United States Patent
Brizgys et al.

(10) Patent No.: US 9,951,043 B2
(45) Date of Patent: Apr. 24, 2018

(54) THERAPEUTIC COMPOUNDS

(71) Applicant: Gilead Sciences, Inc., Foster City, CA (US)

(72) Inventors: Gediminas Brizgys, Menlo Park, CA (US); Eda Canales, San Mateo, CA (US); Chien-hung Chou, Dublin, CA (US); Michael Graupe, Pacifica, CA (US); Randall L. Halcomb, Foster City, CA (US); Yunfeng Eric Hu, San Mateo, CA (US); Scott E. Lazerwith, Burlingame, CA (US); John O. Link, San Francisco, CA (US); Qi Liu, Union City, CA (US); Yafan Lu, Foster City, CA (US); Roland D. Saito, San Mateo, CA (US); Scott D. Schroeder, Union City, CA (US); John R. Somoza, Foster City, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/771,779

(22) PCT Filed: Feb. 28, 2014

(86) PCT No.: PCT/US2014/019663
§ 371 (c)(1),
(2) Date: Aug. 31, 2015

(87) PCT Pub. No.: WO2014/134566
PCT Pub. Date: Sep. 4, 2014

(65) Prior Publication Data
US 2016/0108030 A1 Apr. 21, 2016

Related U.S. Application Data

(60) Provisional application No. 61/771,655, filed on Mar. 1, 2013, provisional application No. 61/857,636, filed on Jul. 23, 2013.

(51) Int. Cl.
| | |
|---|---|
| *C07D 401/12* | (2006.01) |
| *C07D 401/04* | (2006.01) |
| *C07D 487/04* | (2006.01) |
| *C07D 413/14* | (2006.01) |
| *C07D 491/052* | (2006.01) |
| *C07D 417/14* | (2006.01) |
| *C07D 401/14* | (2006.01) |
| *C07D 471/04* | (2006.01) |
| *C07D 403/14* | (2006.01) |
| *A61K 31/437* | (2006.01) |

(Continued)

(52) U.S. Cl.
CPC .......... *C07D 401/12* (2013.01); *A61K 31/437* (2013.01); *A61K 31/444* (2013.01); *A61K 31/4439* (2013.01); *A61K 31/4725* (2013.01); *A61K 31/496* (2013.01); *A61K 31/506* (2013.01); *A61K 31/517* (2013.01); *A61K 31/5377* (2013.01); *A61K 45/06* (2013.01); *C07D 401/04* (2013.01); *C07D 401/14* (2013.01); *C07D 403/14* (2013.01); *C07D 413/14* (2013.01); *C07D 417/14* (2013.01); *C07D 471/04* (2013.01); *C07D 487/04* (2013.01); *C07D 491/052* (2013.01)

(58) Field of Classification Search
CPC .. C07D 401/12; C07D 401/04; C07D 487/04; C07D 401/14; C07D 471/04; C07D 417/14; C07D 413/14; C07D 491/052
See application file for complete search history.

(56) References Cited

U.S. PATENT DOCUMENTS

| | | | |
|---|---|---|---|
| 8,263,627 B2 | 9/2012 | Barrow et al. | |
| 8,748,412 B2 | 6/2014 | Liao et al. | |

(Continued)

FOREIGN PATENT DOCUMENTS

| | | |
|---|---|---|
| WO | WO-2009/062285 A1 | 5/2009 |
| WO | WO-2010/130034 A1 | 11/2010 |

(Continued)

OTHER PUBLICATIONS

Berge, S.M. et al. (1977) "Pharmaceutical Salts," *J. Pharma. Sci.* 66(1):1-19.
Brown, M.K. et al. ( 2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," *Angew Chem. Int. Ed. Engl.* 44(33):5306-5310.
Cos, P. et al. (1998) "Structure-Activity Relationship and Classification of Flavonoids as Inhibitors of Xanthine Oxidase and Superoxide Seavengers," J. Natl. Prod. 61:71-76.
First Examination Report dated Nov. 2, 2015 for New Zealand Patent Application No. 631754.

(Continued)

*Primary Examiner* — Matthew P Coughlin
(74) *Attorney, Agent, or Firm* — Fish & Richardson P.C.

(57) ABSTRACT

Compounds of formula (I) or salts thereof are disclosed. Also disclosed are pharmaceutical compositions comprising a compound of formula I, processes for preparing compounds of formula I, intermediates useful for preparing compounds of formula I and therapeutic methods for treating a Retroviridae viral infection including an infection caused by the HIV virus.

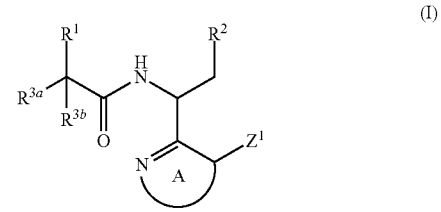

(I)

34 Claims, No Drawings

(51) Int. Cl.

| | | |
|---|---|---|
| A61K 31/4439 | (2006.01) | |
| A61K 31/444 | (2006.01) | |
| A61K 31/4725 | (2006.01) | |
| A61K 31/496 | (2006.01) | |
| A61K 31/506 | (2006.01) | |
| A61K 31/517 | (2006.01) | |
| A61K 31/5377 | (2006.01) | |
| A61K 45/06 | (2006.01) | |

(56) References Cited

U.S. PATENT DOCUMENTS

| | | | |
|---|---|---|---|
| 8,835,488 | B2 | 9/2014 | Yamashita et al. |
| 9,012,441 | B2 | 4/2015 | Bondy et al. |
| 9,050,344 | B2 | 6/2015 | Brizgys et al. |
| 9,220,710 | B2 | 12/2015 | Bondy et al. |
| 9,540,343 | B2 | 1/2017 | Bondy et al. |
| 2010/0249176 | A1 | 9/2010 | Barrow et al. |
| 2012/0045761 | A1 | 2/2012 | Jagannath et al. |
| 2013/0165489 | A1 | 6/2013 | Cocklin et al. |
| 2014/0142085 | A1 | 5/2014 | Bondy et al. |
| 2014/0221346 | A1 | 8/2014 | Halcomb et al. |
| 2014/0296266 | A1 | 10/2014 | Hu et al. |
| 2014/0303164 | A1 | 10/2014 | Brizgys et al. |
| 2016/0067224 | A1 | 3/2016 | Bondy et al. |
| 2016/0083368 | A1 | 3/2016 | Brizgys et al. |
| 2016/0368881 | A1 | 12/2016 | Bondy et al. |

FOREIGN PATENT DOCUMENTS

| | | | | |
|---|---|---|---|---|
| WO | WO-2011/143772 | A1 | 11/2011 | |
| WO | WO-2012/003497 | A1 | 1/2012 | |
| WO | WO-2012/003498 | A1 | 1/2012 | |
| WO | WO-2012065062 | A1 | 5/2012 | |
| WO | WO-2012/145728 | A1 | 10/2012 | |
| WO | WO-2013/006738 | A1 | 1/2013 | |
| WO | WO-2013/006792 | A1 | 1/2013 | |
| WO | WO 2013006738 | A1 * | 1/2013 | ........... C07D 213/40 |
| WO | WO-2013006738 | A1 | 1/2013 | |
| WO | WO-2013/159064 | A1 | 10/2013 | |
| WO | WO-2014/016358 | A1 | 1/2014 | |
| WO | WO-2014/028931 | A2 | 2/2014 | |
| WO | WO-2014/134566 | A1 | 9/2014 | |
| WO | WO-2015/008097 | A1 | 1/2015 | |
| WO | WO-2015/061518 | A1 | 4/2015 | |
| WO | WO-2015/130966 | A1 | 9/2015 | |
| WO | WO-2016/040084 | A1 | 3/2016 | |
| WO | WO-2016/172424 | A1 | 10/2016 | |
| WO | WO-2016/172425 | A1 | 10/2016 | |

OTHER PUBLICATIONS

Hammer, S.M. et al. (2008) "Antiretroviral Treatment of Adult HIV Infection: 2008 Recommendations of the International AIDS Society-USA Panel," JAMA 300(5):555-570.
Hodgson, D.M. et al. (2007) "Intramolecular Cyclopropanation of Unsaturated Terminal Epoxides and Chlorohydrins," JACS 129(14):4456-4462.
International Search Report and Written Opinion mailed Oct. 14, 2014 for PCT/US2014/019663.
Jeong, .J.U. (2010) "Synthesis of Tetrasubstituted Pyrazones and Pyrazone N-Oxides," Tetrahedron Letters 51(6):974-976.
Lemke, C.T. et al. (2012) "Distinct Effects of Two HIV-1 Capsid Assembly Inhibitor Familes That Bind the Same Site Within the N-Terminal Domain of the Viral CA Protein," J. Virol. 86(12):6643-6655.
Notification No. 34475 dated Oct. 13, 2015 for Vietnam Patent Application No. 1-2015-03220.
Office Action dated Dec. 7, 2015 for Colombian Patent Application No. 15-199.357 1 with English translation.
Office Action Dated Jun. 4, 2015 for U.S. Appl. No. 14/194,611.
Office Action Dated Jun. 19, 2015 for U.S. Appl. No. 14/194,623.
Office Action dated Dec. 1, 2015 for Australian Patent Application No. 2014223973.
Office Action dated Dec. 4, 2015 for EP14712844.1-1462.
Office Action dated Dec. 7, 2015 for Colombian Patent Application No. 15-199.357 1.
Powers, J.J. et al. (2009) "Synthesis of Methyl-, Fluoro-, and Chloro-Substituted 6-Hydroxyisoindolin 1-Ones," Tetrahedron Letters 50(12):1267-1269.
Siddiqui, A. et al. (1999) "The Presence of SUbstituents on the Aryl Moiety of the Aryl Phosphoramidate Derivative of d4T Enhances Anti-HIV Efficacy in Cell Culture: A Structure Activity Relationship" J. Med. Chem. 42:393-399.
Smith, R.J. et al. (2010) "Evolutionary Dynamics of Complex Networks of HIV Drug-Resistant Strains: The Case of San Francisco," Science 327(5966):697-701.
Taiwo, B. (2009) "Understanding Transmitted HIV Resistance Through the Experience in the USA," Int. J. Infect. Dis. 13(5):552-559.
Tanaka, R. et al. (2005) "One-Pot Synthesis of Metalated Pyridines from Two Acetylenes, a Nitrile, and a Titanium(II) Alkoxide," J. Am. Chem. Soc. 127(21):7774-7780.
Office Action dated Jun. 28, 2016 for Eurasian Patent Application No. 201591457/28.
Office Action dated Sep. 8, 2016 for Colombia Application No. 15199357.
Office Action dated Sep. 8, 2016 English Translation for Colombia Application No. 15199357.
Bhattacharya et al. (2014) Structural Basis of HIV-1 Capsid Recognition by PF74 and CPSF6, PNAS; 111(52):18625-18630.
Blair et al., (2010) "HIV Capsid is a Tractable Target for Small Molecule Therapeutic Intervention," PLOS Pathog. 6(12): e1001220.
Briggs et al., (2003) "Structural Organization of Authentic, Mature HIV-1 Virions and Cores," The EMBO Journal; vol. 22 No. 7 pp. 1707-1715.
Campbell et al., (2015) "HIV-1 Capsid: The Multifaceted Key Player in HIV-1 Infection," Nat Rev Microbiol.; 13(8): 471-483.
Chin et al. (2015) "Direct Visualization of HIV-1 Replication Intermediates Shows That Capsid and CPSF6 Modulate HIV-1 Intra-Nuclear Invasion and Integration", Cell Reports 13:1717-1731.
Curreli et al., (2011) "Virtual Screening Based Identification of Novel Small-molecule Inhibitors Targeted to the HIV-1 Capsid," Bioorganic & Medicinal Chemistry 19:77-90.
Fader et al., (2013) Optimization of a 1,5-dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistry Letters, doi: <http://dx.doi.org/10.1016/j.bmcl.2013.03.074>.
Forshey et al., (2002) "Formation of a Human Immunodeficiency Virus Type 1 Core of Optimal Stability Is Crucial for Viral Replication," J. Virology, 76(11) p. 5667-5677.
Ganser et al., (1999) "Assembly and Analysis of Conical Models for the HIV-1 Core," Science 283, 80-82.
Ganser-Pornillos et al., (2007) "Structure of Full-Length HIV-1 CA: A Model for the Mature Capsid Lattice," Cell.; 131(1):70-9.
Hung et al. (2013) "Large-Scale Functional Purification of Recombinant HIV- 1 Capsid" PLOS One, vol. 8, Issue 3, e58035.
Jin et al., (2010) "SAR and Molecular Mechanism Study of Novel Acylhydrazone Compounds Targeting HIV-1 CA," Bioorganic & Medicinal Chemistry; 18: 2135-2140.
Jouvenet et al., (2006) "Plasma Membrane Is the Site of Productive HIV-1 Particle Assembly," PLOS Biol.;4(12):e435.
Kelly, et al., (2007) "Structure of the Antiviral Assembly Inhibitor CAP-1 Bound to the HIV-1 CA Protein," Journal of Molecular Biology, doi: 10.1016/j.jmb.2007.07.070.
Kim et al., (2013) "Discovery of a New HIV-1 Inhibitor Scaffold and Synthesis of Potential Prodrugs of Indazoles," Bioorganic & Medicinal Chemistry Letters, doi: <http://dx.doi.org/10.1016/j.bmcl.2013.03.075>.
Lad et al., (2015) "Functional Label-Free Assays for Characterizing the in Vitro Mechanism of Action of Small Molecule Modulators of Capsid Assembly" Biochemistry, 54, 2240-2248.

(56) References Cited

OTHER PUBLICATIONS

Lamorte et al. (2015) "Discovery of Novel Small-Molecule HIV-1 Replication Inhibitors That Stabilize Capsid Complexes" *Antimicrobial Agents and Chemotherapy*, 57(10): 4622-4631.
Lazerwith et al., (2017) "New Antiretrovirals for HIV and Antivirals for HBV," in *Comprehensive Medicinal Chemistry*, 3rd Edition, 1-36.
Lee et al., (2010) "Flexible Use of Nuclear Import Pathways by HIV-1," *Cell Host & Microbe*; 7, 221-233.
Matreyek et al., (2013) "Nucleoporin NUP153 Phenylalanine-Glycine Motifs Engage a Common Binding Pocket within the HIV-1 Capsid Protein to Mediate Lentiviral Infectivity" *PLOS Pathogens* vol. 9 | Issue 10 | e1003693.
Office Action dated Mar. 30, 2017 for Chile Application No. 2445-2015.
English language translation of Office Action dated Mar. 30, 2017 for Chile Application No. 2445-2015.
Office Action dated Jan. 18, 2017 for Eurasian Patent Application No. 201591457.
English language translation of Office Action dated Jan. 18, 2017 for Eurasian Patent Application No. 201591457.
Office Action dated Mar. 29, 2017 for European Patent Application No. 14712844.1.
Office Action dated Feb. 22, 2017 for New Zealand Application No. 728537.
Office Action dated Jan. 18, 2017 for Panama Application No. 90820-01.
English language translation of Office Action dated Jan. 18, 2017 for Panama Application No. 90820-01.
Office Action dated Jan. 16, 2017 for Chinese Application No. 201480020587.0.
English language translation of Office Action dated Jan. 16, 2017 for Chinese Application No. 201480020587.0.
Search Report dated Jan. 6, 2017 for Chinese Application No. 201480020587.0.
English language translation of Search Report dated Jan. 6, 2017 for Chinese Application No. 201480020587.0.
Pre-grant opposition dated Jun. 15, 2016 for Chilean Application No. 2445-2015.
English language translation of Pre-grant opposition dated Jun. 15, 2016 for Chilean Application No. 2445-2015.
Pornillos et al., (2009) "X-ray Structures of the Hexameric Building Block of the HIV Capsid" *Cell.*; 137(7):1282-92.
Pornillos et al., (2009) Supplemental Data for "X-ray Structures of the Hexameric Building Block of the HIV Capsid" *Cell.* Jun. 26, 2009;137(7):1282-92.
Price et al. (2012) "CPSF6 Defines a Conserved Capsid Interface That Modulates HIV-1 Replication" *PLOS Pathogens*, 8(8):e1002896.
Rihn et al., (2013) "Extreme Genetic Fragility of the HIV-1 Capsid" *PLOS One*, vol. 9 Issue 6 e1003461.
Shi et al., (2011) "Small-Molecule Inhibition of Human Immunodeficiency Virus Type 1 Infection by Virus Capsid Destabilization," *J. Virology*, p. 542-549.
Sticht et al., (2005) "A peptide inhibitor of HIV-1 assembly in vitro" *Nature Structural & Molecular Biology*, vol. 12 No. 8 671-677.
Tang et al., (2003) "Antiviral Inhibition of the HIV-1 Capsid Protein," *J. Mol. Biol.*, 327, 1013-1020.
Tse et al., (2017) "Discovery of Novel Potent HIV Capsid Inhibitors with Long-Acting Potential," Oral Presentation at the Conference on Retroviruses and Opportunistic Infections (CROI), Seattle, WA.
Tse et al., (2017) "Discovery of Novel Potent HIV Capsid Inhibitors with Long-Acting Potential," Abstract for Oral Presentation at the Conference on Retroviruses and Opportunistic Infections (CROI), Seattle, WA.
Tsiang et al., (2012) "A Trimer of Dimers Is the Basic Building Block for Human Immunodeficiency Virus-1 Capsid Assembly" *Biochemistry*, 51, 4416-4428.
U.S. Appl. No. 15/357,290 (Not attached) dated Nov. 21, 2016.
Wong et al., (2014) "SPR Assay Development to Characterize Capsid Inhibitors Binding & MOA," Poster Presented at the Developments in Protein Interaction (DiPIA), La Jolla, CA.
Yant et al., (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston, Massachusetts.
Yant et al., (2014) "PF74 Inhibits Multiple HIV Capsid Functions Independently of Host Cyclophilin A and CPSF6" Abstract for Poster Presented at the Conference on Retroviruses and Opportunistic Infections (CROI), Boston, Massachusetts.
Zhou et al. (2015) "HIV-1 Resistance to the Capsid-Targeting Inhibitor PF74 Results in Altered Dependence on Host Factors Required for Virus Neclear Entry" *Journal of Virology*, doi 10.1128/JVI.00340-15. Published online Jun. 24, 2015.
Office Action dated Apr. 12, 2017 for Gulf Cooperation Council Application No. 2014/26552.
U.S. Appl. No. 15/680,041 (not attached). 2017.
Office Action dated Oct. 18, 2017 for Australian Application No. 2016262671.
Office Action dated Jul. 19, 2017 for Chinese Application No. 2014800205870.
Office Action dated Jul. 19, 2017 for Chinese Application No. 2014800205870—English translation.
Office Action dated Oct. 17, 2017 for Taiwan Patent Application No. 103106785.
Office Action dated Oct. 17, 2017 for Taiwan Patent Application No. 103106785—English translation.

\* cited by examiner

THERAPEUTIC COMPOUNDS

CROSS-REFERENCE TO RELATED APPLICATIONS

This application claims the benefit of and priority to U.S. Provisional Patent Application Ser. Nos. 61/771,655, filed Mar. 1, 2013 and 61/857,636, filed Jul. 23, 2013, the disclosures of each of which are hereby incorporated herein by reference in their entirety.

BACKGROUND

Positive-single stranded RNA viruses comprising the Retroviridae family include those of the subfamily Orthoretrovirinae and genera Alpharetrovirus, Betaretrovirus, Gamaretrovirus, Deltaretrovirus, Epsilonretrovirus, Lentivirus, and Spumavirus which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

SUMMARY

Provided herein are compounds and methods for the treatment of HIV (i.e., human immunodeficiency virus) infection.

One embodiment provides a compound of formula IIId:

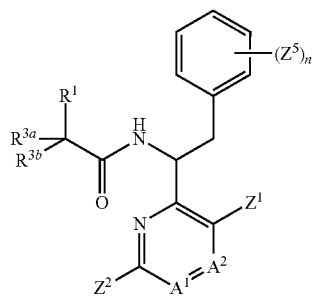

IIId wherein $A^1$ is CH, C—$Z^3$, or nitrogen;

$A^2$ is CH or nitrogen;

$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;

each $R^{3a}$ and $R^{3b}$ is independently H or $(C_1-C_3)$alkyl;

$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;

each $Z^{1a}$ is independently $(C_3-C_7)$carbocycle, 5-12 membered heteroaryl, 3-12 membered heterocycle, halogen, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, —$C(O)R^{n1}$, —$C(O)OR^{n1}$, —$C(O)NR^{q1}R^{r1}$ and —$S(O)_2NR^{n1}COR^{p1}$, wherein any $(C_3-C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;

each $Z^{1b}$ is independently $(C_1-C_8)$alkyl optionally substituted with 1, 2, 3, 4 or 5 halogen, which are the same or different;

each $Z^{1c}$ is independently halogen, —CN, —OH, —$NH_2$, —$C(O)NR^{q2}R^{r2}$, or $(C_1-C_8)$heteroalkyl;

each $Z^{1d}$ is independently $(C_1-C_8)$alkyl or $(C_1-C_8)$haloalkyl;

each $R^{n1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{n1}$ is optionally substituted with 1, 2, 3, 4 or 5 $Z^{1c}$ groups, wherein the $Z^{1c}$ groups are the same or different;

each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^c$ and $Z^{1d}$ groups are the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is $(C_2-C_8)$alkenyl, $(C_2-C_8)$alkynyl, 6-12 membered aryl, 5-12 membered C-linked-heteroaryl, 3-12 membered C-linked-heterocycle, —$C(O)R^{n3}$, or —$C(O)NR^{q3}R^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, wherein the $Z^{2b}$ and $Z^{2c}$ groups are the same or different, and wherein any $(C_2-C_8)$alkenyl or $(C_2-C_8)$alkynyl of $Z^2$ is optionally substituted with 1, 2, 3, 4, or 5 $Z^{2c}$ groups, wherein the $Z^{2c}$ groups are the same or different;

each $R^{n3}$ is independently H or $(C_1-C_4)$alkyl;

each $R^{q3}$ and $R^{r3}$ is independently H or $(C_1-C_4)$alkyl;

each $Z^{2b}$ is independently oxo, $(C_1-C_4)$alkyl, $(C_1-C_4)$heteroalkyl or $(C_1-C_4)$haloalkyl;

each $Z^{2c}$ is independently oxo, halogen, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, —$NO_2$, —$C(O)R^{n4}$, —$C(O)OR^{n4}$, or —$C(O)NR^{q4}R^{r4}$;

each $R^{n4}$ is independently H, $(C_1-C_4)$alkyl, $(C_1-C_4)$haloalkyl, or $(C_1-C_4)$heteroalkyl;

each $R^{p4}$ is independently $(C_1-C_8)$alkyl, $(C_1-C_4)$haloalkyl, or $(C_1-C_4)$heteroalkyl;

each $R^{q4}$ and $R^{r4}$ is independently H, $(C_1-C_4)$alkyl, $(C_1-C_4)$haloalkyl, or $(C_1-C_4)$heteroalkyl;

each $Z^3$ is independently a $(C_1-C_4)$heteroalkyl;

each $Z^4$ is independently oxo, $(C_1-C_8)$alkyl, $(C_3-C_7)$carbocycle, halogen, —CN, —$OR^{n5}$, —$NR^{q5}R^{r5}$, —$NR^{n5}COR^{p5}$, —$NR^{n5}CO_2R^{p5}$, —$C(O)R^{n5}$, —$C(O)OR^{n5}$, or —$C(O)NR^{q5}R^{r5}$, wherein any $(C_3-C_7)$carbocycle or $(C_1-C_8)$alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —$OR^{n6}$;

each $R^{n5}$, $R^{p5}$, $R^{q5}$, $R^{r5}$, and $R^{n6}$ is independently H or $(C_1-C_4)$alkyl;

each $Z^5$ is independently halogen, which may be same or different; and n is 0, 1, 2, or 3;

or a pharmaceutically acceptable salt thereof.

One embodiment provides a compound of formula III:

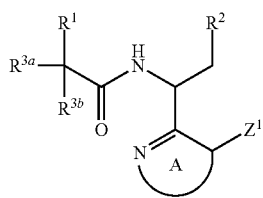

III wherein

A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with 1 or 2 $Z^3$ groups, wherein the $Z^3$ groups are the same or different;

$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;

$R^2$ is phenyl optionally substituted with 1, 2, 3, 4 or 5 halogen, which are the same or different;

each $R^{3a}$ and $R^{3b}$ is independently H or $(C_1-C_3)$alkyl;

$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;

each $Z^{1a}$ is independently $(C_3-C_7)$carbocycle, 5-12 membered heterocycle, 3-12 membered heterocycle, halogen, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{1l}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, —$C(O)R^{n1}$, —$C(O)OR^{n1}$, —$C(O)NR^{q1}R^{r1}$ and —$S(O)_2NR^{n1}COR^{p1}$, wherein any $(C_3-C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;

each $Z^{1b}$ is independently $(C_1-C_8)$alkyl optionally substituted with 1, 2, 3, 4 or 5 halogen, which are the same or different;

each $Z^{1c}$ is independently halogen, —CN, —OH, —$NH_2$, —$C(O)NR^{q2}R^{r2}$, or $(C_1-C_8)$heteroalkyl;

each $Z^{1d}$ is independently $(C_1-C_8)$alkyl or $(C_1-C_8)$haloalkyl;

each $R^{n1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{n1}$ is optionally substituted with 1, 2, 3, 4 or 5 $Z^{1c}$ groups, wherein the $Z^{1c}$ groups are the same or different;

each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^c$ and $Z^{1d}$ groups are the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is $(C_2-C_8)$alkenyl, $(C_2-C_8)$alkynyl, 6-12 membered aryl, 5-12 membered C-linked-heteroaryl, 3-12 membered C-linked-heterocycle, —$C(O)R^{n3}$, or —$C(O)NR^{q3}R^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, wherein the $Z^{2b}$ and $Z^{2c}$ groups are the same or different, and wherein any $(C_2-C_8)$alkenyl or $(C_2-C_8)$alkynyl of $Z^2$ is optionally substituted with 1, 2, 3, 4, or 5 $Z^{2c}$ groups, wherein the $Z^{2c}$ groups are the same or different;

each $R^{n3}$ is independently H or $(C_1-C_4)$alkyl;

each $R^{q3}$ and $R^{r3}$ is independently H or $(C_1-C_4)$alkyl;

each $Z^{2b}$ is independently oxo, $(C_1-C_4)$alkyl, $(C_1-C_4)$heteroalkyl, or $(C_1-C_4)$haloalkyl;

each $Z^{2c}$ is independently oxo, halogen, —CN, —$OR^{n4}$, —OC(O)$R^{p4}$, —OC(O)$NR^{q4}R^{r4}$, —$SR^{n4}$, —S(O)$R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, —$NO_2$, —C(O)$R^{n4}$, —C(O)$OR^{n4}$, or —C(O)$NR^{q4}R^{r4}$;

each $R^{n4}$ is independently H, $(C_1-C_4)$alkyl, $(C_1-C_4)$haloalkyl, or $(C_1-C_4)$heteroalkyl;

each $R^{p4}$ is independently $(C_1-C_8)$alkyl, $(C_1-C_4)$haloalkyl, or $(C_1-C_4)$heteroalkyl;

each $R^{q4}$ and $R^{r4}$ is independently H, $(C_1-C_4)$alkyl, $(C_1-C_4)$haloalkyl, or $(C_1-C_4)$heteroalkyl;

each $Z^3$ is independently a $(C_1-C_4)$heteroalkyl or halogen;

each $Z^4$ is independently oxo, $(C_1-C_8)$alkyl, $(C_3-C_7)$carbocycle, halogen, —CN, —$OR^{n5}$, —$NR^{q5}R^{r5}$, —$NR^{n5}COR^{p5}$, —$NR^{n5}CO_2R^{p5}$, —C(O)$R^{n5}$, —C(O)$OR^{n5}$, or —C(O)$NR^{q5}R^{r5}$, wherein any $(C_3-C_7)$carbocycle or $(C_1-C_8)$alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —$OR^{n6}$; and each $R^{n5}$, $R^{p5}$, $R^{q5}$, $R^{r5}$, and $R^{n6}$ is independently H or $(C_1-C_4)$alkyl;

or a pharmaceutically acceptable salt thereof.

One embodiment provides a compound of formula I

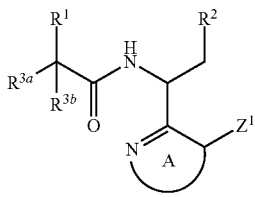

I wherein:

A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with one or more (e.g., 1 or 2) $Z^3$ groups;

$R^1$ is 6-12 membered aryl, 5-12 membered heteroaryl or 3-12 membered heterocycle, wherein any 6-12 membered aryl, 5-12 membered heteroaryl or 3-12 membered heterocycle of $R^1$ is optionally substituted with one or more (e.g., 1, 2, 3, 4 or 5) $Z^4$ groups;

$R^2$ is phenyl, 5-membered monocyclic-heteroaryl, 6-membered monocyclic-heteroaryl or $(C_3-C_7)$carbocycle, wherein any phenyl, 5-membered monocyclic-heteroaryl, 6-membered monocyclic-heteroaryl or $(C_3-C_7)$carbocycle of $R^2$ is optionally substituted with one or more (e.g., 1, 2, 3, 4 or 5) $Z^5$ groups;

each $R^{3a}$ and $R^{3b}$ is independently selected from H, halogen, $(C_1-C_3)$alkyl and $(C_1-C_3)$haloalkyl, or $R^{3a}$ is selected from H, $(C_1-C_3)$alkyl and $(C_1-C_3)$haloalkyl and $R^{3b}$ is selected from —OH and —CN;

$Z^1$ is selected from 6-12 membered aryl, 5-14 membered heteroaryl and 3-14 membered heterocycle, wherein any 6-12 membered aryl, 5-14 membered heteroaryl and 3-14 membered heterocycle of $Z^1$ is optionally substituted with one or more (e.g., 1, 2, 3, 4 or 5) $Z^{1a}$ or $Z^b$;

each $Z^{1a}$ is independently selected from $(C_3-C_7)$carbocycle, 6-12 membered aryl, 5-12 membered heteroaryl, 3-12 membered heterocycle, halogen, —CN, —$OR^{n1}$, —OC(O)$R^{p1}$, —OC(O)$NR^{q1}R^{r1}$, —$SR^{n1}$, —S(O)$R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2R^{p1}$, —$NR^{n1}S(O)_2NR^{q1}R^{r1}$, $NO_2$, —C(O)$R^{n1}$, —C(O)$OR^{n1}$, —C(O)$NR^{q1}R^{r1}$ and —$S(O)_2NR^{n1}COR^{p1}$, wherein any $(C_3-C_7)$carbocycle, 6-12 membered aryl, 5-12 membered heteroaryl and 3-12 membered heterocycle of $Z^{1a}$ is optionally substituted with one or more (e.g., 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with one or more (e.g., 1, 2, 3, 4 or 5) $Z^{1c}$ groups;

each $Z^{1c}$ is independently selected from $(C_3-C_7)$carbocycle, phenyl, 5-6 membered monocyclic-heteroaryl, 3-7 membered heterocycle, halogen, —CN, —$OR^{n2}$, —OC(O)$R^{p2}$, —OC(O)$NR^{q2}R^{r2}$, —$SR^{n2}$, —S(O)$R^{p2}$, —$S(O)_2OH$, —$S(O)_2R^{p2}$, —$S(O)_2NR^{q2}R^{r2}$, —$NR^{q2}R^{r2}$, —$NR^{n2}COR^{p2}$, —$NR^{n2}CO_2R^{p2}$, —$NR^{n2}CONR^{q2}R^{r2}$, —$NR^{n2}S(O)_2R^{p2}$, —$NR^{n2}S(O)_2OR^{p2}$, —$NR^{n2}S(O)_2NR^{q2}R^{r2}$, $NO_2$, —C(O)$R^{n2}$, —C(O)$OR^{n2}$, —C(O)$NR^{q2}R^{r2}$, halophenyl, 5-6 membered haloheteroaryl, 3-7 membered haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R^{n1}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{n1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{n1}$ is optionally substituted with one or more (e.g., 1, 2, 3, 4 or 5) $Z^{1c}$ groups;

each $R^{p1}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{p1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{p1}$ is optionally substituted with one or more (e.g., 1, 2, 3, 4 or 5) $Z^{1c}$ groups;

$R^{q1}$ and $R^{r1}$ are each independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{q1}$ or $R^{r1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{q1}$ or $R^{r1}$ is optionally substituted with one or more (e.g., 1, 2, 3, 4 or 5) $Z^{1c}$ groups, or $R^{q1}$ and $R^{r1}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{1c}$ or $Z^{1d}$ groups;

each $R^{n2}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl;

each $R^{p2}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl;

$R^{q2}$ and $R^{r2}$ are each independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl, or $R^{q2}$ and $R^{r2}$ together with the nitrogen to which they are attached form a 5, 6 or 7-membered heterocycle;

$Z^2$ is selected from $(C_2-C_8)$alkenyl, $(C_2-C_8)$alkynyl, 6-12 membered aryl, 5-12 membered C-linked-heteroaryl, 3-12 membered C-linked-heterocycle, —C(O)$R^{n3}$ and —C(O)NR$^{q3}$R$^{r3}$, wherein any 6-12 membered aryl, 5-12 membered C-linked-heteroaryl and 3-12 membered C-linked-heterocycle of $Z^2$ is optionally substituted with one or more (e.g., 1, 2, 3, 4 or 5) $Z^{2b}$ or $Z^{2c}$ groups, and wherein any $(C_2-C_8)$alkenyl and $(C_2-C_8)$alkynyl of $Z^2$ is optionally substituted with one or more (e.g., 1, 2, 3, 4, or 5) $Z^{2c}$ groups;

each $Z^{2a}$ is independently selected from $(C_3-C_7)$carbocycle, 6-12 membered aryl, 5-12 membered heteroaryl, 3-12 membered heterocycle, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{r4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$, wherein any $(C_3-C_7)$carbocycle, 6-12 membered aryl, 5-12 membered heteroaryl and 3-12 membered heterocycle of $Z^{2a}$ is optionally substituted with one or more (e.g., 1, 2, 3, 4 or 5) $Z^{2b}$ or $Z^{2c}$ groups;

each $Z^{2b}$ is independently selected from $(C_1-C_4)$alkyl, $(C_1-C_4)$heteroalkyl and $(C_1-C_4)$haloalkyl;

each $Z^{2c}$ is independently selected from halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^4$, —NR$^{q4}$R$^4$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$;

each $R^{n3}$ is independently selected from H, $(C_1-C_4)$alkyl, $(C_2-C_4)$alkenyl, $(C_3-C_7)$carbocycle, 3-12 membered heterocycle, 5-12 membered heteroaryl and 6-12 membered aryl, wherein any $(C_3-C_7)$carbocycle, 3-12 membered heterocycle, 5-12 membered heteroaryl and 6-12 membered aryl of $R^{n3}$ is optionally substituted with one or more (e.g., 1, 2, 3, 4 or 5) $Z^{2b}$ or $Z^{2c}$ groups, and wherein any $(C_1-C_4)$alkyl, $(C_2-C_4)$alkenyl and $(C_2-C_4)$alkynyl of $R^{n3}$ is optionally substituted with one or more (e.g., 1, 2, 3, 4 or 5) $Z^{2a}$ groups;

$R^{q3}$ and $R^{r3}$ are each independently selected from H, $(C_1-C_4)$alkyl, $(C_2-C_4)$alkenyl, $(C_3-C_7)$carbocycle, 3-12 membered heterocycle, 5-12 membered heteroaryl and 6-12 membered aryl, wherein any $(C_3-C_7)$carbocycle, 3-12 membered heterocycle, 5-12 membered heteroaryl and 6-12 membered aryl of $R^{q3}$ or $R^{r3}$ is optionally substituted with one or more (e.g., 1, 2, 3, 4 or 5) $Z^{2b}$ or $Z^{2c}$ groups, and wherein any $(C_1-C_4)$alkyl and $(C_2-C_4)$alkenyl of $R^{q3}$ or $R^{r3}$ is optionally substituted with one or more (e.g., 1, 2, 3, 4 or 5) $Z^{2a}$ groups, or $R^{q3}$ and $R^{r3}$ together with the nitrogen to which they are attached form a heterocycle or heteroaryl, wherein the heterocycle or heteroaryl is optionally substituted with one or more (e.g., 1, 2, 3, 4 or 5) $Z^{2b}$ or $Z^{2c}$ groups;

each $R^{n4}$ is independently selected from H, $(C_1-C_4)$alkyl, $(C_2-C_8)$alkenyl, $(C_2-C_8)$alkynyl, $(C_1-C_4)$haloalkyl and $(C_1-C_4)$heteroalkyl;

each $R^{p4}$ is independently selected from $(C_1-C_8)$alkyl, $(C_2-C_4)$alkenyl, $(C_2-C_4)$alkynyl, $(C_1-C_4)$haloalkyl and $(C_1-C_4)$heteroalkyl;

$R^{q4}$ and $R^{r4}$ are each independently selected from H, $(C_1-C_4)$alkyl, $(C_2-C_4)$alkenyl, $(C_2-C_4)$alkynyl, $(C_1-C_4)$haloalkyl and $(C_1-C_4)$heteroalkyl;

each $Z^3$ is independently selected from halogen, $(C_1-C_4)$alkyl, —OH, —CN, $(C_1-C_4)$heteroalkyl and $(C_1-C_4)$haloalkyl;

each $Z^4$ is independently selected from $(C_1-C_8)$alkyl, $(C_2-C_8)$alkenyl, $(C_2-C_8)$alkynyl, $(C_3-C_7)$carbocycle, halogen, —CN, —OR$^{n5}$, —OC(O)R$^{p5}$, —OC(O)NR$^{q5}$R$^{r5}$, —SR$^{n5}$, —S(O)R$^{p5}$, —S(O)$_2$OH, —S(O)$_2$R$^{p5}$, —S(O)$_2$NR$^{q5}$R$^{r5}$, —NR$^{q5}$R$^{r5}$, —NR$^{n5}$COR$^{p5}$, —NR$^{n5}$CO$_2$R$^{p5}$, —NR$^{n5}$CONR$^{q5}$R$^{r5}$, —NR$^{n5}$S(O)$_2$R$^{p5}$, —NR$^{n5}$S(O)$_2$OR$^{p5}$, —NR$^{n5}$S(O)$_2$NR$^{q5}$SR$^5$, NO$_2$, —C(O)R$^{n5}$, —C(O)OR$^{n5}$ and —C(O)NR$^{q5}$R$^{r5}$, wherein any $(C_3-C_7)$carbocycle, of $Z^4$ is optionally substituted with one or more (e.g., 1, 2, 3, 4 or 5) $Z^{4a}$ or $Z^{4b}$ groups, and wherein any $(C_1-C_8)$alkyl, $(C_2-C_8)$alkenyl and $(C_2-C_8)$alkynyl of $Z^4$ is optionally substituted with one or more (e.g., 1, 2, 3, 4 or 5) $Z^{4a}$ groups;

each $Z^{4a}$ is independently selected from halogen, —CN, —OR$^{n6}$, —OC(O)R$^{p6}$, —OC(O)NR$^{q6}$R$^{r6}$, —SR$^{n6}$, —S(O)R$^{p6}$, —S(O)$_2$OH, —S(O)$_2$R$^{p6}$, —S(O)$_2$NR$^{q6}$R$^{r6}$, —NR$^{q6}$R$^{r6}$, —NR$^{n6}$COR$^{p6}$, —NR$^{n6}$CO$_2$R$^{p6}$, —NR$^{n6}$CONR$^{q6}$R$^{r6}$, —NR$^{n6}$S(O)$_2$R$^{p6}$, —NR$^{n6}$S(O)$_2$OR$^{p6}$, —NR$^{n6}$S(O)$_2$NR$^{q6}$R$^{r6}$, NO$_2$, —C(O)R$^{n6}$, —C(O)OR$^{n6}$ and —C(O)NR$^{q6}$R$^{r6}$;

each $Z^{4b}$ is independently selected from $(C_1-C_4)$alkyl, $(C_2-C_4)$alkenyl $(C_2-C_4)$alkynyl and $(C_1-C_4)$haloalkyl;

each $R^{n5}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p5}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q5}$ and $R^{r5}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{n6}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p6}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q6}$ and $R^{r6}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $Z^5$ is independently selected from $(C_1-C_6)$alkyl, halogen, —CN and —OR$^{n7}$ wherein any $(C_1-C_6)$alkyl of $Z^5$ is optionally substituted with one or more (e.g., 1, 2, 3, 4 or 5) halogen; and each $R^{n7}$ is independently selected from H, $(C_1-C_3)$alkyl, $(C_1-C_3)$haloalkyl and $(C_3-C_7)$carbocycle;

or a pharmaceutically acceptable salt thereof.

One embodiment provides a pharmaceutical composition comprising a compound of formula I or a pharmaceutically acceptable salt thereof, and a pharmaceutically acceptable carrier. Another embodiment provides a pharmaceutical composition comprising a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, and a pharmaceutically acceptable carrier.

One embodiment provides a pharmaceutical composition comprising a compound of formula I or a pharmaceutically acceptable salt thereof; and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof. Another embodiment provides a pharmaceutical composition comprising a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof; and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

One embodiment provides a method for treating a Retroviridae viral infection (e.g., an HIV viral infection) in a mammal (e.g., a human), comprising administering a compound of formula I, or a pharmaceutically acceptable salt thereof, to the mammal. Another embodiment provides a method for treating a Retroviridae viral infection (e.g., an HIV viral infection) in a mammal (e.g., a human), comprising administering a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, to the mammal. Another embodiment provides a method for treating a HIV infection in a patient in need thereof comprising administering a therapeutically effective amount of a compound as detailed herein, or a pharmaceutically acceptable salt thereof, to the patient.

One embodiment provides a method for inhibiting the proliferation of the HIV virus, treating AIDS or delaying the onset of AIDS or ARC symptoms in a mammal (e.g., a human), comprising administering a compound of formula I, or a pharmaceutically acceptable salt thereof, to the mammal. Another embodiment provides a method for inhibiting the proliferation of the HIV virus, treating AIDS or delaying the onset of AIDS or ARC symptoms in a mammal (e.g., a human), comprising administering a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, to the mammal.

One embodiment provides a method for treating an HIV infection in a mammal (e.g., a human), comprising administering a compound of formula I, or a pharmaceutically acceptable salt thereof, to the mammal. Another embodiment provides a method for treating an HIV infection in a mammal (e.g., a human), comprising administering a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, to the mammal.

One embodiment provides a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof. Another embodiment provides a method for treating an HIV infection in a mammal (e.g., a human), comprising administering to the mammal in need thereof a therapeutically effective amount of a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof. Another embodiment provides a method for treating an HIV infection in a patient in need thereof comprising administering to the patient a therapeutically effective amount of a compound as described herein, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor and combinations thereof.

One embodiment provides a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and non-catalytic site HIV integrase inhibitors, and combinations thereof. Another embodiment provides a method for treating an HIV infection in a mammal (e.g., a human), comprising administering to the mammal in need thereof a therapeutically effective amount of a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and non-catalytic site HIV integrase inhibitors, and combinations thereof.

One embodiment provides a compound of formula I, or a pharmaceutically acceptable salt thereof for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)). Another embodiment provides a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)).

One embodiment provides a compound of formula I, or a pharmaceutically acceptable salt thereof for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human). Another embodiment provides a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human).

One embodiment provides a compound of formula I, or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS or ARC symptoms. Another embodiment provides a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS or ARC symptoms.

One embodiment provides a compound of formula I, or a pharmaceutically acceptable salt thereof, for use in the prophylactic or therapeutic treatment of a Retroviridae virus infection (e.g., an HIV virus infection). Another embodiment provides a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, for use in the prophylactic or therapeutic treatment of a Retroviridae virus infection (e.g., an HIV virus infection).

One embodiment provides the use of a compound of formula I, or a pharmaceutically acceptable salt thereof, for the manufacture of a medicament for a Retroviridae virus infection (e.g., an HIV virus infection) in a mammal (e.g., a human). Another embodiment provides a compound as detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, for the manufacture of a medicament for a Retroviridae virus infection (e.g., an HIV virus infection) in a mammal (e.g., a human).

One embodiment provides processes and intermediates disclosed herein that are useful for preparing compounds of formula I or salts thereof. Another embodiment provides processes and intermediates disclosed herein that are useful for preparing compounds of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

DEFINITIONS

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms (i.e., ($C_1$-$C_4$)alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, and octyl (—(CH$_2$)$_7$CH$_3$).

"Alkenyl" is a straight or branched hydrocarbon with at least one carbon-carbon, sp$^2$ double bond. For example, an alkenyl group can have 2 to 8 carbon atoms (i.e., C$_2$-C$_8$ alkenyl), or 2 to 6 carbon atoms (i.e., C$_2$-C$_6$ alkenyl). Examples of suitable alkenyl groups include, but are not limited to, ethylene or vinyl (—CH═CH$_2$), allyl (—CH$_2$CH═CH$_2$) and 5-hexenyl (—CH$_2$CH$_2$CH$_2$CH$_2$CH═CH$_2$).

"Alkynyl" is a straight or branched hydrocarbon with at least one carbon-carbon, sp triple bond. For example, an alkynyl group can have 2 to 8 carbon atoms (i.e., C$_2$-C$_8$ alkyne) or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms of the alkyl are each independently replaced by a halo substituent. For example, (C$_1$-C$_6$)haloalkyl is a (C$_1$-C$_6$)alkyl wherein one or more of the hydrogen atoms of the (C$_1$-C$_6$)alkyl have been replaced by a halo substituent. Examples of haloalkyls include but are not limited to fluoromethyl, fluorochloromethyl, difluoromethyl, difluorochloromethyl, trifluoromethyl, 1,1,1, trifluoroethyl and pentafluoroethyl.

The term "heteroalkyl" as used herein refers to an alkyl as defined herein, wherein one or more of the carbon atoms of the alkyl are replaced by an O, S, or NR$^q$, (or if the carbon atom being replaced is a terminal carbon with an OH, SH or N(R$^q$)$_2$) wherein each R$^{q1}$ is independently H or (C$_1$-C$_6$) alkyl. For example, (C$_1$-C$_8$)heteroalkyl includes a heteroalkyl of one to eight carbons and one or more heteroatoms (e.g., O, S, NR$^q$, OH, SH or N(R$^q$)$_2$). Thus, for example, a C$_1$ heteroalkyl encompasses, e.g., —CH$_2$—NH$_2$. Examples of heteroalkyls include but are not limited to methoxymethyl, ethoxymethyl, methoxy, 2-hydroxyethyl and N,N'-dimethylpropylamine.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. It is also to be understood that when reference is made to a certain atom-range membered aryl (e.g., 6-12 membered aryl), the atom range is for the total ring atoms of the aryl. For example, a 6-membered aryl would include phenyl and a 10-membered aryl would include naphthyl and 1, 2, 3,4-tetrahydronaphthyl. Non-limiting examples of aryl groups include, but are not limited to, phenyl, indenyl, naphthyl, 1,2,3,4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5-14 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "C-linked-heteroaryl" (carbon-linked heteroaryl) as used herein refers to a heteroaryl that is linked at a carbon atom of the heteroaryl to the remainder of the compound of formula I (e.g., a C-linked-heteroaryl of $Z^2$ bonded to the A ring of formula I through a carbon atom of the C-linked-heteroaryl).

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). It is also to be understood that when reference is made to a certain atom-range membered heterocycle (e.g., a 3-14 membered heterocycle), the atom range is for the total ring atoms of the heterocycle and includes carbon atoms and heteroatoms. For example, a 3-membered heterocycle would include an aziridinyl and a 10-membered heterocycle would include a 1,2,3,4-tetrahydroquinolyl. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one and pyrrolidin-2-one.

The term "C-linked-heterocycle" (carbon-linked heterocycle) as used herein refers to a "heterocycle that is linked at a carbon atom of the heterocycle to the remainder of the compound of formula I (e.g., a C-linked-heterocycle of $Z^2$ bonded to the A ring of formula I through a carbon atom of the C-linked-heterocycle).

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., $(C_3-C_7)$carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halophenyl" as used herein refers to phenyl, wherein one or more (e.g., 1, 2, 3, 4 or 5) hydrogen atoms of the phenyl are each replaced independently by a halo substituent. Examples of halophenyl include but are not limited to fluorophenyl, 2,3-dichlorophenyl, 3-bromo-4-fluorophenyl and pentafluorophenyl.

The term "haloheteroaryl" as used herein refers to a heteroaryl, wherein one or more (e.g., 1, 2, 3, 4 or 5) hydrogen atoms of the heteroaryl are each replaced independently by a halo substituent. Examples of haloheteroaryl include but are not limited to 2-fluorofuryl, 2,3-dichloropyridinyl and 8-chloro-3-fluoroquinolinyl.

The term "haloheterocycle" as used herein refers to a heterocycle, wherein one or more (e.g., 1, 2, 3, 4 or 5) hydrogen atoms of the heterocycle are each replaced independently by a halo substituent. Examples of haloheteroaryl include but are not limited to 2-fluoropiperidinyl, 2-chloro-3-fluoropiperazinyl and 3-bromopyrrolidinyl.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention. Similarly, one skilled in the art will recognize that substituents and other moieties of the compounds detailed herein, including a compound of any one of formulas I, Ia, Ib, Ic, Id, Ie, If, Ig, III, IIIa, IIIb, IIIc, IIId, IIIe, IIIf, IIIg, IIIh, IIIi, IIIj, and IIIk, or a pharmaceutically acceptable salt thereof, should be selected in order to provide a compound which is sufficiently stable to provide a pharmaceutically useful compound which can be formulated into an acceptably stable pharmaceutical composition. Compounds as detailed herein which have such stability are contemplated as falling within the scope of the present invention.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.

In one embodiment, "treatment" or "treating" include one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. Similarly, compositions disclosed herein also include racemic mixtures of all stereoisomers, including enantiomers, diastereomers, and atropisomers of compounds disclosed herein. In addition, the compounds and compositions disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

The invention includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Compositions comprising a compound of the invention are also intended, such as a composition of substantially pure compound, including a specific stereochemical form, including a specific geometric isomer, thereof. Compositions comprising a mixture of compounds of the invention in any ratio are also embraced by the invention, including mixtures of two or more stereochemical forms of a compound of the invention in any ratio, such that racemic, non-racemic, enantio-enriched and scalemic mixtures of a compound are embraced, or mixtures thereof.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Accordingly, in one embodiment, a composition disclosed herein is greater than 50% a single enantiomer. In another embodiment, a composition disclosed herein is at least 80% a single enantiomer. In another embodiment, a composition disclosed herein is at least 90% a single enantiomer. In another embodiment, a composition disclosed herein is at least 98% a single enantiomer. In another embodiment, a composition disclosed herein is at least 99% a single enantiomer. In another embodiment, a composition disclosed herein is greater than 50% a single diastereomer. In another embodiment, a composition disclosed herein is at least 80% a single diastereomer. In another embodiment, a composition disclosed herein is at least 90% a single diastereomer. In another embodiment, a composition disclosed herein is at least 98% a single diastereomer. In another embodiment, a composition disclosed herein is at least 99% a single diastereomer.

In certain embodiments, the compounds disclosed herein display atropisomerism resulting from steric hindrance affecting the axial rotation rate around a single bond. In certain circumstances, the resultant conformational isomers are observed as distinct entities by characterization techniques such as NMR and HPLC. In certain embodiments, the compounds disclosed herein exist as a mixture of atropisomers. The synthetic examples provided herein note where such mixtures of atropisomers have been observed. However, the detection of atropisomers is dependent on factors such as temperature, solvent, conditions of purification, and timescale of spectroscopic technique. Characterization data presented herein may not represent the equilibrium state depending on the conditions of purification, isolation, handling, solvents used, and temperature.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention. Another non-limiting example includes keto-enol tautomers of heteroaryls. Such tautomers are exemplified by T1/T1', T2/T2' and T3/T3'. All such tautomeric forms are also within the scope of the invention.

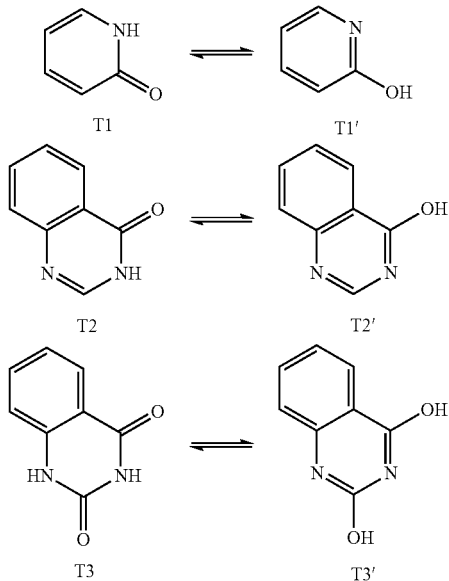

Protecting Groups

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Salts and Hydrates

"Pharmaceutically acceptable salt" refers to a salt of a compound that is pharmaceutically acceptable and that possesses (or can be converted to a form that possesses) the desired pharmacological activity of the parent compound. Pharmaceutically acceptable salts are generally regarded as safe and suitable for use without undue toxicity, irritation, allergic response, and the like, commensurate with a reasonable benefit/risk ratio. Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-napthhalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their unionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, in certain embodiments, a —CH$_3$ group is replaced with —CD$_3$.

Specific values listed below for radicals, substituents, and ranges in the embodiments of the invention are for illustration only; they do not exclude other defined values or other values within defined ranges for the radicals and substituents.

Compounds of Formula I.

A specific group of compounds of formula I are compounds of formula Ia.

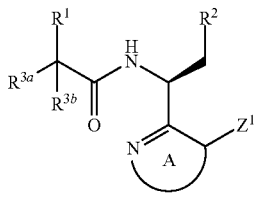

Ia or a pharmaceutically acceptable salt thereof.

Another specific group of compounds of formula I are compounds of formula Ib.

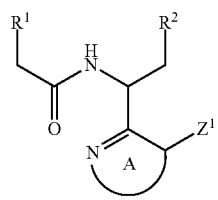

Ib or a pharmaceutically acceptable thereof.

Another specific group of compounds of formula I are compounds of formula Ic.

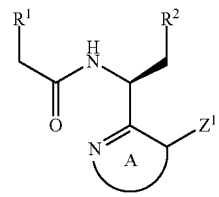

Ic or a pharmaceutically acceptable thereof.

Another specific group of compounds of formula I are compounds of formula Id.

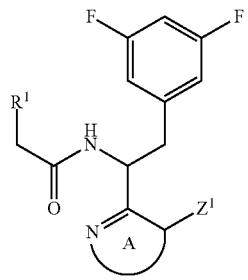

Id or a pharmaceutically acceptable thereof.

Another specific group of compounds of formula I are compounds of formula Ie.

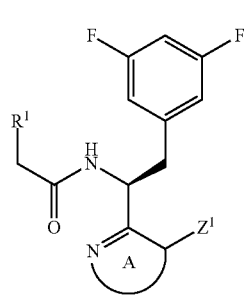

Ie or a pharmaceutically acceptable thereof.

Another specific group of compounds of formula I are compounds of formula If.

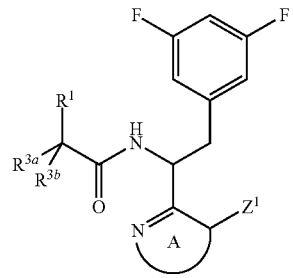

If or a pharmaceutically acceptable thereof.

Another specific group of compounds of formula I are compounds of formula Ig.

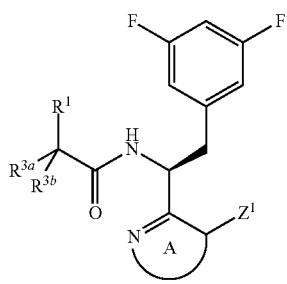

or a pharmaceutically acceptable thereof.

Specific values listed below are values for compounds of formula I as well as all related formulas (e.g., formulas Ia, Ib, Ic, Id, Ie, If, Ig). It is to be understood that two or more values may combined. Thus, it is to be understood that any variable for compounds of formula I may be combined with any other variable for compounds of formula I the same as if each and every combination of variables were specifically and individually listed. For example, it is understood that any specific value of $R^1$ detailed herein for compounds of formula I may be combined with any other specific value for one or more of the variables A, $Z^1$, $R^2$, $R^{3a}$ or $R^{3b}$ the same as if each and every combination were specifically and individually listed.

Specific values listed for compounds of formula I may apply equally to compounds of formula III and all related formulas (e.g., formulas IIIa, IIIb, IIIc, IIId, IIIe, IIIf, IIIg, IIIh, IIIi, IIIj, and IIIk) as applicable. For example, specific values for ring A of formula I may apply equally to ring A of formula III provided that the ring A of formula III encompasses within its scope the specific values. It is also understood that any combination of variables for compounds of formula I may apply equally to compounds of formula III and all related formulas (e.g., formulas IIIa, IIIb, IIIc, IIId, IIIe, IIIf, IIIg, IIIh, IIIi, IIIj, and IIIk) as applicable, the same as if each and every combination were specifically and individually listed. For example, specific values for ring A and $Z^1$ may apply equally to the A-$Z^1$ moiety of formula III provided that the scope of the A-$Z^1$ moiety of formula III encompasses the specific value.

A specific group of compounds of formula I are compounds wherein each $R^{3a}$ and $R^{3b}$ is independently selected from H, halogen, $(C_1-C_3)$alkyl, and $(C_1-C_3)$haloalkyl.

A specific group of compounds of formula I are compounds wherein each $R^{3a}$ and $R^{3b}$ is independently selected from H, $(C_1-C_3)$alkyl, and $(C_1-C_3)$haloalkyl.

A specific group of compounds of formula I are compounds wherein each $R^{3a}$ and $R^{3b}$ is independently selected from H and $(C_1-C_3)$alkyl.

A specific group of compounds of formula I are compounds wherein each $R^{3a}$ and $R^{3b}$ is independently selected from H, methyl and ethyl.

A specific group of compounds of formula I are compounds wherein each $R^{3a}$ and $R^{3b}$ is independently selected from H and methyl.

A specific group of compounds of formula I are compounds wherein $R^{3a}$ is H and $R^{3b}$ is $(C_1-C_3)$alkyl.

A specific group of compounds of formula I are compounds wherein $R^{3a}$ is H and $R^{3b}$ is methyl or ethyl.

A specific group of compounds of formula I are compounds wherein $R^{3a}$ is H and $R^{3b}$ is methyl.

A specific value for $R^{3a}$ and $R^{3b}$ is H.

A specific value for $R^2$ is phenyl or a 5-membered monocyclic-heteroaryl, wherein any phenyl or 5-membered monocyclic-heteroaryl of $R^2$ is optionally substituted with one or more (e.g., 1, 2, 3, 4 or 5) $Z^5$ groups.

A specific value for $R^2$ is phenyl or a 5-membered monocyclic-heteroaryl, wherein any phenyl or 5-membered monocyclic-heteroaryl of $R^2$ is substituted with one or more (e.g., 1, 2, 3, 4 or 5) $Z^5$ groups.

A specific value for $R^2$ is phenyl optionally substituted with one or more (e.g., 1, 2, 3, 4 or 5) $Z^5$ groups.

A specific value for $R^2$ is phenyl substituted with one or more (e.g., 1, 2, 3, 4 or 5) $Z^5$ groups.

A specific value for $Z^5$ is halogen.

A specific value for $Z^5$ is fluoro.

A specific value for $R^2$ is 3,5-difluorophenyl.

A specific value for A is pyridinyl, pyrimidinyl, pyrazinyl or pyridazinyl, wherein any pyridinyl, pyrimidinyl, pyrazinyl or pyridazinyl of A is substituted with one $Z^1$ group at the position shown, one $Z^2$ group and optionally substituted with one or more (e.g., 1 or 2) $Z^3$ groups.

A specific value for A is pyridinyl, pyrimidinyl, pyrazinyl or pyridazinyl, wherein any pyridinyl, pyrimidinyl, pyrazinyl or pyridazinyl of A is substituted with one $Z^1$ group at the position shown and one $Z^2$ group.

A specific value for A is pyridinyl, wherein any pyridinyl of A is substituted with one $Z^1$ group at the position shown, one $Z^2$ group, and optionally substituted with one or more (e.g., 1 or 2) $Z^3$ groups.

A specific value for A is pyridinyl, wherein any pyridinyl of A is substituted with one $Z^1$ group at the position shown and one $Z^2$ group A specific value for A is selected from:

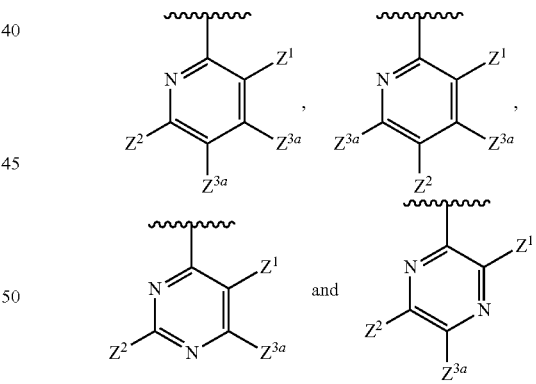

wherein each $Z^{3a}$ is independently selected from H and $Z^3$.

A specific value for A is selected from:

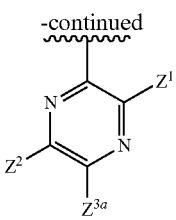

wherein each $Z^{3a}$ is independently selected from H and $Z^3$.

A specific value for A is selected from:

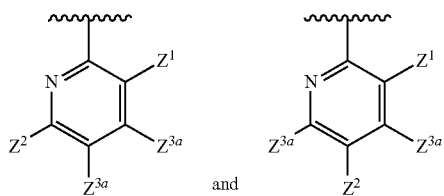

wherein each $Z^{3a}$ is independently selected from H and $Z^3$.

A specific value for A is:

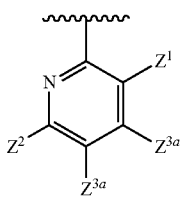

wherein each $Z^{3a}$ is independently selected from H and $Z^3$.

A specific value for A is:

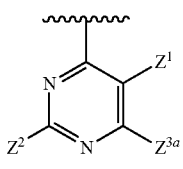

wherein each $Z^{3a}$ is independently selected from H and $Z^3$.

A specific value for A is:

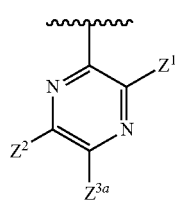

wherein each $Z^{3a}$ is independently selected from H and $Z^3$.

A specific value for $Z^{3a}$ is H.

A specific value for $Z^1$ is selected from phenyl, 5-14 membered heteroaryl and 3-14 membered heterocycle, wherein any phenyl, 5-14 membered heteroaryl and 3-14 membered heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, 5-12 membered heteroaryl and 3-12 membered heterocycle, wherein any phenyl, 5-12 membered heteroaryl and 3-12 membered heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, 5-14 membered heteroaryl and 3-14 membered heterocycle, wherein any phenyl, 5-14 membered heteroaryl and 3-14 membered heterocycle of $Z^1$ is optionally substituted with one or more (e.g., 1, 2, 3, 4 or 5) $Z^{1a}$ groups.

A specific value for $Z^1$ is selected from phenyl, 5-12 membered heteroaryl and 3-12 membered heterocycle, wherein any phenyl, 5-12 membered heteroaryl and 3-12 membered heterocycle of $Z^1$ is optionally substituted with one or more (e.g., 1, 2, 3, 4 or 5) $Z^{1a}$ groups.

A specific value for $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more (e.g., 1, 2, 3, 4 or 5) $Z^{1a}$ groups.

A specific value for $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle, wherein the 5-6 membered monocyclic-heteroaryl, 8-10 membered bicyclic-heteroaryl, 8-10 membered bicyclic-heterocycle and 9-12 membered tricyclic-heterocycle have 1-11 carbon atoms and 1-5 heteroatoms in the ring system, and wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle, wherein the 5-6 membered monocyclic-heteroaryl, 8-10 membered bicyclic-heteroaryl, 8-10 membered bicyclic-heterocycle and 9-12 membered tricyclic-heterocycle have 1-11 carbon atoms and 1-5 heteroatoms in the ring system, and wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more (e.g., 1, 2, 3, 4 or 5) $Z^{1a}$ groups.

A specific value for $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle, wherein the 5-6 membered monocyclic-heteroaryl, 8-10 membered bicyclic-heteroaryl, 8-10 membered bicyclic-heterocycle and 9-12 membered tricyclic-heterocycle have 4-11 carbon atoms and 1-3 heteroatoms in the ring system, and wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more (e.g., 1, 2, 3, 4 or 5) $Z^{1a}$ or $Z^{1b}$ groups.

A specific value for $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle, wherein the 5-6 membered monocyclic-heteroaryl, 8-10 membered bicyclic-heteroaryl, 8-10 membered bicyclic-heterocycle and 9-12 membered tricyclic-heterocycle have 4-11 carbon atoms and 1-3 heteroatoms in the ring system, and wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more (e.g., 1, 2, 3, 4 or 5) $Z^{1a}$ groups.

A specific value for $Z^1$ is selected from 8-10 membered bicyclic-heteroaryl and 8-10 membered bicyclic-heterocycle, wherein any from 8-10 membered bicyclic-heteroaryl and 8-10 membered bicyclic-heterocycle of $Z^1$ is optionally substituted with one or more $Z^{1a}$ or $Z^{1b}$ groups.

A specific value for $Z^1$ is selected from 8-10 membered bicyclic-heteroaryl and 8-10 membered bicyclic-heterocycle, wherein any from 8-10 membered bicyclic-heteroaryl and 8-10 membered bicyclic-heterocycle of $Z^1$ is optionally substituted with one or more $Z^{1a}$ groups.

A specific value for $Z^1$ is selected from 8-10 membered bicyclic-heteroaryl and 8-10 membered bicyclic-heterocycle, wherein the 8-10 membered bicyclic-heteroaryl and 8-10 membered bicyclic-heterocycle have 3-9 carbon atoms and 1-5 heteroatoms in the ring system, and wherein any 8-10 membered bicyclic-heteroaryl and 8-10 membered bicyclic-heterocycle of $Z^1$ is optionally substituted with one or more $Z^{1a}$ or $Z^{1b}$ groups.

A specific value for $Z^1$ is selected from 8-10 membered bicyclic-heteroaryl and 8-10 membered bicyclic-heterocycle, wherein the 8-10 membered bicyclic-heteroaryl and 8-10 membered bicyclic-heterocycle have 3-9 carbon atoms and 1-5 heteroatoms in the ring system, and wherein any 8-10 membered bicyclic-heteroaryl and 8-10 membered bicyclic-heterocycle of $Z^1$ is optionally substituted with one or more $Z^{1a}$ groups.

A specific value for $Z^1$ is selected from phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl, wherein any phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl of $Z^1$ is optionally substituted with one or more (e.g., 1, 2, 3, 4 or 5) $Z^{1a}$ or $Z^{1b}$ groups. A specific value for $Z^1$ is 1H-indazol-7-yl, wherein $Z^1$ is optionally substituted with one or more $Z^{1a}$ or $Z^{1b}$ groups.

A specific value for $Z^1$ is selected from phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl as shown by the following formulas;

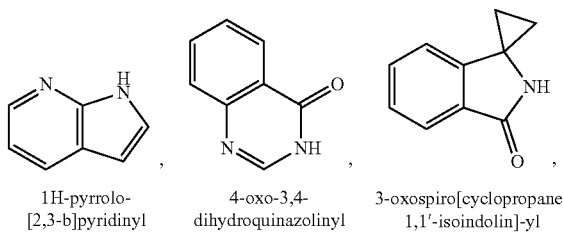

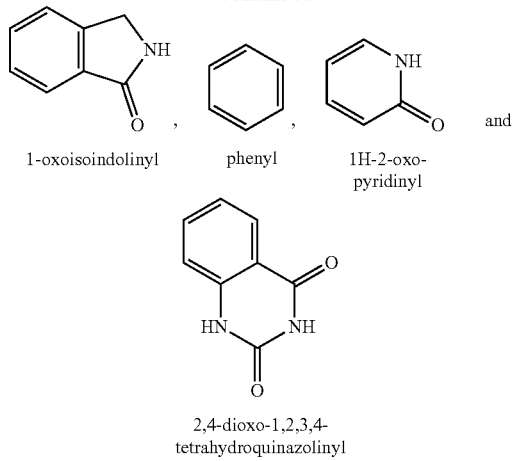

wherein any phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl of $Z^1$ is optionally substituted with one or more (e.g., 1, 2, 3, 4 or 5) $Z^{1a}$ or $Z^{1b}$ groups. A specific value for $Z^1$ is

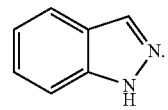

A specific value for $Z^1$ is

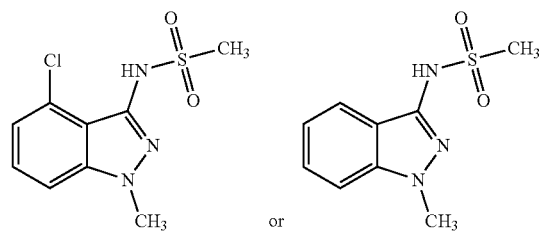

A specific value for $Z^1$ is selected from phenyl, 1H-pyrrolo[2,3-b]pyridinyl, 1-oxoisoindolinyl, 3-oxospiro[cyclopropane-1,1'-isoindolin]-yl, pyridinyl and quinazolinyl, wherein any phenyl, 1H-pyrrolo[2,3-b]pyridinyl, 1-oxoisoindolinyl, 3-oxospiro[cyclopropane-1,1'-isoindolin]-yl, pyridinyl and quinazolinyl of $Z^1$ is optionally substituted with one or more (e.g., 1, 2, 3, 4 or 5) $Z^{1a}$ or $Z^{1b}$ groups.

A specific value for $Z^1$ is selected from phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl, wherein any phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl of $Z^1$ is optionally substituted with one or more (e.g., 1, 2, 3, 4 or 5) $Z^{1a}$ groups.

A specific value for $Z^1$ is selected from phenyl, 1H-pyrrolo[2,3-b]pyridinyl, 1-oxoisoindolinyl, 3-oxospiro[cyclopropane-1,1'-isoindolin]-yl, pyridinyl and quinazolinyl, wherein any phenyl, 1H-pyrrolo[2,3-b]pyridinyl, 1-oxoisoindolinyl, 3-oxospiro[cyclopropane-1,1'-isoindolin]-yl, pyridinyl and quinazolinyl of $Z^1$ is optionally substituted with one or more (e.g., 1, 2, 3, 4 or 5) $Z^{1a}$ groups.

A specific value for $Z^1$ is selected from phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl, wherein any phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl of $Z^1$ is optionally substituted with one or more (e.g., 1, 2, 3, 4 or 5) $Z^{1a}$ or $Z^{1b}$ groups.

A specific value for $Z^1$ is selected from phenyl, 1H-pyrrolo[2,3-b]pyridin-5-yl, 1-oxoisoindolin-5-yl, 1-oxoisoindolin-4-yl, 3'-oxospiro[cyclopropane-1,1'-isoindolin]-5'-yl, pyridin-4-yl and quinazolin-8-yl, wherein any phenyl, 1H-pyrrolo[2,3-b]pyridin-5-yl, 1-oxoisoindolin-5-yl, 1-oxoisoindolin-4-yl, 3'-oxospiro[cyclopropane-1,1'-isoindolin]-5'-yl, pyridin-4-yl and quinazolin-8-yl of $Z^1$ is optionally substituted with one or more (e.g., 1, 2, 3, 4 or 5) $Z^{1a}$ or $Z^{1b}$ groups.

A specific value for $Z^1$ is selected from phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl as shown by the following formulas;

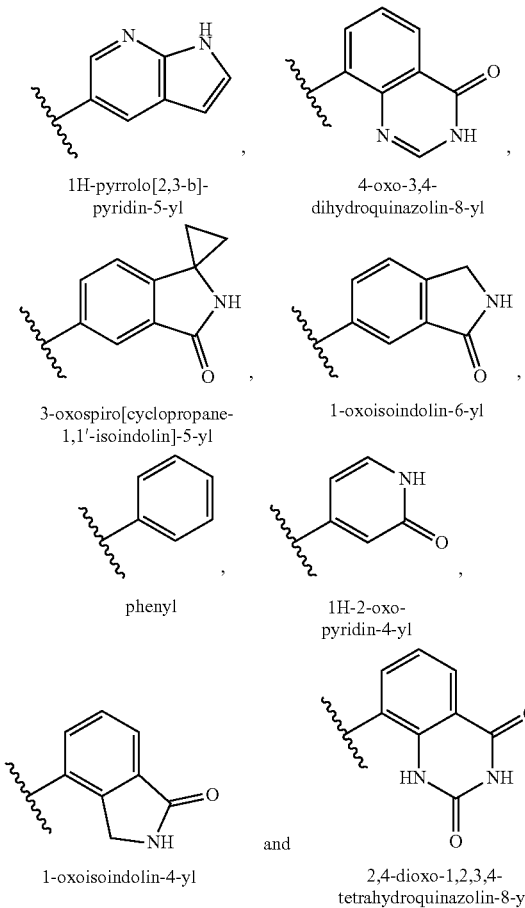

1H-pyrrolo[2,3-b]-pyridin-5-yl, 4-oxo-3,4-dihydroquinazolin-8-yl, 3-oxospiro[cyclopropane-1,1'-isoindolin]-5-yl, 1-oxoisoindolin-6-yl, phenyl, 1H-2-oxo-pyridin-4-yl, 1-oxoisoindolin-4-yl and 2,4-dioxo-1,2,3,4-tetrahydroquinazolin-8-yl wherein any phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl of $Z^1$ is optionally substituted with one or more (e.g., 1, 2, 3, 4 or 5) $Z^{1a}$ or $Z^{1b}$ groups. A specific value for $Z^1$ is

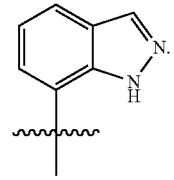 [SMILES: *c1cccc2cn[nH]c12]

A specific value for $Z^1$ is

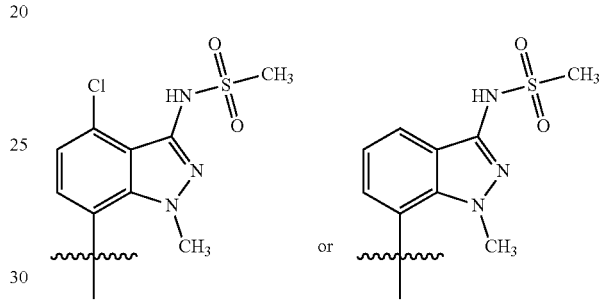

A specific value for $Z^1$ is selected from phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl, wherein any phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl of $Z^1$ is optionally substituted with one or more (e.g., 1, 2, 3, 4 or 5) $Z^{1a}$ groups.

A specific value for $Z^1$ is selected from phenyl, 1H-pyrrolo[2,3-b]pyridin-5-yl, 1-oxoisoindolin-5-yl, 1-oxoisoindolin-4-yl, 3'-oxospiro[cyclopropane-1,1'-isoindolin]-5'-yl, pyridin-4-yl and quinazolin-8-yl, wherein any phenyl, 1H-pyrrolo[2,3-b]pyridin-5-yl, 1-oxoisoindolin-5-yl, 1-oxoisoindolin-4-yl, 3'-oxospiro[cyclopropane-1,1'-isoindolin]-5'-yl, pyridin-4-yl and quinazolin-8-yl of $Z^1$ is optionally substituted with one or more (e.g., 1, 2, 3, 4 or 5) $Z^{1a}$ groups.

A specific group of compounds of formula I are compounds wherein $Z^1$ is not substituted with $Z^{1b}$.

A specific value for each $Z^{1a}$ is independently selected from halogen, —$OR^{n1}$ and —$C(O)NR^{q1}R^{r1}$.

A specific value for each $Z^{1a}$ is independently selected from halogen and —$C(O)NR^{q1}R^{r1}$.

A specific value for each $R^{n1}$, $R^{q1}$ and $R^{r1}$ are each H.

A specific value for each $Z^{1a}$ is independently selected from halogen, —OH and —$C(O)NH_2$.

A specific value for each $Z^{1a}$ is independently selected from fluoro, —OH and —$C(O)NH_2$.

A specific value for $R_{q1}$ and $R_{r1}$ is H.

A specific value for each $Z^{1a}$ is independently selected from halogen and —$NR^{n1}S(O)_2R^{p1}$.

A specific value for each $Z^{1b}$ is $(C_1$-$C_8)$alkyl, which may be same or different.

In certain embodiments, each $Z^{1a}$ is independently selected from halogen and —NR$^{n1}$S(O)$_2$R$^{p1}$ and each $Z^{1b}$ is (C$_1$-C$_8$)alkyl, which may be same or different.

A specific value for $Z^1$ is selected from:

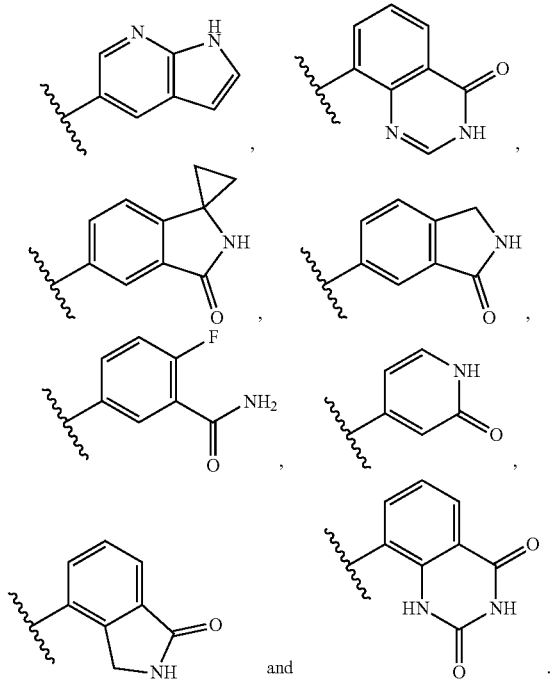

A specific value for $Z^1$ is

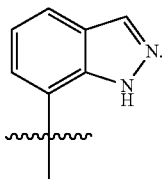

A specific value for $Z^1$ is

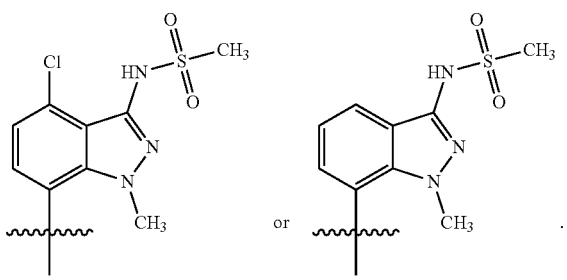 [SMILES: *c1ccc(Cl)c2c(NS(C)(=O)=O)nn(C)c12 ; *c1cccc2c(NS(C)(=O)=O)nn(C)c12]

A specific value for $Z^2$ is selected from (C$_2$-C$_8$)alkynyl, 6-12 membered aryl, 5-12 membered C-linked-heteroaryl, 3-12 membered C-linked-heterocycle and —C(O)NR$^{q3}$R$^{r3}$, wherein any 6-12 membered aryl, 5-12 membered C-linked-heteroaryl and 3-12 membered C-linked-heterocycle of $Z^2$ is optionally substituted with one or more (e.g., 1, 2, 3, 4 or 5) $Z^{2b}$ or $Z^{2c}$ groups, and wherein any (C$_2$-C$_8$)alkynyl of $Z^2$ is optionally substituted with one or more (e.g., 1, 2, 3, 4 or 5) $Z^{2c}$ groups.

A specific value for $Z^2$ is selected from (C$_2$-C$_8$)alkynyl, 6-12 membered aryl, 5-12 membered C-linked-heteroaryl, 3-12 membered C-linked-heterocycle and —C(O)NR$^{q3}$R$^{r3}$, wherein any 6-12 membered aryl, 5-12 membered C-linked-heteroaryl and 3-12 membered C-linked-heterocycle of $Z^2$ is optionally substituted with one or more (e.g., 1, 2, 3, 4 or 5) $Z^{2c}$ groups, and wherein any (C$_2$-C$_8$)alkynyl of $Z^2$ is optionally substituted with one or more (e.g., 1, 2, 3, 4 or 5) $Z^{2c}$ groups.

A specific value for $Z^2$ is selected from (C$_2$-C$_8$)alkynyl, phenyl, 5-6 membered C-linked-monocyclic-heteroaryl, 8-10 membered C-linked-bicyclic-heteroaryl, 8-10 membered C-linked-bicyclic-heterocycle and —C(O)NR$^{q3}$R$^{r3}$, wherein any phenyl, 5-6 membered C-linked-monocyclic-heteroaryl, 8-10 membered C-linked-bicyclic-heteroaryl and 8-10 membered C-linked-bicyclic-heterocycle of $Z^2$ is optionally substituted with one or more (e.g., 1, 2, 3, 4 or 5) $Z^{2b}$ or $Z^{2c}$ groups, and wherein any (C$_2$-C$_8$)alkynyl of $Z^2$ is optionally substituted with one or more (e.g., 1, 2, 3, 4 or 5) $Z^{2c}$ groups.

A specific value for $Z^2$ is selected from (C$_2$-C$_8$)alkynyl, phenyl, 5-6 membered C-linked-monocyclic-heteroaryl, 8-10 membered C-linked-bicyclic-heteroaryl, 8-10 membered C-linked-bicyclic-heterocycle and —C(O)NR$^{q3}$R$^{r3}$, wherein any phenyl, 5-6 membered C-linked-monocyclic-heteroaryl, 8-10 membered C-linked-bicyclic-heteroaryl and 8-10 membered C-linked-bicyclic-heterocycle of $Z^2$ is optionally substituted with one or more (e.g., 1, 2, 3, 4 or 5) $Z^{2c}$ groups, and wherein any (C$_2$-C$_8$)alkynyl of $Z^2$ is optionally substituted with one or more (e.g., 1, 2, 3, 4 or 5) $Z^{2c}$ groups.

A specific value for $Z^2$ is selected from (C$_2$-C$_8$)alkynyl, phenyl, 5-6 membered C-linked-monocyclic-heteroaryl, 8-10 membered C-linked-bicyclic-heteroaryl, 8-10 membered C-linked-bicyclic-heterocycle and —C(O)NR$^{q3}$R$^{r3}$, wherein the 5-6 membered C-linked-monocyclic-heteroaryl, 8-10 membered C-linked-bicyclic-heteroaryl and 8-10 membered C-linked-bicyclic-heterocycle have 1-9 carbon atoms and 1-4 heteroatoms in the ring system, and wherein any phenyl, 5-6 membered C-linked-monocyclic-heteroaryl, 8-10 membered C-linked-bicyclic-heteroaryl, 8-10 membered and C-linked-bicyclic-heterocycle of $Z^2$ is optionally substituted with one or more (e.g., 1, 2, 3, 4 or 5) $Z^{2b}$ or $Z^{2c}$ groups, and wherein any (C$_2$-C$_8$)alkynyl of $Z^2$ is optionally substituted with one or more (e.g., 1, 2, 3, 4 or 5) $Z^{2c}$ groups.

A specific value for $Z^2$ is selected from (C$_2$-C$_8$)alkynyl, phenyl, 5-6 membered C-linked-monocyclic-heteroaryl, 8-10 membered C-linked-bicyclic-heteroaryl, 8-10 membered C-linked-bicyclic-heterocycle and —C(O)NR$^{q3}$R$^{r3}$, wherein the 5-6 membered C-linked-monocyclic-heteroaryl, 8-10 membered C-linked-bicyclic-heteroaryl and 8-10 membered C-linked-bicyclic-heterocycle have 1-9 carbon atoms and 1-4 heteroatoms in the ring system, and wherein any phenyl, 5-6 membered C-linked-monocyclic-heteroaryl, 8-10 membered C-linked-bicyclic-heteroaryl, 8-10 membered and C-linked-bicyclic-heterocycle of $Z^2$ is optionally substituted with one or more (e.g., 1, 2, 3, 4 or 5) $Z^{2c}$ groups, and wherein any (C$_2$-C$_8$)alkynyl of $Z^2$ is optionally substituted with one or more (e.g., 1, 2, 3, 4 or 5) $Z^{2c}$ groups.

A specific value for $Z^2$ is selected from 4-methylpentynyl, phenyl, pyridinyl, 1H-2-oxo-pyridinyl, triazolyl, 1-oxoisoindolinyl, 1H-pyrrolo[2,3-b]pyridinyl and —C(O)NR$^{q3}$R$^{r3}$, wherein any phenyl, pyridinyl, 1H-2-oxo-pyridinyl, triazolyl, 1-oxoisoindolinyl and 1H-pyrrolo[2,3-b]pyridinyl of $Z^2$ is optionally substituted with one or more (e.g., 1, 2, 3, 4 or 5) $Z^{2b}$ or $Z^{2c}$ groups, and wherein any 4-methylpentynyl of $Z^2$ is optionally substituted with one or more (e.g., 1, 2, 3, 4 or 5) $Z^{2c}$ groups.

A specific value for $Z^2$ is selected from 4-methylpentynyl, phenyl, pyridinyl, 1H-2-oxo-pyridinyl, triazolyl, 1-oxoisoindolinyl, 1H-pyrrolo[2,3-b]pyridinyl and —C(O)NR$^{q3}$R$^{r3}$, wherein any phenyl, pyridinyl, 2-oxopyridinyl, triazolyl, 1-oxoisoindolinyl and 1H-pyrrolo[2,3-b]pyridinyl of $Z^2$ is optionally substituted with one or more (e.g., 1, 2, 3, 4 or 5) $Z^{2c}$ groups, and wherein any 4-methylpentynyl of $Z^2$ is optionally substituted with one or more (e.g., 1, 2, 3, 4 or 5) $Z^{2c}$ groups.

A specific value for $Z^2$ is selected from 4-methylpentyn-1-yl, phenyl, pyridin-4-yl, 1H-2-oxo-pyridin-2-yl, triazol-4-yl, 1-oxoisoindolin-6-yl, 1H-pyrrolo[2,3-b]pyridine-5-yl and —C(O)NR$^{q3}$R$^{r3}$, wherein any phenyl, pyridin-4-yl, 1H-2-oxo-pyridin-2-yl, triazol-4-yl, 1-oxoisoindolin-6-yl and 1H-pyrrolo[2,3-b]pyridine-5-yl of $Z^2$ is optionally substituted with one or more (e.g., 1, 2, 3, 4 or 5) $Z^{2b}$ or $Z^{2c}$ groups, and wherein any 4-methylpentyn-1-yl of $Z^2$ is optionally substituted with one or more (e.g., 1, 2, 3, 4 or 5) $Z^{2c}$ groups.

A specific value for $Z^2$ is selected from 4-methylpentyn-1-yl, phenyl, pyridin-4-yl, 1H-2-oxo-pyridin-2-yl, triazol-4-yl, 1-oxoisoindolin-6-yl, 1H-pyrrolo[2,3-b]pyridine-5-yl and —C(O)NR$^{q3}$R$^{r3}$, wherein any phenyl, pyridin-4-yl, 1H-2-oxo-pyridin-2-yl, triazol-4-yl, 1-oxoisoindolin-6-yl and 1H-pyrrolo[2,3-b]pyridine-5-yl of $Z^2$ is optionally substituted with one or more (e.g., 1, 2, 3, 4 or 5) $Z^{2c}$ groups, and wherein any 4-methylpentyn-1-yl of $Z^2$ is optionally substituted with one or more (e.g., 1, 2, 3, 4 or 5) $Z^{2c}$ groups.

A specific group of compounds of formula I are compounds wherein each $Z^2$ is not substituted with $Z^{2b}$.

A specific group of compounds of formula I are compounds wherein each $Z^2$ is optionally substituted with one or more $Z^{2c}$ groups.

A specific value for each $Z^{2c}$ is independently selected from halogen, —OR$_{n4}$ and —C(O)NR$_{q4}$R$_{r4}$.

A specific group of compounds of formula I are compounds wherein R$^{n4}$ is H or methyl, and R$^{q4}$ and R$^{r4}$ are each H.

A specific value for R$^{n4}$ is H or methyl.

A specific value for each R$^{q4}$ and R$^{r4}$ is H.

A specific value for $Z^2$ is selected from:

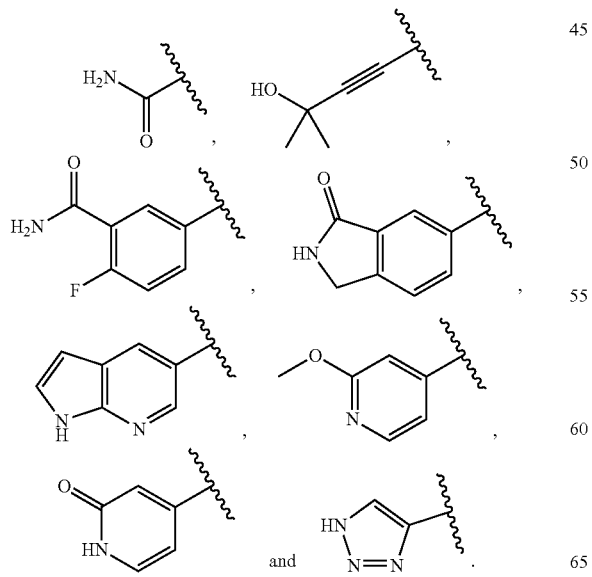

A specific value for A-$Z^1$ is selected from:

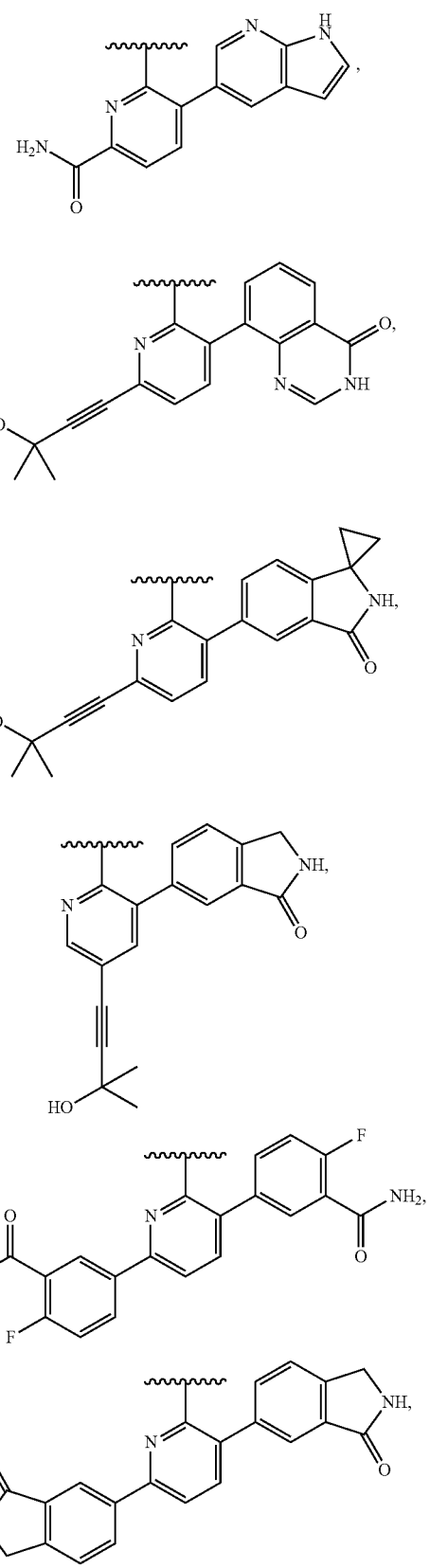

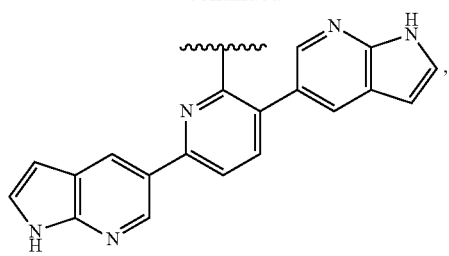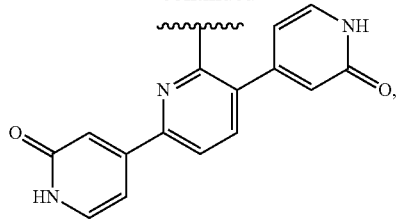

A specific value for A-$Z^1$ is selected from:

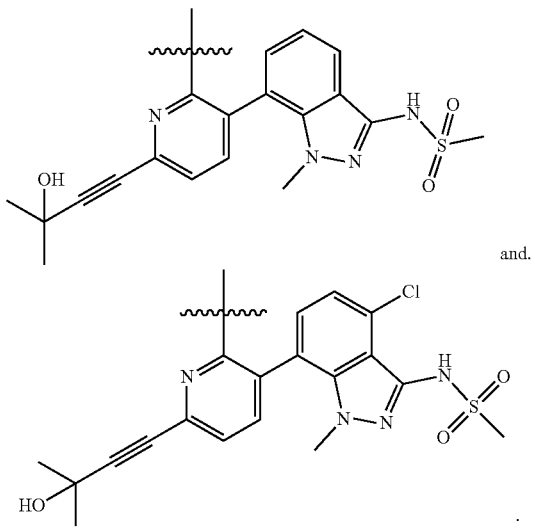

and.

A specific value for $R^1$ is a 5-12 membered heteroaryl, wherein any 5-12 membered heteroaryl of $R^1$ is optionally substituted with one or more (e.g., 1, 2, 3, 4, or 5) $Z^4$ groups.

A specific value for $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with one or more (e.g., 1, 2, 3, 4, or 5) $Z^4$ groups.

A specific value for $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl have 4-10 carbon atoms and 1-5 heteroatoms in the ring system, and wherein any 8-12 membered bicyclic-heteroaryl or 8-12 membered tricyclic-heteroaryl of $R^1$ is optionally substituted with one or more (e.g., 1, 2, 3, 4, or 5) $Z^4$ groups.

A specific value for $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl contains at least one partially unsaturated ring, and wherein any 8-12 membered bicyclic-heteroaryl or 8-12 membered tricyclic-heteroaryl of $R^1$ is optionally substituted with one or more (e.g., 1, 2, 3, 4 or 5) $Z^4$ groups.

A specific value for $R^1$ has the following formula IIa:

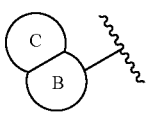

IIa wherein:
C together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with one or more (e.g. 1, 2, 3, 4 or 5) $Z^4$ groups; and B is a 5 or 6 membered monocyclic-heteroaryl with 1, 2 or 3 nitrogen atoms, wherein B is optionally substituted with one or more or (e.g. 1, 2, 3, 4 or 5) $Z^4$ groups.

A specific value for $R^1$ has the following IIb:

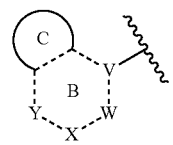

IIb wherein:
C together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with one or more (e.g. 1, 2, 3, 4 or 5) $Z^4$ groups; and B is a 5 or 6 membered monocyclic-heteroaryl having 1, 2 or 3 nitrogen atoms;
V is C or N;
W is $CZ^{4c}$, $NZ^{4c}$ or N;
X is $CZ^{4c}$, $NZ^{4c}$ or N;
Y is $CZ^{4c}$, N or absent;
the dashed bonds are selected from single bonds and double bonds, wherein the dashed bonds, V, W, X and Y are selected so that the 5 or 6 membered monocyclic-heteroaryl B is aromatic; and
each $Z^{4c}$ is independently selected from H or $Z^4$.

A specific value for $R^1$ has the following formula IIc:

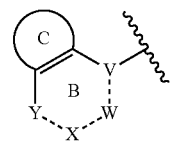

IIc wherein:
C together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with one or more (e.g. 1, 2, 3, 4 or 5) $Z^4$ groups; and B is a 5 or 6 membered monocyclic-heteroaryl having 1, 2 or 3 nitrogen atoms;
V is C or N;
W is $CZ^{4c}$ or N;
X is $CZ^{4c}$, $NZ^{4c}$ or N;
Y is $CZ^{4c}$, N or absent;
the dashed bonds are selected from single bonds and double bonds, wherein the dashed bonds, V, W, X and Y are selected so that the 5 or 6 membered monocyclic-heteroaryl B is aromatic; and
each $Z^{4c}$ is independently selected from H or $Z^4$.

A specific value for R¹ has the following R¹ has the following formula IId:

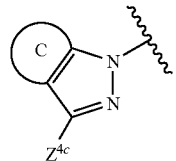

wherein:

C together with the two carbon atoms to which it is attached forms a 3-7 membered monocyclic-carbocycle, 5-9 membered bicyclic-carbocycle, 3-7 membered monocyclic-heterocycle or 5-9 membered bicyclic heterocycle, wherein any 3-7 membered monocyclic-carbocycle, 5-9 membered bicyclic-carbocycle, 3-7 membered monocyclic-heterocycle or 5-9 membered bicyclic heterocycle of C is optionally substituted with one or more (e.g. 1, 2, 3, 4 or 5) $Z^4$ groups; and each $Z^{4c}$ is independently selected from H or $Z^4$.

A specific value for each $Z^4$ is independently selected from ($C_1$-$C_6$)alkyl and halogen, wherein any ($C_1$-$C_6$)alkyl of $Z^4$ is optionally substituted with one or more (e.g., 1, 2, 3, 4, or 5) halogen.

A specific value for each $Z^4$ is independently selected from fluoro, trifluoromethyl and difluoromethyl.

A specific value for R¹ is selected from:

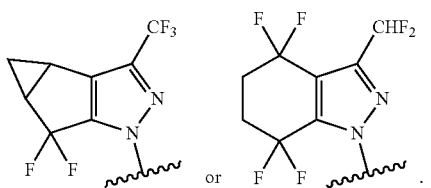 [SMILES: *n1nc(C(F)(F)F)c2c1C(F)(F)C1CC21 ; *n1nc(C(F)F)c2c1C(F)(F)CCC2(F)F]

A specific value for R¹ is selected from:

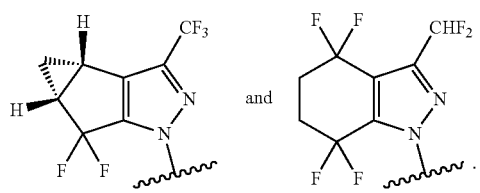 [SMILES: *n1nc(C(F)(F)F)c2c1C(F)(F)[C@@H]1C[C@H]21 ; *n1nc(C(F)F)c2c1C(F)(F)CCC2(F)F]

A specific value for R¹ is

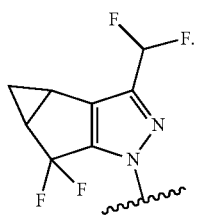

A specific value for R¹ is

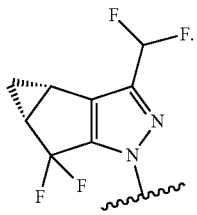

A specific value for R¹ is a 8-12 membered bicyclic-heteroaryl or 8-12 membered tricyclic-heteroaryl, wherein the 8-12 membered bicyclic-heteroaryl or 8-12 membered tricyclic-heteroaryl has 4-9 carbon atoms and 1-5 heteroatoms in the ring system, and wherein any 8-12 membered bicyclic-heteroaryl or 8-12 membered tricyclic-heteroaryl of R¹ is optionally substituted with one or more (e.g., 1, 2, 3, 4 or 5) $Z^4$ groups.

A specific value for R¹ is a 8-12 membered bicyclic-heteroaryl, wherein the 8-12 membered bicyclic-heteroaryl has 6-9 carbon atoms and 1-3 heteroatoms in the ring system, and wherein any 8-12 membered bicyclic-heteroaryl of R¹ is optionally substituted with one or more (e.g., 1, 2, 3, 4 or 5) $Z^4$ groups.

A specific value for R¹ is a 8-12 membered bicyclic-heteroaryl or 8-12 membered tricyclic-heteroaryl, wherein the 8-12 membered bicyclic-heteroaryl or 8-12 membered tricyclic-heteroaryl has 6-9 carbon atoms and 1-3 heteroatoms in the ring system, and wherein any 8-12 membered bicyclic-heteroaryl or 8-12 membered tricyclic-heteroaryl of R¹ is optionally substituted with one or more (e.g., 1, 2, 3, 4 or 5) $Z^4$ groups.

A specific value for R¹ is selected from indolyl and 4,5,6,7-tetrahydro-indazolyl, wherein any indolyl and 4,5,6,7-tetrahydro-indazolyl of R¹ is optionally substituted with one or more (e.g., 1, 2, 3, 4 or 5) $Z^4$ groups.

A specific value for R¹ is selected from indolyl, 4,5,6,7-tetrahydro-indazolyl, 3b,4,4a,5-tetrahydro-cyclopropa[3,4]cyclopenta[1,2-c]pyrazole and 1,4,5,5a,6,6a-hexahydrocyclopropa[g]indazole, wherein any indolyl, 4,5,6,7-tetrahydro-indazolyl, 3b,4,4a,5-tetrahydro-cyclopropa[3,4]cyclopenta[1,2-c]pyrazole and 1,4,5,5a,6,6a-hexahydrocyclopropa[g]indazole of R¹ is optionally substituted with one or more (e.g., 1, 2, 3, 4 or 5) $Z^4$ groups.

A specific value for R¹ is selected from indol-3-yl and 4,5,6,7-tetrahydro-1H-indazol-1-yl, wherein any indol-3-yl and 4,5,6,7-tetrahydro-1H-indazol-1-yl of R¹ is optionally substituted with one or more (e.g., 1, 2, 3, 4 or 5) $Z^4$ groups.

A specific value for R¹ is selected from indol-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl, wherein any indol-3-yl, 4,5,6,7-tetrahydro-1H-indazol-1-yl, 3b,4,4a,5-tetrahydro-1H-cyclopropa[3,4]cyclopenta[1,2-c]pyrazol-1-yl and 1,4,5,5a,6,6a-hexahydrocyclopropa[g]indazol-1-yl of R¹ is optionally substituted with one or more (e.g., 1, 2, 3, 4 or 5) $Z^4$ groups.

A specific value for each $Z^4$ is independently selected from ($C_1$-$C_6$)alkyl and halogen, wherein any ($C_1$-$C_6$)alkyl of $Z^4$ is optionally substituted with one or more (e.g., 1, 2, 3, 4 or 5) halogen.

A specific value for each $Z^4$ is independently selected from ($C_1$-$C_6$)alkyl, —CN and halogen, wherein any ($C_1$-$C_6$)alkyl of $Z^4$ is optionally substituted with one or more (e.g., 1, 2, 3, 4 or 5) halogen.

A specific value for each $Z^4$ is independently selected from fluoro, trifluoromethyl and difluoromethyl.

A specific value for each $Z^4$ is independently selected from fluoro, trifluoromethyl, —CN and difluoromethyl.

A specific value for $R^1$ is selected from:

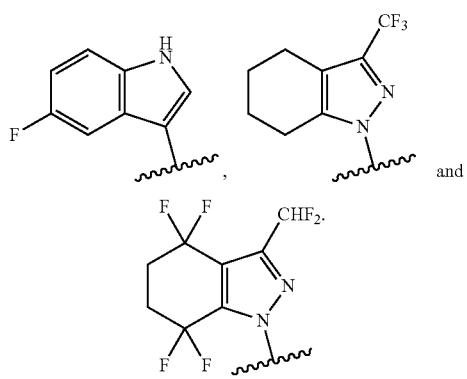

A specific value for $R^1$ is selected from:

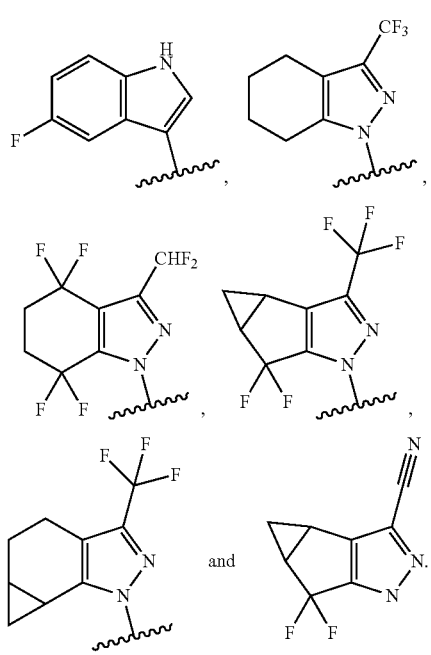

A specific value for $R^1$ is selected from:

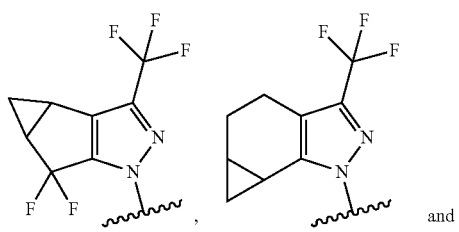

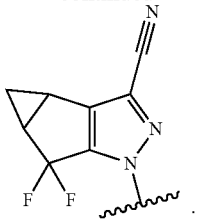

A specific value for $R^1$ is

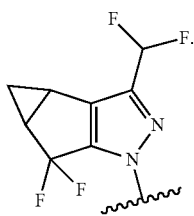 [SMILES: *n1nc(C(F)F)c2c1C(F)(F)C1CC21]

A specific value for $R^1$ is

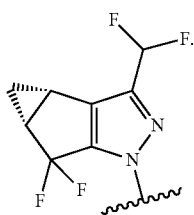 [SMILES: *n1nc(C(F)F)c2c1C(F)(F)[C@@H]1C[C@H]21]

In one variation of formula I, A is pyridinyl, pyrimidinyl, pyrazinyl or pyridazinyl; and $R^1$ is a 5-12 membered heteroaryl, optionally substituted with 1, 2, 3, 4 or 5 $Z^4$ groups, which may be the same or different. In another variation, A is pyridinyl, pyrimidinyl, pyrazinyl or pyridazinyl; and $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups. In another variation, A is pyridinyl, pyrimidinyl, pyrazinyl or pyridazinyl; $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups; and each $Z^4$ is independently fluoro, trifluoromethyl, or difluoromethyl.

In one variation of formula I, A is pyridinyl; and $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups.

In one variation of formula I, A is pyridinyl, pyrimidinyl, pyrazinyl or pyridazinyl; and $R^2$ is 3,5-difluorophenyl. In another variation, A is pyridinyl; and $R^2$ is 3,5-difluorophenyl. In another variation, A is pyrimidinyl; and $R^2$ is 3,5-difluorophenyl. In another variation, A is pyrazinyl; and $R^2$ is 3,5-difluorophenyl. In another variation, A is pyridazinyl; and $R^2$ is 3,5-difluorophenyl.

In one variation of formula I, A is pyridinyl, pyrimidinyl, pyrazinyl or pyridazinyl; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups. In another variation, A is pyridinyl, pyrimidinyl, pyrazinyl or pyridazinyl; and $Z^1$ is phenyl, optionally substituted with 1, 2, 3, 4 or 5 $Z^{1a}$ groups. In another variation, A is pyridinyl, pyrimidinyl, pyrazinyl or pyridazinyl; and $Z^1$ is 5-6 membered monocyclic-heteroaryl or 8-10 membered bicyclic-heteroaryl, wherein any 5-6 membered monocyclic-heteroaryl or 8-10 membered bicyclic-heteroaryl of $Z^1$ is optionally substituted with 1, 2, 3, 4 or 5 $Z^{1a}$ groups. In another variation, A is pyridinyl, pyrimidinyl, pyrazinyl or pyridazinyl; and $Z^1$ is 8-10 membered bicyclic-heterocycle or 9-12 membered tricyclic-heterocycle wherein any 8-10 membered bicyclic-heterocycle or 9-12 membered tricyclic-heterocycle of $Z^1$ is optionally substituted with 1, 2, 3, 4 or 5 $Z^{1a}$ groups.

In one variation of formula I, A is pyridinyl; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups. In another variation, A is pyridinyl; and $Z^1$ is phenyl, optionally substituted with 1, 2, 3, 4 or 5 $Z^{1a}$ groups. In another variation, A is pyridinyl; and $Z^1$ is 5-6 membered monocyclic-heteroaryl or 8-10 membered bicyclic-heteroaryl, wherein any 5-6 membered monocyclic-heteroaryl or 8-10 membered bicyclic-heteroaryl of $Z^1$ is optionally substituted with 1, 2, 3, 4 or 5 $Z^{1a}$ groups. In another variation, A is pyridinyl; and $Z^1$ is 8-10 membered bicyclic-heterocycle or 9-12 membered tricyclic-heterocycle wherein any 8-10 membered bicyclic-heterocycle or 9-12 membered tricyclic-heterocycle of $Z^1$ is optionally substituted with 1, 2, 3, 4 or 5 $Z^{1a}$ groups.

In one variation of formula I, A is pyridinyl, pyrimidinyl, pyrazinyl or pyridazinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyridinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyrimidinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$ wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyrazinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyridazinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups.

In one variation of formula I, A is pyridinyl substituted with one $Z^1$ moiety, one $Z^2$ moiety and no (zero) $Z^3$ moieties; and $Z^2$ is $(C_2-C_8)$alkynyl or aryl, which $Z^2$ may be optionally substituted as provided by formula I. In another variation, A is pyridinyl substituted with one $Z^1$ moiety, one $Z^2$ moiety and no (zero) $Z^3$ moieties; and $Z^2$ is $(C_2-C_8)$alkynyl, which $Z^2$ may be optionally substituted as provided by formula I. In a particular variation, A is pyridinyl substituted with one $Z^1$ moiety, one $Z^2$ moiety at the position alpha to the nitrogen atom of the pyridinyl ring, and no (zero) $Z^3$ moieties, wherein $Z^2$ is $(C_2-C_8)$alkynyl, which $Z^2$ may be optionally substituted as provided by formula I.

In one variation of formula I, $R^1$ is a 5-12 membered heteroaryl optionally substituted with 1, 2, 3, 4 or 5 $Z^4$ groups, which may be the same or different; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups. In another variation, $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups.

In one variation of formula I, $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups; and $Z^1$ is 8-10 membered bicyclic-heteroaryl or 8-10 membered bicyclic-heterocycle wherein any 8-10 membered bicyclic-heteroaryl or 8-10 membered bicyclic-heterocycle of $Z^1$ is optionally substituted with 1, 2, 3, 4 or 5 $Z^{1a}$ groups.

In one variation of formula I, $R^1$ is a 5-12 membered heteroaryl optionally substituted with 1, 2, 3, 4 or 5 $Z^4$ groups, which may be the same or different; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, $R^1$ is a 8-12 membered bicyclic-heteroaryl or 8-12 membered tricyclic-heteroaryl wherein any 8-12 membered bicyclic-heteroaryl or 8-12 membered tricyclic-heteroaryl of $R^1$ is optionally substituted with 1, 2, 3, 4, or 5 $Z^4$ groups; and $Z^2$ is $(C_2\text{-}C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2\text{-}C_8)$alkynyl of $Z^2$ is optionally substituted with 1, 2, 3, 4 or 5 $Z^{2c}$ group.

In one variation of formula I, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups; and $Z^2$ is $(C_2\text{-}C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2\text{-}C_8)$alkynyl of $Z^2$ is optionally substituted with 1, 2, 3, 4 or 5 $Z^{2c}$ groups.

In one variation of formula I, $Z^1$ is bicyclic-heteroaryl optionally substituted with 1, 2, 3, 4 or 5 $Z^{1a}$ groups; and $Z^2$ is $(C_2\text{-}C_8)$alkynyl optionally substituted with 1, 2, 3, 4 or 5 $Z^{2c}$ groups.

In one variation of formula I, $R^1$ is a 5-12 membered heteroaryl; $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups; and $Z^2$ is $(C_2\text{-}C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2\text{-}C_8)$alkynyl of $Z^2$ is optionally substituted with 1, 2, 3, 4 or 5 $Z^{2c}$ groups.

Compounds of Formula III.

The present disclosure provides compounds of formula III:

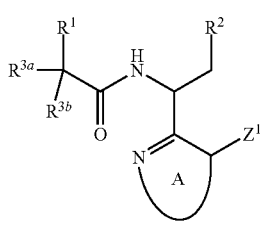

III wherein

A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with 1 or 2 $Z^3$ groups, wherein the $Z^3$ groups are the same or different;

$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;

$R^2$ is phenyl optionally substituted with 1, 2, 3, 4 or 5 halogen, which are the same or different;

each $R^{3a}$ and $R^{3b}$ is independently H or $(C_1\text{-}C_3)$alkyl;

$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;

each $Z^{1a}$ is independently $(C_3\text{-}C_7)$carbocycle, 5-12 membered heteroaryl, 3-12 membered heterocycle, halogen, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, —C(O)R$^{n1}$, —C(O)OR$^{n1}$, —C(O)NR$^{q1}$R$^{r1}$ and —S(O)$_2$NR$^{n1}$COR$^{p1}$, wherein any $(C_3\text{-}C_7)$carbocycle, 5-12 membered heteroaryl and 3-12 membered heterocycle of $Z^{ma}$ is optionally substituted with 1, 2, 3 or 5 $Z^{1c}$ or $Z^{1d}$ groups, wherein the $Z^{1c}$ and $Z^{1d}$ groups are the same or different;

each $Z^{1b}$ is independently $(C_1\text{-}C_8)$alkyl optionally substituted with 1, 2, 3, 4 or 5 halogen, which are the same or different;

each $Z^{1c}$ is independently halogen, —CN, —OH, —NH$_2$, —C(O)NR$^{q2}$R$^{r2}$, or $(C_1\text{-}C_8)$heteroalkyl;

each $Z^{1d}$ is independently $(C_1\text{-}C_8)$alkyl or $(C_1\text{-}C_8)$haloalkyl;

each $R^{n1}$ is independently H, $(C_1\text{-}C_8)$alkyl, $(C_3\text{-}C_7)$carbocycle, 3-7 membered heterocycle, or 5-6 membered monocyclic-heteroaryl, wherein any $(C_3\text{-}C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1\text{-}C_8)$alkyl of $R^{n1}$ is optionally substituted with 1, 2, 3, 4 or 5 $Z^{1c}$ groups, wherein the $Z^{1c}$ groups are the same or different;

each $R^{p1}$ is independently $(C_1\text{-}C_8)$alkyl, $(C_3\text{-}C_7)$carbocycle, 3-7 membered heterocycle, or 5-6 membered monocyclic-heteroaryl, wherein any $(C_3\text{-}C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1\text{-}C_8)$alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1\text{-}C_8)$alkyl, $(C_3\text{-}C_7)$carbocycle, 3-7 membered heterocycle, or 5-6 membered monocyclic-heteroaryl, wherein any $(C_3\text{-}C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1\text{-}C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^c$ and $Z^{1d}$ groups are the same or different;

each $R^{q2}$ and $R^{r2}$ is independently H, $(C_1$-$C_8)$alkyl, $(C_3$-$C_7)$carbocycle, or $R^{q2}$ and $R^{r2}$ together with the nitrogen to which they are attached form a 5, 6, or 7-membered heterocycle;

$Z^2$ is $(C_2$-$C_8)$alkenyl, $(C_2$-$C_8)$alkynyl, 6-12 membered aryl, 5-12 membered C-linked-heteroaryl, 3-12 membered C-linked-heterocycle, —C(O)$R^{n3}$, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, wherein the $Z^{2b}$ and $Z^{2c}$ groups are the same or different, and wherein any $(C_2$-$C_8)$alkenyl or $(C_2$-$C_8)$alkynyl of $Z^2$ is optionally substituted with 1, 2, 3, 4, or 5 $Z^{2c}$ groups, wherein the $Z^{2c}$ groups are the same or different;

each $R^{n3}$ is independently H or $(C_1$-$C_4)$alkyl;

each $R^{q3}$ and $R^{r3}$ is independently H or $(C_1$-$C_4)$alkyl;

each $Z^{2b}$ is independently oxo, $(C_1$-$C_4)$alkyl, $(C_1$-$C_4)$heteroalkyl, or $(C_1$-$C_4)$haloalkyl;

each $Z^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, or —C(O)NR$^{q4}$R$^{r4}$;

each $R^{n4}$ is independently H, $(C_1$-$C_4)$alkyl, $(C_1$-$C_4)$haloalkyl, or $(C_1$-$C_4)$heteroalkyl;

each $R^{p4}$ is independently $(C_1$-$C_8)$alkyl, $(C_1$-$C_4)$haloalkyl, or $(C_1$-$C_4)$heteroalkyl;

each $R^{q4}$ and $R^{r4}$ is independently H, $(C_1$-$C_4)$alkyl, $(C_1$-$C_4)$haloalkyl, or $(C_1$-$C_4)$heteroalkyl;

each $Z^3$ is independently a $(C_1$-$C_4)$heteroalkyl or halogen;

each $Z^4$ is independently oxo, $(C_1$-$C_8)$alkyl, $(C_3$-$C_7)$carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any $(C_3$-$C_7)$carbocycle or $(C_1$-$C_8)$alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —OR$^{n6}$; and each $R^{n5}$, $R^{p5}$, $R^{q5}$, $R^{r5}$, and $R^{n6}$ is independently H or $(C_1$-$C_4)$alkyl;

or a pharmaceutically acceptable salt thereof.

In certain embodiments, a compound of formula III is a compound of formula IIIa.

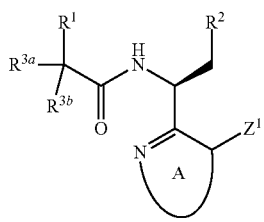

IIIa or a pharmaceutically acceptable salt thereof.

In certain embodiments, a compound of formula III is a compound of formula IIIb.

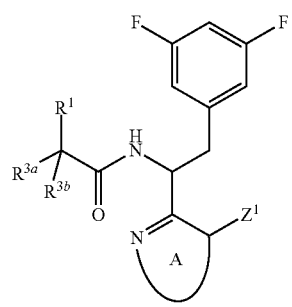

IIIb or a pharmaceutically acceptable thereof.

In certain embodiments, a compound of formula III is a compound of formula IIIc.

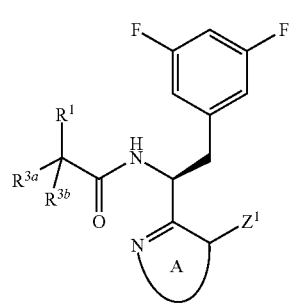

IIIc or a pharmaceutically acceptable thereof.

The present disclosure provides compounds of formula IIId:

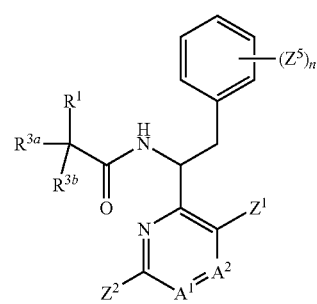

IIId wherein
$A^1$ is CH, C—$Z^3$, or nitrogen;
$A^2$ is CH or nitrogen;
$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;
each $R^{3a}$ and $R^{3b}$ is independently H or $(C_1$-$C_3)$alkyl;
$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;
each $Z^{1a}$ is independently $(C_3$-$C_7)$carbocycle, 5-12 membered heteroaryl, 3-12 membered heterocycle, halogen, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, —C(O)R$^{n1}$, —C(O)OR$^{n1}$, —C(O)NR$^{q1}$R$^{r1}$ and —S(O)$_2$NR$^{n1}$COR$^{p1}$, wherein any (C$_3$-C$_7$) carbocycle, 5-12 membered heteroaryl and 3-12 membered heterocycle of Z$^{1a}$ is optionally substituted with 1, 2, 3, 4 or 5 Z$^{1c}$ or Z$^{1d}$ groups, wherein the Z$^{1c}$ and Z$^{1d}$ groups are the same or different;

each Z$^{1b}$ is independently (C$_1$-C$_8$)alkyl optionally substituted with 1, 2, 3, 4 or 5 halogen, which are the same or different;

each Z$^{1c}$ is independently halogen, —CN, —OH, —NH$_2$, —C(O)NR$^{q2}$R$^{r2}$, or (C$_1$-C$_8$)heteroalkyl;

each Z$^{1d}$ is independently (C$_1$-C$_8$)alkyl or (C$_1$-C$_8$)haloalkyl;

each R$^{n1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{n1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{n1}$ is optionally substituted with 1, 2, 3, 4 or 5 Z$^{1c}$ groups, wherein the Z$^{1c}$ groups are the same or different;

each R$^{p1}$ is independently (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{p1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{p1}$ is optionally substituted with 1, 2, 3, 4 or 5 Z$^{1c}$ groups, wherein the Z$^{1c}$ groups are the same or different;

each R$^{q1}$ and R$^{r1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{q1}$ or R$^{r1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{q1}$ or R$^{r1}$ is optionally substituted with 1, 2, 3, 4 or 5 Z$^{1c}$ groups, wherein the Z$^{1c}$ groups are the same or different, or R$^{q1}$ and R$^{r1}$ together with the nitrogen to which they are attached form a 5, 6 or 7-membered heterocycle, wherein the 5, 6 or 7-membered heterocycle is optionally substituted with 1, 2, 3, 4 or 5 Z$^{1c}$ or Z$^{1d}$ groups, wherein the Z$^c$ and Z$^{1d}$ groups are the same or different;

each R$^{q2}$ and R$^{r2}$ is independently H, (C$_1$-C$_8$)alkyl, (C$_3$-C$_7$)carbocycle, or R$^{q2}$ and R$^{r2}$ together with the nitrogen to which they are attached form a 5, 6, or 7-membered heterocycle;

Z$^2$ is (C$_2$-C$_8$)alkenyl, (C$_2$-C$_8$)alkynyl, 6-12 membered aryl, 5-12 membered C-linked-heteroaryl, 3-12 membered C-linked-heterocycle, —C(O)R$^{n3}$, or —C(O)NR$^{q3}$R$^{r3}$, wherein any 6-12 membered aryl, 5-12 membered C-linked-heteroaryl, or 3-12 membered C-linked-heterocycle of Z$^2$ is optionally substituted with 1, 2, 3, 4 or 5 Z$^{2b}$ or Z$^{2c}$ groups, wherein the Z$^{2b}$ and Z$^{2c}$ groups are the same or different, and wherein any (C$_2$-C$_8$)alkenyl or (C$_2$-C$_8$)alkynyl of Z$^2$ is optionally substituted with 1, 2, 3, 4, or 5 Z$^{2c}$ groups, wherein the Z$^{2c}$ groups are the same or different;

each R$^{n3}$ is independently H or (C$_1$-C$_4$)alkyl;

each R$^{q3}$ and R$^{r3}$ is independently H or (C$_1$-C$_4$)alkyl;

each Z$^{2b}$ is independently oxo, (C$_1$-C$_4$)alkyl, (C$_1$-C$_4$) heteroalkyl or (C$_1$-C$_4$)haloalkyl;

each Z$^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, or —C(O)NR$^{q4}$R$^{r4}$;

each R$^{n4}$ is independently H, (C$_1$-C$_4$)alkyl, (C$_1$-C$_4$)haloalkyl, or (C$_1$-C$_4$)heteroalkyl;

each R$^{p4}$ is independently (C$_1$-C$_8$)alkyl, (C$_1$-C$_4$)haloalkyl, or (C$_1$-C$_4$)heteroalkyl;

each R$^{q4}$ and R$^{r4}$ is independently H, (C$_1$-C$_4$)alkyl, (C$_1$-C$_4$)haloalkyl, or (C$_1$-C$_4$)heteroalkyl;

each Z$^3$ is independently a (C$_1$-C$_4$)heteroalkyl;

each Z$^4$ is independently oxo, (C$_1$-C$_8$)alkyl, (C$_3$-C$_7$)carbocycle, halogen, —CN, —OR$^{n5}$ NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any (C$_3$-C$_7$)carbocycle or (C$_1$-C$_8$)alkyl of Z$^4$ is optionally substituted with 1, 2, 3, 4 or 5 Z$^{4a}$ groups, wherein the Z$^{4a}$ groups are the same or different;

each Z$^{4a}$ is independently halogen, —CN, or —OR$^{n6}$ each R$^{n5}$, R$^{p5}$, R$^{q5}$, R$^{r5}$, and R$^{n6}$ is independently H or (C$_1$-C$_4$)alkyl;

each Z$^5$ is independently halogen, which may be same or different; and n is 0, 1, 2, or 3;

or a pharmaceutically acceptable salt thereof.

In certain embodiments, a compound of formula IIId is a compound of formula IIIe.

IIIe

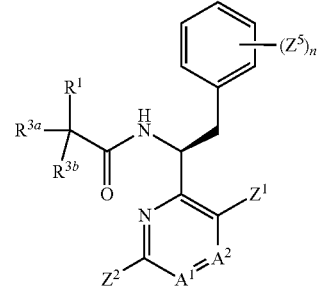

or a pharmaceutically acceptable salt thereof.

The present disclosure provides compounds of formula IIIf:

IIIf

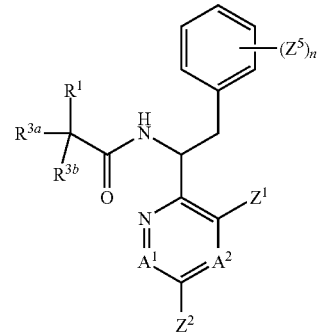

wherein
A$^1$ is CH, C—Z$^3$, or nitrogen;
A$^2$ is CH or nitrogen;

R$^1$ is 6-12 membered aryl, 5-12 membered heteroaryl, or 3-12 membered heterocycle, wherein any 6-12 membered aryl, 5-12 membered heteroaryl, or 3-12 membered heterocycle of R$^1$ is optionally substituted with 1, 2, 3, 4 or 5 Z$^4$ groups, wherein the Z$^4$ groups are the same or different;

each R$^{3a}$ and R$^{3b}$ is independently H or (C$_1$-C$_3$)alkyl;

Z$^1$ is 6-12 membered aryl, 5-14 membered heteroaryl, or 3-14 membered heterocycle, wherein any 6-12 membered aryl, 5-14 membered heteroaryl, or 3-14 membered heterocycle of Z$^1$ is optionally substituted with 1, 2, 3, 4 or 5 Z$^{1a}$ or Z$^{1b}$, wherein the Z$^{1a}$ and Z$^{1b}$ groups are the same or different;

each Z$^{1a}$ is independently (C$_3$-C$_7$)carbocycle, 5-12 membered heteroaryl, 3-12 membered heterocycle, halogen, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, —C(O)R$^{n1}$, —C(O)OR$^{n1}$, —C(O)NR$^{q1}$R$^{r1}$ and —S(O)$_2$NR$^{n1}$COR$^{p1}$, wherein any (C$_3$-C$_7$) carbocycle, 5-12 membered heteroaryl and 3-12 membered heterocycle of Z$^{1a}$ is optionally substituted with 1, 2, 3, 4 or 5 Z$^{1c}$ or Z$^{1d}$ groups, wherein the Z$^{1c}$ and Z$^{1d}$ groups are the same or different;

each Z$^{1b}$ is independently (C$_1$-C$_8$)alkyl optionally substituted with 1, 2, 3, 4 or 5 halogen, which are the same or different;

each Z$^{1c}$ is independently halogen, —CN, —OH, —NH$_2$, —C(O)NR$^{q2}$R$^{r2}$, or (C$_1$-C$_8$)heteroalkyl;

each Z$^{1d}$ is independently (C$_1$-C$_8$)alkyl or (C$_1$-C$_8$)haloalkyl;

each R$^{n1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{n1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{n1}$ is optionally substituted with 1, 2, 3, 4 or 5 Z$^{1c}$ groups, wherein the Z$^{1c}$ groups are the same or different;

each R$^{p1}$ is independently (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{p1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{p1}$ is optionally substituted with 1, 2, 3, 4 or 5 Z$^{1c}$ groups, wherein the Z$^{1c}$ groups are the same or different;

each R$^{q1}$ and R$^{r1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{q1}$ or R$^{r1}$ is optionally substituted with 1, 2, 3, 4 or 5 Z$^{1c}$ or Z$^{1d}$ groups, wherein the Z$^{1c}$ and Z$^{1d}$ groups are the same or different, and wherein any (C$_1$-C$_8$)alkyl of R$^{q1}$ or R$^{r1}$ is optionally substituted with 1, 2, 3, 4 or 5 Z$^{1c}$ groups, wherein the Z$^{1c}$ groups are the same or different, or R$^{q1}$ and R$^{r1}$ together with the nitrogen to which they are attached form a 5, 6 or 7-membered heterocycle, wherein the 5, 6 or 7-membered heterocycle is optionally substituted with 1, 2, 3, 4 or 5 Z$^{1c}$ or Z$^{1d}$ groups, wherein the Z$^c$ and Z$^{1d}$ groups are the same or different;

each R$^{q2}$ and R$^{r2}$ is independently H, (C$_1$-C$_8$)alkyl, (C$_3$-C$_7$)carbocycle, or R$^{q2}$ and R$^{r2}$ together with the nitrogen to which they are attached form a 5, 6, or 7-membered heterocycle;

Z$^2$ is (C$_2$-C$_8$)alkenyl, (C$_2$-C$_8$)alkynyl, 6-12 membered aryl, 5-12 membered C-linked-heteroaryl, 3-12 membered C-linked-heterocycle, —C(O)R$^{n3}$, or —C(O)NR$^{q3}$R$^{r3}$, wherein any 6-12 membered aryl, 5-12 membered C-linked-heteroaryl, or 3-12 membered C-linked-heterocycle of Z$^2$ is optionally substituted with 1, 2, 3, 4 or 5 Z$^{2b}$ or Z$^{2c}$ groups, wherein the Z$^{2b}$ and Z$^{2c}$ groups are the same or different, and wherein any (C$_2$-C$_8$)alkenyl or (C$_2$-C$_8$)alkynyl of Z$^2$ is optionally substituted with 1, 2, 3, 4, or 5 Z$^{2c}$ groups, wherein the Z$^{2c}$ groups are the same or different;

each R$^{n3}$ is independently H or (C$_1$-C$_4$)alkyl;

each R$^{q3}$ and R$^{r3}$ is independently H or (C$_1$-C$_4$)alkyl;

each Z$^{2b}$ is independently oxo, (C$_1$-C$_4$)alkyl, (C$_1$-C$_4$)heteroalkyl or (C$_1$-C$_4$)haloalkyl;

each Z$^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, or —C(O)NR$^{q4}$R$^{r4}$;

each R$^{n4}$ is independently H, (C$_1$-C$_4$)alkyl, (C$_1$-C$_4$)haloalkyl, or (C$_1$-C$_4$)heteroalkyl;

each R$^{p4}$ is independently (C$_1$-C$_8$)alkyl, (C$_1$-C$_4$)haloalkyl, or (C$_1$-C$_4$)heteroalkyl;

each R$^{q4}$ and R$^{r4}$ is independently H, (C$_1$-C$_4$)alkyl, (C$_1$-C$_4$)haloalkyl, or (C$_1$-C$_4$)heteroalkyl;

each Z$^3$ is independently a (C$_1$-C$_4$)heteroalkyl;

each Z$^4$ is independently oxo, (C$_1$-C$_8$)alkyl, (C$_3$-C$_7$)carbocycle, halogen, —CN, —OR$^{n5}$ NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any (C$_3$-C$_7$)carbocycle or (C$_1$-C$_8$)alkyl of Z$^4$ is optionally substituted with 1, 2, 3, 4 or 5 Z$^{4a}$ groups, wherein the Z$^{4a}$ groups are the same or different;

each Z$^{4a}$ is independently halogen, —CN, or —OR$^{n6}$ each R$^{n5}$, R$^{p5}$, R$^{q5}$, R$^{r5}$, and R$^{n6}$ is independently H or (C$_1$-C$_4$)alkyl;

each Z$^5$ is independently halogen, which may be same or different; and n is 0, 1, 2, or 3;

or a pharmaceutically acceptable salt thereof.

In certain embodiments, a compound of formula IIIf is a compound of formula IIIg.

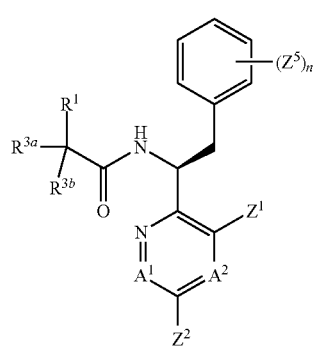

IIIg or a pharmaceutically acceptable salt thereof.

The present disclosure provides compounds of formula IIIh:

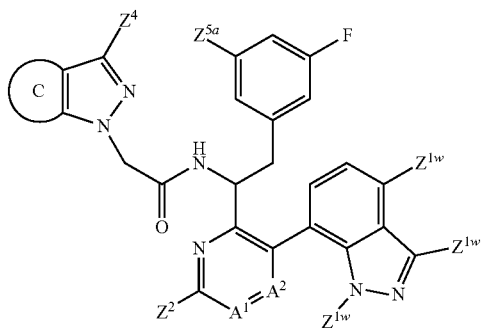

IIIh wherein
$A^1$ is CH, C—$Z^3$, or nitrogen;
$A^2$ is CH or nitrogen;
C together with the two carbon atoms to which it is attached forms a 3-7 membered monocyclic-carbocycle or 5-9 membered bicyclic-carbocycle, wherein any 3-7 membered monocyclic-carbocycle or 5-9 membered bicyclic-carbocycle of C is optionally substituted with 1, 2, 3, 4 or 5 $Z^4$ groups, wherein the $Z^4$ groups are the same or different;

each $Z^{1w}$ is independently $Z^{1a}$, $Z^{1b}$ or H;

each $Z^{1a}$ is independently $(C_3-C_7)$carbocycle, 5-12 membered heteroaryl, 3-12 membered heterocycle, halogen, —CN, —$OR^{n1}$, —OC(O)$R^{p1}$, —OC(O)N$R^{q1}R^{r1}$, —$SR^{n1}$, —S(O)$R^{p1}$, —S(O)$_2$OH, —S(O)$_2R^{p1}$, —S(O)N$R^{q1}R^{r1}$, —S(O)$_2$N$R^{q1}R^{r1}$, —N$R^{q1}R^{r1}$, —N$R^{n1}$COR$^{p1}$, —N$R^{n1}$CO$_2R^{p1}$, —N$R^{n1}$CONR$^{q1}R^{r1}$, —N$R^{n1}$S(O)$_2R^{p1}$, —N$R^{n1}$S(O)$_2$OR$^{p1}$, —N$R^{n1}$S(O)$_2$N$R^{q1}R^{r1}$, —C(O)$R^{n1}$, —C(O)O$R^{n1}$, —C(O)N$R^{q1}R^{r1}$ and —S(O)$_2$N$R^{n1}$COR$^{p1}$, wherein any $(C_3-C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^c$ and $Z^{1d}$ groups are the same or different;

each $Z^{1b}$ is independently $(C_1-C_8)$alkyl optionally substituted with 1, 2, 3, 4 or 5 halogen, which are the same or different;

each $Z^{1c}$ is independently halogen, —CN, —OH, —NH$_2$, —C(O)N$R^{q2}R^{r2}$, or $(C_1-C_8)$heteroalkyl;

each $Z^{1d}$ is independently $(C_1-C_8)$alkyl or $(C_1-C_8)$haloalkyl;

each $R^{n1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{n1}$ is optionally substituted with 1, 2, 3, 4 or 5 $Z^{1c}$ groups, wherein the $Z^{1c}$ groups are the same or different;

each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^c$ and $Z^{1d}$ groups are the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is $(C_2-C_8)$alkenyl, $(C_2-C_8)$alkynyl, 6-12 membered aryl, 5-12 membered C-linked-heteroaryl, 3-12 membered C-linked-heterocycle, —C(O)$R^{n3}$, or —C(O)N$R^{q3}R^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, wherein the $Z^{2b}$ and $Z^{2c}$ groups are the same or different, and wherein any $(C_2-C_8)$alkenyl or $(C_2-C_8)$alkynyl of $Z^2$ is optionally substituted with 1, 2, 3, 4, or 5 $Z^{2c}$ groups, wherein the $Z^{2c}$ groups are the same or different;

each $R^{n3}$ is independently H or $(C_1-C_4)$alkyl;

each $R^{q3}$ and $R^{r3}$ is independently H or $(C_1-C_4)$alkyl;

each $Z^{2b}$ is independently oxo, $(C_1-C_4)$alkyl, $(C_1-C_4)$heteroalkyl or $(C_1-C_4)$haloalkyl;

each $Z^{2c}$ is independently oxo, halogen, —CN, —$OR^{n4}$, —OC(O)$R^{p4}$, —OC(O)N$R^{q4}R^{r4}$, —$SR^{n4}$, —S(O)$R^{p4}$, —S(O)$_2$OH, —S(O)$_2R^{p4}$, —S(O)$_2$N$R^{q4}R^{r4}$, —N$R^{q4}R^{r4}$, —N$R^{n4}$COR$^{p4}$, —N$R^{n4}$CO$_2R^{p4}$, —N$R^{n4}$CONR$^{q4}R^{r4}$, —N$R^{n4}$S(O)$_2R^{p4}$, —N$R^{n4}$S(O)$_2$OR$^{p4}$, —N$R^{n4}$S(O)$_2$N$R^{q4}R^{r4}$, —NO$_2$, —C(O)$R^{n4}$, —C(O)O$R^{n4}$, or —C(O)N$R^{q4}R^{r4}$;

each $R^{n4}$ is independently H, $(C_1-C_4)$alkyl, $(C_1-C_4)$haloalkyl, or $(C_1-C_4)$heteroalkyl;

each $R^{p4}$ is independently $(C_1-C_8)$alkyl, $(C_1-C_4)$haloalkyl, or $(C_1-C_4)$heteroalkyl;

each $R^{q4}$ and $R^{r4}$ is independently H, $(C_1-C_4)$alkyl, $(C_1-C_4)$haloalkyl, or $(C_1-C_4)$heteroalkyl;

$Z^3$ is independently a $(C_1-C_4)$heteroalkyl;

each $Z^4$ is independently oxo, $(C_1-C_8)$alkyl, $(C_3-C_7)$carbocycle, halogen, —CN, —$OR^{n5}$, —N$R^{q5}R^{r5}$, —N$R^{n5}$COR$^{p5}$, —N$R^{n5}$CO$_2R^{p5}$, —C(O)$R^{n5}$, —C(O)O$R^{n5}$, or —C(O)N$R^{q5}R^{r5}$, wherein any $(C_3-C_7)$carbocycle or $(C_1-C_8)$alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —$OR^{n6}$ each $R^{n5}$, $R^{p5}$, $R^{q5}$, $R^{r5}$, and $R^{n6}$ is independently H or $(C_1-C_4)$alkyl; and $Z^{5a}$ is H or halogen;

or a pharmaceutically acceptable salt thereof.

In certain embodiments, a compound of formula IIIh is a compound of formula IIIi.

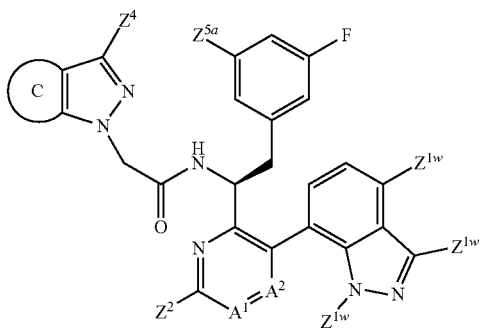

IIIi or a pharmaceutically acceptable salt thereof.

The present disclosure provides compounds of formula IIIj:

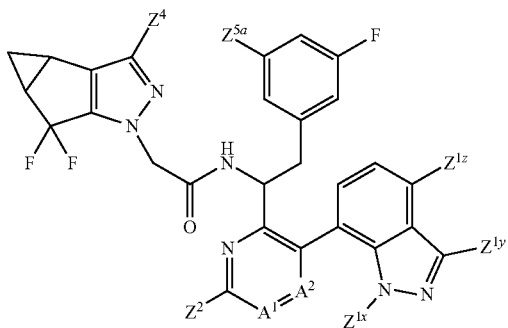

IIIj wherein
$A^1$ is CH, C—$Z^3$, or nitrogen;
$A^2$ is CH or nitrogen;
$Z^{1x}$ is H or $(C_1-C_8)$alkyl;
$Z^{1y}$ is —$NR^{n1}S(O)_2R^{p1}$, —$NR^{n1}S(O)_2NR^{q1}R^{r1}$, —$NR^{q1}R^{r1}$, —$NR^{n1}COR^{p1}$, —$NR^{n1}CONR^{q1}R^{r1}$, or —$NR^{n1}CO_2R^{p1}$;
$Z^{1z}$ is H, halogen, —CN, —$OR^{n1}$, $(C_1-C_8)$alkyl, wherein the $(C_1-C_8)$alkyl is optionally substituted with 1, 2, or 3 halogen, which are the same or different;
each $R^{n1}$ is independently H or $(C_1-C_8)$alkyl;
each $R^{p1}$ is independently $(C_1-C_8)$alkyl;
each $R^{q1}$ and $R^{r1}$ is independently H or $(C_1-C_8)$alkyl;
$Z^3$ is $(C_1-C_4)$heteroalkyl;
$Z^2$ is $(C_2-C_8)$alkynyl, optionally substituted with 1, 2, 3, 4, or 5 $Z^{2c}$ group, wherein the $Z^{2c}$ groups are the same or different; wherein $Z^{2c}$ is independently halogen, —$OR^{n4}$, —$NR^4CO_2R^{p4}$, —$C(O)OR^{n4}$, or —$NR^{q4}R^{r4}$;
each $R^{n4}$ is independently H or $(C_1-C_4)$alkyl;
each $R^{p4}$ is independently $(C_1-C_4)$alkyl;
each $R^{q4}$ and $R^{r4}$ is independently H, $(C_1-C_4)$alkyl, or $(C_1-C_4)$heteroalkyl;
$Z^4$ is hydrogen, $(C_1-C_8)$alkyl, halogen, —CN, $C(O)R^{n5}$, —$C(O)OR^{n5}$, —$C(O)NR^{q5}R^{r5}$, —$NR^{n5}COR^{p5}$, —$NR^{q5}R^{r5}$, or $(C_3-C_7)$carbocycle, wherein any $(C_3-C_7)$carbocycle or $(C_1-C_8)$alkyl of $Z^4$ is optionally substituted with halogen or hydroxyl;
each $R^{n5}$ is independently H or $(C_1-C_4)$alkyl;
each $R^{p5}$ is independently H or $(C_1-C_4)$alkyl;
each $R^{q5}$ and $R^{r5}$ is independently H or $(C_1-C_4)$alkyl; and
$Z^{5a}$ is H or halogen;
or a pharmaceutically acceptable salt thereof.
In certain embodiments, a compound of formula IIIj is a compound of formula IIIk.

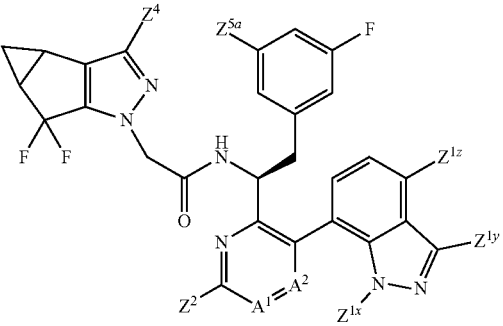

IIIk or a pharmaceutically acceptable salt thereof.

Specific values listed below are values for compounds of formula III as well as all related formulas (e.g., formulas IIIa, IIIb, IIIc, IIId, IIIe, IIIf, IIIg, IIIh, IIIi, IIIj, and IIIk) where applicable. For example, values recited below as applying to formula III apply equally to all related formulas of formula III (e.g., formulas IIIa, IIIb, IIIc, IIId, IIIe, IIIf, IIIg, IIIh, IIIi, IIIj, and IIIk) that permit the presence of such variable. It is to be understood that two or more values may combined. Thus, it is to be understood that any variable for compounds of formula III may be combined with any other variable for compounds of formula III the same as if each and every combination of variables were specifically and individually listed. For example, it is understood that any specific value of $R^1$ detailed herein for compounds of formula III may be combined with any other specific value for one or more of the variables A, $Z^1$, $R^2$, $R^{3a}$ or $R^{3b}$ of formula III the same as if each and every combination were specifically and individually listed.

In certain embodiments of formula III, $A^1$ is CH. In certain embodiments, $A^1$ is C—$Z^3$. In certain embodiments, $A^1$ is nitrogen.

In certain embodiments of formula III, $A^2$ is CH. In certain embodiments, $A^2$ is nitrogen.

In certain embodiments of formula III, $A^1$ is CH; and $A^2$ is CH. In certain embodiments, $A^1$ is C—$Z^3$; and $A^2$ is CH. In certain embodiments, $A^1$ is nitrogen; and $A^2$ is CH.

In certain embodiments of formula III, $A^1$ is CH; and $A^2$ is nitrogen. In certain embodiments, $A^1$ is C—$Z^3$; and $A^2$ is nitrogen. In certain embodiments, $A^1$ is nitrogen; and $A^2$ is nitrogen.

In certain embodiments of formula III, $Z^5$ is F. In certain embodiments of formula III, n is one. In certain embodiments, n is two. In certain embodiments of formula III, n is one and $Z^5$ is F. In certain embodiments, n is two and each $Z^5$ is F.

In certain embodiments of formula III, $Z^{5a}$ is H. In certain embodiments, $Z^{5a}$ is F.

In certain embodiments of formula III, each $Z^{1w}$ is independently $Z^{1a}$ or $Z^{1b}$, wherein the $Z^{1a}$ and $Z^b$ groups may be the same or different. In certain embodiments, each $Z^{1w}$ is independently $(C_1-C_8)$alkyl, halogen, or —$NR^{n1}S(O)_2R^{p1}$, which may be same or different.

In certain embodiments of formula III, $Z^{1x}$ is H. In certain embodiments, $Z^{1x}$ is $(C_1-C_8)$alkyl. In certain embodiments, $Z^{1x}$ is $(C_1-C_4)$alkyl. In certain embodiments, $Z^{1x}$ is $(C_1-C_3)$ alkyl. In certain embodiments, $Z^{1x}$ is methyl.

In certain embodiments of formula III, $Z^{1y}$ is —$NR^{n1}S(O)_2R^{p1}$, —$NR^{n1}S(O)_2NR^{q1}R^{r1}$, or —$NR^{q1}R^{r1}$. In certain embodiments, $Z^{1y}$ is —$NR^{n1}S(O)_2R^{p1}$ or —$NR^{n1}S(O)_2NR^{q1}R^{r1}$. In certain embodiments, $Z^y$ is —$NR^{n1}S(O)_2R^{p1}$.

In certain embodiments, $Z^{1y}$ is $-NR^{n1}S(O)_2NR^{q1}R^{r1}$. In certain embodiments, $Z^{1y}$ is $-NR^{q1}R^{r1}$.

In certain embodiments of formula III, $Z^{1z}$ is H or halogen. In certain embodiments, $Z^{1z}$ is H. In certain embodiments, $Z^{1z}$ is halogen. In certain embodiments, $Z^{1z}$ is Cl. In certain embodiments, $Z^{1z}$ is F. In certain embodiments, $Z^{1z}$ is Br.

In certain embodiments of formula III, $Z^{1y}$ is $-NR^{n1}S(O)_2R^{p1}$ or $-NR^{n1}S(O)_2NR^{q1}R^{r1}$ and $Z^{1z}$ is halogen. In certain embodiments, $Z^{1y}$ is $-NR^{n1}S(O)_2R^{p1}$ and $Z^{1z}$ is halogen. In certain embodiments, $Z^{1x}$ is $(C_1-C_4)$alkyl; $Z^{1y}$ is $-NR^{n1}S(O)_2R^{p1}$ or $-NR^{n1}S(O)_2NR^{q1}R^{r1}$; and $Z^{1z}$ is halogen. In certain embodiments, $Z^{1x}$ is $(C_1-C_4)$alkyl; $Z^{1y}$ is $-NR^{n1}S(O)_2R^{p1}$; and $Z^{1z}$ is halogen.

In certain embodiments of formula III, A is pyridinyl, pyrimidinyl, pyrazinyl, or pyridazinyl, wherein any pyridinyl, pyrimidinyl, pyrazinyl or pyridazinyl of A is substituted with one $Z^1$ group at the position shown, one $Z^2$ group and optionally substituted with 1 or 2 $Z^3$ groups. In certain embodiments, A is pyridinyl, pyrimidinyl, pyrazinyl, or pyridazinyl, wherein any pyridinyl, pyrimidinyl, pyrazinyl or pyridazinyl of A is substituted with one $Z^1$ group at the position shown, one $Z^2$ group and optionally substituted with 1 $Z^3$ group.

In certain embodiments, A is pyridinyl, pyrimidinyl, pyrazinyl or pyridazinyl, wherein any pyridinyl, pyrimidinyl, pyrazinyl or pyridazinyl of A is substituted with one $Z^1$ group at the position shown and one $Z^2$ group. In one aspect, A is not substituted with a $Z^3$ group.

In certain embodiments, A is pyridinyl, wherein any pyridinyl of A is substituted with one $Z^1$ group at the position shown, one $Z^2$ group, and optionally substituted with 1 or 2 $Z^3$ groups. In certain embodiments, A is pyridinyl, wherein any pyridinyl of A is substituted with one $Z^1$ group at the position shown, one $Z^2$ group, and optionally substituted with 1 $Z^3$ group.

In certain embodiments, A is pyridinyl, wherein any pyridinyl of A is substituted with one $Z^1$ group at the position shown and one $Z^2$ group. In one aspect, the $Z^2$ group attached at the position alpha to the nitrogen of the pyridinyl group. In a further aspect, A is not substituted with a $Z^3$ group.

In certain embodiments, A is pyrimidinyl, wherein any pyridinyl of A is substituted with one $Z^1$ group at the position shown, one $Z^2$ group, and optionally substituted with 1 or 2 $Z^3$ groups. In certain embodiments, A is pyrimidinyl, wherein any pyridinyl of A is substituted with one $Z^1$ group at the position shown, one $Z^2$ group, and optionally substituted with 1 $Z^3$ group.

In certain embodiments, A is pyrimidinyl, wherein any pyridinyl of A is substituted with one $Z^1$ group at the position shown and one $Z^2$ group. In one aspect, A is not substituted with a $Z^3$ group.

In certain embodiments, A is pyrazinyl, wherein any pyridinyl of A is substituted with one $Z^1$ group at the position shown, one $Z^2$ group, and optionally substituted with 1 or 2 $Z^3$ groups. In certain embodiments, A is pyrazinyl, wherein any pyridinyl of A is substituted with one $Z^1$ group at the position shown, one $Z^2$ group, and optionally substituted with 1 $Z^3$ group.

In certain embodiments, A is pyrazinyl, wherein any pyridinyl of A is substituted with one $Z^1$ group at the position shown and one $Z^2$ group. In one aspect, A is not substituted with a $Z^3$ group.

In certain embodiments, A is:

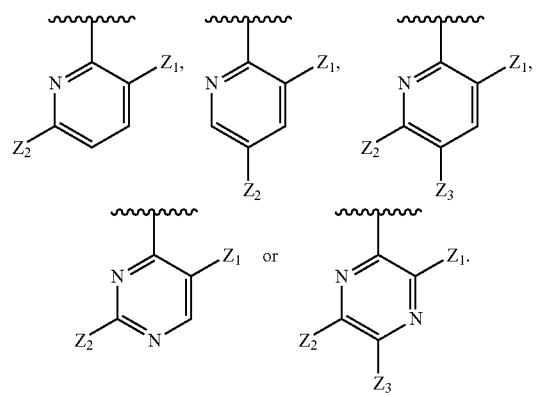

In certain embodiments, A is:

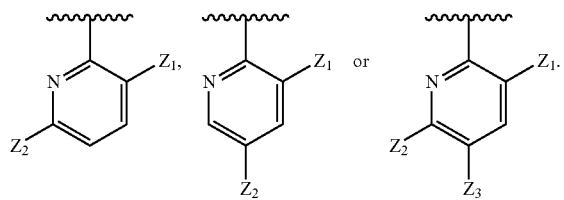

In certain embodiments, A is:

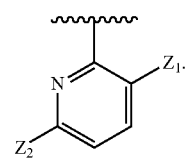

In certain embodiments, A is:

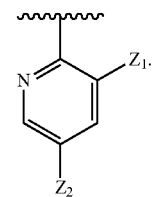

In certain embodiments, A is:

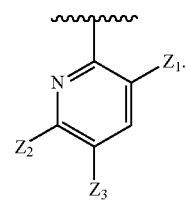

In certain embodiments of formula III, $R^2$ is phenyl optionally substituted with 1, 2, or 3 halogens, which may be the same or different. In certain embodiments, $R^2$ is phenyl optionally substituted with 1 or 2 halogens, which may be the same or different. In certain embodiments, R² is phenyl optionally substituted with 2 halogens, which may be the same or different. In certain embodiments, R² is phenyl optionally substituted with 1 halogen.

In certain embodiments, R² is 3,5-difluorophenyl or 3-fluorophenyl. In certain embodiments, R² is 3,5-difluorophenyl. In certain embodiments, R² is 3-fluorophenyl.

In certain embodiments, the moiety

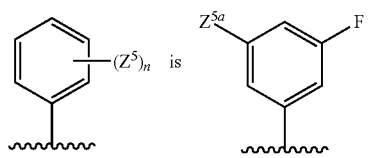

wherein $Z^{5a}$ is H or halogen.

In certain embodiments of formula III, each $Z^3$, where present, is independently methoxy, dimethylamino, or methylamino. In certain embodiments, $Z^3$, where present, is methoxy. In certain embodiments, $Z^3$, where present, is dimethylamino. In certain embodiments, $Z^3$, where present, is methylamino. In certain embodiments, $Z^3$, where present, is halogen. In certain embodiments, $Z^3$, where present, is fluoro. In certain embodiments, $Z^3$, where present, is chloro. In certain embodiments, $Z^3$, where present, is bromo.

In certain embodiments of formula III, each $R^{3a}$ and $R^{3b}$ are each H. In certain embodiments, $R^{3a}$ is methyl and $R^{3b}$ is H.

In certain embodiments of formula III, $Z^2$ is $(C_2$-$C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2$-$C_8)$alkynyl of $Z^2$ is optionally substituted with 1, 2, 3, 4 or 5 $Z^{2c}$ groups.

In certain embodiments, $Z^2$ is $(C_2$-$C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2c}$ groups, and wherein any $(C_2$-$C_8)$alkynyl of $Z^2$ is optionally substituted with 1, 2, 3, 4 or 5 $Z^{2c}$ groups.

In certain embodiments, $Z^2$ is $(C_2$-$C_8)$alkynyl, phenyl, 5-6 membered C-linked-monocyclic-heteroaryl, 8-10 membered C-linked-bicyclic-heteroaryl, 8-10 membered C-linked-bicyclic-heterocycle, or —C(O)NR$^{q3}$R$^{r3}$, wherein any phenyl, 5-6 membered C-linked-monocyclic-heteroaryl, 8-10 membered C-linked-bicyclic-heteroaryl, or 8-10 membered C-linked-bicyclic-heterocycle of $Z^2$ is optionally substituted with 1, 2, 3, 4 or 5 $Z^{2b}$ or $Z^{2c}$ groups, and wherein any $(C_2$-$C_8)$alkynyl of $Z^2$ is optionally substituted with 1, 2, 3, 4 or 5 $Z^{2c}$ groups.

In certain embodiments, $Z^2$ is $(C_2$-$C_8)$alkynyl, phenyl, 5-6 membered C-linked-monocyclic-heteroaryl, 8-10 membered C-linked-bicyclic-heteroaryl, 8-10 membered C-linked-bicyclic-heterocycle, or —C(O)NR$^{q3}$R$^{r3}$, wherein any phenyl, 5-6 membered C-linked-monocyclic-heteroaryl, 8-10 membered C-linked-bicyclic-heteroaryl, or 8-10 membered C-linked-bicyclic-heterocycle of $Z^2$ is optionally substituted with 1, 2, 3, 4 or 5 $Z^{2c}$ groups, and wherein any $(C_2$-$C_8)$alkynyl of $Z^2$ is optionally substituted with 1, 2, 3, 4 or 5 $Z^{2c}$ groups.

In certain embodiments, $Z^2$ is $(C_2$-$C_8)$alkynyl, phenyl, 5-6 membered C-linked-monocyclic-heteroaryl, 8-10 membered C-linked-bicyclic-heteroaryl, 8-10 membered C-linked-bicyclic-heterocycle, or —C(O)NR$^{q3}$R$^{r3}$, wherein the 5-6 membered C-linked-monocyclic-heteroaryl, 8-10 membered C-linked-bicyclic-heteroaryl, or 8-10 membered C-linked-bicyclic-heterocycle have 1-9 carbon atoms and 1-4 heteroatoms in the ring system, and wherein any phenyl, 5-6 membered C-linked-monocyclic-heteroaryl, 8-10 membered C-linked-bicyclic-heteroaryl, 8-10 membered and C-linked-bicyclic-heterocycle of $Z^2$ is optionally substituted with 1, 2, 3, 4 or 5 $Z^{2b}$ or $Z^{2c}$ groups, and wherein any $(C_2$-$C_8)$alkynyl of $Z^2$ is optionally substituted with 1, 2, 3, 4 or 5 $Z^{2c}$ groups.

In certain embodiments, $Z^2$ is $(C_2$-$C_8)$alkynyl, phenyl, 5-6 membered C-linked-monocyclic-heteroaryl, 8-10 membered C-linked-bicyclic-heteroaryl, 8-10 membered C-linked-bicyclic-heterocycle, or —C(O)NR$^{q3}$R$^{r3}$, wherein the 5-6 membered C-linked-monocyclic-heteroaryl, 8-10 membered C-linked-bicyclic-heteroaryl, or 8-10 membered C-linked-bicyclic-heterocycle have 1-9 carbon atoms and 1-4 heteroatoms in the ring system, and wherein any phenyl, 5-6 membered C-linked-monocyclic-heteroaryl, 8-10 membered C-linked-bicyclic-heteroaryl, 8-10 membered, or C-linked-bicyclic-heterocycle of $Z^2$ is optionally substituted with 1, 2, 3, 4 or 5 $Z^{2c}$ groups, and wherein any $(C_2$-$C_8)$ alkynyl of $Z^2$ is optionally substituted with 1, 2, 3, 4 or 5 $Z^{2c}$ groups.

In certain embodiments of formula III, $Z^2$ is $(C_2$-$C_8)$ alkynyl, optionally substituted with 1, 2, 3, 4, or 5 $Z^{2c}$ groups. In certain embodiments, $Z^2$ is $(C_2$-$C_8)$alkynyl, optionally substituted with 1, 2, 3, or 4 $Z^{2c}$ groups. In certain embodiments, $Z^2$ is $(C_2$-$C_8)$alkynyl, optionally substituted with 1, 2, or 3 $Z^{2c}$ groups. In certain embodiments, $Z^2$ is $(C_2$-$C_8)$alkynyl, optionally substituted with 1 or 2 $Z^{2c}$ groups.

In certain embodiments, $Z^2$ is of the formula:

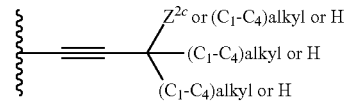

wherein each of the $(C_1$-$C_4)$alkyl moieties of $Z^2$, if present, is optionally substituted with 1, 2 or 3 $Z^{2c}$ groups, wherein the $Z^{2b}$ groups may be the same or different.

In certain embodiments, $Z^2$ is of the formula:

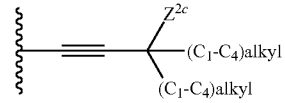

wherein each of the $(C_1$-$C_4)$alkyl moieties of $Z^2$ is optionally substituted with 1, 2 or 3 $Z^{2c}$ groups, wherein the $Z^{2b}$ groups may be the same or different.

In certain embodiments, $Z^2$ is of the formula:

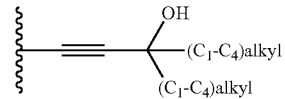

wherein each of the $(C_1-C_4)$alkyl moieties of $Z^2$ is optionally substituted with 1, 2 or 3 $Z^{2c}$ groups, wherein the $Z^{2b}$ groups may be the same or different.

In certain embodiments of formula III, $Z^2$ is substituted with 1, 2, 3, or 4 $Z^{2b}$ or $Z^{2c}$ groups, wherein the $Z^{2b}$ and $Z^{2c}$ groups may be the same or different. In certain embodiments, $Z^2$ is substituted with 1, 2, or 3 $Z^{2b}$ or $Z^{2c}$ groups, wherein the $Z^{2b}$ and $Z^{2c}$ groups may be the same or different. In certain embodiments, $Z^2$ is substituted with 1 or 2 $Z^{2b}$ or $Z^{2c}$ groups, wherein the $Z^{2b}$ and $Z^{2c}$ groups may be the same or different. In certain embodiments, $Z^2$ is substituted with 1 $Z^{2b}$ or $Z^{2c}$ group.

In certain embodiments of formula III, $Z^2$ is optionally substituted with 1, 2, or 3 $Z^{2b}$ or $Z^{2c}$ groups, wherein the $Z^{2b}$ and $Z^{2c}$ groups may be the same or different. In certain embodiments, $Z^2$ is substituted with 1 $Z^{2b}$ or $Z^{2c}$ group. In certain embodiments, $Z^2$ is substituted with 2 $Z^{2b}$ or $Z^{2c}$ groups, wherein the $Z^{2b}$ and $Z^{2c}$ groups may be the same or different. In certain embodiments, $Z^2$ is substituted with 3 $Z^{2b}$ or $Z^{2c}$ groups, wherein the $Z^{2b}$ and $Z^{2c}$ groups may be the same or different.

In certain embodiments of formula III, $Z^2$ is substituted with 1, 2, 3, or 4 $Z^{2c}$ groups, wherein the $Z^{2c}$ groups may be the same or different. In certain embodiments, $Z^2$ is substituted with 1, 2, or 3 $Z^{2c}$ groups, wherein the $Z^{2c}$ groups may be the same or different. In certain embodiments, $Z^2$ is substituted with 1 or 2 $Z^{2c}$ groups, wherein the $Z^{2c}$ groups may be the same or different. In certain embodiments, $Z^2$ is substituted with 1 $Z^{2c}$ group.

In certain embodiments of formula III, $Z^2$ is optionally substituted with 1, 2, or 3 $Z^{2c}$ groups, wherein the $Z^{2c}$ groups may be the same or different. In certain embodiments, $Z^2$ is substituted with 1 $Z^{2c}$ group. In certain embodiments, $Z^2$ is substituted with 2 $Z^{2c}$ groups, wherein the $Z^{2c}$ groups may be the same or different. In certain embodiments, $Z^2$ is substituted with 3 $Z^{2c}$ groups, wherein the $Z^{2c}$ groups may be the same or different.

In certain embodiments, each $Z^{2c}$ is independently halogen, —$OR^{n4}$, $NR^{q4}R^{r4}$, $NR^{n4}CO_2R^{p4}$, —$C(O)OR^{n4}$, or —$C(O)NR^{q4}R^{r4}$. In certain embodiments, each $Z^{2c}$ is independently halogen or —$OR^{n4}$.

In certain embodiments, $Z^2$ optionally substituted with 1, 2, 3, 4, or 5 $Z^{2b}$ or $Z^{2c}$ groups is

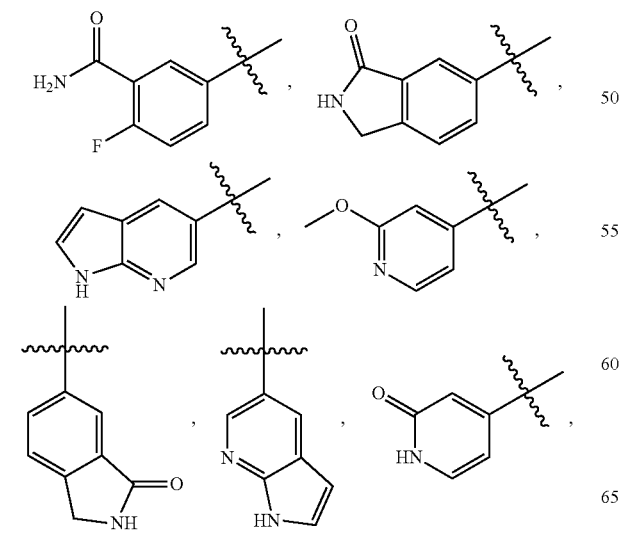

-continued

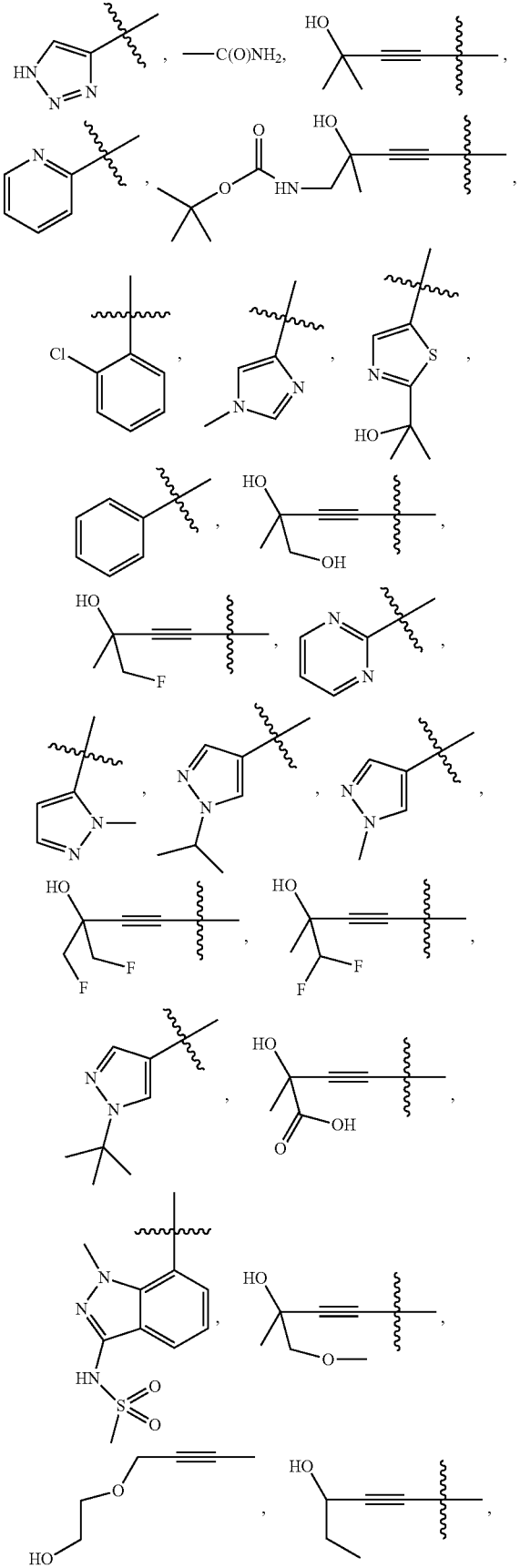

-continued
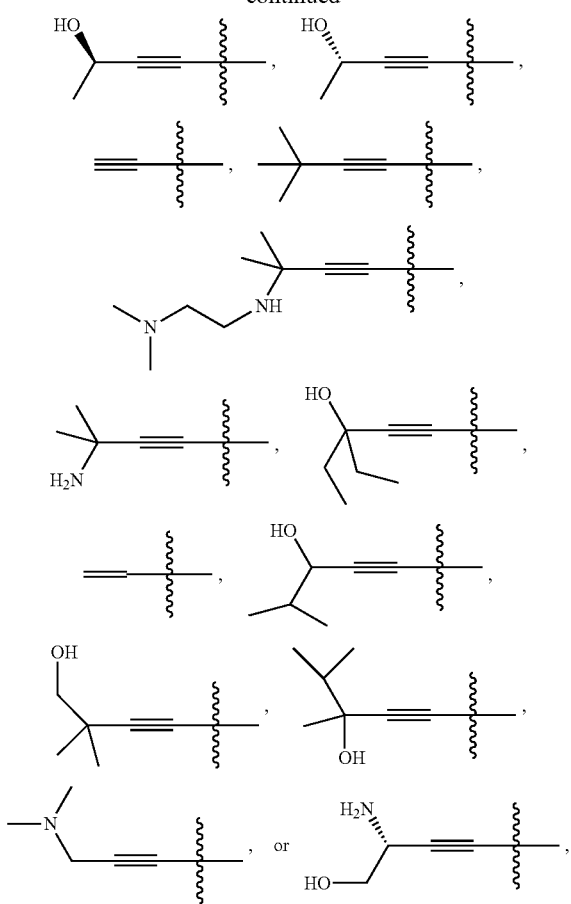
In certain embodiments, $Z^2$ optionally substituted with 1, 2, 3, 4, or 5 $Z^{2b}$ or $Z^{2c}$ groups is
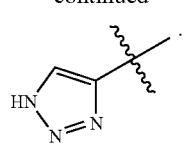
In certain embodiments, $Z^2$ optionally substituted with 1, 2, 3, 4, or 5 $Z^{2b}$ or $Z^{2c}$ groups is
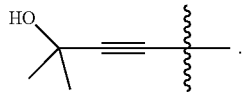
In certain embodiments, $Z^2$ optionally substituted with 1, 2, 3, 4, or 5 $Z^{2b}$ or $Z^{2c}$ groups is
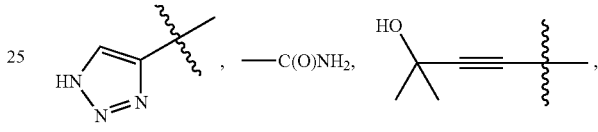
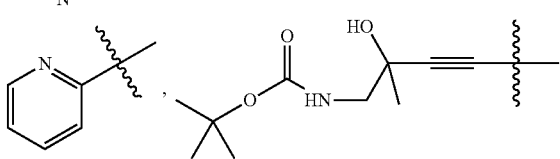
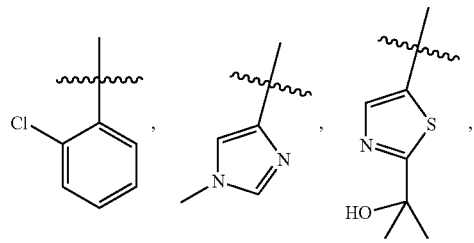
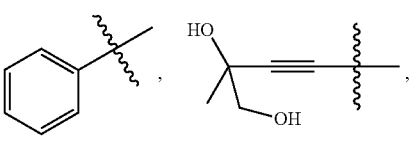
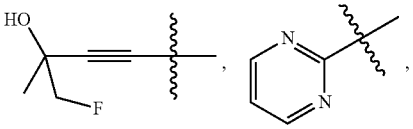
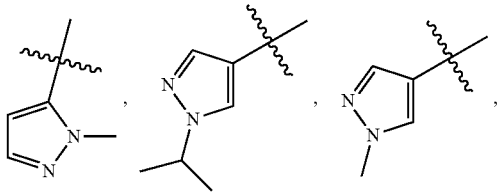
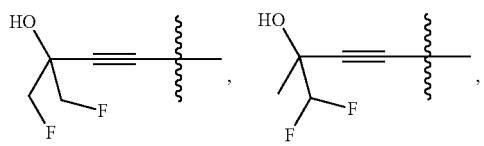
In certain embodiments, $Z^2$ optionally substituted with 1, 2, 3, 4, or 5 $Z^{2b}$ or $Z^{2c}$ groups is
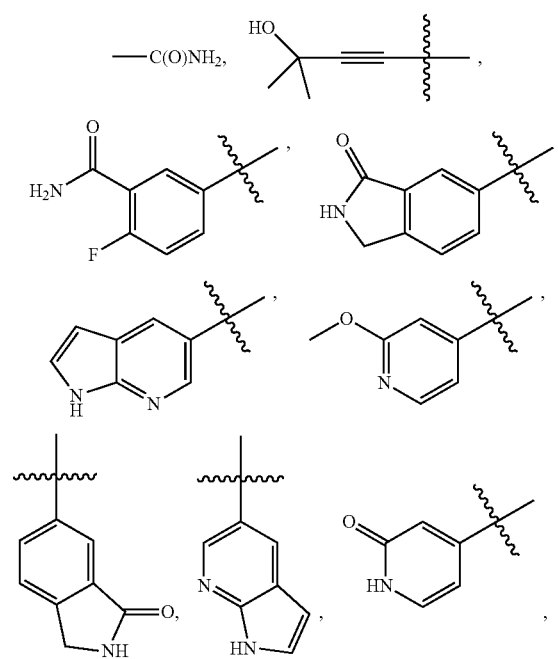
, or

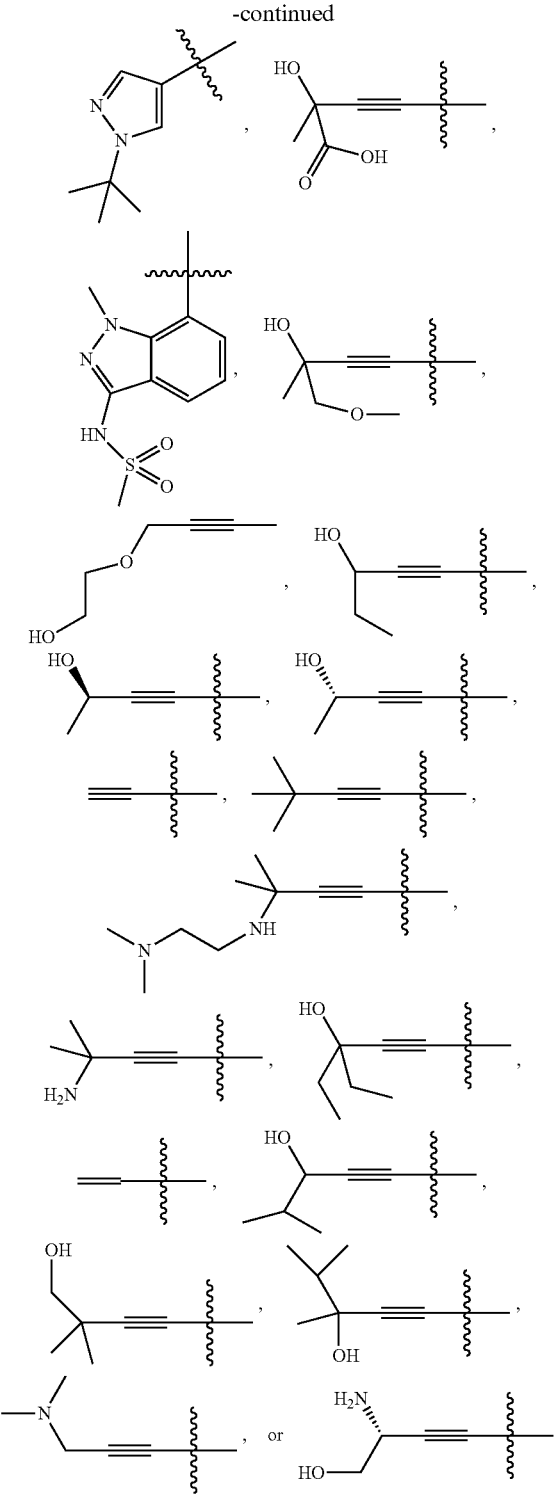
In certain embodiments, $Z^2$ optionally substituted with 1, 2, 3, 4, or 5 $Z^{2b}$ or $Z^{2c}$ groups is
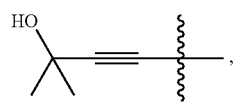
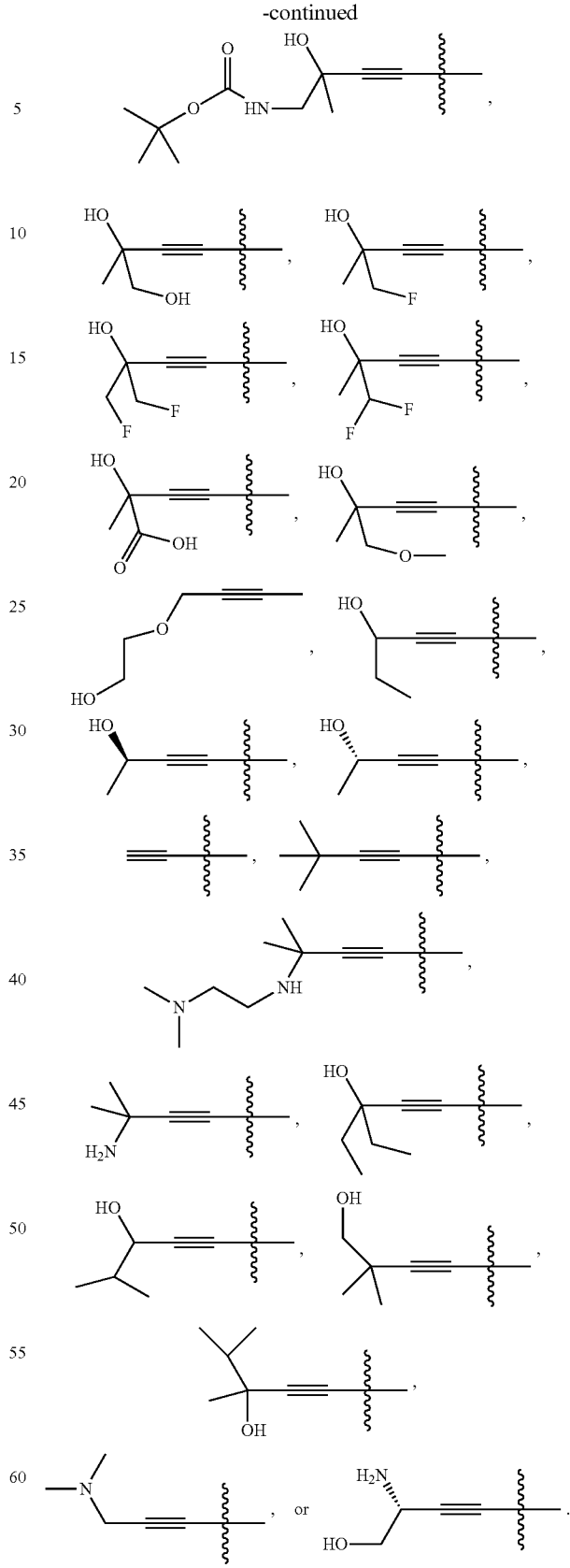
In certain embodiments, $Z^2$ optionally substituted with 1, 2, 3, 4, or 5 $Z^{2b}$ or $Z^{2c}$ groups is

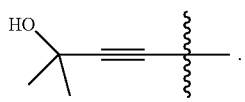

In certain embodiments of formula III, $R^1$ is a 5-12 membered heteroaryl, wherein any 5-12 membered heteroaryl of $R^1$ is optionally substituted with 1, 2, 3, 4, or 5 $Z^4$ groups.

In certain embodiments of formula III, $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups.

In certain embodiments, $R^1$ is a 8-12 membered tricyclic-heteroaryl, wherein the 8-12 membered tricyclic-heteroaryl of $R^1$ is optionally substituted with 1, 2, 3, 4, or 5 $Z^4$ groups.

In certain embodiments, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl have 4-10 carbon atoms and 1-5 heteroatoms in the ring system, and wherein any 8-12 membered bicyclic-heteroaryl or 8-12 membered tricyclic-heteroaryl of $R^1$ is optionally substituted with 1, 2, 3, 4, or 5 $Z^4$ groups.

In certain embodiments, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl contains at least one partially unsaturated ring, and wherein any 8-12 membered bicyclic-heteroaryl or 8-12 membered tricyclic-heteroaryl of $R^1$ is optionally substituted with 1, 2, 3, 4 or 5 $Z^4$ groups.

In certain embodiments, $R^1$ is a 8-12 membered tricyclic-heteroaryl, wherein the 8-12 membered tricyclic-heteroaryl contains at least one partially unsaturated ring, and wherein any 8-12 membered bicyclic-heteroaryl or 8-12 membered tricyclic-heteroaryl of $R^1$ is optionally substituted with 1, 2, 3, 4 or 5 $Z^4$ groups.

In certain embodiments of formula III, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl has 4-9 carbon atoms and 1-5 heteroatoms in the ring system, and wherein any 8-12 membered bicyclic-heteroaryl or 8-12 membered tricyclic-heteroaryl of $R^1$ is optionally substituted with 1, 2, 3, 4 or 5 $Z^4$ groups.

In certain embodiments, $R^1$ is a 8-12 membered bicyclic-heteroaryl, wherein the 8-12 membered bicyclic-heteroaryl has 6-9 carbon atoms and 1-3 heteroatoms in the ring system, and wherein any 8-12 membered bicyclic-heteroaryl of $R^1$ is optionally substituted with 1, 2, 3, 4 or 5 $Z^4$ groups.

In certain embodiments, $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl has 6-9 carbon atoms and 1-3 heteroatoms in the ring system, and wherein any 8-12 membered bicyclic-heteroaryl or 8-12 membered tricyclic-heteroaryl of $R^1$ is optionally substituted with 1, 2, 3, 4 or 5 $Z^4$ groups.

In certain embodiments of formula III, $R^1$ has the following formula IIa:

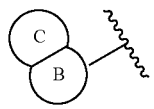

IIa wherein:

C together with the two carbon atoms of ring B to which it is attached forms a 3-7 membered monocyclic-carbocycle, 5-8 membered bicyclic-carbocycle, 3-7 membered monocyclic-heterocycle, or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with 1, 2, 3, 4 or 5 $Z^4$ groups, wherein the $Z^4$ groups are the same or different; and B is a 5 or 6 membered monocyclic-heteroaryl with 1, 2 or 3 nitrogen atoms, wherein B is optionally substituted with 1, 2, 3, 4 or 5 $Z^4$ groups, wherein the $Z^4$ groups are the same or different.

In certain embodiments of formula III, $R^1$ has the following formula IIb:

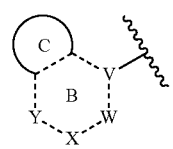

IIb wherein:

C together with the two carbon atoms of ring B to which it is attached forms a 3-7 membered monocyclic-carbocycle, 5-8 membered bicyclic-carbocycle, 3-7 membered monocyclic-heterocycle, or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with 1, 2, 3, 4 or 5 $Z^4$ groups, wherein the $Z^4$ groups are the same or different; and B is a 5 or 6 membered monocyclic-heteroaryl having 1, 2 or 3 nitrogen atoms;

V is C or N;

W is $CZ^{4c}$, $NZ^{4c}$ or N;

X is $CZ^{4c}$, $NZ^{4c}$ or N;

Y is $CZ^{4c}$, N or absent;

the dashed bonds are selected from single bonds and double bonds, wherein the dashed bonds, V, W, X and Y are selected so that the 5 or 6 membered monocyclic-heteroaryl B is aromatic; and each $Z^{4c}$ is independently selected from H or $Z^4$, wherein the $Z^4$ groups are the same or different.

In certain embodiments of formula III, $R^1$ has the following formula IIc:

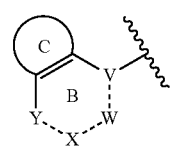

IIc wherein:

C together with the two carbon atoms of ring B to which it is attached forms a 3-7 membered monocyclic-carbocycle, 5-8 membered bicyclic-carbocycle, 3-7 membered monocyclic-heterocycle, or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with 1, 2, 3, 4 or 5 $Z^4$ groups, wherein the $Z^4$ groups are the same or different; and B is a 5 or 6 membered monocyclic-heteroaryl having 1, 2 or 3 nitrogen atoms;

V is C or N;

W is $CZ^{4c}$ or N;

X is $CZ^{4c}$, $NZ^{4c}$ or N;

Y is $CZ^{4c}$, N or absent;

the dashed bonds are selected from single bonds and double bonds, wherein the dashed bonds, V, W, X and Y are selected so that the 5 or 6 membered monocyclic-heteroaryl B is aromatic; and each $Z^{4c}$ is independently selected from H or $Z^4$, wherein the $Z^4$ groups are the same or different.

In certain embodiments of formula III, $R^1$ has the following formula IId:

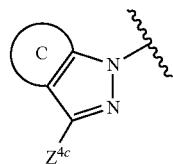

IId wherein:

C together with the two carbon atoms to which it is attached forms a 3-7 membered monocyclic-carbocycle, 5-9 membered bicyclic-carbocycle, 3-7 membered monocyclic-heterocycle, or 5-9 membered bicyclic heterocycle, wherein any 3-7 membered monocyclic-carbocycle, 5-9 membered bicyclic-carbocycle, 3-7 membered monocyclic-heterocycle or 5-9 membered bicyclic heterocycle of C is optionally substituted with 1, 2, 3, 4 or 5 $Z^4$ groups, wherein the $Z^4$ groups are the same or different; and each $Z^{4c}$ is independently selected from H or $Z^4$, wherein the $Z^4$ groups are the same or different.

In certain embodiments of formula III, $R^1$ has the following formula:

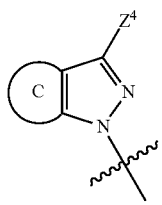

wherein:

C together with the two carbon atoms to which it is attached forms a 3-7 membered monocyclic-carbocycle or 5-9 membered bicyclic-carbocycle, wherein any 3-7 membered monocyclic-carbocycle or 5-9 membered bicyclic-carbocycle of C is optionally substituted with 1, 2, 3, 4 or 5 $Z^4$ groups, wherein the $Z^4$ groups are the same or different.

In certain embodiments of formula III, $R^1$ has the following formula:

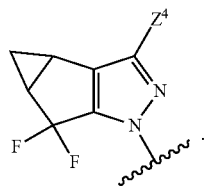

In certain embodiments of formula III, C together with the two carbon atoms to which it is attached forms a 5-7 membered monocyclic-carbocycle or 5-7 membered bicyclic-carbocycle, wherein any 5-7 membered monocyclic-carbocycle or 5-7 membered bicyclic-carbocycle of C is optionally substituted with 1, 2, 3, or 4 $Z^4$ groups, wherein the $Z^4$ groups are the same or different.

In certain embodiments of formula III, each $Z^4$ is independently $(C_1-C_8)$alkyl, $(C_3-C_7)$carbocycle, halogen, —CN, —$NR^{q5}R^{r5}$, —$NR^{n5}COR^{p5}$, —$NR^{n5}CO_2R^{p5}$, —$C(O)OR^{n5}$, or —$C(O)NR^{q5}R^{r5}$, wherein any $(C_3-C_7)$carbocycle or $(C_1-C_8)$alkyl of $Z^4$ is optionally substituted with 1, 2, 3, 4 or 5 $Z^{4a}$ groups.

In certain embodiments, each $Z^4$ is independently $(C_1-C_6)$alkyl or halogen, wherein any $(C_1-C_6)$alkyl of $Z^4$ is optionally substituted with 1, 2, 3, 4 or 5 halogen, which may be the same or different. In certain embodiments, each $Z^4$ is independently $(C_1-C_4)$alkyl or halogen, wherein any $(C_1-C_6)$alkyl of $Z^4$ is optionally substituted with 1, 2, 3, 4 or 5 halogen, which may be the same or different. In certain embodiments, each $Z^4$ is independently $(C_1-C_3)$alkyl or halogen, wherein any $(C_1-C_3)$alkyl of $Z^4$ is optionally substituted with 1, 2, 3, 4 or 5 halogen, which may be the same or different.

In certain embodiments, each $Z^4$ is independently fluoro, trifluoromethyl, or difluoromethyl.

In certain embodiments of formula III, $R^1$ optionally substituted with 1, 2, 3, 4, or 5 $Z^4$ groups is

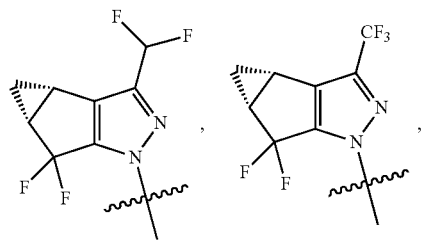

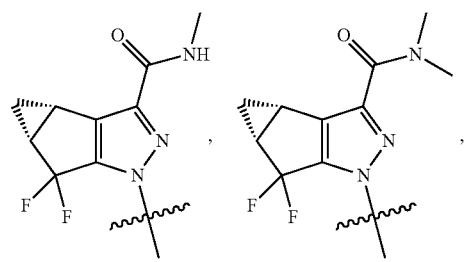

-continued
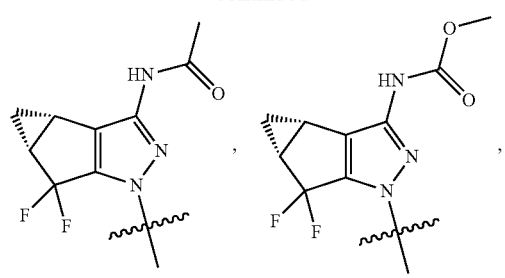
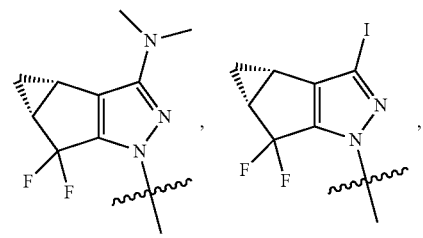
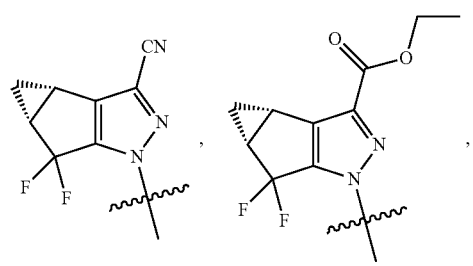
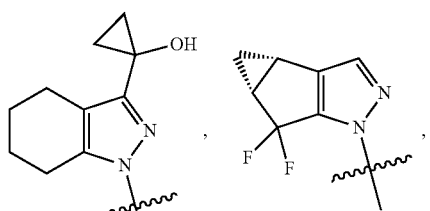
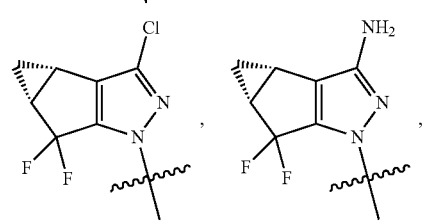
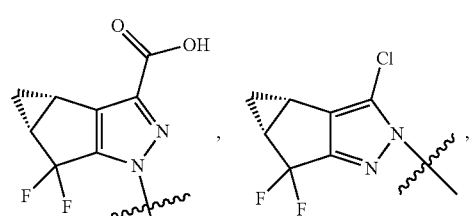
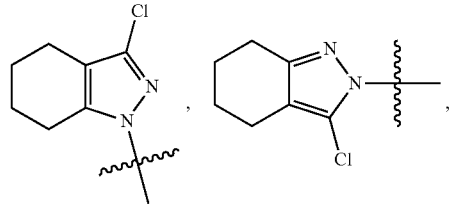
-continued
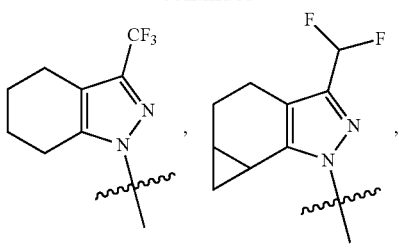
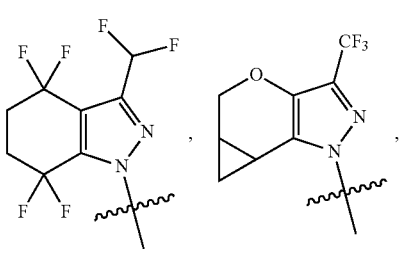
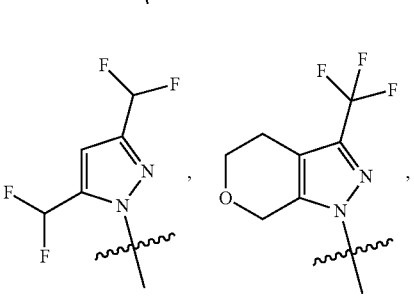
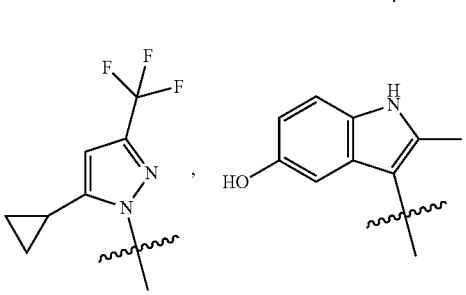
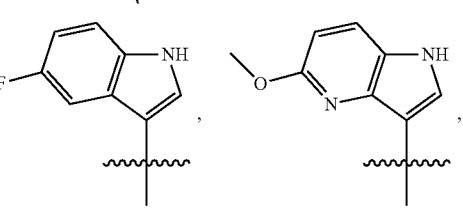
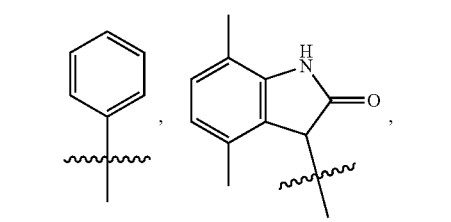
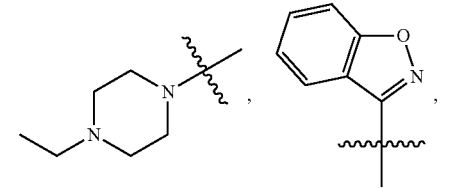

-continued

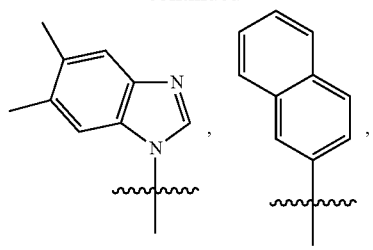,

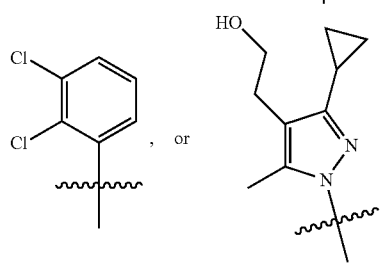.

In certain embodiments, $R^1$ optionally substituted with 1, 2, 3, 4, or 5 $Z^4$ groups is

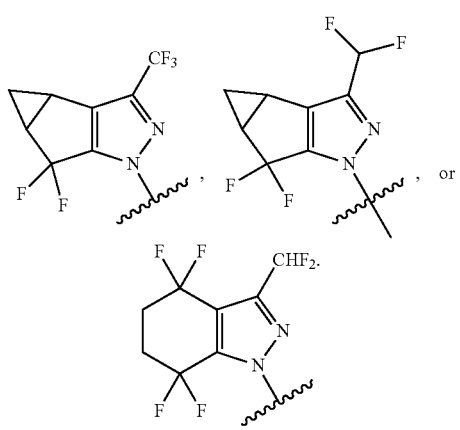

In certain embodiments, $R^1$ optionally substituted with 1, 2, 3, 4, or 5 $Z^4$ groups is

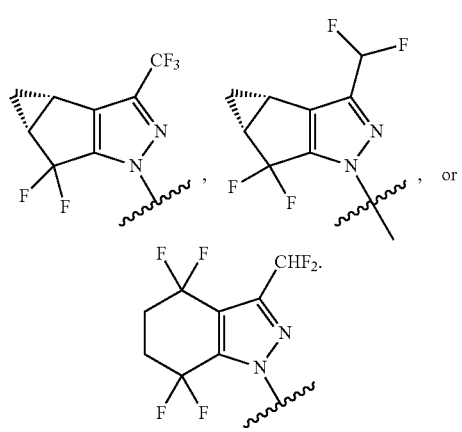

In certain embodiments, $R^1$ optionally substituted with 1, 2, 3, 4, or 5 $Z^4$ groups is

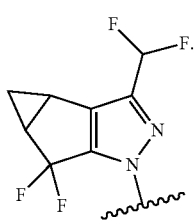 [SMILES: *n1nc(C(F)F)c2c1C(F)(F)C1CC21]

In certain embodiments, $R^1$ optionally substituted with 1, 2, 3, 4, or 5 $Z^4$ groups is

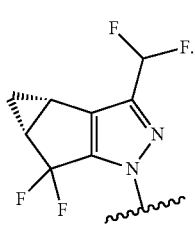 [SMILES: *n1nc(C(F)F)c2c1C(F)(F)[C@@H]1C[C@H]21]

In certain embodiments, $R^1$ optionally substituted with 1, 2, 3, 4, or 5 $Z^4$ groups is

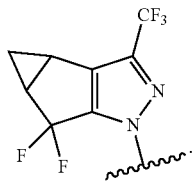 [SMILES: *n1nc(C(F)(F)F)c2c1C(F)(F)C1CC21]

In certain embodiments, $R^1$ optionally substituted with 1, 2, 3, 4, or 5 $Z^4$ groups is

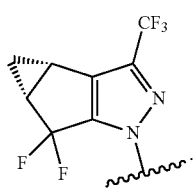

In certain embodiments, $R^1$ optionally substituted with 1, 2, 3, 4, or 5 $Z^4$ groups is

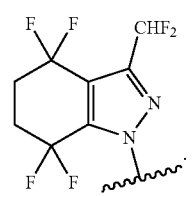 [SMILES: *n1nc(C(F)F)c2c1C(F)(F)CCC2(F)F]

In certain embodiments, $R^1$ is

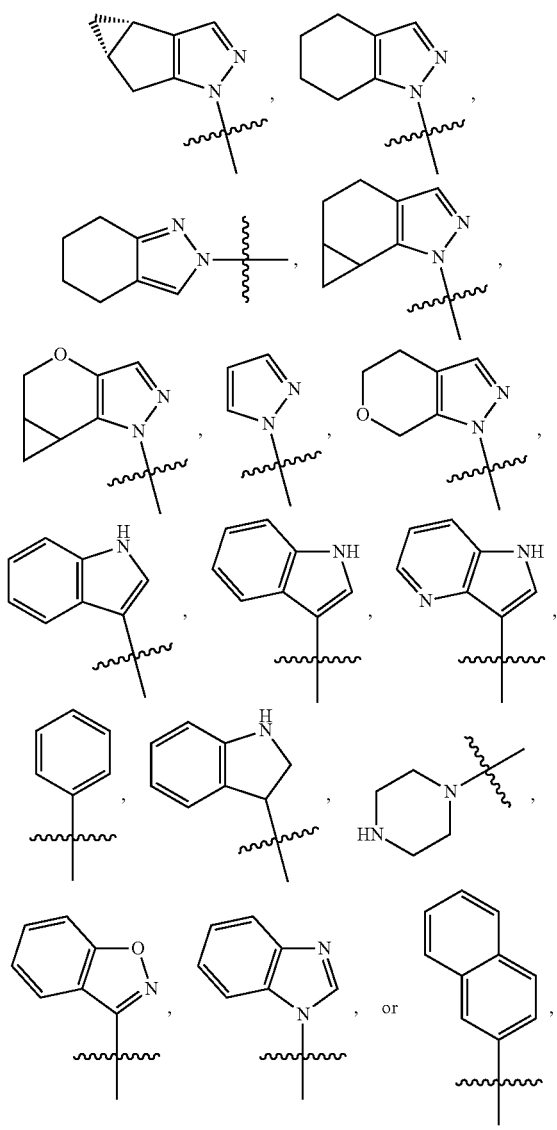

optionally substituted with 1, 2, 3, 4 or 5 $Z^4$ groups.

In certain embodiments, $R^1$ is

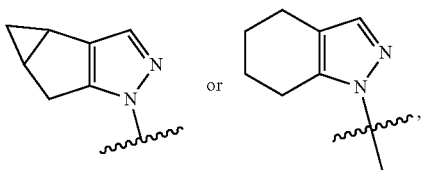 [SMILES: *n1ncc2c1CC1CC21 ; *n1ncc2c1CCCC2]

optionally substituted with 1, 2, 3, 4 or 5 $Z^4$ groups.

In certain embodiments of formula III, each $Z^4$ is independently $(C_1-C_6)$alkyl or halogen, wherein any $(C_1-C_6)$ alkyl of $Z^4$ is optionally substituted with 1, 2, 3, 4 or 5 halogen, which may be the same or different.

In certain embodiments, each $Z^4$ is independently $(C_1-C_6)$alkyl, —CN, or halogen, wherein any $(C_1-C_6)$alkyl of $Z^4$ is optionally substituted with 1, 2, 3, 4 or 5 halogen, which may the same or different.

In certain embodiments, each $Z^4$ is independently fluoro, trifluoromethyl, or difluoromethyl.

In certain embodiments, each $Z^4$ is independently fluoro, trifluoromethyl, —CN, or difluoromethyl.

In certain embodiments of Formula III, $Z^1$ is phenyl, 5-14 membered heteroaryl, or 3-14 membered heterocycle, wherein any phenyl, 5-14 membered heteroaryl, or 3-14 membered heterocycle of $Z^1$ is optionally substituted with 1, 2, 3, 4 or 5 $Z^{1a}$ or $Z^{1b}$ groups.

In certain embodiments, $Z^1$ is phenyl, 5-12 membered heteroaryl, or 3-12 membered heterocycle, wherein any phenyl, 5-12 membered heteroaryl, or 3-12 membered heterocycle of $Z^1$ is optionally substituted with 1, 2, 3, 4 or 5 $Z^{1a}$ or $Z^{1b}$ groups.

In certain embodiments, $Z^1$ is phenyl, 5-14 membered heteroaryl, or 3-14 membered heterocycle, wherein any phenyl, 5-14 membered heteroaryl, or 3-14 membered heterocycle of $Z^1$ is optionally substituted with 1, 2, 3, 4 or 5 $Z^{1a}$ groups.

In certain embodiments, $Z^1$ is phenyl, 5-12 membered heteroaryl, or 3-12 membered heterocycle, wherein any phenyl, 5-12 membered heteroaryl, or 3-12 membered heterocycle of $Z^1$ is optionally substituted with 1, 2, 3, 4 or 5 $Z^{1a}$ groups.

In certain embodiments, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ or $Z^{1b}$ groups.

In certain embodiments, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups.

In certain embodiments, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle, wherein the 5-6 membered monocyclic-heteroaryl, 8-10 membered bicyclic-heteroaryl, 8-10 membered bicyclic-heterocycle, or 9-12 membered tricyclic-heterocycle have 1-11 carbon atoms and 1-5 heteroatoms in the ring system, and wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ or $Z^{1b}$ groups.

In certain embodiments, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle, wherein the 5-6 membered monocyclic-heteroaryl, 8-10 membered bicyclic-heteroaryl, 8-10 membered bicyclic-heterocycle, or 9-12 membered tricyclic-heterocycle have 1-11 carbon atoms and 1-5 heteroatoms in the ring system, and wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups.

In certain embodiments, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle, wherein the 5-6 membered monocyclic-heteroaryl, 8-10 membered bicyclic-heteroaryl, 8-10 membered bicyclic-heterocycle, or 9-12 membered tricyclic-heterocycle have 4-11 carbon atoms and 1-3 heteroatoms in the ring system, and wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ or $Z^{1b}$ groups.

In certain embodiments, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle, wherein the 5-6 membered monocyclic-heteroaryl, 8-10 membered bicyclic-heteroaryl, 8-10 membered bicyclic-heterocycle, or 9-12 membered tricyclic-heterocycle have 4-11 carbon atoms and 1-3 heteroatoms in the ring system, and wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups.

In certain embodiments, $Z^1$ is 8-10 membered bicyclic-heteroaryl or 8-10 membered bicyclic-heterocycle, wherein any from 8-10 membered bicyclic-heteroaryl or 8-10 membered bicyclic-heterocycle of $Z^1$ is optionally substituted with 1, 2, 3, 4 or 5 $Z^{1a}$ or $Z^{1b}$ groups.

In certain embodiments, $Z^1$ is 8-10 membered bicyclic-heteroaryl or 8-10 membered bicyclic-heterocycle, wherein any from 8-10 membered bicyclic-heteroaryl or 8-10 membered bicyclic-heterocycle of $Z^1$ is optionally substituted with 1, 2, 3, 4 or 5 $Z^{1a}$ groups.

In certain embodiments, $Z^1$ is 8-10 membered bicyclic-heteroaryl or 8-10 membered bicyclic-heterocycle, wherein the 8-10 membered bicyclic-heteroaryl or 8-10 membered bicyclic-heterocycle has 3-9 carbon atoms and 1-5 heteroatoms in the ring system, and wherein any 8-10 membered bicyclic-heteroaryl or 8-10 membered bicyclic-heterocycle of $Z^1$ is optionally substituted with 1, 2, 3, 4 or 5 $Z^{1a}$ or $Z^{1b}$ groups.

In certain embodiments, $Z^1$ is 8-10 membered bicyclic-heteroaryl or 8-10 membered bicyclic-heterocycle, wherein the 8-10 membered bicyclic-heteroaryl or 8-10 membered bicyclic-heterocycle has 3-9 carbon atoms and 1-5 heteroatoms in the ring system, and wherein any 8-10 membered bicyclic-heteroaryl or 8-10 membered bicyclic-heterocycle of $Z^1$ is optionally substituted with 1, 2, 3, 4 or 5 $Z^{1a}$ groups.

In certain embodiments of formula III, $Z^1$ is not substituted with $Z^{1b}$.

In certain embodiments of formula III, each $Z^{1a}$ is independently oxo, $(C_3-C_7)$carbocycle, halogen, —CN, —O—$(C_1-C_8)$alkyl, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$NR$^{q1}$R$^{r1}$, or —C(O)NR$^{q1}$R$^{r1}$.

In certain embodiments, each $Z^{1a}$ is independently —NR$^{n1}$S(O)$_2$R$^{p1}$, —NR$^{n1}$S(O)$_2$NR$^{q1}$R$^{r1}$, or halogen. In certain embodiments, each $Z^{1a}$ is independently halogen or —NR$^{n1}$S(O)$_2$R$^{p1}$. In certain embodiments, each $Z^{1a}$ is independently halogen or —NR$^{n1}$S(O)$_2$NR$^{q1}$R$^{r1}$.

In certain embodiments, $Z^1$ is substituted with 2 $Z^{1a}$ groups, wherein each $Z^{1a}$ is independently —NR$^{n1}$S(O)$_2$R$^{p1}$, —NR$^{n1}$S(O)$_2$N$_R$R$^{r1}$, or halogen.

In certain embodiments, each $Z^{1a}$ is independently halogen or —NR$^{n1}$S(O)$_2$R$^{p1}$ and each $Z^{1b}$ is $(C_1-C_8)$alkyl, which may be same or different.

In certain embodiments, $Z^{1a}$ is —NR$^{n1}$S(O)$_2$R$^{p1}$ or —NR$^{n1}$S(O)$_2$NR$^{q1}$R$^{r1}$. In certain embodiments, $Z^{1a}$ is halogen. In certain embodiments, $Z^{1a}$ is —NR$^{q1}$R$^{r1}$, —NR$^{n1}$COR$^{p1}$, —NR$^{n1}$CO$_2$R$^{p1}$, or —NR$^{n1}$CONR$^{q1}$R$^{r1}$.

In certain embodiments, $Z^{1a}$ is halogen, —OR$^{n1}$, or —C(O)NR$^{q1}$R$^{r1}$.

In certain embodiments, $Z^{1a}$ is halogen or —C(O)NR$^{q1}$R$^{r1}$.

In certain embodiments, $Z^{1a}$ is halogen, —OH, or —C(O)NH$_2$.

In certain embodiments, $Z^{1a}$ is fluoro, —OH, or —C(O)NH$_2$.

In certain embodiments, each $Z^{1b}$ is $(C_1-C_8)$alkyl, which may be same or different.

In certain embodiments, each $Z^{1b}$ is independently methyl or difluoromethyl.

In certain embodiments of formula III, $Z^1$ is

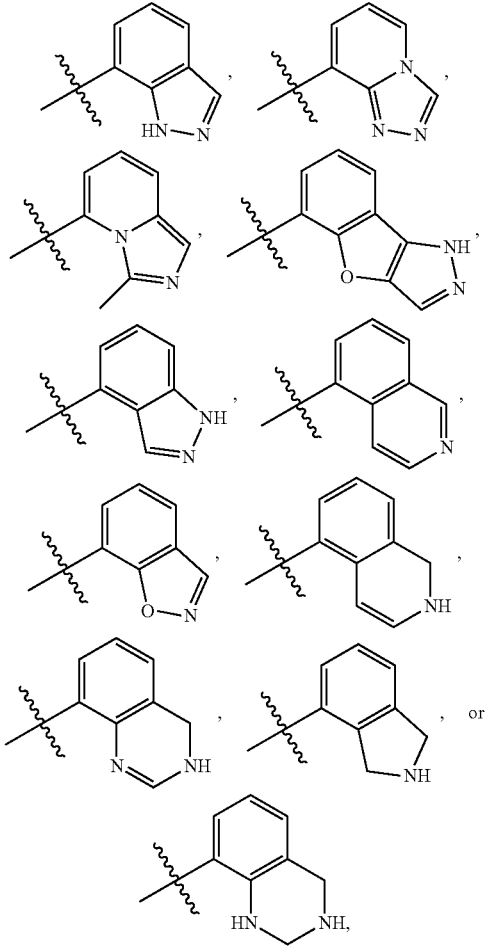

optionally substituted with 1, 2, 3, 4 or 5 $Z^{1a}$ or $Z^{1b}$.

In certain embodiments, $Z^1$ is

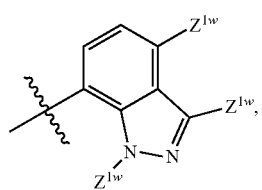

wherein each $Z^{1w}$ is independently $Z^{1a}$, $Z^{1b}$, or H. In certain embodiments, each $Z^{1a}$ is independently halogen, —CN, —OR$^{n1}$, —NR$^{n1}$S(O)$_2$R$^{p1}$, —NR$^{n1}$S(O)$_2$NR$^{q1}$R$^{r1}$, —NR$^{q1}$R$^{r1}$, —NR$^{n1}$COR$^{p1}$, —NR$^{n1}$CONR$^{q1}$R$^{r1}$, or —NR$^{n1}$CO$_2$R$^{p1}$; each $Z^{1b}$ is independently (C$_1$-C$_8$alkyl), wherein the (C$_1$-C$_8$alkyl) is optionally substituted with 1, 2, or 3 halogen, which are the same or different; and at least one of $Z^{1w}$ is $Z^{1a}$ or $Z^{1b}$. In certain embodiments, at least two of $Z^{1w}$ are independently $Z^{1a}$. In certain embodiments, each $Z^{1a}$ is independently halogen, —NR$^{n1}$S(O)$_2$R$^{p1}$, or —NR$^{n1}$S(O)$_2$NR$^{q1}$R$^{r1}$.

In certain embodiments, $Z^1$ is

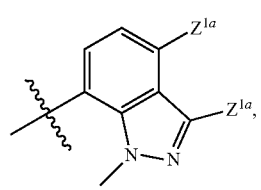

wherein each $Z^{1a}$ is independently halogen, —NR$^{n1}$S(O)$_2$R$^{p1}$ or —NR$^{n1}$S(O)$_2$NR$^{q1}$R$^{r1}$.

In certain embodiments, $Z^1$ is

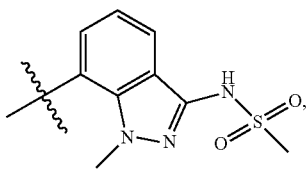 [SMILES: *c1cccc2c(NS(C)(=O)=O)nn(C)c12]

optionally substituted with 1, 2, 3, or 4 $Z^{1a}$ or $Z^{1b}$.

In certain embodiments, $Z^1$ is

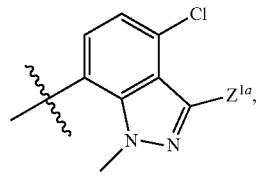

In certain embodiments, $Z^1$ optionally substituted with 1, 2, 3, 4, or 5 $Z^{1a}$ or $Z^{1b}$ groups is

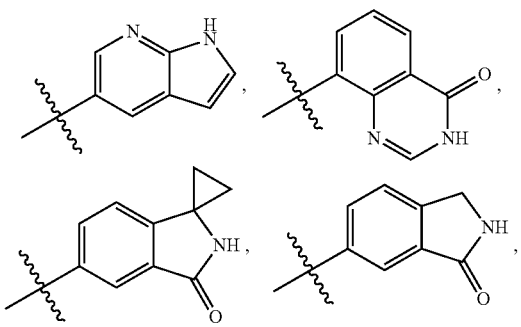

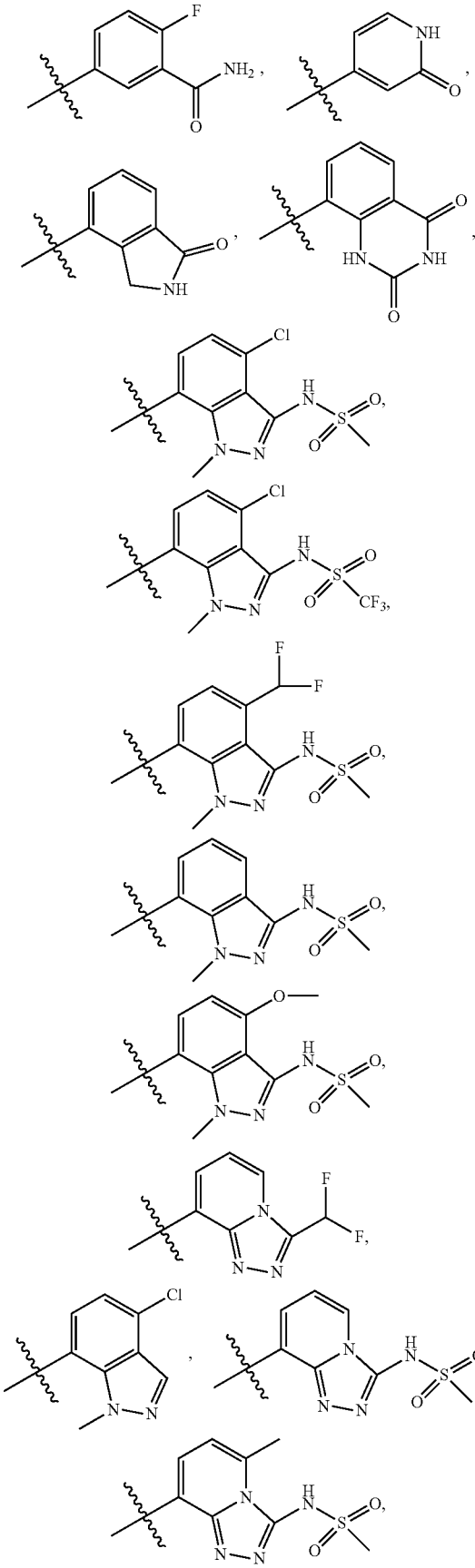

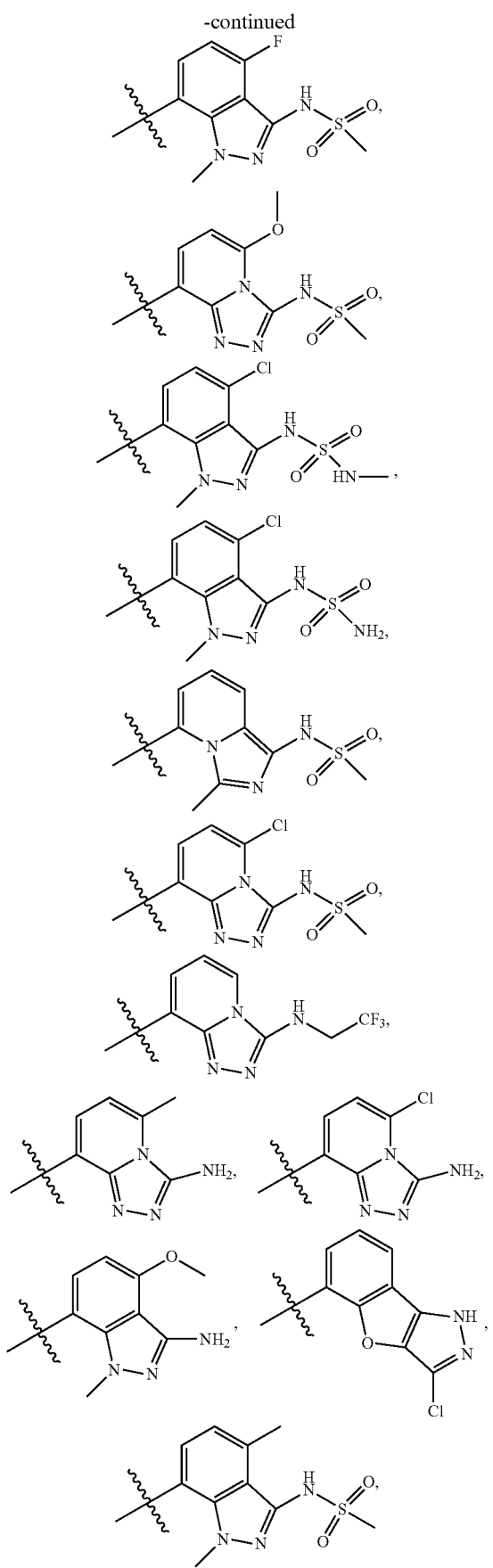
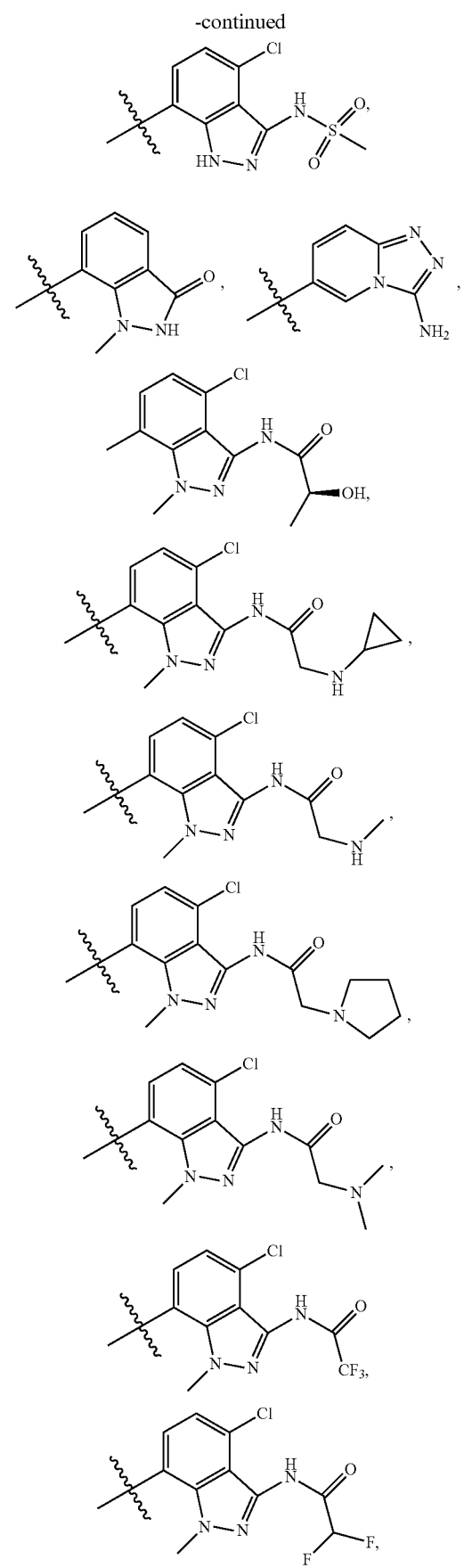

83
-continued
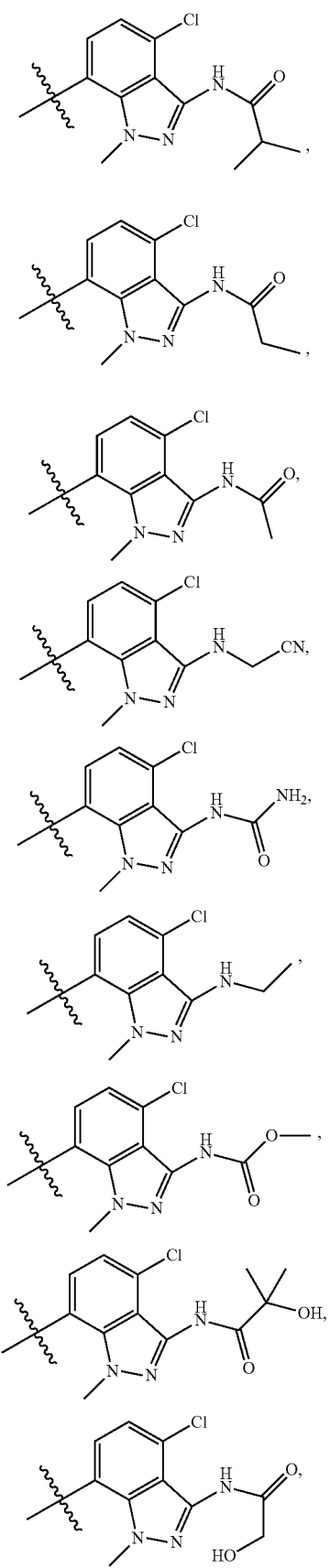
84
-continued
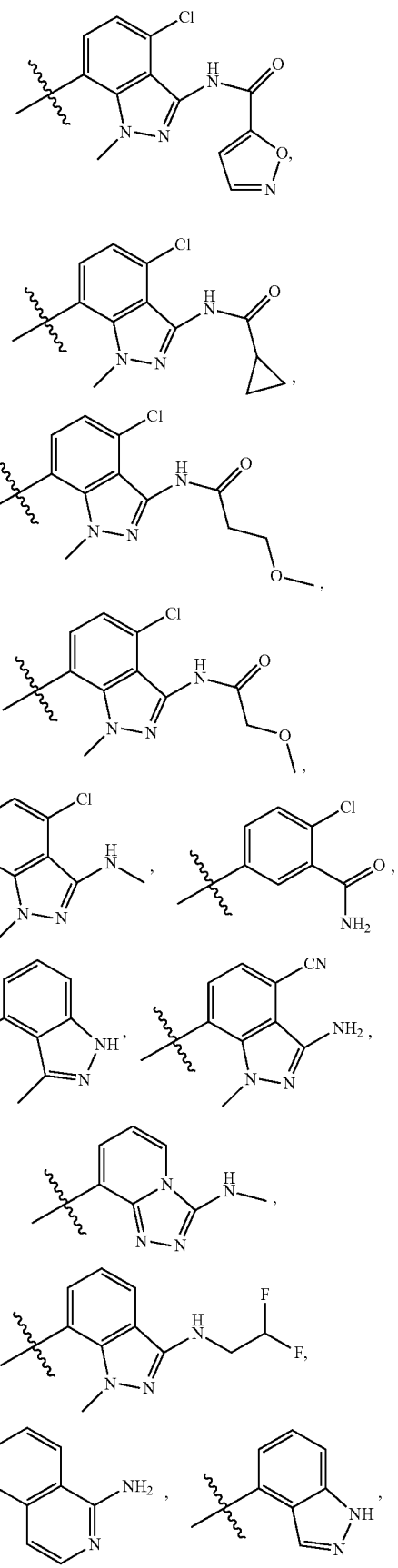

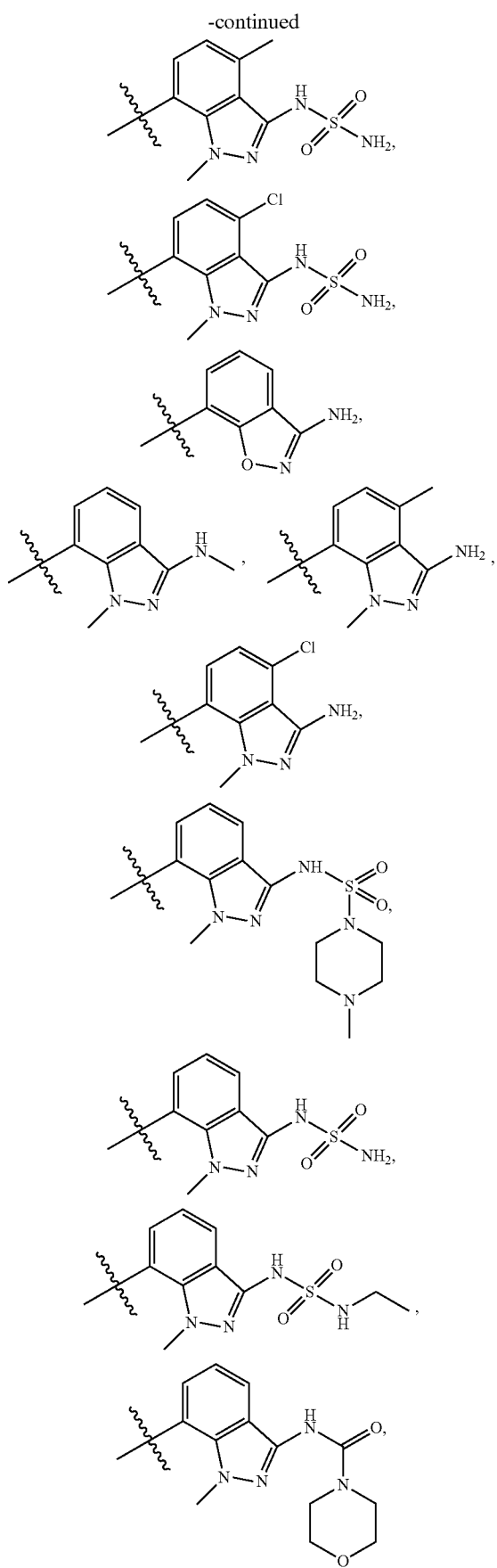
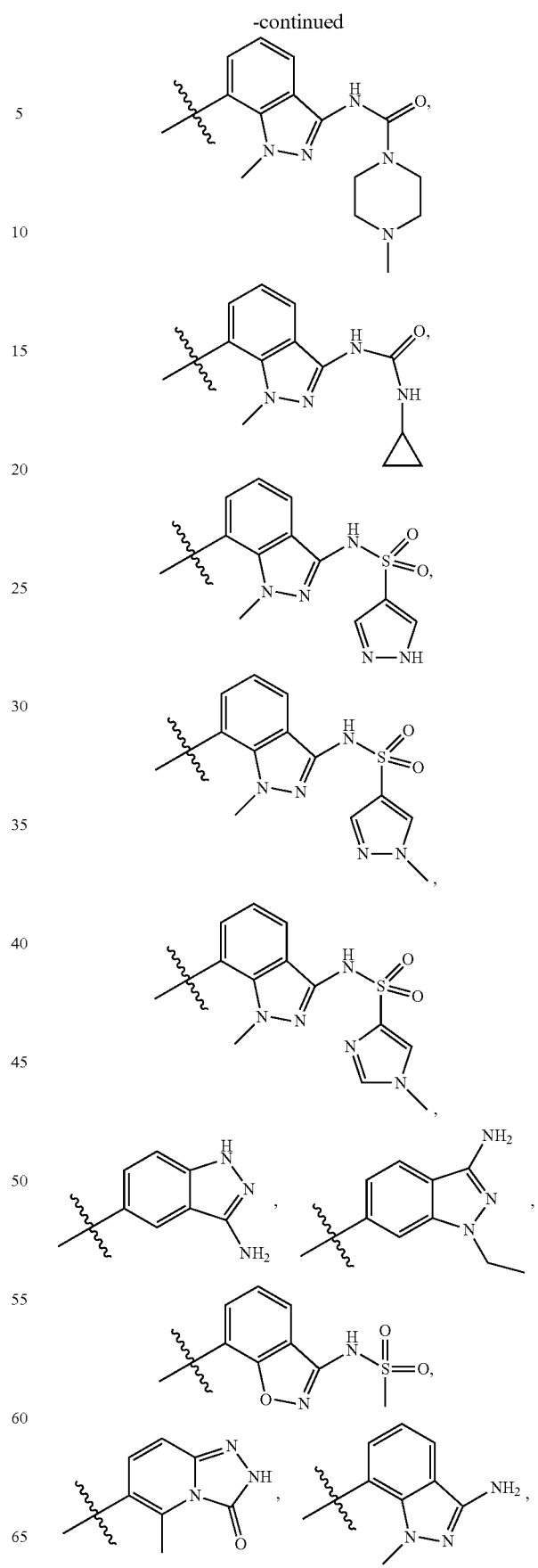

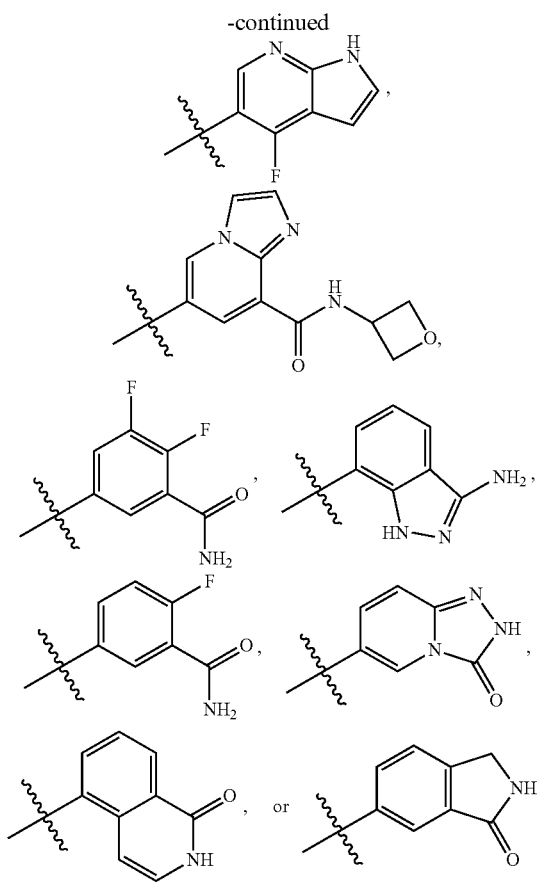
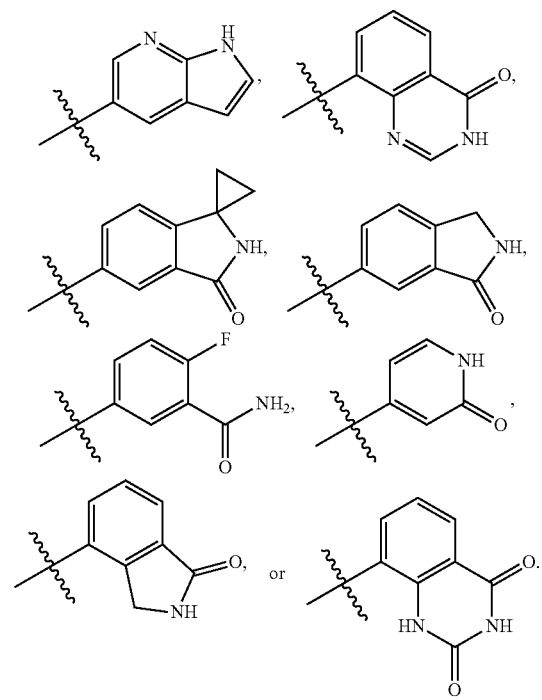
In certain embodiments, $Z^1$ optionally substituted with 1, 2, 3, 4, or 5 $Z^{1a}$ or $Z^{1b}$ groups is
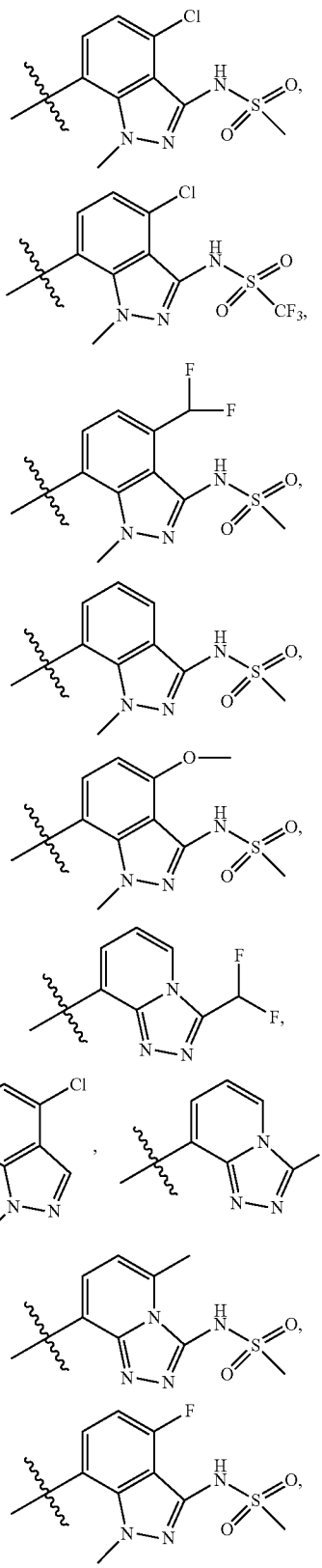

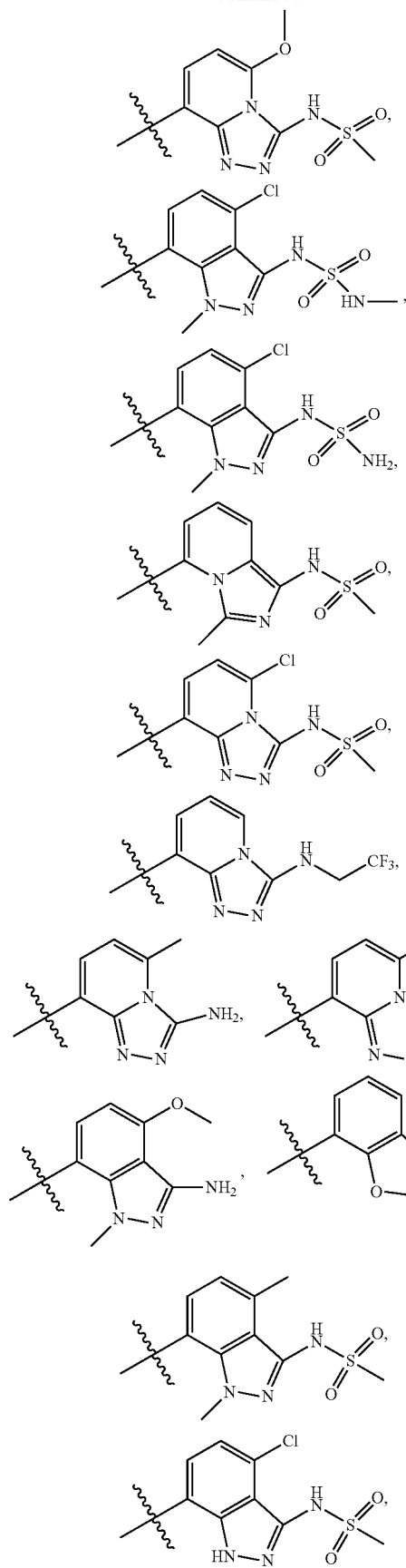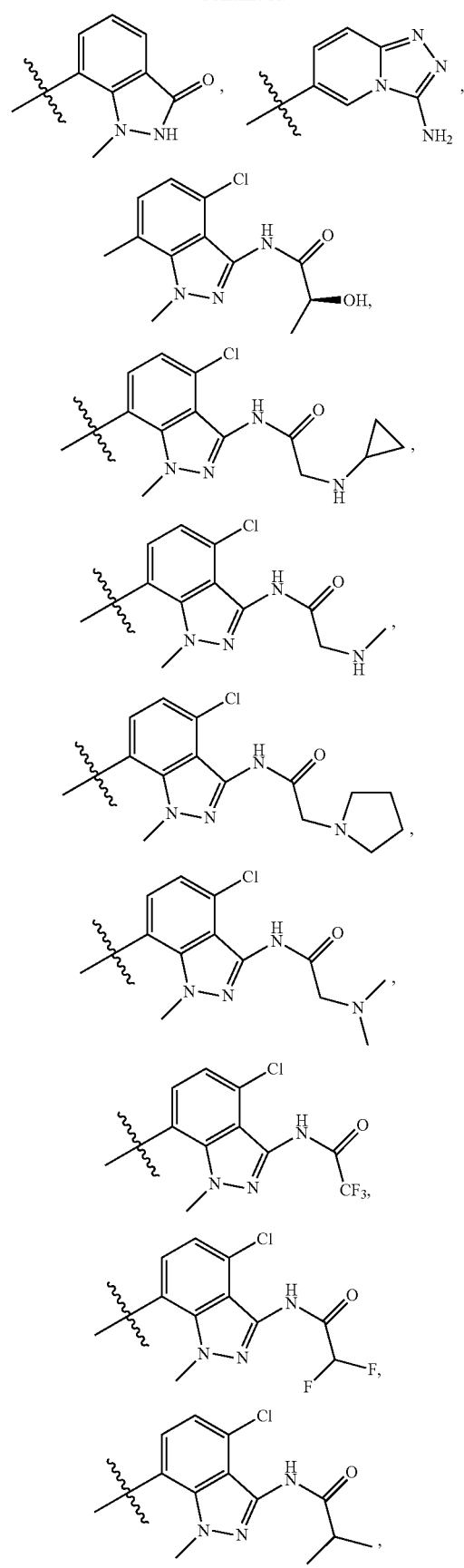

91
-continued
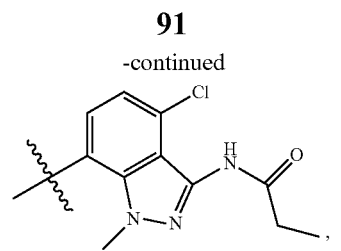
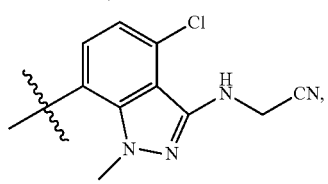
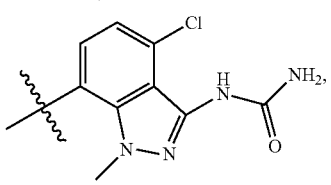
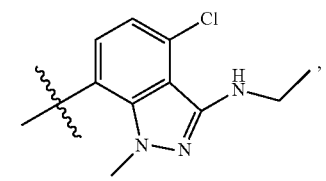
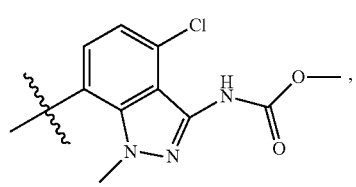
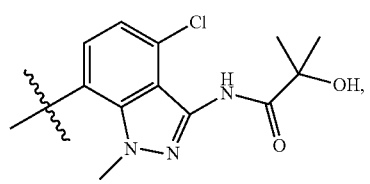
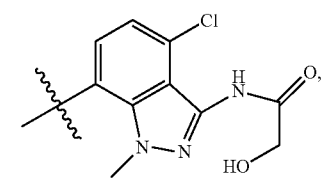
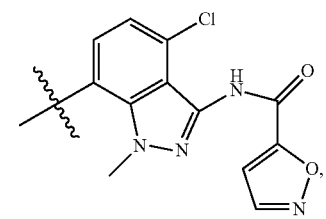
92
-continued
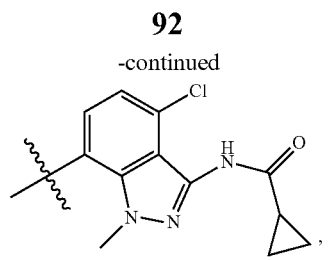
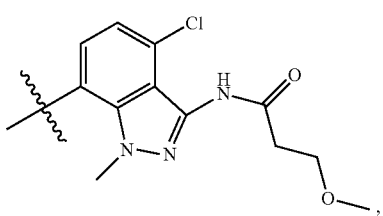
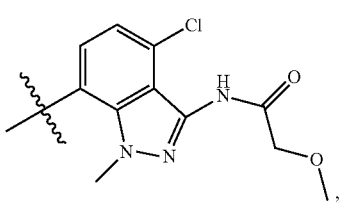
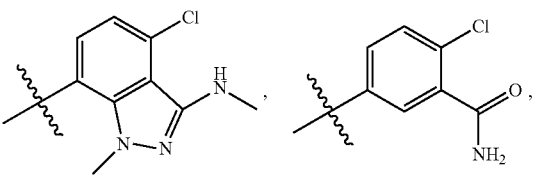
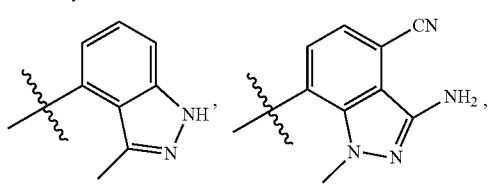
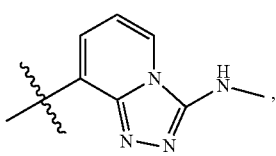
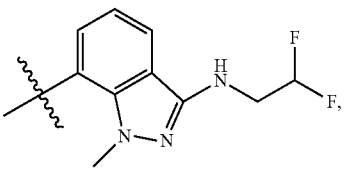
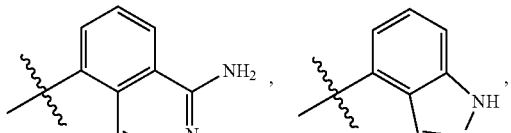
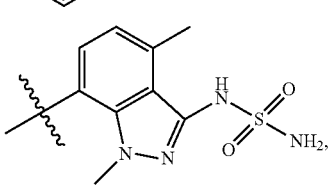

93
-continued
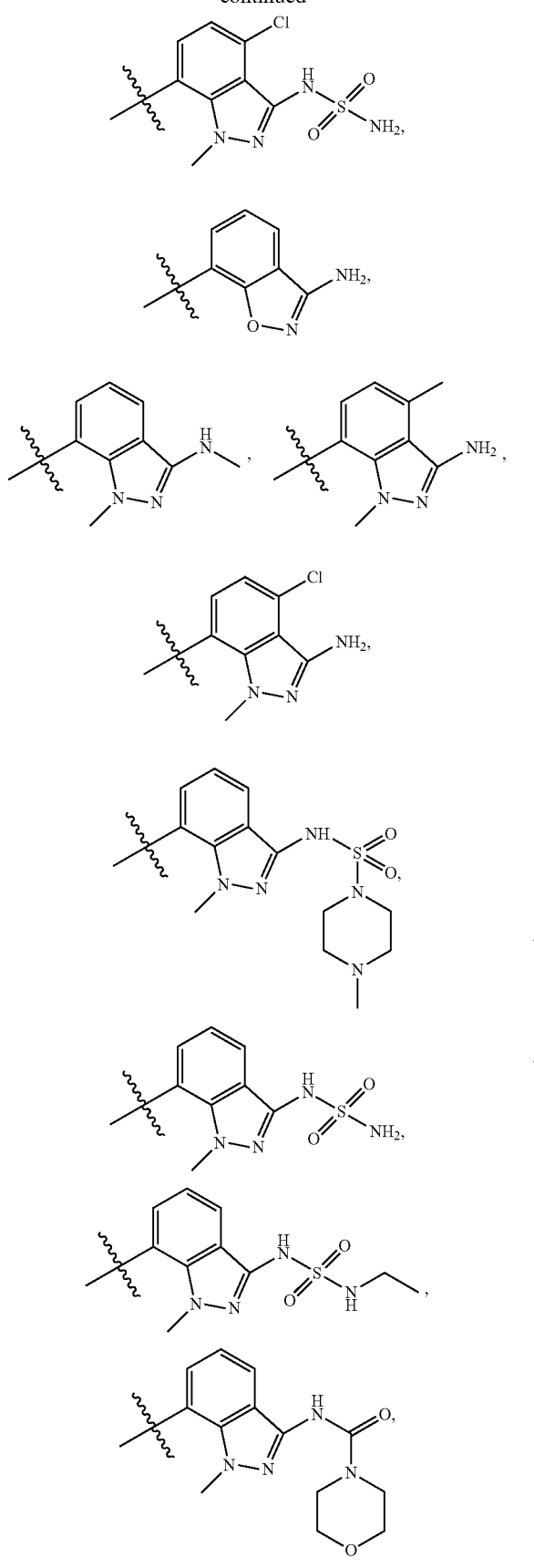
94
-continued
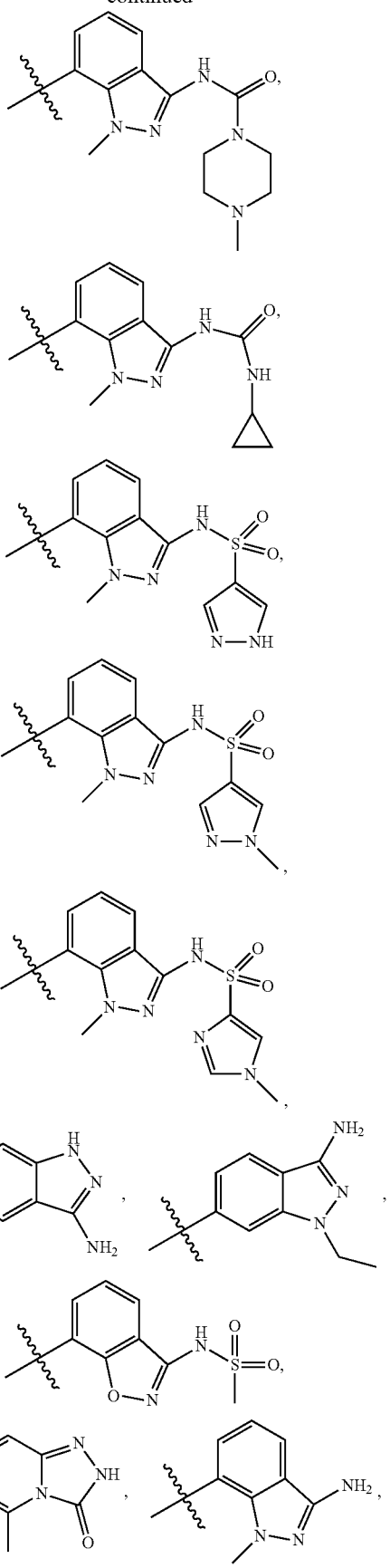

-continued

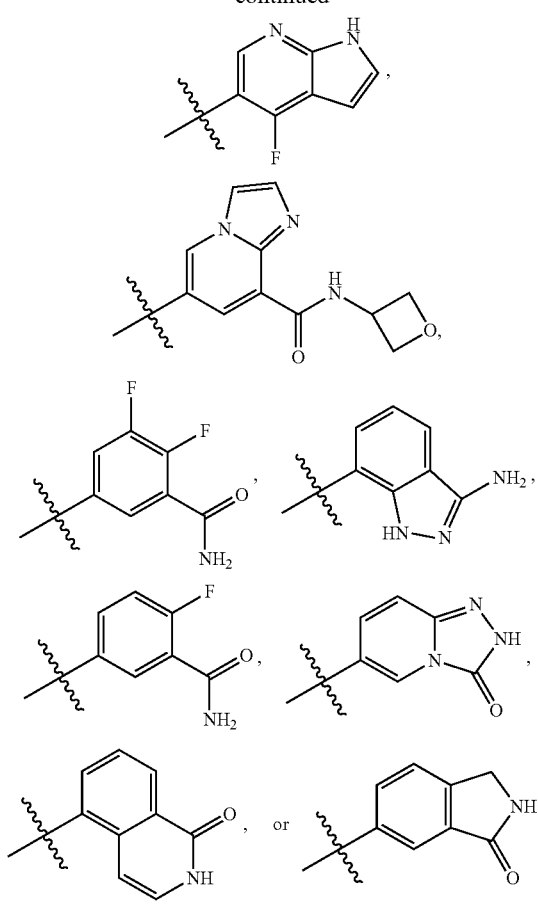

In certain embodiments, $Z^1$ optionally substituted with 1, 2, 3, 4, or 5 $Z^{1a}$ or $Z^{1b}$ groups is

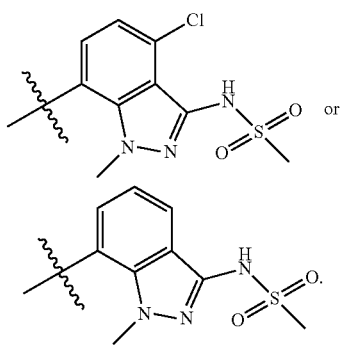

In certain embodiments, $Z^1$ optionally substituted with 1, 2, 3, 4, or 5 $Z^{1a}$ or $Z^{1b}$ groups is

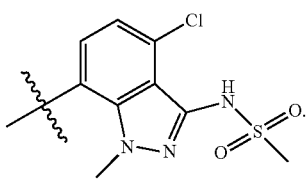 [SMILES: *c1ccc(Cl)c2c(NS(C)(=O)=O)nn(C)c12]

In certain embodiments, $Z^1$ is

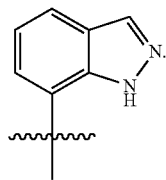 [SMILES: *c1cccc2cn[nH]c12]

In certain embodiments, $Z^2$-A-$Z^1$ is:

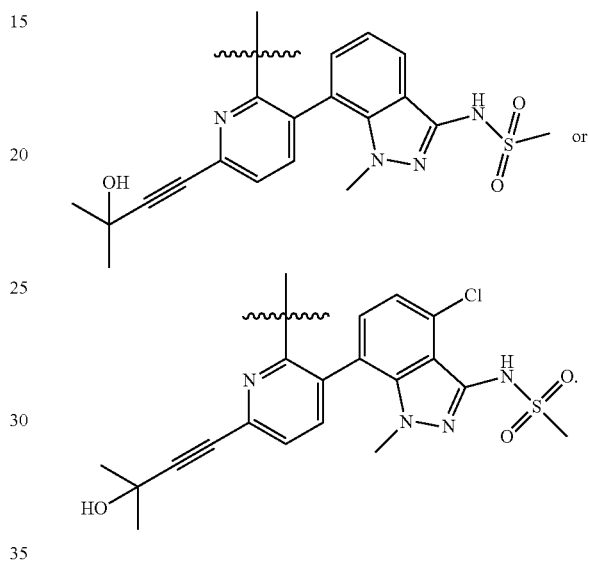

In one variation of formula III, A is pyridinyl, pyrimidinyl, pyrazinyl or pyridazinyl; and $R^1$ is a 5-12 membered heteroaryl, optionally substituted with 1, 2, 3, 4 or 5 $Z^4$ groups, which may be the same or different. In another variation, A is pyridinyl, pyrimidinyl, pyrazinyl or pyridazinyl; and $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups. In another variation, A is pyridinyl, pyrimidinyl, pyrazinyl or pyridazinyl; $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups; and each $Z^4$ is independently fluoro, trifluoromethyl, or difluoromethyl.

In one variation of formula III, A is pyridinyl; and $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups, which may be the same or different.

In one variation of formula III, A is pyridinyl, pyrimidinyl, pyrazinyl or pyridazinyl; and $R^2$ is 3,5-difluorophenyl. In another variation, A is pyridinyl; and $R^2$ is 3,5-difluorophenyl. In another variation, A is pyrimidinyl; and $R^2$ is 3,5-difluorophenyl. In another variation, A is pyrazinyl; and $R^2$ is 3,5-difluorophenyl. In another variation, A is pyridazinyl; and $R^2$ is 3,5-difluorophenyl.

In one variation of formula III, A is pyridinyl, pyrimidinyl, pyrazinyl or pyridazinyl; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups, which may be the same or different. In another variation, A is pyridinyl, pyrimidinyl, pyrazinyl or pyridazinyl; and $Z^1$ is phenyl, optionally substituted with 1, 2, 3, 4 or 5 $Z^{1a}$ groups. In another variation, A is pyridinyl, pyrimidinyl, pyrazinyl or pyridazinyl; and $Z^1$ is 5-6 membered monocyclic-heteroaryl or 8-10 membered bicyclic-heteroaryl, wherein any 5-6 membered monocyclic-heteroaryl or 8-10 membered bicyclic-heteroaryl of $Z^1$ is optionally substituted with 1, 2, 3, 4 or 5 $Z^{1a}$ groups. In another variation, A is pyridinyl, pyrimidinyl, pyrazinyl or pyridazinyl; and $Z^1$ is 8-10 membered bicyclic-heterocycle or 9-12 membered tricyclic-heterocycle wherein any 8-10 membered bicyclic-heterocycle or 9-12 membered tricyclic-heterocycle of $Z^1$ is optionally substituted with 1, 2, 3, 4 or 5 $Z^{1a}$ groups.

In one variation of formula III, A is pyridinyl; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups, which may be the same or different. In another variation, A is pyridinyl; and $Z^1$ is phenyl, optionally substituted with 1, 2, 3, 4 or 5 $Z^{1a}$ groups. In another variation, A is pyridinyl; and $Z^1$ is 5-6 membered monocyclic-heteroaryl or 8-10 membered bicyclic-heteroaryl, wherein any 5-6 membered monocyclic-heteroaryl or 8-10 membered bicyclic-heteroaryl of $Z^1$ is optionally substituted with 1, 2, 3, 4 or 5 $Z^{1a}$ groups. In another variation, A is pyridinyl; and $Z^1$ is 8-10 membered bicyclic-heterocycle or 9-12 membered tricyclic-heterocycle wherein any 8-10 membered bicyclic-heterocycle or 9-12 membered tricyclic-heterocycle of $Z^1$ is optionally substituted with 1, 2, 3, 4 or 5 $Z^{1a}$ groups.

In one variation of formula III, A is pyridinyl, pyrimidinyl, pyrazinyl or pyridazinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, which may be the same or different, and wherein any $(C_2-C_8)$alkynyl of $Z^2$ is optionally substituted with 1, 2, 3, 4 or 5 $Z^{2c}$ groups, which may be the same or different. In another variation, A is pyridinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyrimidinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyrazinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups. In another variation, A is pyridazinyl; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$alkynyl of $Z^2$ is optionally substituted with 1, 2, 3, 4 or 5 $Z^{2c}$ groups.

In one variation of formula III, A is pyridinyl substituted with one $Z^1$ moiety, one $Z^2$ moiety and no (zero) $Z^3$ moieties; and $Z^2$ is $(C_2-C_8)$alkynyl or aryl, which $Z^2$ may be optionally substituted as provided by formula III. In another variation, A is pyridinyl substituted with one $Z^1$ moiety, one $Z^2$ moiety and no (zero) $Z^3$ moieties; and $Z^2$ is $(C_2-C_8)$alkynyl, which $Z^2$ may be optionally substituted as provided by formula III. In a particular variation, A is pyridinyl substituted with one $Z^1$ moiety, one $Z^2$ moiety at the position alpha to the nitrogen atom of the pyridinyl ring, and no (zero) $Z^3$ moieties, wherein $Z^2$ is $(C_2-C_8)$alkynyl, which $Z^2$ may be optionally substituted as provided by formula III.

In one variation of formula III, $R^1$ is a 5-12 membered heteroaryl optionally substituted with 1, 2, 3, 4 or 5 $Z^4$ groups, which may be the same or different; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups, which may be the same or different. In another variation, $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups; and $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups.

In one variation of formula III, $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with 1, 2, 3, 4, or 5 $Z^4$ groups, which may be the same or different; and $Z^1$ is 8-10 membered bicyclic-heteroaryl or 8-10 membered bicyclic-heterocycle wherein any 8-10 membered bicyclic-heteroaryl or 8-10 membered bicyclic-heterocycle of $Z^1$ is optionally substituted with 1, 2, 3, 4 or 5 $Z^{1a}$ groups, which may be the same or different.

In one variation of formula III, $R^1$ is a 5-12 membered heteroaryl optionally substituted with 1, 2, 3, 4 or 5 $Z^4$ groups, which may be the same or different; and $Z^2$ is $(C_2-C_8)$alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any $(C_2-C_8)$ alkynyl of $Z^2$ is optionally substituted with 1, 2, 3, 4 or 5 $Z^{2c}$ groups, which may be the same or different. In another variation, $R^1$ is a 8-12 membered bicyclic-heteroaryl or 8-12 membered tricyclic-heteroaryl wherein any 8-12 membered bicyclic-heteroaryl or 8-12 membered tricyclic-heteroaryl of $R^1$ is optionally substituted with 1, 2, 3, 4, or 5 $Z^4$ groups; and $Z^2$ is ($C_2$-$C_8$)alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, and wherein any ($C_2$-$C_8$)alkynyl of $Z^2$ is optionally substituted with 1, 2, 3, 4 or 5 $Z^{2c}$ group.

In one variation of formula III, $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups, which may be the same or different; and $Z^2$ is ($C_2$-$C_8$)alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, which may be the same or different, and wherein any ($C_2$-$C_8$)alkynyl of $Z^2$ is optionally substituted with 1, 2, 3, 4 or 5 $Z^{2c}$ groups, which may be the same or different.

In one variation of formula III, $Z^1$ is bicyclic-heteroaryl optionally substituted with 1, 2, 3, 4 or 5 $Z^{1a}$ groups, which may be the same or different; and $Z^2$ is ($C_2$-$C_8$)alkynyl optionally substituted with 1, 2, 3, 4 or 5 $Z^{2c}$ groups, which may be the same or different.

In one variation of formula III, $R^1$ is a 5-12 membered heteroaryl; $Z^1$ is phenyl, 5-6 membered monocyclic-heteroaryl, 8-10 membered bicyclic-heteroaryl, 8-10 membered bicyclic-heterocycle, or 9-12 membered tricyclic-heterocycle wherein any phenyl, 5-6 membered monocyclic-heteroaryl, 8-10 membered bicyclic-heteroaryl, 8-10 membered bicyclic-heterocycle, or 9-12 membered tricyclic-heterocycle of $Z^1$ is optionally substituted with 1, 2, 3, 4 or 5 $Z^{1a}$ groups, which may be the same or different; and $Z^2$ is ($C_2$-$C_8$)alkynyl, 6-12 membered aryl, 5-12 membered C-linked-heteroaryl, 3-12 membered C-linked-heterocycle, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, which may be the same or different, and wherein any ($C_2$-$C_8$)alkynyl of $Z^2$ is optionally substituted with 1, 2, 3, 4 or 5 $Z^{2c}$ groups, which may be the same or different.

In certain embodiments of formula III,

A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with 1 or 2 $Z^3$ groups, which may be the same or different;

$R^1$ is 6-12 membered aryl, 5-12 membered heteroaryl, or 3-12 membered heterocycle, wherein any 6-12 membered aryl, 5-14 membered heteroaryl, or 3-12 membered heterocycle of $R^1$ is optionally substituted with 1, 2, 3, 4 or 5 $Z^4$ groups, which may be the same or different;

$R^2$ is phenyl optionally substituted with 1, 2, 3, 4 or 5 halogen, which may be the same or different;

each $R^{3a}$ and $R^{3b}$ is independently H or ($C_1$-$C_3$)alkyl;

$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, which may be the same or different;

each $Z^{1a}$ is independently oxo, ($C_3$-$C_7$)carbocycle, halogen, —CN, —O—($C_1$-$C_8$)alkyl, —OC(O)R$^{p1}$, —OC(O)NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$NR$^{q1}$R$^{r1}$, —C(O)R$^{n1}$, —C(O)OR$^{n1}$, or —C(O)NR$^{q1}$R$^{r1}$;

each $Z^{1b}$ is independently ($C_1$-$C_8$)alkyl optionally substituted with 1, 2, 3, 4 or 5 halogen, which may be the same or different;

each $R^{n1}$ is independently H or ($C_1$-$C_8$)alkyl;

each $R^{p1}$ is independently ($C_1$-$C_8$)alkyl, ($C_3$-$C_7$)carbocycle, 3-7 membered heterocycle, or 5-6 membered monocyclic-heteroaryl, wherein any ($C_3$-$C_7$)carbocycle, 3-7 membered heterocycle, or 5-6 membered monocyclic-heteroaryl of $R^{p1}$ is optionally substituted with 1, 2, 3, 4 or 5 ($C_1$-$C_8$)alkyl, which may be the same or different, and wherein any ($C_1$-$C_8$)alkyl of $R^{p1}$ is optionally substituted with 1, 2, 3, 4 or 5 halogen, hydroxyl, —O($C_1$-$C_8$)alkyl, or —NR$^{q2}$R$^{r2}$, which may be the same or different;

each $R^{q1}$ and $R^{r1}$ is independently H, ($C_1$-$C_8$)alkyl, ($C_3$-$C_7$)carbocycle, or 3-7-membered heterocycle, wherein any ($C_1$-$C_8$)alkyl of $R^{q1}$ or $R^{r1}$ is optionally substituted with 1, 2, 3, 4 or 5 halogen or —CN, which may be the same or different, or $R^{q1}$ and $R^{r1}$ together with the nitrogen to which they are attached form a 5, 6, or 7-membered heterocycle, wherein the 5, 6, or 7-membered heterocycle is optionally substituted with 1, 2, 3, 4 or 5 ($C_1$-$C_8$)alkyl, which may be the same or different;

each $R^{q2}$ and $R^{r2}$ is independently H, ($C_1$-$C_8$)alkyl, ($C_3$-$C_7$)carbocycle, or $R^{q2}$ and $R^{r2}$ together with the nitrogen to which they are attached form a 5, 6, or 7-membered heterocycle;

$Z^2$ is ($C_2$-$C_8$)alkenyl, ($C_2$-$C_8$)alkynyl, 6-12 membered aryl, 5-12 membered C-linked-heteroaryl, 3-12 membered C-linked-heterocycle, —C(O)R$^{n3}$, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, which may be the same or different, and wherein any ($C_2$-$C_8$)alkenyl or ($C_2$-$C_8$)alkynyl of $Z^2$ is optionally substituted with 1, 2, 3, 4, or 5 $Z^{2c}$ groups, which may be the same or different;

each $R^{n3}$ is independently H or ($C_1$-$C_4$)alkyl;

each $R^{q3}$ and $R^{r3}$ is independently H or ($C_1$-$C_4$)alkyl;

each $Z^{2b}$ is independently oxo, ($C_1$-$C_4$)alkyl, ($C_1$-$C_4$)heteroalkyl or ($C_1$-$C_4$)haloalkyl;

each $Z^{2c}$ is independently oxo, halogen, —CN, —OR$^{n4}$, NR$^{q4}$R$^{r4}$, —NR$^{n4}$COR$^4$, —NR$^{n4}$CO$_2$R$^{p4}$, —NR$^{n4}$S(O)$_2$R$^{p4}$, —C(O)R$^{n4}$, —C(O)OR$^{n4}$ or —C(O)NR$^{q4}$R$^{r4}$;

each $R^{n4}$ is independently H, ($C_1$-$C_4$)alkyl, or ($C_1$-$C_4$)heteroalkyl;

each $R^{p4}$ is independently ($C_1$-$C_8$)alkyl;

each $R^{q4}$ and $R^{r4}$ is independently H, ($C_1$-$C_4$)alkyl, or ($C_1$-$C_4$)heteroalkyl;

each $Z^3$ is independently a ($C_1$-$C_4$)heteroalkyl or halogen;

each $Z^4$ is independently oxo, ($C_1$-$C_8$)alkyl, ($C_3$-$C_7$)carbocycle, halogen, —CN, —OR$^{n5}$ NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any ($C_3$-$C_7$)carbocycle or ($C_1$-$C_8$)alkyl of $Z^4$ is optionally substituted with 1, 2, 3, 4 or 5 $Z^{4a}$ groups, which may be the same or different;

each $Z^{4a}$ is independently halogen, —CN, or —OR$^{n6}$; and each $R^{n5}$, $R^{p5}$, $R^{q5}$, $R^{r5}$, and $R^{n6}$ is independently H or $(C_1-C_4)$alkyl.

In certain embodiments of formula III, $A^1$ is CH, C—$Z^3$, or nitrogen;

$A^2$ is CH or nitrogen;

$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, which may be the same or different;

each $R^{3a}$ and $R^{3b}$ is independently H or $(C_1-C_3)$alkyl;

$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, which may be the same or different;

each $Z^{1a}$ is independently oxo, $(C_3-C_7)$carbocycle, halogen, —CN, —O—$(C_1-C_8)$alkyl, —OC(O)$R^{p1}$, —OC(O)N$R^{q1}R^{r1}$, —N$R^{q1}R^{r1}$, —N$R^{n1}$CO$R^{p1}$, —N$R^{n1}$CO$_2R^{p1}$, —N$R^{n1}$CON$R^{q1}R^{r1}$, —N$R^{n1}$S(O)$_2R^{p1}$, —N$R^{n1}$S(O)$_2$N$R^{q1}R^{r1}$, —C(O)$R^{n1}$, —C(O)O$R^{n1}$, or —C(O)N$R^{q1}R^{r1}$;

each $Z^{1b}$ is independently $(C_1-C_8)$alkyl optionally substituted with 1, 2, 3, 4 or 5 halogen, which may be the same or different;

each $R^{n1}$ is independently H or $(C_1-C_8)$alkyl;

each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $(C_1-C_8)$alkyl, which may be the same or different, and wherein any $(C_1-C_8)$alkyl of $R^{p1}$ is optionally substituted with 1, 2, 3, 4 or 5 halogen, hydroxyl, —O$(C_1-C_8)$alkyl, or —N$R^{q2}R^{r2}$, which may be the same or different;

each $R^{q1}$ and $R^{r1}$ is independently H, $(C_1-C_8)$alkyl, $(C_3-C_7)$carbocycle, or 3-7-membered heterocycle, wherein any $(C_1-C_8)$alkyl of $R^{q1}$ or $R^{r1}$ is optionally substituted with 1, 2, 3, 4 or 5 halogen or —CN, which may be the same or different, or $R^{q1}$ and $R^{r1}$ together with the nitrogen to which they are attached form a 5, 6, or 7-membered heterocycle, wherein the 5, 6, or 7-membered heterocycle is optionally substituted with 1, 2, 3, 4 or 5 $(C_1-C_8)$alkyl, which may be the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is $(C_2-C_8)$alkenyl, $(C_2-C_8)$alkynyl, 6-12 membered aryl, 5-12 membered C-linked-heteroaryl, 3-12 membered C-linked-heterocycle, —C(O)$R^{n3}$, or —C(O)N$R^{q3}R^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, which may be the same or different, and wherein any $(C_2-C_8)$alkenyl or $(C_2-C_8)$alkynyl of $Z^2$ is optionally substituted with 1, 2, 3, 4, or 5 $Z^{2c}$ groups, which may be the same or different;

each $R^{n3}$ is independently H or $(C_1-C_4)$alkyl;

each $R^{q3}$ and $R^{r3}$ is independently H or $(C_1-C_4)$alkyl;

each $Z^{2b}$ is independently oxo, $(C_1-C_4)$alkyl, $(C_1-C_4)$heteroalkyl or $(C_1-C_4)$haloalkyl;

each $Z^{2c}$ is independently oxo, halogen, —CN, —O$R^{n4}$, N$R^{q4}R^{r4}$, —N$R^{n4}$CO$R^4$, —N$R^{n4}$CO$_2R^{p4}$, —N$R^{n4}$S(O)$_2$R$^{p4}$, —C(O)N$R^{n4}$, —C(O)O$R^{n4}$ or —C(O)N$R^{q4}R^{r4}$;

each $R^{n4}$ is independently H, $(C_1-C_4)$alkyl, or $(C_1-C_4)$heteroalkyl;

each $R^{p4}$ is independently $(C_1-C_8)$alkyl;

each $R^{q4}$ and $R^{r4}$ is independently H, $(C_1-C_4)$alkyl, or $(C_1-C_4)$heteroalkyl;

$Z^3$ is independently a $(C_1-C_4)$heteroalkyl or halogen;

each $Z^4$ is independently oxo, $(C_1-C_8)$alkyl, $(C_3-C_7)$carbocycle, halogen, —CN, —O$R^{n5}$, —N$R^{q5}R^{r5}$, —N$R^{n5}$CO$R^{p5}$, —N$R^{n5}$CO$_2R^{p5}$, —C(O)$R^{n5}$, —C(O)O$R^{n5}$, or —C(O)N$R^{q5}R^{r5}$, wherein any $(C_3-C_7)$carbocycle or $(C_1-C_8)$alkyl of $Z^4$ is optionally substituted with 1, 2, 3, 4 or 5 $Z^{4a}$ groups, which may be the same or different;

each $Z^{4a}$ is independently halogen, —CN, or —O$R^{n6}$; and each $R^{n5}$, $R^{p5}$, $R^{q5}$, $R^{r5}$, and $R^{n6}$ is independently H or $(C_1-C_4)$alkyl;

each $Z^5$ is independently halogen, which may be same or different; and n is 0, 1, 2, or 3.

In one embodiment the compound of formula I is selected from:

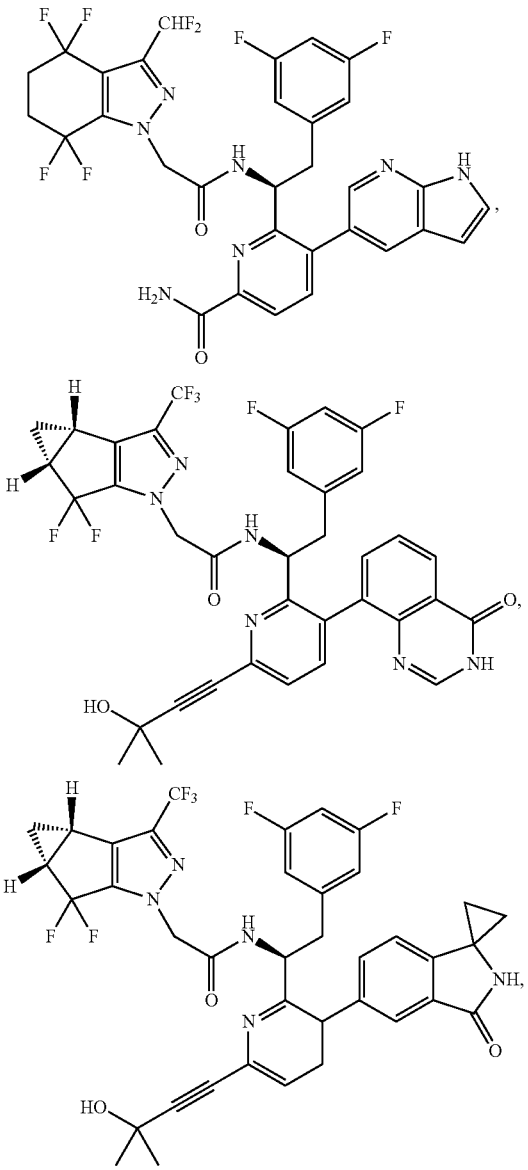

103
-continued
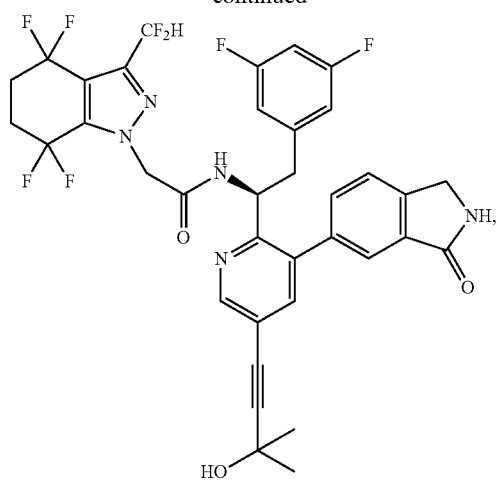
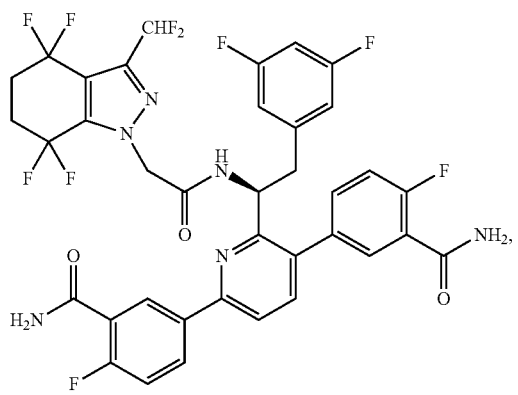
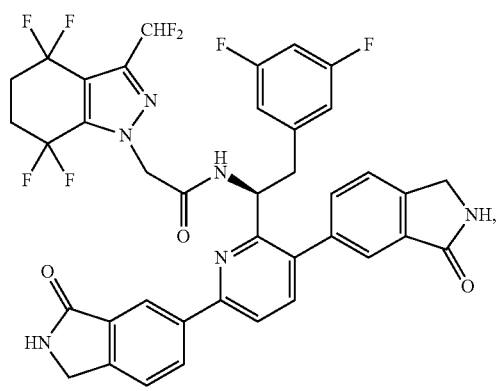
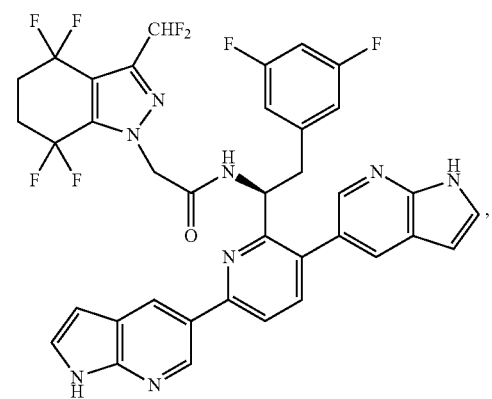
104
-continued
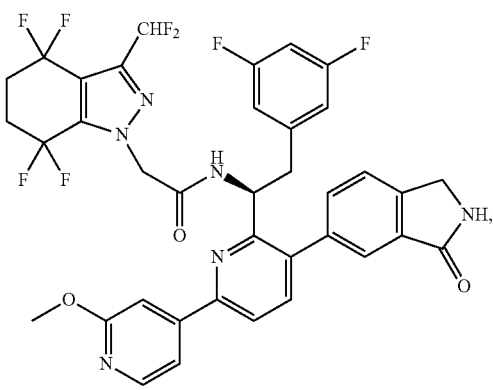
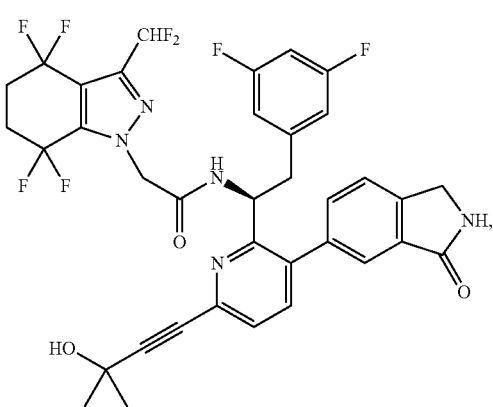
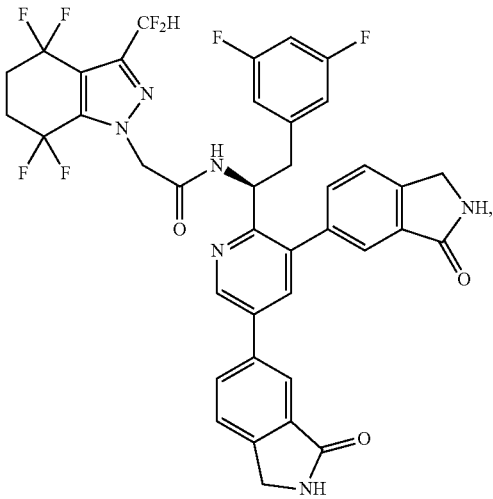

105
-continued
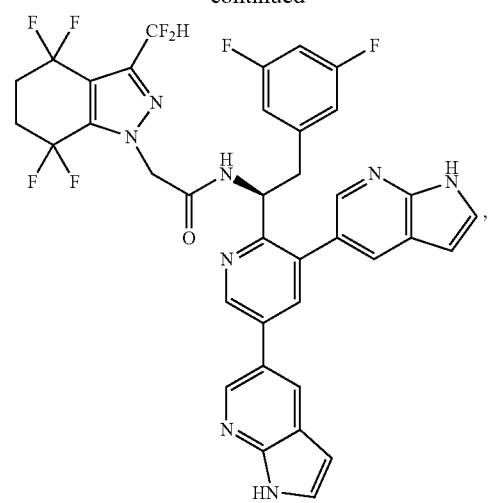
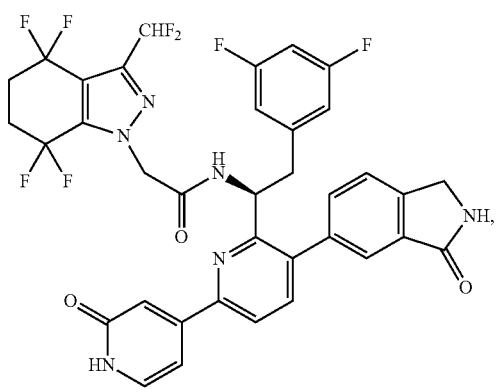
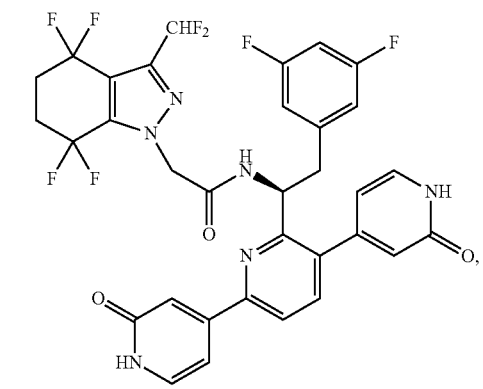
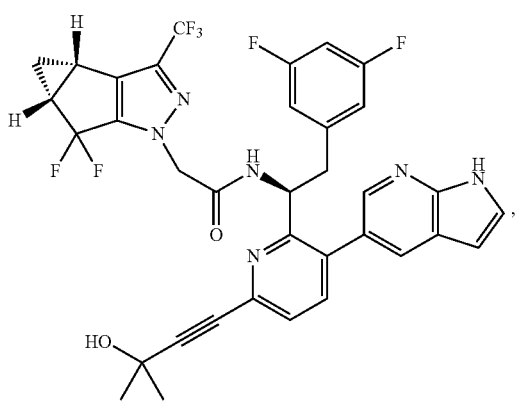
106
-continued
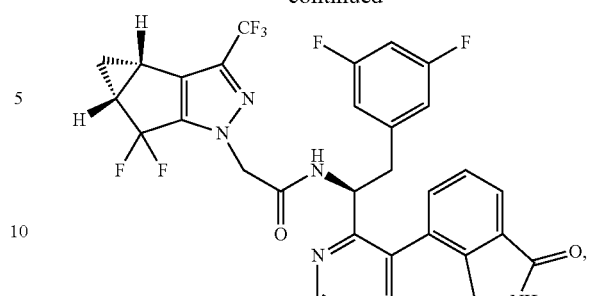
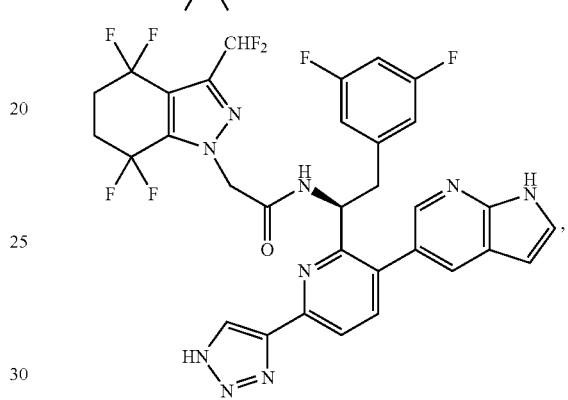
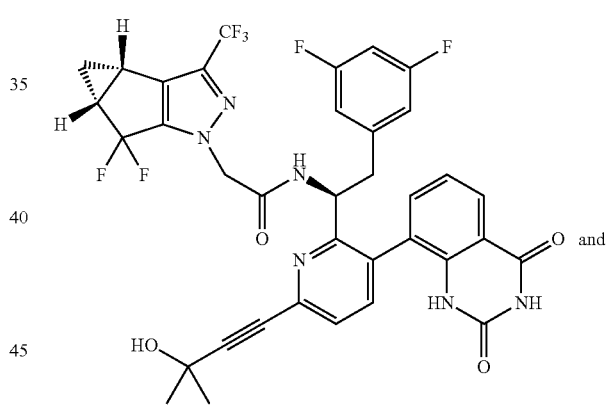
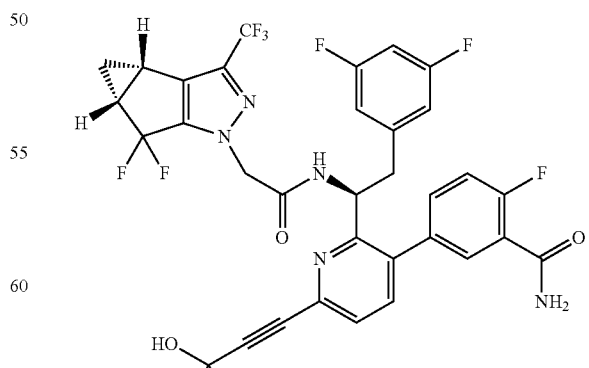
and pharmaceutically acceptable salts thereof.

In certain embodiments, a compound is:
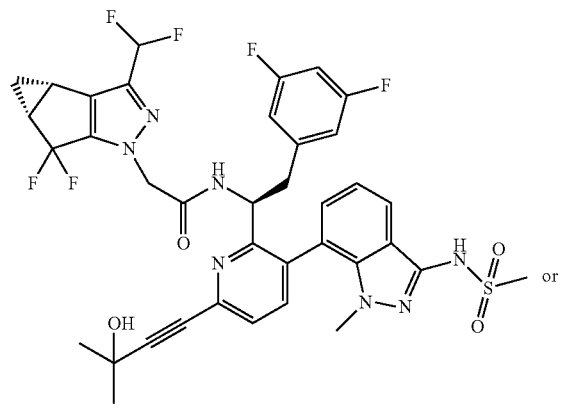
In certain embodiments, a compound or a pharmaceutically acceptable salt thereof is:
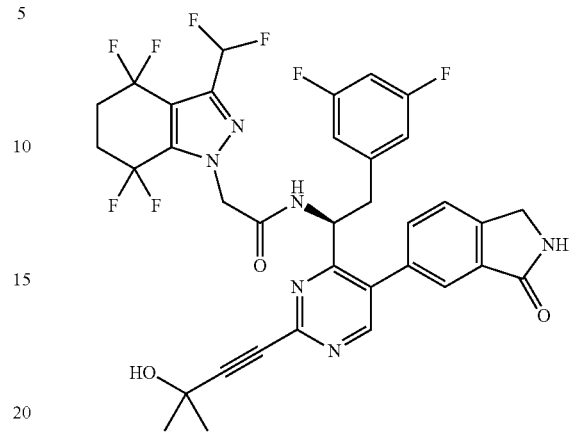
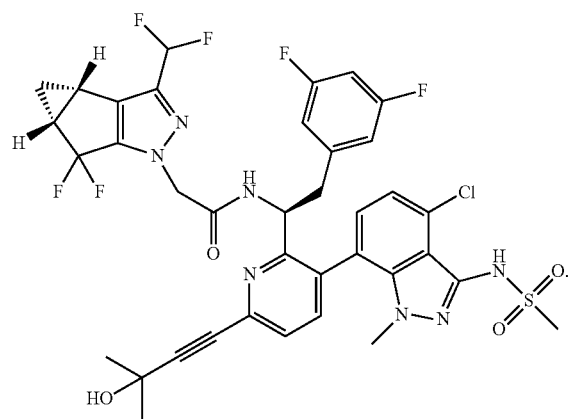
or a pharmaceutically acceptable salt thereof.
In certain embodiments, a compound is:
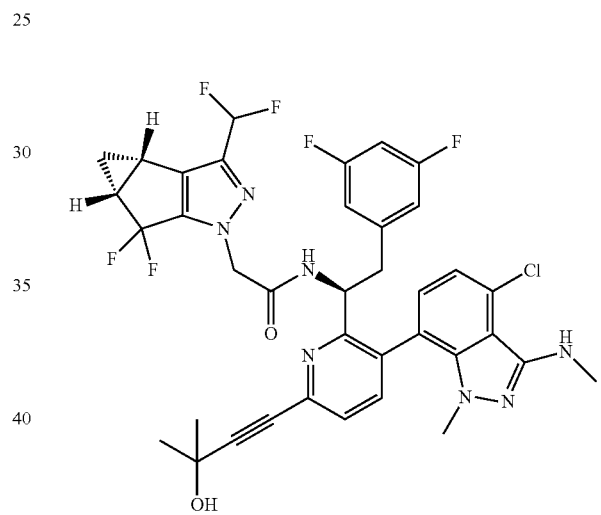
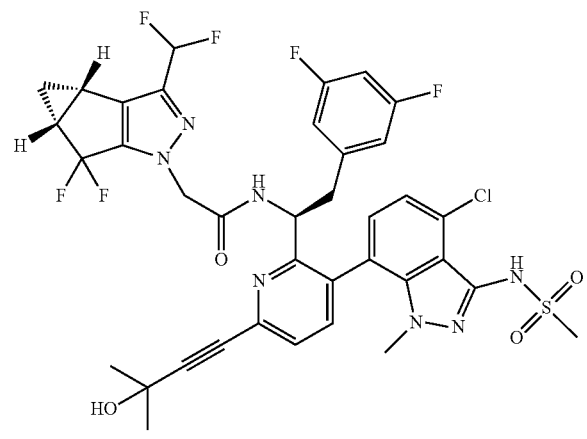 [SMILES: Cn1nc(NS(C)(=O)=O)c2c(Cl)ccc(-c3ccc(C#CC(C)(C)O)nc3[C@H](Cc3cc(F)cc(F)c3)NC(=O)Cn3nc(C(F)F)c4c3C(F)(F)[C@@H]3C[C@H]43)c21]
or a pharmaceutically acceptable salt thereof.

109
-continued
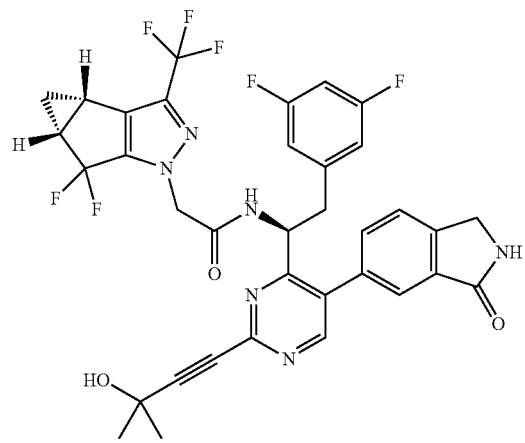
110
-continued
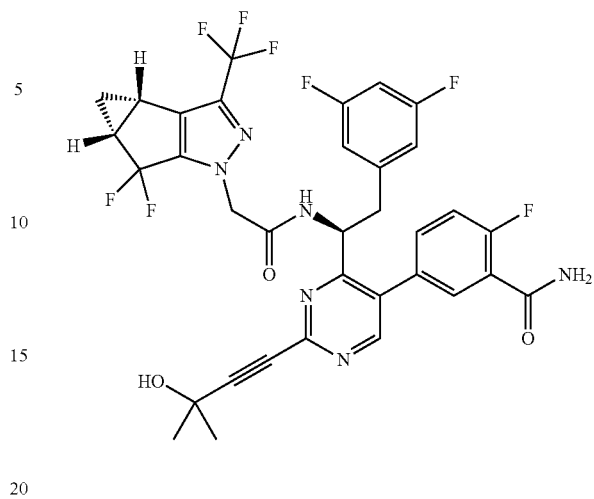
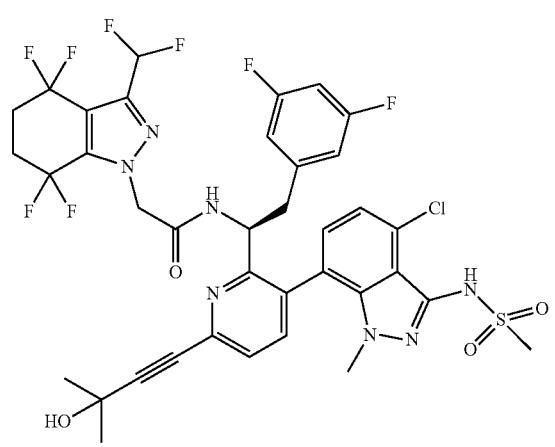
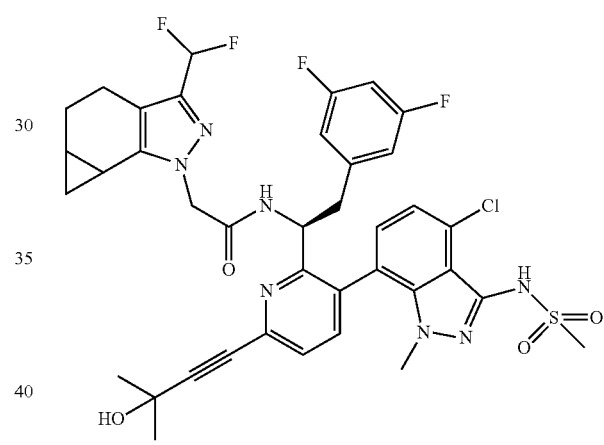
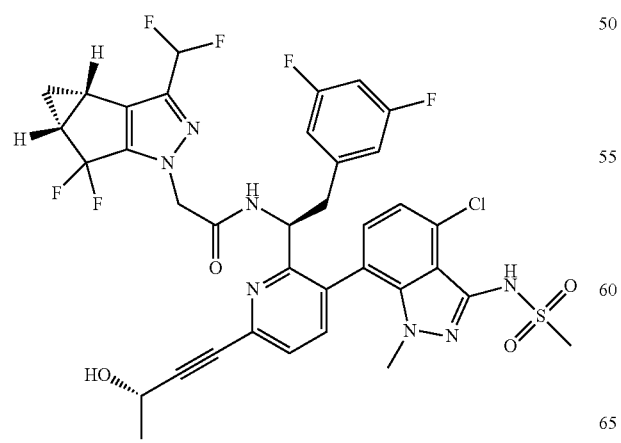
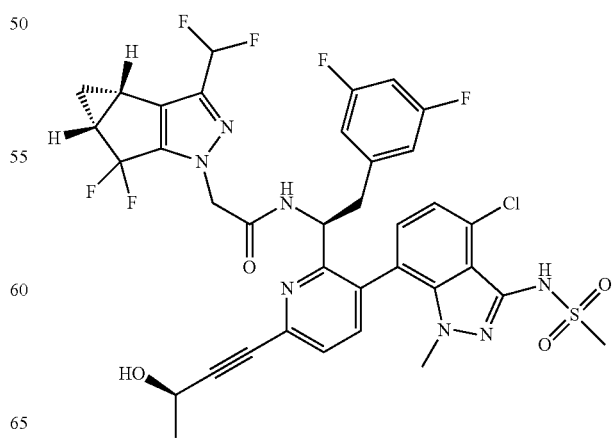

111
-continued
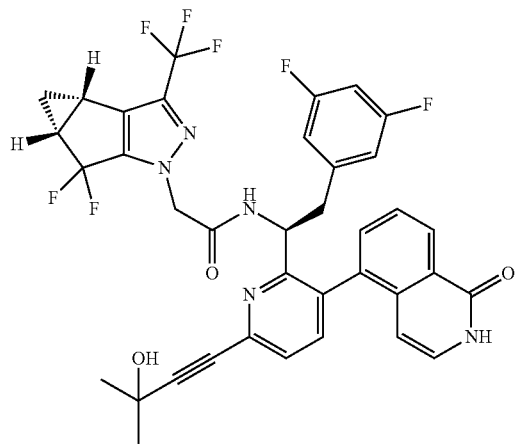
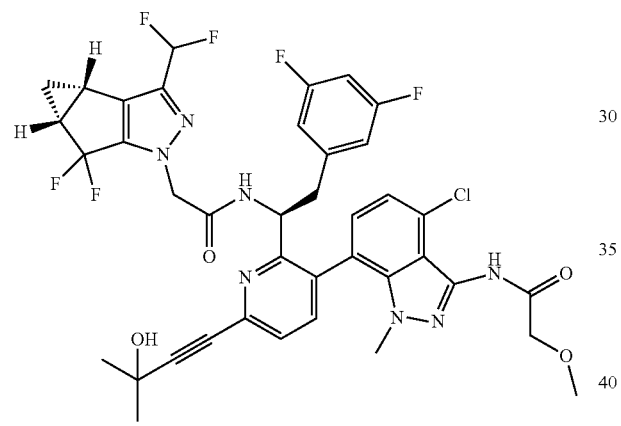
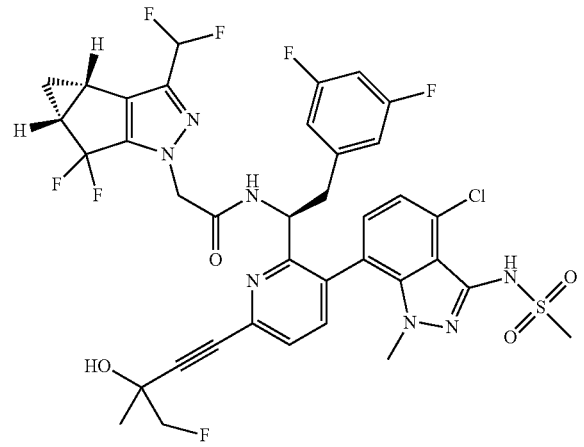
112
-continued
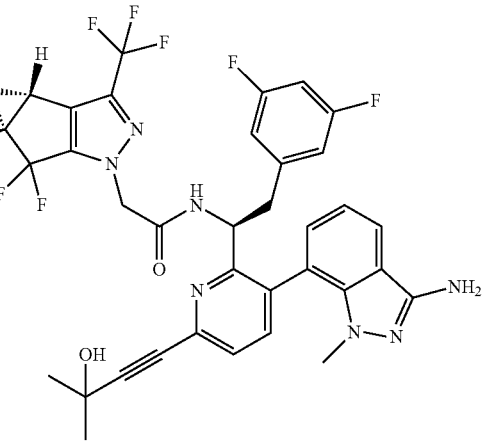
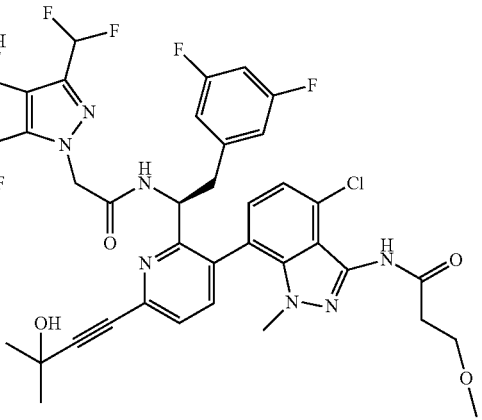
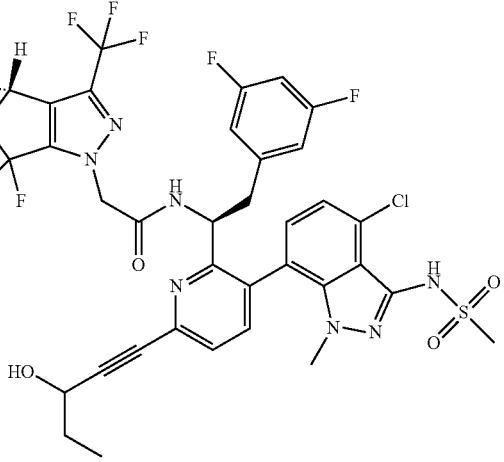

113
-continued
114
-continued
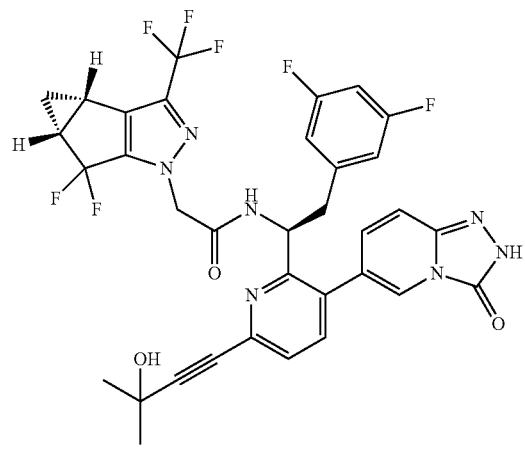
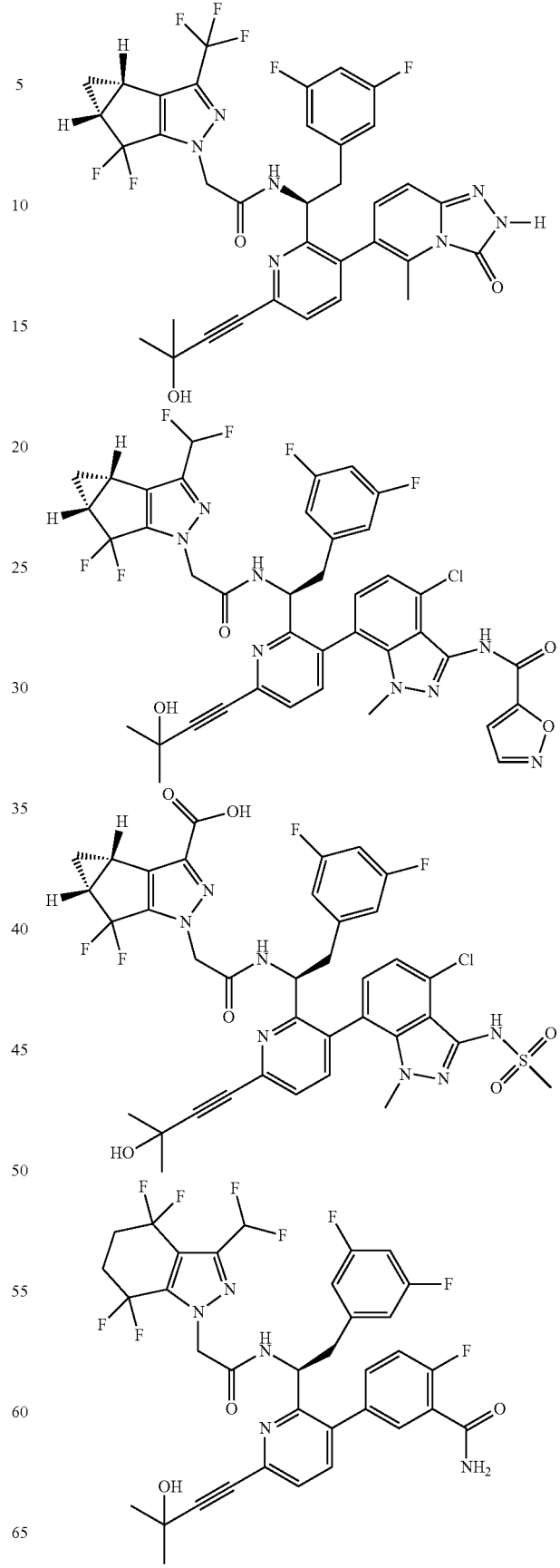

115
-continued
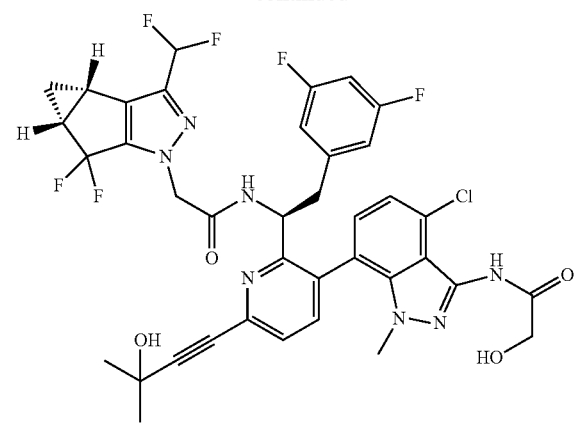
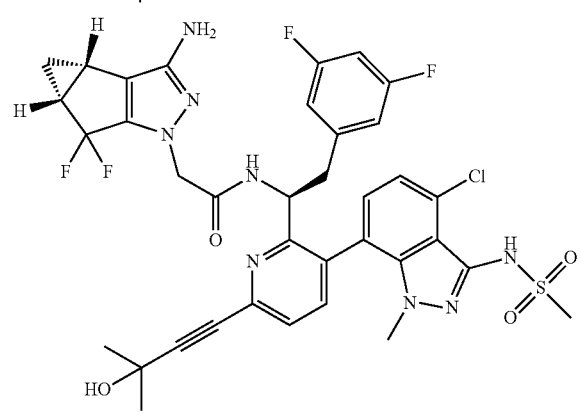
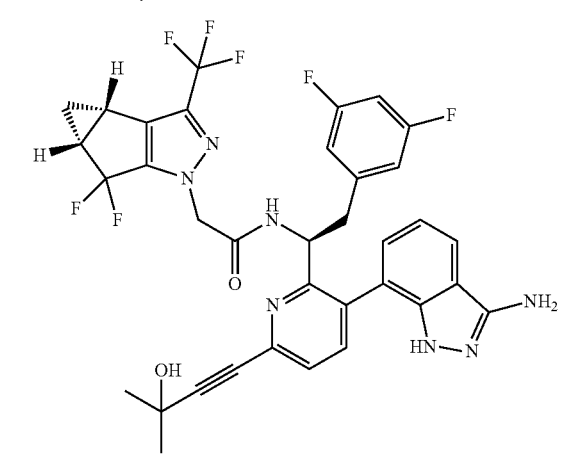
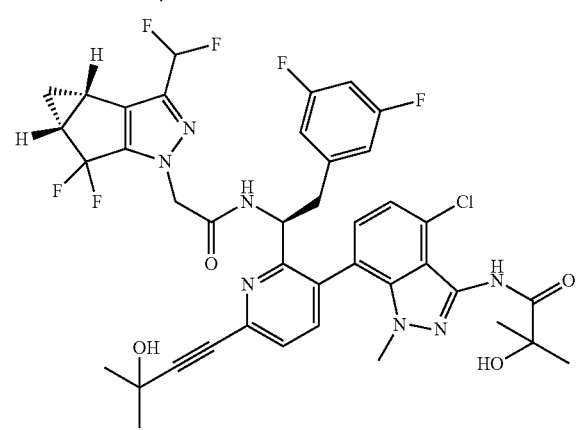
116
-continued
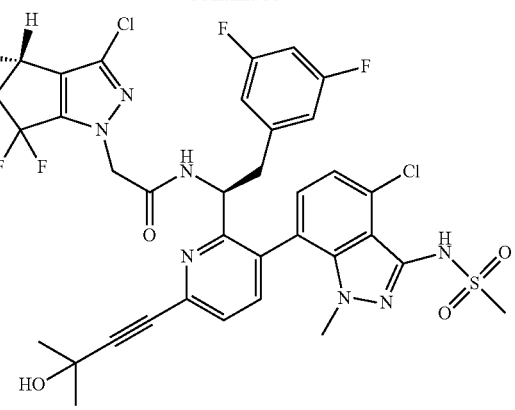
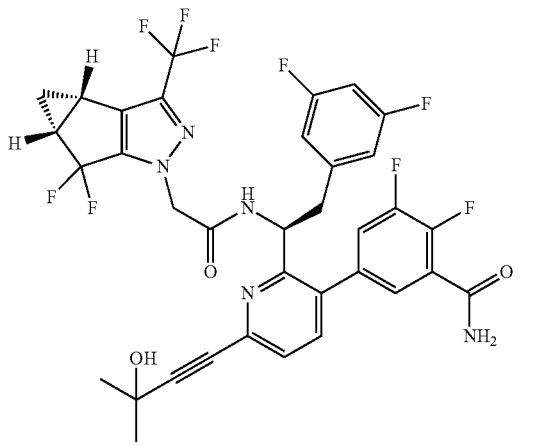
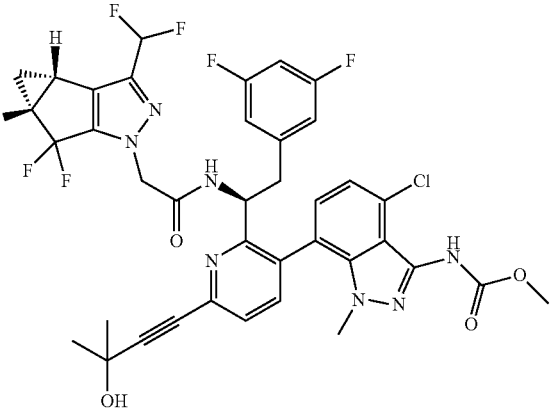
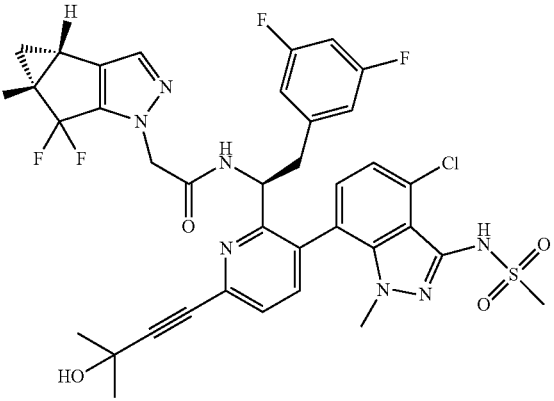

117
-continued
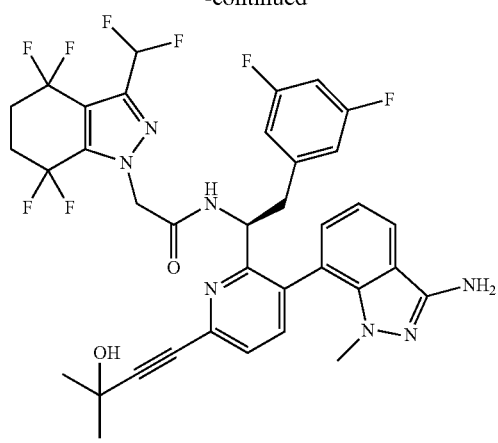
118
-continued
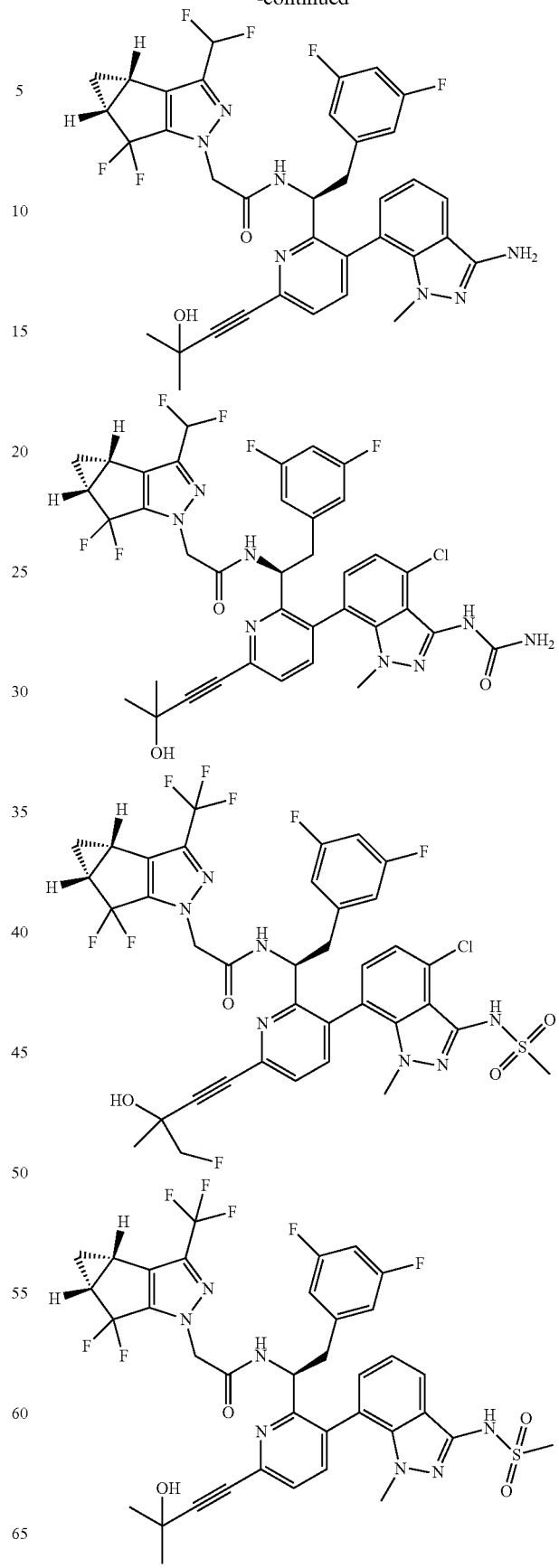

119
-continued
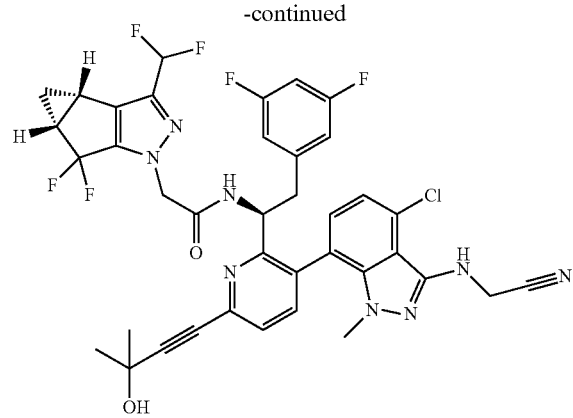
120
-continued
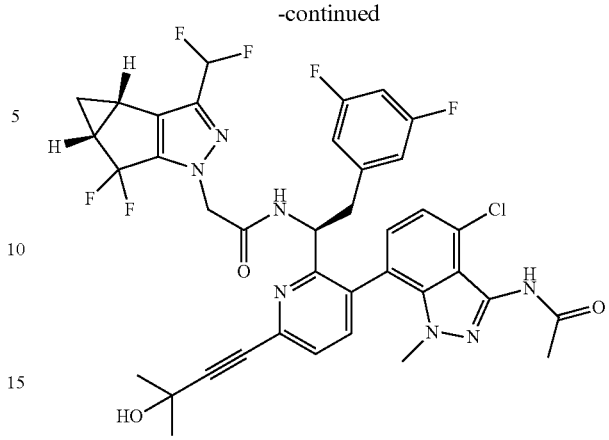
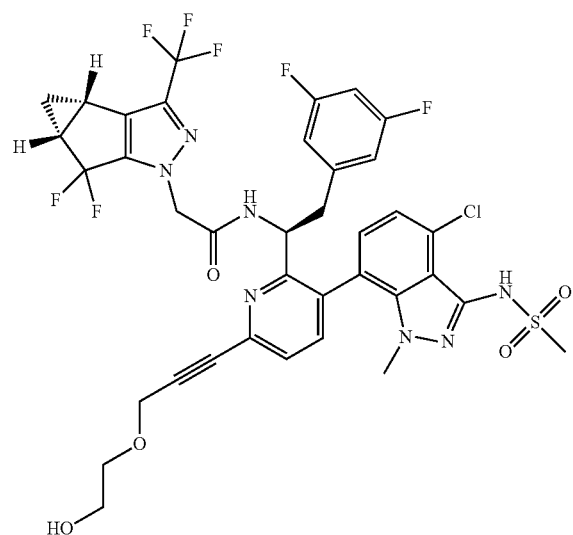
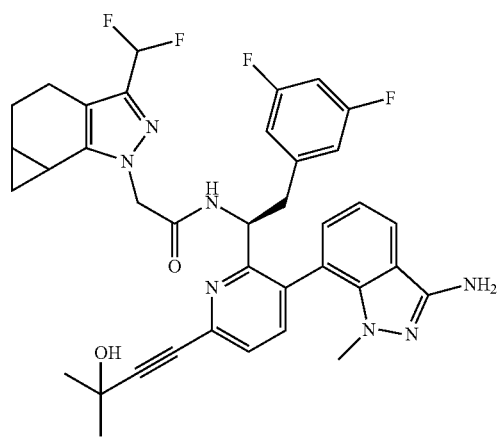
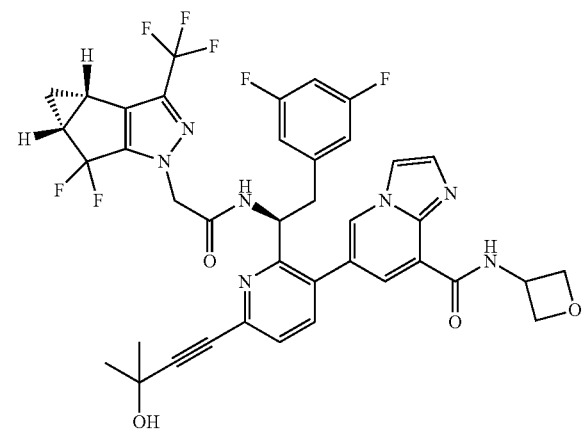

121
-continued
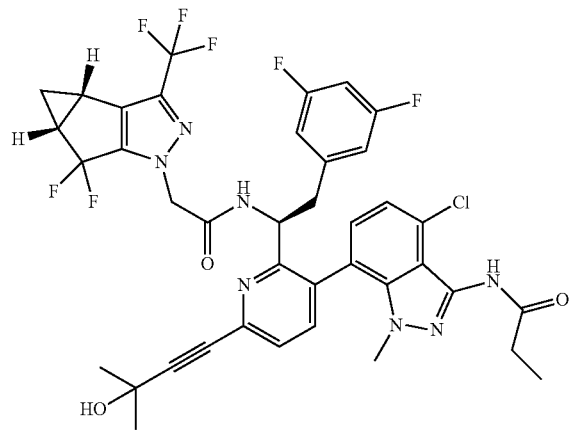
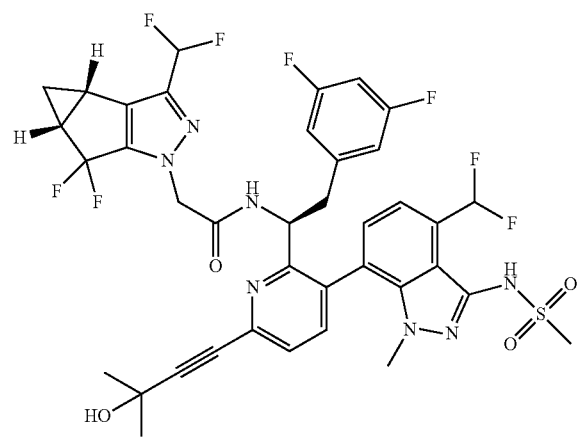
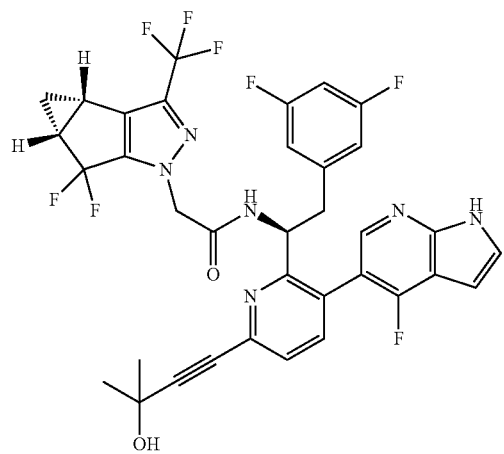
122
-continued
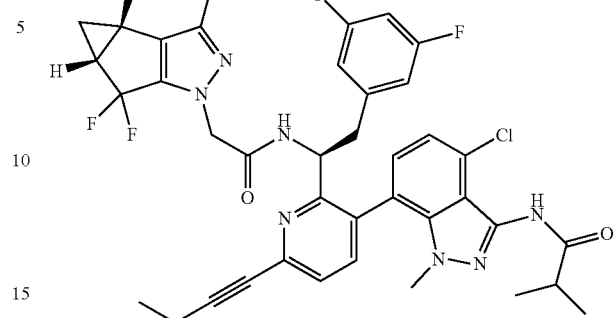
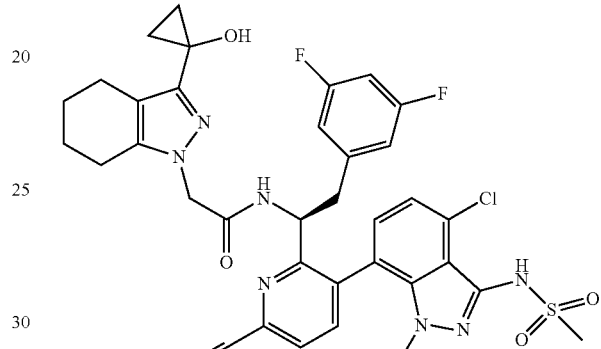
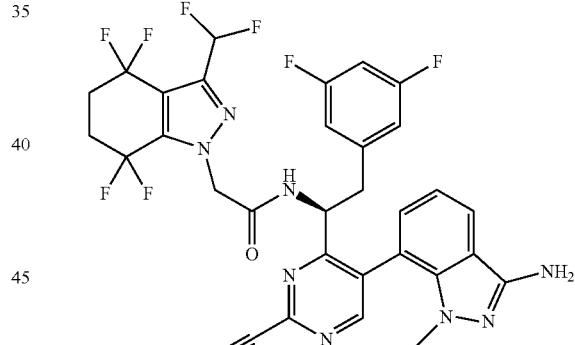
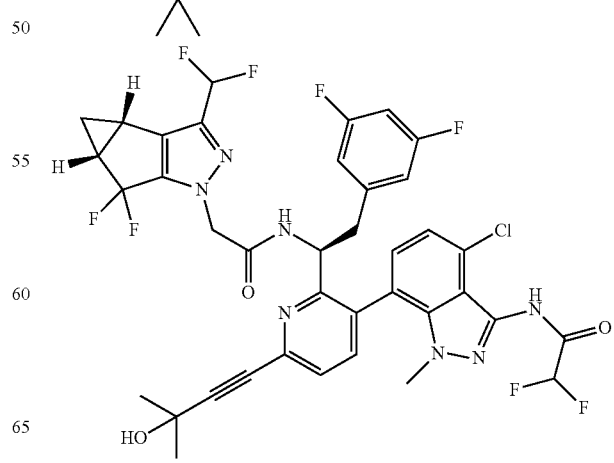

123
-continued
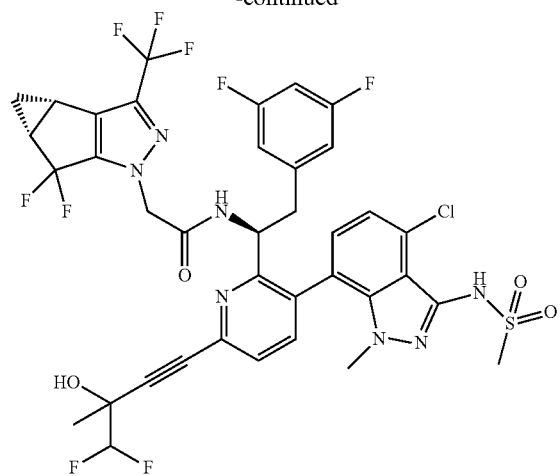
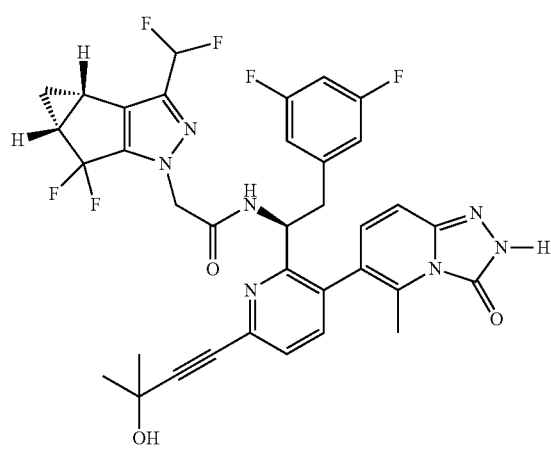
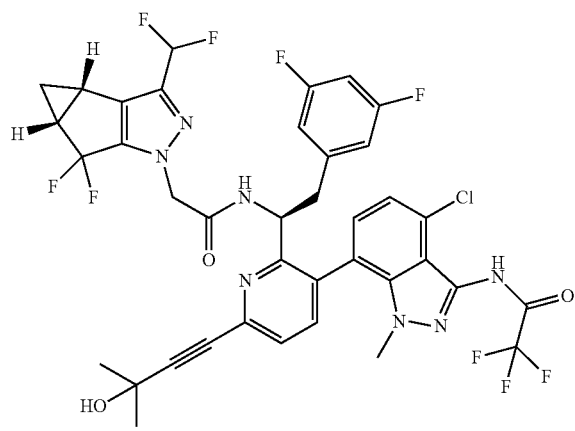
124
-continued
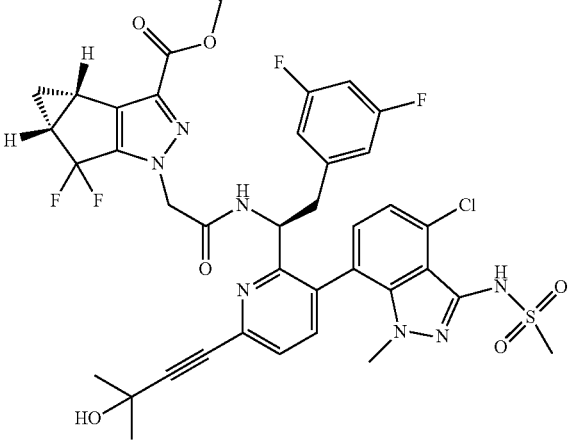
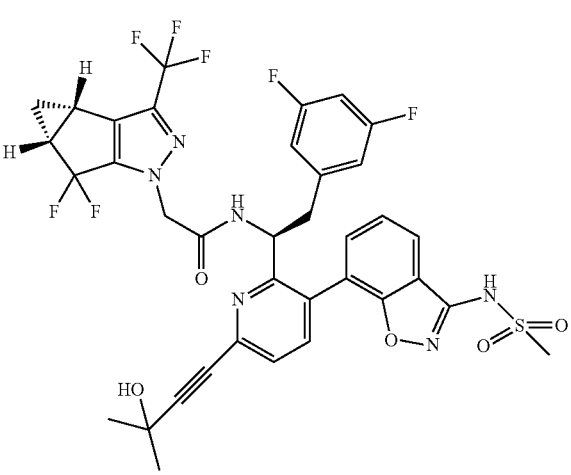
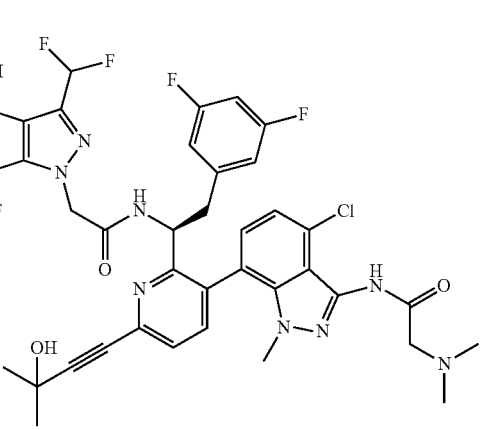

125
-continued
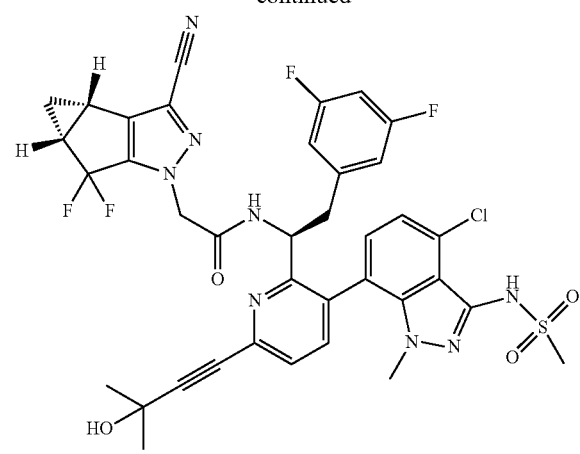
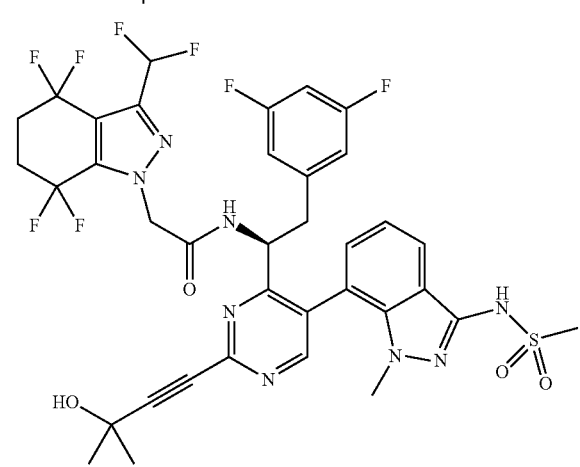
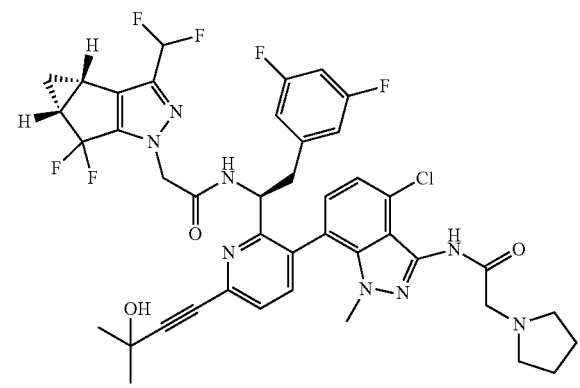
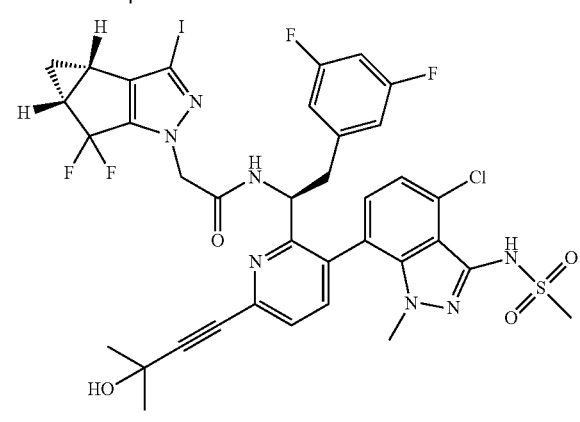
126
-continued
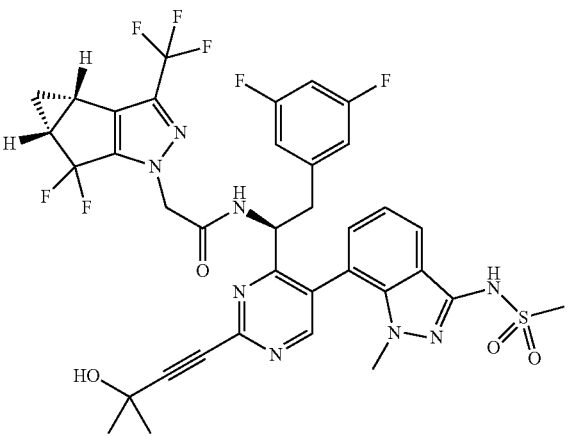
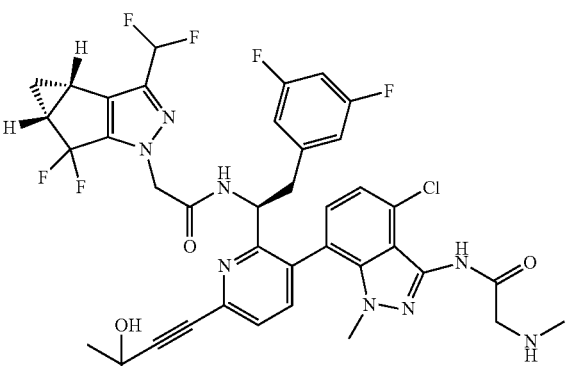
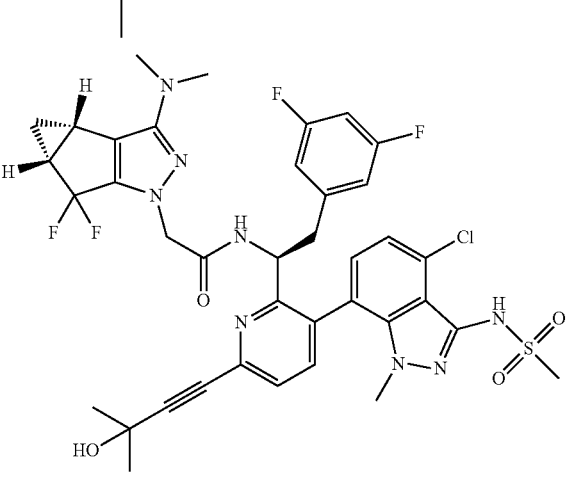
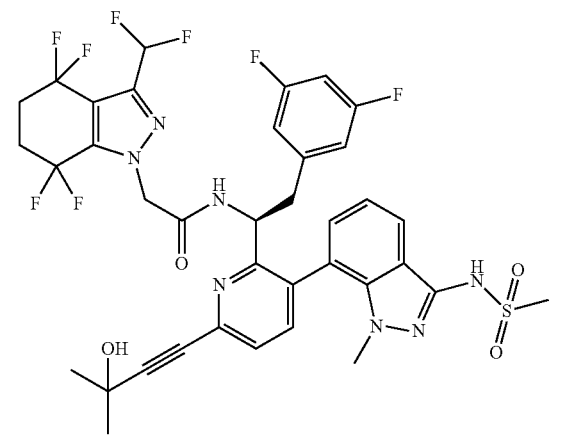

127
-continued
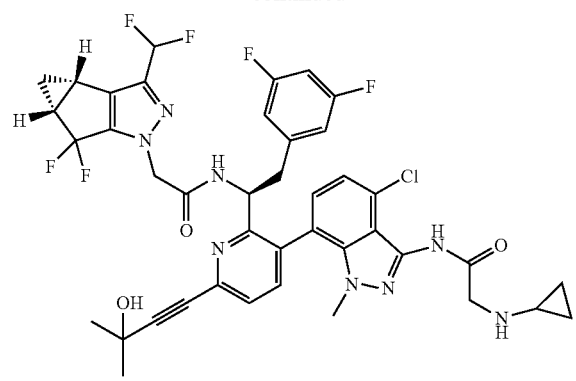
128
-continued
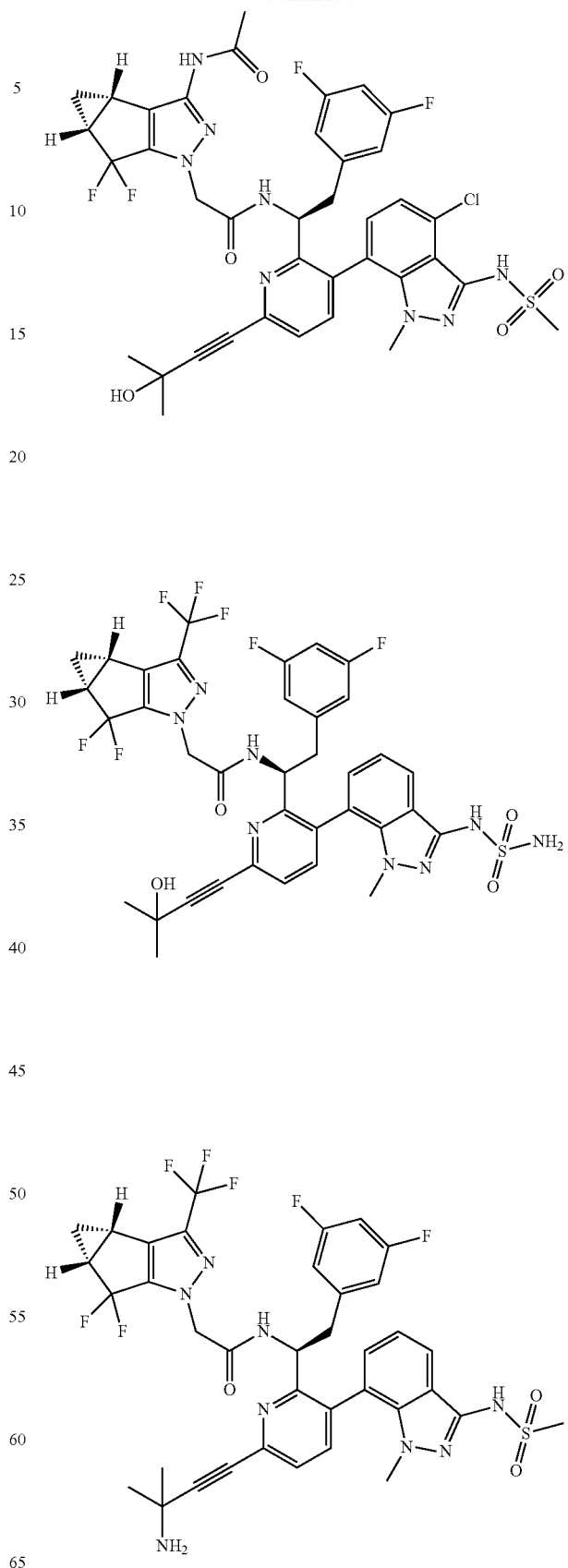

129
-continued
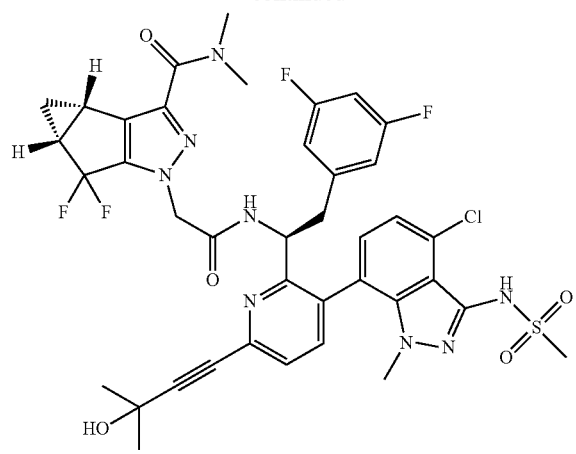
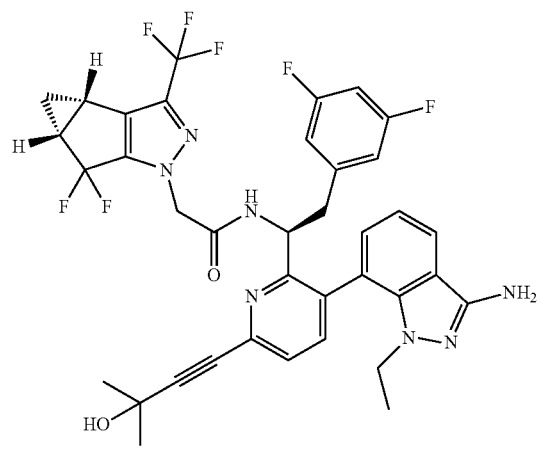
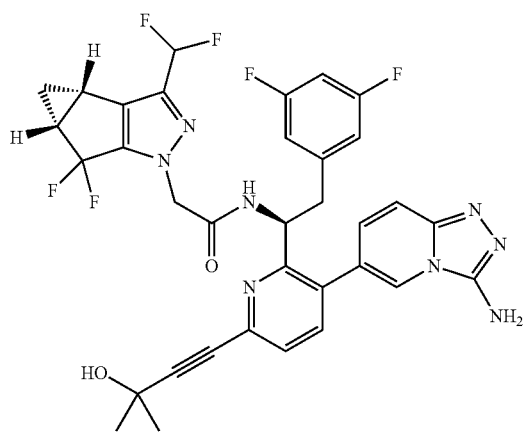
130
-continued
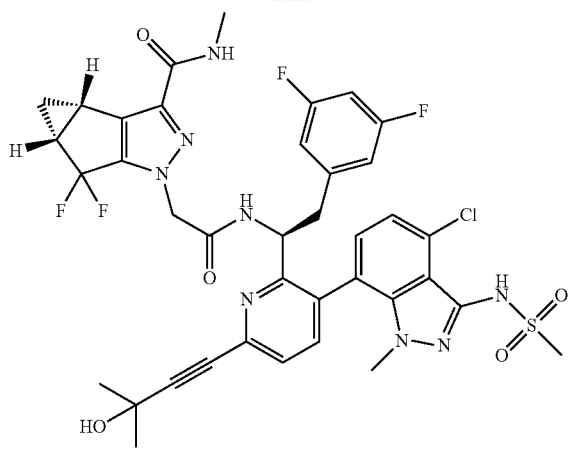
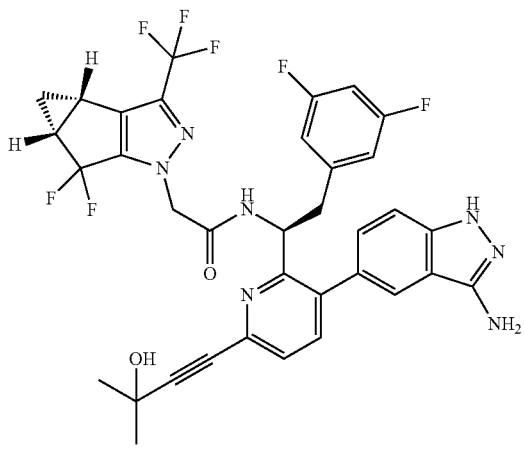
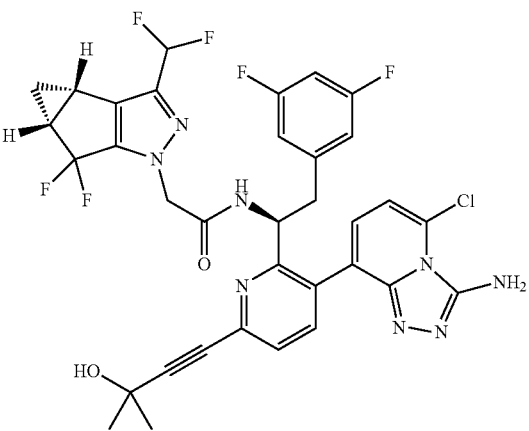

131
-continued
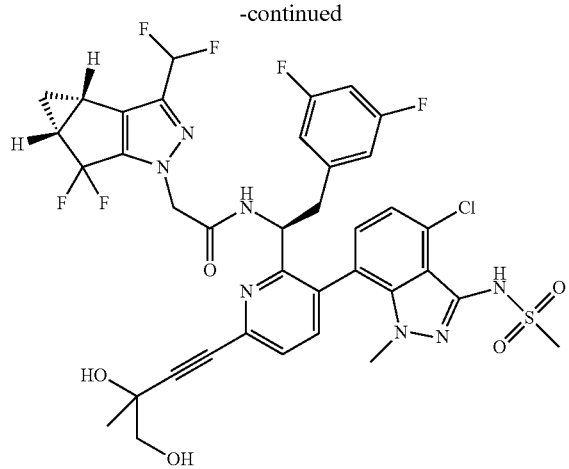
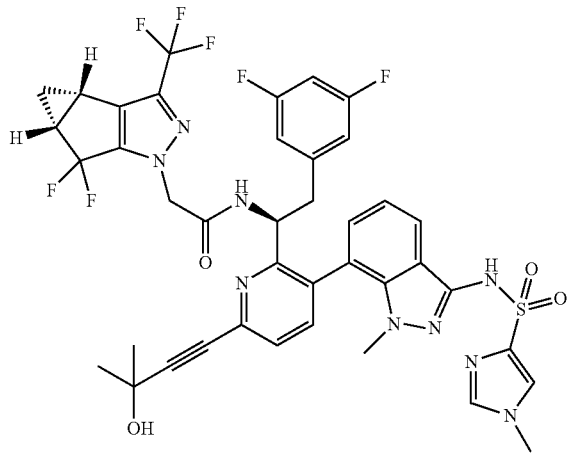
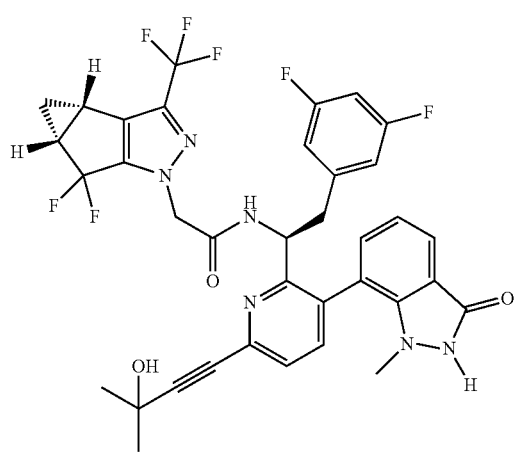
132
-continued
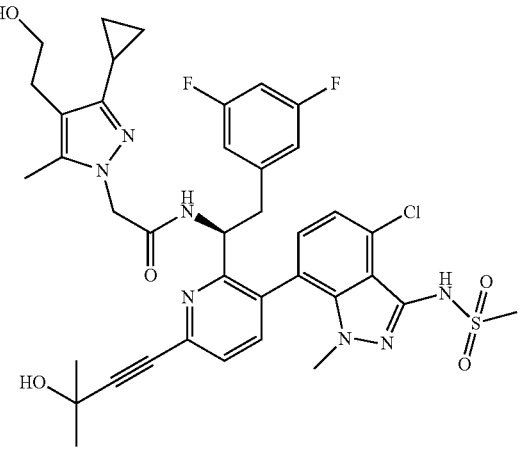
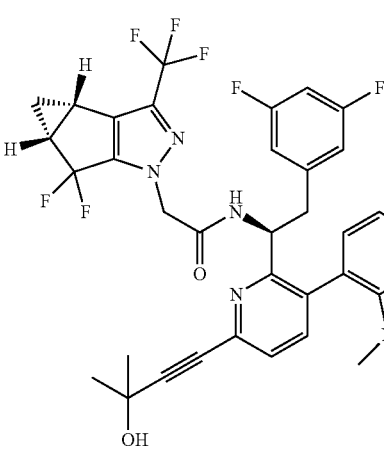
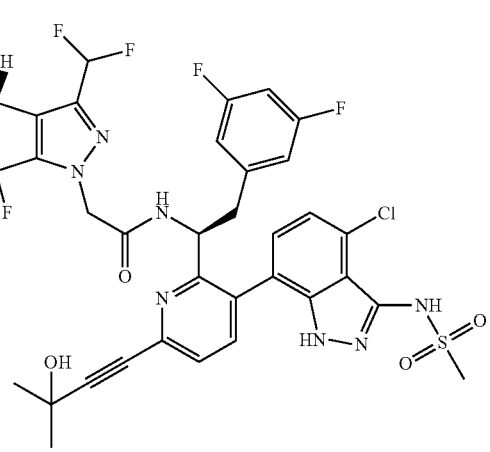

133
-continued
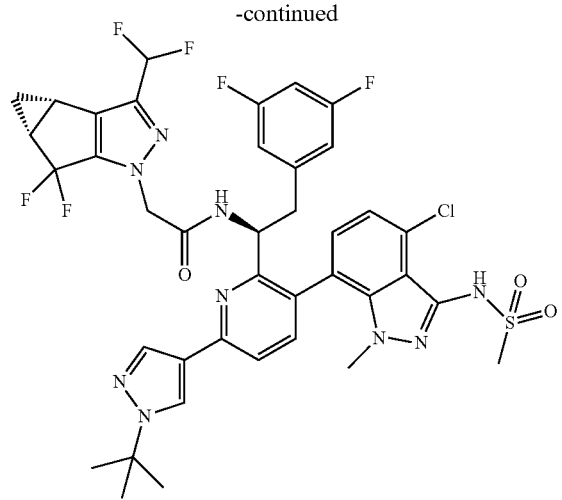
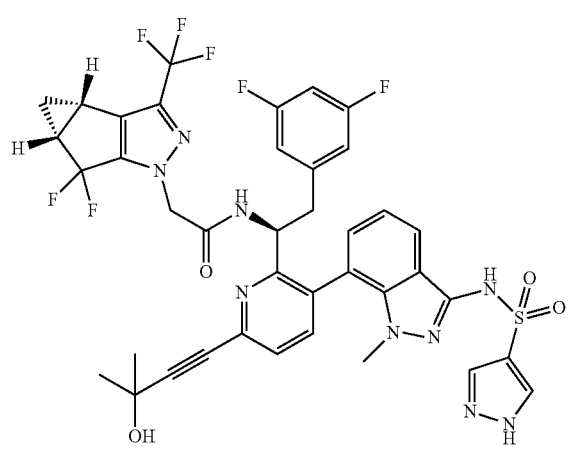
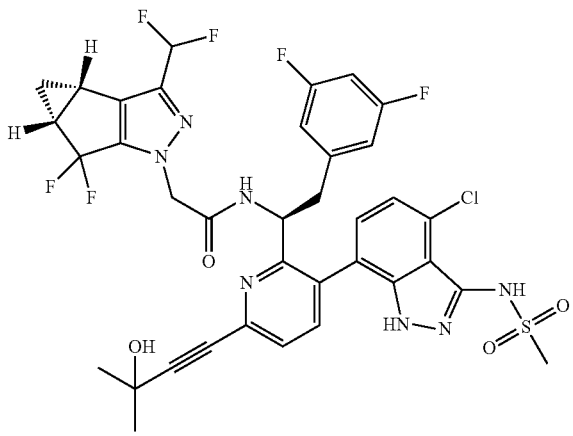
134
-continued
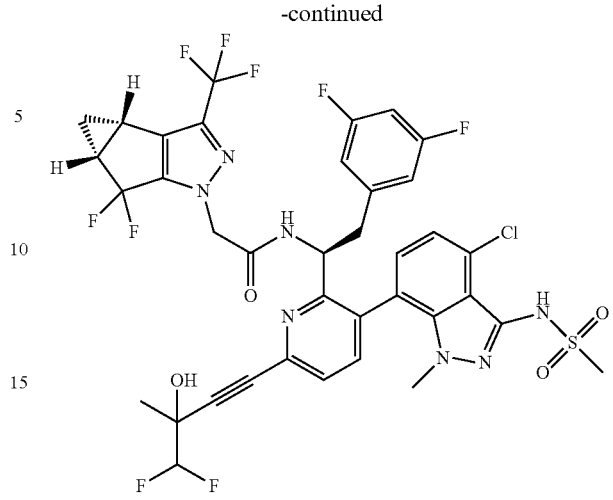
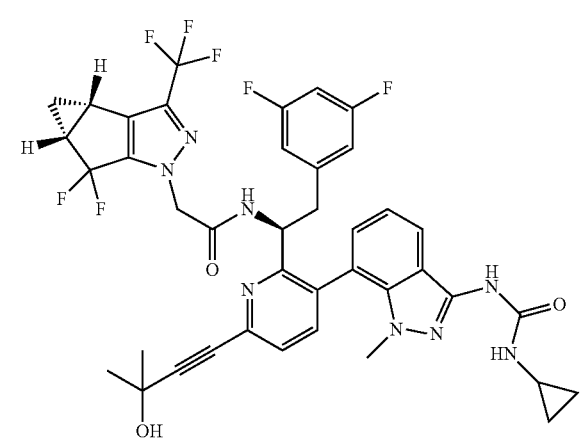
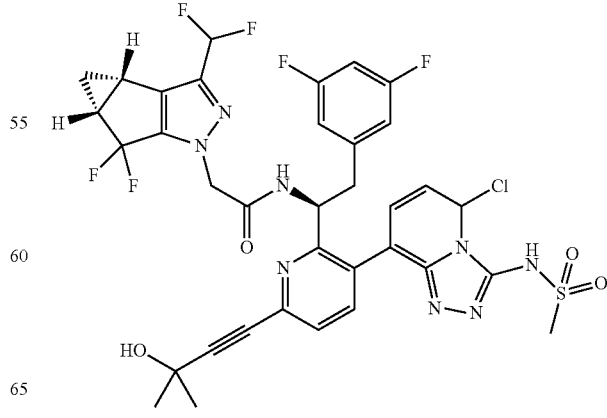

135
-continued
136
-continued
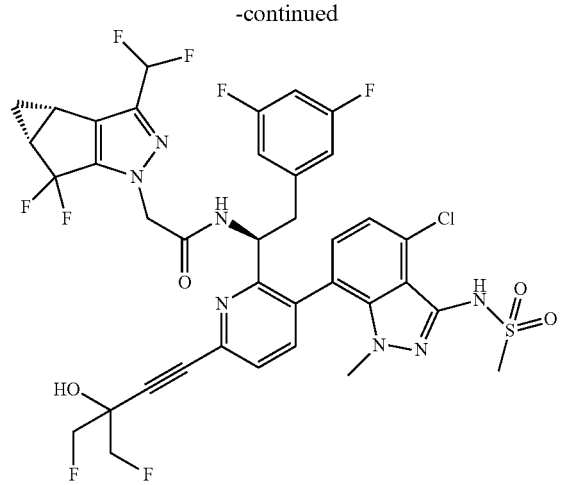
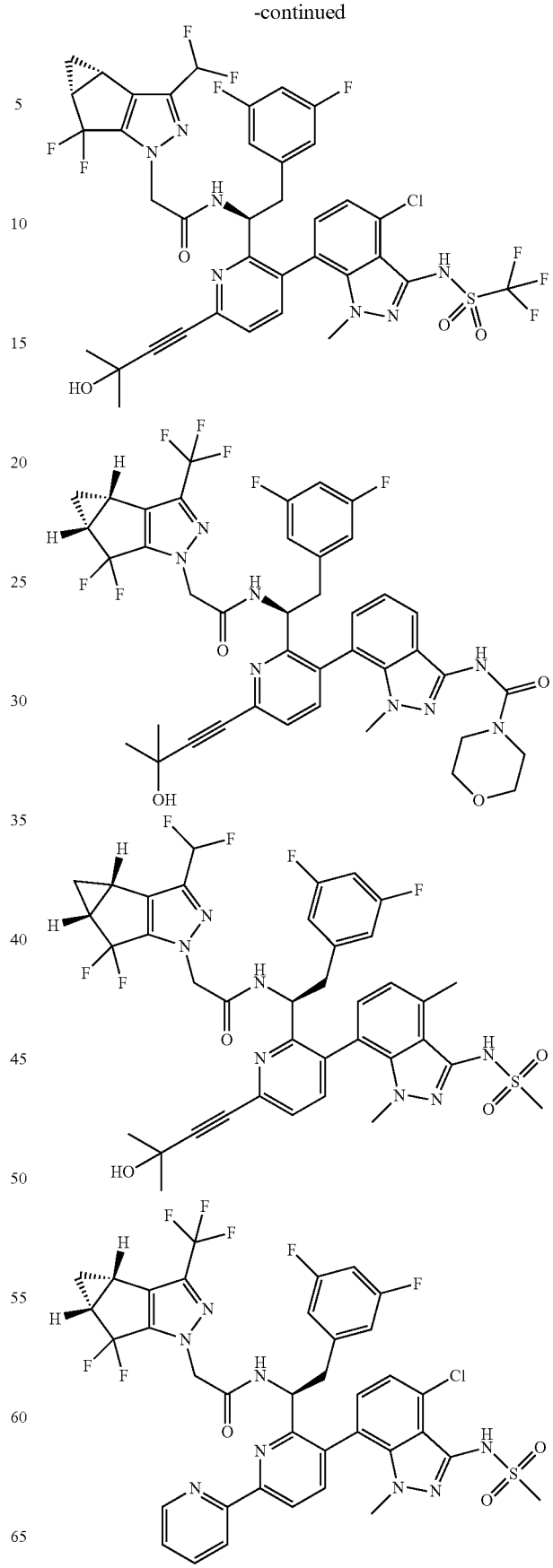

137
-continued
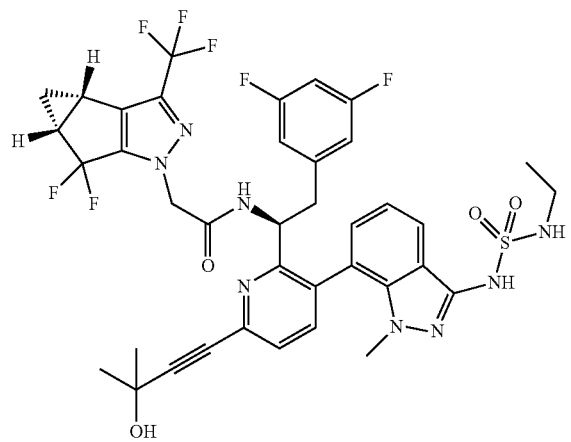
138
-continued
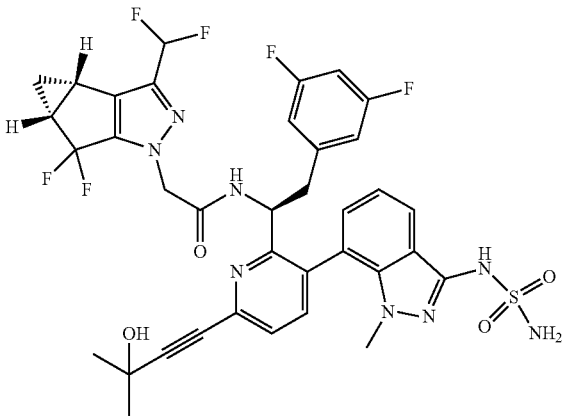
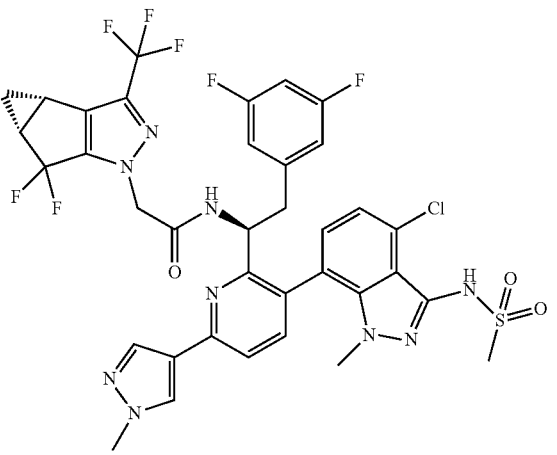
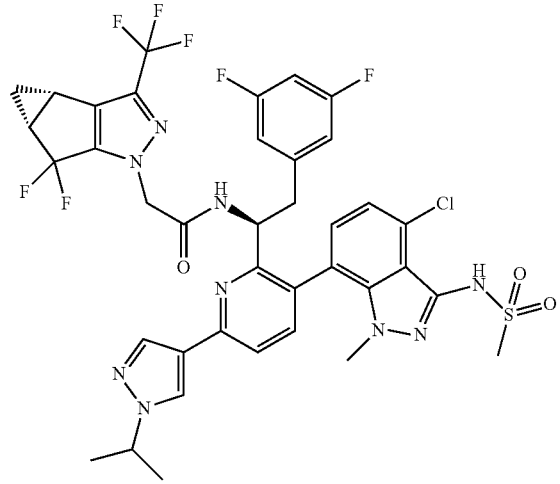

139
-continued
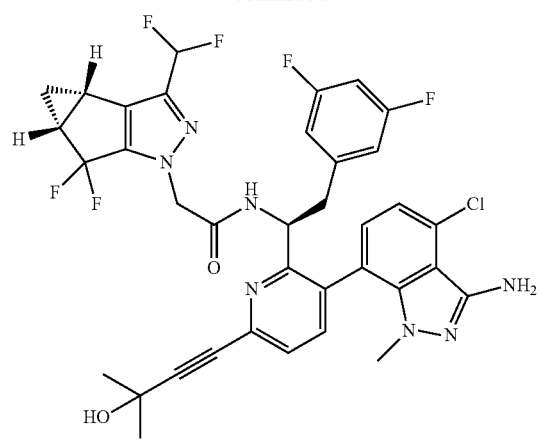
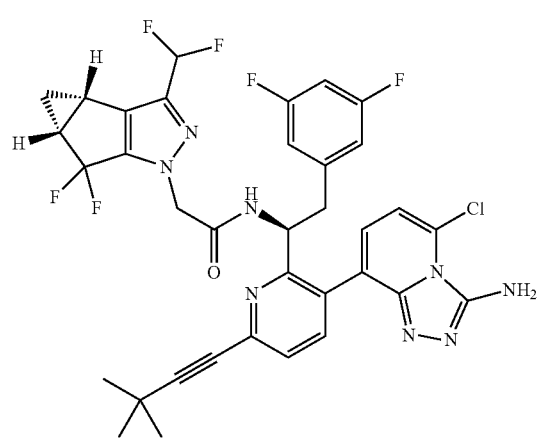
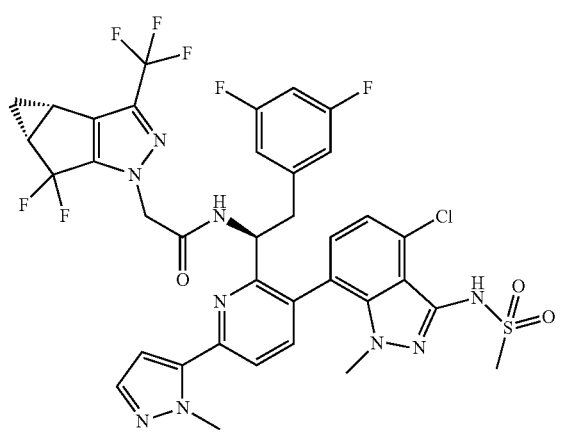
140
-continued
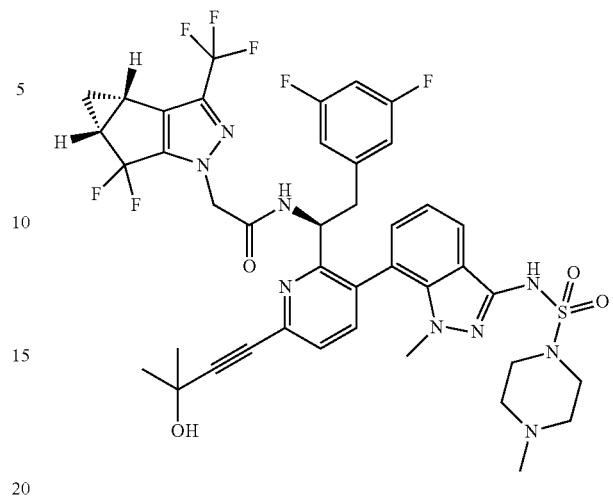
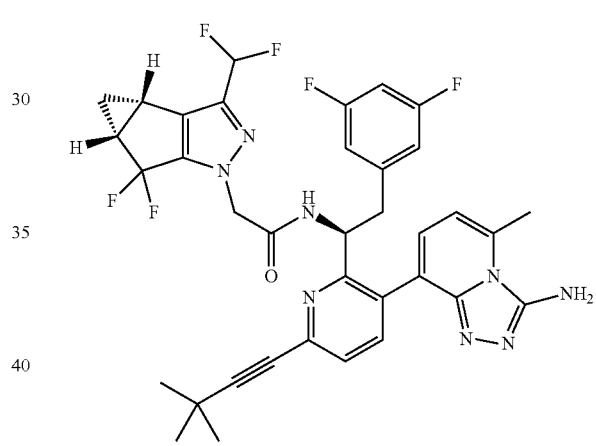
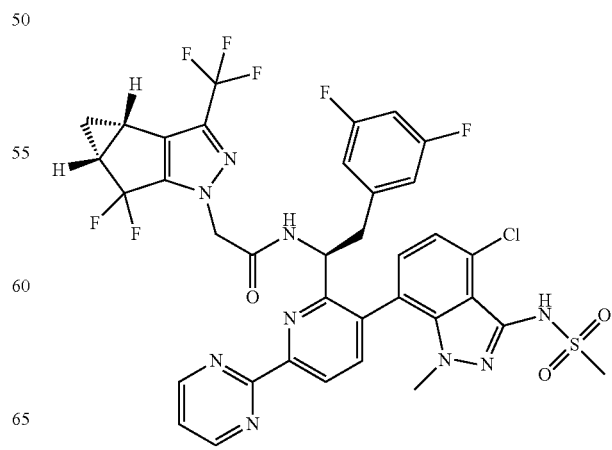

141
-continued
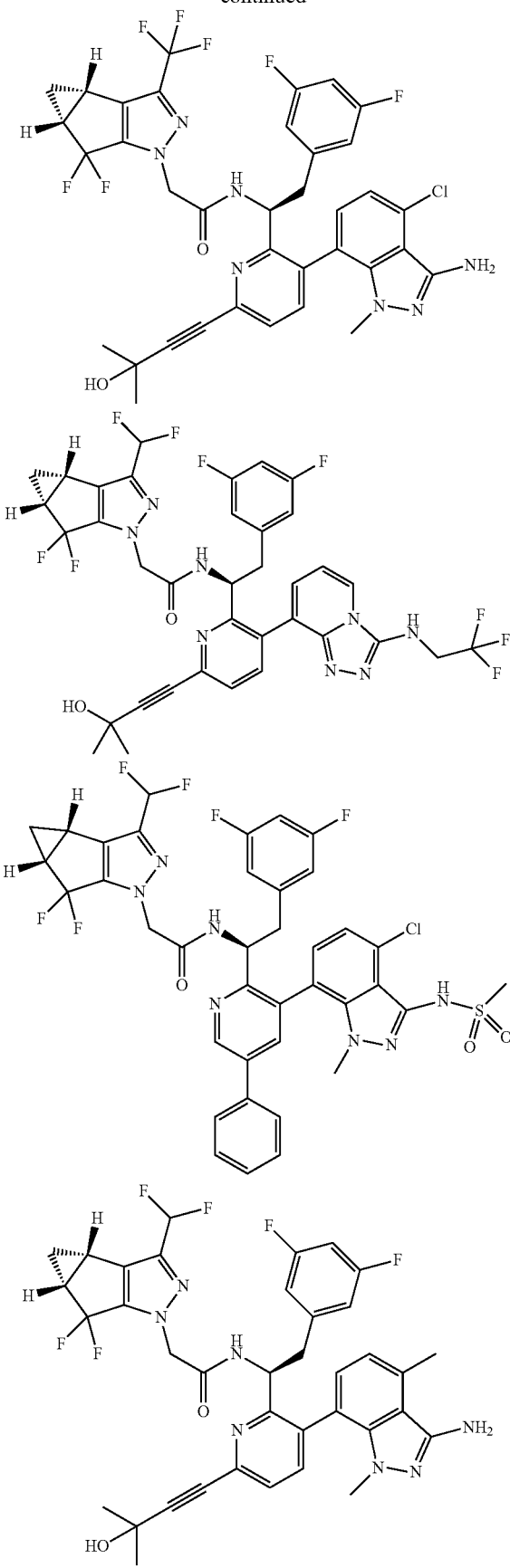
142
-continued
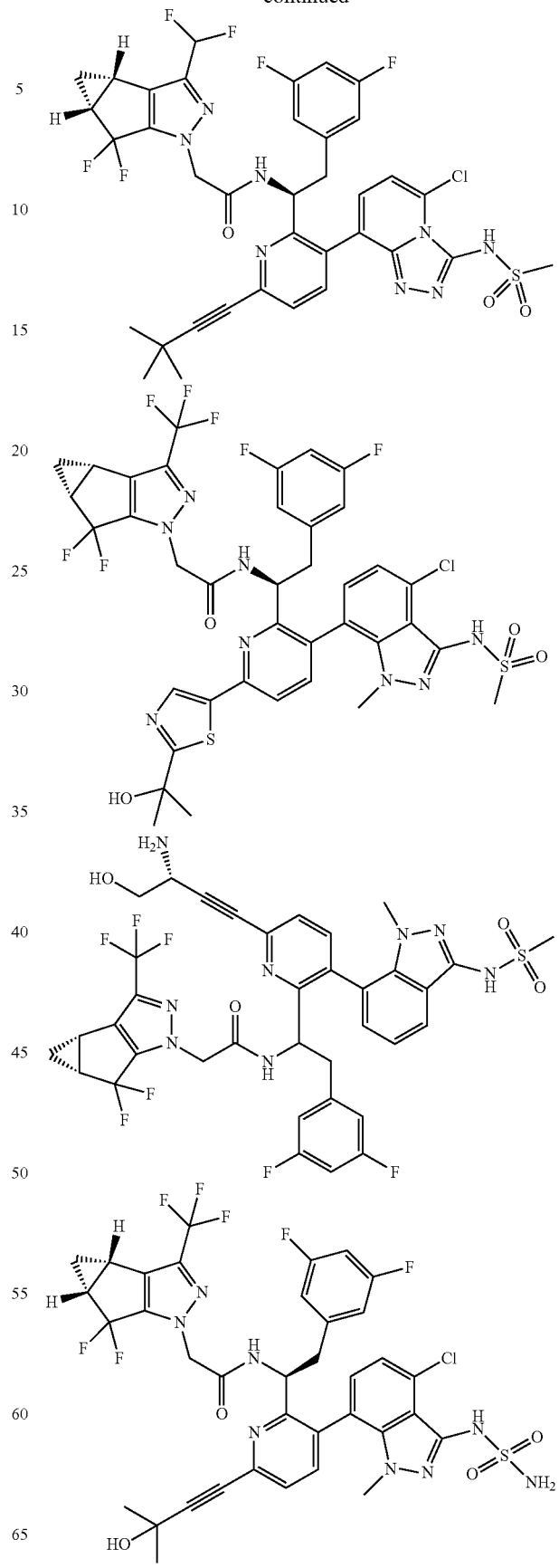

143
-continued
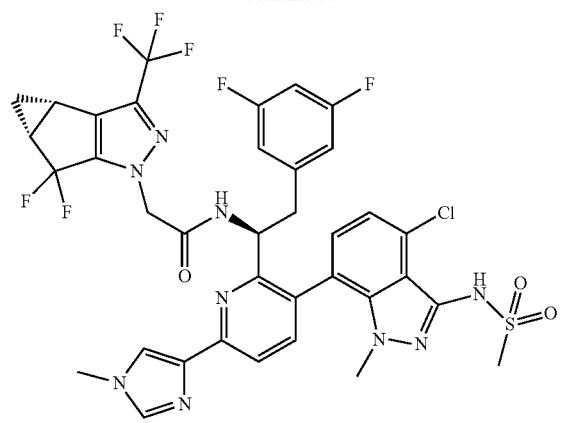
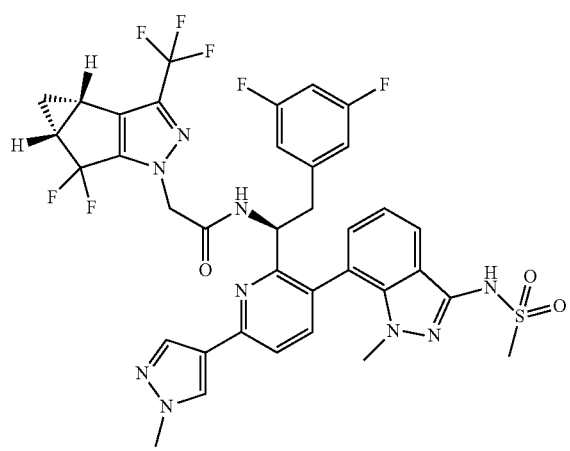
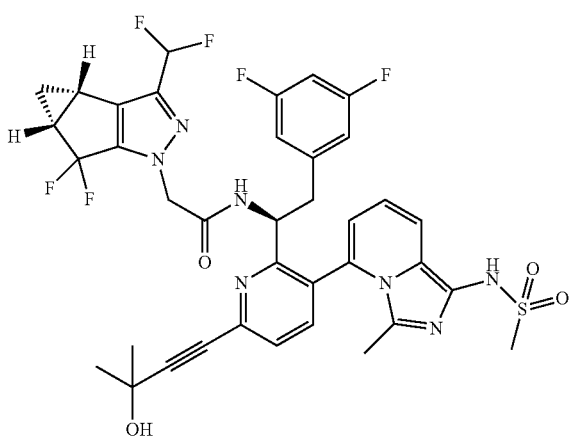
144
-continued
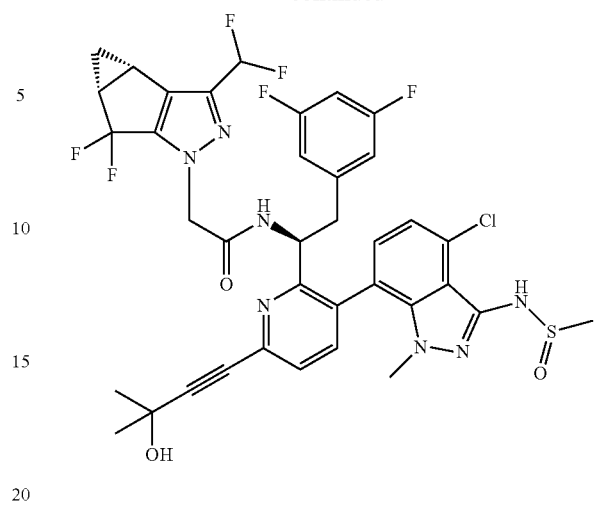
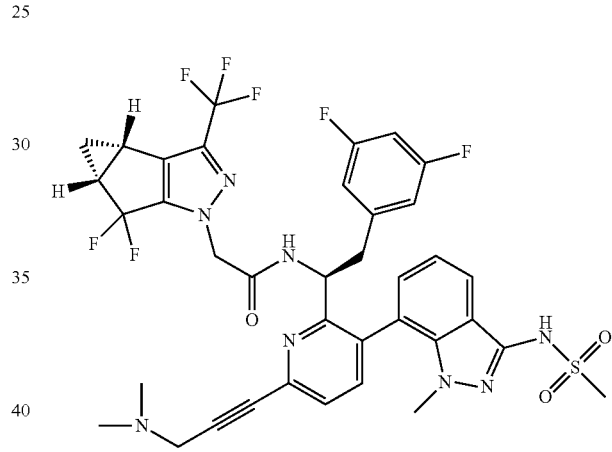
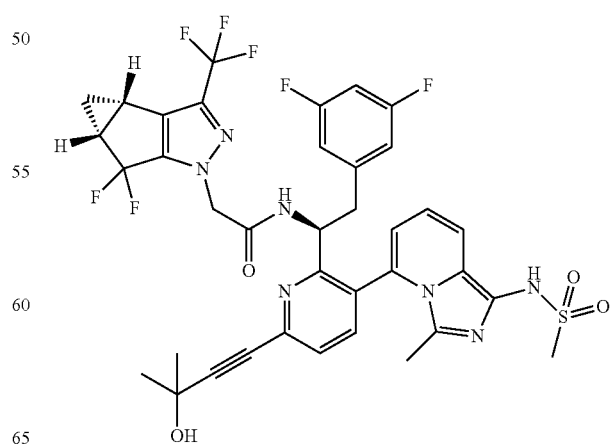

145
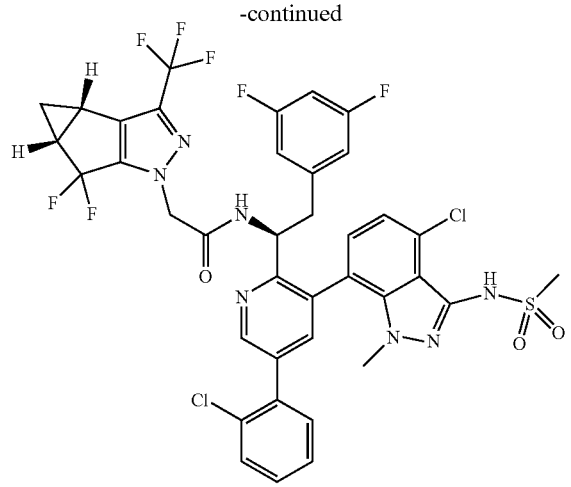
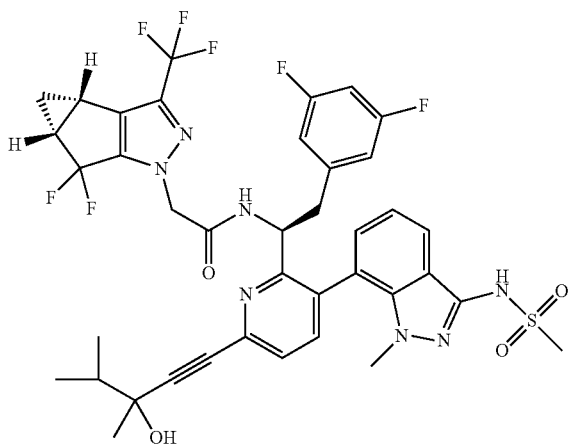
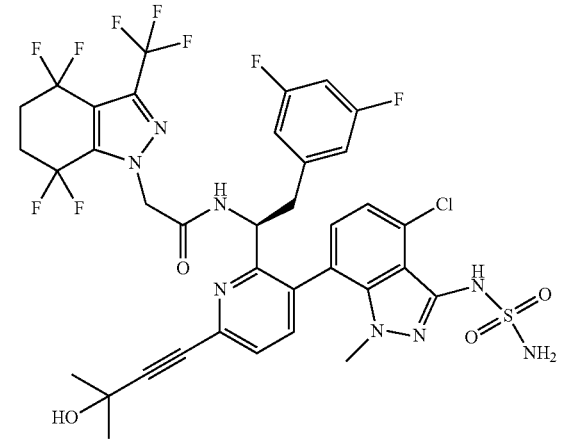
146
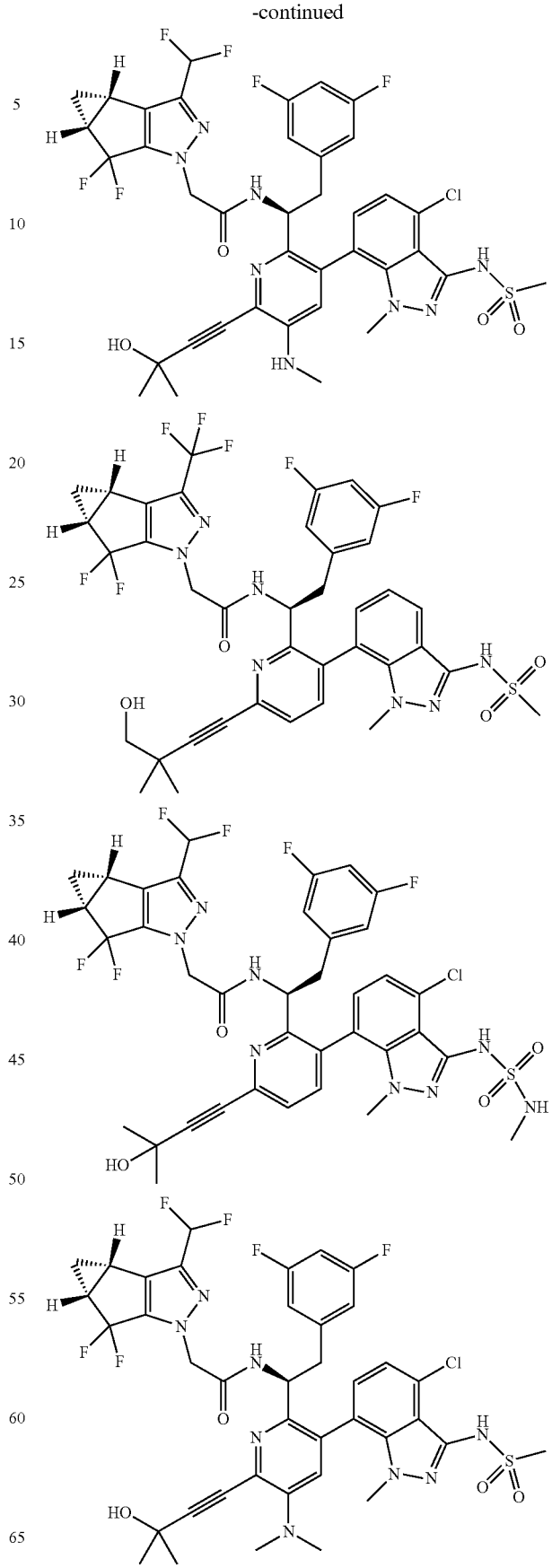

147
-continued
148
-continued
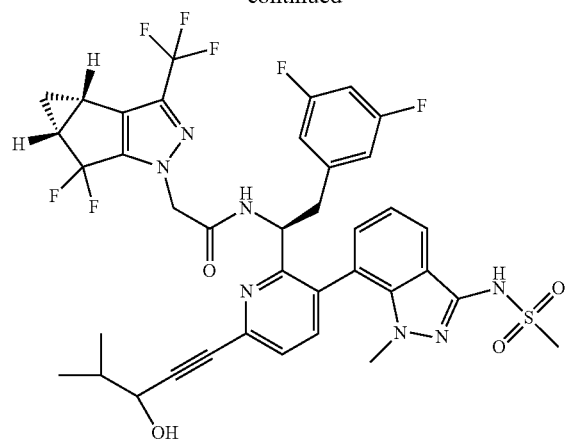
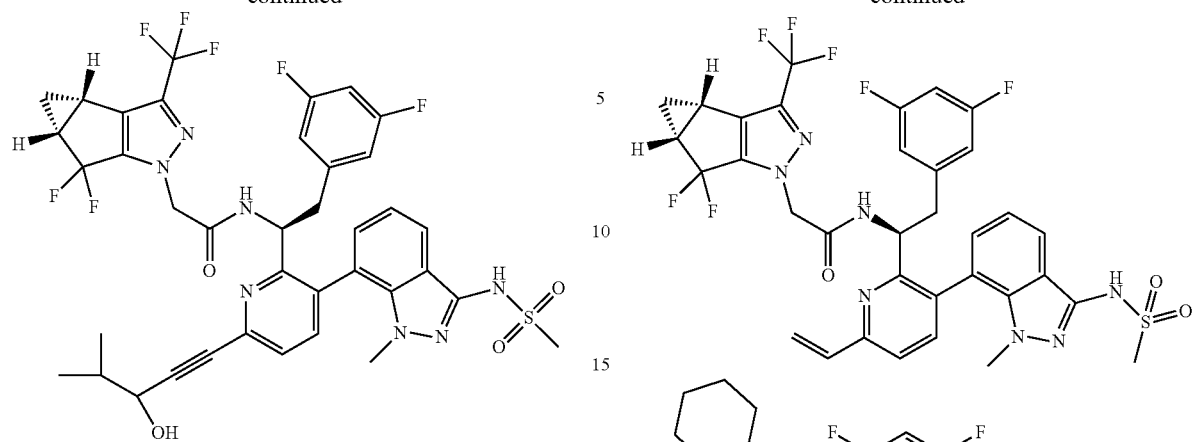
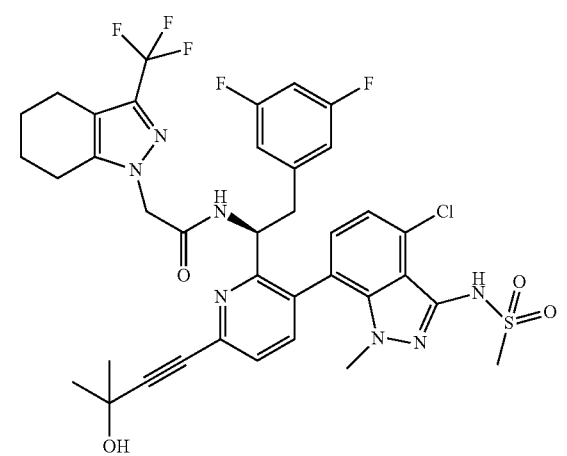
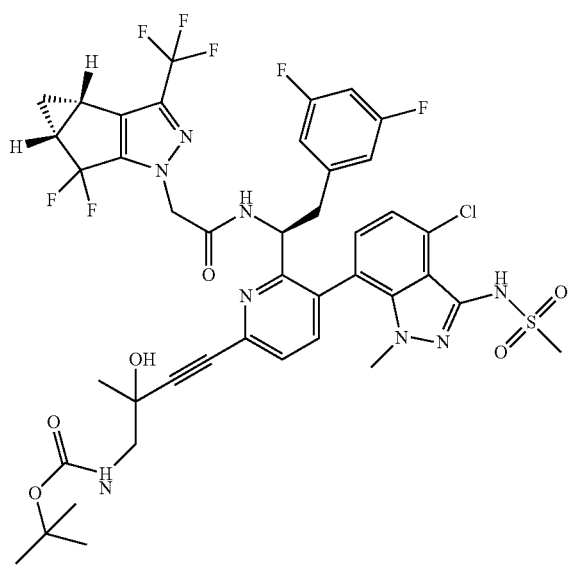

149
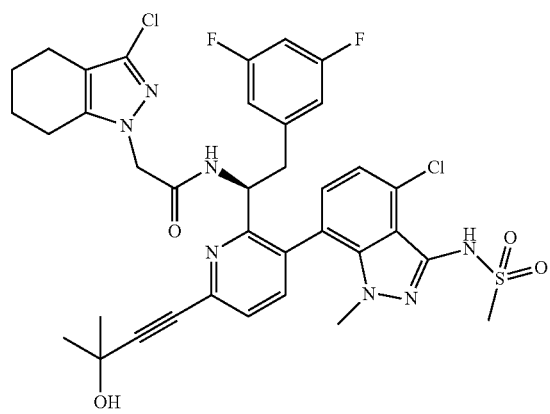
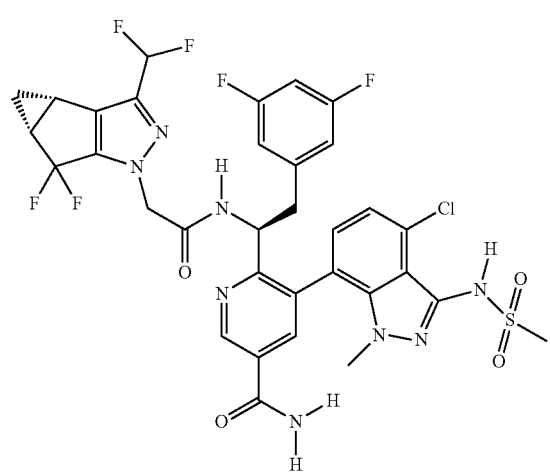
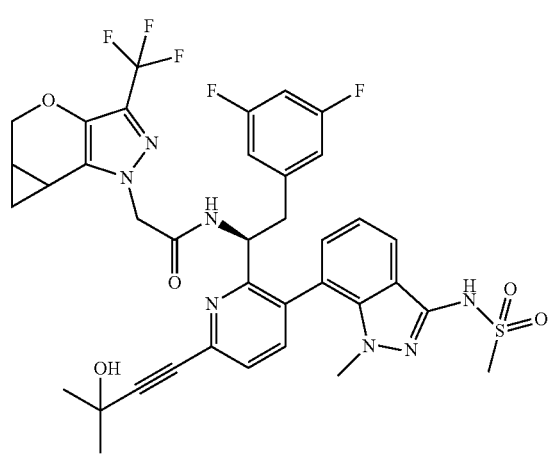
150
-continued
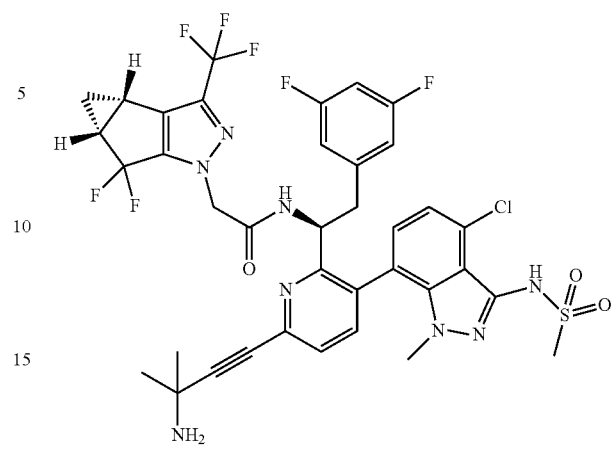
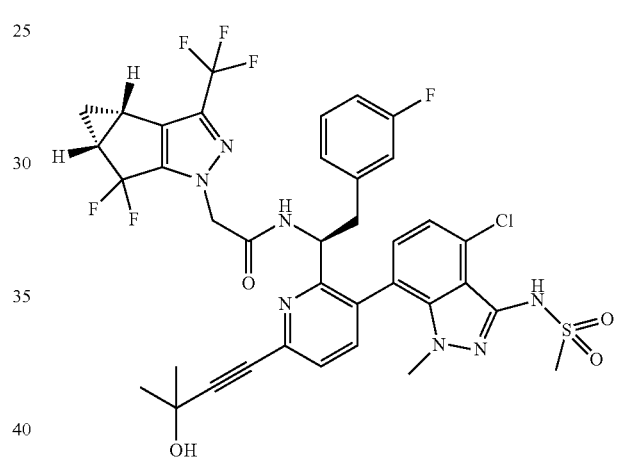
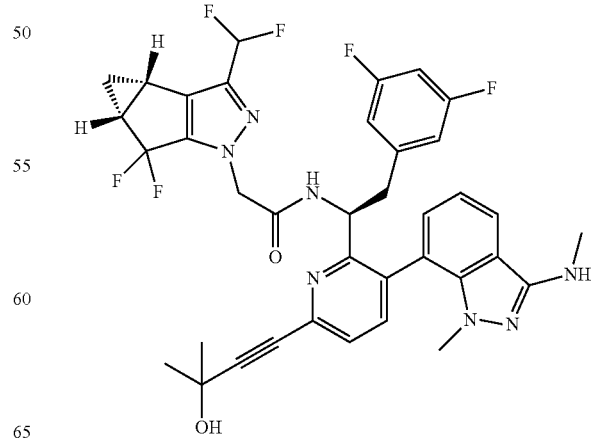

151
-continued
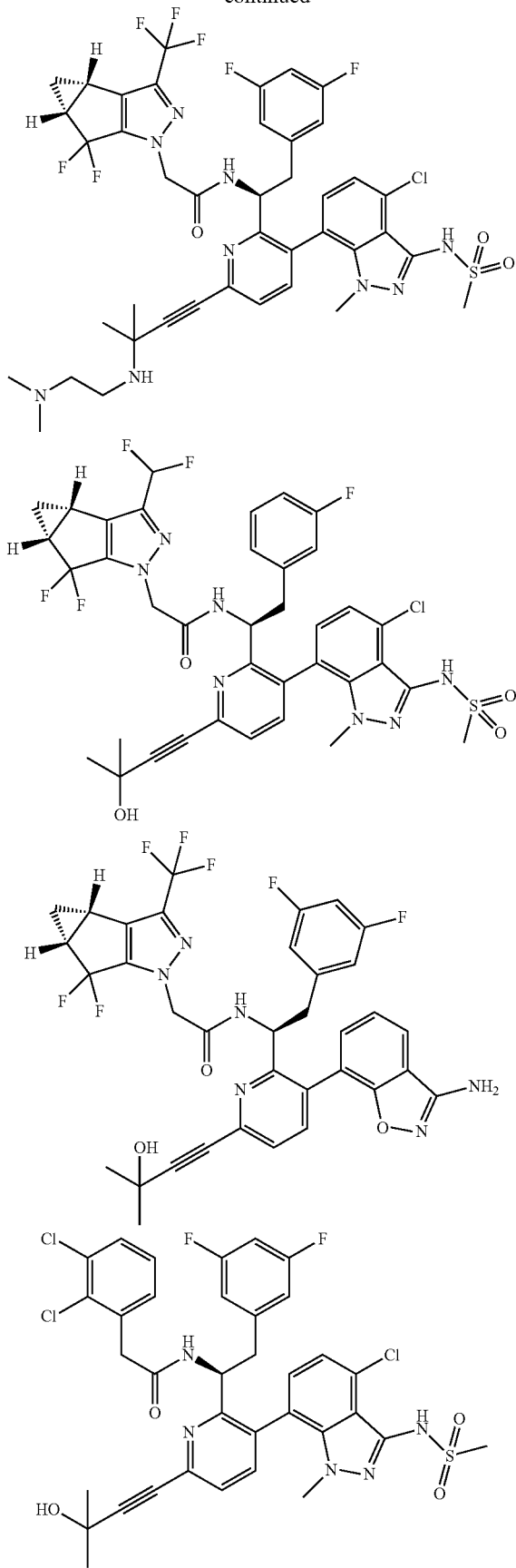
152
-continued
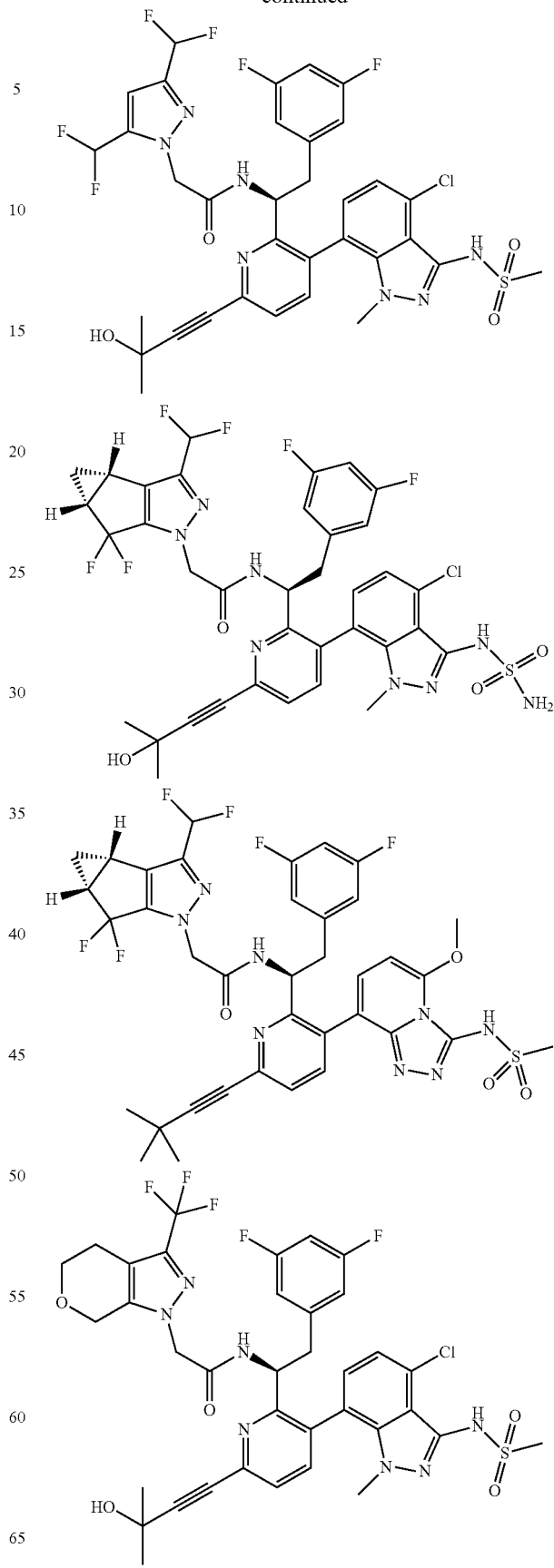

153
-continued
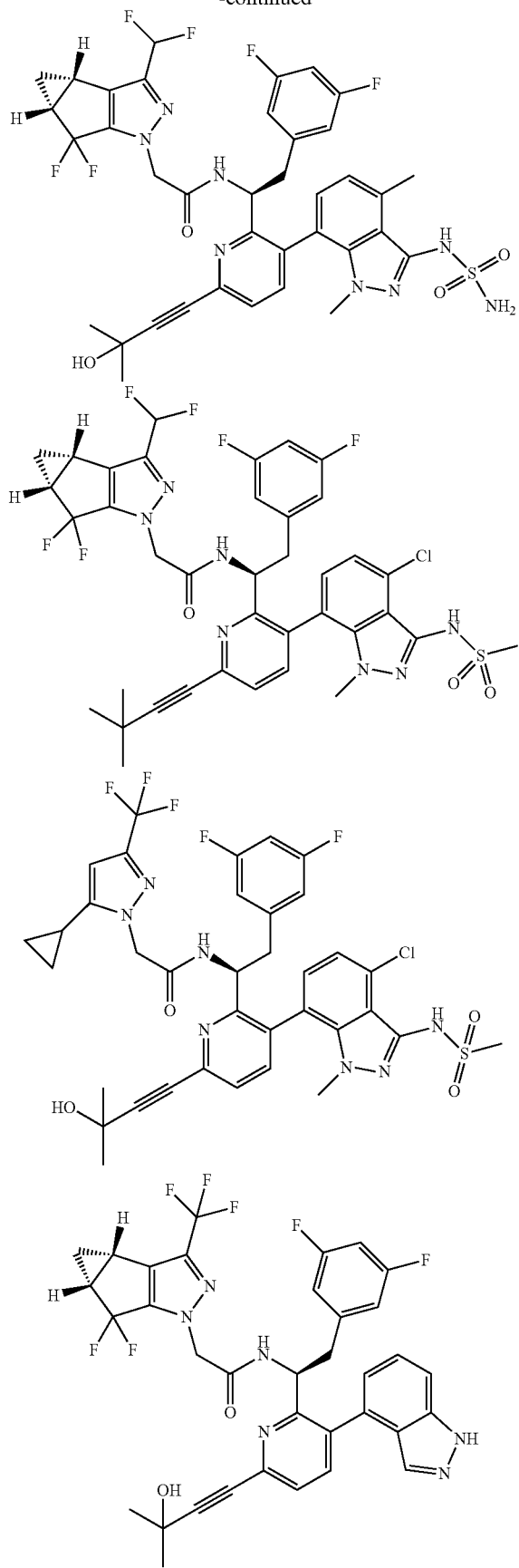
154
-continued
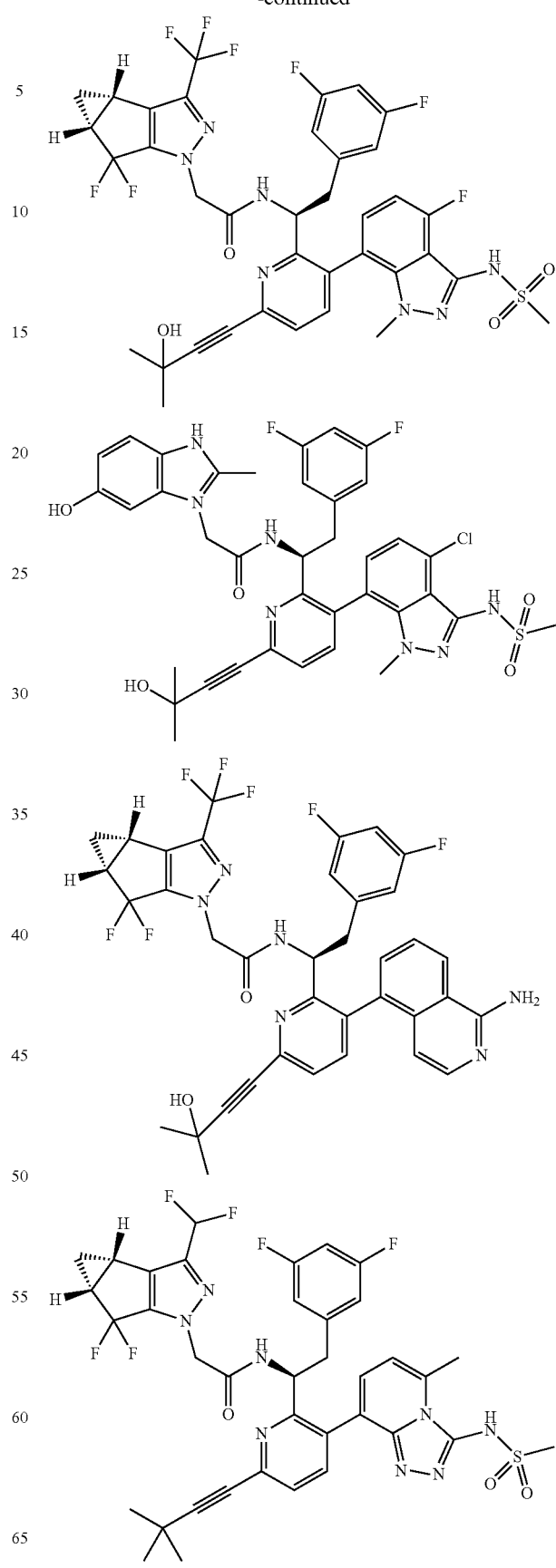

155
-continued
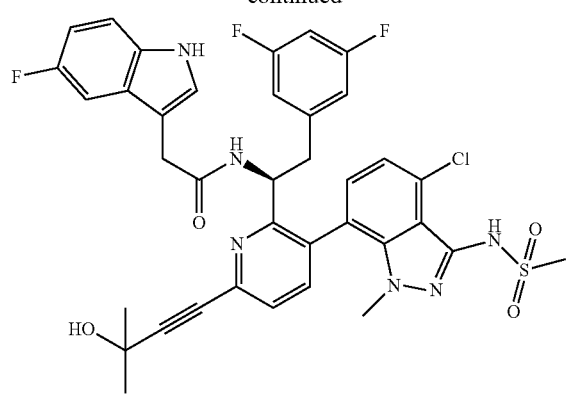
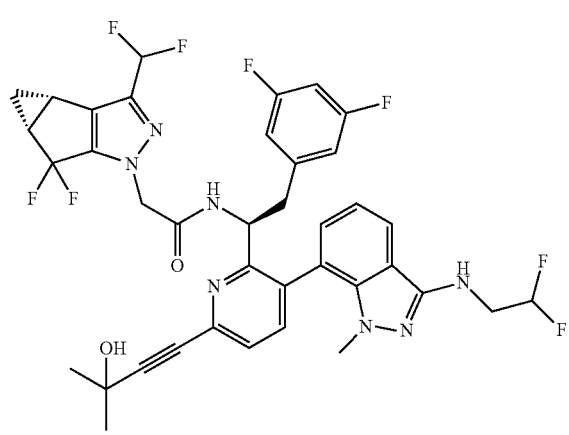
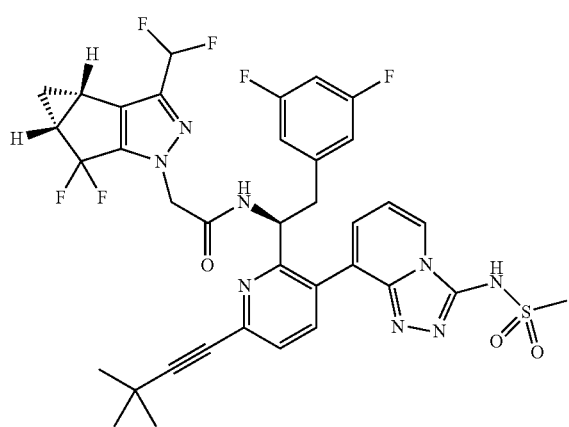
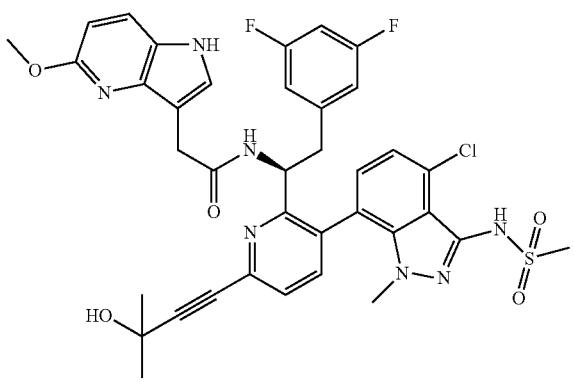
156
-continued
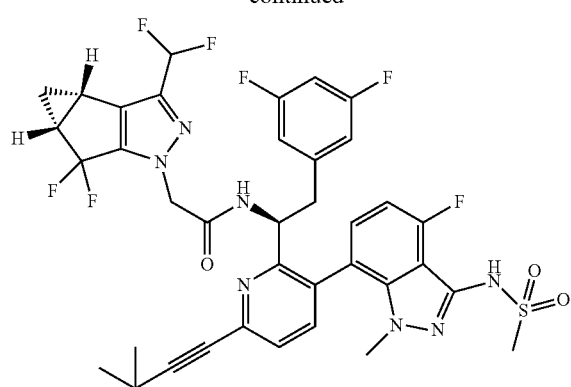
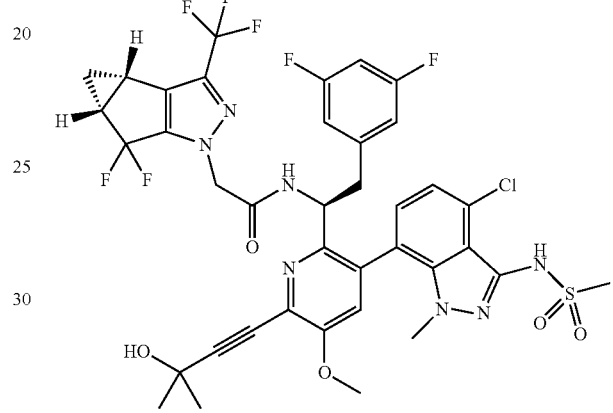
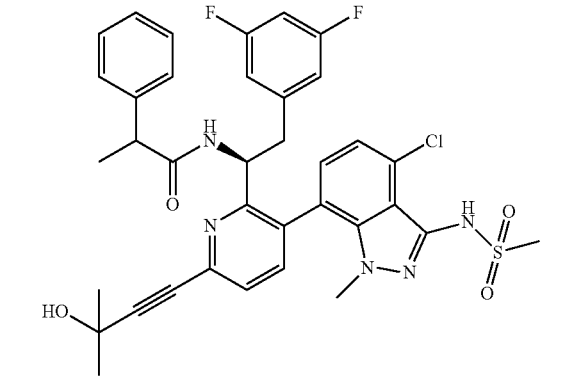
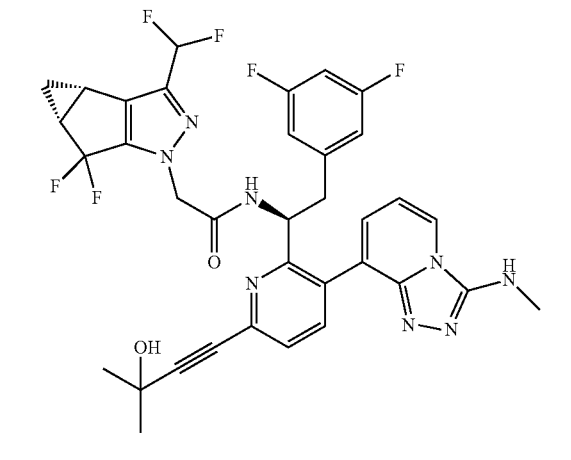

157
-continued
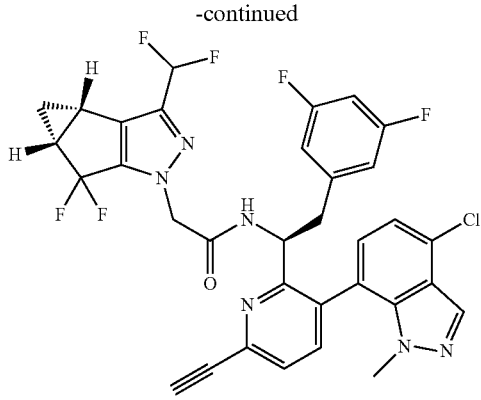
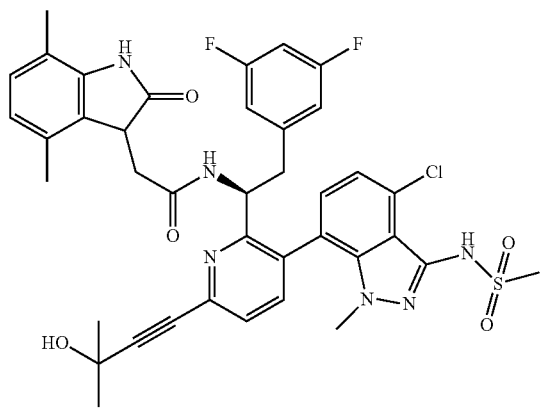
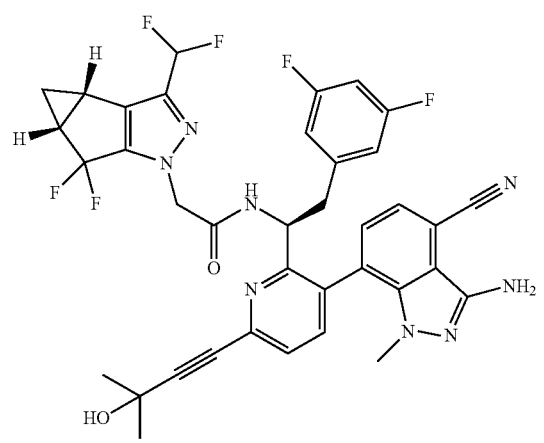
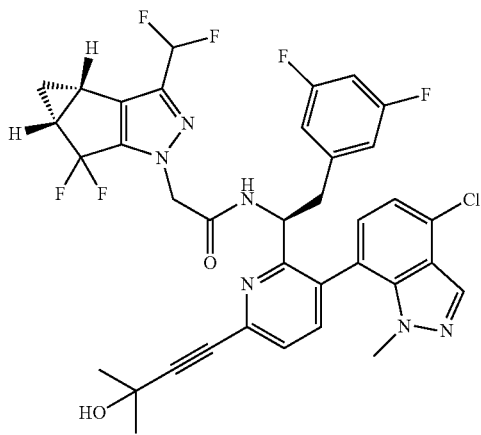
158
-continued
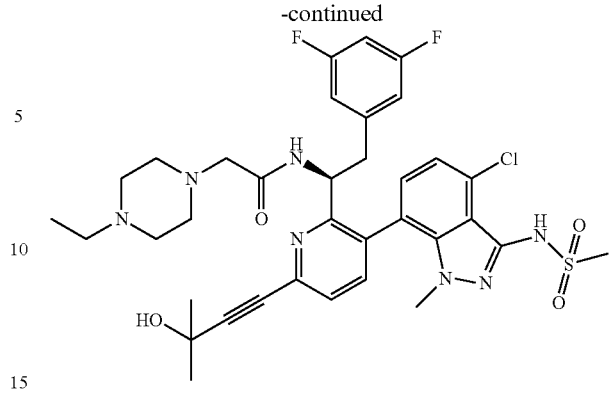
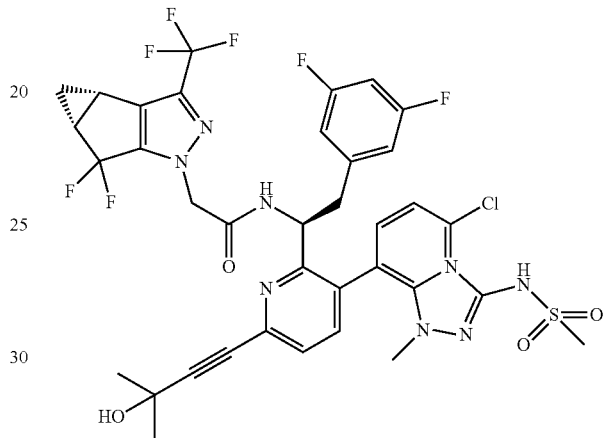
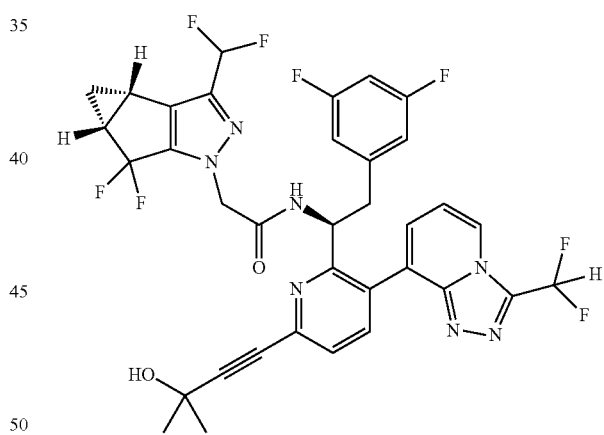
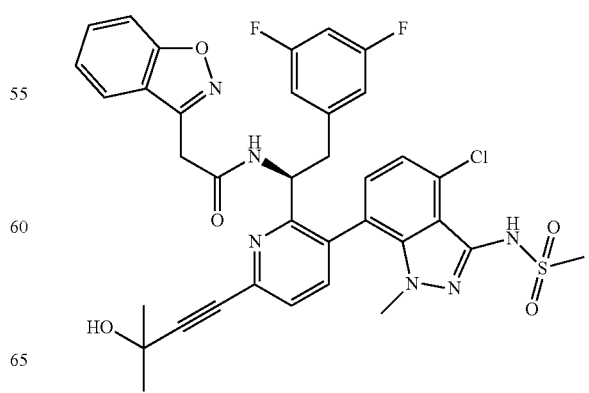

159
-continued
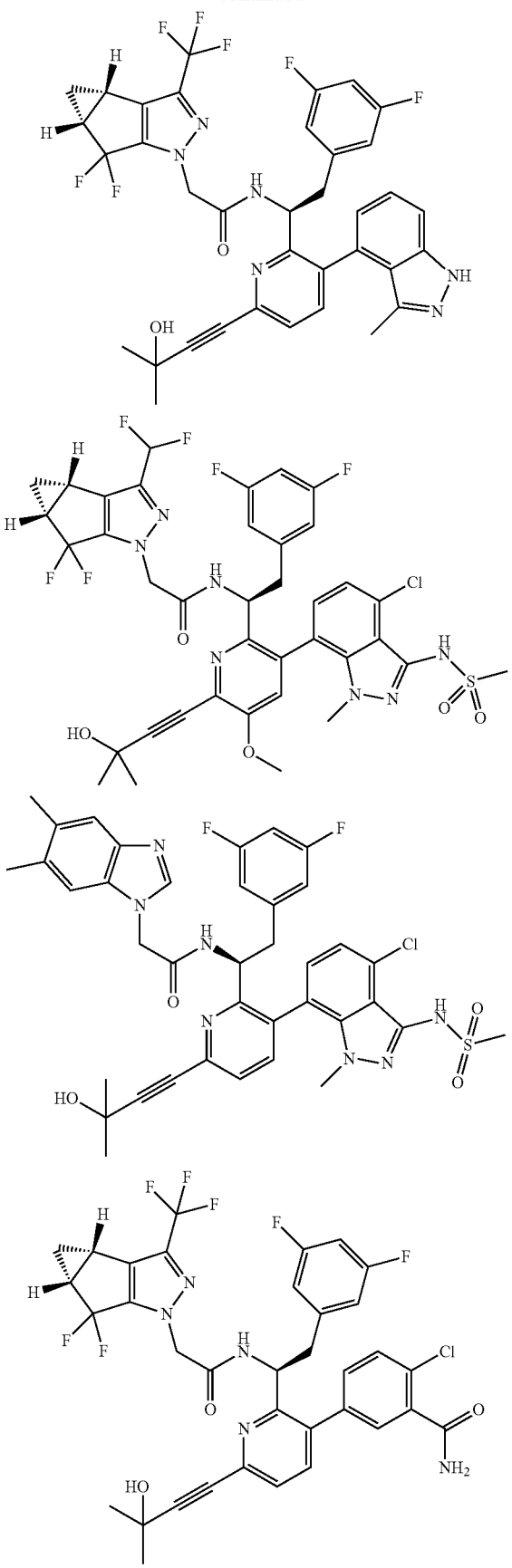
160
-continued
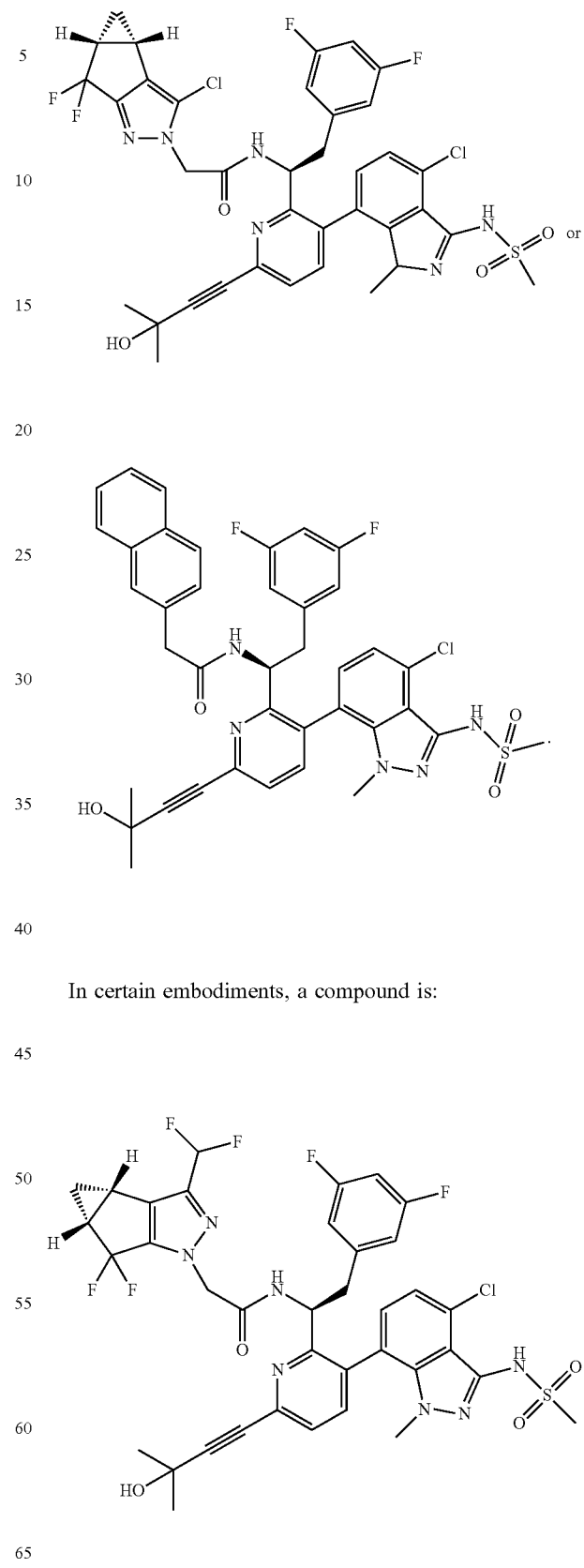
In certain embodiments, a compound is:
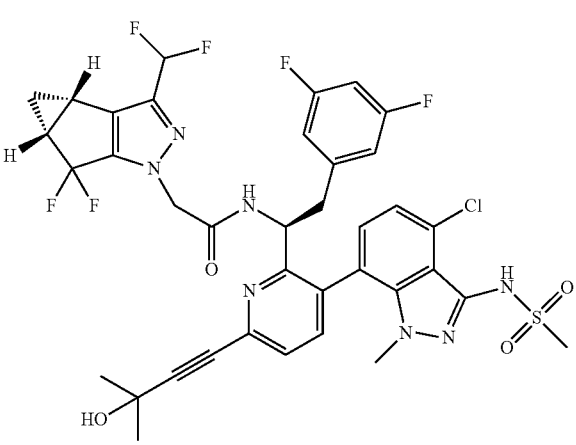 [SMILES: Cn1nc(NS(C)(=O)=O)c2c(Cl)ccc(-c3ccc(C#CC(C)(C)O)nc3[C@H](Cc3cc(F)cc(F)c3)NC(=O)Cn3nc(C(F)F)c4c3C(F)(F)[C@@H]3C[C@H]43)c21]
or a pharmaceutically acceptable salt thereof.

In certain embodiments, a compound is:

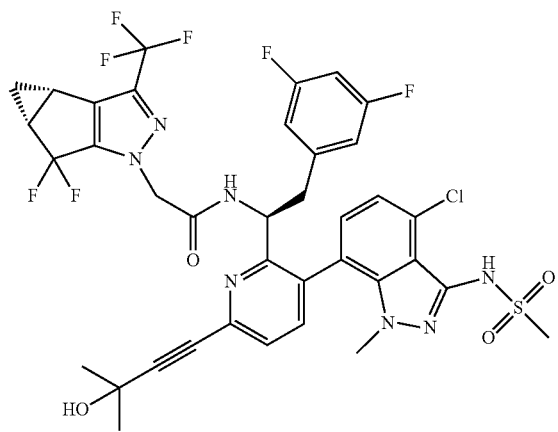 [SMILES: Cn1nc(NS(C)(=O)=O)c2c(Cl)ccc(-c3ccc(C#CC(C)(C)O)nc3[C@H](Cc3cc(F)cc(F)c3)NC(=O)Cn3nc(C(F)(F)F)c4c3C(F)(F)[C@@H]3C[C@H]43)c21]

or a pharmaceutically acceptable salt thereof.

In certain embodiments, a compound is:

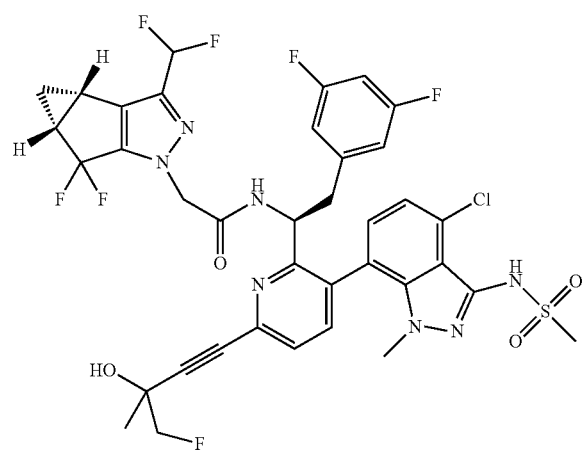 [SMILES: Cn1nc(NS(C)(=O)=O)c2c(Cl)ccc(-c3ccc(C#CC(C)(O)CF)nc3[C@H](Cc3cc(F)cc(F)c3)NC(=O)Cn3nc(C(F)F)c4c3C(F)(F)[C@@H]3C[C@H]43)c21]

or a pharmaceutically acceptable salt thereof.

In certain embodiments, a compound is:

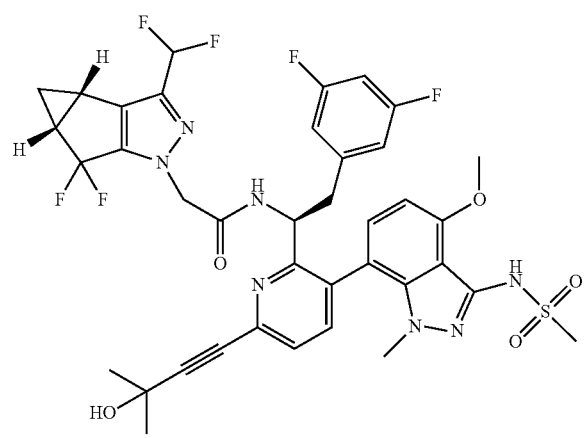 [SMILES: COc1ccc(-c2ccc(C#CC(C)(C)O)nc2[C@H](Cc2cc(F)cc(F)c2)NC(=O)Cn2nc(C(F)F)c3c2C(F)(F)[C@@H]2C[C@H]32)c2c1c(NS(C)(=O)=O)nn2C]

or a pharmaceutically acceptable salt thereof.

In certain embodiments, a compound is:

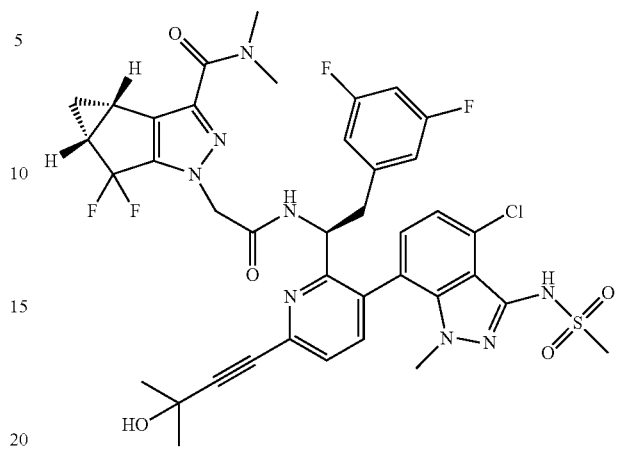

or a pharmaceutically acceptable salt thereof.

In certain embodiments, a compound is:

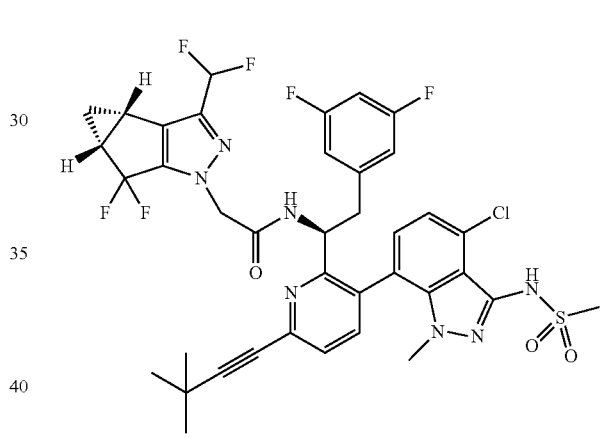

or a pharmaceutically acceptable salt thereof.

General Synthetic Procedures

The following schemes describe methods that are useful for preparing compounds of formula I. The following schemes similarly describe methods that are useful for preparing compounds of formula III.

Scheme 1

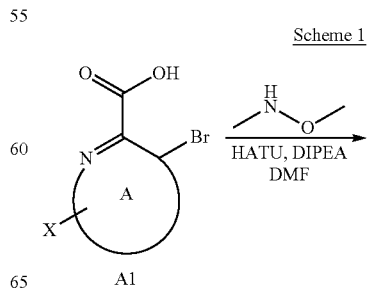

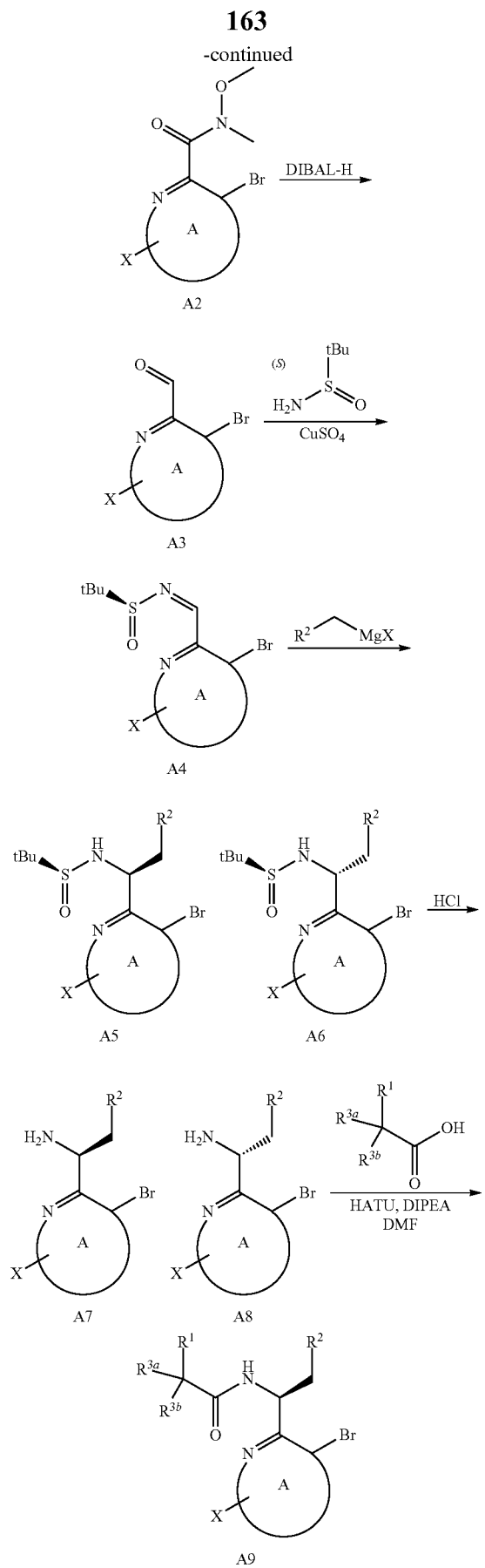

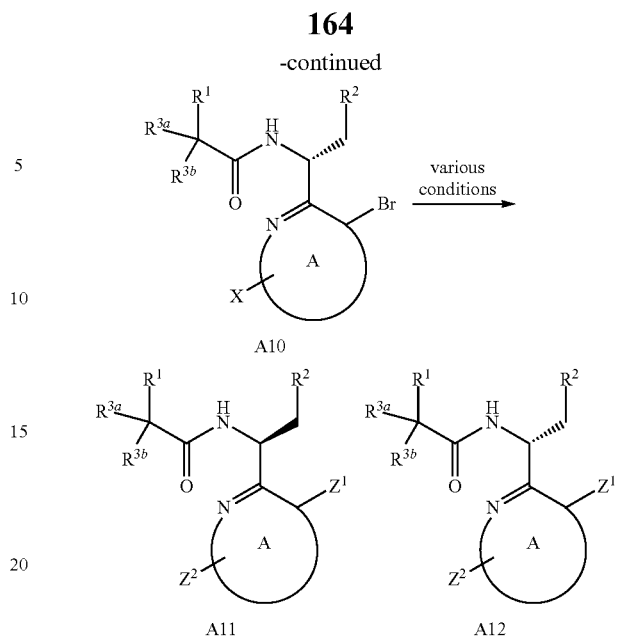

Scheme 1 describes a general stereoselective route which is used to prepare compounds of formula I. The scheme is also be used to prepare compounds of formula III. Heteroaryl acids of formula A1 (where X represents diversifiable chemical group such as $NH_2$, SH, or halogen that are suitably protected) are converted to the corresponding aldehydes then condensed with a chiral auxiliary to provide a stereoselective addition of a nucleophilic reagent. Depicted in Scheme 1 is the conversion of a heteroaryl acid A1 containing two diversifiable functional groups (e.g., X and Br) to the corresponding aldehyde. This is followed by the condensation of the aldehyde A3 with (S) tert-butane sulfinamide and the addition of a Grignard reagent to provide a mixture of A5 and A6 enriched in A5. This mixture is separated by column chromatography on silica gel to provide pure diastereomers. Removal of the auxiliary provides amines A7 and A8 which are coupled to a variety of carboxylic acids to provide heteroaryl compounds of formula A9 and A10. Diversification of A9 and A10 is accomplished by a variety of methods including alkylation, acylation, cyanation, nucleophilic aromatic displacement, and metal catalyzed cross coupling reactions such as Suzuki couplings, Buchwald-Hartwig type couplings, and Sonogashira couplings.

Scheme 2 describes a general stereoselective route which can be used to prepare compounds of formulas I and III.

Scheme 2

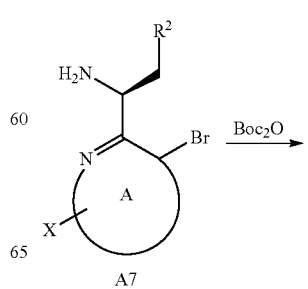

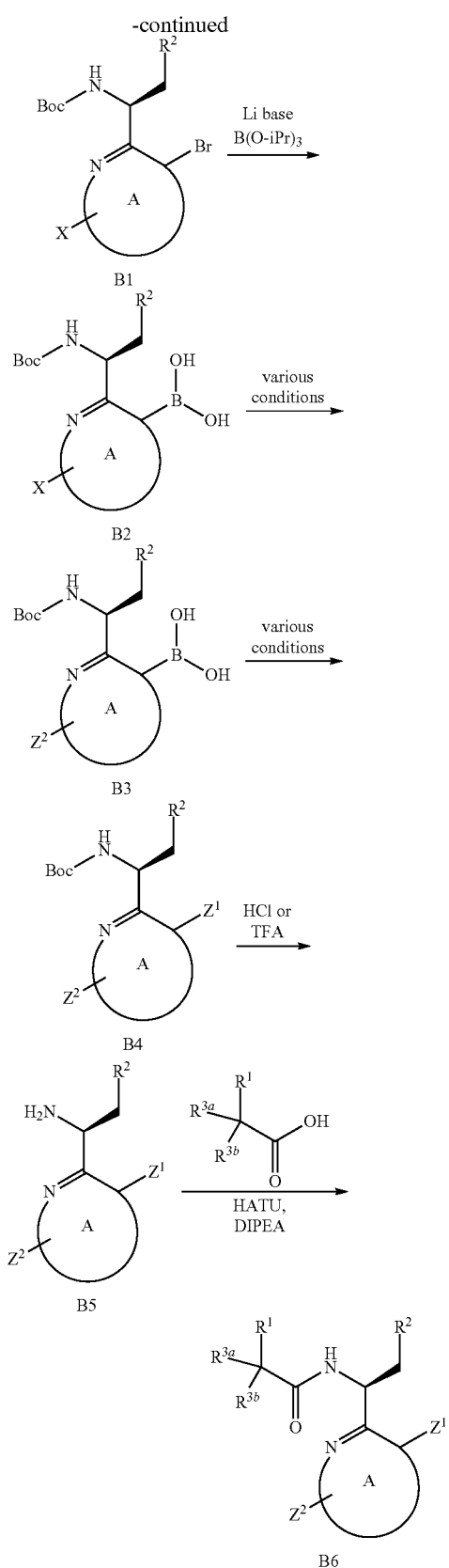

Depicted in Scheme 2 is the protection of amine A7 to a compound of formula B1. This is followed by the conversion of the Br to the corresponding boronic acid. Diversi-fication of the functional group X and boronic acid is accomplished by a variety of methods including alkylation, acylation, cyanation, nucleophilic aromatic displacement, and metal catalyzed cross coupling reactions such as Suzuki couplings, Buchwald-Hartwig type couplings, and Sonogashira couplings to provide compounds of formulas B3 and B4. Deprotection followed by amide formation with a variety of carboxylic acids provides compounds of formula I.

Combination Therapy

In one embodiment, the invention provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

A compound as disclosed herein (e.g., a compound of any of formulas I and III or a pharmaceutically acceptable salt thereof) may be combined with one or more additional therapeutic agents in any dosage amount of the compound (e.g., from 50 mg to 300 mg of compound).

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents.

In one embodiment, the invention provides pharmaceutical compositions comprising a compound disclosed herein, or a pharmaceutically acceptable salt thereof, in combination with at least one additional therapeutic agent, and a pharmaceutically acceptable carrier. For example, the therapeutic agent used in combination with the compound disclosed herein can be any anti-HIV agent.

In one embodiment, combination pharmaceutical agents comprising a compound disclosed herein, or a pharmaceutically acceptable salt thereof, in combination with one or more additional therapeutic agents are provided.

One embodiment provides pharmaceutical compositions comprising a compound disclosed herein, or a pharmaceutically acceptable salt thereof, in combination with at least one additional therapeutic agent, and a pharmaceutically acceptable carrier. In one embodiment, the additional therapeutic agent may be an anti-HIV agent. For example, in some embodiments, the additional therapeutic agent is selected from the group consisting of HIV protease inhibiting compounds (HIV protease inhibitors), HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, capsid polymerization inhibitors or capsid disrupting compounds such as those disclosed in US 2013/0165489 (University of Pennsylvania), and WO 2013/006792 (Pharma Resources), pharmacokinetic enhancers, and other drug for treating HIV, and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP- 450), JE-2147 (AG1776), L-756423, RO0334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir disoproxil hemifumarate, tenofovir disoproxil, tenofovir alafenamide fumarate, tenofovir alafenamide hemifumarate, tenofovir alafenamide, GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by reference in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB 15050, PF-232798 (Pfizer), and CCR5mAb004;

(13) CD4 attachment inhibitors selected from the group consisting of ibalizumab (TMB-355) and BMS-068 (BMS-663068);

(14) pharmacokinetic enhancers selected from the group consisting of cobicistat, ritonavir, and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In certain embodiments, a compound disclosed herein, or a pharmaceutically acceptable salt thereof, is combined with two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleotide inhibitor of reverse transcriptase, and an HIV protease inhibiting compound. In a further embodiment, a compound disclosed herein, or a pharmaceutically acceptable salt thereof, is combined with an HIV nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleotide inhibitor of reverse transcriptase, an HIV non-nucleoside inhibitor of reverse transcriptase, and a pharmacokinetic enhancer.

In a specific embodiment, a compound disclosed herein, or a pharmaceutically acceptable salt thereof, is combined with tenofovir, tenofovir disoproxil fumarate, tenofovir disoproxil hemifumarate, tenofovir disoproxil, tenofovir alafenamide fumarate, tenofovir alafenamide hemifumarate, or tenofovir alafenamide. In another specific embodiment, a compound disclosed herein, or a pharmaceutically acceptable salt thereof, is combined with tenofovir disoproxil fumarate, tenofovir disoproxil hemifumarate, or tenofovir alafenamide. In a specific embodiment, a compound disclosed herein, or a pharmaceutically acceptable salt thereof, is combined with emtricitibine, abacavir or lamivudine.

In a specific embodiment, a compound disclosed herein, or a pharmaceutically acceptable salt thereof, is combined with one of: tenofovir, tenofovir disoproxil fumarate, tenofovir disoproxil hemifumarate, tenofovir disoproxil, tenofovir alafenamide fumarate, tenofovir alafenamide hemifumarate, or tenofovir alafenamide and one of: emtricitibine, abacavir or lamivudine. In a specific embodiment, a compound disclosed herein, or a pharmaceutically acceptable salt thereof, is combined with one of: tenofovir disoproxil fumarate, tenofovir disoproxil hemifumarate, tenofovir alafenamide fumarate, or tenofovir alafenamide and one of: emtricitibine or abacavir.

In some embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of any of formulas I and III or a pharmaceutically acceptable salt thereof) may be combined with the agents provided herein in any dosage amount of the compound (e.g., from 50 mg to 300 mg of compound) the same as if each combination of dosages were specifically and individually listed.

In some embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In some embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In some embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of any of formulas I and III or a pharmaceutically acceptable salt thereof) may be combined with the agents provided herein in any dosage amount of the compound (e.g., from 50 mg to 300 mg of compound) the same as if each combination of dosages were specifically and individually listed.

In some embodiments, one or more of the compounds disclosed herein are combined with one or more other active therapeutic agents in a unitary dosage form for simultaneous or sequential administration to a patient. In certain embodiments, a pharmaceutical composition including one or more of the compounds disclosed herein combined with one or more other active therapeutic agents is provided. In certain embodiments, the compounds disclosed herein are combined with one or more other active therapeutic agents in a solid dosage form. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations described herein that are suitable for oral administration may be presented as discrete units including but not limited to capsules, cachets or tablets each containing a predetermined amount of the active ingredient.

Pharmaceutical formulations disclosed herein comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In some embodiments, a dosage form (e.g., for oral administration to humans) contains: from 10 mg to 1000 mg or from 50 mg to 1000 mg or from 100 mg to 1000 mg or from 200 mg to 1000 mg or from 300 mg to 1000 mg or from 10 mg to 800 mg or from 10 mg to 600 mg or from 10 mg to 500 mg or from 10 mg to 400 mg or from 10 mg to 300 mg or from 50 mg to 800 mg or from 100 mg to 600 mg or from 150 mg to 500 mg or from 200 mg to 400 mg or from 50 mg to 500 mg or from 10 mg to 300 mg or from 50 mg to 300 mg or from 10 mg to 200 mg or from 50 mg to 200 mg or from 100 mg to 300 mg or from 100 mg to 200 mg or from 200 mg to 300 mg of active material (e.g., a compound of any of formulae I or III). In some embodiments, a dosage form for oral administration to humans contains at least any of 10, 25, 50, 100, 150, 200, 250 or 300 mg and no more than 500 or 800 or 1000 mg of active material (e.g., from at least 50 mg to no more than 500 mg). In some embodiments, a dosage form for oral administration to humans contains at least any of 10, 25, 50, 100, 150, 200, 250 or 300 mg or no more than 500 or 800 or 1000 mg of active material. In some embodiments, a dosage form for oral administration to humans contains any of 10, 25, 50, 100, 150, 200, 250, 300, 350, 400, 450, 500, 550, 600, 650, 700, 750, 800, 850, 900, 950, or 1000 mg of active material. It is understood that a dosage form in an amount provided herein may be administered to a patient (e.g., a human in need thereof) in accordance with a dosing regimen provided herein, such as once, twice or thrice daily dosing. In one aspect, a dosing regimen provides for administration of at least 10 mg and no more that 1,000 mg of active material (e.g., a compound of any of formulas I or III) daily, and it is understood that the amount may be provided in any suitable dosage form and amount (e.g., 500 mg twice daily or 1,000 mg once daily would provide the same amount of 1,000 mg/day dosing). The invention embraces once daily dosing to an individual (e.g., a human in need thereof) of a dosage form of compound (e.g., a compound of any of formulas I or III) containing at least 50 mg and not more than 300 mg of compound. In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds disclosed herein is that they are orally bioavailable and can be dosed orally.

Dosing Regimen

The compound, such as a compound of any of Formulas I and III, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of any of Formulas I and III may be adjusted over the course of the treatment, e.g., based on the judgment of the administering physician.

The compound may be administered to an individual (e.g., a human) in an effective amount. In one aspect, the compound is administered once daily. In one aspect, the compound is administered twice a day. In one aspect, the compound is administered three times daily. It is understood that the compound may be administered in any dosage amount provided herein, such as a dosage amount that would provide at least 10 mg/day dosing and no more than 1,000 mg/day dosing. Once daily oral dosing is embraced, such as by administering a dosage form containing from 50 mg to 300 mg of compound.

The antiviral properties of a compound of the invention may be determined using Test A described below.

Test A: Antiviral Assay in MT4 Cells

For the antiviral assay, 40 µL of a concentration required to achieve a final effective 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glo™ Reagent (catalog #G7571, Promega Biosciences, Inc., Madison, Wis.) was added to each well containing MT-4 cells. Cell lysis was carried out by incubating at room temperature for 10 min and then chemiluminescence was read. EC50 values were calculated as the compound concentration that caused a 50% decrease in luminescence signal, a measure of HIV-1 replication. Percent inhibition of virus-induced cell killing calculated from the dose response curve at 2 µM and 0.2 µM drug concentration is shown in the table below.

Test B: Cytotoxicity Assay

Compound cytotoxicity and the corresponding CC50 values was determined using the same protocol as described in the antiviral assay (Test A) except that uninfected cells were used.

Compounds of the present invention demonstrate antiviral activity (Test A) as depicted in the table below. Shown below are the corresponding values for CC50 and percent inhibition of virus-induced cell killing in the presence of 2 µM and 0.2 µM drug concentration.

| Compound | % inhibition at 2 µM | % inhibition at 0.2 µM | CC50 (nM) |
|---|---|---|---|
| 1B | 77 | 17 | 8569 |
| 2 | 90 | 79 | 14347 |
| 3D | 82 | 82 | 4149 |
| 4H | 74 | 8 | 22793 |
| 5G | 58 | 3 | >53192 |
| 6 | 73 | 5 | >53192 |

| Compound | % inhibition at 2 μM | % inhibition at 0.2 μM | CC50 (nM) |
|---|---|---|---|
| 7 | 92 | 8 | 5664 |
| 8C | 86 | 6 | 21955 |
| 9B | 95 | 92 | 14557 |
| 10B | 85 | 1 | >53192 |
| 11 | 66 | 3 | >53192 |
| 12 | 58 | 1 | >53192 |
| 13 | 0 | — | >53192 |
| 14E | 89 | 87 | 6824 |
| 15 | 94 | 93 | 10261 |
| 16C | 65 | 23 | 3670 |
| 17 | 80 | 95 | 12556 |
| 18 | 90 | 96 | 6934 |
| 19G | 93 | 97 | 19626 |
| 20 | 80 | 96 | 11162 |
| 21H | 92 | 92 | 7628 |
| 22C | 92 | 92 | 4949 |
| 23B | 88 | 83 | 7619 |
| 24B | 83 | 78 | 5921 |
| 25 | 89 | 89 | 9139 |
| 26 | 100 | 84 | 10014 |
| 27G | 89 | 89 | 10412 |
| 28 | 84 | 71 | 12175 |
| 29B | 81 | 80 | 15266 |
| 30 | 91 | 1 | 8582 |
| 31 | 89 | 89 | 8034 |
| 32 | 84 | 84 | 9177 |
| 33F | 93 | 93 | 12867 |
| 34 | 78 | 78 | 8758 |
| 35D | 91 | 28 | 14204 |
| 36C | 92 | 88 | 3150 |
| 37F | 90 | 90 | 6352 |
| 38 | 96 | 96 | 13516 |
| 39C | 91 | 7 | 26475 |
| 40 | 87 | 87 | 8719 |
| 41 | 98 | 98 | 7631 |
| 42 | 100 | 100 | 11765 |
| 43 | 100 | 100 | 15419 |
| 44 | 94 | 94 | 6816 |
| 45G | 92 | 92 | 10401 |
| 46 | 89 | 87 | 10490 |
| 47 | 100 | 100 | 21441 |
| 48 | 88 | 88 | 23969 |
| 49 | 87 | 87 | 23967 |
| 50 | 96 | 95 | 11736 |
| 51 | 95 | 95 | 11128 |
| 52 | 93 | 92 | 31753 |
| 53 | 92 | 92 | 8026 |
| 54 | 98 | 98 | 8076 |
| 55C | 92 | 92 | 9559 |
| 56F | 97 | 97 | 18961 |
| 57 | 93 | 93 | 7634 |
| 58G | 95 | 95 | 8440 |
| 59B | 94 | 94 | 22443 |
| 60 | 96 | 86 | 14337 |
| 61B | 96 | 96 | 14309 |
| 62 | 100 | 100 | 5695 |
| 63 | 91 | 91 | 8888 |
| 64 | 98 | 98 | 7696 |
| 65 | 100 | 85 | 19301 |
| 66 | 97 | 97 | 6956 |
| 67I | 94 | 94 | 21471 |
| 68G | 96 | 96 | 9638 |
| 69 | 77 | 77 | 718 |
| 70 | 94 | 94 | 9976 |
| 71 | 87 | 87 | 9509 |
| 72 | 87 | 85 | 5865 |
| 73 | 86 | 86 | 4494 |
| 74D | 99 | 99 | 6905 |
| 75 | 93 | 92 | >40267 |
| 76F | 98 | 98 | 22571 |
| 77E | 97 | 96 | 11804 |
| 78 | 98 | 98 | 14418 |
| 79 | 100 | 100 | 4716 |
| 80 | 100 | 96 | 8579 |
| 81 | 100 | 100 | 12466 |
| 82 | 99 | 99 | 9698 |
| 83 | 94 | 94 | 9935 |
| 84 | 100 | 100 | 8734 |
| 85 | 96 | 96 | 7850 |
| 86 | 99 | 99 | 6471 |
| 87 | 96 | 95 | 6803 |
| 88 | 100 | 100 | 8488 |
| 89 | 95 | 95 | 7773 |
| 90D | 97 | 97 | 7620 |
| 91E | 100 | 100 | 9382 |
| 92 | 100 | 100 | 6244 |
| 93 | 92 | 92 | 4809 |
| 94 | 100 | 100 | 7577 |
| 95 | 93 | 93 | 6513 |
| 96 | 100 | 100 | 6998 |
| 97 | 100 | 100 | 7596 |
| 98 | 100 | 100 | 8410 |
| 99B | 100 | 100 | 6366 |
| 100 | 99 | 99 | 5136 |
| 101 | 95 | 95 | 6526 |
| 102 | 100 | 100 | 5815 |
| 103 | 100 | 100 | 6792 |
| 104 | 100 | 100 | 7463 |
| 105E | 74 | — | 31484 |
| 106E | 96 | 95 | 12404 |
| 107B | 95 | 95 | 5303 |
| 108C | 94 | 94 | >53076 |
| 109 | 97 | 97 | 29567 |
| 110E | 98 | 15 | >53192 |
| 111 | 90 | 89 | 9593 |
| 112D | 97 | 97 | 13891 |
| 113D | 97 | — | 1092 |
| 114G | 100 | 100 | 14834 |
| 115C | 91 | 84 | 9313 |
| 116A | 93 | 62 | 10484 |
| 117F | 100 | 93 | 27833 |
| 118 | 96 | 96 | 23924 |
| 119C | 99 | 99 | 9242 |
| 120H | 88 | 51 | 11699 |
| 121 | 98 | 46 | 9184 |
| 122 | 88 | 88 | 9072 |
| 123 | 90 | 90 | 7904 |
| 124 | 97 | 97 | 9145 |
| 125D | 97 | 96 | 13628 |
| 126 | 92 | 92 | 15507 |
| 127 | 92 | 92 | 8762 |
| 128B | 94 | 93 | 4181 |
| 129 | 82 | 54 | 12115 |
| 130 | 85 | 80 | 23158 |
| 131E | 96 | 95 | 22533 |
| 132C | 92 | 92 | 24161 |
| 133 | 90 | 90 | 16784 |
| 134 | 83 | 82 | 28027 |
| 135B | 93 | 93 | 14242 |
| 136D | — | — | 7427 |
| 137C | 100 | 93 | 7881 |
| 138 | 83 | 61 | 33392 |
| 139B | 94 | 94 | 15437 |
| 140M | 98 | 98 | 20364 |
| 141D | 100 | 100 | 19761 |
| 142 | 92 | 92 | 12621 |
| 143 | 98 | 98 | 11253 |
| 144 | 95 | 95 | 16236 |
| 145 | 99 | 99 | 8687 |
| 146I | — | — | 33468 |
| 147 | — | — | >53192 |
| 148B | 83 | 83 | 23264 |
| 149 | 86 | 86 | 26728 |
| 150 | 87 | 87 | 28895 |
| 151 | 92 | 92 | 25316 |
| 152 | 89 | 89 | 11872 |
| 153 | 98 | 98 | 18649 |
| 154 | 97 | 97 | 12488 |
| 155I | 99 | 99 | 26782 |
| 156E | 78 | 78 | 25584 |
| 157G | 87 | 87 | 10904 |
| 158G | 71 | 71 | 26745 |

-continued

| Compound | % inhibition at 2 µM | % inhibition at 0.2 µM | CC50 (nM) |
|---|---|---|---|
| 159 | 95 | 95 | 27427 |
| 160 | 100 | 100 | 20477 |
| 161 | 84 | 84 | 21843 |
| 162 | 81 | 81 | 22412 |
| 163 | 86 | 79 | 8853 |
| 164 | 97 | 96 | 40504 |
| 165 | 72 | 72 | 5456 |
| 166 | 92 | 92 | 24421 |
| 167 | 93 | 93 | 34110 |
| 168B | 90 | 90 | >53192 |
| 169 | 92 | 92 | 12421 |
| 170 | 88 | 88 | 16958 |
| 171D | — | — | >42470 |
| 172 | — | — | 61 |
| 173 | 92 | 92 | >43678 |
| 174 | 85 | 85 | >53192 |
| 175 | 95 | 95 | >46082 |
| 176 | 100 | 100 | 17402 |
| 177D | 100 | 100 | >53192 |
| 178 | 100 | 95 | 13999 |
| 179 | 100 | 100 | 15481 |
| 180C | 100 | 100 | 21252 |
| 181C | 100 | 100 | >53192 |
| 182L | 100 | 100 | 9829 |
| 183F | 84 | 84 | 12400 |
| 184 | 90 | 90 | 7694 |
| 185C | 89 | 89 | 18160 |
| 186D | 87 | 87 | 1517 |
| 187G | 84 | 84 | 19776 |
| 188 | 92 | 92 | 26275 |
| 189 | 88 | 88 | 17249 |
| 190 | 98 | 98 | 13907 |
| 191 | 91 | 91 | 10142 |
| 192 | 98 | 95 | 28776 |
| 193 | 92 | 92 | 23055 |
| 194 | 99 | 84 | 21268 |
| 195 | 90 | 88 | 11235 |
| 196 | 92 | 76 | 10783 |
| 197 | 63 | — | 15373 |
| 198 | 98 | 64 | 23690 |
| 199 | 95 | 95 | 22472 |
| 200 | 90 | 89 | 12230 |

The data above represent an average over time of each assay for each compound. For certain compounds, multiple assays have been conducted over the life of the project. Thus, the data reported in the tables include the data reported in the priority document, as well as data from assays run in the intervening period. In the above table, percent inhibition values have been normalized to 100% where the calculation of percent inhibition would have resulted in a value greater than 100.

In one embodiment, the compounds demonstrate >10% inhibition at 2 µM. In one embodiment, the compounds demonstrate >30% inhibition at 2 µM. In one embodiment, the compounds demonstrate >50% inhibition at 2 µM. In one embodiment, the compounds demonstrate >70% inhibition at 2 µM. In one embodiment, the compounds demonstrate >75% inhibition at 2 µM. In one embodiment, the compounds demonstrate >80% inhibition at 2 µM. In one embodiment, the compounds demonstrate >85% inhibition at 2 µM. In one embodiment, the compounds demonstrate >90% inhibition at 2 µM. In one embodiment, the compounds demonstrate >95% inhibition at 2 µM. It is to be understood that the compounds disclosed herein can be grouped according to their % inhibition as described above.

In one embodiment, the compounds demonstrate >10% inhibition at 0.2 µM. In one embodiment, the compounds demonstrate >30% inhibition at 0.2 µM. In one embodiment, the compounds demonstrate >50% inhibition at 0.2 µM. In one embodiment, the compounds demonstrate >70% inhibition at 0.2 µM. In one embodiment, the compounds demonstrate >75% inhibition at 0.2 µM. In one embodiment, the compounds demonstrate >80% inhibition at 0.2 µM. In one embodiment, the compounds demonstrate >85% inhibition at 0.2 µM. In one embodiment, the compounds demonstrate >90% inhibition at 0.2 µM. In one embodiment, the compounds demonstrate >95% inhibition at 0.2 µM. It is to be understood that the compounds disclosed herein can be grouped according to their % inhibition as described above.

In one variation, a compound is of any formulae provided herein, wherein the compound exhibits from 85%-100% inhibition of virus-induced cell killing at 2 µM. In one variation, a compound is of any formulae provided herein, wherein the compound exhibits from 85%-100% inhibition of virus-induced cell killing at 0.2 µM. In other embodiments, a compound is of any formulae provided herein wherein the compound exhibits from 50-100, 60-100, 70-100, 80-100, or 90-100% inhibition of virus-induced cell killing at 2 jµM or at 0.2 jµM.

It is understood that % inhibition may be evaluated by techniques known in the art. In a particular variation, a compound is of any formulae provided herein wherein the compound exhibits from 85%-110% inhibition of virus-induced cell killing at 2 µM or at 0.2 µM as measured by the method provided in the Test A and Test B sections discussed above.

Percent inhibition was also calculated for certain compounds as compared to previously published compounds (WO 2013/006738) and is shown below. The percent inhibition of virus-induced cell killing at 2 µM and 0.2 µM was measured by the method provided in the Test A and Test B sections discussed above.

| Compound | Response at 2 µM | Response at 0.2 µM |
|---|---|---|
| 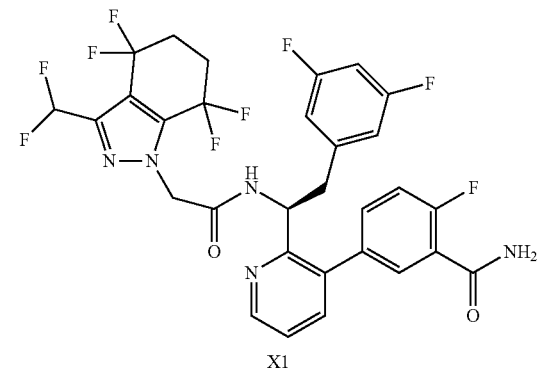 | 94 | 21 |

X1

-continued
| Compound | Response at 2 μM | Response at 0.2 μM |
|---|---|---|
| 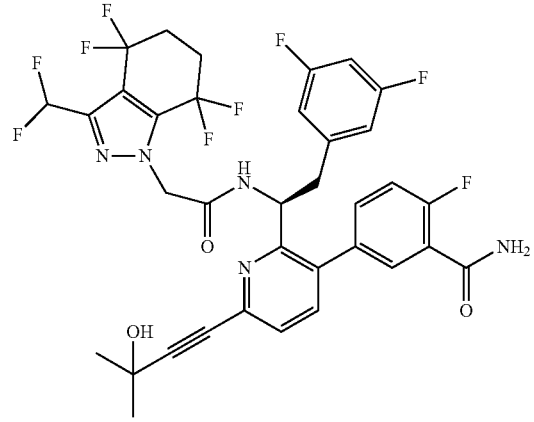<br>28 | 84 | 71 |
| 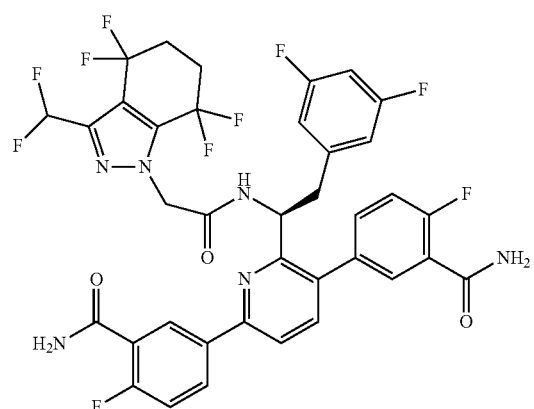<br>5G | 58 | 3 |
| Compound | Response at 2 μM | Response at 0.2 μM |
|---|---|---|
| 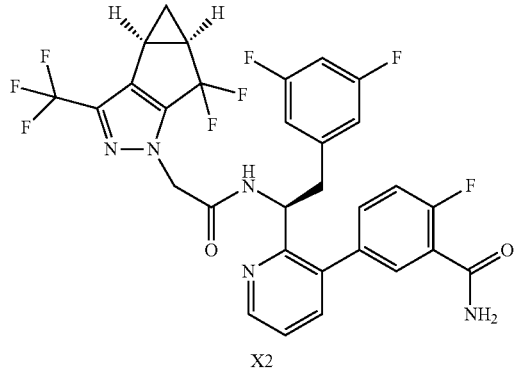<br>X2 | 91 | 65 |

| Compound | Response at 2 μM | Response at 0.2 μM |
|---|---|---|
| 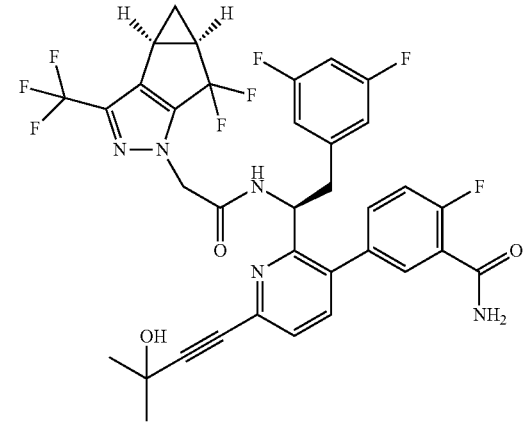 18 | 90 | 96 |

The specific pharmacological responses observed may vary according to and depending on the particular active compound selected and whether there are present pharmaceutical carriers and/or pharmaceutically active compounds, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

Example 1

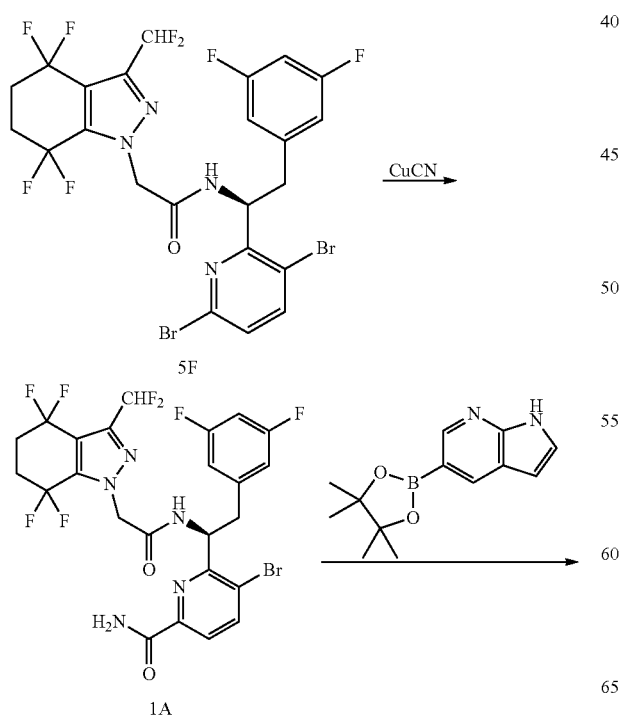

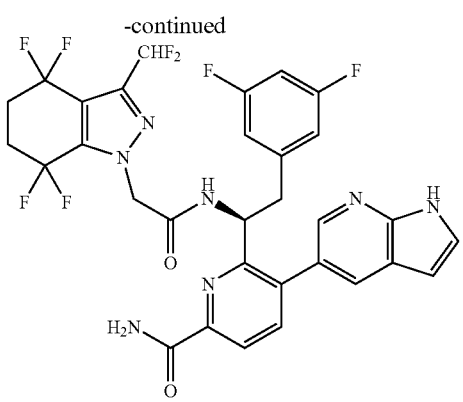

Synthesis of (S)-5-bromo-6-(1-(2-(3-(difluoromethyl)-4,4,7,7-tetrafluoro-4,5,6,7-tetrahydro-1H-indazol-1-yl)acetamido)-2-(3,5-difluorophenyl)ethyl)picolinamide (A)

Compound 5F (100 mg, 0.15 mmol) and CuCN (16 mg, 0.18 mmol) was dissolved in 0.3 mL of DMF. The reaction mixture was heated at 100° C. overnight. After cooled down to room temperature it was diluted with water and extracted with EtOAc. The organic phase was dried (Na$_2$SO$_4$), filtered and concentrated. The crude material was purified on reverse phase HPLC eluting with acetonitrile and water (with 0.1% TFA) to afford (S)—N-(1-(3-bromo-6-cyanopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide and the title product (1A). MS (m/z) 640.05 [M+H]$^+$.

Synthesis of (S)-6-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-5-(1H-pyrrolo[2,3-b]pyridin-5-yl)picolinamide The title compound (1B) was prepared according to the method presented for the synthesis of compound 4H of Example 4 utilizing 5-(4,4,5,5-tetramethyl-1,3,2-dioxaborolan-2-yl)-1H-pyrrolo[2,3-b]pyridine and 1A. ¹H NMR (400 MHz, CD₃OD) δ 9.00 (d, J=8.5 Hz, 1H), 8.12 (d, J=7.9 Hz, 1H), 8.01 (s, 1H), 7.92-7.77 (m, 2H), 7.56 (d, J=3.5 Hz, 1H), 6.97-6.53 (m, 3H), 6.26 (d, J=6.1 Hz, 2H), 5.53 (m, 1H), 5.11 (s, 2H), 3.07 (m, 2H), 2.63-2.25 (m, 4H). MS (m/z) 678.08 [M+H]⁺.

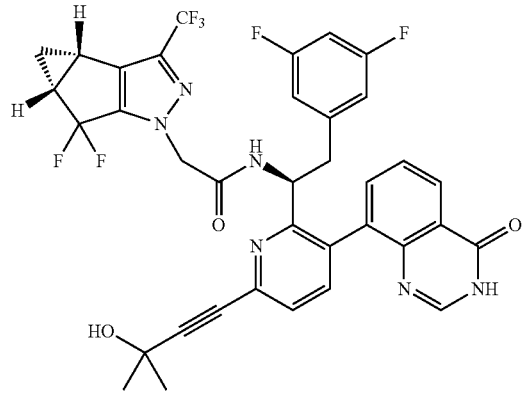

2

Example 2

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(4-oxo-3,4-dihydroquinazolin-8-yl)pyridin-2-yl)ethyl)acetamide (2)

The title compound (2) was prepared according to the method presented for the synthesis of compound 4H of Example 4 utilizing (4-oxo-3,4-dihydroquinazolin-8-yl)boronic acid and 14D. ¹H NMR (400 MHz, CD₃OD) δ 8.27 (m, 1H), 7.82 (m, 1H), 7.75 (m, 1H), 7.50 (s, 1H), 7.44 (m, 2H), 6.86 (m, 1H), 6.61 (m, 2H), 6.32 (m, 1H), 6.15 (m, 2H), 5.21 (m, 1H), 4.76 (s, 2H), 3.11 (m, 2H), 2.92 (m, 2H), 2.48 (m, 4H), 1.62 (d, J=6.6 Hz, 6H), 1.33 (m, 1H), 1.12 (m, 1H). MS (m/z) 725.14 [M+H]⁺.

Example 3

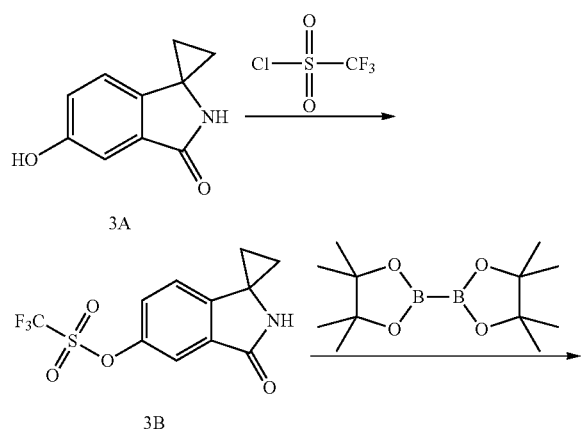

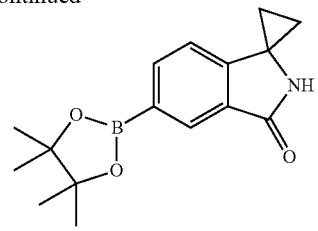

3C

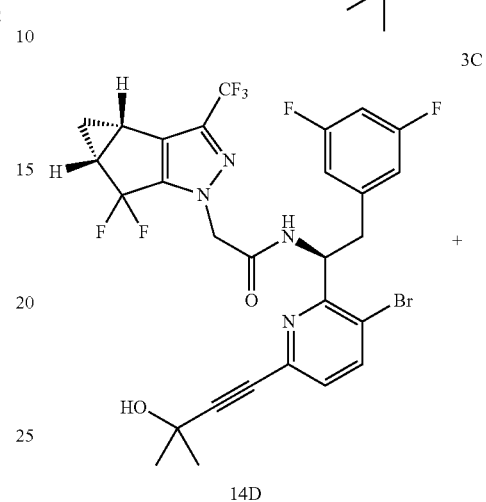

14D

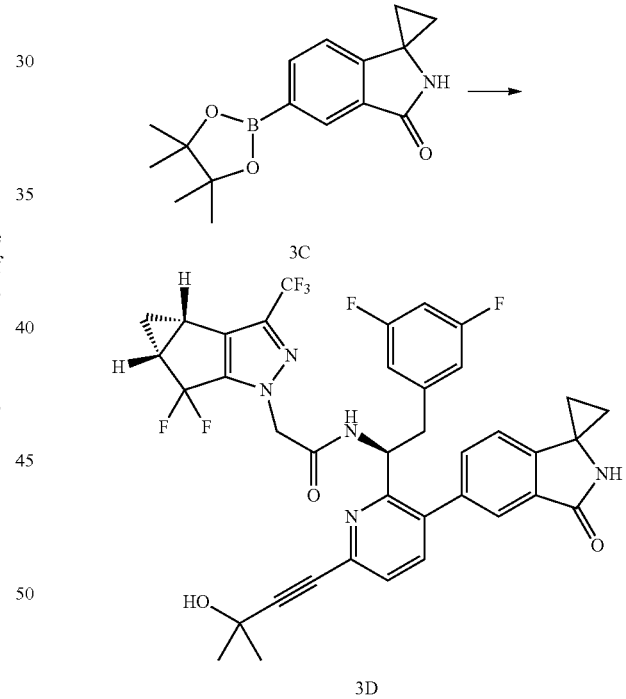

3D

Synthesis of 3'-oxospiro[cyclopropane-1,1'-isoindolin]-5'-yl trifluoromethanesulfonate (3B)

The mixture of compound 3A (1 g, 5.7 mmol, prepared according to the method presented in Tetrahedron Letters 50 (2009) 1267-1269), DCM (20 mL), and Et₃N (0.9 mL, 6.8 mmol) was cooled to 0° C. using an ice/water bath. Trifluoromethanesulfonyl chloride (0.91 mL, 8.5 mmol) was added dropwise via syringe. The mixture was then stirred for 1 h in ambient temperature. More Trifluoromethanesulfonyl chloride (0.8 mL) was added and the mixture was stirred at ambient temperature for another hour. Then diluted with DCM (150 mL) and washed with 1.0 N HCl (50 mL), saturated aqueous sodium bicarbonate (1×50 mL), and saturated aqueous sodium chloride (1×50 mL). The organic layer was dried over MgSO$_4$, filtered through Celite®, and concentrated in vacuo to give the title product (3B). MS (m/z) 308.29 [M+H]$^+$.

Synthesis of 5'-(4,4,5,5-tetramethyl-1,3,2-dioxaborolan-2-yl)spiro[cyclopropane-1,1'-isoindolin]-3'-one (3C)

In a microwave tube were charged 3B (200 mg, 0.65 mmol), bis(pinacolato)diboron (330 mg, 1.3 mmol) and potassium acetate (191 mg, 1.95 mmol), [1,1'-Bis(diphenylphosphino)ferrocene]dichloropalladium(II)(14 mg, 0.02 mmol) and 1,4-dioxane (8 mL) The mixture was heated up to 150° C. for 20 min in a Microwave Synthesizer. Upon completion the solution was diluted in EtOAc and the organic layer was washed with water and a saturated NaCl solution, dried over MgSO$_4$ and concentrated in vacuum to give the title compound as a dark brown solid. A half amount of the product was purified by silica gel chromatography eluting with EtOAc/hexanes to afford the title product. MS (m/z) 286.23 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3'-oxospiro[cyclopropane-1,1'-isoindolin]-5'-yl)pyridin-2-yl)ethyl)acetamide (3D)

In a microwave tube were charged with 14D (33 mg, 0.05 mmol), 3C (21 mg, 0.075 mmol), LiCl (6 mg, 0.15 mmol), K$_2$CO$_3$ (21 mg, 0.15 mmol), Pd(PPh$_3$)$_2$Cl$_2$ (3 mg) and Pd(dppf)Cl$_2$ (3 mg). To the mixture was added 1 mL of DME and 0.2 mL of H$_2$O. The mixture was heated up to 165° C. for 12 min in a Microwave Synthesizer. After cooled down and filtered through a syringe filter, purified on reverse phase HPLC eluting with acetonitrile and water (with 0.1% TFA) to afford the title product. $^1$H NMR (400 MHz, CD$_3$OD) δ 8.77 (d, J=8.4 Hz, 1H), 7.55 (d, J=8.0 Hz, 1H), 7.46 (d, J=8.0 Hz, 1H), 7.40 (d, J=7.8 Hz, 1H), 7.32-7.16 (m, 2H), 6.64 (t, J=9.2 Hz, 1H), 6.24 (d, J=6.5 Hz, 2H), 5.39 (t, J=7.3 Hz, 1H), 4.86 (s, 2H), 3.08-2.92 (m, 2H), 2.58-2.31 (m, 2H), 1.62 (s, 6H), 1.60-1.33 (m, 5H), 1.12 (m, 1H). MS (m/z) 738.15 [M+H]$^+$.

Example 4

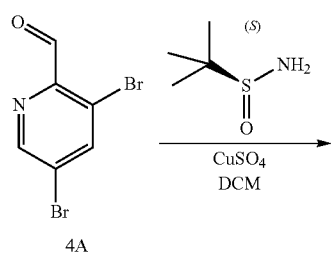

4A

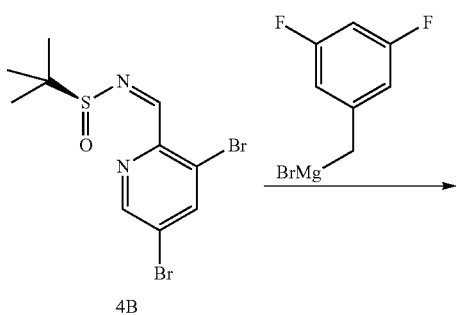

4B

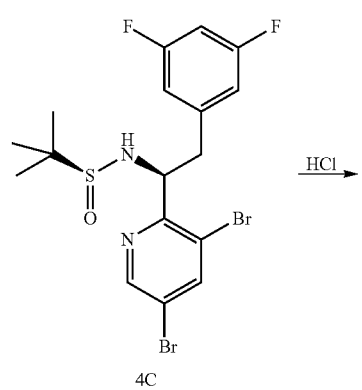

4C

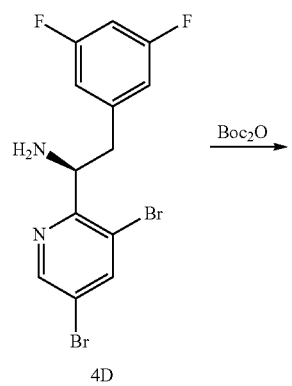

4D

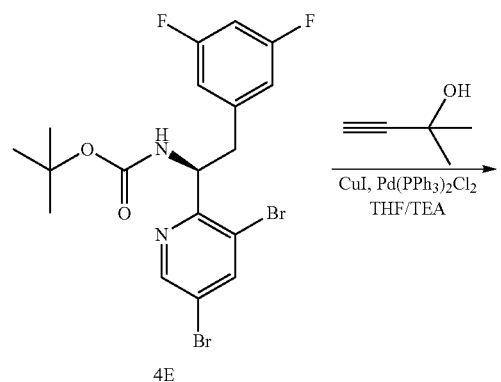

4E

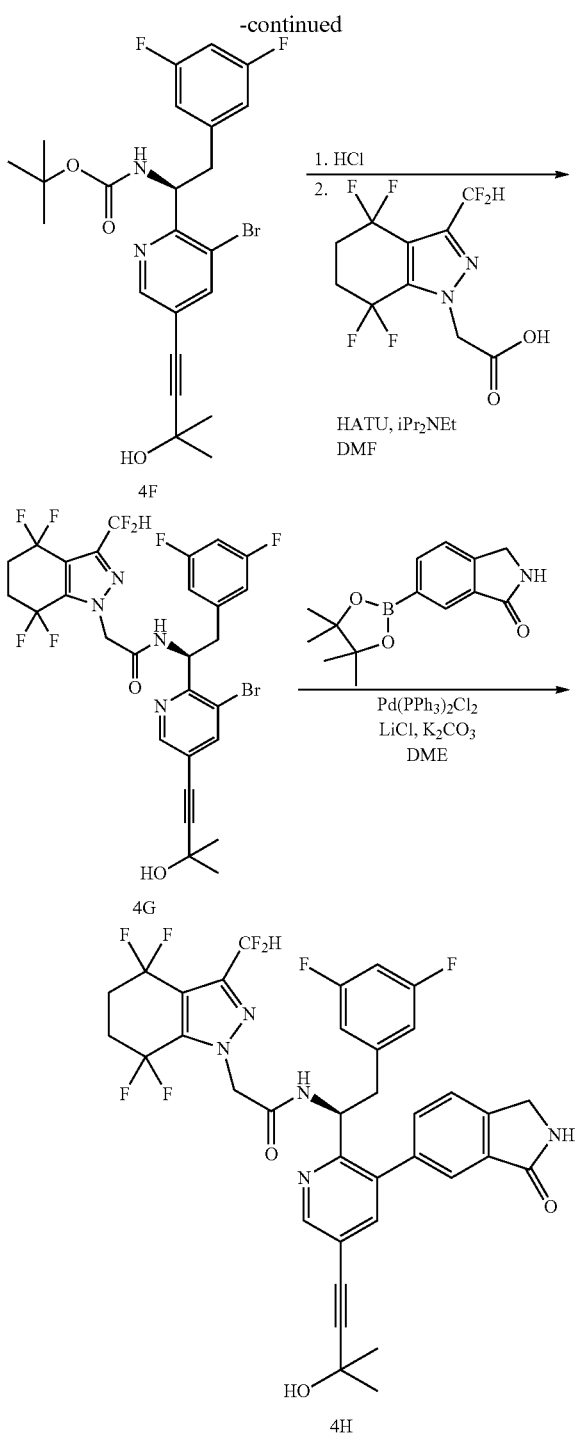

Synthesis of (S)—N—((3,5-dibromopyridin-2-yl)methylene)-2-methylpropane-2-sulfinamide (4B)

To 3,5-dibromopicolinaldehyde (1.9 g0, 7.17 mmol) in DCM (30 mL) was added (S)-2-methylpropane-2-sulfinamide (870 mg, 7.17 mmol) and CuSO$_4$ (2.29 g, 14.3 mmol). The reaction mixture was stirred for 15 h. Solids were filtered over celite. The solvents were removed in vacuo and the residue purified by column chromatography on silica to provide 2.6 g of the title compound. MS (m/z) 368.9 [M+H]$^+$.

Synthesis of (S)—N—((S)-1-(3,5-dibromopyridin-2-yl)-2-(3,5-difluorophenyl)ethyl)-2-methylpropane-2-sulfinamide (4C)

(S)—N-((3,5-dibromopyridin-2-yl)methylene)-2-methylpropane-2-sulfinamide (2.6 g, 7.1 mmol) was dissolved in THF (24 mL) and cooled to −78° C. (3,5-difluorobenzyl)magnesium bromide (34 mL, 0.25 M in Et$_2$O) was added dropwise. The reaction was stirred at −78° C. for 3 hr then let warm to 0° C. and quenched. The reaction was partitioned between EtOAc and aq. NH$_4$Cl. The organics were separated, dried, and removed in vacuo. The residue purified by column chromatography on silica to provide the title compound. MS (m/z) 496.6 [M+H]$^+$.

Synthesis of (S)-1-(3,5-dibromopyridin-2-yl)-2-(3,5-difluorophenyl)ethanamine (4D)

To (S)—N—((S)-1-(3,5-dibromopyridin-2-yl)-2-(3,5-difluorophenyl)ethyl)-2-methylpropane-2-sulfinamide (650 mg) dissolved in DCM (3 mL) was added 4N HCl in dioxanes (4 mL). The reaction was stirred for 2 hr at ambient temperature. Solvents were removed in vacuo and the crude desired product was used without further purification. MS (m/z) 393.0 [M+H]$^+$.

Synthesis of (S)-tert-butyl 1-(3,5-dibromopyridin-2-yl)-2-(3,5-difluorophenyl)ethylcarbamate (4E)

(S)-1-(3,5-Dibromopyridin-2-yl)-2-(3,5-difluorophenyl)ethanamine (780 mg, 1.84 mmol) was combined with di-tert-butyl dicarbonate (400 mg, 1.84 mmol) and TEA (515 μL, 3.7 mmol) in DCM (9 mL). The reaction was stirred for 2 hr at ambient temperature. The reaction was partitioned between EtOAc and H$_2$O. The organics were separated, dried, and removed in vacuo. The residue purified by column chromatography on silica to provide the title compound. MS (m/z) 492.9 [M+H]$^+$.

Synthesis of (S)-tert-butyl 1-(3-bromo-5-(3-hydroxy-3-methylbut-1-ynyl)pyridin-2-yl)-2-(3,5-difluorophenyl)ethylcarbamate (4F)

To (S)-tert-butyl 1-(3,5-dibromopyridin-2-yl)-2-(3,5-difluorophenyl)ethylcarbamate (140 mg, 0.29 mmol) in THF (18 mL) was added 2-methylbut-3-yn-2-ol (42 μL, 0.43 mmol), TEA (0.9 mL), Pd(PPh$_3$)$_2$Cl$_2$ (30 mg) and CuI (16 mg). The reaction was stirred for 2 hr at ambient temperature and then partitioned between EtOAc and H$_2$O. The organics were separated, dried, and removed in vacuo. The residue purified by column chromatography on silica to provide the title compound as a mixture with 4E which was used in the next step. MS (m/z) 496.7 [M+H]$^+$.

Synthesis of (S)—N-(1-(3-bromo-5-(3-hydroxy-3-methylbut-1-ynyl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (4G)

A mixture of (S)-tert-butyl 1-(3-bromo-5-(3-hydroxy-3-methylbut-1-ynyl)pyridin-2-yl)-2-(3,5-difluorophenyl)ethylcarbamate and (S)-tert-butyl 1-(3,5-dibromopyridin-2-yl)-2-(3,5-difluorophenyl)ethylcarbamate (105 mg) obtained from the previous step was dissolved in DCM (3 mL) and treated with 4N HCl in dioxanes (4 mL). The reaction was stirred for 2 hr then solvents removed in vacuo. The residue purified by column chromatography on silica to provide 18 mg of (S)-4-(6-(1-amino-2-(3,5-difluorophenyl)ethyl)-5-bromopyridin-3-yl)-2-methylbut-3-yn-2-ol (MS (m/z) 395.0 [M+H]⁺). To (S)-4-(6-(1-amino-2-(3,5-difluorophenyl)ethyl)-5-bromopyridin-3-yl)-2-methylbut-3-yn-2-ol (18 mg, 0.046 mmol) in DMF (1 mL) was added 2-(3-(difluoromethyl)-4,4,7,7-tetrafluoro-4,5,6,7-tetrahydro-1H-indazol-1-yl)acetic acid (15 mg, 0.05 mmol), iPr₂NEt (17 μL, 0.1 mmol) and HATU (26 mg, 0.07 mmol). The reaction was stirred 30 min and then partitioned between EtOAc and H₂O. The organics were separated, dried, and removed in vacuo. The crude product was used directly in the next reaction. MS (m/z) 679.2[M+H]⁺.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(5-(3-hydroxy-3-methylbut-1-ynyl)-3-(3-oxoisoindolin-5-yl)pyridin-2-yl)ethyl) acetamide (4H)

To (S)—N-(1-(3-bromo-5-(3-hydroxy-3-methylbut-1-ynyl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (16 mg, 0.02 mmol) in DME (0.7 mL) was added 6-(4,4,5,5-tetramethyl-1,3,2-dioxaborolan-2-yl)isoindolin-1-one (7 mg, 0.03 mmol), Pd(PPh₃)₂Cl₂ (2 mg), LiCl (1 mg), and aq 2M K₂CO₃ (30 μL). The reaction was heated in a microwave reactor to 150° C. for 20 min. The reaction was purified by RP HPLC to provide the desired product. ¹H NMR (400 MHz, Methanol-d₄) δ 8.69 (d, 1H), 7.62-7.49 (m, 2H), 7.43 (s, 1H), 7.28 (s, 1H), 6.98-6.58 (m, 4H), 6.26 (d, 2H), 5.34 (d, 2H), 5.18 (s, 1H), 5.05 (s, 2H), 4.48 (s, 2H), 3.02 (t, J=7.5 Hz, 3H), 2.49 (s, 7H), 1.56 (s, 5H). MS (m/z) 732.1[M+H]⁺.

Example 5

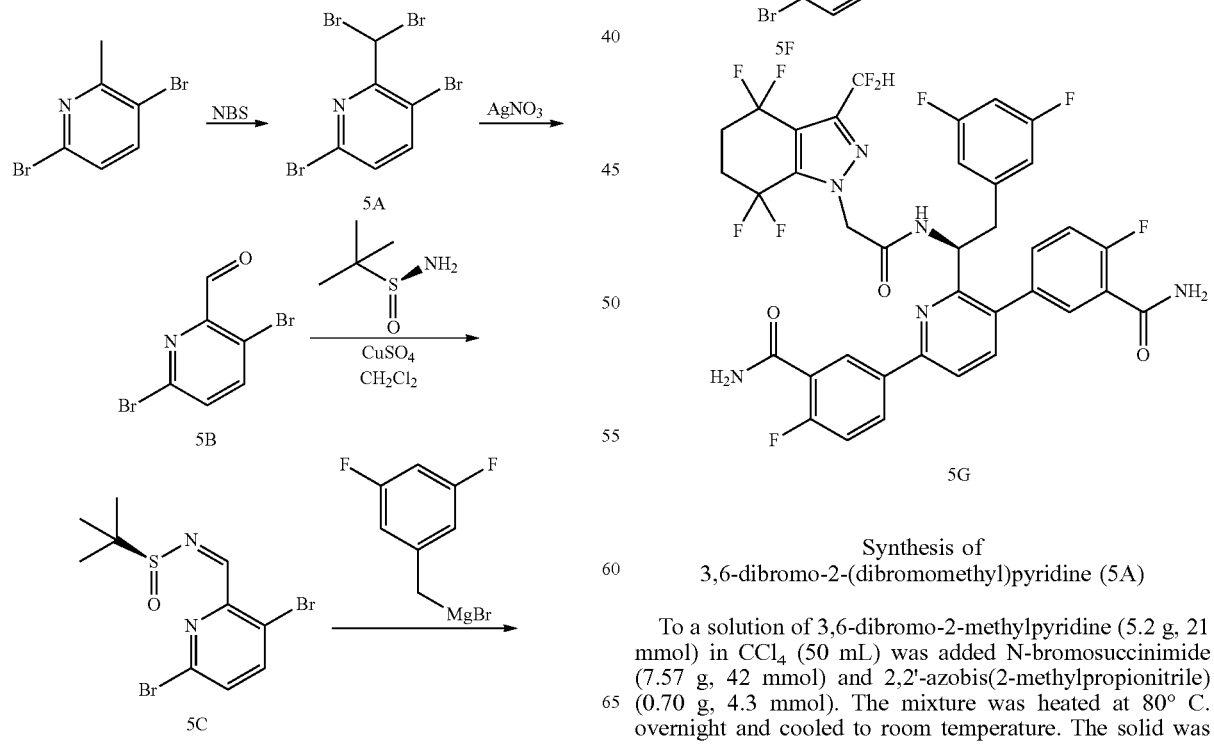

Synthesis of 3,6-dibromo-2-(dibromomethyl)pyridine (5A)

To a solution of 3,6-dibromo-2-methylpyridine (5.2 g, 21 mmol) in CCl₄ (50 mL) was added N-bromosuccinimide (7.57 g, 42 mmol) and 2,2'-azobis(2-methylpropionitrile) (0.70 g, 4.3 mmol). The mixture was heated at 80° C. overnight and cooled to room temperature. The solid was removed by filtration and the filtrate was concentrated under reduced pressure. The product (5A) was obtained after flash chromatography eluding with 0-10 percent EtOAc in hexane (7.36 g). MS (m/z): 409.66 [M+H]$^+$ Synthesis of 3,6-dibromopicolinaldehyde (5B)

A solution of silver nitrate (7.6 g, 45 mmol) in water (24 mL) was added dropwise to a solution of 5A (7.36 g, 18 mmol) in refluxing EtOH (90 mL). The mixture was stirred at 80° C. for 5 hours. After the mixture was cooled to room temperature, it was diluted with water (100 mL), extracted with EtOAc (3 times), dried over Na$_2$SO$_4$, filtered and concentrated under reduced pressure. The crude product (5B, 4.6 G) was directly used for next step. MS (m/z): 265.96. [M+H]$^+$ Synthesis of (S,Z)—N-((3,6-dibromopyridin-2-yl) methylene)-2-methylpropane-2-sulfinamide (5C)

The title compound (5C) was prepared according to the method presented for the synthesis of compound 4B of Example 4 utilizing 5B. MS (m/z) 368.86 [M+H]$^+$ Synthesis of (S)—N—((S)-1-(3,6-dibromopyridin-2-yl)-2-(3,5-difluorophenyl)ethyl)-2-methylpropane-2-sulfinamide (5D)

The title compound (5D) was prepared according to the method presented for the synthesis of compound 4C of Example 4 utilizing 5C. MS (m/z) 496.99 [M+H]$^+$ Synthesis of (S)-1-(3,6-dibromopyridin-2-yl)-2-(3,5-difluorophenyl)ethanamine hydrochloride (5E)

The title compound (5E) was prepared according to the method presented for the synthesis of compound 4D of Example 4 utilizing 5D. MS (m/z) 393.29 [M+H]$^+$ Synthesis of (S)—N-(1-(3,6-dibromopyridin-2-yl)-2-(3-(difluoromethyl)-4,4,7,7-tetrafluoro-4,5,6,7-tetrahydro-1H-indazol-1-yl)acetamide (5F)

The title compound (5F) was prepared according to the method presented for the synthesis of compound 10A of Example 10 utilizing 5E. MS (m/z) 676.96 [M+H]$^+$.

Synthesis of (S)-5,5'-(6-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyridine-2,5-diyl)bis(2-fluorobenzamide) (5G)

In a microwave tube was charged with 5F (100 mg, 0.15 mmol), (3-carbamoyl-4-fluorophenyl)boronic acid (81 mg, 0.45 mmol), LiCl (19 mg, 0.45 mmol), Na$_2$CO$_3$ (50 mg, 0.6 mmol) and 5 mg of Pd(PPh$_3$)$_2$Cl$_2$. To the mixture was added 1.4 mL of 1,4-dioxane/methanol/H$_2$O (5/1/1). The mixture was heated up to 170° C. for 15 min in a Microwave Synthesizer. After cooled down and filtered through a syringe filter, purified on reverse phase HPLC eluting with acetonitrile and water (with 0.1% TFA) to afford the title compound. $^1$H NMR (400 MHz, CD$_3$OD) δ 8.90 (d, J=8.6 Hz, 1H), 8.74 (dd, J=7.2, 2.4 Hz, 1H), 8.51-8.30 (m, 1H), 7.91 (d, J=8.1 Hz, 1H), 7.64 (d, J=8.1 Hz, 1H), 7.41 (m, 2H), 7.23 (dd, J=10.7, 8.5 Hz, 1H), 7.02-6.49 (m, 2H), 6.35 (d, J=6.2 Hz, 2H), 5.45 (m, 1H), 5.16-5.02 (m, 2H), 3.23-2.97 (m, 2H), 2.49 (m, 4H). MS (m/z) 793.19 [M+H]$^+$.

Example 6

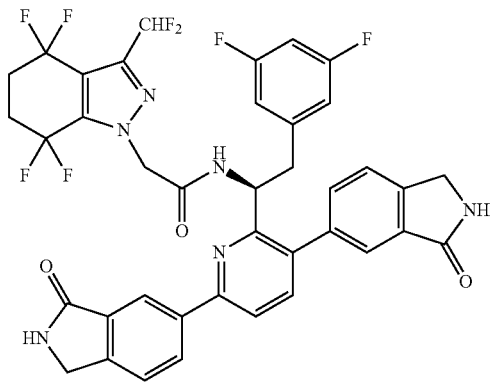

6

Synthesis of (S)—N-(1-(3,6-bis(3-oxoisoindolin-5-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (6)

The title compound (6) was prepared according to the method presented for the synthesis of compound 5G of Example 5 utilizing 6-(4,4,5,5-tetramethyl-1,3,2-dioxaborolan-2-yl)isoindolin-1-one and 5F. $^1$H NMR (400 MHz, CD$_3$OD) δ 8.84 (d, J=8.1 Hz, 1H), 8.72 (s, 1H), 8.49 (d, J=7.9 Hz, 1H), 7.98 (d, J=8.1 Hz, 2H), 7.72 (dd, J=23.8, 8.0 Hz, 2H), 7.60 (d, J=7.9 Hz, 1H), 7.49 (d, J=8.0 Hz, 1H), 7.39 (s, 1H), 6.97-6.57 (m, 2H), 6.33 (m, 2H), 5.49 (m, 2H), 5.10 (s, 2H), 4.57 (s, 2H), 4.49 (s, 2H), 3.24-2.95 (m, 2H), 2.47 (m, 4H). MS (m/z) 781.02[M+H]$^+$.

Example 7

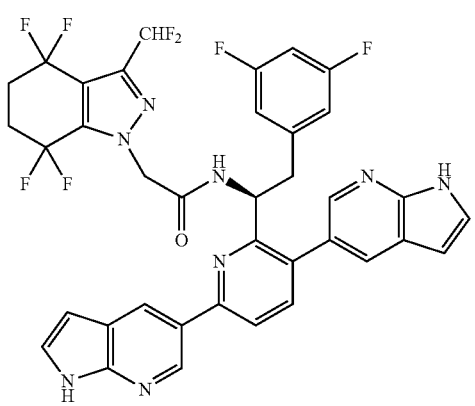

7

Synthesis of (S)—N-(1-(3,6-bis(1H-pyrrolo[2,3-b]pyridin-5-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (7)

The title compound (7) was prepared according to the method presented for the synthesis of compound 5G of Example 5 utilizing 6 5-(4,4,5,5-tetramethyl-1,3,2-dioxaborolan-2-yl)-1H-pyrrolo[2,3-b]pyridine and 5F. $^1$H NMR (400 MHz, CD$_3$OD) δ 9.23-9.17 (m, 2H), 9.04 (d, J=8.1 Hz, 1H), 8.03 (m, 3H), 7.75 (d, J=8.1 Hz, 1H), 7.61 (dd, J=7.3, 3.5 Hz, 2H), 6.93-6.52 (m, 4H), 6.34 (d, J=6.2 Hz, 2H), 5.45 (m, 1H), 5.10 (m, 2H), 3.27-3.06 (m, 2H), 2.48 (m, 4H). MS (m/z) 751.22 [M+H]⁺.

Example 8

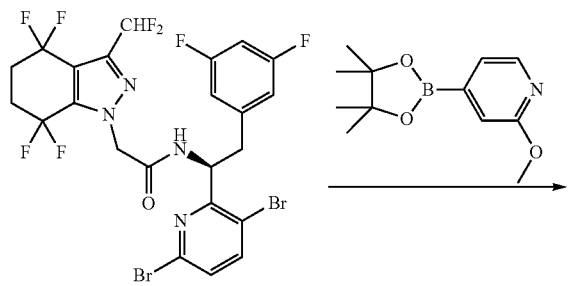

5F

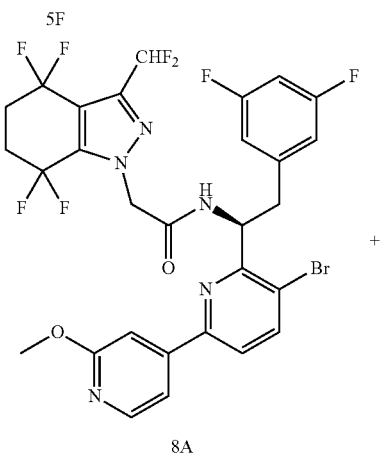

8A

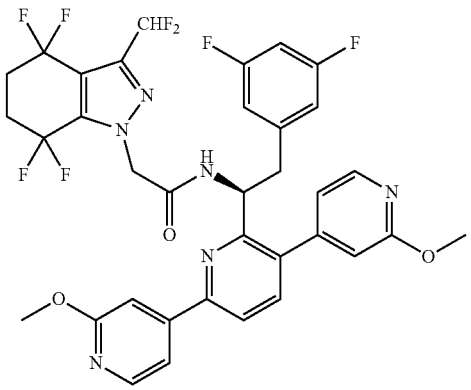

8B

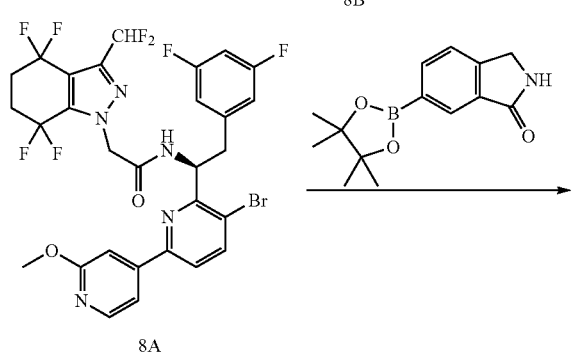

8A

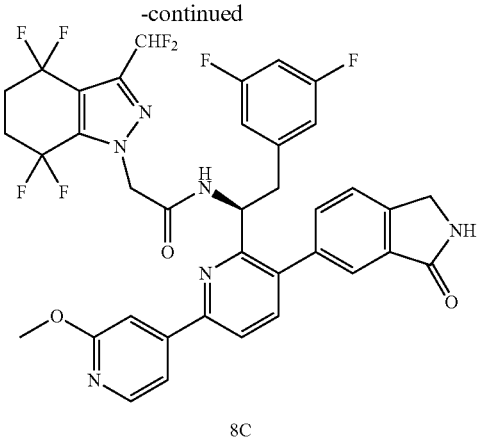

8C

Synthesis of (S)—N-(1-(5-bromo-2'-methoxy-[2,4'-bipyridin]-6-yl)-2-(3,5-difluorophenyl)ethyl)-2-(3-(difluoromethyl)-4,4,7,7-tetrafluoro-4,5,6,7-tetrahydro-1H-indazol-1-yl)acetamide (8A) and (S)—N-(1-(2',5'-di(methoxy-[2,4'-bipyridin]-6-yl))-2-(3,5-difluorophenyl)ethyl)-2-(3-(difluoromethyl)-4,4,7,7-tetrafluoro-4,5,6,7-tetrahydro-1H-indazol-1-yl) acetamide (8B)

The title compounds (8A and 8B) were prepared according to the method presented for the synthesis of compound 5G of Example 5 utilizing 2-methoxy-4-(4,4,5,5-tetramethyl-1,3,2-dioxaborolan-2-yl)pyridine (2 equiv.) and 5F.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2'-methoxy-5-(3-oxoisoindolin-5-yl)-[2,4'-bipyridin]-6-yl)ethyl)acetamide (8C)

The title compound (8C) was prepared according to the method presented for the synthesis of compound 4H of Example 4 utilizing 8A. ¹H NMR (400 MHz, CD₃OD) δ 8.85 (d, J=8.1 Hz, 1H), 8.33 (d, J=5.7 Hz, 1H), 8.06 (d, J=8.0 Hz, 1H), 7.91 (d, J=5.7 Hz, 1H), 7.82 (s, 1H), 7.74 (d, J=8.0 Hz, 1H), 7.61 (d, J=6.3 Hz, 1H), 7.53 (d, J=7.8 Hz, 1H), 7.38 (s, 1H), 6.91-6.44 (m, 2H), 6.29 (d, J=6.3 Hz, 2H), 5.51 (dd, J=14.8, 8.2 Hz, 1H), 5.18-4.98 (m, 2H), 4.50 (s, 2H), 4.09 (s, 3H), 3.12 (m, 2H), 2.49 (m, 4H). MS (m/z) 757.25 [M+H]⁺.

Example 9

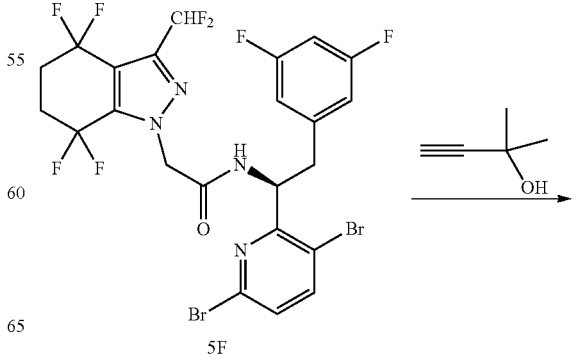

5F

193
-continued

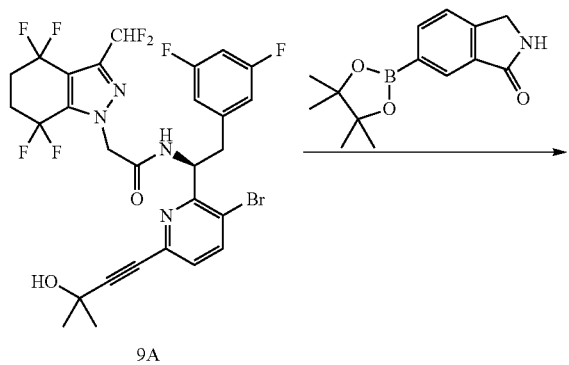

9A

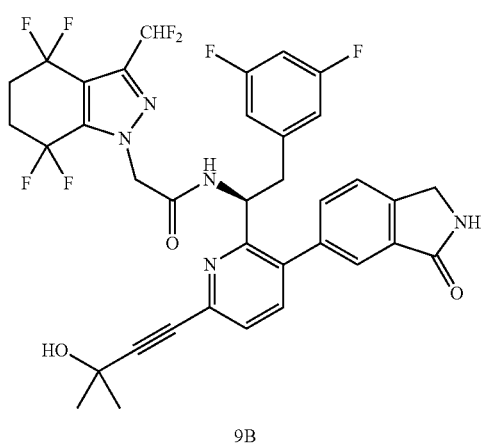

9B

Synthesis of (S)—N-(1-(3-bromo-6-(3-hydroxy-3-methylbut-1-yn-1-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (9A)

The title compound (9A) was prepared according to the method presented for the synthesis of compound 4F of Example 4 utilizing 2-methylbut-3-yn-2-ol and 5F. MS (m/z) 681.17 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(6-(3-hydroxy-3-methylbut-1-yn-1-yl)-3-(3-oxoisoindolin-5-yl)pyridin-2-yl)ethyl)acetamide (9B)

The title compound (9B) was prepared according to the method presented for the synthesis of compound 4H of Example 4 utilizing 9A. $^1$H NMR (400 MHz, CD$_3$OD) δ 7.63-7.53 (m, 2H), 7.50-7.40 (m, 2H), 7.30 (s, 1H), 6.95-6.56 (m, 2H), 6.28 (d, J=6.3 Hz, 2H), 5.39 (t, J=7.4 Hz, 1H), 5.05 (s, 2H), 4.48 (s, 2H), 3.13-2.91 (m, 2H), 2.66-2.35 (m, 4H), 1.61 (s, 6H). MS (m/z) 732.23 [M+H]$^+$.

194
Example 10

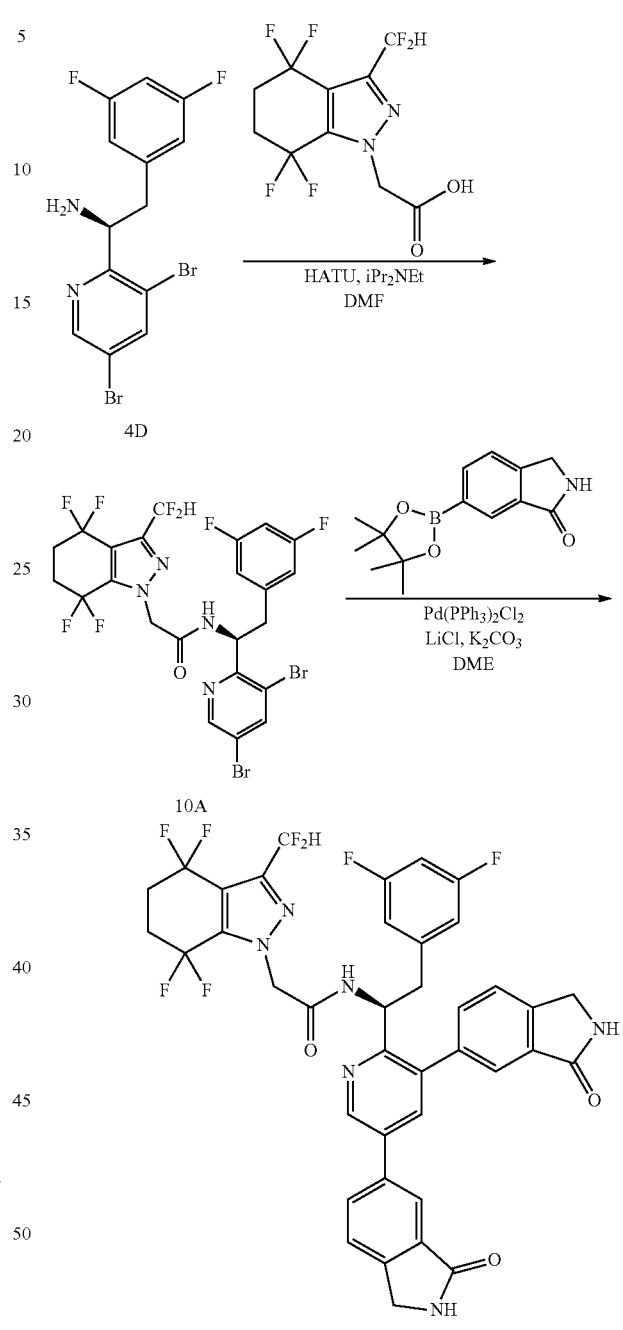

Synthesis of (S)—N-(1-(3,5-dibromopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (10A)

To (S)-1-(3,5-dibromopyridin-2-yl)-2-(3,5-difluorophenyl)ethanamine (380 mg, 0.97 mmol) dissolved in DMF (10 mL) was added iPr$_2$NEt (350 μL, 2 mmol) and 2-(3-(difluoromethyl)-4,4,7,7-tetrafluoro-4,5,6,7-tetrahydro-1H-indazol-1-yl)acetic acid (293 mg, 0.97 mmol). HATU (442 mg, 1.16 mmol) was added and the reaction stirred for 30 min. The reaction was partitioned between EtOAc and H$_2$O. The organics were separated, dried, and removed in vacuo. The residue purified by column chromatography on silica to provide the title compound. MS (m/z) 677.1 [M+H]$^+$.

Synthesis of (S)—N-(1-(3,5-bis(3-oxoisoindolin-5-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (10B)

To (S)—N-(1-(3,5-dibromopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (50 mg, 0.074 mmol) in DME (0.8 mL) and DMF (0.2 mL) was added 6-(4,4,5,5-tetramethyl-1,3,2-dioxaborolan-2-yl)isoindolin-1-one (48 mg, 0.19 mmol), Pd(PPh$_3$)$_2$Cl$_2$ (5 mg), LiCl (2 mg), and aq 2M K$_2$CO$_3$ (110 μL). The reaction was heated in a microwave reactor to 150° C. for 20 min. The reaction was purified by RP HPLC to provide the desired product. $^1$H NMR (400 MHz, Methanol-d$_4$) δ 9.02 (d, 1H), 8.11 (d, 1H), 7.97 (dd, 1.7 Hz, 1H), 7.89 (d, 1H), 7.72 (d, 1H), 7.67-7.48 (m, 3H), 7.42 (d, 1H), 6.70-6.61 (m, 2H), 6.37-6.30 (m, 2H), 5.44 (t, 1H), 5.07 (s, 2H), 4.51 (d, 4H), 3.18-3.01 (m, 3H), 2.50 (dd, 4H). MS (m/z) 798.1[M+H]$^+$.

Example 11

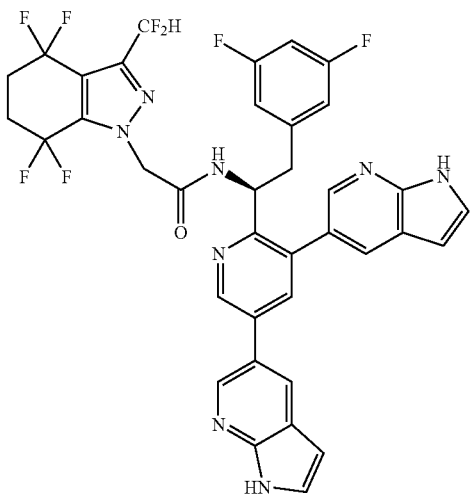

Synthesis of (S)—N-(1-(3,5-di(1H-pyrrolo[2,3-b]pyridin-5-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (11)

The title compound was prepared according to the method presented for the synthesis of 10B of Example 10 utilizing 10A and 5-(4,4,5,5-tetramethyl-1,3,2-dioxaborolan-2-yl)-1H-pyrrolo[2,3-b]pyridine. $^1$H NMR (400 MHz, Methanol-d$_4$) δ 9.10 (s, 1H), 8.62 (s, 1H), 8.56 (s, 1H), 8.14 (s, 1H), 8.05-7.94 (m, 2H), 7.58 (dd, 2H), 6.99-6.61 (m, 4H), 6.36 (d, 2H), 5.47-5.27 (m, 2H), 5.15-5.00 (m, 2H), 3.24-3.01 (m, 3H), 2.66-2.32 (m, 5H). MS (m/z) 751.1[M+H]$^+$.

Example 12

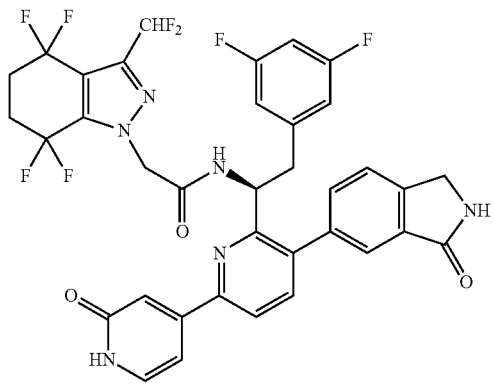

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2'-oxo-5-(3-oxoisoindolin-5-yl)-1',2'-dihydro-[2,4'-bipyridin]-6-yl)ethyl)acetamide (12)

In a microwave tube were charged with (S)-2-(3-(difluoromethyl)-4,4,7,7-tetrafluoro-4,5,6,7-tetrahydro-1H-indazol-1-yl)-N-(2-(3,5-difluorophenyl)-1-(2'-methoxy-5-(3-oxoisoindolin-5-yl)-[2,4'-bipyridin]-6-yl)ethyl)acetamide (8C, 5 mg), HCl in 1,4-dioxane (4N, 0.3 mL) and ethanol (0.3 mL). The mixture was heated up to 100° C. for 20 min in a Microwave Synthesizer. After cooled down, After cooled down, the solvent was removed and the residue was purified on reverse phase HPLC eluting with acetonitrile and water (with 0.1% TFA) to afford the title product. $^1$H NMR (400 MHz, CD$_3$OD) δ 8.88 (m, 1H), 7.96 (d, J=8.0 Hz, 1H), 7.73 (d, J=8.0 Hz, 1H), 7.60 (m, 2H), 7.53 (m, 1H), 7.43 (s, 1H), 7.37 (s, 1H), 7.27 (d, J=6.8 Hz, 1H), 6.96-6.53 (m, 2H), 6.30 (d, J=6.2 Hz, 2H), 5.49 (m, 1H), 5.09 (s, 2H), 4.49 (s, 2H), 3.12 (m, 2H), 2.48 (m, 4H). MS (m/z) 742.99 [M+H]$^+$.

Example 13

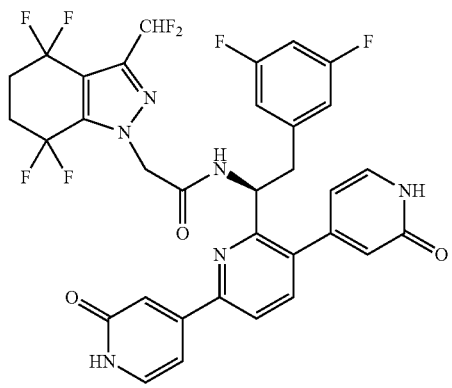

Synthesis of (S)-2-(3-(difluoromethyl)-4,4,7,7-tetra-fluoro-4,5,6,7-tetrahydro-1H-indazol-1-yl)-N-(2-(3,5-difluorophenyl)-1-(2,2''-dioxo-1,1'',2,2''-tetra-hydro-[4,2':5',4''-terpyridin]-6'-yl)ethyl)acetamide (13)

The title compound (13) was prepared according to the method presented for the synthesis of compound 12 of Example 12 utilizing 8B. $^1$H NMR (400 MHz, CD$_3$OD) δ 8.95 (d, J=7.8 Hz, 1H), 7.95 (d, J=8.1 Hz, 1H), 7.71 (d, J=8.1 Hz, 1H), 7.60 (d, J=6.8 Hz, 1H), 7.43 (d, J=7.2 Hz, 1H), 7.25 (d, J=6.9 Hz, 1H), 6.98-6.61 (m, 2H), 6.45 (d, J=6.3 Hz, 2H), 6.33 (d, J=6.6 Hz, 1H), 6.19 (s, 1H), 5.51 (m, 1H), 5.08 (m, 2H), 3.15 (m, 2H), 2.49 (m, 4H). MS (m/z) 705.00 [M+H]$^+$.

Example 14

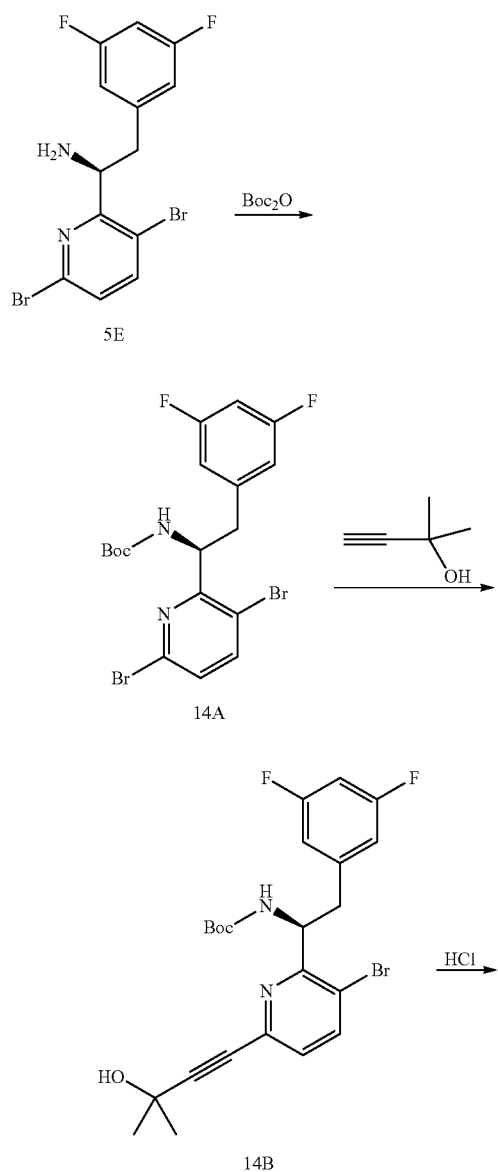

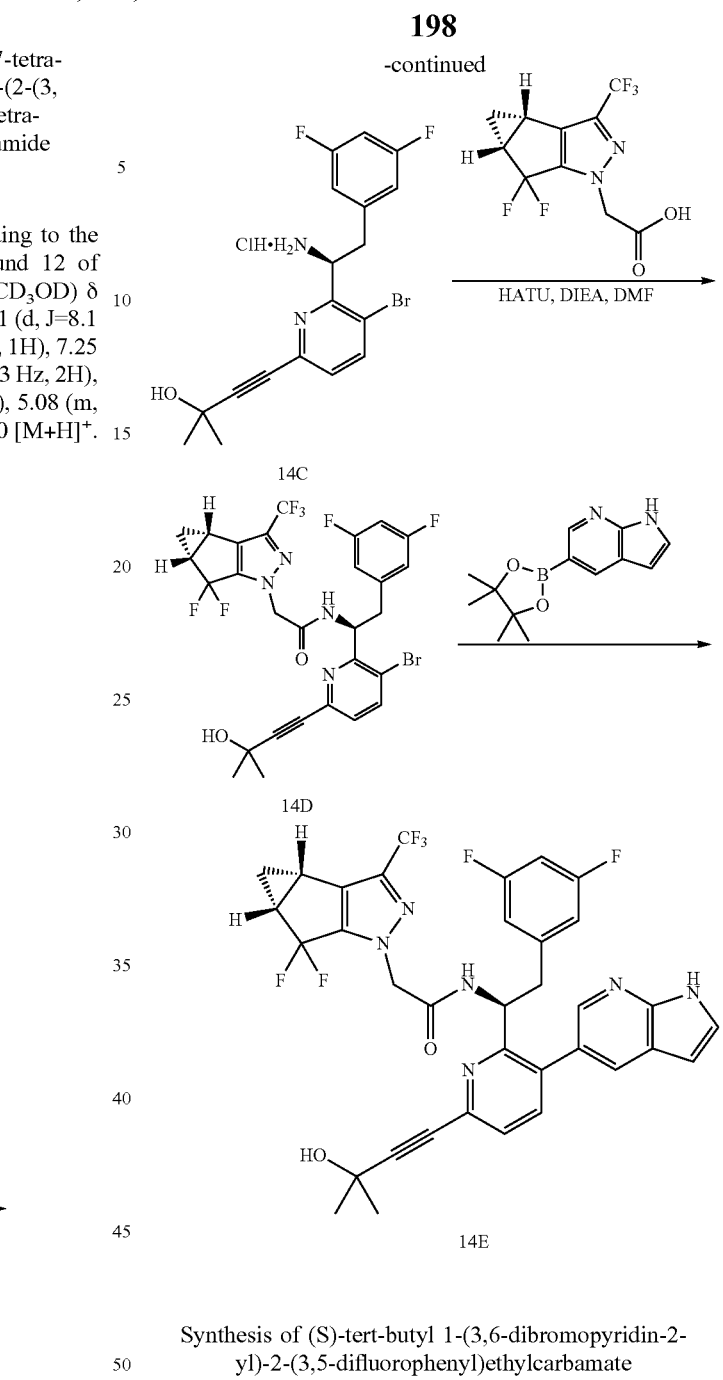

Synthesis of (S)-tert-butyl 1-(3,6-dibromopyridin-2-yl)-2-(3,5-difluorophenyl)ethylcarbamate The title compound was prepared according to the method presented for the synthesis of compound 4E of Example 4 utilizing 5E.

Synthesis of (S)-tert-butyl (1-(3-bromo-6-(3-hydroxy-3-methylbut-1-yn-1-yl)pyridin-2-yl)-2-(3,5-difluorophenyl)ethyl)carbamate (14B)

The title compound (14B) was prepared according to the method presented for the synthesis of compound 4F of Example 4 utilizing 2-methylbut-3-yn-2-ol and (S)-tert-butyl (1-(3,6-dibromopyridin-2-yl)-2-(3,5-difluorophenyl) ethyl)carbamate. MS (m/z) 496.90 [M+H]$^+$. Synthesis of (S)-4-(6-(1-amino-2-(3,5-difluorophenyl)ethyl)-5-bromopyridin-2-yl)-2-methylbut-3-yn-2-ol compound with 2-methylbut-3-yn-2-ol (1:1) hydrochloride (14C)

The title compound (14C) was prepared according to the method presented for the synthesis of compound 4G of Example 4 utilizing 14B. MS (m/z) 397.09 [M+H]⁺.

Synthesis of N—((S)-1-(3-bromo-6-(3-hydroxy-3-methylbut-1-yn-1-yl)pyridin-2-yl)-2-(3,5-difluorophenyl)ethyl)-2-((3b,4aR)-5,5-difluoro-3-(trifluoromethyl)-3b,4,4a,5-tetrahydro-1H-cyclopropa[3,4]cyclopenta[1,2-c]pyrazol-1-yl)acetamide (14D)

The title compound (14D) was prepared according to the method presented for the synthesis of compound 4G of Example 4 utilizing 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid and 14C. MS (m/z) 659.23 [M+H]⁺.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-oxoisoindolin-4-yl)pyridin-2-yl)ethyl)acetamide (14E)

The title compound (14E) was prepared according to the method presented for the synthesis of compound 4H of Example 4 utilizing 5-(4,4,5,5-tetramethyl-1,3,2-dioxaborolan-2-yl)-1H-pyrrolo[2,3-b]pyridine and 14D. ¹H NMR (400 MHz, CD₃OD) δ 8.92 (d, J=8.7 Hz, 1H), 8.00 (s, 2H), 7.85 (s, 1H), 7.59 (m, 2H), 7.48 (d, J=7.9 Hz, 1H), 6.77-6.56 (m, 2H), 6.28 (d, J=6.3 Hz, 2H), 5.33 (m, 1H), 4.87 (s, 2H), 3.17-2.99 (m, 4H), 2.48 (m, 4H), 1.6 (s, 6H), 1.40 (m, 1H), 1.10 (m, 1H). MS (m/z) 697.28 [M+H]⁺.

Example 15

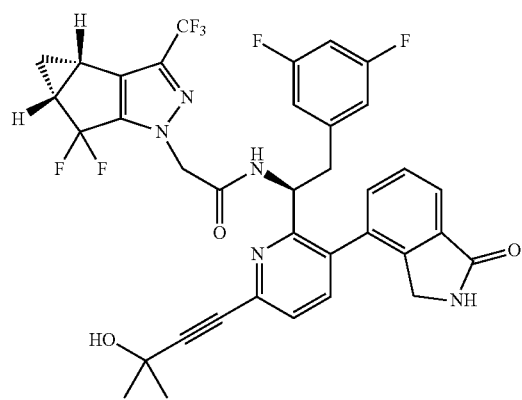

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-oxoisoindolin-4-yl)pyridin-2-yl)ethyl)acetamide (15)

The title compound (15) was prepared according to the method presented for the synthesis of compound 4H of Example 4 utilizing 14D and 2,3-dihydro-1H-isoindol-1-one-4-boronic acid pinacol ester. ¹H NMR (400 MHz, CD₃OD) δ 7.82 (m, 1H), 7.53 (m, 4H), 6.78 (m, 1H), 6.30 (m, 2H), 5.35 (m, 1H), 4.83 (m, 2H), 4.17 (m, 2H), 3.16-3.04 (m, 1H), 2.98 (m, 1H), 2.48 (m, 2H), 1.53 (s, 6H), 1.43 (m, 1H), 1.08 (m, 1H). MS (m/z) 712.18 [M+H]⁺.

Example 16

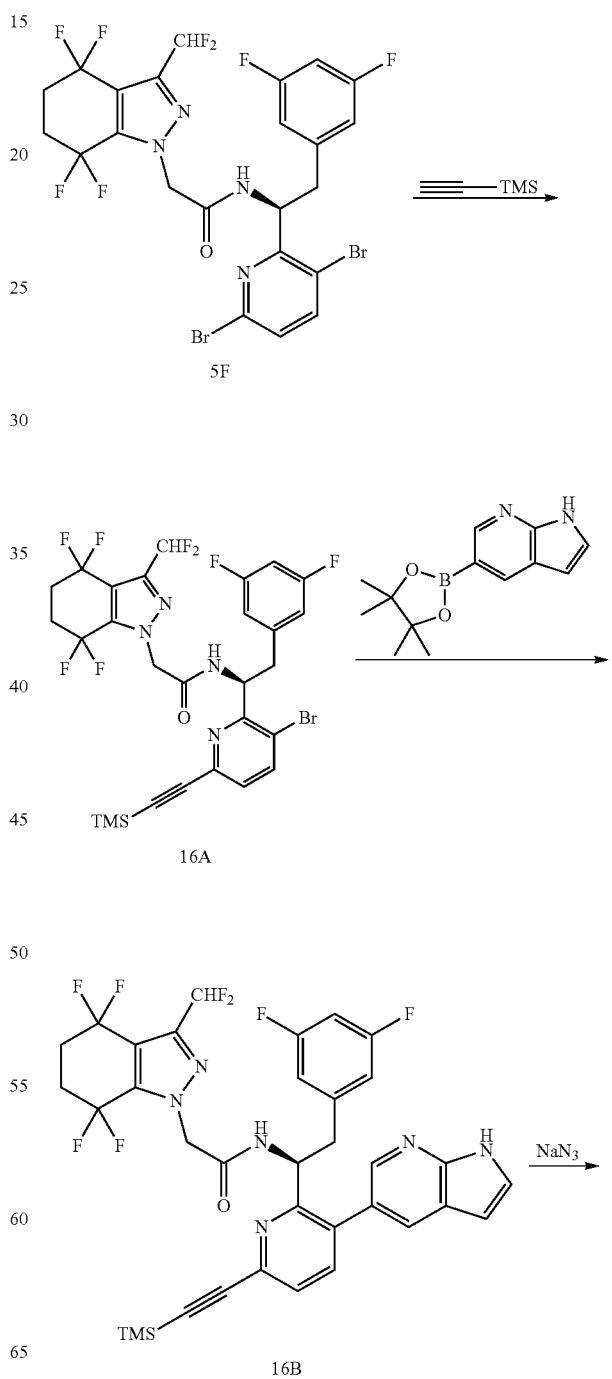

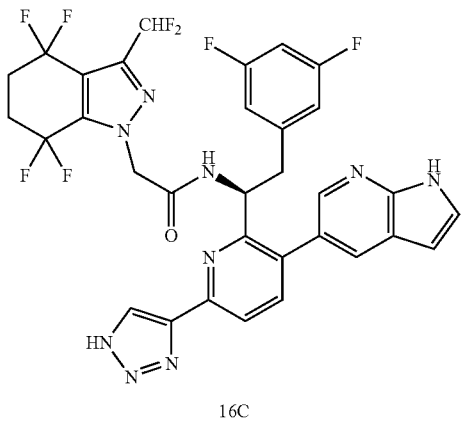

16C

Synthesis of (S)—N-(1-(3-bromo-6-((trimethylsilyl) ethynyl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (16A)

The title compound (16A) was prepared according to the method presented for the synthesis of compound 4F of Example 4 utilizing ethynyltrimethylsilane and 5F. MS (m/z) 694.59 [M+H]$^+$.

Synthesis of (S)—N-(1-(3-(1H-pyrrolo[2,3-b]pyridin-5-yl)-6-((trimethylsilyl)ethynyl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (16B)

The title compound (16B) was prepared according to the method presented for the synthesis of compound 4H of Example 4 utilizing 5-(4,4,5,5-tetramethyl-1,3,2-dioxaborolan-2-yl)-1H-pyrrolo[2,3-b]pyridine and 16A. MS (m/z) 731.22 [M+H]$^+$.

Synthesis of (S)—N-(1-(3-(1H-pyrrolo[2,3-b]pyridin-5-yl)-6-(1H-1,2,3-triazol-4-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (16C)

Compound 16B (75 mg, 0.1 mmol), NaN$_3$ (13 mg, 0.2 mmol) and NH$_4$Cl (5 mg, 0.1 mmol) were dissolved in DMF (0.5 mL) and stirred at 100° C. for overnight. The reaction mixture was cooled down to room temperature and diluted with water and extracted with EtOAc. The organic phase was dried (Na$_2$SO$_4$), filtered and concentrated. The crude material was purified on reverse phase HPLC eluting with acetonitrile and water (with 0.1% TFA) to afford the title product. $^1$H NMR (400 MHz, CD$_3$OD) δ 9.01 (d, J=7.7 Hz, 1H), 8.54 (s, 1H), 7.99 (m, 3H), 7.73 (d, J=8.0 Hz, 1H), 7.59 (d, J=3.5 Hz, 1H), 6.97-6.55 (m, 3H), 6.31 (d, J=6.3 Hz, 2H), 5.45 (m, 1H), 5.11 (s, 2H), 3.13 (m, 2H), 2.49 (m, 4H). MS (m/z) 702.02 [M+H]$^+$.

Example 17

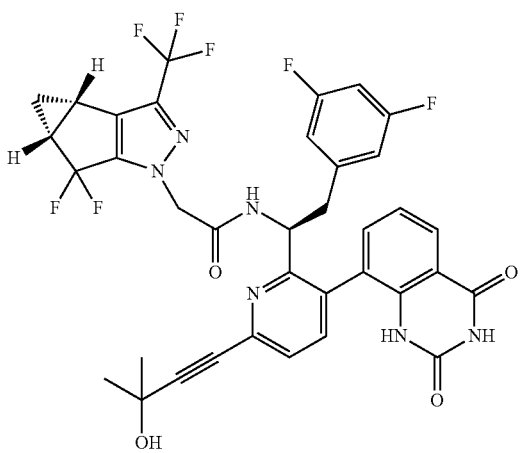

17

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(2,4-dioxo-1,2,3,4-tetrahydroquinazolin-8-yl)-6-(3-hydroxy-3-methylbut-1-ynyl)pyridin-2-yl)ethyl)acetamide (17)

The title compound was prepared according to the method presented for the synthesis of compound 4F of Example 4 utilizing 8-(4,4,5,5-tetramethyl-1,3,2-dioxaborolan-2-yl)quinazoline-2,4(1H,3H)-dione and 14D. $^1$H NMR (400 MHz, DMSO) δ 11.36 (d, 1H), 10.12 (d, 1H), 8.87 (m, 1H), 7.98 (d, 1H), 7.75-6.70 (m, 7H), 6.47-6.57 (m, 2H), 4.74-4.50 (m, 2H), 3.01-2.90 (m, 2H), 2.48-2.60 (m, 2H), 1.49 (s, 6H), 1.45-1.24 (m, 1H), 0.96 (m, 1H). MS (m/z) 741.1 [M+H]$^+$.

Example 18

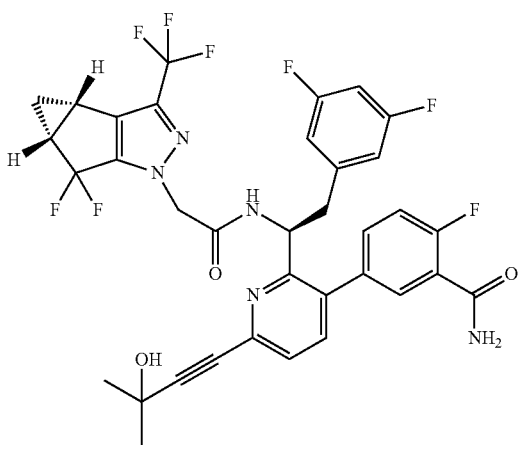

18

Synthesis of 5-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-2-fluorobenzamide (18)

The title compound was prepared according to the method presented for the synthesis of compound 4F of Example 4 utilizing (3-carbamoyl-4-fluorophenyl)boronic acid and 14D. $^1$H NMR (400 MHz, DMSO) δ 9.08 (d, 1H), 7.79-7.14 (m, 8H), 6.92 (m, 1H), 6.62 (d, 2H), 5.12 (m, 1H), 4.77-4.83 (m, 2H), 3.01 (m, 2H), 2.55 (m, 1H), 1.51 (s, 6H), 1.38 (m, 1H), 0.98 (m, 1H). MS (m/z) 718.2 [M+H]$^+$.

Example 19

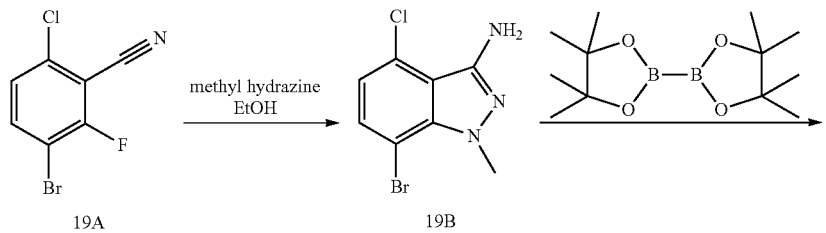

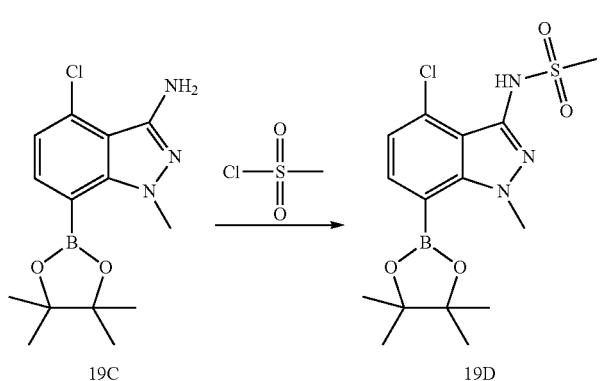

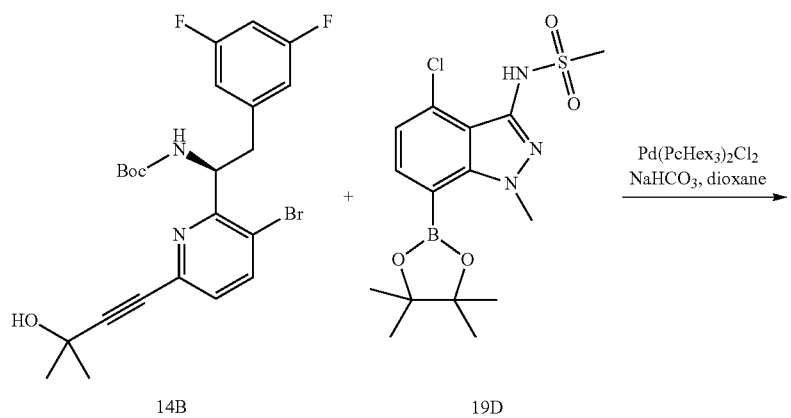

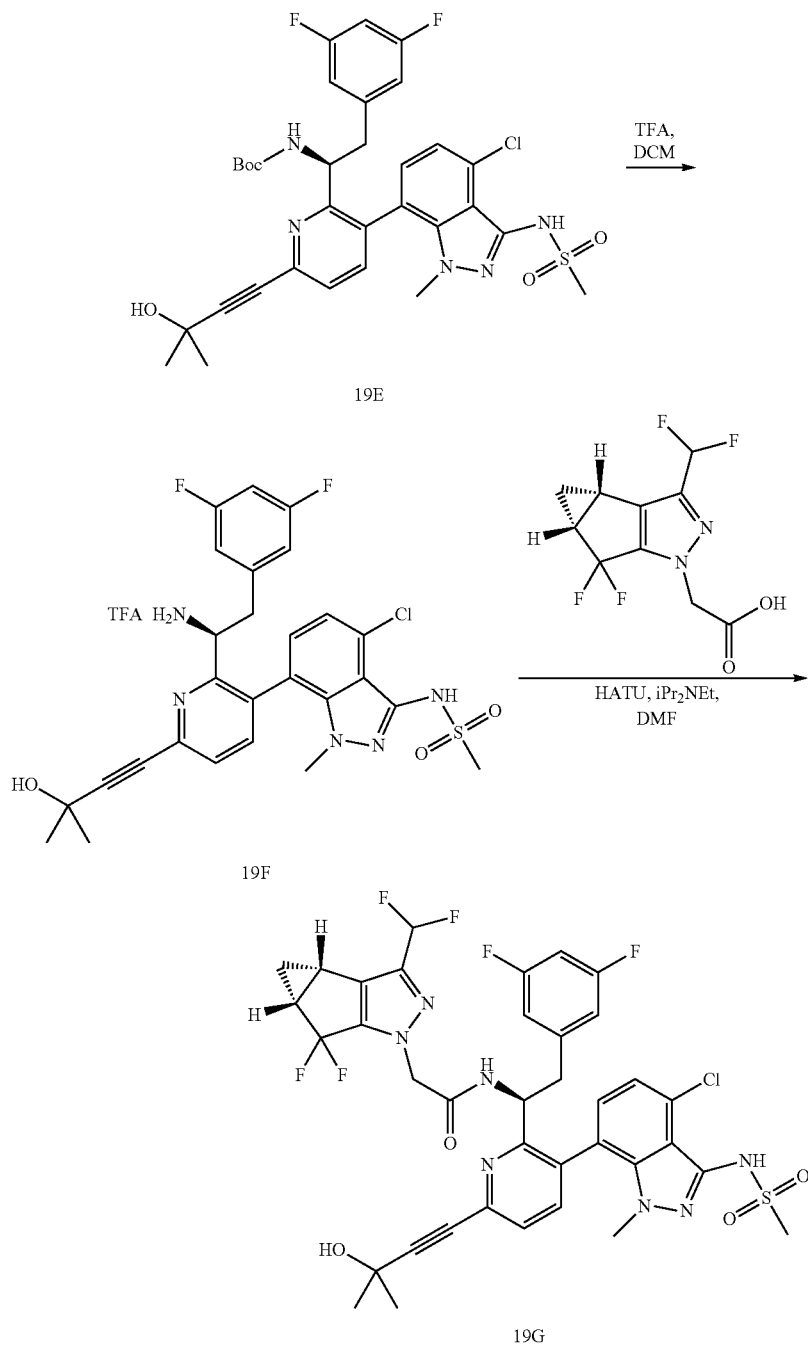

Synthesis of 7-bromo-4-chloro-1-methyl-1H-indazol-3-amine (19B)

To 3-bromo-6-chloro-2-fluorobenzonitrile (10 g, 42.7 mmol) in EtOH (100 mL) was added methylhydrazine (9 ml, 171 mmol). The reaction mixture was stirred for 4 hours at 110° C. The reaction was allowed to slowly cool over 4 hours, then the solids were filtered off and used with no further purification to provide 7 g of the title compound (including minor amounts of the other regioisomer). MS (m/z) 262.0 [M+H]$^+$.

Synthesis of 4-chloro-1-methyl-7-(4,4,5,5-tetramethyl-1,3,2-dioxaborolan-2-yl)-1H-indazol-3-amine (19C)

To 7-bromo-4-chloro-1-methyl-1H-indazol-3-amine (3 g, 11.5 mmol) in dioxane (40 mL) and DMF (25 ml) was added bis (pinacolato)diborane (8.8 g, 34.6 mmol), potassium acetate (3.4 g, 34.6 mmol), and trans-dichlorobis(triphenylphosphine)palladium (II) (486.35 mg, 0.69 mmol). The reaction mixture was stirred for 3 hours at 130° C. The reaction was cooled, diluted with EtOAc, and then the solids were filtered off over Celite and silica gel eluting with EtOAc. The mixture was concentrated and purified by flash column chromatography to provide 1.8 g of the title compound. MS (m/z) 308.3 [M+H]$^+$.

Synthesis of N-(4-chloro-1-methyl-7-(4,4,5,5-tetramethyl-1,3,2-dioxaborolan-2-yl)-1H-indazol-3-yl)methanesulfonamide (19D)

To 7-bromo-4-chloro-1-methyl-1H-indazol-3-amine (2.6 g, 8.5 mmol) in DCM (30 mL) was added N,N-Diisopropylethylamine (5.9 ml, 33.8 mmol) then the reaction was cooled in an ice bath and methansulfonyl chloride (2 ml, 25.4 mmol) was added. The reaction mixture was stirred for 20 minutes at 0° C. The reaction was diluted with water and extracted 2× with DCM. The organic layer was dried over sodium sulfate and concentrated. The resulting mixture was taken up in EtOH (30 ml) and 8 ml of 10N NaOH was added. The reaction was followed by LC/MS and once done (10 minutes) the reaction was diluted with water and quenched with concentrated HCl to pH 2. The mixture was extracted 3× with DCM. The organic layer was dried over sodium sulfate and concentrated until solid starts to fall out. The mixture is then cooled in a brine/ice bath for 20 minutes and filtered to recover desired as two lots and used with no further purification to provide 2.1 g of the title compound. MS (m/z) 386.4 [M+H]$^+$.

Synthesis of (S)-tert-butyl 1-(3-(4-chloro-1-methyl-3-(methylsulfonamido)-1H-indazol-7-yl)-6-(3-hydroxy-3-methylbut-1-ynyl)pyridin-2-yl)-2-(3,5-difluorophenyl)ethylcarbamate (19E)

To N-(4-chloro-1-methyl-7-(4,4,5,5-tetramethyl-1,3,2-dioxaborolan-2-yl)-1H-indazol-3-yl)methanesulfonamide (39 mg, 0.1 mmol) in dioxane (5 mL) and DMF (0.3 ml) was added 14B (50 mg, 0.1 mmol), 1N sodium bicarbonate (0.9 ml, 0.9 mmol), and dichlorobis(tricyclohexylphosphine)palladium (II) (1.9 mg, 0.003 mmol). The reaction mixture was stirred for 4 hours at 140° C. The reaction was cooled, diluted with EtOAc and brine. The mixture was extracted 2× with EtOAc, the organic layer was dried over sodium sulfate, was concentrated and purified by flash column chromatography to provide 30 mg of the title compound. MS (m/z) 674.7 [M+H]$^+$.

Synthesis of (S)—N-(7-(2-(1-amino-2-(3,5-difluorophenyl)ethyl)-6-(3-hydroxy-3-methylbut-1-ynyl)pyridin-3-yl)-4-chloro-1-methyl-1H-indazol-3-yl)methanesulfonamide TFA salt (19F)

To (S)-tert-butyl 1-(3-(4-chloro-1-methyl-3-(methylsulfonamido)-1H-indazol-7-yl)-6-(3-hydroxy-3-methylbut-1-ynyl)pyridin-2-yl)-2-(3,5-difluorophenyl)ethylcarbamate (30 mg, 0.04 mmol) in DCM (4 mL) was added TFA (2 ml). The reaction mixture was stirred for 0.5 hours at RT. The reaction was concentrated and used with no further purification to provide the title compound. MS (m/z) 574.4 [M+H]$^+$.

Synthesis of (S)—N-(1-(3-(4-chloro-1-methyl-3-(methylsulfonamido)-1H-indazol-7-yl)-6-(3-hydroxy-3-methylbut-1-ynyl)pyridin-2-yl)-2-(3,5-difluorophenyl)ethyl)-2-((3bS,4aR)-5,5-difluoro-3-(difluoromethyl)-3b,4,4a,5-tetrahydro-1H-cyclopropa[3,4]cyclopenta[1,2-c]pyrazol-1-yl)acetamide (19G)

The title compound (19G) was prepared according to the method presented for the synthesis of compound 4G of Example 4 utilizing 2-((3bS,4aR)-5,5-difluoro-3-(difluoromethyl)-3b,4,4a,5-tetrahydro-1H-cyclopropa[3,4]cyclopenta[1,2-c]pyrazol-1-yl)acetic acid and (S)—N-(7-(2-(1-amino-2-(3,5-difluorophenyl)ethyl)-6-(3-hydroxy-3-methylbut-1-ynyl)pyridin-3-yl)-4-chloro-1-methyl-1H-indazol-3-yl)methanesulfonamide to provide 20 mg of the title compound. $^1$H NMR (400 MHz, Methanol-d$_4$) δ 8.69 (t, 1H), 7.69 (dd, 1H), 7.53 (dd, 1H), 7.17 (s, 1H), 7.06 (d, 1H), 6.88-6.52 (m, 2H), 6.44-6.33 (m, 2H), 5.28 (d, 1H), 5.02-4.92 (m, 1H), 4.78-4.64 (m, 2H), 3.33 (s, 3H), 3.24 (d, 3H), 3.19-3.08 (m, 2H), 3.05-2.92 (m, 2H), 2.44 (ddd, 2H), 1.64 (d, 6H), 1.38 (dt, 1H), 1.02 (s, 1H).
MS (m/z) 820.8 [M+H]$^+$.

Example 20

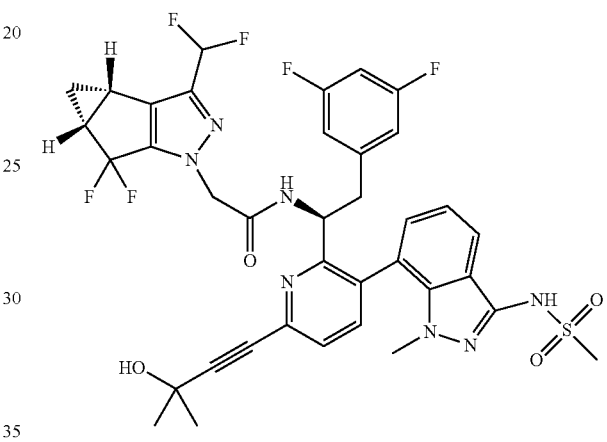

Synthesis of (S)—N-(1-(3-(1-methyl-3-(methylsulfonamido)-1H-indazol-7-yl)-6-(3-hydroxy-3-methylbut-1-ynyl)pyridin-2-yl)-2-(3,5-difluorophenyl)ethyl)-2-((3bS,4aR)-5,5-difluoro-3-(difluoromethyl)-3b,4,4a,5-tetrahydro-1H-cyclopropa[3,4]cyclopenta[1,2-c]pyrazol-1-yl)acetamide (20)

The title compound was prepared according to the method presented for the synthesis of compound 19G of utilizing N-(1-methyl-7-(4,4,5,5-tetramethyl-1,3,2-dioxaborolan-2-yl)-1H-indazol-3-yl)methanesulfonamide and compound 14B. $^1$H NMR (400 MHz, Methanol-d$_4$) δ 8.69 (t, 1H), 7.88-7.80 (dd, 1H), 7.69 (dd, 1H), 7.53 (dd, 1H), 7.20 (s, 1H), 7.09 (d, 1H), 6.88-6.52 (m, 2H), 6.38-6.27 (m, 2H), 5.35 (m, 1H), 5.02-4.95 (m, 1H), 4.80-4.65 (m, 2H), 3.33 (s, 3H), 3.19-3.08 (m, 4H), 3.05-2.92 (m, 2H), 2.44 (m, 2H), 1.64 (d, 6H), 1.38 (m, 1H), 1.02 (m, 1H).
MS (m/z) 786.1 [M+H]$^+$.

Example 21

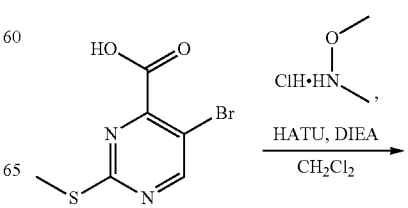

US 9,951,043 B2

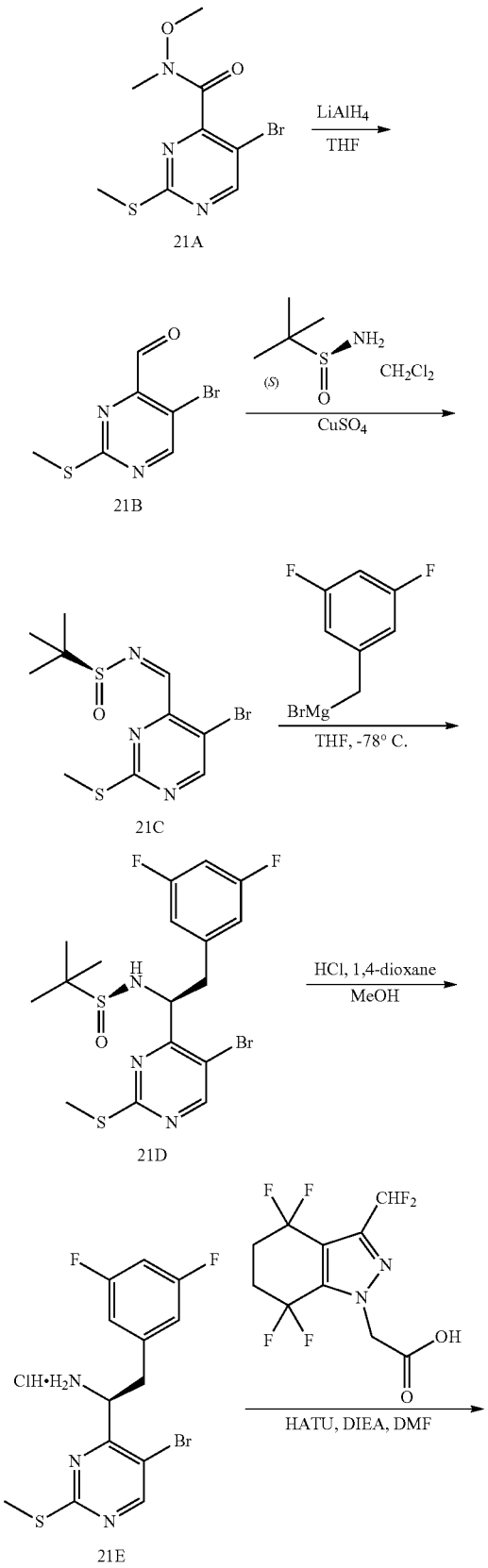

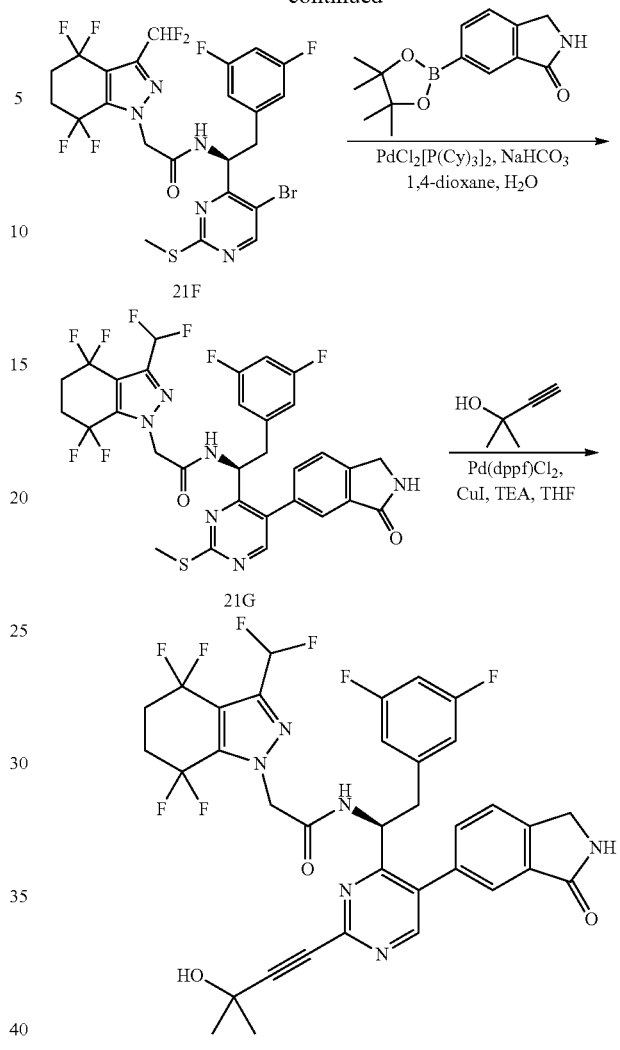

Synthesis of 5-bromo-N-methoxy-N-methyl-2-(methylthio)pyrimidine-4-carboxamide (21A)

To a mixture of 5-bromo-2-(methylthio)pyrimidine-4-carboxylic acid (5 g, 20 mmol), N,O-dimethylhydroxylamine hydrochloride (2.9 g, 30 mmol) and HATU (9.1 g, 24 mmol) in 100 mL of $CH_2Cl_2$ at 0° C. was added N,N-diisopropylethylamine (17.4 mL, 100 mmol). The reaction mixture was allowed to stir at 0° C. for 30 min and then diluted with $CH_2Cl_2$. It was washed with water and half brine. The organic layer was separated, dried over $MgSO_4$, filtered and concentrated. The crude product was purified by silica gel chromatography to afford the title compound 21A. MS (m/z) 292.16 [M+H]$^+$.

Synthesis of 5-bromo-2-(methylthio)pyrimidine-4-carbaldehyde (21B)

A solution of 5-bromo-N-methoxy-N-methyl-2-(methylthio)pyrimidine-4-carboxamide (21A, 8.2 g, 28 mmol) in THF (120 mL) was added dropwise to a suspension of lithium aluminum hydride (1.06 g, 28 mmol) and THF (120 mL) at −78° C. The mixture was stirred for 10 minutes after addition finish. H$_2$O (1.06 mL), 15% aqueous NaOH solution (1.06 mL) and H$_2$O (3.18 mL) were successively added to the mixture at 0° C. very slowly. The resulting precipitate was filtered and washed with THF. The filtrate was concentrated in vacuo to afford crude of the title compound. MS (m/z): 233.14, [M+H]$^+$.

Synthesis of (S)—N-((5-bromo-2-(methylthio)pyrimidin-4-yl)methylene)-2-methylpropane-2-sulfinamide (21C)

Copper(II) sulfate (anhydrous, 8.9 g, 56 mmol) was added to a solution of 5-bromo-2-(methylthio)pyrimidine-4-carbaldehyde (21B, ~28 mmol) and (S)-2-methylpropane-2-sulfinamide (3.4 g, 28 mmol) in CH$_2$Cl$_2$ (100 mL). The suspension was stirred for 3 days at room temperature. The reaction was filtered and washed with CH$_2$Cl$_2$ (3×20 ml). The filtrate was concentrated. The crude product was purified by silica gel chromatography to yield the title compound 21C. MS (m/z) 337.7 [M+H]$^+$ Synthesis of (S)—N—((S)-1-(5-bromo-2-(methylthio)pyrimidin-4-yl)-2-(3,5-difluorophenyl)ethyl)-2-methylpropane-2-sulfinamide (21D)

To a solution of (S)—N-((5-bromo-2-(methylthio)pyrimidin-4-yl)methylene)-2-methylpropane-2-sulfinamide (21C, 2.97 g. 8.8 mmol) in THF (18 mL) cooled to −78° C. was drop wise added 3,5-Difluorobenzylmagnesium bromide (53 mL, 0.25 M in Ether, 13.3 mmol). After stirring at −78° C. for 10 min, NH$_4$Cl (sat. aq.) (10 ml) was added to the reaction and warmed up to ambient temperature. Extracted with EtOAc and the organic layer was dried over Na$_2$SO$_4$(s). The solvent was removed and the residue was purified by silica gel chromatography to yield 1.44 g of the title compound 21D MS (m/z) 465.87 [M+H]$^+$ Synthesis of (S)-1-(5-bromo-2-(methylthio)pyrimidin-4-yl)-2-(3,5-difluorophenyl)ethanamine hydrochloride (21E)

Compound 21D (8 g, 17.23 mmol) was dissolved in 35 mL of methanol and cooled to 0° C. To it was added 4N HCl/1,4-dioxane (10.7 mL). The reaction mixture was allowed to stir for 20 minutes and to it was added diethyl ether. The resulting precipitate was collected by vacuum filtration then dried to afford the title product 21E. MS (m/z) 362.02 [M+H]$^+$.

Synthesis of (S)—N-(1-(5-bromo-2-(methylthio)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (21F)

A mixture of 2-(3-(difluoromethyl)-4,4,7,7-tetrafluoro-4,5,6,7-tetrahydro-1H-indazol-1-yl)acetic acid (604 mg, 2 mmol), compound 21E (793 mg, 2 mmol) and HATU (912 mg, 2.4 mmol) in 10 mL of DMF was cooled to 0° C. To it was drop wise added N,N-diisopropylethylamine (1.05 mL, 6 mmol). The reaction mixture was allowed to stir at 0° C. for 10 minutes then slowly poured it into ice water with stirring. The resulting precipitate was collected by vacuum filtration then dried to afford the title product 21F. MS (m/z) 644.22 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-(methylthio)-5-(3-oxoisoindolin-5-yl)pyrimidin-4-yl)ethyl)acetamide (21G)

In a microwave tube were charged with compound 21F (300 mg, 0.47 mmol), 6-(4,4,5,5-tetramethyl-1,3,2-dioxaborolan-2-yl)isoindolin-1-one (181 mg, 0.7 mmol) and PdCl$_2$[P(Cy)$_3$]$_2$(17 mg, 0.023 mmol). To the mixture was added 10 mL of 1,4-dioxane and 1.4 mL of sodium bicarbonate aqueous solution (1M). The mixture was heated to 155° C. for 25 min in a microwave synthesizer. After cooled to room temperature, it was partitioned between EtOAc and water. The organic layer was separated and washed with brine, then dried over MgSO$_4$, filtered and concentrated. The residue was purified by silica gel chromatography to afford the title compound 21G. MS (m/z) 697.32 [M+H]$^+$).

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-(3-hydroxy-3-methylbut-1-yn-1-yl)-5-(3-oxoisoindolin-5-yl)pyrimidin-4-yl)ethyl)acetamide (21H)

To the mixture of solid CuI (3.3 mg, 0.017 mmol), Pd(dppf)Cl$_2$ (7 mg, 0.009 mmol), 2-methylbut-3-yn-2-ol (22 mg, 0.26 mmol) and compound 21G (60 mg, 0.086 mmol) were added THF (1 mL) and Et$_3$N (0.06 mL, 0.4 mmol). The reaction mixture was heated in a microwave at 160° C. for 20 min. After cooled to room temperature it was diluted with EtOAc. To it was added Si-Thiol (130 mg, 1.37 mmol/g) and the mixture was stirred at 40° C. for 1 hour. Then it was filtered and the filtrate was washed with 10% aqueous NH$_4$OH, water and brine. The organic layer was dried over MgSO$_4$, filtered, concentrated, and purified by reverse phase HPLC to afford the title compound (21H). $^1$H NMR (400 MHz, Methanol-d4): δ 9.09 (d), 8.54 (s), 7.64 (dd), 7.58 (dd), 7.40 (d), 6.78 (t), 6.67 (tt), 6.43-6.20 (m), 5.40 (q), 4.50 (s), 3.05 (d), 2.50 (tdd), 1.62 (s). MS (m/z): 732.99 [M+H]$^+$.

Example 22

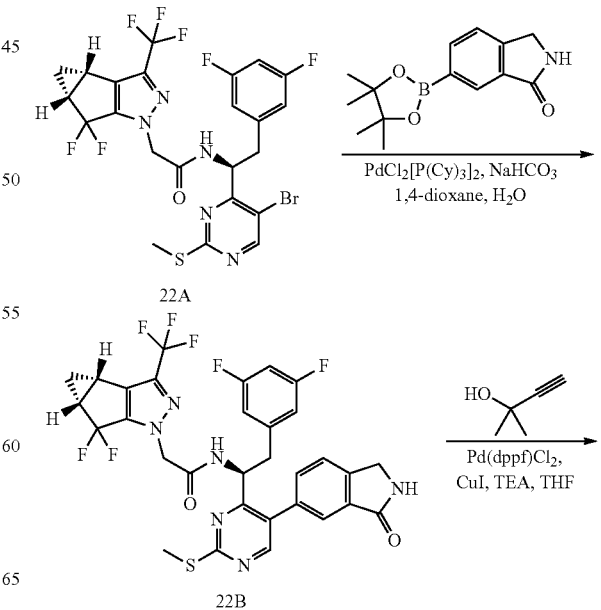

22A

22B

213
-continued

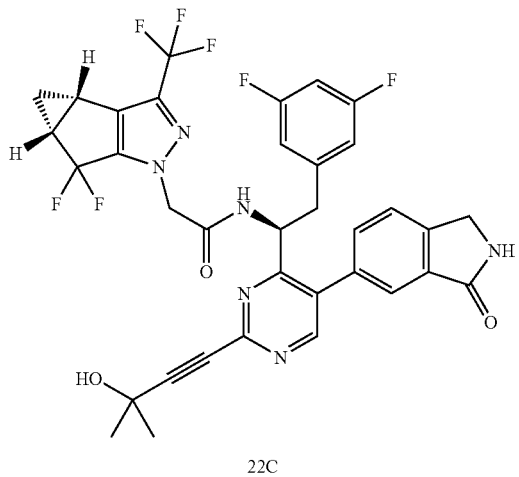

22C

Synthesis of N—((S)-1-(5-bromo-2-(methylthio)
pyrimidin-4-yl)-2-(3,5-difluorophenyl)ethyl)-2-
((3bS,4aR)-5,5-difluoro-3-(trifluoromethyl)-3b,4,4a,
5-tetrahydro-1H-cyclopropa[3,4]cyclopenta[1,2-c]
pyrazol-1-yl)acetamide (22A)

The title compound (22A) was prepared according to the method presented for the synthesis of compound 21F of Example 21 utilizing 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid and compound 21E. MS (m/z) 624.13 [M+H]$^+$.

Synthesis of 2-((3bS,4aR)-5,5-difluoro-3-(trifluoromethyl)-3b,4,4a,5-tetrahydro-1H-cyclopropa[3,4]
cyclopenta[1,2-c]pyrazol-1-yl)-N—((S)-2-(3,5-difluorophenyl)-1-(2-(methylthio)-5-(3-oxoisoindolin-
5-yl)pyrimidin-4-yl)ethyl)acetamide (22B)

The title compound (22B) was prepared according to the method presented for the synthesis of compound 21G of Example 21 utilizing compound 22A and 6-(4,4,5,5-tetramethyl-1,3,2-dioxaborolan-2-yl)isoindolin-1-one. MS (m/z) 677.05 [M+H]$^+$.

Synthesis of 2-((3bS,4aR)-5,5-difluoro-3-(trifluoromethyl)-3b,4,4a,5-tetrahydro-1H-cyclopropa[3,4]
cyclopenta[1,2-c]pyrazol-1-yl)-N—((S)-2-(3,5-difluorophenyl)-1-(2-(3-hydroxy-3-methylbut-1-yn-1-
yl)-5-(3-oxoisoindolin-5-yl)pyrimidin-4-yl)ethyl)
acetamide (22C)

The title compound (22C) was prepared according to the method presented for the synthesis of compound 21H of Example 21 utilizing compound 22B and 2-methylbut-3-yn-2-ol. $^1$H NMR (400 MHz, Methanol-d4): δ 9.05 (d), 8.53 (s), 7.63 (dd), 7.58 (dd), 7.37 (d), 6.75-6.55 (m), 6.41-6.21 (m), 5.41 (q), 4.85 (s), 4.50 (s), 3.05 (dd), 2.48-2.45 (m), 1.62 (s), 1.38 (q), 1.18-0.97 (m, 1H). MS (m/z) 713.01 [M+H]$^+$.

214
Example 23

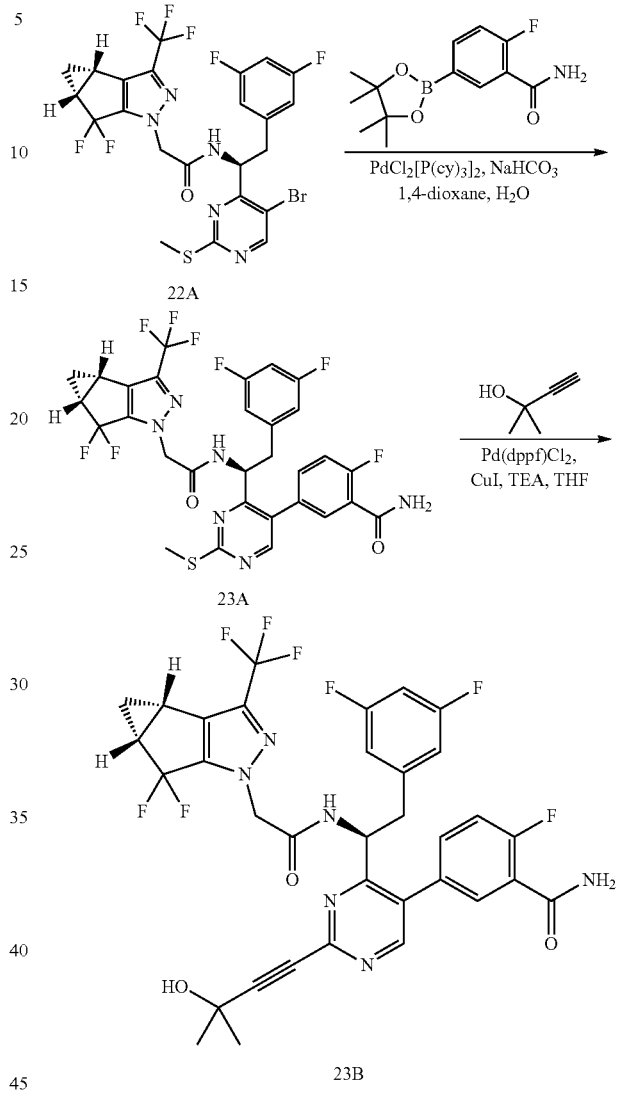

Synthesis of 5-(4-((S)-1-(2-((3bS,4aR)-5,5-difluoro-
3-(trifluoromethyl)-3b,4,4a,5-tetrahydro-1H-cyclopropa[3,4]cyclopenta[1,2-c]pyrazol-1-yl)acetamido)-
2-(3,5-difluorophenyl)ethyl)-2-(methylthio)
pyrimidin-5-yl)-2-fluorobenzamide (23A)

The title compound (23A) was prepared according to the method presented for the synthesis of compound 21G of Example 21 utilizing compound 22A and 2-fluoro-5-(4,4,5,5-tetramethyl-1,3,2-dioxaborolan-2-yl)benzamide. MS (m/z) 683.06 [M+H]$^+$.

Synthesis of 5-(4-((S)-1-(2-((3bS,4aR)-5,5-difluoro-
3-(trifluoromethyl)-3b,4,4a,5-tetrahydro-1H-cyclopropa[3,4]cyclopenta[1,2-c]pyrazol-1-yl)acetamido)-
2-(3,5-difluorophenyl)ethyl)-2-(3-hydroxy-3-
methylbut-1-yn-1-yl)pyrimidin-5-yl)-2-
fluorobenzamide (23B)

The title compound (23B) was prepared according to the method presented for the synthesis of compound 21H of Example 21 utilizing compound 23A and 2-methylbut-3-yn-2-ol. ¹H NMR (400 MHz, Methanol-d₄): δ 9.09 (t), 8.51 (d), 7.46 (ddq), 7.27 (ddd), 6.69 (tt), 6.40 (h), 5.36 (q), 4.84 (s), 3.10-3.01 (m), 2.48-2.45 (m), 1.61 (s), 1.38 (q), 1.07 (dd). MS (m/z) 719.06 [M+H]⁺.

Example 24

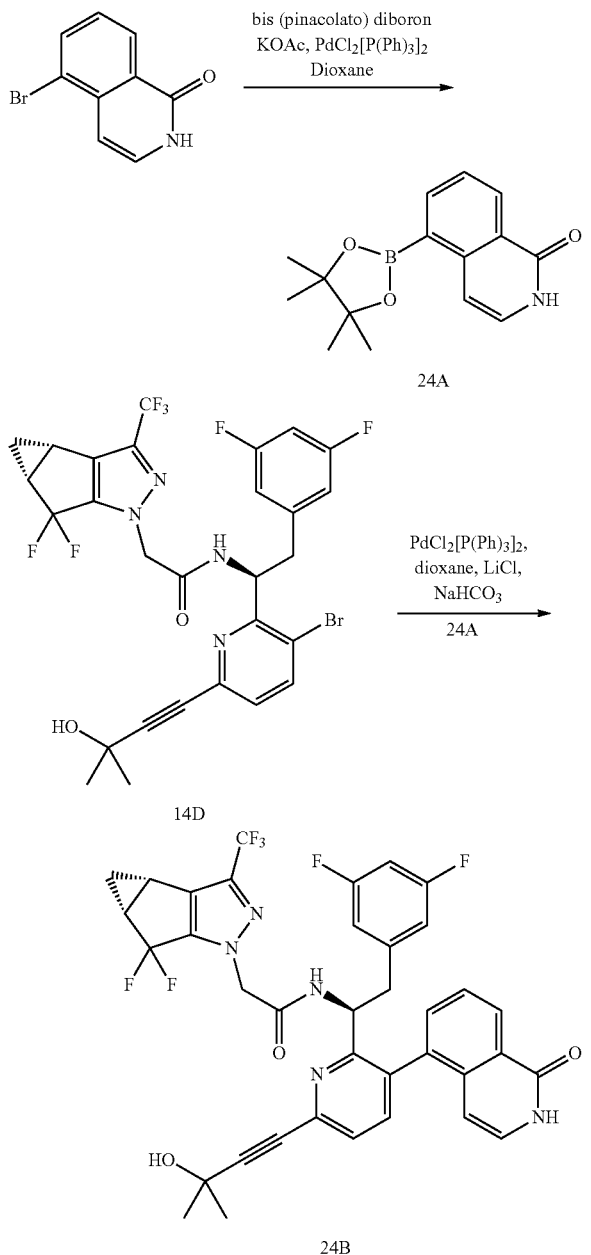

Synthesis of 5-(4,4,5,5-tetramethyl-1,3,2-dioxaborolan-2-yl)isoquinolin-1(2H)-one (24A)

To 5-bromoisoquinolin-1(2H)-one (40 mg, 0.18 mmol) in dioxane (1 mL) was added bis(pinacolato)diboron (63 mg, 0.25 mmol), and PdCl₂[P(Ph)₃]₂ (6 mg, 0.01 mmol). The reaction mixture sealed and heated to 100° C. for 1 h. The reaction was cooled to room temperature and telescoped to the next reaction. MS (m/z) 272.3 [M+H]⁺.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-oxo-1,2-dihydroisoquinolin-5-yl)pyridin-2-yl)ethyl)acetamide (24B)

To the reaction vial containing 24A (0.18 mmol) was added 14D (50 mg, 0.07 mmol), PdCl₂[P(Ph)₃]₂ (5 mg, 0.01 mmol), LiCl (11 mg, 0.22 mmol) and aq 1M NaHCO₃ (0.22 mL, 0.22 mmol). The reaction mixture was sealed and heated in a microwave reactor to 160° C. for 20 min. Upon cooling, the reaction mixture was diluted with EtOAc and washed with three portions of brine. The organic layer were dried over Na₂SO₄, filtered, concentrated in vacuo, and purified by reverse phase HPLC to provide the title compound 24B as a mixture of atropisomers. MS (m/z) 724.2 [M+H]⁺. HPLC retention time 6.95 min and 7.09 min (2-98% acetonitrile: water with 0.1% trifluoroacetic acid, 8.5 min gradient on a Phenomonex Kinetex C18 column).

Example 25

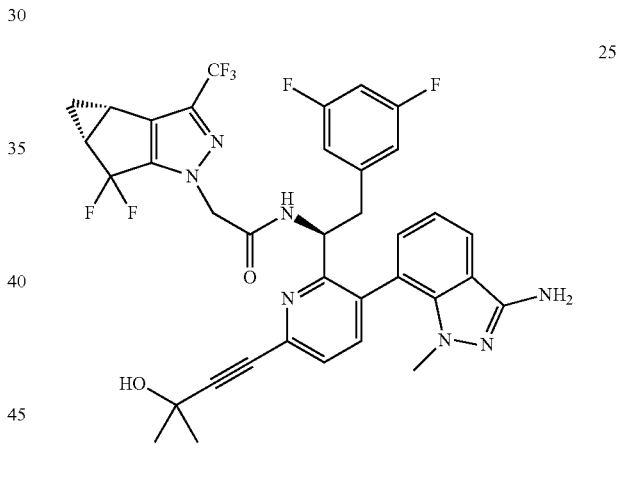

Synthesis of N—((S)-1-(3-(3-amino-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (25)

The title compound (25) was prepared as a mixture of atropisomers according to the method presented for the synthesis of compound 33F of Example 33 utilizing 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid and 37A. ¹H NMR (400 MHz, cd₃od) δ 9.04-8.52 (m), 7.7-7.61 (m), 7.52 (dd), 7.17 (d), 7.04 (t), 7.00-6.90 (m), 6.77-6.66 (m), 6.60 (t), 6.48 9 (d), 6.40-6.25 (m), 5.32-5.25 (m), 5.11-5.04 (m), 4.80-4.79 (m), 3.22-3.06 (m), 2.96-2.85 (m), 2.52-2.46 (m), 1.64 (s), 1.43-1.39 (m), 1.14-1.07 (m). MS (m/z) 726.2 [M+H]⁺.

Example 26

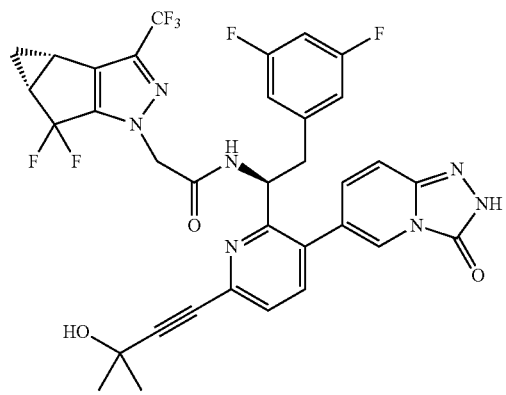

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-oxo-2,3-dihydro-[1,2,4]triazolo[4,3-a]pyridin-6-yl)pyridin-2-yl)ethyl)acetamide (26)

The title compound (26) was prepared according to the method presented for the synthesis of compound 24B of Example 24 utilizing 6-(4,4,5,5-tetramethyl-1,3,2-dioxaborolan-2-yl)-[1,2,4]triazolo[4,3-a]pyridin-3(2H)-one MS (m/z) 714.1 [M+H]$^+$. HPLC retention time 6.58 min (2-98% acetonitrile: water with 0.1% trifluoroacetic acid, 8.5 min gradient on a Phenomonex Kinetex C18 column).

Example 27

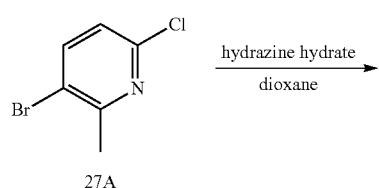

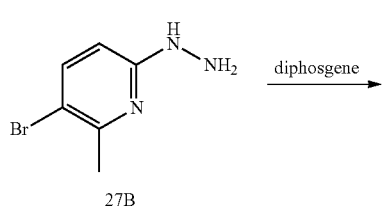

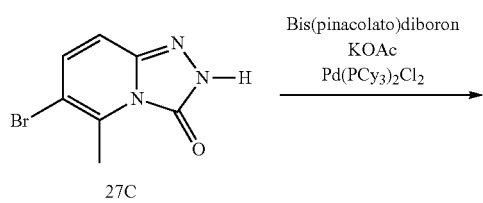

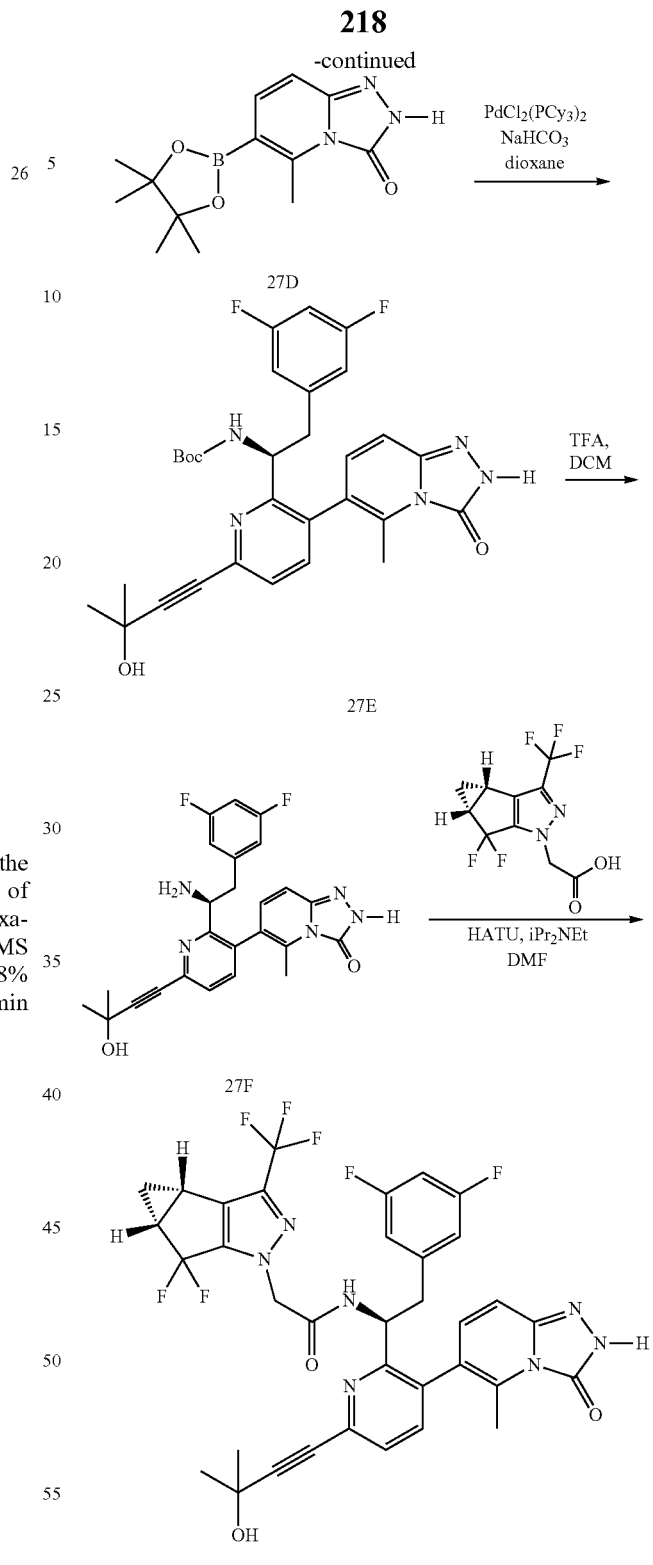

Synthesis of 3-bromo-6-hydrazinyl-2-methylpyridine (27B)

To 3-bromo-6-chloro-2-methylpyridine (1.53 g, 7.41 mmol) in dioxane (4.5 ml) was added hydrazine hydrate (1.8 ml, 37 mmol). The reaction was heated in a microwave reactor at 160° C. for 55 min. After cooling to ambient temperature, the reaction mixture was partitioned between EtOAc and saturated aqueous NaCl. The organics were separated and evaporated in vacuo. The product was used directly in the following step. MS (m/z) 202.0 [M+H]+.

Synthesis of 6-bromo-5-methyl-1-[1,2,4]triazolo[4, 3-a]pyridin-3(2H)-one (27C)

3-bromo-6-hydrazinyl-2-methylpyridine (4.55 g, 22.52 mmol) was dissolved in DCE (35 ml) to which trichloromethyl chloroformate (2.72 ml, 22.52 mmol) was added. The reaction was stirred at ambient temperature for 1 h. Hexanes (15 ml) was added and the solids filtered to provide the desired product. The eluent was reduced in a volume and a second crop of precipitate was isolated. The combined solids were used without further purification. MS (m/z) 228.0 [M+H]+.

Synthesis of 5-methyl-6-(4,4,5,5-tetramethyl-1,3,2-dioxaborolan-2-yl)-[1,2,4]triazolo[4,3-a]pyridin-3(2H)-one (27D)

6-bromo-5-methyl-[1,2,4]triazolo[4,3-a]pyridin-3(2H)-one (3.62 g, 15.87 mmol) was combined with bis(pinacolato)diboron (6.05 g, 23.81 mmol), KOAc (3.12 g, 31.75 mmol), and PdCl$_2$(PCy$_3$)$_2$ (0.23 g, 0.32 mmol) in dioxane (80 ml). Argon was bubbled into the reaction solution for 15 min. The reaction was then heated to 85 deg C. for 15 h. Additional PdCl$_2$(PCy$_3$)$_2$ (250 mg) was added and the temperature was raised to 125 deg C. Heated for 15 h. After cooling to ambient temperature, the reaction was partitioned between EtOAc and water. The organics were separated, dried, and removed in vacuo. The residue was suspended in EtOAc (50 ml) and the resultant solids filtered to provide the title compound. MS (m/z) 276.2 [M+H]+.

Synthesis of (S)-tert-butyl (2-(3,5-difluorophenyl)-1-(6-(3-hydroxy-3-methylbut-1-yn-1-yl)-3-(5-methyl-3-oxo-2,3-dihydro-[1,2,4]triazolo[4,3-a]pyridin-6-yl)pyridin-2-yl)ethyl)carbamate (27E)

In a microwave reaction vessel, 14B (66 mg, 0.13 mmol) and 5-methyl-6-(4,4,5,5-tetramethyl-1,3,2-dioxaborolan-2-yl)-[1,2,4]triazolo[4,3-a]pyridin-3 (2H)-one (55 mg, 0.2 mmol) were dissolved in dioxane (2 mL) and treated with aqueous 1M NaHCO$_3$ (0.4 mL) and PdCl$_2$(PCy$_3$)$_2$ (10 mg). The mixture was heated to 150° C. for 20 min. After cooling to ambient temperature, the reaction was partitioned between EtOAc and water. The organics were separated, dried, and removed in vacuo and the residue was purified by column chromatography on silica to provide the title compound as a mixture of atropisomers. MS (m/z) 563.8 [M+H]+.

Synthesis of (S)-6-(2-(1-amino-2-(3,5-difluorophenyl)ethyl)-6-(3-hydroxy-3-methylbut-1-yn-1-yl)pyridin-3-yl)-5-methyl-[1,2,4]triazolo[4,3-a]pyridin-3(2H)-one (27F)

The title compound (27F) was prepared as a mixture of atropisomers according to the method presented for the synthesis of 19F in Example 19 utilizing 27E. MS (m/z) 464.1 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(5-methyl-3-oxo-2,3-dihydro-[1,2,4]triazolo[4,3-a]pyridin-6-yl)pyridin-2-yl)ethyl)acetamide (27G)

The title compound (27G) was prepared as a mixture of atropisomers according to the method presented for the synthesis of 37E in Example 37 utilizing 27F and 2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, Methanol-d$_4$) δ 8.75 (dd), 7.44-7.54 (m), 6.83-6.92 (m), 6.68-6.80 (m), 6.47-6.56 (dd), 5.98 (d), 5.16-5.24 (m), 3.13-3.26 (m), 3.03-3.08 (m), 2.45-2.51 (m), 2.37 (s), 2.11 (s), 1.36-1.43 (m), 1.05-1.15 (m). MS (m/z) 728.0 [M+H]+.

Example 28

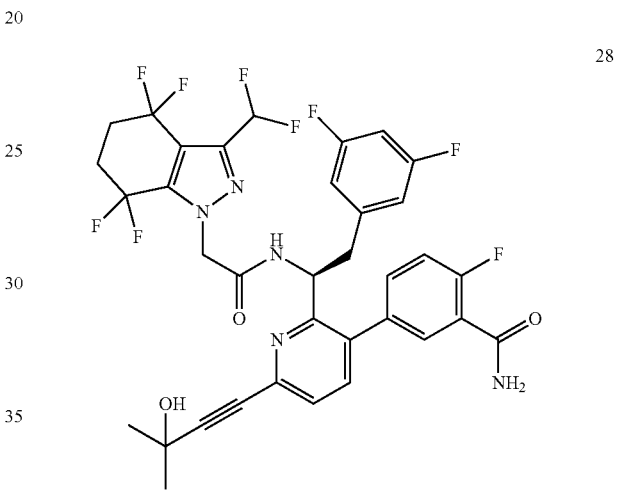

28

Synthesis of (S)-5-(2-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-6-(3-hydroxy-3-methylbut-1-yn-1-yl)pyridin-3-yl)-2-fluorobenzamide (28)

The title compound (28) was prepared according to the method presented for the synthesis of compound 33F of Example 33 utilizing (3-carbamoyl-4-fluorophenyl)boronic acid and 2-(3-(difluoromethyl)-4,4,7,7-tetrafluoro-4,5,6,7-tetrahydro-1H-indazol-1-yl)acetic acid. 1H NMR (400 MHz, cd$_3$od) δ 8.88 (d), 7.55 (d), 7.50-7.36 (m), 7.32 (s), 7.23 (dd), 6.94 (d), 6.82 (d), 6.72-6.62 (m), 6.40-6.31 (m), 5.40-5.32 (m), 5.22 (s), 5.06 (s), 4.36-4.29 (m), 3.75-3.57 (m), 3.14-2.98 (m), 2.66-2.42 (m), 1.62 (s). MS (m/z) 738.2 [M+H]+.

Example 29

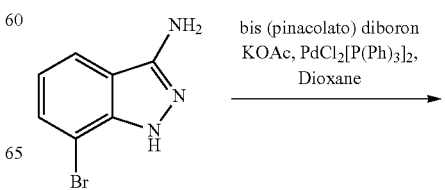

Example 30

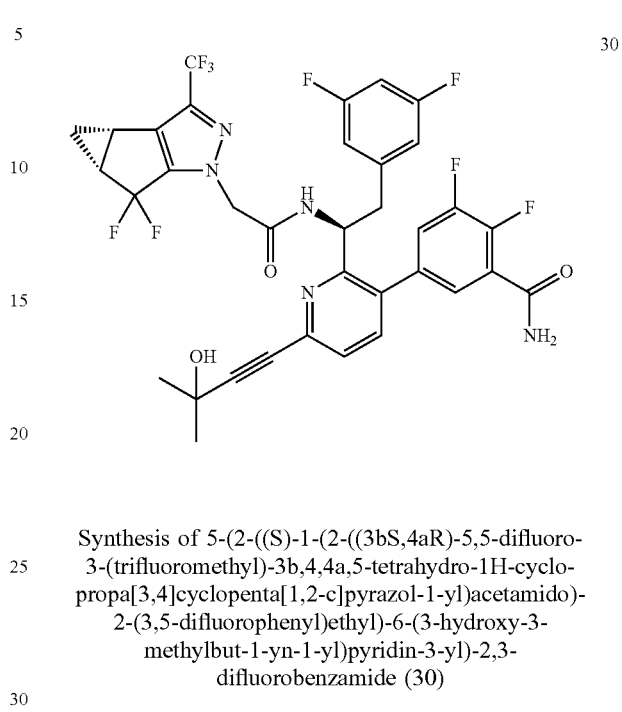

Synthesis of 5-(2-(((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-2,3-difluorobenzamide (30)

The title compound (30) was prepared according to the method presented for the synthesis of compound 33F of Example 33 utilizing 5-bromo-2,3-difluorobenzamide and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, cd$_3$od) δ 8.80 (d), 7.71-7.65 (m), 7.60-7.50 (m), 7.49-7.40 (m), 7.25-7.18 (m), 7.17-7.10 (m), 6.79-6.65 (m), 6.43-6.31 (m), 5.33 (m, 1H), 5.03 (s), 4.33-4.30 (m), 3.20-3.00 (m), 2.59-2.45 (m), 1.65-1.55 (m), 1.49-1.37 (m), 1.15-1.04 (m). MS (m/z) 736.1 [M+H]$^+$.

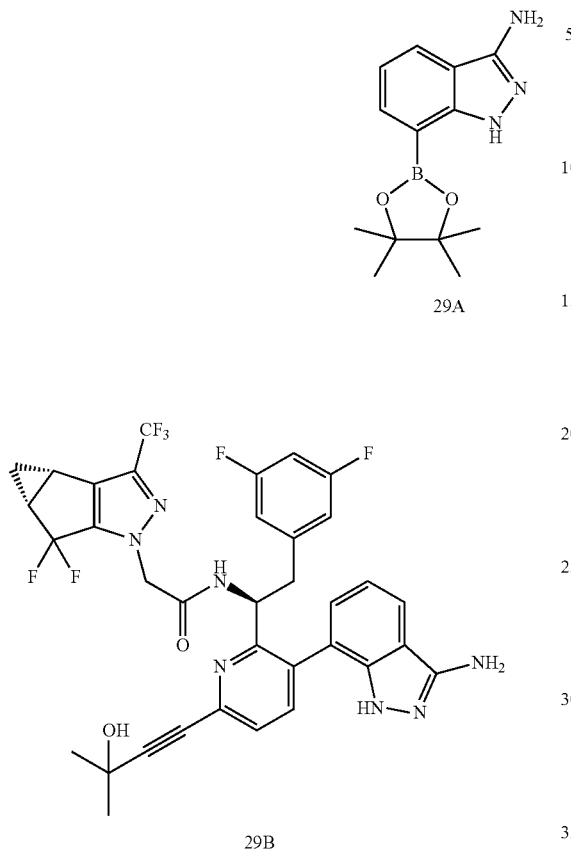

29A

Synthesis of 7-(4,4,5,5-tetramethyl-1,3,2-dioxaborolan-2-yl)-1H-indazol-3-amine (29A)

To 7-bromo-1H-indazol-3-amine (75 mg, 0.35 mmol) in dioxane (3 mL) was added bis(pinacolato)diboron (126 mg, 0.5 mmol), and PdCl$_2$[P(Ph)$_3$]$_2$ (12 mg, 0.01 mmol). The reaction mixture sealed and heated to 100° C. for 16 h. The reaction was cooled to room temperature and telescoped to the next reaction. MS (m/z) 260.2 [M+H]$^+$. Synthesis of N—((S)-1-(3-(3-amino-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (29B)

The title compound (29) was prepared according to the method presented for the synthesis of compound 24B of Example 24 utilizing 29A. MS (m/z) 712.4 [M+H]$^+$. PLC retention time 6.02 min (2-98% acetonitrile: water with 0.1% trifluoroacetic acid, 8.5 min gradient on a Phenomonex Kinetex C18 column).

Example 31

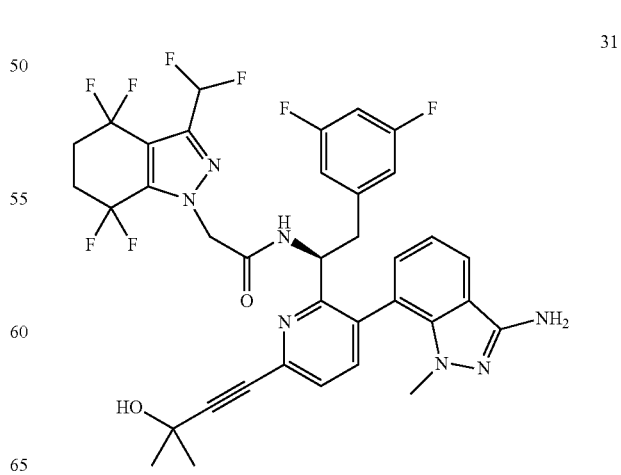

Synthesis of (S)—N-(1-(3-(3-amino-1-methyl-1H-indazol-7-yl)-6-(3-hydroxy-3-methylbut-1-yn-1-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (31)

The title compound (31) was prepared as a mixture of atropisomers according to the method presented for the synthesis of compound 33F of Example 33 utilizing 37A and 2-(3-(difluoromethyl)-4,4,7,7-tetrafluoro-4,5,6,7-tetrahydro-H-indazol-1-yl)acetic acid. $^1$H NMR (400 MHz, cd$_3$od) δ 8.85 (m), 7.87-7.85 (m), 7.70 (d), 7.54-7.46 (d), 7.33 (d), 7.25-7.15 (m), 6.81-6.71 (m), 6.40-6.32 (m), 5.35-5.24 (m), 5.03-4.98 (m), 3.19 (s), 3.08-2.95 (m), 2.61-2.40 (m), 1.64 (s). MS (m/z) 746.2 [M+H]$^+$.

Example 32

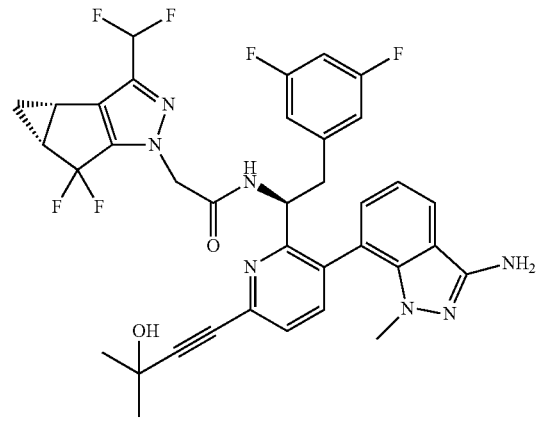

32

Synthesis of N—((S)-1-(3-(3-amino-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (32)

The title compound (32) was prepared as a mixture of atropisomers according to the method presented for the synthesis of compound 33F of Example 33 utilizing 37A. $^1$H NMR (400 MHz, cd$_3$od) δ 8.68 (d), 7.89-7.79 (m), 7.74-7.65 (m), 7.59-7.48 (m), 7.29 (d), 7.16-7.11 (m), 6.79-6.60 (m), 6.39 (d), 6.35-6.28 (m), 5.27-5.22 (m), 5.06-4.95 (m), 4.73 (d), 3.16 (s), 3.13-3.03 (m), 3.02-2.84 (m), 2.50-2.39 (m), 1.64 (s), 1.42-1.34 (m), 1.03 (s). MS (m/z) 708.2 [M+H]$^+$.

Example 33

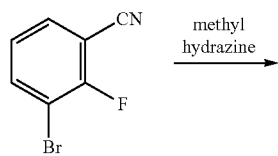

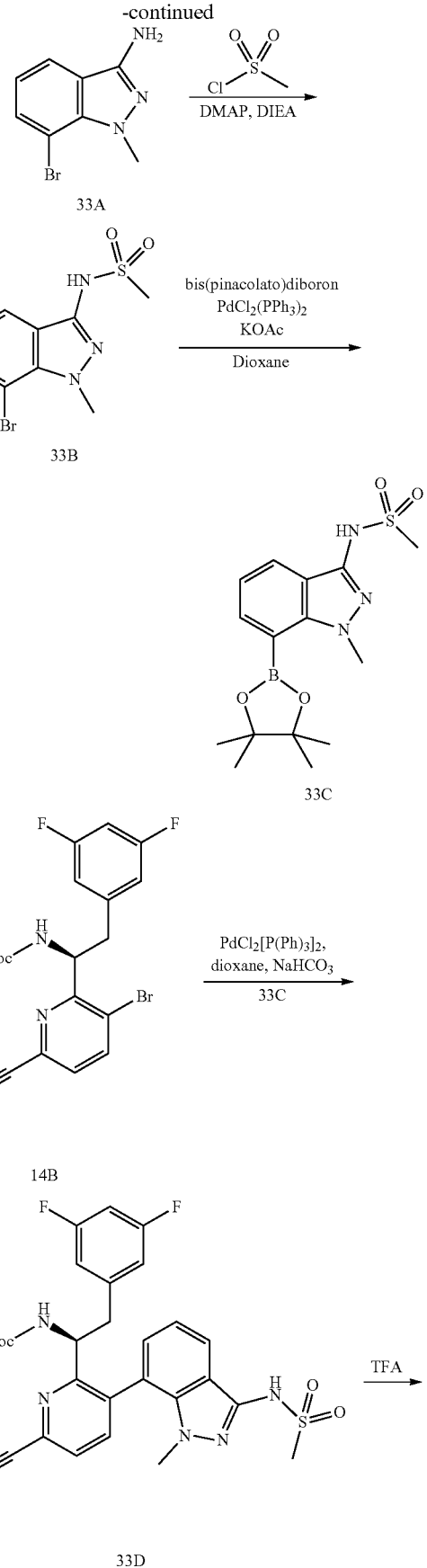

-continued

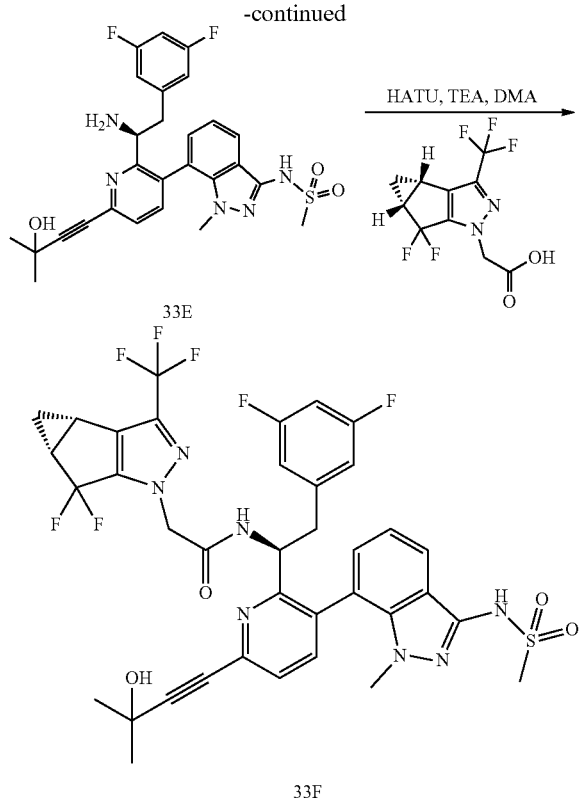

Synthesis of 7-bromo-1-methyl-1H-indazol-3-amine (33A)

In a microwave vial a solution of 3-bromo-2-fluorobenzonitrile (2 g, 10 mmol) ethanol (10 mL) was treated with methylhydrazine (2.1 mL, 40 mmol), sealed, and heated to 120° C. in a microwave reactor for 35 minutes. The reaction was concentrated in vacuo and the crude product dissolved with EtOAc (30 mL) and washed with water (30 mL), then 2M NaCl (aq, 30 mL). The organics were dried with $Na_2SO_4$, filtered, and concentrated. Product was purified by silica chromatography to give the title compound. MS (m/z) 227.1 $[M+H]^+$.

Synthesis of N-(7-bromo-1-methyl-1H-indazol-3-yl)methanesulfonamide (33B)

To a stirred solution of 33A (500 mg, 2.21 mmol), 4-Dimethylaminopyridine (13.5 mg, 0.11 mmol), and N,N-diisopropylethylamine (714.6 mg, 5.53 mmol) in DCM (20 ml) was added dropwise methanesulfonyl chloride (532.0 mg, 4.64 mmol) at 0° C. The reaction was warmed to RT and stirred for 2 h. The reaction was washed with water, dried with $Na_2SO_4$, filtered, and concentrated. The crude product dissolved with EtOH (10 mL) and treated with 8N NaOH (1.65 ml). The reaction mixture was heated at 60° C. for 0.5 h. The ethanol was removed under vacuum, pH to ~2 with 1.0 HCl then, extracted with EtOAc. The organics were dried with $Na_2SO_4$, filtered, and concentrated. The product was purified by silica chromatography to give the title compound. MS (m/z) 305.9 $[M+H]^+$.

Synthesis of N-(1-methyl-7-(4,4,5,5-tetramethyl-1,3,2-dioxaborolan-2-yl)-1H-indazol-3-yl)methanesulfonamide (33C)

To 33B (1.2 g, 3.9 mmol) in dioxane (15 mL) was added bis(pinacolato)diboron (1.9 mg, 5.5 mmol), and $PdCl_2[P(Ph)_3]_2$ (138 mg, 0.19 mmol). The reaction mixture sealed and heated to 100° C. for 1 h. The reaction was cooled to rt and filtered through Celite using ethyl acetate to rinse the pad. The collected organic phase was concentrated in vacuo and purified by silica gel chromatography to give the title compound. MS (m/z) 352.1 $[M+H]^+$.

Synthesis of (S)-tert-butyl (2-(3,5-difluorophenyl)-1-(6-(3-hydroxy-3-methylbut-1-yn-1-yl)-3-(1-methyl-3-(methylsulfonamido)-1H-indazol-7-yl)pyridin-2-yl)ethyl)carbamate (33D)

To 14B (250 mg, 0.5 mmol) in dioxane (12 mL) was added N-(1-methyl-7-(4,4,5,5-tetramethyl-1,3,2-dioxaborolan-2-yl)-1H-indazol-3-yl)methanesulfonamide (33C, 253 mg, 0.72 mmol), $PdCl_2[P(Ph)_3]_2$ (35 mg, 0.05 mmol), and aq 1M $NaHCO_3$ (1.5 mL, 1.5 mmol). The reaction mixture sealed and heated in a microwave reactor to 150° C. for 20 min. Upon cooling, the reaction mixture was diluted with EtOAc and washed with three portions of brine. The organic layer were dried over $Na_2SO_4$, filtered, concentrated in vacuo, and purified by silica gel column chromatography, eluting with 0-100% EtOAc in hexanes to give the title compound 33D as a mixture of atropisomers.

Synthesis of (S)—N-(7-(2-(1-amino-2-(3,5-difluorophenyl)ethyl)-6-(3-hydroxy-3-methylbut-1-yn-1-yl)pyridin-3-yl)-1-methyl-1H-indazol-3-yl)methanesulfonamide (33E)

To a solution of 33D (47 mg, 0.07 mmol) in DCM was added 4M HCl in dioxane (0.7 mL, 2.9 mmol). The reaction mixture was stirred at room temperature for 0.5 hours. Upon complete removal of the Boc protecting group, the reaction was concentrated in vacuo to give the title compound 33E as a mixture of atropisomers.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(methylsulfonamido)-1H-indazol-7-yl)pyridin-2-yl)ethyl)acetamide (33F)

To a solution of 33E (70 mg) in DMA (3 mL) was added triethylamine (0.046 mL, 0.32 mmol), followed by 2-((3bS,4aR)-3-(trifluoromethyl)-5,5-difluoro-3b,4,4a,5-tetrahydro-1H-cyclopropa[3,4]cyclopenta[1,2-c]pyrazol-1-yl)acetic acid (31 mg, 0.1 mmol) and HATU (46 mg, 0.12 mmol). After stirring for 30 minutes, the reaction mixture was filtered and purified by reverse phase HPLC to provide the product 33F as a mixture of atropisomers. $^1$H NMR (400 MHz, $cd_3od$) δ 7.83 (dd), 7.72-7.64 (m), 7.50-7.55 (m), 7.32-7.07 (m), 6.78-6.70 (m), 6.52-6.48 (m), 6.33-6.31 (m), 5.35-5.28 (m), 5.05-4.37 (m), 3.56 (s), 3.21-3.09 (m), 3.00-2.90 (m), 2.54-2.40 (m), 1.64 (s), 1.50-1.39 (m), 1.10-0.88 (m). MS (m/z) 804.1 $[M+H]^+$.

Example 34

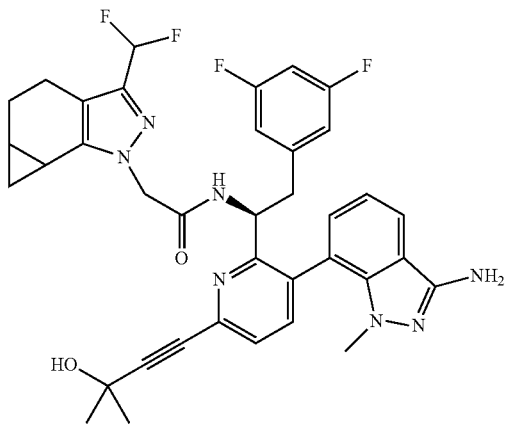

Synthesis of N—((S)-1-(3-(3-amino-1-methyl-1H-indazol-7-yl)-6-(3-hydroxy-3-methylbut-1-yn-1-yl)pyridin-2-yl)-2-(3,5-difluorophenyl)ethyl)-2-(3-(difluoromethyl)-5,5a,6,6a-tetrahydrocyclopropa[g]indazol-1 (4H)-yl)acetamide (34)

The title compound (34) was prepared as a mixture of atropisomers according to the method presented for the synthesis of compound 33F of Example 33 utilizing 37A and 2-(3-(difluoromethyl)-5,5a,6,6a-tetrahydrocyclopropa[g]indazol-1(4H)-yl)acetic acid (WO2013006738). $^1$H NMR (400 MHz, cd$_3$od) δ 7.91-7.86 (m), 7.71 (dd), 7.54 (dd), 7.22-7.17 (m), 6.87-6.69 (m), 6.66-6.56 (m), 6.41-6.30 (m), 5.35-5.25 (m), 5.08-4.97 (m), 4.90-4.71 (m), 4.36-4.29 (m), 3.76-3.66 (m), 3.65-3.57 (m), 3.18-3.13 (m), 3.07 (dt), 3.01-2.90 (m), 2.75-2.64 (m), 2.21-2.04 (m), 1.76-1.61 (m), 1.10-1.03 (m), 1.00-0.90 (m), 0.75-0.70 (m), 0.69-0.62 (m). MS (m/z) 686.2 [M+H]$^+$.

Example 35

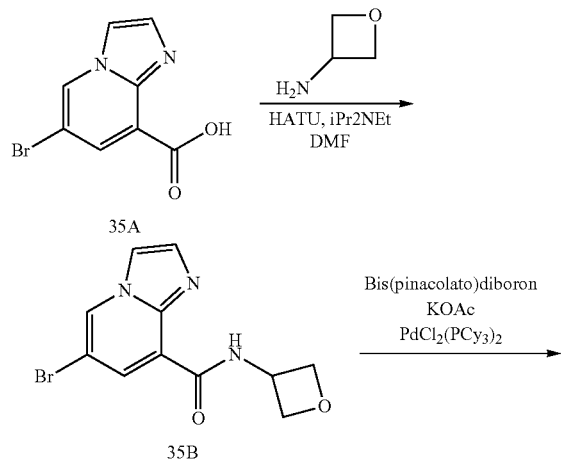

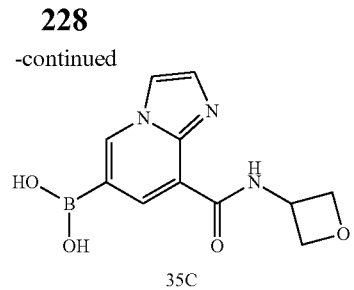

Synthesis of 6-bromo-N-(oxetan-3-yl)imidazo[1,2-a]pyridine-8-carboxamide (35B)

6-bromoimidazo[1,2-a]pyridine-8-carboxylic acid hydrochloride (235 mg, 0.85 mmol) and HATU (386.16 mg, 1.02 mmol) were combined in DMF (4 ml) and treated with iPr$_2$NEt (0.37 ml, 2.12 mmol). 3-Oxetamine hydrochloride (92.31 mg, 0.85 mmol) was added and the reaction stirred at ambient temperature for 1 h. Water (2 ml) was added and a solid precipitated. The solids were collected by filtration to provide the desired product. MS (m/z) 296.0 [M+H]$^+$.

Synthesis of (8-(oxetan-3-ylcarbamoyl)imidazo[1,2-a]pyridin-6-yl)boronic acid (35C)

The title compound (35C) was prepared according to the method presented for the synthesis of 27D in Example 27 utilizing 35B wherein the boronic ester hydrolyzed and the corresponding boronic acid was isolated. MS (m/z) 262.1 [M+H]$^+$.

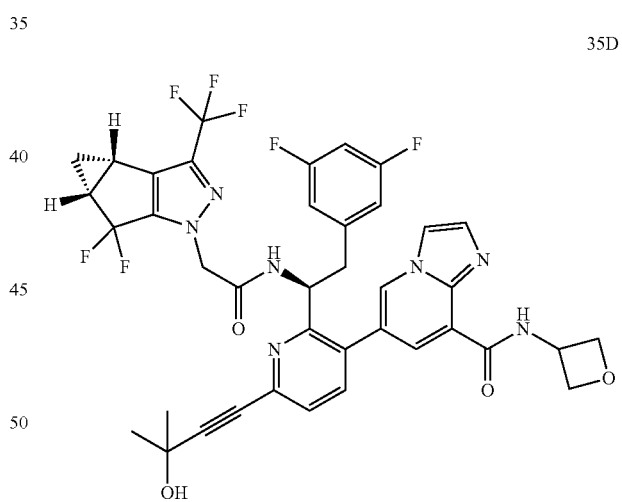

Synthesis of 6-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-N-(oxetan-3-yl)imidazo[1,2-a]pyridine-8-carboxamide (35D)

The title compound (35D) was prepared according to the method presented for the synthesis of 27G in Example 27 utilizing 14B and 35C. $^1$H NMR (400 MHz, Methanol-d$_4$) δ 9.15 (d), 8.80 (d), 8.27 (d), 8.11 (d), 7.84-7.69 (m), 7.65 (dd), 7.53 (dd), 6.89-6.64 (m), 6.53-6.37 (m), 5.34-5.13 (m), 4.73-4.49 (m), 4.49-4.34 (m), 3.96-3.58 (m), 3.25-3.03 (m), 2.59-2.36 (m), 1.51-1.29 (m), 1.18-0.95 (m). MS (m/z) 796.2 [M+H]⁺.

Example 36

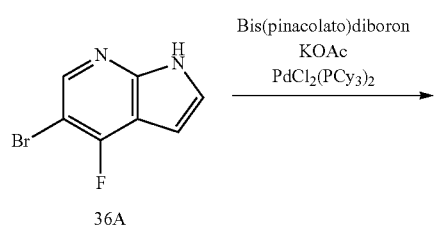

36A

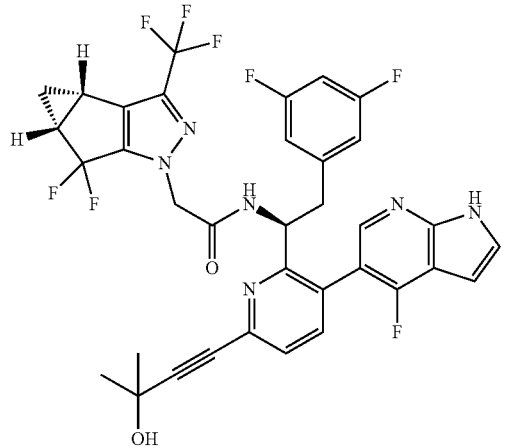

36C

Synthesis of (4-fluoro-1H-pyrrolo[2,3-b]pyridin-5-yl)boronic acid (36B)

In a microwave vessel, 5-bromo-4-fluoro-1H-pyrrolo[2,3-b]pyridine (100 mg, 0.47 mmol) was combined with bis(pinacolato)diboron (177 mg, 0.7 mmol), KOAc (91 mg, 0.93 mmol), and PdCl₂(PCy₃)₂ (34 mg) in dioxane (4.5 ml). Argon was bubbled into the reaction solution for 15 min. The reaction was heated in a microwave reactor at 155° C. for 15 min. After cooling to ambient temperature, the reaction was partitioned between EtOAc and water. The organics were separated, dried, and removed in vacuo to provide the title compound. MS (m/z) 181.1 [M+H]⁺.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(4-fluoro-1H-pyrrolo[2,3-b]pyridin-5-yl)-6-(3-hydroxy-3-methylbut-1-yn-1-yl)pyridin-2-yl)ethyl)acetamide (36C)

The title compound (36C) was prepared according to the method presented for the synthesis of 27G in Example 27 utilizing 14B and 36B. ¹H NMR (400 MHz, Methanol-d₄) δ 8.71 (s), 7.63 (s), 7.53-7.42 (m), 6.64 (s), 6.57 (s), 6.32 (s), 3.14-2.97 (m), 2.56-2.40 (m), 1.62 (s), 1.42-1.34 (m), 1.16-1.04 (m). MS (m/z) 715.1 [M+H]⁺.

Example 37

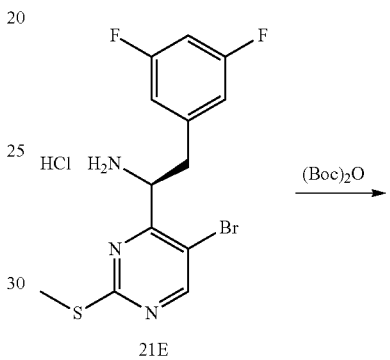

21E

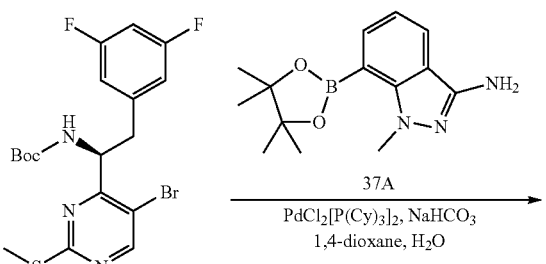

37B

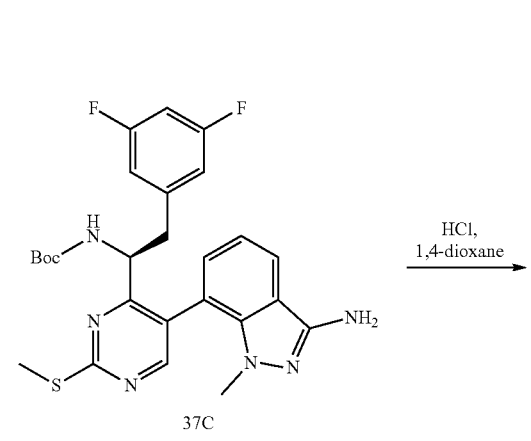

37C

-continued

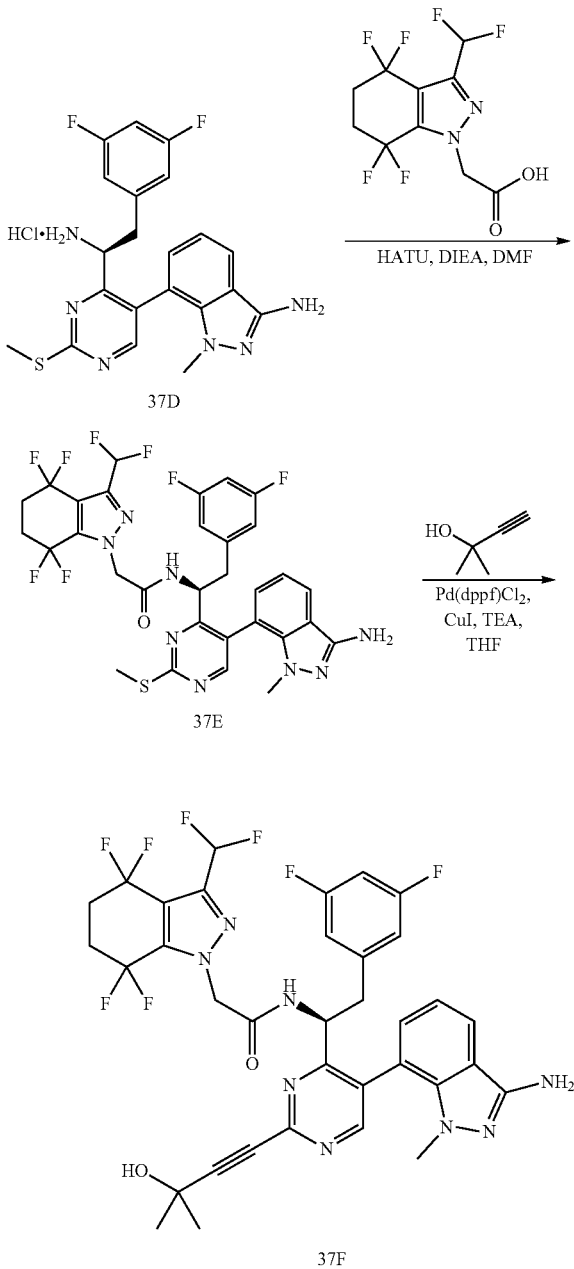

Synthesis of 1-methyl-7-(4,4,5,5-tetramethyl-1,3,2-dioxaborolan-2-yl)-1H-indazol-3-amine (37A)

The title compound (37A) was prepared according to the method presented for the synthesis of compound 39B of Example 39 utilizing 33A. MS (m/z) 274.2 [M+H]⁺.

Synthesis of (S)-tert-butyl (1-(5-bromo-2-(methylthio)pyrimidin-4-yl)-2-(3,5-difluorophenyl)ethyl)carbamate (37B)

To compound 21E (310 mg, 0.78 mmol) in dichloromethane (3 ml) was added triethylamine (217 µL, 1.56 mmol) and di-tert-butyldicarbonate (170 mg, 0.78 mmol). The mixture was stirred for one hour at ambient temperature then concentrated in vacuo.

The residue was purified by silica gel chromatography to afford the title compound (37B). MS (m/z) 459.86 [M+H]⁺.

Synthesis of (S)-tert-butyl (1-(5-(3-amino-1-methyl-1H-indazol-7-yl)-2-(methylthio)pyrimidin-4-yl)-2-(3,5-difluorophenyl)ethyl)carbamate (37C)

The title compound (37C) was prepared as a mixture of atropisomers according to the method presented for the synthesis of compound 21G of Example 21 utilizing compound 37B and 37A. MS (m/z) 526.81 [M+H]⁺.

Synthesis of (S)-7-(4-(1-amino-2-(3,5-difluorophenyl)ethyl)-2-(methylthio)pyrimidin-5-yl)-1-methyl-1H-indazol-3-amine hydrochloride (37D)

Compound 37C (78 mg, 0.15 mmol) was dissolved in 2 mL of 1,4-dioxane and cooled to 0° C. To it was added 4N HCl/1,4-dioxane (2 mL). The reaction mixture was stirred at room temperature for 7 hours. The solvent was removed and dried to afford the title compound 37D as a mixture of atropisomers. MS (m/z) 427.01 [M+H]⁺.

Synthesis of (S)—N-(1-(5-(3-amino-1-methyl-1H-indazol-7-yl)-2-(methylthio)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (37E)

A mixture of 2-(3-(difluoromethyl)-4,4,7,7-tetrafluoro-4,5,6,7-tetrahydro-1H-indazol-1-yl)acetic acid (44 mg, 0.14 mmol), compound 37D (69 mg, 0.15 mmol) and HATU (68 mg, 0.18 mmol) in 1.5 mL of DMF was cooled to 0° C. To it was added N,N-diisopropylethylamine (0.1 mL, 0.6 mmol). The reaction mixture was allowed to stir at 0° C. for 5 minutes then partitioned between EtOAc and 5% aqueous LiCl solution. The organic layer was separated, washed with brine and concentrated. The residue was purified by reverse phase HPLC) to afford the title product 37E as a mixture of atropisomers. MS (m/z) 710.95 [M+H]⁺.

Synthesis of (S)—N-(1-(5-(3-amino-1-methyl-1H-indazol-7-yl)-2-(3-hydroxy-3-methylbut-1-yn-1-yl)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (37F)

The title compound (37F) was prepared as a mixture of atropisomers according to the method presented for the synthesis of compound 21H of Example 21 utilizing compound 37E and 2-methylbut-3-yn-2-ol. ¹H NMR (400 MHz, Methanol-d₄) δ 9.01 (d), 8.69 (d), 7.88-7.78 (m), 7.70-7.41 (m), 7.40-7.28 (m), 7.10 (dt), 6.96-6.52 (m), 6.35 (d), 5.41-5.23 (m), 5.15-5.05 (m), 5.04-4.91 (m), 3.45-3.47 (m), 3.20 (s), 3.13-2.83 (m), 2.62-2.35 (m), 1.62 (s). MS (m/z) 747.03 [M+H]⁺.

Example 38

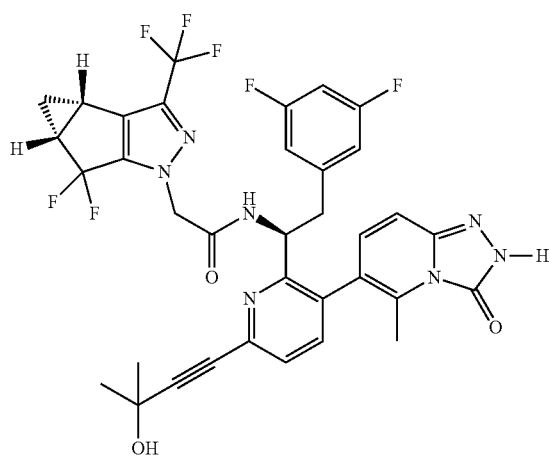

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(5-methyl-3-oxo-2,3-dihydro-[1,2,4]triazolo[4,3-a]pyridin-6-yl)pyridin-2-yl)ethyl)acetamide (38)

The title compound (38) was prepared as a mixture of atropisomers according to the method presented for the synthesis of 27G in Example 27 utilizing 27F and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. HPLC retention time 6.48 min and 6.58 min corresponding to each atropisomer (2-98% acetonitrile: water with 0.1% trifluoroacetic acid, 8.5 min gradient on a Phenomonex Kinetex C18 column 4.6×100 mm). MS (m/z) 710.1 [M+H]+.

Example 39

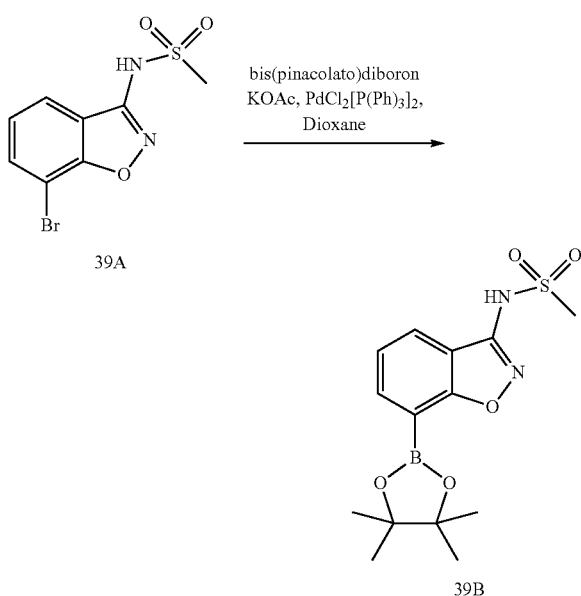

Synthesis of N-(7-(4,4,5,5-tetramethyl-1,3,2-dioxaborolan-2-yl)benzo[d]isoxazol-3-yl)methanesulfonamide (39B)

To 39A (prepared similarly to 33B of example 33 utilizing 7-bromobenzo[d]isoxazol-3-amine instead of 7-bromo-1-methyl-1H-indazol-3-amine) (87 mg, 0.3 mmol) in dioxane (3 mL) was added bis(pinacolato)diboron (107 mg, 0.4 mmol), and PdCl₂[P(Ph)₃]₂ (21 mg, 0.03 mmol). The reaction mixture sealed and heated to 100° C. for 16 h. The reaction was cooled to room temperature and telescoped to the next reaction. MS (m/z) 260.2 [M+H]+.

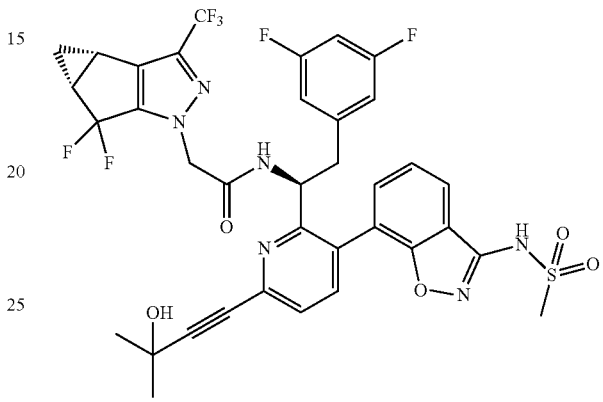

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-(methylsulfonamido)benzo[d]isoxazol-7-yl)pyridin-2-yl)ethyl)acetamide (39C)

The title compound (39C) was prepared according to the method presented for the synthesis of compound 33F of Example 33 utilizing 39B and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. MS (m/z) 791.1 [M+H]+. HPLC retention time 7.25 min (2-98% acetonitrile: water with 0.1% trifluoroacetic acid, 8.5 min gradient on a Phenomonex Kinetex C18 column).

Example 40

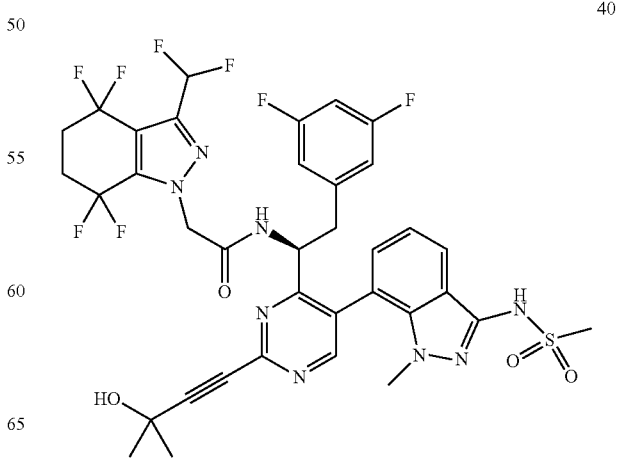

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-(3-hydroxy-3-methylbut-1-yn-1-yl)-5-(1-methyl-3-(methylsulfonamido)-1H-indazol-7-yl)pyrimidin-4-yl)ethyl)acetamide (40)

The title compound (40) was prepared as a mixture of atropisomers according to the method presented for the synthesis of compound 37F of Example 37 utilizing compound 37B and N-(1-methyl-7-(4,4,5,5-tetramethyl-1,3,2-dioxaborolan-2-yl)-1H-indazol-3-yl)methanesulfonamide (compound 33C). $^1$H NMR (400 MHz, Methanol-$d_4$): δ 8.73 (d), 7.90 (ddd), 7.48-7.40 (m), 7.25 (dd), 7.18 (dd), 7.04-6.53 (m), 6.44-6.25 (m), 5.42-5.38 (m), 5.09-4.88 (m), 3.41 (s), 3.19 (s), 3.14-2.90 (m), 2.63-2.20 (m), 1.64 (d). MS (m/z) 824.90 [M+H]$^+$ Example 41

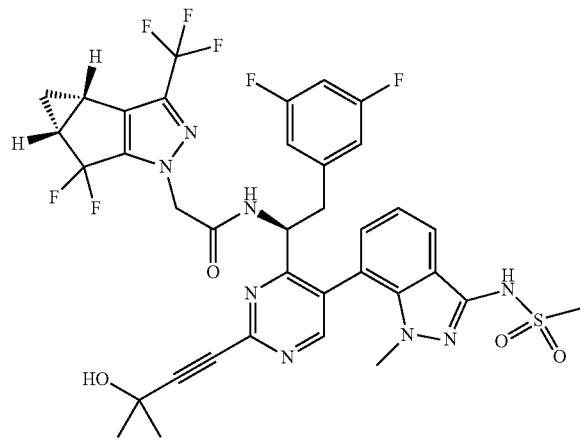

41

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-hydroxy-3-methylbut-1-yn-1-yl)-5-(1-methyl-3-(methylsulfonamido)-1H-indazol-7-yl)pyrimidin-4-yl)ethyl)acetamide (41)

The title compound (41) was prepared as a mixture of atropisomers according to the method presented for the synthesis of compound 23B of Example 23 utilizing compound 22A and N-(1-methyl-7-(4,4,5,5-tetramethyl-1,3,2-dioxaborolan-2-yl)-1H-indazol-3-yl)methanesulfonamide (33C). $^1$H NMR (400 MHz, Methanol-$d_4$) δ 9.12-8.90 (m), 8.73 (dd), 7.90 (dd), 7.42 (d), 7.24 (t), 7.17 (t), 6.87-6.68 (m), 6.61 (t), 6.37 (dd), 5.47-5.35 (m), 5.02 (q), 4.85-4.46 (m), 3.40 (d), 3.19 (d), 3.12 (dd), 3.07-2.83 (m), 2.62-2.33 (m) 1.64 (d), 1.48-1.31 (m), 1.16-0.95 (m). MS (m/z) 804.85 [M+H]$^+$.

Example 42

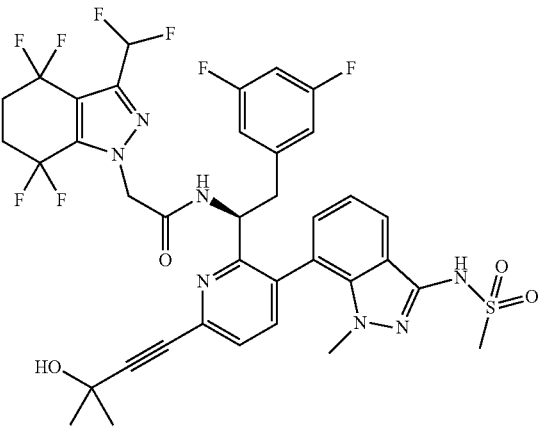

42

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(6-(3-hydroxy-3-methylbut-1-yn-1-yl)-3-(1-methyl-3-(methylsulfonamido)-1H-indazol-7-yl)pyridin-2-yl)ethyl)acetamide (42)

The title compound (42) was prepared as a mixture of atropisomers according to the method presented for the synthesis of compound 33F of Example 33 utilizing 2-(3-(difluoromethyl)-4,4,7,7-tetrafluoro-4,5,6,7-tetrahydro-H-indazol-1-yl)acetic acid. $^1$H NMR (400 MHz, $cd_3od$) δ 8.80 (d), 7.82 (d), 7.75-7.69 (m), 7.59-7.51 (m), 7.40-7.20 (m), 7.19-7.05 (m), 6.80 (d), 6.60-6.52 (m), 6.30 (d), 5.08-4.97 (m), 4.90-4.71 (m), 3.34 (s), 3.25-3.00 (m), 2.90-2.75 (m), 2.76-2.64 (m), 2.25-2.00 (m, 5H), 1.64 (s). MS (m/z) 824.2 [M+H]$^+$.

Example 43

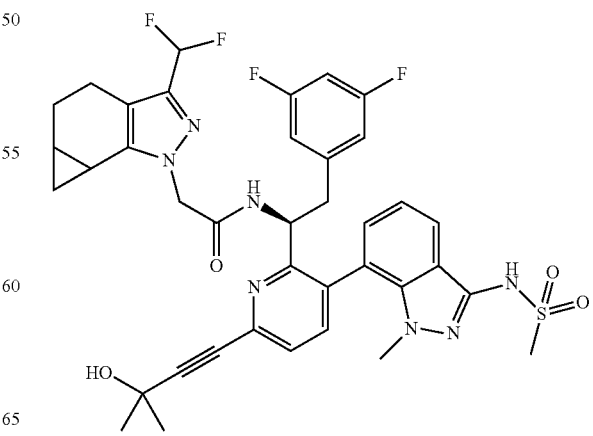

43

Synthesis of 2-(3-(difluoromethyl)-5,5a,6,6a-tetrahydrocyclopropara[g]indazol-1(4H)-yl)-N-((S)-2-(3,5-difluorophenyl)-1-(6-(3-hydroxy-3-methylbut-1-yn-1-yl)-3-(1-methyl-3-(methylsulfonamido)-1H-indazol-7-yl)pyridin-2-yl)ethyl)acetamide (43)

The title compound (43) was prepared as a mixture of atropisomers according to the method presented for the synthesis of compound 33F of Example 33 utilizing 20C and 2-(3-(difluoromethyl)-5,5a,6,6a-tetrahydrocyclopropa[g]indazol-1(4H)-yl)acetic acid. $^1$H NMR (400 MHz, cd$_3$od) δ 7.80 (d), 7.45 (d), 7.51 (d), 7.25-7.20 (m, 1H), 6.80-6.52 (m), 6.45 (d), 5.35-5.25 (m), 5.08-4.97 (m), 4.90-4.71 (m), 3.34 (s), 3.25-3.02 (m), 2.98-2.64 (m), 2.75-2.35 (m), 2.25-2.00 (m), 1.80-1.70 (m), 1.64 (d), 1.00-0.90 (m), 0.65-0.58 (m). MS (m/z) 764.2 [M+H]$^+$.

heated at 60° C. for 1 h. Upon cooling, the reaction mixture was concentrated in vacuo, diluted with EtOAc and washed with water then 1 M HCl. The organic layer was dried over Na$_2$SO$_4$, filtered, concentrated in vacuo, and purified by reverse phase HPLC to provide the title compound 44 as a mixture of atropisomers. $^1$H NMR (400 MHz, cd$_3$od) δ 8.86-6.25 (m, 8H), 5.38-4.97 (m, 1H), 4.85-4.73 (m, 2H), 3.26-3.06 (m, 1H), 3.04-2.90 (m, 2H), 2.63-2.37 (m, 2H), 1.69-1.56 (m, 6H), 1.52-1.32 (m, 1H), 1.19-0.98 (m, 1H). MS (m/z) 805.1 [M+H]$^+$.

Example 44

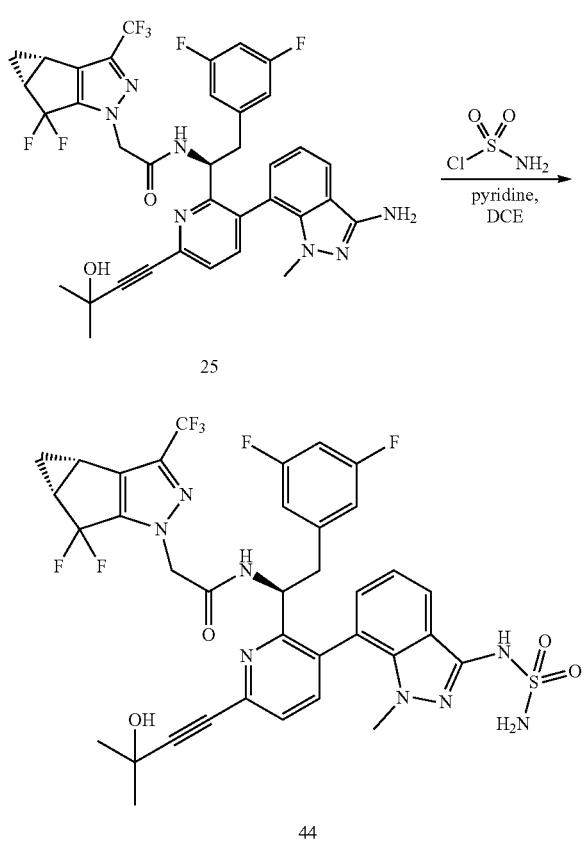

Example 45

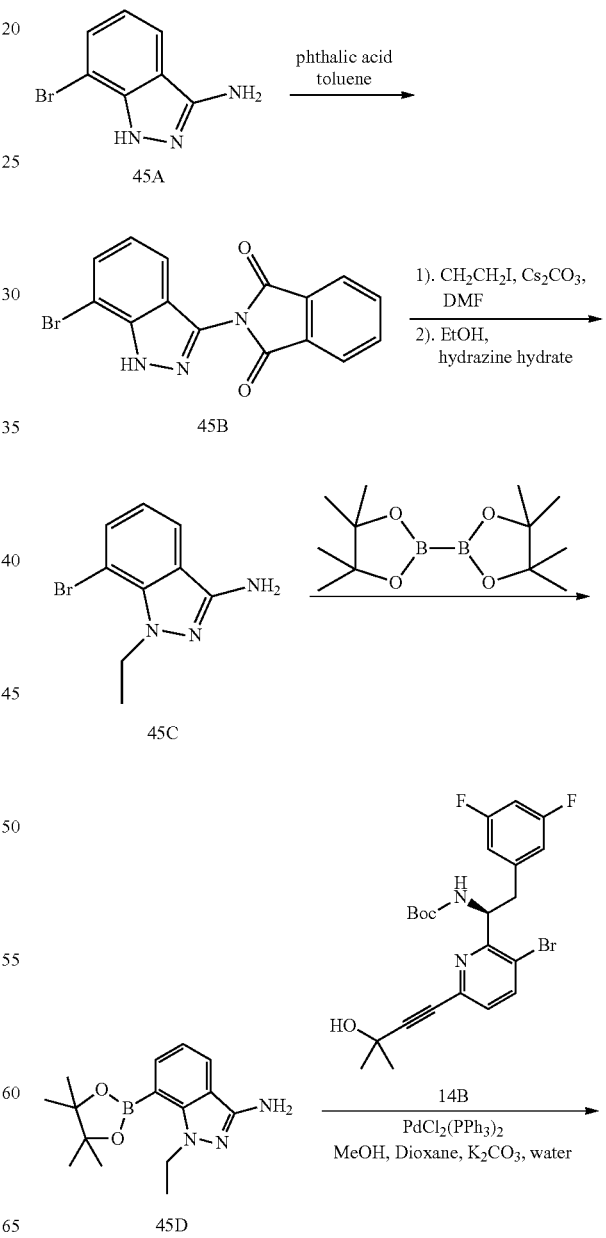

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(sulfamoylamino)-1H-indazol-7-yl)pyridin-2-yl)ethyl)acetamide (44)

To a stirred solution of 25 (31 mg, 0.04 mmol) and pyridine (0.024 mL, 0.03 mmol) in dichloroethane (0.5 mL) was added a solution of sulfamoyl chloride (12 mg, 0.1 mmol) in dichloroethane (~0.2 mL). The reaction was

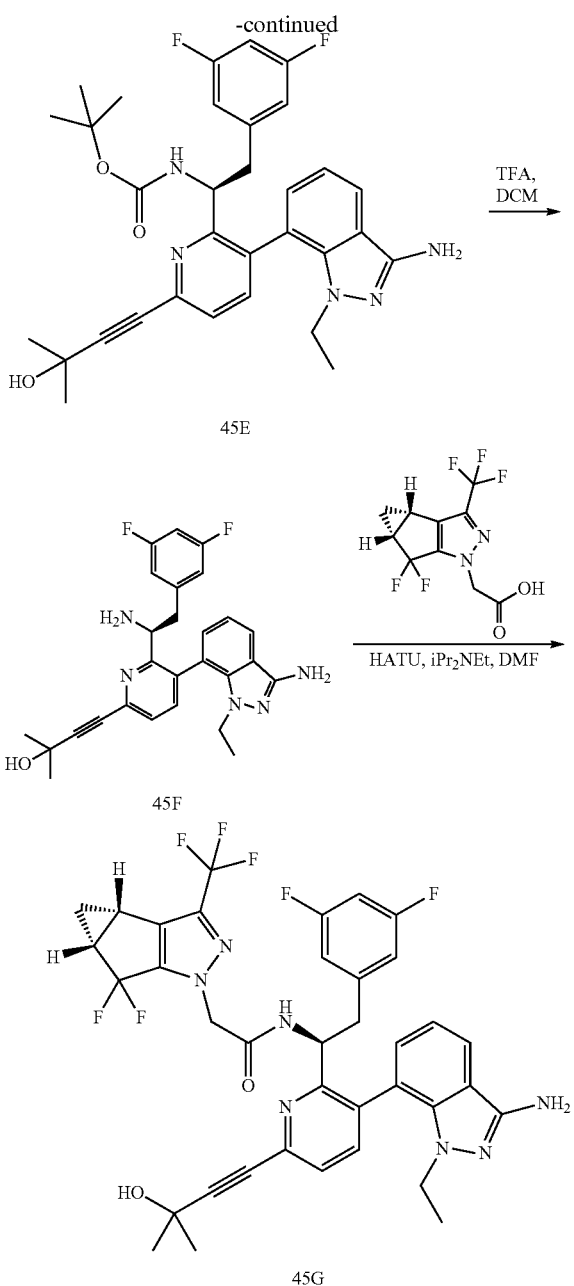

45E

45F

45G

Synthesis of 2-(7-bromo-1H-indazol-3-yl)isoindoline-1,3-dione (45B)

To 7-bromo-1H-indazol-3-amine (45A, 1.2 g, 5.5 mmol) in toluene (30 mL) was added phthalic acid (990 mg, 6.0 mmol). The flask was fitted with a Dean-Stark trap and the reaction mixture was stirred for 12 hours at 180° C. The reaction was allowed to cool, the solids were filtered off and used with no further purification to provide the title compound. MS (m/z) 343.1 [M+H]+.

Synthesis of 7-bromo-1-ethyl-1H-indazol-3-amine (45C)

To 45B (100 mg, 0.3 mmol) in DMF (2 mL) was added $Cs_2CO_3$ (95.2 mg, 0.3 mmol) and iodoethane (0.028 ml, 0.35 mmol). The reaction mixture was stirred for 10 minutes. The reaction mixture was diluted with EtOAc and brine, extracted 2× with EtOAc, organic layer dried over sodium sulfate, and concentrated. To the crude mixture was added EtOH (2 ml) and hydrazine hydrate (1 ml) the reaction mixture was stirred for 30 minutes. The mixture was concentrated and purified by flash column chromatography to provide the title compound. MS (m/z) 240.1 [M+H]+.

Synthesis of 1-ethyl-7-(4,4,5,5-tetramethyl-1,3,2-dioxaborolan-2-yl)-1H-indazol-3-amine (45D)

To 45C (80 mg, 0.3 mmol) in dioxane (5 mL) was added bis(pinacolato)diboron (84.6 mg, 0.3 mmol), potassium acetate (32.7 mg, 0.3 mmol), and $Pd(PCy_3)_2Cl_2$ (12.3 mg, 0.02 mmol). The reaction mixture was heated in the microwave for 30 minutes at 150° C. The reaction was cooled and the solids were filtered off. The mixture was concentrated and purified by flash column chromatography to provide the title compound. MS (m/z) 288.2 [M+H]+.

Synthesis of (S)-tert-butyl (1-(3-(3-amino-1-ethyl-1H-indazol-7-yl)-6-(3-hydroxy-3-methylbut-1-yn-1-yl)pyridin-2-yl)-2-(3,5-difluorophenyl)ethyl)carbamate (45E)

To 45D (40 mg, 0.1 mmol) in dioxane (4 mL) and MeOH (0.75 ml) was added 14B (69 mg, 0.1 mmol), 2M $K_2CO_3$ (0.4 ml), LiCl (17.7 mg, 0.4 mmol) and $Pd(PPh_3)_2Cl_2$ (4.9 mg, 0.007 mmol). The reaction mixture was heated in the microwave for 30 minutes at 150° C. The reaction was cooled, diluted with EtOAc and brine, and extracted 2× EtOAc. The organic layer was dried over sodium sulfate, concentrated and purified by flash column chromatography to provide the title compound as a mixture of atropisomers. MS (m/z) 576.0 [M+H]+.

Synthesis of (S)-4-(5-(3-amino-1-ethyl-1H-indazol-7-yl)-6-(1-amino-2-(3,5-difluorophenyl)ethyl)pyridin-2-yl)-2-methylbut-3-yn-2-ol (45F)

The title compound (45F) was prepared as a mixture of atropisomers according to the method presented for the synthesis of compound 19F of Example 19 utilizing 45E. MS (m/z) 476.1 [M+H]+.

Synthesis of N—((S)-1-(3-(3-amino-1-ethyl-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (45G)

The title compound (45G) was prepared as a mixture of atropisomers according to the method presented for the synthesis of compound 10A of Example 10 utilizing 45F and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR $^1$H NMR (400 MHz, Methanol-$d_4$) δ 8.67 (d), 7.87-7.75 (m), 7.71 (d), 7.59-7.50 (m), 7.26-7.19 (m), 7.18-7.12 (m), 7.12-7.04 (m), 6.76-6.63 (m), 6.60 (d), 6.47-6.41 (m), 6.27 (d), 5.11-5.01 (m), 4.81 (d), 4.72 (d), 3.67-3.55 (m), 3.51-3.43 (m), 3.39-3.24 (m), 3.15-3.10 (m), 3.09-2.84 (m), 2.56-2.40 (m), 1.64 (s), 1.45-1.33 (m), 1.31-1.25 (m), 1.14-1.03 (m), 0.87 (dt). MS (m/z) 740.2 [M+H]+.

Example 46

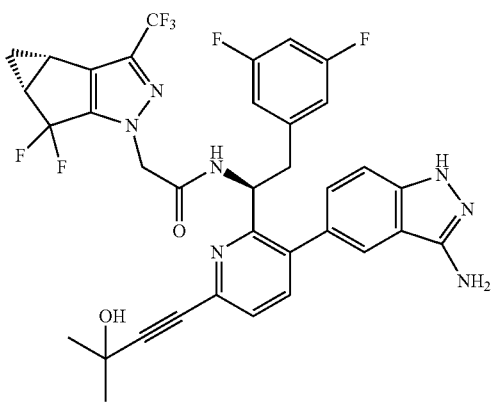

46

Synthesis of N—((S)-1-(3-(3-amino-1H-indazol-5-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (46)

The title compound (46) was prepared according to the method presented for the synthesis of compound 33F of Example 33 utilizing 5-(4,4,5,5-tetramethyl-1,3,2-dioxaborolan-2-yl)-1H-indazol-3-amine and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, cd₃od) δ 8.99 (d), 7.62-7.54 (m), 7.51-7.40 (m), 7.33 (d), 6.72-6.62 (m), 6.29-6.22 (m), 5.53-5.43 (m), 4.92 (d), 3.03 (d), 2.60-2.45 (m), 1.63 (s), 1.48-1.37 (m), 1.16-1.04 (m). MS (m/z) 712.1 [M+H]⁺.

Example 47

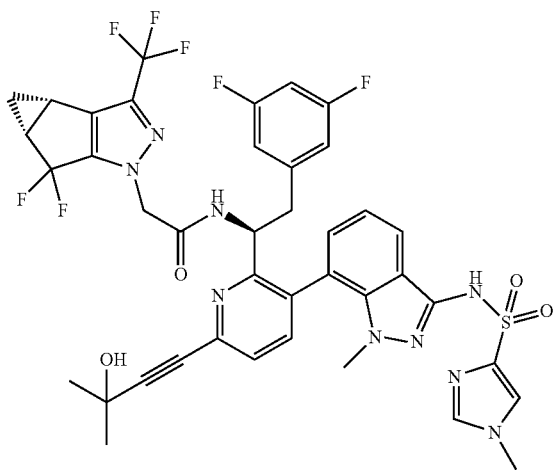

47

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(1-methyl-1H-imidazole-4-sulfonamido)-1H-indazol-7-yl)pyridin-2-yl)ethyl)acetamide (47)

To a solution of N—((S)-1-(3-(3-amino-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (25, 10 mg, 0.014 mmol) in dichloromethane (0.2 mL) was added pyridine (6.6 µL, 0.083 mmol), followed by 1-methyl-1H-imidazole-4-sulfonyl chloride (3.7 mg, 0.021 mmol). After stirring for 1 h, the reaction mixture was concentrated and purified by reverse phase HPLC to provide the title product as a mixture of atropisomers. ¹H NMR (400 MHz, Methanol-d₄) δ 7.75 (dd), 7.71-7.63 (m), 7.57-7.48 (m), 7.30 (s), 7.14-7.03 (m), 6.79-6.70 (m), 6.66-6.55 (m), 6.38-6.26 (m), 5.25 (dd), 4.96 (dd), 4.87-4.72 (m), 3.67 (s), 3.46 (s), 3.27 (s), 3.25-3.18 (m), 3.09-3.02 (m), 3.00-2.87 (m), 2.58-2.43 (m), 1.64 (s), 1.64 (s), 1.50-1.37 (m), 1.16-1.06 (m). MS (m/z) 870.10 [M+H]⁺.

Example 48

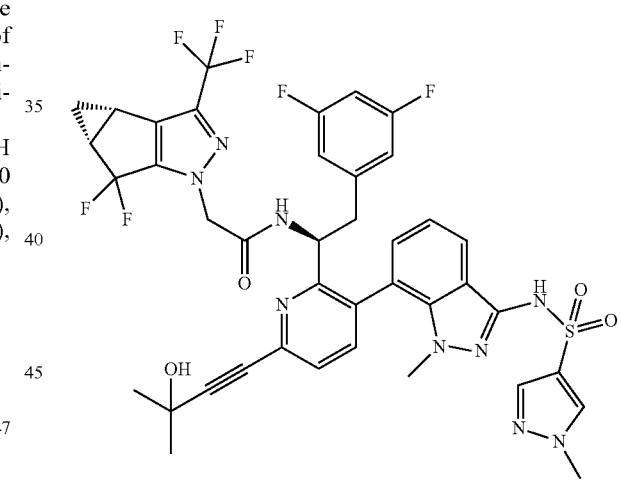

48

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(1-methyl-1H-pyrazole-4-sulfonamido)-1H-indazol-7-yl)pyridin-2-yl)ethyl)acetamide (48)

The title compound (48) was prepared as a mixture of atropisomers according to the method presented for the synthesis of compound (47) of Example 47 utilizing 1-methyl-1H-pyrazole-4-sulfonyl chloride. ¹H NMR (400 MHz, Methanol-d₄) δ 7.95 (s), 7.77-7.66 (m), 7.61 (s), 7.57-7.48 (m), 7.24-7.18 (m), 7.17-7.10 (m), 7.07 (dd), 6.78-6.68 (m), 6.63 (dd), 6.60-6.50 (m), 6.40-6.26 (m), 5.26 (dd), 5.02 (dd), 4.88-4.71 (m), 3.83 (s), 3.60 (s), 3.29 (s), 3.27-3.21 (m), 3.09-3.01 (m), 3.00-2.87 (m), 2.58-2.39 (m), 1.64 (s), 1.49-1.36 (m), 1.16-1.04 (m). MS (m/z) 870.03 [M+H]⁺.

Example 49

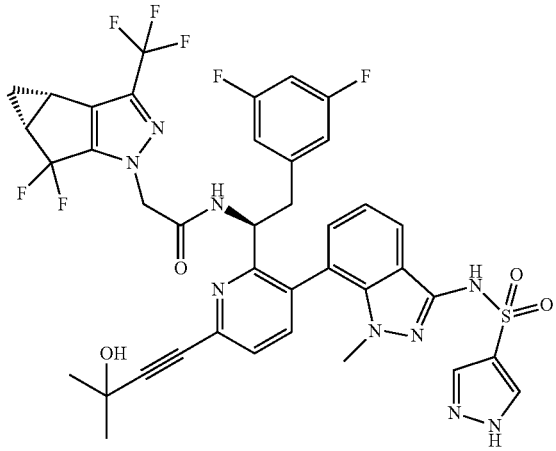

49

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(1H-pyrazole-4-sulfonamido)-1H-indazol-7-yl)pyridin-2-yl)ethyl)acetamide (49)

The title compound (49) was prepared as a mixture of atropisomers according to the method presented for the synthesis of compound (47) of Example 47 utilizing 1H-pyrazole-4-sulfonyl chloride. ¹H NMR (400 MHz, Methanol-d₄) δ 8.74 (d), 8.60 (q), 7.91 (s), 7.83 (s), 7.76-7.63 (m), 7.57-7.47 (m), 7.21 (dd), 7.13 (dd), 7.03 (dd), 6.79-6.68 (m), 6.61-6.50 (m), 6.46 (dd), 6.38-6.25 (m), 5.34-5.22 (m), 5.05-4.94 (m), 4.87-4.78 (m), 3.28 (s), 3.26-3.16 (m), 3.15-3.07 (m), 3.00-2.90 (m), 2.58-2.43 (m), 1.64 (s), 1.64-1.64 (m), 1.49-1.37 (m), 1.17-1.07 (m). MS (m/z) 856.03 [M+H]⁺.

Example 50

50

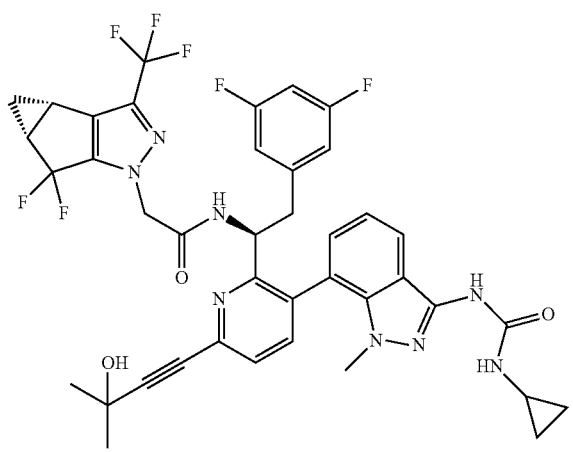

Synthesis of N—((S)-1-(3-(3-(3-cyclopropylureido)-1-methyl-1H-indazol-7-yl)-6-(3-hydroxy-3-methylbut-1-yn-1-yl)pyridin-2-yl)-2-(3,5-difluorophenyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (50)

To a solution of N—((S)-1-(3-(3-amino-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (25, 10 mg, 0.014 mmol) and DIPEA (3.5 μL, 0.021 mmol) in dichloromethane (0.1 mL) was added triphosgene (4.5 mg, 0.015 mmol). After stirring for 1 minute cyclopropylamine (3.5 μL, 0.055 mmol) was added. After stirring for 15 minutes, the reaction mixture was concentrated and purified by reverse phase HPLC to provide the title product as a mixture of atropisomers. ¹H NMR (400 MHz, Methanol-d₄) δ 7.87 (m), 7.68 (dd), 7.53 (dd), 7.23 (dd), 7.13 (dd), 7.02 (dd), 6.77-6.68 (m), 6.63-6.54 (m), 6.49 (dd), 6.38-6.32 (m), 6.32-6.25 (m), 5.25 (dd), 5.01 (t), 4.79 (t), 3.26 (s), 3.25-3.19 (m), 3.14-3.04 (m), 3.00-2.89 (m), 2.73-2.64 (m), 2.56-2.41 (m), 1.64 (s), 1.64 (s), 1.49-1.36 (m), 1.17-1.04 (m), 0.81-0.71 (m), 0.61-0.51 (m). MS (m/z) 809.12 [M+H]⁺.

Example 51

51

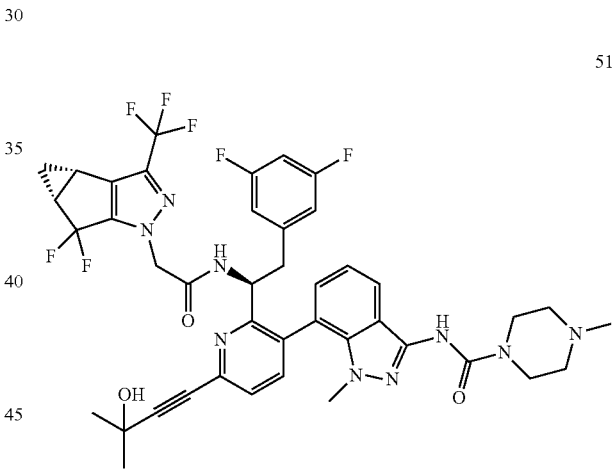

Synthesis of N-(7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)-4-methylpiperazine-1-carboxamide (51)

The title compound (51) was prepared as a mixture of atropisomers according to the method presented for the synthesis of compound (50) of Example 50 utilizing 1-methylpiperazine. ¹H NMR (400 MHz, Methanol-d₄) δ 7.79-7.66 (m), 7.54 (dd), 7.23 (dd), 7.16 (dd), 7.09 (dd), 6.78-6.68 (m), 6.66-6.57 (m), 6.43-6.36 (m), 6.36-6.28 (m), 5.29 (dd), 5.02 (dd), 4.85-4.71 (m), 4.39 (s), 3.67-3.45 (m), 3.27-3.22 (m), 3.14-3.06 (m), 3.03-2.89 (m), 2.58-2.41 (m), 1.65 (s), 1.64 (s), 1.49-1.36 (m), 1.17-1.10 (m), 1.10-1.04 (m). MS (m/z) 852.11 [M+H]⁺.

Example 52

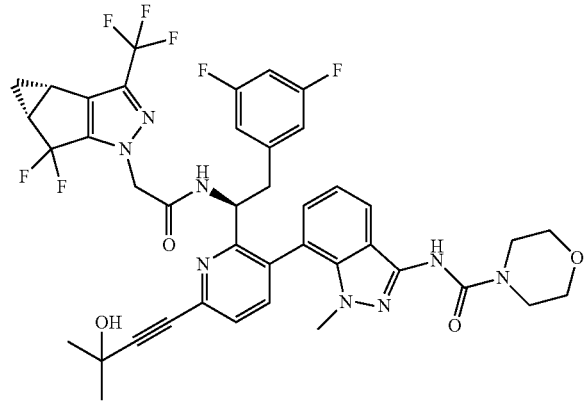

Synthesis of N-(7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)morpholine-4-carboxamide (52)

The title compound (52) was prepared as a mixture of atropisomers according to the method presented for the synthesis of compound (50) of Example 50 utilizing morpholine. $^1$H NMR (400 MHz, Methanol-$d_4$) δ 7.77-7.66 (m), 7.54 (dd), 7.22 (dd), 7.15 (dd), 7.08 (dd), 6.77-6.69 (m), 6.66-6.60 (m), 6.58 (dd), 6.42-6.36 (m), 6.36-6.29 (m), 5.32 (dd), 5.03 (dd), 4.85-4.79 (m), 4.79-4.71 (m), 3.74 (dd), 3.61-3.53 (m), 3.27-3.20 (m), 3.15-3.07 (m), 3.02 (s), 3.00-2.90 (m), 2.58-2.41 (m), 1.65 (s), 1.64 (s), 1.49-1.35 (m), 1.16-1.10 (m), 1.10-1.04 (m). MS (m/z) 839.13 [M+H]$^+$.

Example 53

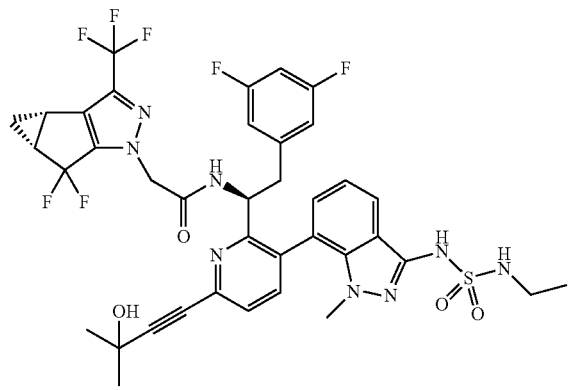

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(3-((N-ethylsulfamoyl)amino)-1-methyl-1H-indazol-7-yl)-6-(3-hydroxy-3-methylbut-1-yn-1-yl)pyridin-2-yl)ethyl)acetamide (53)

The title compound (53) was prepared as a mixture of atropisomers according to the method presented for the synthesis of compound (44) of Example 44 utilizing ethyl sulfamoylchloride. $^1$H NMR (400 MHz, Methanol-$d_4$) δ 8.84-8.74 (m), 7.95-7.85 (m), 7.69 (dd), 7.54 (dd), 7.23 (dd), 7.15 (dd), 7.09 (dd), 6.79-6.69 (m), 6.66-6.56 (m), 6.39-6.34 (m), 6.34-6.26 (m), 5.35-5.25 (m), 5.07-4.98 (m), 4.86-4.71 (m), 3.23 (m), 3.15-3.02 (m), 3.00 (s), 2.98-2.88 (m), 2.58-2.40 (m), 1.65 (s), 1.64 (s), 1.49-1.36 (m), 1.12 (t), 1.10-1.02 (m). MS (m/z) 833.14 [M+H]$^+$.

Example 54

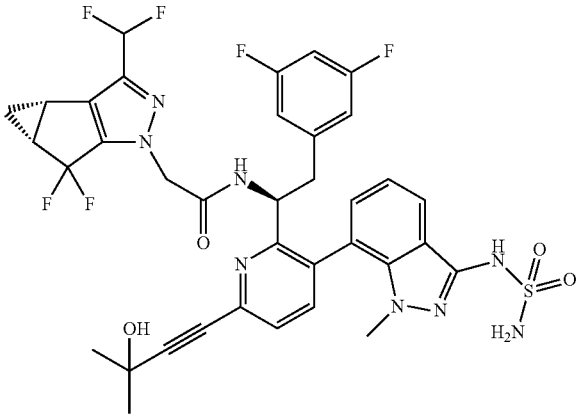

Synthesis of 2-((3bS,4aR)-3-(difluoromethyl)-5,5-difluoro-3b,4,4a,5-tetrahydro-H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(sulfamoylamino)-1H-indazol-7-yl)pyridin-2-yl)ethyl)acetamide (54)

The title compound (54) was prepared as a mixture of atropisomers according to the method presented for the synthesis of compound 44 of Example 44 utilizing and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (400 MHz, $cd_3od$) δ 8.75 (d), 8.01-7.93 (m), 7.72-7.63 (m), 7.53 (dd), 7.28-7.05 (m), 6.87-6.51 (m), 6.34 (m), 5.35-5.25 (m), 5.07-4.96 (m), 4.80-4.65 (m), 3.33 (s), 3.24-2.88 (m), 2.53-2.38 (m), 1.64 (d), 1.45-1.32 (m), 1.13-0.99 (m). MS (m/z) 787.1 [M+H]$^+$.

Example 55

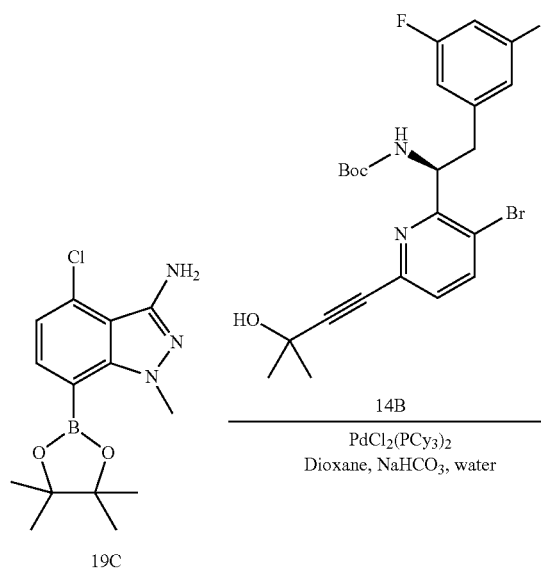

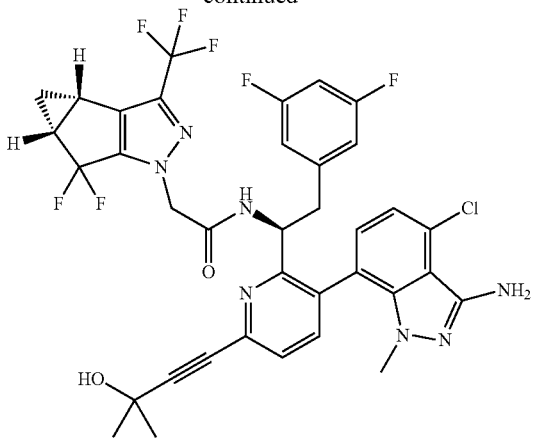

Synthesis of (S)-tert-butyl (1-(3-(3-amino-4-chloro-1-methyl-1H-indazol-7-yl)-6-(3-hydroxy-3-methyl-but-1-yn-1-yl)pyridin-2-yl)-2-(3,5-difluorophenyl)ethyl)carbamate (55A)

To 19C (1.5 g, 4.8 mmol) in dioxane (100 mL) was added 14B (1.6 g, 3.2 mmol), 1N sodium bicarbonate (8.4 ml, 8.4 mmol), and PdCl$_2$(PCy$_3$)$_2$ (238 mg, 0.3 mmol). The reaction mixture was stirred for 30 minutes at 125° C. The reaction was cooled, diluted with EtOAc and brine. The mixture was extracted 2× with EtOAc, the organic layer was dried over sodium sulfate, was concentrated and purified by flash column chromatography to provide the title compound as a mixture of atropisomers. MS (m/z) 596.7 [M+H]$^+$.

Synthesis of (S)-4-(6-(1-amino-2-(3,5-difluorophenyl)ethyl)-5-(3-amino-4-chloro-1-methyl-1H-indazol-7-yl)pyridin-2-yl)-2-methylbut-3-yn-2-ol (55B)

The title compound (55B) was prepared as a mixture of atropisomers according to the method presented for the synthesis of compound 19F of Example 19 utilizing 55A. MS (m/z) 496.5 [M+H]$^+$.

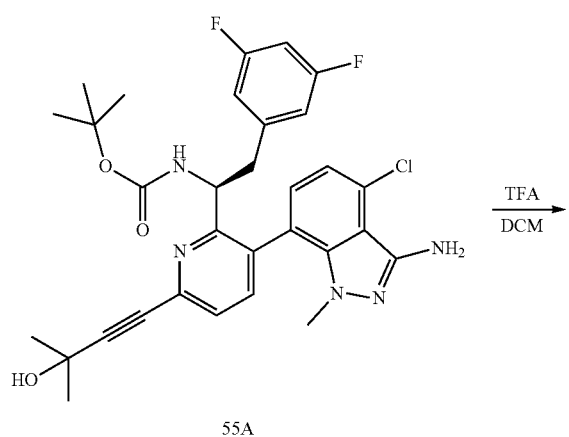

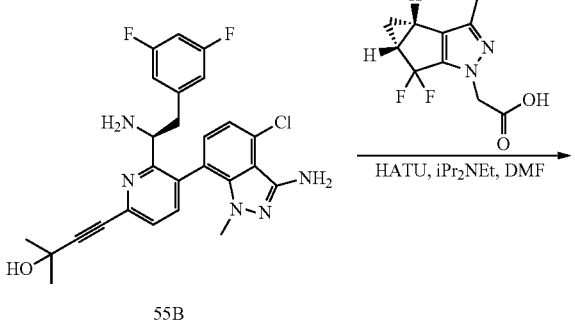

Synthesis of N—((S)-1-(3-(3-amino-4-chloro-1-methyl-1H-indazol-7-yl)-6-(3-hydroxy-3-methylbut-1-yn-1-yl)pyridin-2-yl)-2-(3,5-difluorophenyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (55C)

The title compound (55C) was prepared as a mixture of atropisomers according to the method presented for the synthesis of compound 10A of Example 10 utilizing 55B and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, Methanol-d$_4$) δ 8.83-8.69 (m), 7.65 (d), 7.53 (d), 7.13-7.06 (m), 7.07-6.99 (m), 6.96 (d), 6.81-6.71 (m), 6.67-6.56 (m), 6.48-6.39 (m), 6.41-6.30 (m), 5.30-5.19 (m), 5.07-4.96 (m), 4.83-4.71 (m), 3.27-3.22 (m), 3.17 (s), 3.10 (s), 3.04-2.91 (m), 2.81 (s), 2.61-2.39 (m), 1.63 (s), 1.49-1.37 (m), 1.37-1.24 (m), 1.23-1.00 (m). MS (m/z) 760.3 [M+H]$^+$.

Example 56

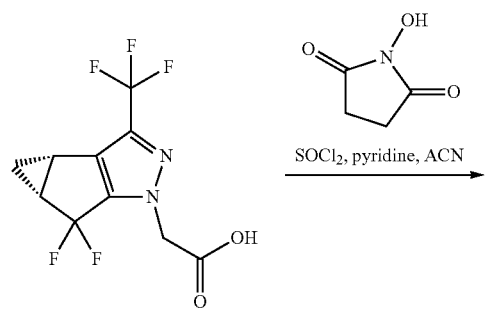

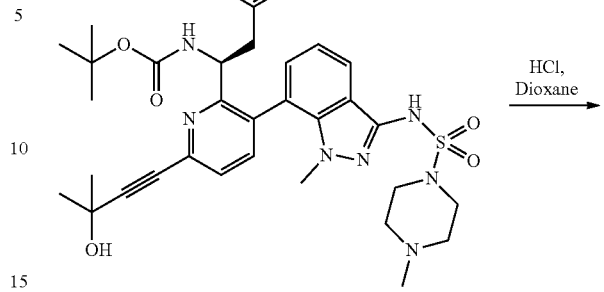

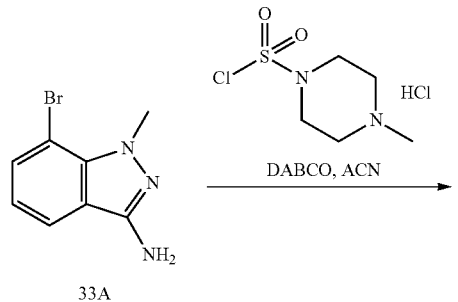

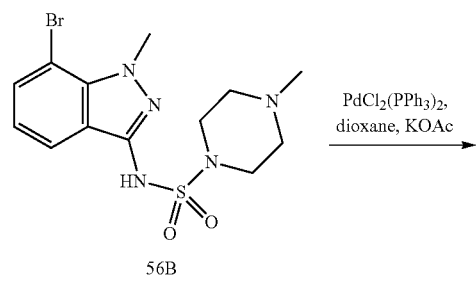

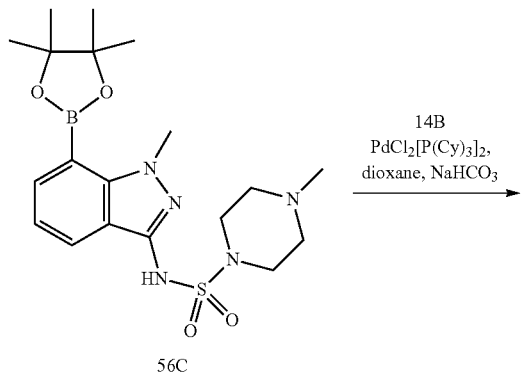

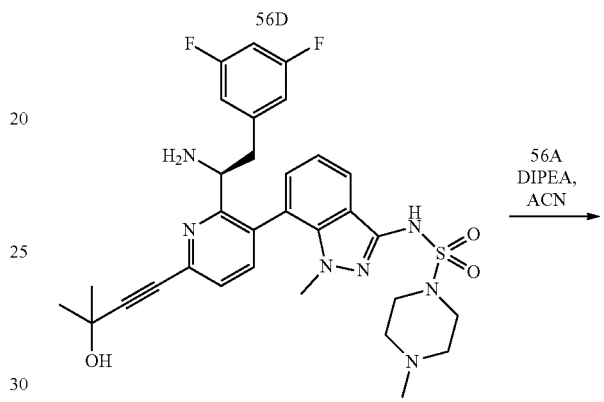

Synthesis of 2,5-dioxopyrrolidin-1-yl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (56A)

To a stirring solution of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (1.00 g, 3.54 mmol), N-hydroxysuccinimide (0.61 g, 5.32 mmol), and pyridine (0.968 mL, 12.1 mmol) was added dropwise at −5° C. thionyl chloride (0.439 mL, 6.02 mmol). After stirring at −5° C. for 20 min, 2.0M aqueous NaCl (10 mL) was added and the product was extracted with two portions of ethyl acetate (12 mL). The combined organic layers were dried over Na₂SO₄, filtered, concentrated in vacuo, and purified by silica gel column chromatography to give the title compound. ¹H NMR (400 MHz, DMSO-d₆) δ 5.88-5.63 (m, 4H), 2.77-2.55 (m, 2H), 1.56-1.31 (m, 2H), 1.12-0.98 (m, 2H).

Synthesis of N-(7-bromo-1-methyl-1H-indazol-3-yl)-4-methylpiperazine-1-sulfonamide (56B)

To a stirring solution of 7-bromo-1-methyl-1H-indazol-3-amine (33A, 250 mg, 1.11 mmol) and DABCO (310 mg, 2.77 mmol) in acetonitrile was added 4-methylpiperazine-1-sulfonyl chloride HCl (650 mg, 2.77 mmol). After stirring at 50° C. for 3 h, the reaction was concentrated, diluted with water and extracted with ethyl acetate. The organic layer was dried over Na₂SO₄, filtered, concentrated in vacuo, and purified by silica gel column chromatography to give the title compound. MS (m/z) 387.97 [M+H]⁺.

Synthesis of 4-methyl-N-(1-methyl-7-(4,4,5,5-tetramethyl-1,3,2-dioxaborolan-2-yl)-1H-indazol-3-yl)piperazine-1-sulfonamide (56C)

The title compound (56C) was prepared according to the method presented for the synthesis of compound (19D) of Example 19 utilizing N-(7-bromo-1-methyl-1H-indazol-3-yl)-4-methylpiperazine-1-sulfonamide (56B). MS (m/z) 436.18 [M+H]⁺.

Synthesis of (S)-tert-butyl (2-(3,5-difluorophenyl)-1-(6-(3-hydroxy-3-methylbut-1-yn-1-yl)-3-(1-methyl-3-(4-methylpiperazine-1-sulfonamido)-1H-indazol-7-yl)pyridin-2-yl)ethyl)carbamate (56D)

The title compound (56D) was prepared as a mixture of atropisomers according to the method presented for the synthesis of compound (19E) of Example 19 utilizing 4-methyl-N-(1-methyl-7-(4,4,5,5-tetramethyl-1,3,2-dioxaborolan-2-yl)-1H-indazol-3-yl)piperazine-1-sulfonamide (56C).

Synthesis of (S)—N-(7-(2-(1-amino-2-(3,5-difluorophenyl)ethyl)-6-(3-hydroxy-3-methylbut-1-yn-1-yl)pyridin-3-yl)-1-methyl-1H-indazol-3-yl)-4-methylpiperazine-1-sulfonamide (56E)

The title compound (56E) was prepared as a mixture of atropisomers according to the method presented for the synthesis of compound (14C) of Example 14 utilizing (S)-tert-butyl (2-(3,5-difluorophenyl)-1-(6-(3-hydroxy-3-methylbut-1-yn-1-yl)-3-(1-methyl-3-(4-methylpiperazine-1-sulfonamido)-1H-indazol-7-yl)pyridin-2-yl)ethyl)carbamate (56D). The resulting crude product was basified to pH-8 with 1M aqueous NaHCO₃ and extracted with ethyl acetate. The organic layer was dried over Na₂SO₄, filtered, concentrated in vacuo, and taken to the next step without further purification.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(4-methylpiperazine-1-sulfonamido)-1H-indazol-7-yl)pyridin-2-yl)ethyl)acetamide (56F)

To a solution of crude (S)—N-(7-(2-(1-amino-2-(3,5-difluorophenyl)ethyl)-6-(3-hydroxy-3-methylbut-1-yn-1-yl)pyridin-3-yl)-1-methyl-1H-indazol-3-yl)-4-methylpiperazine-1-sulfonamide (56E, 62.9 mg, 0.101 mmol assuming 100% purity) and DIPEA (17.5 μL, 0.101 mmol) in acetonitrile (2 mL) was 2,5-dioxopyrrolidin-1-yl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (56A, 38.3 mg, 0.101 mmol). After stirring for 1 h, the reaction mixture was filtered and purified by reverse phase HPLC to provide the title product as a mixture of atropisomers. 1H NMR (400 MHz, Methanol-d₄) δ 8.01 (dd), 7.87-7.77 (m), 7.73-7.52 (m), 7.28-7.15 (m), 6.95 (dd), 6.76-6.61 (m), 6.46-6.41 (m), 6.19-6.11 (m), 5.24 (dd), 5.03-4.90 (m), 4.78 (d), 3.91-3.67 (m), 3.36 (s), 3.13 (dq), 3.00 (s), 2.94-2.87 (m), 2.75 (dd), 2.70 (s), 2.60-2.45 (m), 1.65 (s), 1.64 (s), 1.49-1.38 (m), 1.15-0.94 (m). MS (m/z) 888.35 [M+H]⁺.

Example 57

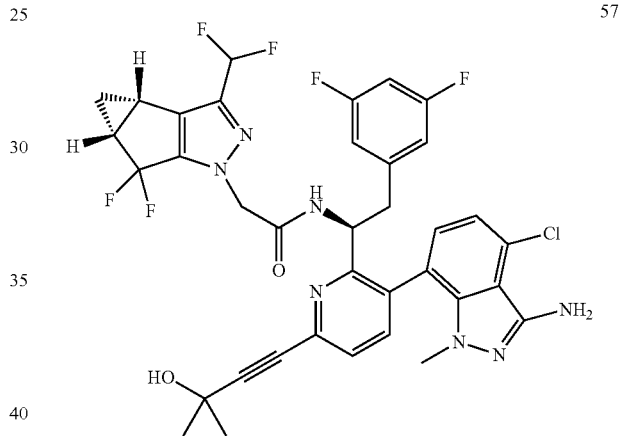

57

Synthesis of N—((S)-1-(3-(3-amino-4-chloro-1-methyl-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (57)

The title compound (57) was prepared as a mixture of atropisomers according to the method presented for the synthesis of compound 10A of Example 10 utilizing 55B and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. ¹H NMR (400 MHz, Chloroform-d) δ 8.02 (s), 7.54-7.37 (m), 7.10 (d), 7.07-6.99 (m), 6.75 (d), 6.72 (t), 6.67-6.56 (m), 6.51-6.44 (m), 6.25-6.13 (m), 6.02 (d), 5.56 (q), 5.01 (td), 4.75-4.69 (m), 3.08 (s), 2.98-2.86 (m), 2.80 (s), 2.55-2.39 (m), 1.71 (s), 1.42 (q), 1.22-1.14 (m). MS (m/z) 742.8 [M+H]⁺.

Example 58
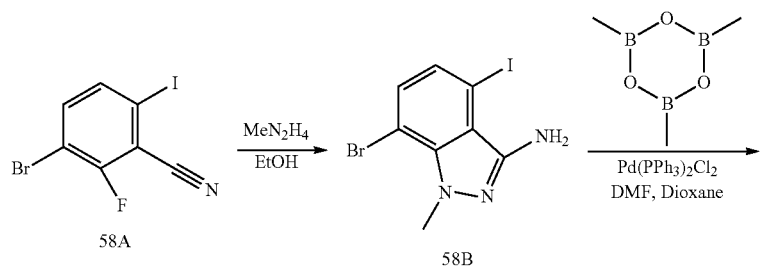
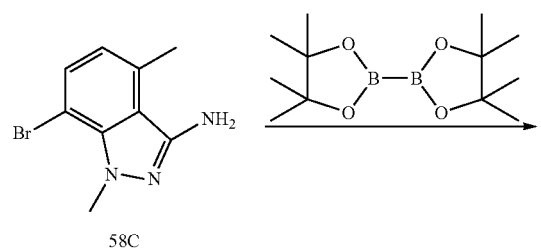
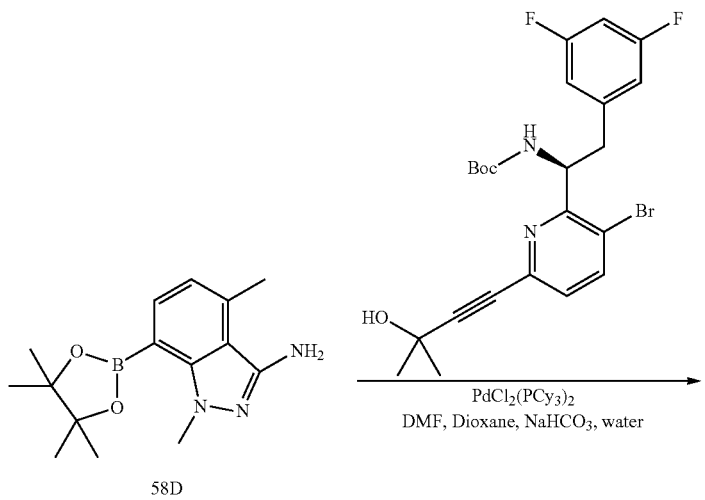
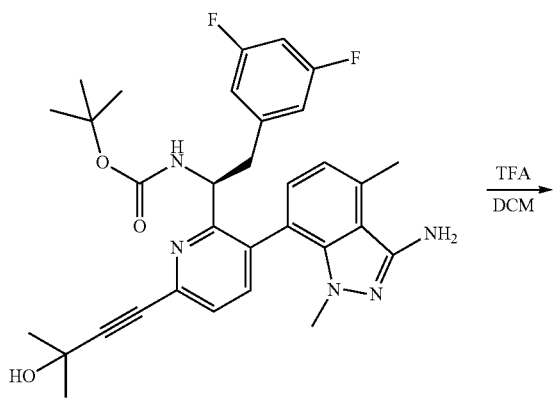

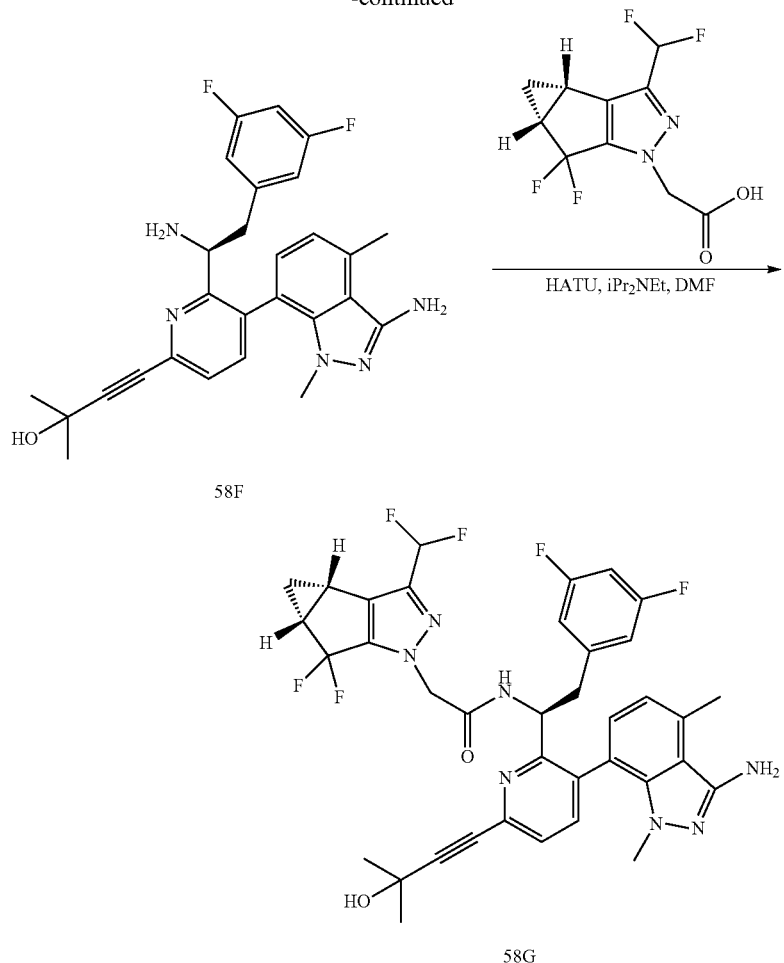

Synthesis of 7-bromo-4-iodo-1-methyl-1H-indazol-3-amine (58B)

The title compound (58B) was prepared according to the method presented for the synthesis of compound 19B of Example 19 utilizing 58A. MS (m/z) 352.4 [M+H]⁺.

Synthesis of 7-bromo-1,4-dimethyl-1H-indazol-3-amine (58C)

To 58B (3.0 g, 8.5 mmol) in dioxane (10 mL) and DMF (10 ml) was added Trimethylboroxine (4.8 ml, 34.1 mmol), 2M $K_2CO_3$ in water (8.5 ml), and $Pd(PPh_3)_2Cl_2$ (600 mg, 0.8 mmol). The reaction mixture was stirred for 5 hours at 160° C. The reaction was cooled, diluted with EtOAc and brine. The mixture was extracted 2× with EtOAc, the organic layer was dried over sodium sulfate, concentrated and purified by flash column chromatography to provide the title compound. MS (m/z) 240.1 [M+H]⁺.

Synthesis of 1,4-dimethyl-7-(4,4,5,5-tetramethyl-1,3,2-dioxaborolan-2-yl)-1H-indazol-3-amine (58D)

The title compound (58D) was prepared according to the method presented for the synthesis of compound 19C of Example 19 utilizing 58C. MS (m/z) 288.2 [M+H]⁺.

Synthesis of (S)-tert-butyl (1-(3-(3-amino-1,4-dimethyl-1H-indazol-7-yl)-6-(3-hydroxy-3-methylbut-1-yn-1-yl)pyridin-2-yl)-2-(3,5-difluorophenyl)ethyl) carbamate (58E)

The title compound (58E) was prepared as a mixture of atropisomers according to the method presented for the synthesis of compound 19E of Example 19 utilizing 58D. MS (m/z) 576.2 [M+H]⁺.

Synthesis of (S)-4-(5-(3-amino-1,4-dimethyl-1H-indazol-7-yl)-6-(1-amino-2-(3,5-difluorophenyl)ethyl)pyridin-2-yl)-2-methylbut-3-yn-2-ol (58F)

The title compound (58F) was prepared as a mixture of atropisomers according to the method presented for the synthesis of compound 19F of Example 19 utilizing 58E. MS (m/z) 476.1 [M+H]⁺.

Synthesis of N—((S)-1-(3-(3-amino-1,4-dimethyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (58G)

The title compound (58G) was prepared as a mixture of atropisomers according to the method presented for the synthesis of compound 10A of Example 10 utilizing 58F and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (Methanol-$d_4$) δ: 8.68-8.57 (m), 7.69-7.45 (m), 7.06 (d), 6.85 (d), 6.80 (d), 6.76-6.66 (m), 6.66-6.53 (m), 6.45 (d), 6.38 (d), 6.31 (d), 5.26 (s), 5.08-4.98 (m), 4.73 (d), 3.27-3.19 (m), 3.16 (s), 3.06 (dd), 2.91 (dd), 2.84 (s), 2.74-2.66 (m), 2.53-2.38 (m), 1.64 (d), 1.43-1.24 (m), 1.12-0.98 (m). MS (m/z) 722.2 [M+H]$^+$.

Example 59

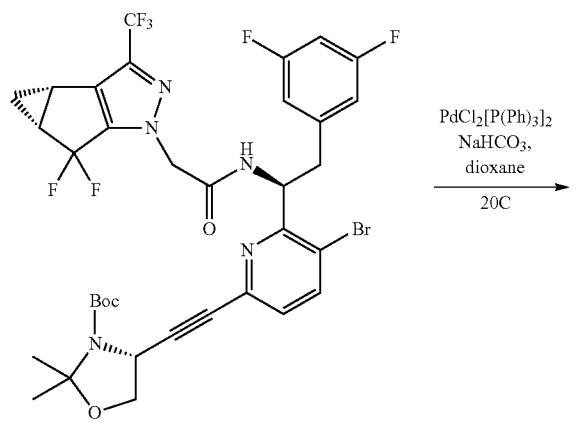

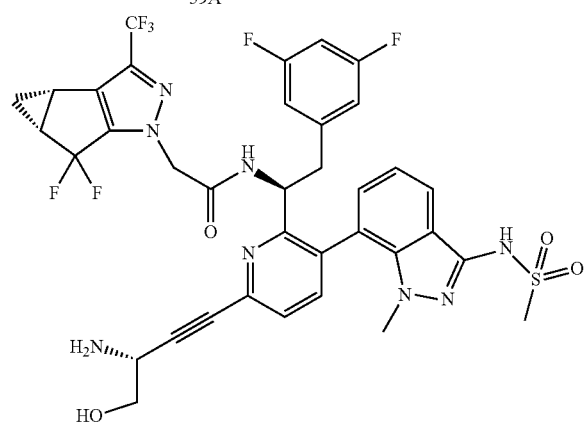

Synthesis of (R)-tert-butyl 4-((5-bromo-6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)ethynyl)-2,2-dimethyloxazolidine-3-carboxylate (59A)

The title compound was prepared similarly to compound 14D in example 14 utilizing (R)-tert-butyl 4-ethynyl-2,2-dimethyloxazolidine-3-carboxylate instead of 2-methylbut-3-yn-2-ol. MS (m/z) 799 [M−H]$^−$.

Synthesis of N—((S)-1-(6-((R)-3-amino-4-hydroxybut-1-yn-1-yl)-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (59B)

To a solution of 59A (110 mg, 0.13 mmol) in dioxane (3 mL) was added 20C (67 mg, 0.19 mmol), sodium bicarbonate (1M, 0.41 mL) followed by PdCl$_2$[P(Ph)$_3$]$_2$ (4.8 mg, 0.06 mmol). The reaction was sealed and heated in a microwave reactor for 20 min at 150° C. Upon cooling, the reaction mixture was first diluted with EtOAc and washed with brine (2×10 mL), dried over Na$_2$SO$_4$, filtered and concentrated. The crude material purified by reverse phase HPLC. Fractions containing the product were pooled and treated with neat TFA to give the title compound 59B as a mixture of atropisomers. $^1$H NMR (400 MHz, cd$_3$od) δ 7.89-7.73 (m), 7.69-7.60 (m), 7.32-7.27 (m), 7.25-7.15 (m), 7.10-7.07 (m), 6.80-6.70 (m), 6.69-6.47 (m), 6.50 (d), 6.40-6.28 (m), 5.32-5.25 (m), 5.05-4.96 (m), 4.80-4.72 (d), 4.52-4.44 (m), 4.09-3.98 (m), 3.94-3.84 (m), 3.21-3.08 (m), 3.05-2.89 (m), 2.59-2.37 (m), 1.46-1.35 (m), 1.11 (s), 1.04 (s). MS (m/z) 805.1 [M+H]$^+$.

Example 60

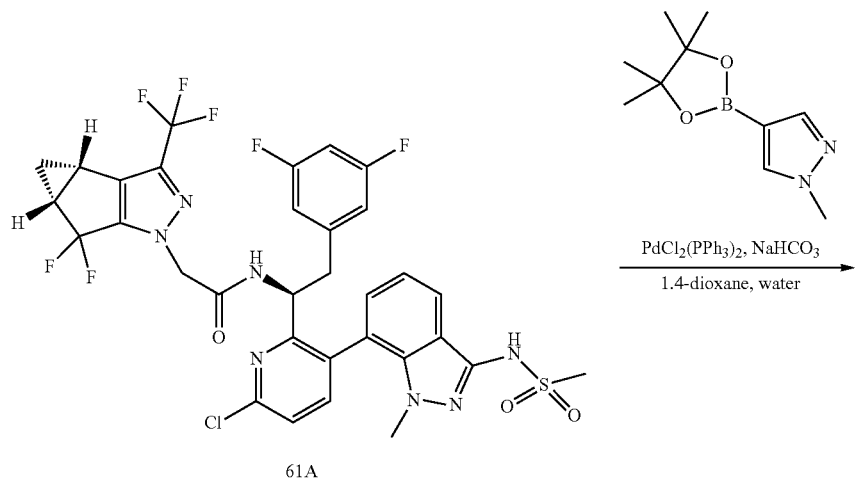

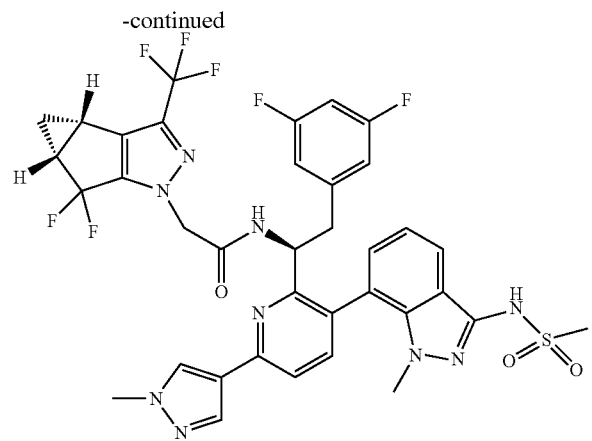

60

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-1H-pyrazol-4-yl)-3-(1-methyl-3-(methylsulfonamido)-1H-indazol-7-yl)pyridin-2-yl)ethyl)acetamide (60)

In a microwave tube were charged with compound 61A (20 mg, 0.026 mmol), 1-methyl-4-(4,4,5,5-tetramethyl-1,3,2-dioxaborolan-2-yl)-1H-pyrazole (11 mg, 0.053 mmol) and PdCl$_2$[PPh$_3$]$_2$ (2 mg, 0.003 mmol). To the mixture was added 0.5 mL of 1,4-dioxane and 0.1 mL of sodium bicarbonate aqueous solution (1M). The mixture was heated to 120° C. for 4 minutes in a microwave synthesizer. After cooled to room temperature, it was partitioned between EtOAc and water. The organic layer was separated and washed with brine, then dried over MgSO$_4$, filtered and concentrated. The residue was purified by reverse phase HPLC to afford the title compound 60 as a mixture of atropisomers. $^1$H NMR (400 MHz, Methanol-d$_4$) δ 8.43-8.29 (m), 8.28-8.09 (m), 7.91-7.72 (m), 7.76-7.58 (m), 7.15-7.00 (m), 6.82-6.68 (m), 6.53 (dd), 6.36-6.14 (m), 5.39-5.18 (m), 5.08-4.91 (m), 4.84 (d), 4.02 (d), 3.38 (s), 3.23-3.14 (m), 3.14 (s), 3.01 (d), 2.93 (dd), 2.63-2.30 (m), 1.50-1.26 (m), 1.17-0.79 (m). MS (m/z): 802.16 [M+H]$^+$ Example 61

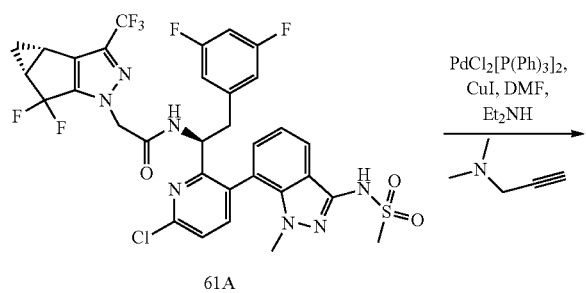

61A

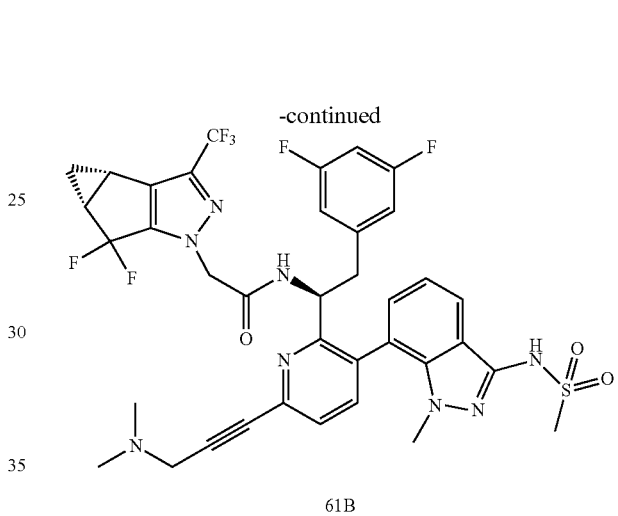

61B

Synthesis of N—((S)-1-(6-chloro-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (61A)

The title compound (61A) was prepared according to the method presented for the synthesis of compound 157F of Example 157 utilizing N-(1-methyl-7-(4,4,5,5-tetramethyl-1,3,2-dioxaborolan-2-yl)-1H-indazol-3-yl)methanesulfonamide (33C) instead of 19D. MS (m/z) 756.1 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-(dimethylamino)prop-1-yn-1-yl)-3-(1-methyl-3-(methylsulfonamido)-1H-indazol-7-yl)pyridin-2-yl)ethyl)acetamide (61B)

To the reaction vial containing 61A (20 mg, 0.026 mmol) in DMF (0.2 mL) was added N,N-dimethylprop-2-yn-1-amine (11 mg, 0.13 mmol), PdCl$_2$[P(Ph)$_3$]$_2$ (1.87 mg, 0.003 mmol), and diethylamine (0.02 mL, 0.26 mmol). The reaction mixture was flushed with argon gas for 5 min then sealed and heated in a microwave reactor to 125° C. for 15 min. Upon cooling, the reaction mixture was filtered and purified by reverse phase HPLC to provide the title product as a mixture of atropisomers. $^1$H NMR δ 8.70 (m), 7.90-7.76 (m), 7.70 (d), 7.16 (m), 6.75 (tt), 6.57 (dd), 6.41-6.28 (m), 5.35-5.25 (m), 5.08-4.97 (m), 4.82-4.68 (m), 4.47 (d), 3.30-3.06 (m), 3.05-2.88 (m), 2.54-2.43 (m), 1.48-1.35 (m), 1.15-1.11 (m), 1.09-1.00 (m). MS (m/z) 803.2 [M+H]$^+$.

Example 62

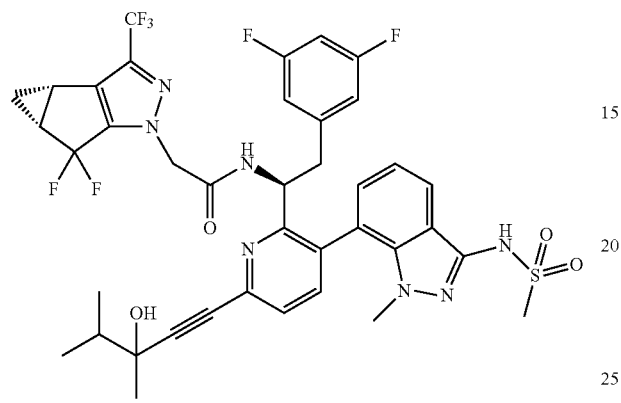

62

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-((1S)-2-(3,5-difluorophenyl)-1-(6-(3-hydroxy-3,4-dimethylpent-1-yn-1-yl)-3-(1-methyl-3-(methylsulfonamido)-1H-indazol-7-yl)pyridin-2-yl)ethyl)acetamide (62)

The title compound (62) was prepared as a mixture of atropisomers according to the method presented for the synthesis of compound 61 of Example 61 utilizing 3,4-dimethylpent-1-yn-3-ol. $^1$H NMR (400 MHz, cd$_3$od) δ 8.73 (m), 7.83-7.79 (m), 7.75-7.70 (m), 7.60-7.54 (m), 7.277.12 (m), 7.05 (t), 6.65 (t), 6.61 (t), 6.52 (t), 6.35-6.21 (m), 5.35-5.21 (m), 5.06-4.97 (m), 4.85-4.70 (m), 3.34 (s), 3.20-3.08 (m), 3.01-2.88 (m), 2.56-2.38 (m), 2.01-1.89 (m), 1.60-1.54 (d), 1.46-1.34 (m), 1.21-1.09 (m), 1.08-1.03 (m). MS (m/z) 832.1 [M+H]$^+$.

Example 63

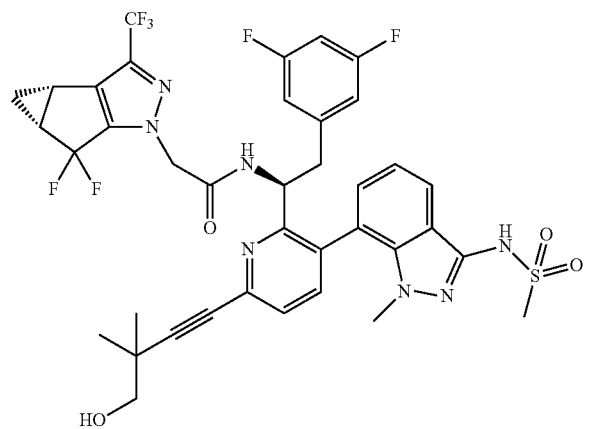

63

Synthesis of 2-((3bS,4aR)-5,5-difluoro-3-(trifluoromethyl)-3b,4,4a,5-tetrahydro-H-cyclopropa[3,4]cyclopenta[1,2-c]pyrazol-1-yl)-N—((S)-2-(3,5-difluorophenyl)-1-(6-(4-hydroxy-3,3-dimethylbut-1-yn-1-yl)-3-(1-methyl-3-(methylsulfonamido)-1H-indazol-7-yl)pyridin-2-yl)ethyl)acetamide (63)

The title compound (63) was prepared as a mixture of atropisomers according to the method presented for the synthesis of compound 61 of Example 61 utilizing 2,2-dimethylbut-3-yn-1-ol. $^1$H NMR (400 MHz, cd$_3$od) δ 8.65 (d), 7.83 (m), 7.66 (dd), 7.51 (dd), 7.08 (dd), 6.73 (tt), 6.50 (dt), 6.38-6.26 (m), 5.35-5.25 (m), 4.98 (t), 4.85-4.71 (m), 3.57 (s), 3.33 (s), 3.15 (d), 3.04-2.87 (m), 2.54-2.43 (m), 1.36 (s), 1.12-1.02 (m). MS (m/z) 818.2 [M+H]$^+$.

Example 64

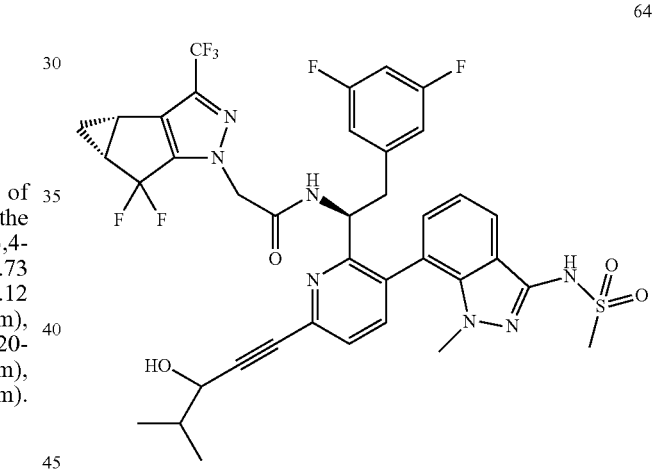

64

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-((1S)-2-(3,5-difluorophenyl)-1-(6-(3-hydroxy-4-methylpent-1-yn-1-yl)-3-(1-methyl-3-(methylsulfonamido)-1H-indazol-7-yl)pyridin-2-yl)ethyl)acetamide (64)

The title compound (64) was prepared as a mixture of atropisomers according to the method presented for the synthesis of compound 61 of Example 61 utilizing 4-methylpent-1-yn-3-ol. $^1$H NMR (400 MHz, cd$_3$od) δ 8.74 (d), 8.67 (d), 7.88-7.79 (m), 7.75-7.66 (m), 7.60-7.50 (m), 7.14-7.05 (m), 6.78-6.68 (m), 6.53 (ddt), 6.41-6.29 (m),5.31-5.25 (m), 5.06-4.95 (m), 4.78 (m), 4.45-4.38 (m), 3.34 (s), 3.15 (d), 3.03-2.88 (m), 2.55-2.43 (m), 2.06-1.91 (m), 1.39 (q), 1.18-1.10 (m), 1.07 (d). MS (m/z) 818.1 [M+H]$^+$.

Example 65

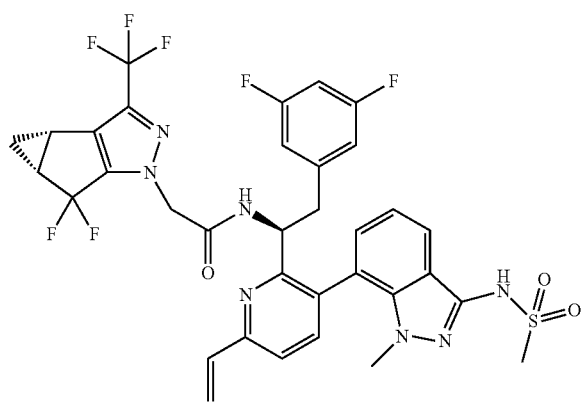

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(1-methyl-1H-imidazole-4-sulfonamido)-1H-indazol-7-yl)-6-vinylpyridin-2-yl)ethyl)acetamide (65)

Argon was bubbled through a solution of N—((S)-1-(6-chloro-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (61A, 100 mg, 0.13 mmol), potassium vinyltrifluoroborate (35.4 mg, 0.26 mmol), dichloro 1,1'-bis(diphenylphosphino)ferrocene palladium (II) dichloromethane (10.8 mg, 0.01 mmol), and triethylamine (0.06 ml, 0.43 mmol) in EtOH (2.6 ml) for 5 mins. The reaction was heated in a microwave reactor at 150° C. for 20 mins. The product was solid loaded onto silica and purified by silica gel chromatography followed by re-purification by reverse phase HPLC to provide the title product as a mixture of atropisomers. $^1$H NMR (400 MHz, Methanol-d4) δ 7.85-7.78 (m), 7.67-7.62 (m), 7.55-7.48 (m), 7.24-7.14 (m), 7.11-7.05 (m), 7.04-6.94 (m), 6.76-6.67 (m), 6.64-6.56 (m), 6.56-6.34 (m), 6.33-6.24 (m), 5.67-5.58 (m), 5.31-5.23 (m), 5.03-4.95 (m), 4.86-4.75 (m), 3.34 (s), 3.32-3.28 (m), 3.24-3.09 (m), 3.02-2.85 (m), 2.57-2.41 (m), 1.41 (m), 1.35-1.24 (m), 1.17-1.10 (m), 1.10-1.03 (m). MS (m/z) 748.15 [M+H]$^+$.

Example 66

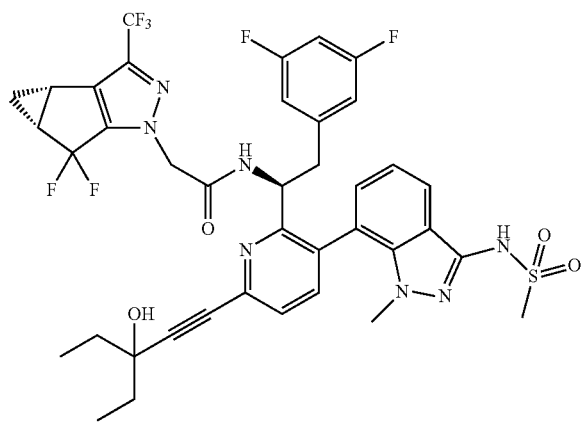

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-ethyl-3-hydroxypent-1-yn-1-yl)-3-(1-methyl-3-(methylsulfonamido)-1H-indazol-7-yl)pyridin-2-yl)ethyl)acetamide (66)

The title compound (66) was prepared as a mixture of atropisomers according to the method presented for the synthesis of compound 61 of Example 61 utilizing 3-ethyl-pent-1-yn-3-ol. $^1$H NMR (400 MHz, cd$_3$od) δ 7.83 (td), 7.74-7.65 (m), 7.54 (dd), 7.28-7.05 (m), 6.78-6.67 (m), 6.62 (s), 6.54 (dd), 6.35 (ddd), 5.00 (t), 5.32-5.25 (m), 4.84-4.70 (m), 3.34 (s), 3.15 (d), 3.03-2.88 (m), 2.55-2.42 (m), 1.93-1.73 (m), 1.41 (dq), 1.16 (td), 1.10-1.01 (m). MS (m/z) 832.1 [M+H]$^+$.

Example 67

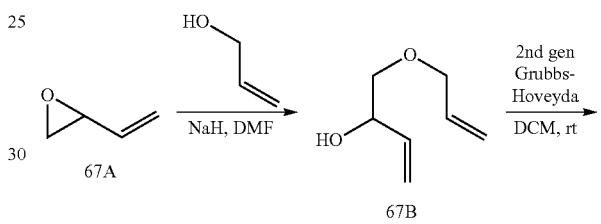

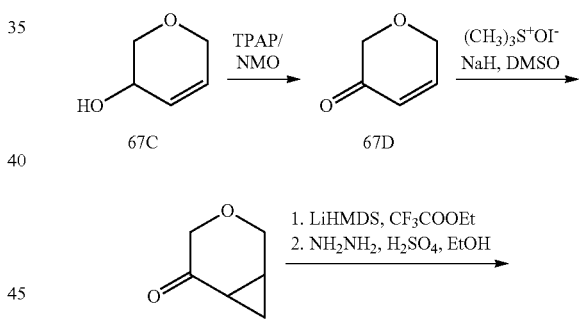

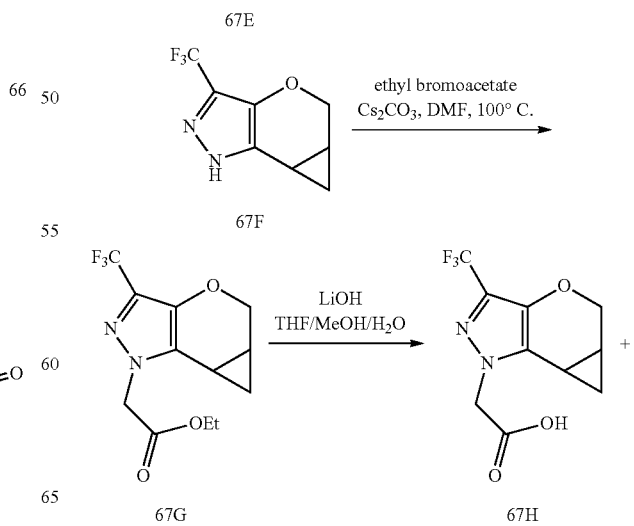

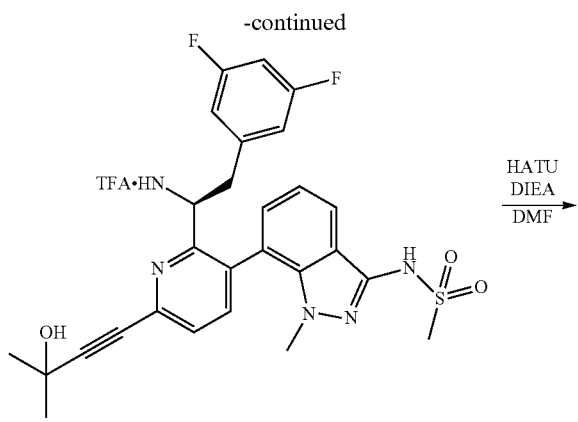

33E

HATU
DIEA
DMF

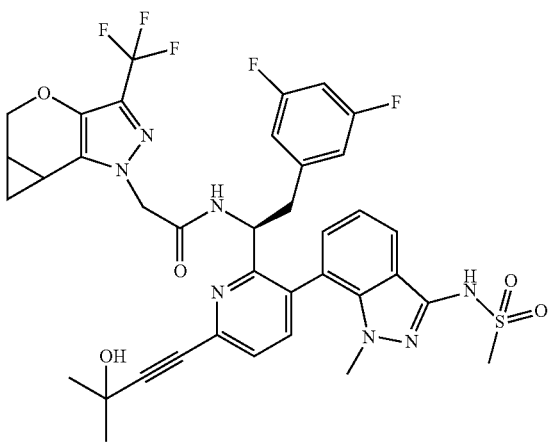

67I

Synthesis of 1-(allyloxy)but-3-en-2-ol (67B)

The epoxide 67A (3.5 g, 50 mmol) and allyl alcohol (5.8 g, 100 mmol) were dissolved in DMF (100 mL) in a pressure bottle. After cooled to 0° C., NaH (60% suspension in mineral oil, 2.4 g) was added portionwise, stirred for 20 min under argon. The bottle was sealed and heated at 60° C. overnight. The reaction was cooled to 0° C. in an ice bath, quenched with 100 mL 2N HCl. The aqueous layer was extracted 3 times with ether (3×100 mL). The combined ether were washed with 5% LiCl and brine, dried over Na$_2$SO$_4$, filtered, and concentrated under reduced pressure. The residue was purified by silica gel column to yield the title compound 67B. $^1$H NMR (400 MHz, Chloroform-d) δ 6.00-5.74 (m, 2H), 5.45-5.08 (m, 4H), 4.31 (tdd, J=7.0, 3.2, 1.5 Hz, 1H), 4.02 (dt, J=5.7, 1.4 Hz, 2H), 3.49 (dd, J=9.7, 3.4 Hz, 1H), 3.32 (dd, J=9.7, 7.9 Hz, 1H), 2.56 (s, 1H).

Synthesis of 3,6-dihydro-2H-pyran-3-ol (67C)

The title compound (67C) was prepared according to reference: Angew. Chem. Intl. Ed. 2005, 44, 5306-5310. $^1$H NMR data: 1H NMR (400 MHz, Chloroform-d) δ 6.06-5.81 (m, 2H), 4.19-3.99 (m, 2H), 3.98-3.89 (m, 1H), 3.86-3.66 (m, 2H), 2.77-2.57 (m, 1H).

Synthesis of 2H-pyran-3(6H)-one (67D)

The title compound (67D) was prepared according to reference: Angew. Chem. Intl. Ed. 2005, 44, 5306-5310.

Synthesis of 3-oxabicyclo[4.1.0]heptan-5-one (67E)

To a suspension of NaH (60% in mineral oil, 0.19 g) in DMSO (20 mL) was added trimethylsulfonium iodide (1.75 g, 8 mmol) at room temperature. After stirring for 15 min, a solution of 67D (0.6 g, 6 mmol) in DMSO (5 mL) was added. After stirring at room temperature for 5 min, the reaction mixture was diluted with ethyl acetate and washed with 5% LiCl aqueous solution. The organic layers were dried over Na$_2$SO$_4$, filtered, concentrated in vacuo, and purified by silica gel column chromatography to give the title compound. $^1$H NMR (400 MHz, Chloroform-d) δ 4.22-4.03 (m, 2H), 3.80 (s, 1H), 3.76 (d, J=6.0 Hz, 1H), 1.95 (ddd, J=9.8, 7.5, 4.7 Hz, 1H), 1.85-1.71 (m, 2H), 1.23 (ddd, J=9.8, 7.1, 4.4 Hz, 1H).

Synthesis of 3-(trifluoromethyl)-5,5a,6,6a-tetrahydro-1H-cyclopropa[4,5]pyrano[3,2-c]pyrazole (67F)

A solution of compound 67E (90 mg, 0.8 mmol) and ethyl trifluoroacetate (0.16 g, 1.2 mmol) in ether was cooled to −78° C. LiHMDS (0.18 g, 1 mmol) was added in one portion. The resulting mixture was stirred at −78° C. for 2 h. The reaction was poured into 1 N HCl aqueous solution and the aqueous layer was extracted with ether. The organic layers were dried over Na$_2$SO$_4$, filtered, concentrated in vacuo to give the title compound which was used without further purification. MS (m/z) 209.06 [M+H]$^+$.

To a solution of crude from last step in ethanol (20 mL) was added concentrated sulfuric acid (0.5 mL) and hydrazine monohydrate (1 mL). The resulting mixture was heated at 90° C. for 5 min. Upon completion of the reaction, the volatiles were removed in vacuo to give the title compound which was used in the next step. MS (m/z) 205.18 [M+H]$^+$.

Synthesis of ethyl 2-(3-(trifluoromethyl)-5,5a,6,6a-tetrahydro-1H-cyclopropa[4,5]pyrano[3,2-c]pyrazol-1-yl)acetate (67G)

To a solution of compound 67F (100 mg, 0.49 mmol) in DMF (2 mL) was added bromoethyl acetate (98 mg, 0.59 mmol) and cesium carbonate (160 mg, 0.5 mmol) at 0° C. The reaction was heated at 50° C. overnight. Upon cooling, the mixture was purified by reverse phase HPLC to give the title compound. MS (m/z) 291.19 [M+H]$^+$.

Synthesis of 2-(3-(trifluoromethyl)-5,5a,6,6a-tetrahydro-1H-cyclopropa[4,5]pyrano[3,2-c]pyrazol-1-yl) acetic acid (67H)

To a solution of compound 67G (16 mg, 0.055 mmol) in a mixture of THF:water:MeOH (1 mL:0.5 mL:0.5 mL) was added solid LiOH monohydrate (7 mg, 0.165 mmol) at 0° C. After stirring at room temperature for 10 min, the reaction mixture was poured into EtOAc and the organic was washed with 2 N HCl. The organic layers were dried over Na$_2$SO$_4$, filtered, concentrated in vacuo to give the title compound which was used in the next step. MS (m/z) 263.04 [M+H]$^+$.

Synthesis of N—((S)-2-(3,5-difluorophenyl)-1-(6-(3-hydroxy-3-methylbut-1-yn-1-yl)-3-(1-methyl-3-(methylsulfonamido)-1H-indazol-7-yl)pyridin-2-yl) ethyl)-2-(3-(trifluoromethyl)-5,5a,6,6a-tetrahydro-1H-cyclopropa[4,5]pyrano[3,2-c]pyrazol-1-yl) acetamide (67I)

The title compound (67I) was prepared as a mixture of atropisomers according to the method presented for the synthesis of compound 10A of Example 10 utilizing 2-(3-(trifluoromethyl)-5,5a,6,6a-tetrahydro-1H-cyclopropa[4,5]pyrano[3,2-c]pyrazol-1-yl)acetic acid (67H) and compound 33E. $^1$H NMR (400 MHz, Methanol-$d_4$) δ 7.93-7.78 (m), 7.75-7.65 (m), 7.61-7.45 (m), 7.39-6.98 (m), 6.73 (tq), 6.68-6.56 (m), 6.34 (tdd), 5.43-4.93 (m), 4.83-4.71 (m), 4.30-3.97 (m), 3.22-3.00 (m), 3.02-2.76 (m), 2.10-1.70 (m), 1.16 (dddd), 0.86-0.64 (m). MS (m/z) 784.34 [M+H]$^+$.
Example 68
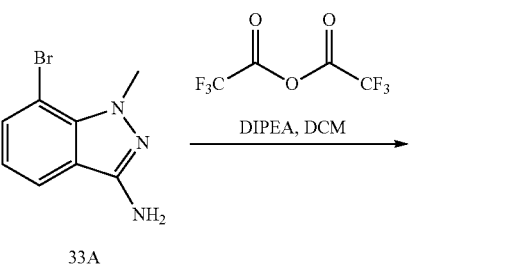
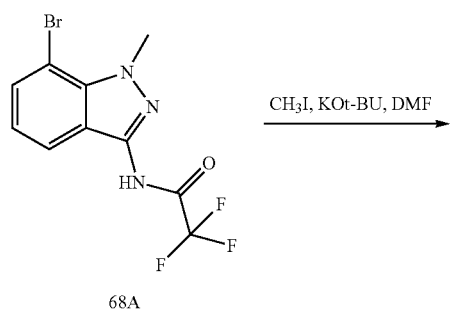
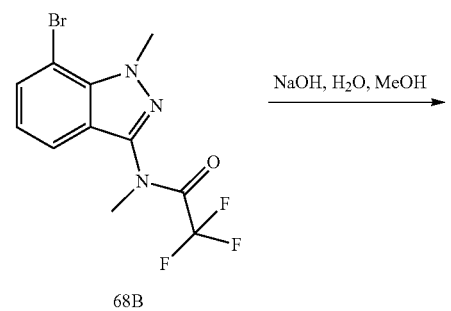
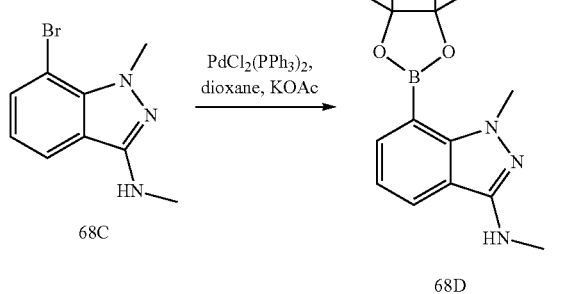
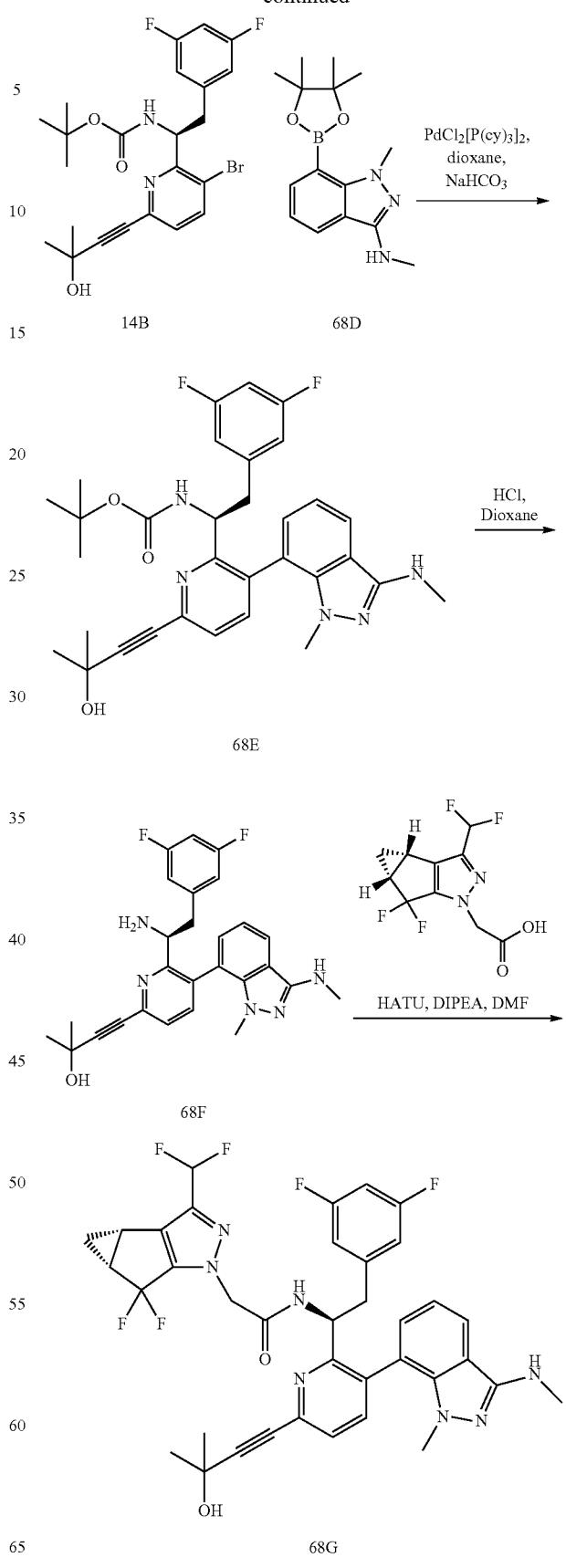

Synthesis of N-(7-bromo-1-methyl-1H-indazol-3-yl)-2,2,2-trifluoroacetamide (68A)

To a solution of 7-bromo-1-methyl-1H-indazol-3-amine (33A, 500 mg, 2.21 mmol) and N,N-diisopropylethylamine (0.578 mL, 3.32 mmol) in dichloromethane (5 ml) was added dropwise at 0° C. trifluoroacetic anhydride (697 mg, 3.32 mmol). The reaction was warmed to room temperature and stirred for 30 min. The reaction mixture was washed with water. The aqueous layer was back-extracted with dichloromethane. The combined organic layers were dried over $Na_2SO_4$, filtered, concentrated in vacuo, and purified by silica gel column chromatography to give the title compound. $^1H$ NMR (400 MHz, Chloroform-d) δ 8.51 (s, 1H), 7.87 (d, 1H), 7.60 (d, 1H), 7.01 (t, 1H), 4.37 (s, 3H).

Synthesis of N-(7-bromo-1-methyl-1H-indazol-3-yl)-2,2,2-trifluoro-N-methylacetamide (68B)

To a stirred solution of N-(7-bromo-1-methyl-1H-indazol-3-yl)-2,2,2-trifluoroacetamide (68A, 100 mg, 0.31 mmol) in DMF (0.6 ml) was added potassium t-butoxide (36.6 mg, 0.33 mmol). The reaction was sonicated until the solution became homogeneous and the reaction was stirred at room temperature for 30 mins. To the reaction was added iodomethane (29 µL, 0.47 mmol). After stirring for 1 h, the reaction was diluted with ethyl acetate and washed with water, followed by 0.5M aqueous NaCl. The combined organic layers were dried over $Na_2SO_4$, filtered, and concentrated in vacuo. The crude product was used in the next step without further purification.

Synthesis of 7-bromo-N,1-dimethyl-1H-indazol-3-amine (68C)

To a solution of N-(7-bromo-1-methyl-1H-indazol-3-yl)-2,2,2-trifluoro-N-methylacetamide (68B, 104 mg) in methanol (3 ml) was added 8M NaOH (46.6 µl). After stirring for 30 mins, the solution was concentrated, extracted with ethyl acetate (4 mL) and washed water (4 mL), followed by 2M aqueous NaCl (4 mL). The organic layer was dried over $Na_2SO_4$, filtered, and concentrated in vacuo. The crude product was used in the next step without further purification. MS (m/z) 240.15 $[M+H]^+$.

Synthesis of N,1-dimethyl-7-(4,4,5,5-tetramethyl-1,3,2-dioxaborolan-2-yl)-1H-indazol-3-amine (68D)

The title compound (68D) was prepared according to the method presented for the synthesis of compound 19C of Example 19 utilizing 7-bromo-N,1-dimethyl-1H-indazol-3-amine (68C). MS (m/z) 288.22 $[M+H]^+$.

Synthesis of ((S)-tert-butyl (2-(3,5-difluorophenyl)-1-(6-(3-hydroxy-3-methylbut-1-yn-1-yl)-3-(1-methyl-3-(methylamino)-1H-indazol-7-yl)pyridin-2-yl)ethyl)carbamate (68E)

The title compound (68E) was prepared as a mixture of atropisomers according to the method presented for the synthesis of compound 55A of Example 55 utilizing N,1-dimethyl-7-(4,4,5,5-tetramethyl-1,3,2-dioxaborolan-2-yl)-1H-indazol-3-amine (68D). MS (m/z) 576.06 $[M+H]^+$.

Synthesis of (S)-4-(6-(1-amino-2-(3,5-difluorophenyl)ethyl)-5-(1-methyl-3-(methylamino)-1H-indazol-7-yl)pyridin-2-yl)-2-methylbut-3-yn-2-ol (68F)

The title compound (68F) was prepared as a mixture of atropisomers according to the method presented for the synthesis of compound 14C of Example 14 utilizing ((S)-tert-butyl (2-(3,5-difluorophenyl)-1-(6-(3-hydroxy-3-methylbut-1-yn-1-yl)-3-(1-methyl-3-(methylamino)-1H-indazol-7-yl)pyridin-2-yl)ethyl)carbamate (68E). MS (m/z) 476.13 $[M+H]^+$.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-(methylamino)-1H-indazol-7-yl)pyridin-2-yl)ethyl)acetamide (68G)

The title compound (68G) was prepared according to the method presented for the synthesis of compound 33F of Example 33 utilizing (S)-4-(6-(1-amino-2-(3,5-difluorophenyl)ethyl)-5-(1-methyl-3-(methylamino)-1H-indazol-7-yl)pyridin-2-yl)-2-methylbut-3-yn-2-ol (68F) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1H$ NMR (400 MHz, Methanol-$d_4$) δ 7.90-7.86 (m), 7.86-7.80 (m), 7.71 (dd), 7.55 (dd), 7.34 (d), 7.22-7.12 (m), 6.84-6.77 (m), 6.77-6.70 (m), 6.70-6.67 (m), 6.66-6.62 (m), 6.56 (s), 6.54 (s), 6.47-6.41 (m), 6.36-6.29 (m), 5.22 (dd), 5.05 (t), 4.76 (d), 4.71 (s), 3.30-3.22 (m), 3.14-3.03 (m), 3.03-2.91 (m), 2.85 (s), 2.46 (ddt), 1.64 (s), 1.44-1.33 (m), 1.11-0.97 (m). MS (m/z) 722.18 $[M+H]^+$.

Example 69

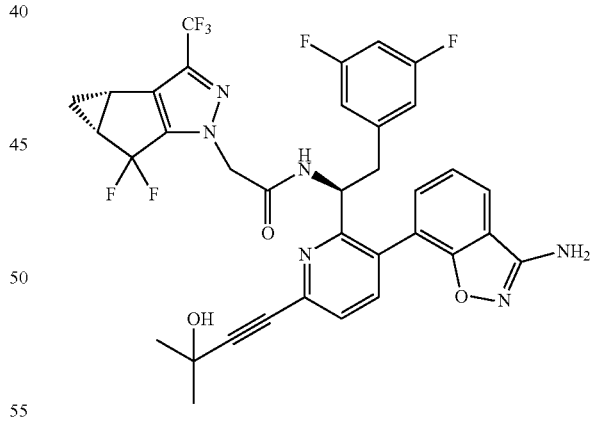

69

Synthesis of N—((S)-1-(3-(3-aminobenzo[d]isoxazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (69)

The title compound (69) was prepared as a mixture of atropisomers according to the method presented for the synthesis of compound 33F of Example 33 utilizing tert-butyl (7-(4,4,5,5-tetramethyl-1,3,2-dioxaborolan-2-yl)benzo[d]isoxazol-3-yl)carbamate and 2-((3bS,4aR)-5,5-difluoro-3-(trifluoromethyl)-3b,4,4a,5-tetrahydro-H-cyclopropa[3,4]cyclopenta[1,2-c]pyrazol-1-yl)acetic acid. ¹H NMR (400 MHz, cd₃od) δ 7.80 (dd), 7.69 (d), 7.54-7.40 (m), 7.33 (dt), 6.57 (ddd), 6.36-6.27 (m), 5.31 (t), 4.82 (s), 3.13-2.96 (m), 2.52-2.43 (m), 1.63 (s), 1.45-1.35 (m), 1.15-1.07 (m). MS (m/z) 713.3 [M+H]⁺.

Example 70

HPLC to provide the title compound as a mixture of atropisomers. ¹H NMR (400 MHz, Methanol-d₄) δ 8.69 (d), 7.68 (dd), 7.53 (dd), 7.19-7.10 (m), 7.06 (d), 6.87-6.52 (m), 6.49-6.31 (m), 5.35-5.22 (m), 5.05-4.94 (m), 4.79-4.65 (m), 3.24 (dd), 3.12 (dd), 3.04-2.91 (m), 2.45 (ddt), 1.64 (d), 1.44-1.32 (m), 1.12-0.99 (m). MS (m/z) 820.9 [M+H]⁺.

Example 71

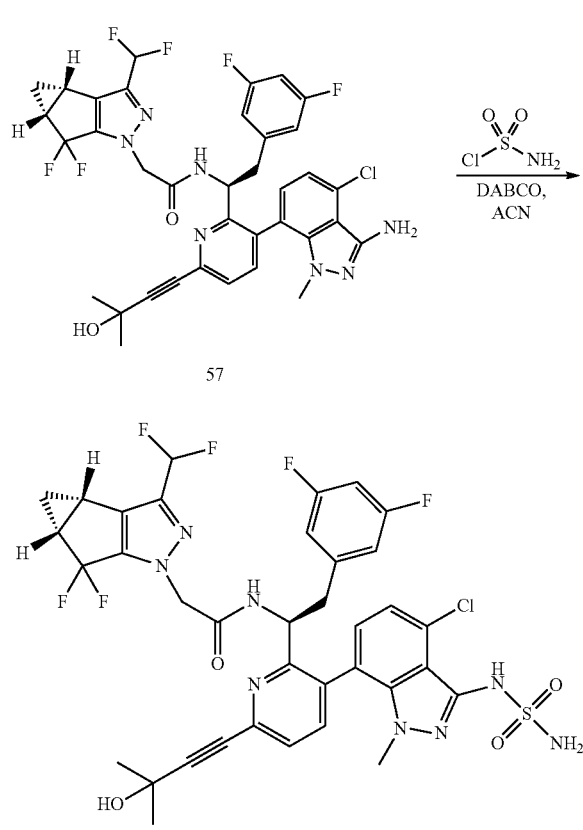

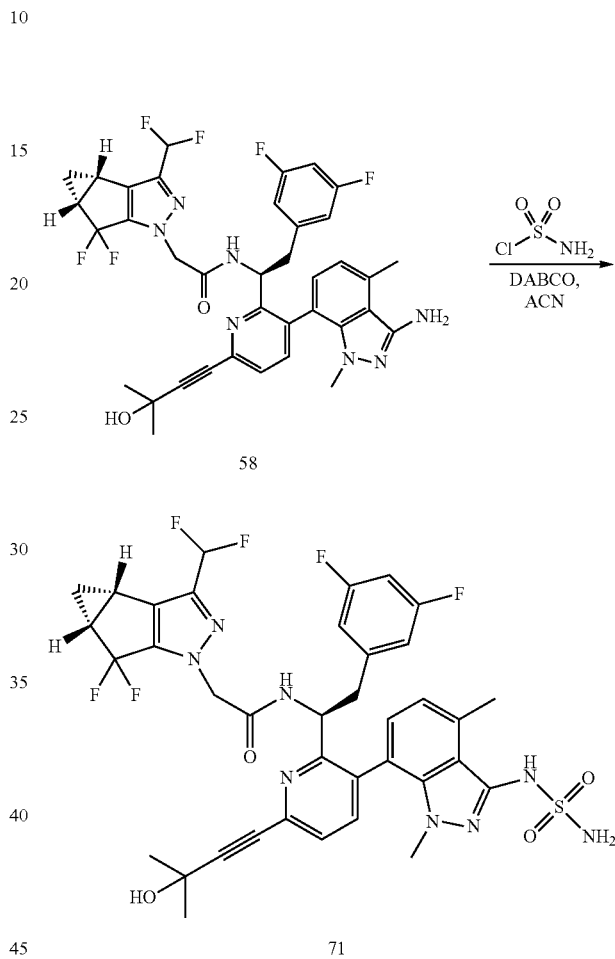

Synthesis of N—((S)-1-(3-(4-chloro-1-methyl-3-(sulfamoylamino)-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (70)

Compound 57 (20 mg, 0.03 mmol) was dissolved in ACN (0.5 ml) and cooled in a salt-ice bath to −10° C. The reaction solution was treated with DABCO (6 mg, 0.05 mmol) then a solution of sulfamoyl chloride (5 mg, 0.04 mmol) in ACN (0.2 ml) and let warm to ambient temperature. After 1 h, an additional aliquot of DABCO (2 eq) and sulfamoyl chloride (1.5 eq) were added. After another 1.5 hr, the reaction was diluted with KH₂PO₄ buffer and partitioned between brine and EtOAc. The organics were separated, dried, and removed in vacuo. The residue was purified by reverse phase Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1,4-dimethyl-3-(sulfamoylamino)-1H-indazol-7-yl)-6-(3-hydroxy-3-methylbut-1-yn-1-yl)pyridin-2-yl)ethyl)acetamide (71)

The title compound (71) was prepared as a mixture of atropisomers according to the method presented for the synthesis of 70 in Example 70 utilizing compound 58. ¹H NMR (400 MHz, Methanol-d₄) δ 8.71-8.54 (m), 7.73-7.60 (m), 7.57-7.45 (m), 7.08 (d), 7.00-6.89 (m), 6.89-6.77 (m), 6.77-6.64 (m), 6.66-6.56 (m), 6.54 (s), 6.44 (d), 6.41-6.33 (m), 6.33-6.25 (m), 5.40-5.29 (m), 5.08-4.94 (m), 4.75-4.67 (m), 3.12-2.86 (m), 2.86-2.74 (m), 2.54-2.35 (m), 1.44-1.29 (m), 1.12-0.98 (m). MS (m/z) 801.0 [M+H]⁺.

Example 72

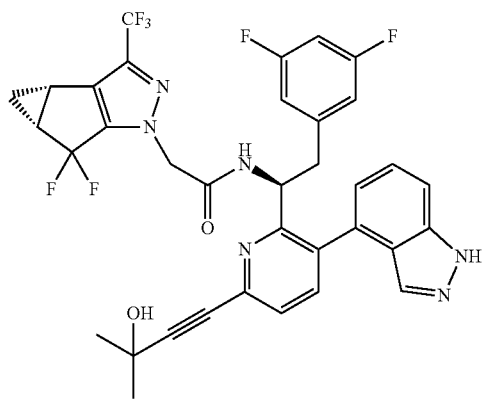

72

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(1H-indazol-4-yl)pyridin-2-yl)ethyl)acetamide (72)

The title compound (72) was prepared according to the method presented for the synthesis of compound 33F of Example 33 utilizing 4-(4,4,5,5-tetramethyl-1,3,2-dioxaborolan-2-yl)-1H-indazole and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, cd₃od) δ 8.74 (d), 8.61 (m), 7.63 (dd), 7.56-7.46 (m), 7.39 (dd), 7.32 (dd), 6.99 (d), 6.72 (tt), 6.56-6.45 (m), 6.31 (d), 6.27-6.20 (m), 5.44-5.34 (m), 5.10-4.99 (m), 4.93-4.83 (m), 4.76 (s), 3.18-3.04 (m), 2.97-2.83 (m), 2.58-2.42 (m), 1.86 (s), 1.67-1.57 (m), 1.48-1.33 (m), 1.15 (s), 1.08 (s). MS (m/z) 697.2 [M+H]⁺.

Example 73

73

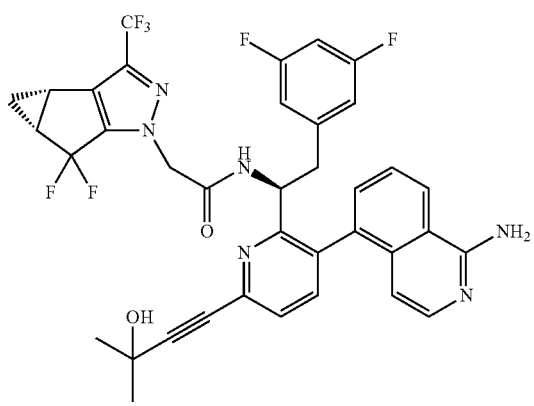

Synthesis of N—((S)-1-(3-(1-aminoisoquinolin-5-yl)-6-(3-hydroxy-3-methylbut-1-yn-1-yl)pyridin-2-yl)-2-(3,5-difluorophenyl)ethyl)-2-((3b,4aR)-5,5-difluoro-3-(trifluoromethyl)-3b,4,4a,5-tetrahydro-1H-cyclopropa[3,4]cyclopenta[1,2-c]pyrazol-1-yl)acetamide (73)

The title compound (73) was prepared as a mixture of atropisomers according to the method presented for the synthesis of compound 33F of Example 33 utilizing 5-(4,4,5,5-tetramethyl-1,3,2-dioxaborolan-2-yl)isoquinolin-1-amine and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, cd₃od) δ 8.89 (d), 8.76 (d), 8.47 (d), 7.90-7.84 (m), 7.81-7.73 (m), 7.68-7.50 (m), 7.32 (dd), 7.07 (dd), 6.81-6.69 (m), 6.63-6.53 (m), 6.48 (dd), 6.35-6.25 (m), 6.05 (dd), 5.07 (td), 4.86-4.71 (m), 3.25-3.09 (m), 3.03-2.92 (m), 2.55-2.45 (m), 1.65 (s), 1.48-1.38 (m), 1.16-1.07 (m). MS (m/z) 723.3 [M+H]⁺.

Example 74

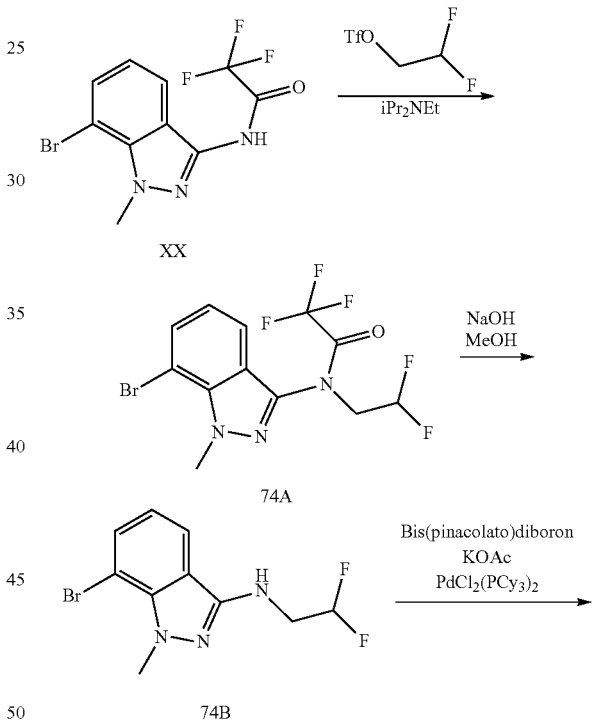

Synthesis of N-(7-bromo-1-methyl-1H-indazol-3-yl)-N-(2,2-difluoroethyl)-2,2,2-trifluoroacetamide (74A)

To N-(7-bromo-1-methyl-1H-indazol-3-yl)-2,2,2-trifluoroacetamide (150 mg, 0.47 mmol) in DCE (2 ml) was added iPr₂NEt (0.122 ml, 0.7 mmol) followed by 2,2-difluoroethyl trifluoromethanesulfonate (100 mg, 0.47 mmol). The reaction was stirred 15 h at ambient temperature. The reaction was partitioned between EtOAc and water. The organics were separated, dried, and removed in vacuo to provide the title compound which was used directly in the next reaction. MS (m/z) 387.9 [M+H]⁺.

Synthesis of 7-bromo-N-(2,2-difluoroethyl)-1-methyl-1H-indazol-3-amine (74B)

N-(7-bromo-1-methyl-1H-indazol-3-yl)-N-(2,2-difluoroethyl)-2,2,2-trifluoroacetamide (0.18 g, 0.47 mmol) was dissolved in MeOH (2 ml) and treated with aqueous NaOH (1M, 3 ml). After 10 min, the reaction was neutralized and partitioned between EtOAc and 20% aqueous KH₂PO₄. The organics were separated, dried, and removed in vacuo to provide the title compound which was used directly in the next reaction. MS (m/z) 290.1 [M+H]⁺.

Synthesis of N-(2,2-difluoroethyl)-1-methyl-7-(4,4,5,5-tetramethyl-1,3,2-dioxaborolan-2-yl)-1H-indazol-3-amine (74C)

The title compound (74C) was prepared according to the method presented for the synthesis of 27D in Example 27 utilizing 74B. MS (m/z) 338.1 [M+H]⁺.

74D

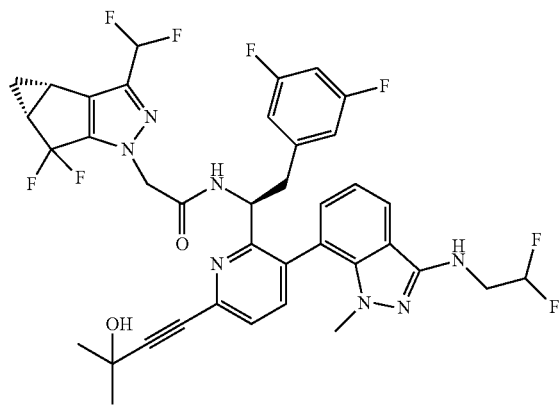

Synthesis of N—((S)-1-(3-(3-((2,2-difluoroethyl)amino)-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (74D)

The title compound (36C) was prepared as a mixture of atropisomers according to the method presented for the synthesis of 27G in Example 27 utilizing 14B and 74C. ¹H NMR (400 MHz, Methanol-d₄) δ 7.75 (d), 7.67 (dd), 7.52 (dd), 7.18 (d), 7.04 (t), 6.95 (t), 6.85-6.49 (m), 6.39-6.26 (m), 6.26-6.20 (m), 6.12-6.04 (m), 5.99-5.91 (m), 5.32-5.22 (m), 5.05 (t), 4.74 (s), 3.79-3.56 (m), 3.23-3.11 (m), 3.07 (dd), 3.00-2.89 (m), 2.88 (s), 2.54-2.38 (m), 1.64 (s), 1.44-1.27 (m), 1.13-0.94 (m).
MS (m/z) 772.5 [M+H]⁺.

Example 75

75

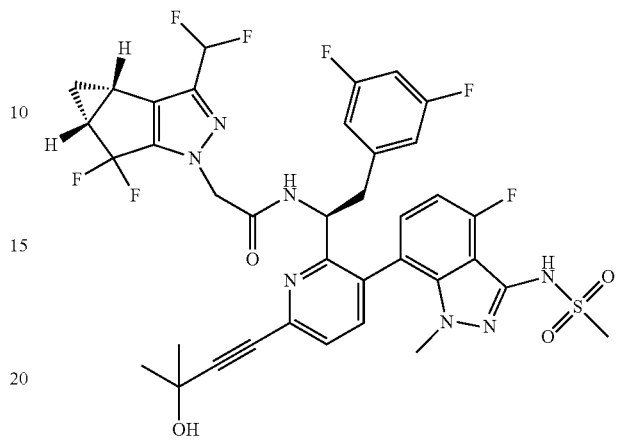

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-fluoro-1-methyl-3-(methylsulfonamido)-1H-indazol-7-yl)-6-(3-hydroxy-3-methylbut-1-yn-1-yl)pyridin-2-yl)ethyl)acetamide (75)

The title compound (75) was prepared as a mixture of atropisomers according to the method presented for the synthesis of compound 132C of Example 132 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid. ¹H NMR (400 MHz, cd₃od) δ 8.68 (dd), 7.72-7.65 (m), 7.54 (d), 7.51 (d), 7.21 (dd), 6.87-6.81 (m), 6.80-6.71 (m), 6.69 (s), 6.66-6.59 (m), 6.58 (s), 6.55 (s), 6.45-6.34 (m), 5.35-5.27 (m), 5.03-4.96 (m), 4.88 (s), 4.77 (s), 4.72 (d), 3.27-3.08 (m), 3.03-2.92 (m), 2.56-2.37 (m), 1.94 (s), 1.64 (d), 1.44-1.26 (m), 1.13-1.06 (m), 1.05-0.98 (m). MS (m/z) 804.1 [M+H]⁺.

Example 76

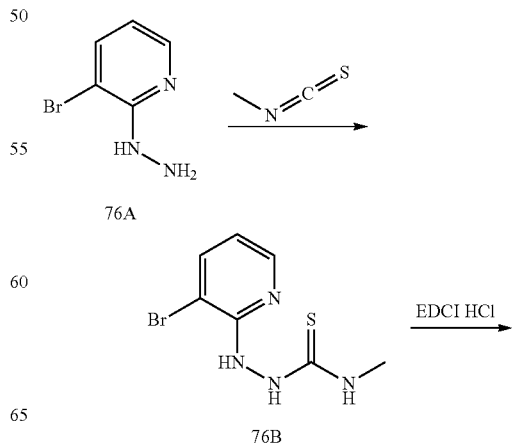

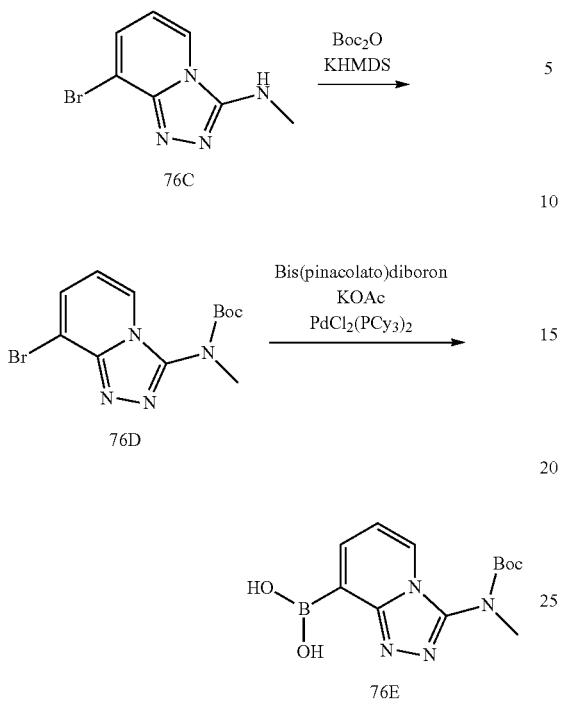

organics were separated, dried, and removed in vacuo and the residue was purified by column chromatography on silica to provide the title compound. MS (m/z) 326.9 [M+H]+.

Synthesis of (3-((tert-butoxycarbonyl)(methyl) amino)-[1,2,4]triazolo[4,3-a]pyridin-8-yl)boronic acid (76E)

tert-Butyl (8-bromo-[1,2,4]triazolo[4,3-a]pyridin-3-yl)(methyl)carbamate (0.46 g, 1.41 mmol) was combined with bis (pinacolato)diboron (0.54 g), KOAc (0.41 g, 0 mol), and PdCl$_2$(PCy$_3$)$_2$ (0.05 g) in dioxane and DMF. Argon was bubbled into the reaction mixture for 10 min and then heated to 140 deg C. for 2 h. The reaction was partitioned between EtOAc and water. The organics were separated, dried, and removed in vacuo to provide the title compound as a crude product contaminated with byproducts. The material was used directly in the following reaction. MS (m/z) 293.0 [M+H]+.

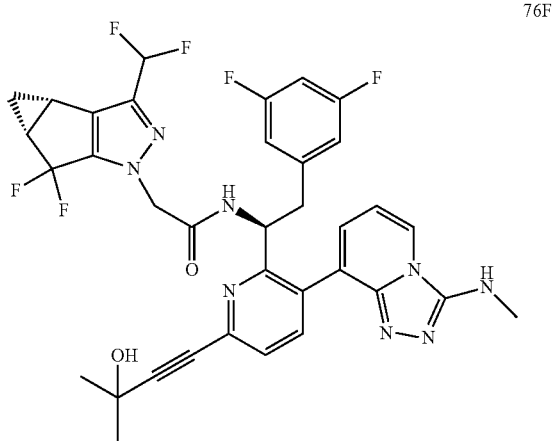 [SMILES: CNc1nnc2c(-c3ccc(C#CC(C)(C)O)nc3[C@H](Cc3cc(F)cc(F)c3)NC(=O)Cn3nc(C(F)F)c4c3C(F)(F)[C@@H]3C[C@H]43)cccn12]

Synthesis of 2-(3-bromopyridin-2-yl)-N-methylhydrazinecarbothioamide (76B)

3-Bromo-2-hydrazinylpyridine (1500 mg, 7.98 mmol) was dissolved in DCM (50 ml) and treated with dropwise addition of methyl isothiocyanate (700 mg, 9.57 mmol) in DCM. The reaction was heated to 45° C. and stirred for 2 hr. After cooling to ambient temperature, the solids were filtered to provide the title compound. MS (m/z) 261.0 [M+H]+.

Synthesis of 8-bromo-N-methyl-[1,2,4]triazolo[4,3-a]pyridin-3-amine (76C)

2-(3-Bromopyridin-2-yl)-N-methylhydrazinecarbothioamide (1.6 g, 6.1 mmol) was treated with EDCI HCl (1.76 g, 9 mmol) in toluene and heated to 105° C. After 1 hr, the hot toluene was decanted. To the residue was added H$_2$O (50 ml). The slurry was mixed thoroughly and heated to 100° C. for 15 min. After cooling to 0° C., the resultant solids were filtered to provide the title compound. MS (m/z) 227.1 [M+H]+.

Synthesis of tert-butyl (8-bromo-[1,2,4]triazolo[4,3-a]pyridin-3-yl)(methyl)carbamate (76D)

8-bromo-N-methyl-[1,2,4]triazolo[4,3-a]pyridin-3-amine (0.55 g, 2.42 mmol) was dissolved in DMF (10 ml) and treated with KHMDS (0.58 g, 2.91 mmol). Di-tert-butyl dicarbonate (0.79 g, 3.63 mmol) was then added. The reaction was stirred at ambient temperature for 2 d. The reaction was partitioned between EtOAc and water. The Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-(methylamino)-[1,2,4]triazolo[4,3-a]pyridin-8-yl)pyridin-2-yl)ethyl)acetamide (76F)

The title compound (76F) was prepared according to the method presented for the synthesis of 27G in Example 27 utilizing 14B and 76E. $^1$H NMR (400 MHz, Methanol-d$_4$) δ 8.88 (d), 8.22 (d), 7.75 (d), 7.56 (d), 7.37 (s), 7.18 (t), 6.67 (t), 6.70-6.59 (m), 6.55-6.44 (m), 5.31-5.17 (m), 4.69 (d), 3.23-3.08 (m), 2.55-2.39 (m), 1.63 (s), 1.46-1.25 (m), 1.08-1.00 (m). MS (m/z) 709.2 [M+H]+.

Example 77
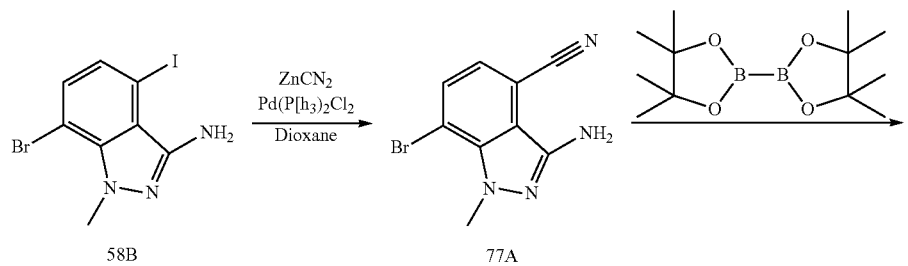
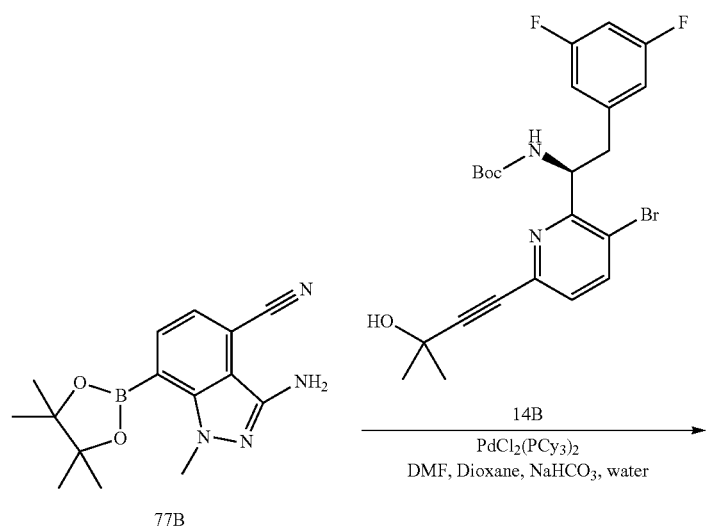
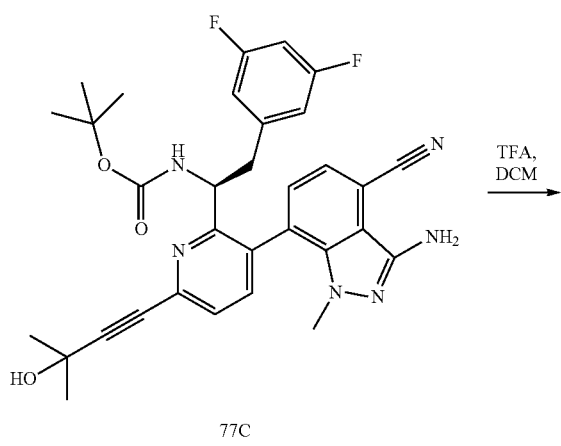

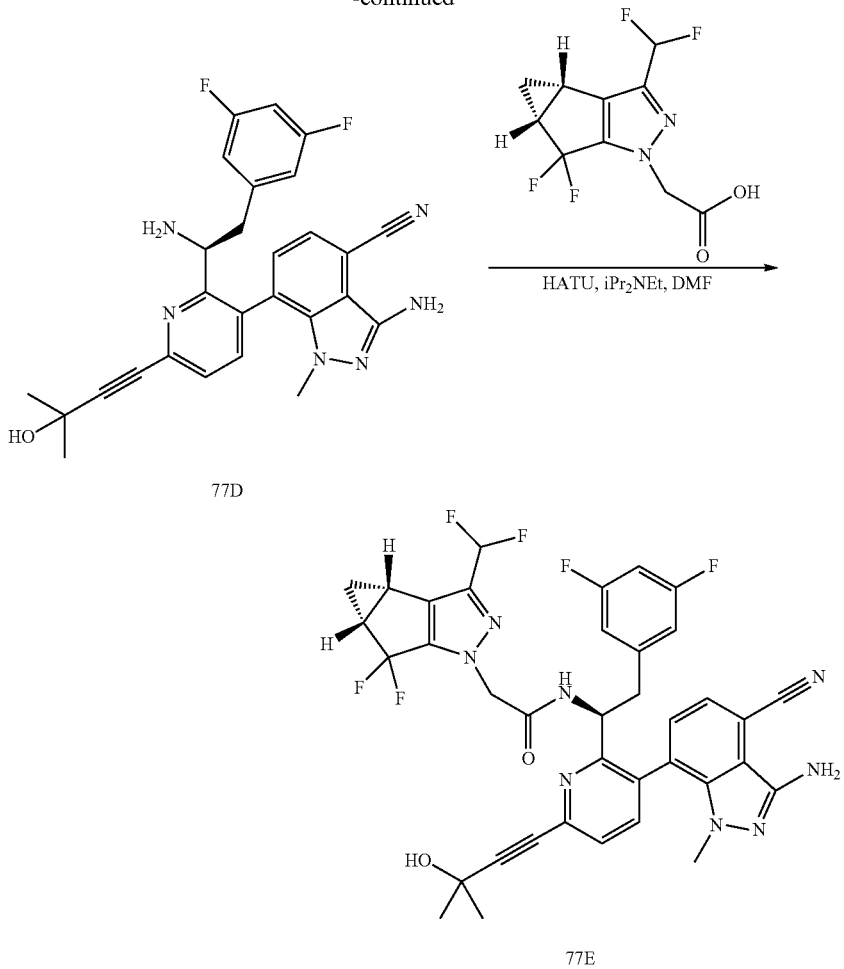

77D

77E

Synthesis of 3-amino-7-bromo-1-methyl-1H-indazole-4-carbonitrile (77A)

To 58B (3 g, 8.5 mmol) in dioxane (32 mL) and DMF (32 ml) was added zinc (6.7 g, 102.3 mmol) and Pd(PPh$_3$)$_2$Cl$_2$ (600 mg, 0.9 mmol). The reaction mixture was stirred at 160° C. and ZnCN$_2$ (500 mg, 4.3 mmol) was added to the reaction. After an hour another aliquot of ZnCN$_2$ (500 mg, 4.3 mmol) was added. The reaction was cooled, diluted with EtOAc and brine. The mixture was extracted 2× with EtOAc, the organic layer was dried over sodium sulfate, was concentrated and purified by flash column chromatography to provide the title compound. MS (m/z) 251.1 [M+H]$^+$.

Synthesis of 3-amino-1-methyl-7-(4,4,5,5-tetramethyl-1,3,2-dioxaborolan-2-yl)-1H-indazole-4-carbonitrile (77B)

The title compound (77B) was prepared according to the method presented for the synthesis of compound 19C of Example 19 utilizing 77A. MS (m/z) 299.3 [M+H]$^+$.

Synthesis of (S)-tert-butyl (1-(3-(3-amino-4-cyano-1-methyl-1H-indazol-7-yl)-6-(3-hydroxy-3-methylbut-1-yn-1-yl)pyridin-2-yl)-2-(3,5-difluorophenyl)ethyl)carbamate (77C)

The title compound (77C) was prepared as a mixture of atropisomers according to the method presented for the synthesis of compound 19E of Example 19 utilizing 77B. MS (m/z) 587.0 [M+H]$^+$.

Synthesis of (S)-3-amino-7-(2-(1-amino-2-(3,5-difluorophenyl)ethyl)-6-(3-hydroxy-3-methylbut-1-yn-1-yl)pyridin-3-yl)-1-methyl-1H-indazole-4-carbonitrile (77D)

The title compound (77D) was prepared as a mixture of atropisomers according to the method presented for the synthesis of compound 19F of Example 19 utilizing 77C. MS (m/z) 487.2 [M+H]$^+$.

Synthesis of N—((S)-1-(3-(3-amino-4-cyano-1-methyl-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (77E)

The title compound (77E) was prepared as a mixture of atropisomers according to the method presented for the synthesis of compound 10A of Example 10 utilizing 77D and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. ¹H NMR (Chloroform-d) δ: 7.54 (t), 7.52-7.45 (m), 7.33 (d), 7.19 (t), 6.85 (t), 6.71-6.62 (m), 6.49 (d), 6.24-6.17 (m), 6.15 (d), 5.47 (d), 4.99-4.88 (m), 4.78-4.68 (m), 3.12 (s), 3.03-2.94 (m), 2.92 (s), 2.56-2.39 (m), 1.72 (s), 1.42 (q), 1.21-1.10 (m) MS (m/z) 733.3 [M+H]⁺.

Example 78

78

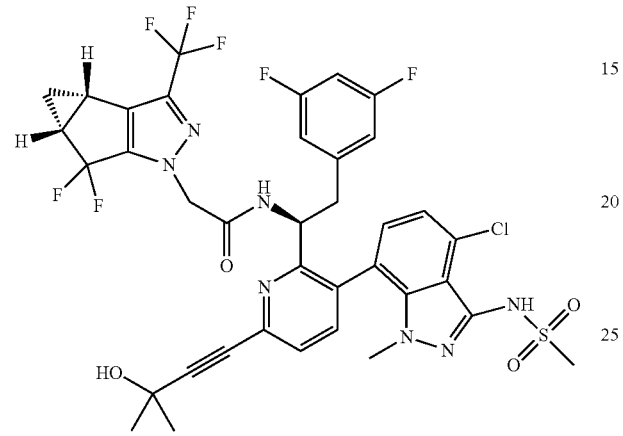

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (78)

The title compound (78) was prepared as a mixture of atropisomers according to the method presented for the synthesis of compound 19G of Example 19 utilizing 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (Chloroform-d) δ: 7.60-7.46 (m), 7.32-7.24 (m), 7.24-7.15 (m), 6.92 (d), 6.71-6.62 (m), 6.48 (s), 6.27-6.17 (m), 6.08 (d), 5.55 (d), 4.98 (q), 4.79 (d), 4.73 (d), 3.56 (d), 3.40 (d), 3.27 (s), 3.07-2.91 (m), 2.66-2.40 (m), 1.71 (s), 1.44 (q), 1.28-1.15 (m). MS (m/z) 838.9 [M+H]⁺.

Example 79

79

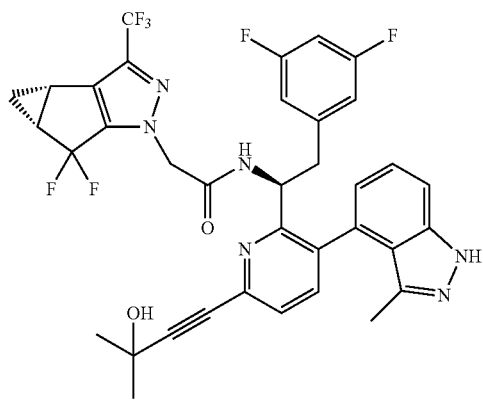

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-methyl-1H-indazol-4-yl)pyridin-2-yl)ethyl)acetamide (79)

The title compound (79) was prepared as a mixture of atropisomers according to the method presented for the synthesis of compound 20F of Example 20 utilizing (3-carbamoyl-4-chlorophenyl)boronic acid and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, cd3od) δ 8.75 (d), 8.61 (d), 7.63 (dd), 7.56-7.46 (m), 7.39 (dd), 7.32 (dd), 6.99 (d), 6.72 (tt), 6.56-6.45 (m), 6.31 (d), 6.27-6.20 (m), 5.39 (dt), 5.10-4.99 (m), 4.76 (s), 3.18-3.04 (m), 2.97-2.83 (m), 2.58-2.42 (m), 1.86 (s), 1.64 (d), 1.60 (s), 1.48-1.33 (m), 1.18-1.11 (m), 1.11-1.03 (m). MS (m/z) 711.7 [M+H]⁺.

Example 80

80

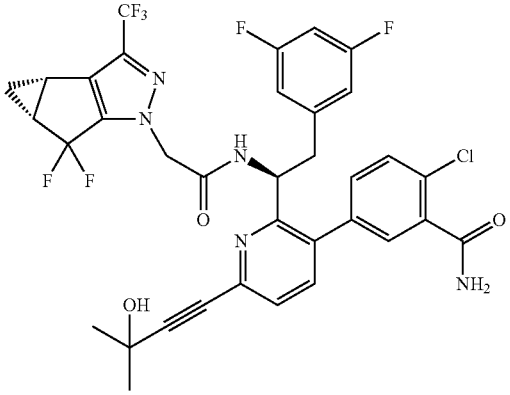

Synthesis of 2-chloro-5-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)benzamide (80)

The title compound (80) was prepared according to the method presented for the synthesis of compound 33F of Example 33 utilizing (3-carbamoyl-4-chlorophenyl)boronic acid and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, cd₃od) δ 8.86 (d), 7.54 (d), 7.46 (dd), 7.17 (d), 7.07-6.99 (m), 6.70 (tt), 6.44-6.34 (m), 5.35 (dd), 4.84 (d), 3.19-3.00 (m), 2.57-2.42 (m), 1.62 (s), 1.46-1.36 (m), 1.15-1.06 (m). MS (m/z) 736.0 [M+H]⁺.

Example 81

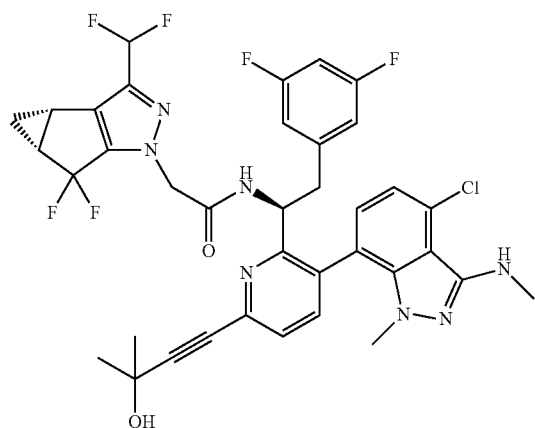

Synthesis of N—((S)-1-(3-(4-chloro-1-methyl-3-(methylamino)-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (81)

The title compound (81) was prepared as a mixture of atropisomers according to the method presented in Example 68 utilizing 7-bromo-4-chloro-1-methyl-1H-indazol-3-amine (19B) in place of 7-bromo-1-methyl-1H-indazol-3-amine (33A). $^1$H NMR (400 MHz, Methanol-$d_4$) δ 7.90-7.86 (m), 7.86-7.80 (m), 7.71 (dd), 7.55 (dd), 7.34 (d), 7.22-7.12 (m), 6.84-6.77 (m), 6.77-6.70 (m), 6.70-6.67 (m), 6.66-6.62 (m), 6.56 (s), 6.54 (s), 6.47-6.41 (m), 6.36-6.29 (m), 5.22 (dd), 5.05 (t), 4.76 (d), 4.71 (s), 3.30-3.22 (m), 3.14-3.03 (m), 3.03-2.91 (m), 2.85 (s), 2.46 (ddt), 1.64 (s), 1.44-1.33 (m), 1.11-0.97 (m). MS (m/z) 756.14 [M+H]$^+$.

Example 82

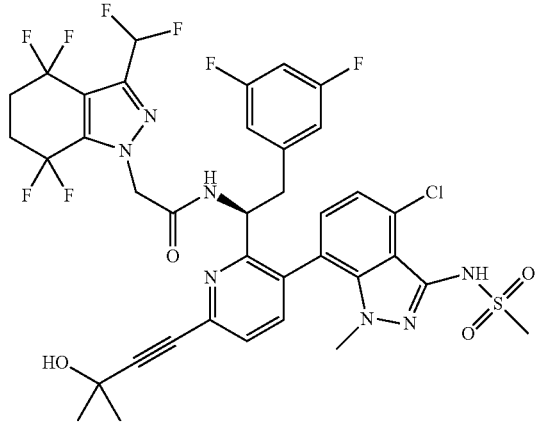

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (82)

The title compound (82) was prepared as a mixture of atropisomers according to the method presented for the synthesis of compound 19G of Example 19 utilizing 2-(3-(difluoromethyl)-4,4,7,7-tetrafluoro-4,5,6,7-tetrahydro-1H-indazol-1-yl)acetic acid. $^1$H NMR (Chloroform-d) δ: 7.60-7.47 (m), 7.31-7.16 (m), 7.02-6.80 (m), 6.72-6.59 (m), 6.51-6.43 (m), 6.27-6.12 (m), 5.66-5.52 (m), 5.08-4.97 (m), 4.94 (d), 3.40 (s), 3.38 (s), 3.28 (t), 3.07 (s), 3.01-2.89 (m), 2.63-2.42 (m), 2.03 (s), 1.71 (s). MS (m/z) 858.8 [M+H]$^+$.

Example 83

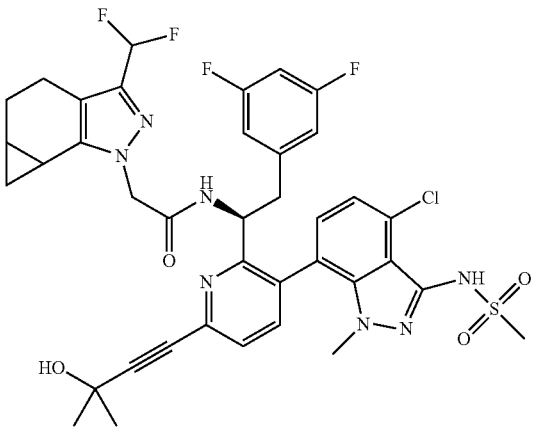

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-(difluoromethyl)-5,5a,6,6a-tetrahydrocyclopropa[g]indazol-1(4H)-yl)acetamide (83)

The title compound (83) was prepared as a mixture of atropisomers according to the method presented for the synthesis of compound 19G of Example 19 utilizing 2-(3-(difluoromethyl)-5,5a,6,6a-tetrahydrocyclopropa[g]indazol-1(4H)-yl)acetic acid. $^1$H NMR (Chloroform-d) δ: 7.55-7.43 (m), 7.38 (d), 7.29 (d), 7.18 (d), 6.96 (dd), 6.86 (d), 6.72 (d), 6.67-6.59 (m), 6.57 (d), 6.29 (d), 6.18 (td), 4.94 (dq), 4.84-4.79 (m), 4.76 (s), 3.39 (d), 3.30 (s), 3.24 (s), 3.07 (d), 3.01-2.89 (m), 2.89-2.74 (m), 2.63-2.47 (m), 2.29-2.08 (m), 1.82-1.62 (m), 1.71 (d), 1.05 (td), 0.96 (td), 0.74 (q), 0.65 (q). MS (m/z) 798.9 [M+H]$^+$.

Example 84

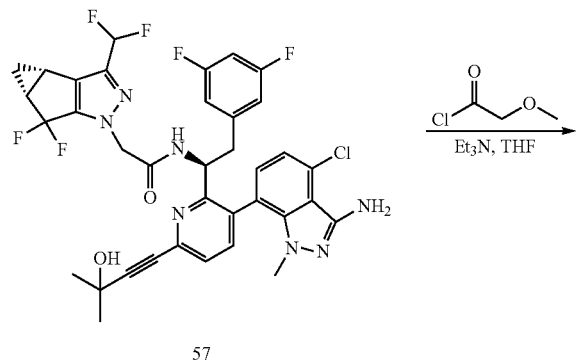

57

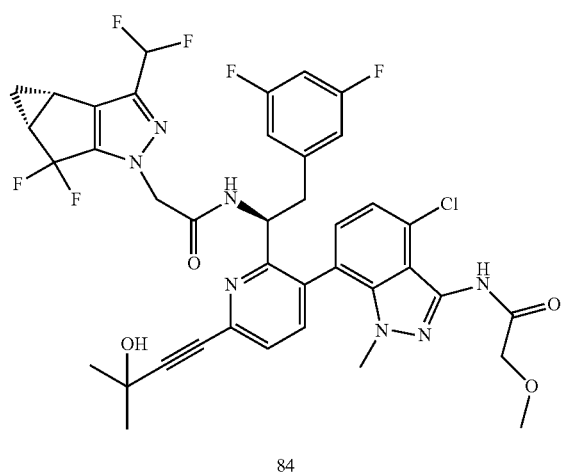

84

Synthesis of N—((S)-1-(3-(4-chloro-3-(2-methoxyacetamido)-1-methyl-H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (84)

To the reaction vial containing 57 (13 mg, 0.017 mmol) in THF (0.25 mL) was added 2-methoxyacetyl chloride (2 mg, 0.019 mmol), and triethylamine (0.004 mL, 0.026 mmol). The reaction mixture was stirred at room temperature until the majority of 57 was consumed. The reaction mixture was concentrated in vacuo and dissolved in methanol and treated with several drops of 2 M NaOH for 30 min. The reaction mixture was then acidified with TFA and purified by reverse phase HPLC to provide the title compound 84 as a mixture of atropisomers. $^1$H NMR (400 MHz, cd$_3$od) δ 8.72-8.67 (m), 7.70 (dd), 7.54 (dd), 7.22-7.13 (m), 7.08 (d), 6.87-6.59 (m), 6.50-6.36 (m), 5.32-5.25 (m), 5.02-4.94 (m), 4.72 (dd), 4.14 (d), 3.56 (s), 3.34 (s), 3.15 (dd), 3.05-2.93 (m), 2.51-2.38 (m), 1.64 (d), 1.45-1.31 (m), 1.11-1.05 (m), 1.06-0.97 (m). MS (m/z) 815.2 [M+H]$^+$.

Example 85

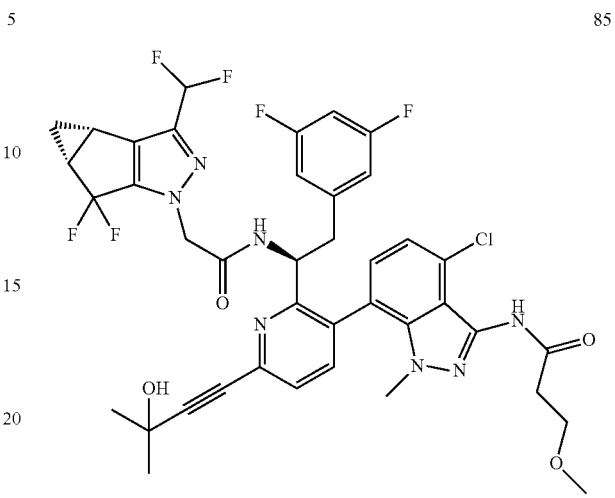

85

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)-3-methoxypropanamide (85)

The title compound (85) was prepared as a mixture of atropisomers according to the method presented for the synthesis of compound 84 of Example 84 utilizing 3-methoxypropanoyl chloride. $^1$H NMR (400 MHz, cd$_3$od) δ 8.75-8.65 (m), 7.69 (dd), 7.53 (dd), 7.21-7.12 (m), 7.07 (d), 6.87-6.52 (m), 6.47-6.35 (m), 5.35-5.25 (m), 4.98 (t), 4.79-4.63 (m), 3.79-3.73 (m), 3.39 (s), 3.14 (dd), 3.05-2.93 (m), 2.76-2.68 (m), 2.51-2.39 (m), 1.64 (d), 1.45-1.32 (m), 1.11-1.05 (m), 1.06-0.97 (m). MS (m/z) 829.2 [M+H]$^+$.

Example 86

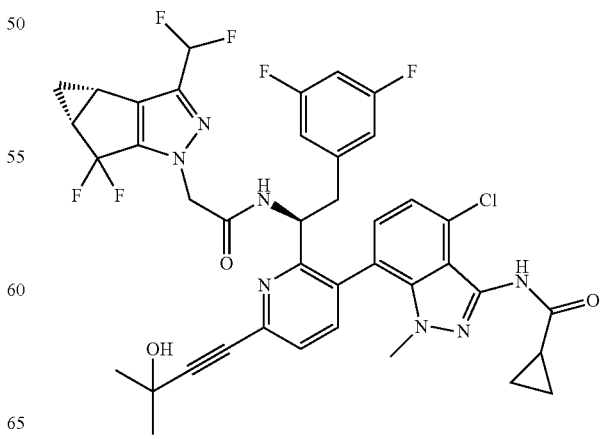

86

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)cyclopropanecarboxamide (86)

The title compound (86) was prepared as a mixture of atropisomers according to the method presented for the synthesis of compound 84 of Example 84 utilizing cyclopropanecarbonyl chloride. $^1$H NMR (400 MHz, cd$_3$od) δ 8.75-8.52 (m), 7.69 (dd), 7.53 (dd), 7.16 (d), 7.06 (d), 6.87-6.52 (m), 6.46-6.35 (m), 5.35-5.21 (m), 4.98 (t), 4.79-4.63 (m), 3.14 (dd), 3.00 (d), 2.53-2.39 (m), 1.90 (s), 1.64 (d), 1.45-1.32 (m), 1.06-0.96 (m), 0.90 (s). MS (m/z) 811.2 [M+H]$^+$.

Example 87

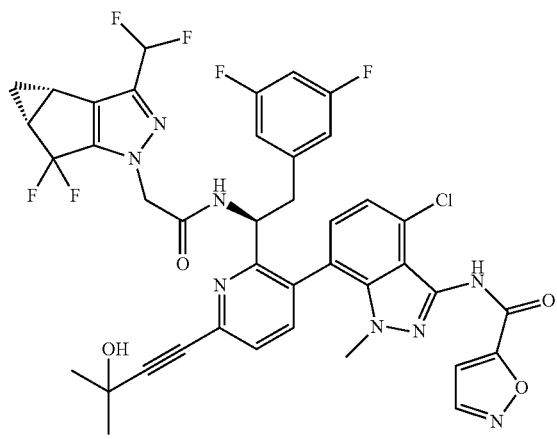

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)isoxazole-5-carboxamide (87)

The title compound (87) was prepared as a mixture of atropisomers according to the method presented for the synthesis of compound 84 of Example 84 utilizing isoxazole-5-carbonyl chloride. $^1$H NMR (400 MHz, cd$_3$od) δ 8.71 (t), 8.60 (s), 7.72 (dd), 7.55 (dd), 7.24-7.07 (m), 6.87-6.61 (m), 6.60-6.37 (m), 5.35-5.25 (m), 5.00 (t), 4.79-4.64 (m), 3.37 (s), 3.21-3.12 (m), 3.08-2.95 (m), 2.52-2.39 (m), 1.92 (d), 1.64 (s), 1.42-132 (m), 1.08 (s), 1.02 (s). MS (m/z) 838.1 [M+H]$^+$.

Example 88

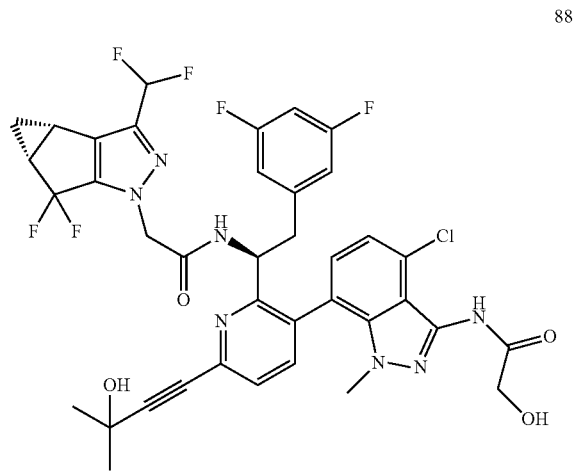 [SMILES: Cn1nc(NC(=O)CO)c2c(Cl)ccc(-c3ccc(C#CC(C)(C)O)nc3[C@H](Cc3cc(F)cc(F)c3)NC(=O)Cn3nc(C(F)F)c4c3C(F)(F)[C@@H]3C[C@H]43)c21]

Synthesis of N—((S)-1-(3-(4-chloro-3-(2-hydroxyacetamido)-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (88)

The title compound (88) was prepared as a mixture of atropisomers according to the method presented for the synthesis of compound 84 of Example 84 utilizing 2-chloro-2-oxoethyl acetate. $^1$H NMR (400 MHz, cd$_3$od) δ 7.74-7.66 (m), 7.54 (dd), 7.23-7.13 (m), 7.08 (d), 6.87-6.58 (m), 6.50-6.35 (m), 5.25-5.31 (m), 4.99 (t), 4.76 (d), 4.68 (s), 4.21 (d), 3.34 (s), 3.30-3.11 (m), 3.04-2.94 (m), 2.51-2.38 (m), 1.64 (d), 1.45-1.33 (m), 1.11-1.05 (m), 1.06-0.97 (m). MS (m/z) 802.1 [M+H]$^+$.

Example 89

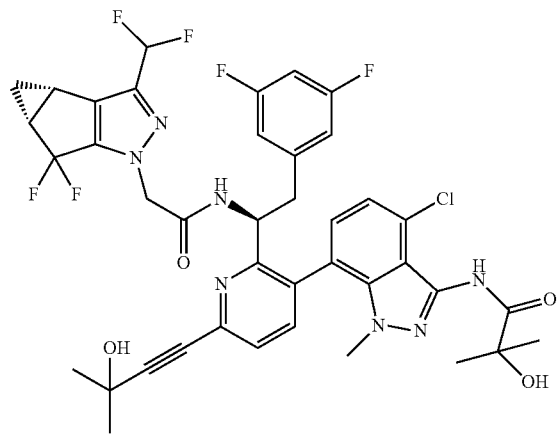

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)-2-hydroxy-2-methylpropanamide (89)

The title compound (89) was prepared as a mixture of atropisomers according to the method presented for the synthesis of compound 84 of Example 84 utilizing 1-chloro-2-methyl-1-oxopropan-2-yl acetate. $^1$H NMR (400 MHz, cd$_3$od) δ 8.75-8.65 (m), 7.70 (t), 7.54 (dd), 7.22-7.12 (m), 7.07 (d), 6.87-6.66 (m), 6.49-6.36 (m), 5.30-5.22 (m), 4.99 (t), 4.75 (d), 4.67 (s), 3.35 (s), 3.28-3.12 (m), 3.04-2.93 (m), 2.49-2.38 (m), 1.64 (d), 1.51 (dd), 1.43-1.33 (m), 1.08 (s), 1.05-0.98 (m). MS (m/z) 829.2 [M+H]$^+$.

Example 90

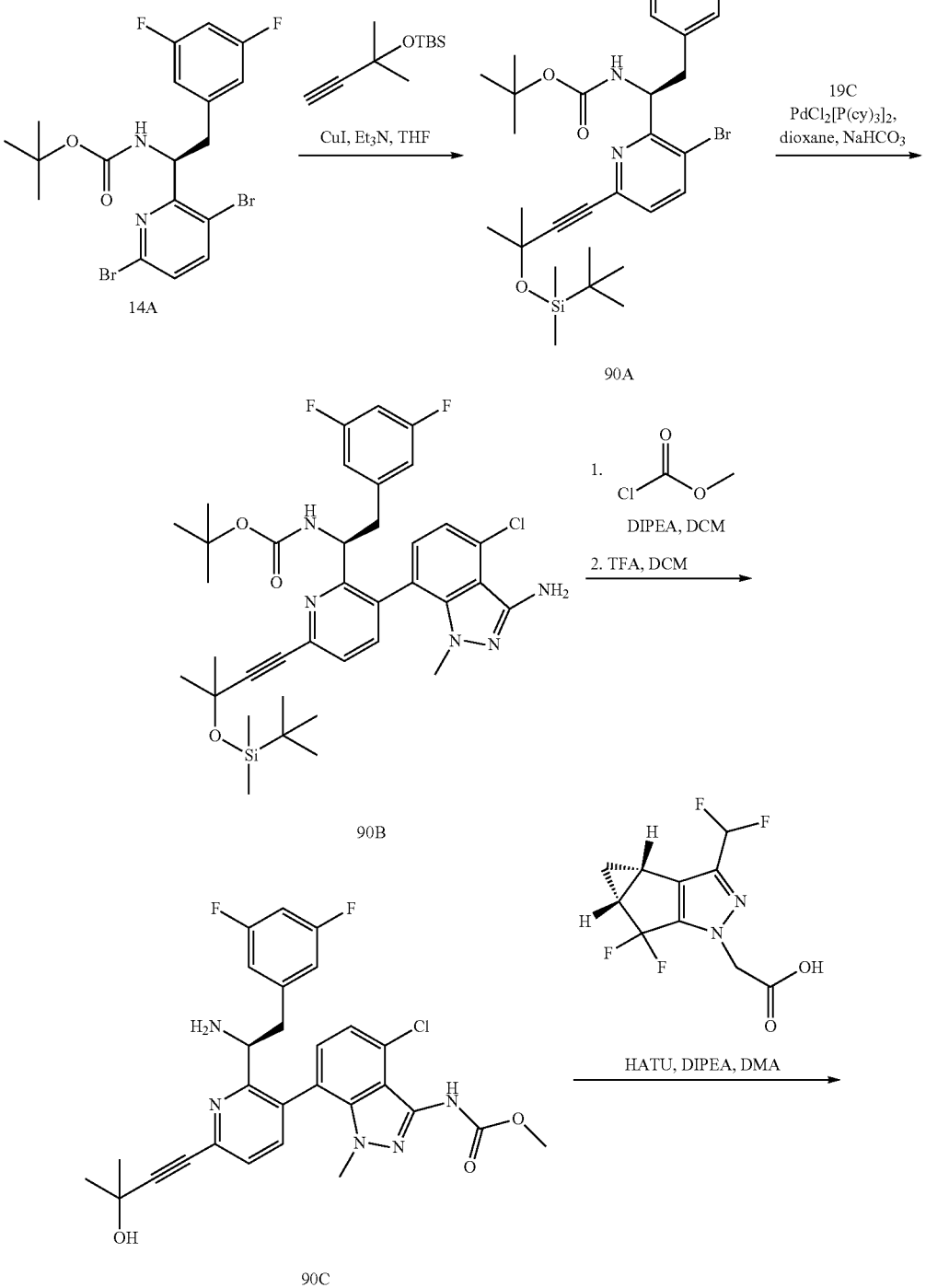

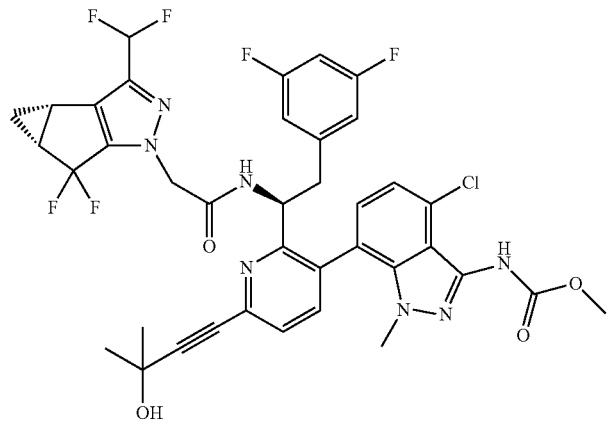

90D

Synthesis of (S)-tert-butyl (1-(3-bromo-6-(3-((tert-butyldimethylsilyl)oxy)-3-methylbut-1-yn-1-yl)pyridin-2-yl)-2-(3,5-difluorophenyl)ethyl)carbamate (90A)

The title compound (90A) was prepared according to the method presented for the synthesis of compound (14B) of Example 14 utilizing tert-butyldimethyl((2-methylbut-3-yn-2-yl)oxy)silane. MS (m/z) 609.10 [M+H]$^+$.

Synthesis of (S)-tert-butyl (1-(3-(3-amino-4-chloro-1-methyl-H-indazol-7-yl)-6-(3-((tert-butyldimethylsilyl)oxy)-3-methylbut-1-yn-1-yl)pyridin-2-yl)-2-(3,5-difluorophenyl)ethyl)carbamate (90B)

The title compound (90B) was prepared as a mixture of atropisomers according to the method presented for the synthesis of compound (19E) of Example 19 utilizing (S)-tert-butyl (1-(3-bromo-6-(3-((tert-butyldimethylsilyl)oxy)-3-methylbut-1-yn-1-yl)pyridin-2-yl)-2-(3,5-difluorophenyl)ethyl)carbamate (90A) and 4-chloro-1-methyl-7-(4,4,5,5-tetramethyl-1,3,2-dioxaborolan-2-yl)-1H-indazol-3-amine (19C). MS (m/z) 710.01 [M+H]$^+$.

Synthesis of (S)-methyl (7-(2-(1-amino-2-(3,5-difluorophenyl)ethyl)-6-(3-hydroxy-3-methylbut-1-yn-1-yl)pyridin-3-yl)-4-chloro-1-methyl-1H-indazol-3-yl)carbamate (90C)

To a solution of (S)-tert-butyl (1-(3-(3-amino-4-chloro-1-methyl-1H-indazol-7-yl)-6-(3-((tert-butyldimethylsilyl)oxy)-3-methylbut-1-yn-1-yl)pyridin-2-yl)-2-(3,5-difluorophenyl)ethyl)carbamate (90B) (20 mg, 0.03 mmol) and DIPEA (0.08 µl, 0.06 mmol) in dichloromethane (0.5 ml) was added methyl chloroformate (3.27 µl, 0.04 mmol). After stirring overnight, trifluoroacetic acid (0.5 ml) was added and the reaction was stirred at room temperature for 1 hour. The reaction was concentrated, extracted with ethyl acetate, and basified with 2 M aqueous K$_2$CO$_3$. The organic layer was washed with 0.5 M NaCl and the organic layer was dried with Na$_2$SO$_4$, filtered, and concentrated. The crude product as a mixture of atropisomers was taken to the next step without further purification. MS (m/z) 554.13 [M+H]$^+$.

Synthesis of methyl (4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)carbamate (90D)

The title compound (90D) was prepared as a mixture of atropisomers according to the method presented for the synthesis of compound (33F) of Example 33 utilizing (S)-methyl (7-(2-(1-amino-2-(3,5-difluorophenyl)ethyl)-6-(3-hydroxy-3-methylbut-1-yn-1-yl)pyridin-3-yl)-4-chloro-1-methyl-1H-indazol-3-yl)carbamate (90C) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. 1H NMR (400 MHz, Methanol-d$_4$) δ 8.72 (d), 8.66 (d), 7.74-7.63 (m), 7.59-7.48 (m), 7.20-7.14 (m), 7.07 (d), 6.87-6.53 (m), 6.46-6.33 (m), 5.35-5.26 (m), 5.05-4.95 (m), 4.80-4.64 (m), 3.75 (d), 3.33 (s), 3.28-3.07 (m), 2.99 (q), 2.53-2.39 (m), 1.64 (s), 1.50-1.28 (m), 1.09 (d), 1.06-0.99 (m). MS (m/z) 800.15 [M+H]$^+$.

Example 91
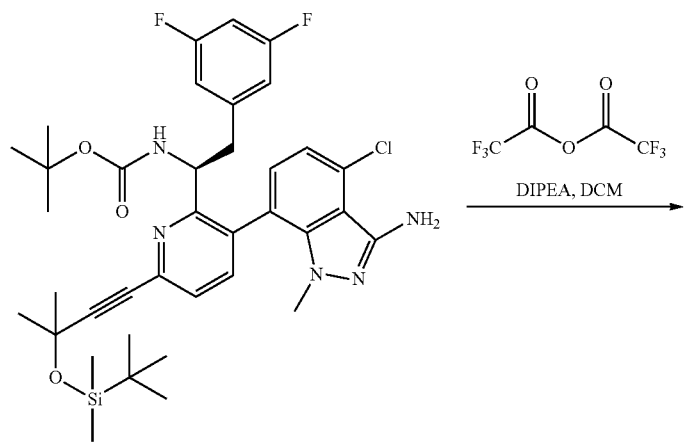
90B
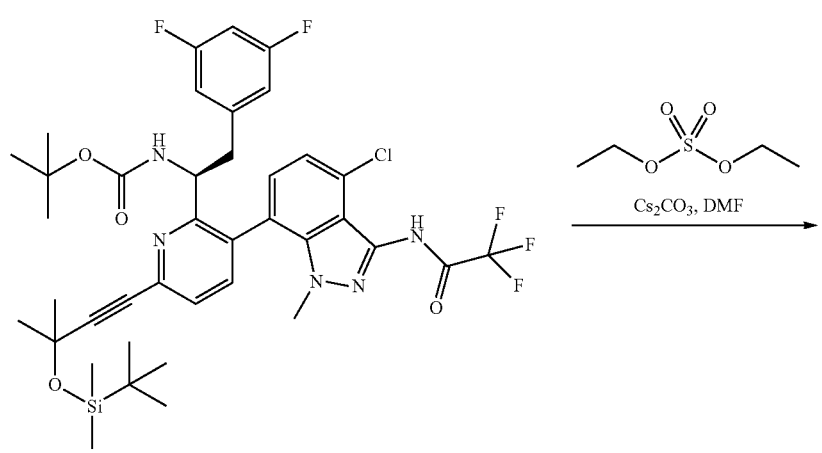
91A
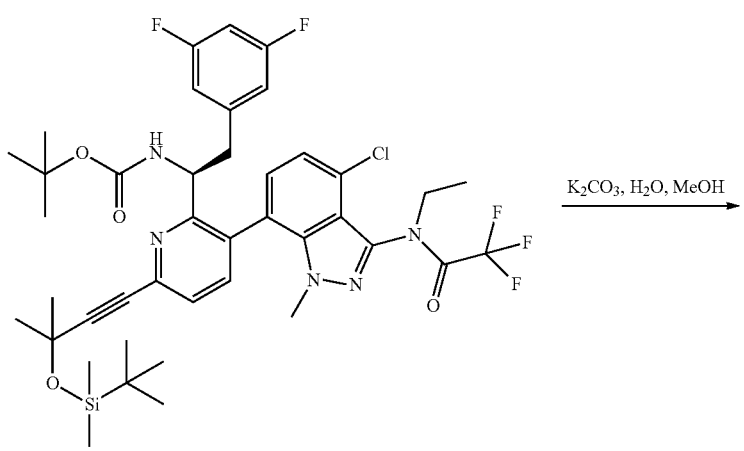
91B

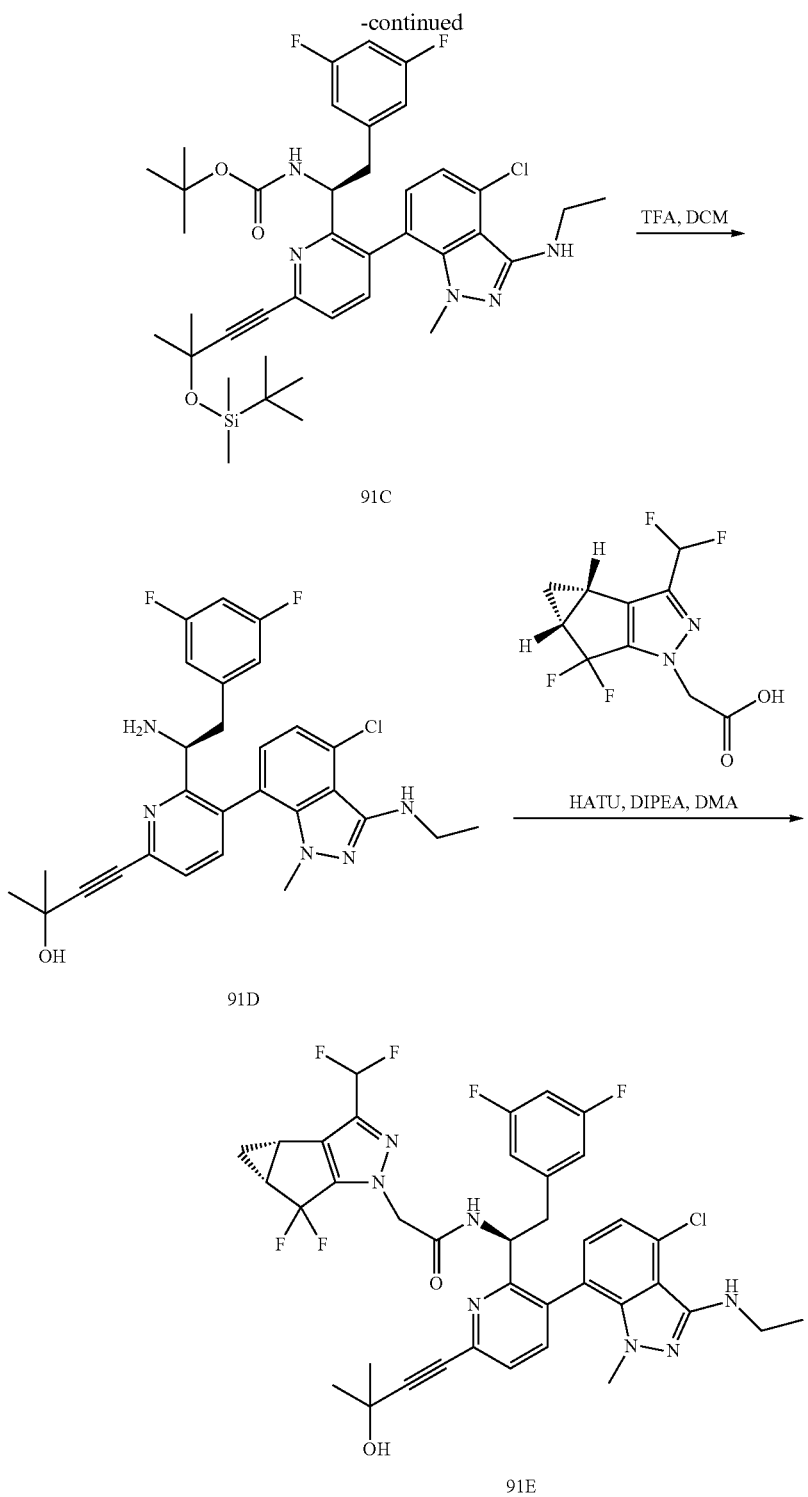

Synthesis of (S)-tert-butyl (1-(6-(3-((tert-butyldimethylsilyl)oxy)-3-methylbut-1-yn-1-yl)-3-(4-chloro-1-methyl-3-(2,2,2-trifluoroacetamido)-1H-indazol-7-yl)pyridin-2-yl)-2-(3,5-difluorophenyl)ethyl) carbamate (91A)

To a solution of (S)-tert-butyl (1-(3-(3-amino-4-chloro-1-methyl-1H-indazol-7-yl)-6-(3-((tert-butyldimethylsilyl)oxy)-3-methylbut-1-yn-1-yl)pyridin-2-yl)-2-(3,5-difluorophenyl)ethyl)carbamate (90B) (93 mg, 0.13 mmol) in dichloromethane (0.5 ml) was added DIPEA (34.14 μl, 0.2 mmol), followed by trifluoroacetic anhydride (25.5 μl, 0.18 mmol). After stirring at room temperature for 1 h, the product was extracted with dichloromethane and water. The organic layer was dried with $Na_2SO_4$, filtered, concentrated in vacuo, and purified by silica gel chromatography to provide the title compound. MS (m/z) 806.04 $[M+H]^+$.

Synthesis of (S)-tert-butyl (1-(6-(3-((tert-butyldimethylsilyl)oxy)-3-methylbut-1-yn-1-yl)-3-(4-chloro-3-(N-ethyl-2,2,2-trifluoroacetamido)-1-methyl-1H-indazol-7-yl)pyridin-2-yl)-2-(3,5-difluorophenyl)ethyl)carbamate (91B)

To a solution of (S)-tert-butyl (1-(6-(3-((tert-butyldimethylsilyl)oxy)-3-methylbut-1-yn-1-yl)-3-(4-chloro-1-methyl-3-(2,2,2-trifluoroacetamido)-1H-indazol-7-yl)pyridin-2-yl)-2-(3,5-difluorophenyl)ethyl)carbamate (91A) (20 mg, 0.02 mmol) in DMF (0.5 ml) was added cesium carbonate (20.2 mg, 0.06 mmol), followed by diethylsulfate (4.6 mg, 0.03 mmol). After stirring at room temperature overnight, the reaction mixture was extracted with ethyl acetate and water. The organic layer was dried with $Na_2SO_4$, filtered, and concentrated in vacuo. The crude product was taken to the next step without further purification.

Synthesis of (S)-tert-butyl (1-(6-(3-((tert-butyldimethylsilyl)oxy)-3-methylbut-1-yn-1-yl)-3-(4-chloro-3-(ethylamino)-1-methyl-1H-indazol-7-yl)pyridin-2-yl)-2-(3,5-difluorophenyl)ethyl)carbamate (91C)

To a solution of (S)-tert-butyl (1-(6-(3-((tert-butyldimethylsilyl)oxy)-3-methylbut-1-yn-1-yl)-3-(4-chloro-3-(N-ethyl-2,2,2-trifluoroacetamido)-1-methyl-1H-indazol-7-yl)pyridin-2-yl)-2-(3,5-difluorophenyl)ethyl)carbamate (21 mg) (91B) in methanol (0.5 mL) was added 2M aqueous $K_2CO_3$ (0.25 mL). After stirring at room temperature for 2 h, the reaction mixture was concentrated in vacuo. The mixture was extracted with ethyl acetate and water. The organic layer was dried with $Na_2SO_4$, filtered, and concentrated in vacuo. The crude product was taken to the next step without further purification.

Synthesis of (S)-4-(6-(1-amino-2-(3,5-difluorophenyl)ethyl)-5-(4-chloro-3-(ethylamino)-1-methyl-1H-indazol-7-yl)pyridin-2-yl)-2-methylbut-3-yn-2-ol (91D)

The title compound (91D) was prepared according to the method presented for the synthesis of compound (90C) of Example 90 utilizing (S)-tert-butyl (1-(6-(3-((tert-butyldimethylsilyl)oxy)-3-methylbut-1-yn-1-yl)-3-(4-chloro-3-(ethylamino)-1-methyl-1H-indazol-7-yl)pyridin-2-yl)-2-(3,5-difluorophenyl)ethyl)carbamate (91C). MS (m/z) 524.55 $[M+H]^+$.

Synthesis of N—((S)-1-(3-(4-chloro-3-(ethylamino)-1-methyl-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (91E)

The title compound (91E) was prepared as a mixture of atropisomers according to the method presented for the synthesis of compound (90D) of Example 90 utilizing (S)-4-(6-(1-amino-2-(3,5-difluorophenyl)ethyl)-5-(4-chloro-3-(ethylamino)-1-methyl-1H-indazol-7-yl)pyridin-2-yl)-2-methylbut-3-yn-2-ol (91D). $^1$H NMR (400 MHz, Methanol-d$_4$) δ 7.73-7.60 (m), 7.58-7.48 (m), 7.12 (d), 7.04 (d), 6.93 (d), 6.85-6.79 (m), 6.78-6.71 (m), 6.71-6.66 (m), 6.67-6.58 (m), 6.58-6.53 (m), 6.49-6.32 (m), 6.32-6.28 (m), 5.26-5.20 (m), 5.04 (t), 4.80-4.67 (m), 4.10 (q), 3.42-3.28 (m), 3.27-3.17 (m), 3.17-3.05 (m), 3.05-2.91 (m), 2.82 (s), 2.53-2.40 (m), 2.01 (s), 1.64 (s), 1.41-1.21 (m), 0.96-0.82 (m). MS (m/z) 770.15 $[M+H]^+$.

Example 92

92

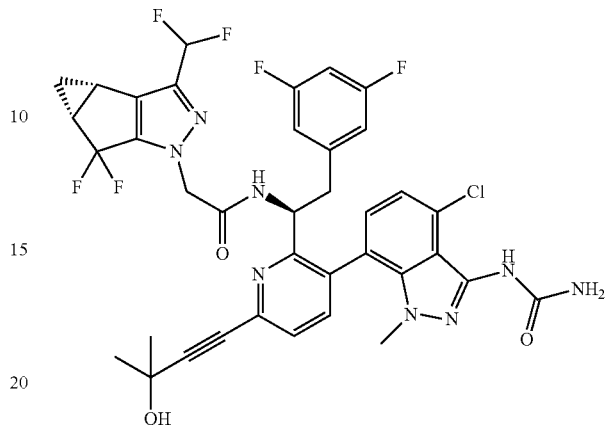

Synthesis of N—((S)-1-(3-(4-chloro-1-methyl-3-ureido-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (92)

To a solution of N—((S)-1-(3-(3-amino-4-chloro-1-methyl-H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (57) (30 mg, 0.04 mmol) in acetic acid (0.4 ml) was added a solution of potassium cyanate (3.9 mg, 0.049 mmol) in water (0.05 ml). After stirring at 50° C. for 2 h, the reaction was concentrated and purified by reverse phase HPLC to provide the title product as a mixture of atropisomers. $^1$H NMR (400 MHz, Methanol-d$_4$) δ 8.72 (dd), 7.69 (dd), 7.54 (dd), 7.22-7.10 (m), 7.04 (d), 6.88-6.52 (m), 6.47-6.32 (m), 5.31-5.22 (m), 5.03-4.92 (m), 4.76 (s), 4.72 (d), 3.28 (s), 3.18-3.10 (m), 3.04-2.94 (m), 2.94 (s), 2.53-2.40 (m), 1.64 (s), 1.46-1.25 (m), 1.12-1.05 (m), 1.05-0.99 (m). MS (m/z) 785.15 $[M+H]^+$.

Example 93

93

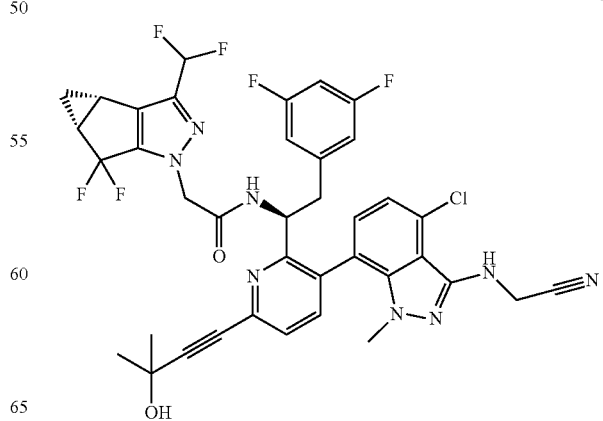

Synthesis of N—((S)-1-(3-(4-chloro-3-((cyanomethyl)amino)-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (93)

The title compound (93) was prepared as a mixture of atropisomers according to the method presented for the synthesis of compound (91D) of Example 91 utilizing bromoacetonitrile in place of diethyl sulfate during the synthesis of compound (91B). $^1$H NMR (400 MHz, Methanol-$d_4$) δ 8.69 (d), 8.63-8.55 (m), 7.67 (dd), 7.56-7.48 (m), 7.11 (d), 6.99 (d), 6.86 (dd), 6.78-6.72 (m), 6.70 (d), 6.67-6.60 (m), 6.57 (d), 6.45-6.31 (m), 5.35-5.28 (m), 5.08-5.00 (m), 4.77 (s), 4.73 (s), 4.35-4.23 (m), 3.20 (s), 3.12 (dd), 3.05-2.92 (m), 2.89 (s), 2.54-2.39 (m), 1.64 (s), 1.44-1.30 (m), 1.12-1.07 (m), 1.07-1.01 (m). MS (m/z) 828.18 [M+H]$^+$.

Example 94

94

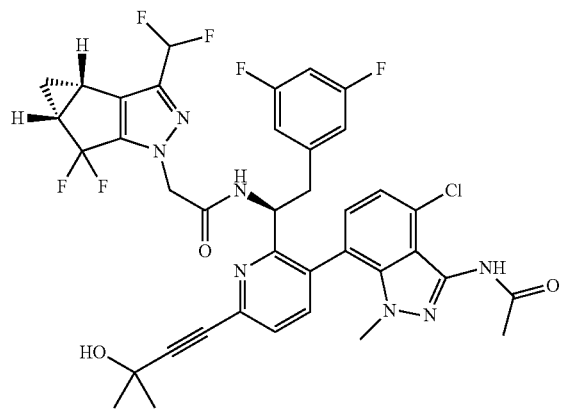

Synthesis of N—((S)-1-(3-(3-acetamido-4-chloro-1-methyl-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (94)

The title compound (94) was prepared as a mixture of atropisomers according to the method presented for the synthesis of compound 84 of Example 84 utilizing acetyl chloride. 1H NMR (Chloroform-d) δ: 7.63-7.57 (m), 7.54-7.48 (m), 7.25-7.22 (m), 6.97 (d), 6.70 (t), 6.70-6.63 (m), 6.48 (t), 6.24 (d), 6.19 (d), 6.15 (d), 5.63-5.55 (m), 4.99 (q), 4.76 (d), 4.70 (d), 3.29 (s), 3.09-2.94 (m), 2.55-2.40 (m), 2.30 (d), 1.72 (d), 1.41 (q), 1.21-1.12 (m). MS (m/z) 784.9 [M+H]$^+$.

Example 95

95

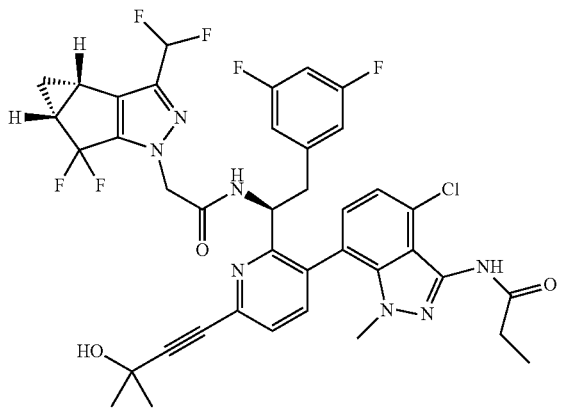

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)propionamide (95)

The title compound (95) was prepared as a mixture of atropisomers according to the method presented for the synthesis of compound 84 of Example 84 utilizing propionyl chloride. $^1$H NMR (Chloroform-d) δ: 7.62-7.43 (m), 7.35-7.17 (m), 6.95 (d), 6.71 (t), 6.69-6.62 (m), 6.53-6.44 (m), 6.30-6.16 (m), 6.12 (d), 5.61-5.50 (m), 4.96 (q), 4.75 (d), 4.70 (d), 3.28 (s), 3.07 (s), 2.95 (d), 2.56 (qd), 2.61-2.36 (m), 1.71 (s), 1.41 (q), 1.36-1.21 (m), 1.20-1.08 (m). MS (m/z) 798.9 [M+H]$^+$.

Example 96

96

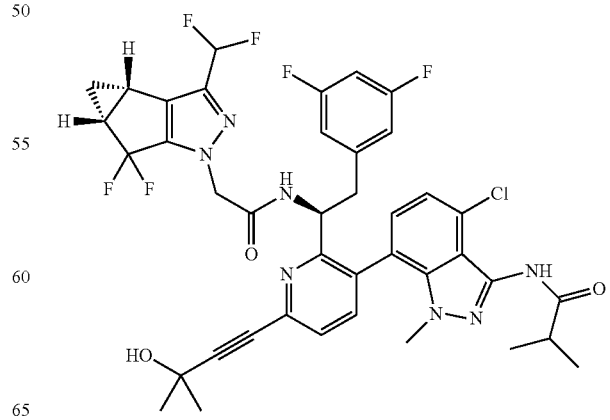

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)isobutyramide (96)

The title compound (96) was prepared as a mixture of atropisomers according to the method presented for the synthesis of compound 84 of Example 84 utilizing isobutyryl chloride. $^1$H NMR (Chloroform-d) δ: 7.59-7.52 (m), 7.48 (dd), 7.31-7.23 (m), 7.22 (s), 6.94 (d), 6.70 (t), 6.69-6.61 (m), 6.48 (d), 6.22 (d), 6.18 (d), 6.11 (d), 5.56 (d), 4.96 (q), 4.75 (d), 4.69 (d), 3.28 (s), 3.15 (s), 3.09 (s), 2.96 (d), 2.72 (s), 2.55-2.40 (m), 1.71 (s), 1.41 (q), 1.33 (s), 1.21-1.13 (m). MS (m/z) 813.1 [M+H]$^+$.

Example 97

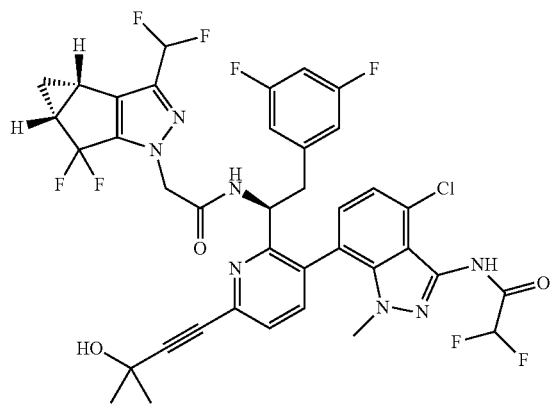

97

Synthesis of N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)-2,2-difluoroacetamide (97)

The title compound (97) was prepared as a mixture of atropisomers according to the method presented for the synthesis of compound 84 of Example 84 utilizing 2,2-difluoroacetic anhydride. $^1$H NMR (Chloroform-d) δ: 8.80 (d), 7.63-7.55 (m), 7.54-7.46 (m), 7.43-7.30 (m), 7.30-7.23 (m), 6.99 (d), 6.71 (t), 6.70-6.63 (m), 6.53-6.46 (m), 6.25 (d), 6.19 (d), 6.17-6.11 (m), 6.04-5.95 (m), 5.65-5.53 (m), 4.98 (q), 4.79-4.73 (m), 4.69 (d), 3.33 (s), 3.12 (s), 3.07-2.94 (m), 2.60-2.34 (m), 1.71 (s), 1.41 (q), 1.26 (s), 1.23-1.12 (m) MS (m/z) 820.9 [M+H]$^+$.

Example 98

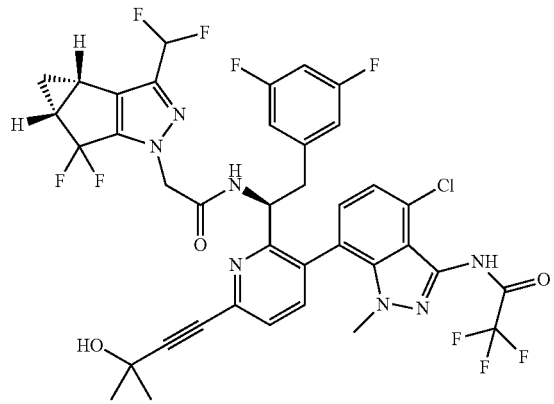

98

Synthesis N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)-2,2,2-trifluoroacetamide (98)

The title compound (98) was prepared as a mixture of atropisomers according to the method presented for the synthesis of compound 84 of Example 84 utilizing 2,2,2-trifluoroacetic anhydride. $^1$H NMR (Chloroform-d) δ: 8.77-8.72 (m), 8.69-8.63 (m), 7.56-7.43 (m), 7.31-7.19 (m), 7.18-7.06 (m), 7.01-6.95 (m), 6.71 (t), 6.70-6.61 (m), 6.52-6.45 (m), 6.24-6.16 (m), 6.11 (d), 5.60-5.52 (m), 4.93 (q), 4.75 (d), 4.69 (d), 3.32 (s), 3.10 (s), 3.01-2.91 (m), 2.57-2.38 (m), 2.23-2.02 (m), 1.72 (s), 1.47-1.37 (m), 1.25 (s), 1.22-1.12 (m). MS (m/z) 838.8 [M+H]$^+$.

Example 99

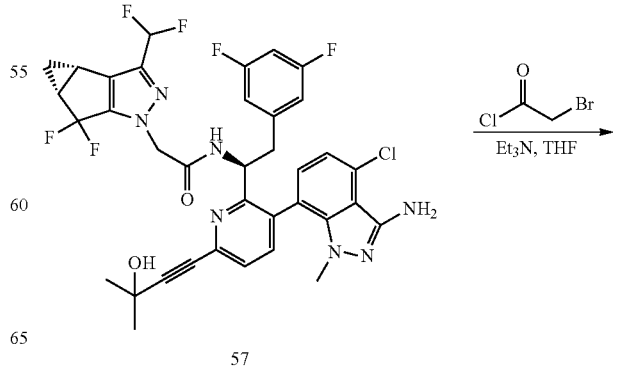

57

-continued

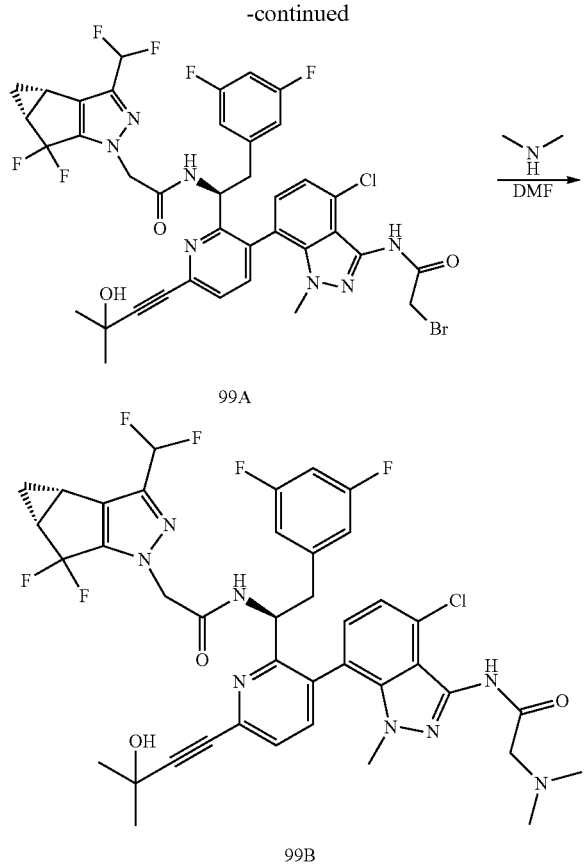

99A

99B

Synthesis of 2-bromo-N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)acetamide (99A)

To the reaction vial containing 57 (32 mg, 0.043 mmol) in THF (0.25 mL) was added 2-bromoacetyl chloride (7 mg, 0.047 mmol), and triethylamine (0.009 mL, 0.06 mmol). The reaction mixture was stirred at room temperature until the majority of 57 was consumed. The reaction mixture was concentrated in vacuo and telescoped to the next reaction. MS (m/z) 862.1 [M+H]⁺.

Synthesis of N—((S)-1-(3-(4-chloro-3-(2-(dimethylamino)acetamido)-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (99B)

The crude 99A material was dissolved in DMF (0.1 mL) and treated with excess dimethylamine at room temperature for 30 min. The reaction mixture was then acidified with TFA and purified by reverse phase HPLC to provide the title compound 99B as a mixture of atropisomers. ¹H NMR (400 MHz, cd₃od) δ 8.90-8.69 (m, 1H), 7.73-7.65 (m, 1H), 7.59-7.49 (m, 1H), 7.23-7.06 (m, 1H), 6.89-6.59 (m, 2H), 6.53-6.29 (m, 3H), 5.03-4.93 (m, 1H), 4.80-4.68 (m, 2H), 4.28 (s, 2H), 3.38-2.96 (m, 9H), 2.91-2.73 (m, 2H), 2.61-2.33 (m, 2H), 1.64 (s, 6H), 1.43-1.28 (m, 1H), 1.15-0.98 (m, 1H). MS (m/z) 829.2 [M+H]⁺.

Example 100

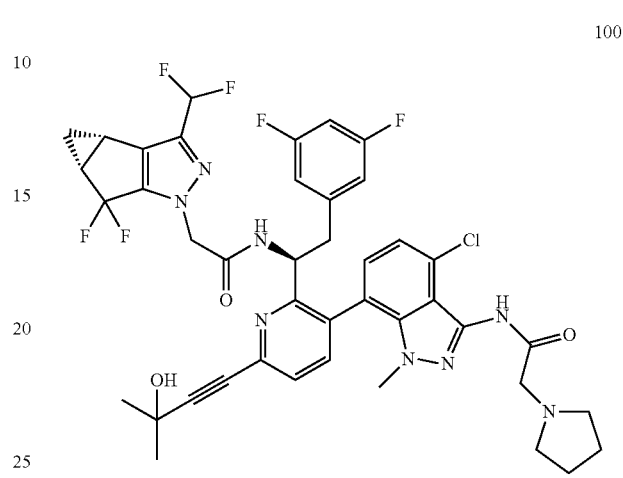

100

Synthesis of N—((S)-1-(3-(4-chloro-1-methyl-3-(2-(pyrrolidin-1-yl)acetamido)-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (100)

The title compound (100) was prepared as a mixture of atropisomers according to the method presented for the synthesis of compound 99B of Example 99 utilizing pyrrolidine. 1H NMR (400 MHz, cd₃od) δ 8.87-8.69 (m), 7.73-7.68 (m), 7.59-7.49 (m), 7.20 (s), 7.10 (s), 6.90-6.69 (m), 6.45-6.32 (m), 5.30-5.25 (m), 5.03-4.98 (m), 4.79-4.63 (m), 4.37 (s), 3.82-3.64 (m), 3.35 (s), 3.24-3.19 (m), 3.01 (s), 2.51-2.43 (m, 2H), 2.30-2.13 (m), 1.64 (d), 1.42-1.25 (m), 1.10 (s), 1.00 (s). MS (m/z) 854.4 [M+H]⁺.

Example 101

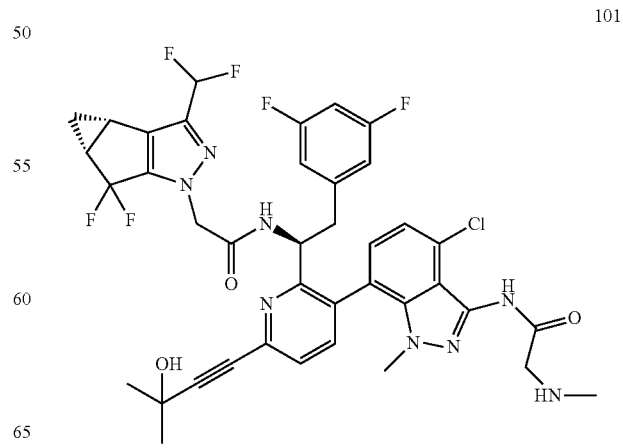

101

Synthesis of N—((S)-1-(3-(4-chloro-1-methyl-3-(2-(methylamino)acetamido)-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (101)

The title compound (101) was prepared as a mixture of atropisomers according to the method presented for the synthesis of compound 99B of Example 99 utilizing methylamine. 1H NMR (400 MHz, cd₃od) δ 8.85-8.65 (m), 7.79-7.62 (m), 7.60-7.50 (m), 7.21-7.15 (m), 7.13-7.09 (m), 6.91-6.50 (m), 6.45-6.23 (m), 5.32-5.21 (m), 5.00-4.98 (m), 4.82-4.68 (m), 4.20-4.15 (s), 4.14-4.08 (s), 3.35 (s), 3.13-3.08 (m), 3.03-2.98 (m), 2.81 (s), 2.48-2.43 (m), 1.64 (d), 1.50-1.29 (m), 1.12-1.05 (m), 1.03-0.98 (m). MS (m/z) 814.2 [M+H]⁺.

Example 102

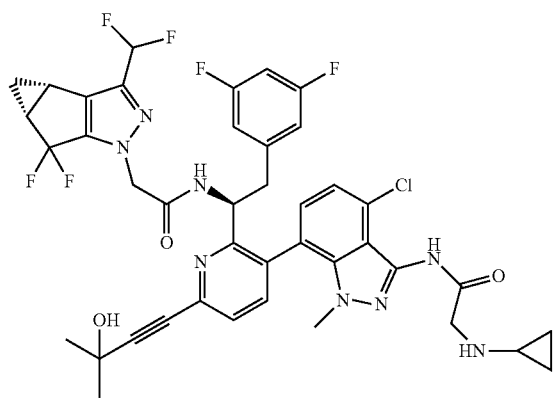

102

Synthesis of N—((S)-1-(3-(4-chloro-3-(2-(cyclopropylamino)acetamido)-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (102)

The title compound (102) was prepared as a mixture of atropisomers according to the method presented for the synthesis of compound 99B of Example 99 utilizing cyclopropylamine. ¹H NMR (400 MHz, cd₃od) δ 8.74-8.69 (m), 7.74-7.65 (m), 7.59-7.49 (m), 7.19 (s), 7.12 (s) 6.91-6.53 (m), 6.38 (m), 5.35-5.20 (m), 5.01-4.94 (m), 4.79-4.64 (m), 4.21 (s), 3.35 (s), 3.03-2.98 (m), 2.91-2.86 (m), 2.53-2.38 (m), 1.64 (s), 1.45-1.36 (m), 1.11-0.70 (m). MS (m/z) 840.2 [M+H]⁺.

Example 103

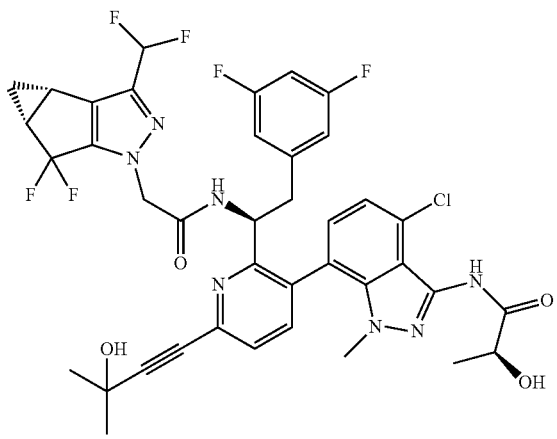

103

Synthesis of (S)—N-(4-chloro-7-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-1-methyl-1H-indazol-3-yl)-2-hydroxypropanamide (103)

The title compound (103) was prepared as a mixture of atropisomers according to the method presented for the synthesis of compound 84 of Example 84 utilizing (S)-1-chloro-1-oxopropan-2-yl acetate. ¹H NMR (400 MHz, cd₃od) δ 8.72-8.64 (m), 7.70 (dd), 7.54 (dd), 7.22-7.12 (m), 7.07 (d), 6.87-6.66 (m), 6.50-6.36 (m), 5.30-5.25 9 (m), 4.99 (t), 4.75 (d), 4.68 (s), 4.38-4.28 (m), 3.33 (s), 3.26-3.12 (m)), 3.04-2.93 (m), 2.52-2.38 (m), 1.64 (d), 1.50 (dd), 1.43-1.31 (m), 1.10-1.05 (m), 1.04-0.98 (m). MS (m/z) 815.2 [M+H]⁺.

Example 104

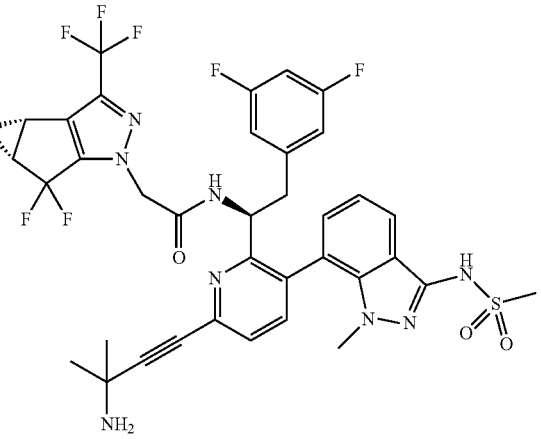

104

309

Synthesis of N—((S)-1-(6-(3-amino-3-methylbut-1-yn-1-yl)-3-(1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (104)

The title compound (104) was prepared as a mixture of atropisomers according to the method presented for the synthesis of compound (61) of Example 61 utilizing 2-methylbut-3-yn-2-amine. $^1$H NMR (400 MHz, Methanol-d4) δ 8.71 (d), 7.89-7.81 (m), 7.78 (t), 7.63 (dd), 7.27 (dd), 7.20 (dd), 7.10 (dd), 6.79-6.71 (m), 6.68-6.58 (m), 6.52 (dd), 6.40-6.27 (m), 5.33-5.24 (m), 5.02 (q), 4.80-4.68 (m), 3.32 (s), 3.28-3.20 (m), 3.18 (s), 3.16-3.10 (m), 3.04-2.91 (m), 2.58-2.40 (m), 1.83 (s), 1.47-1.36 (m), 1.15-1.10 (m), 1.08-1.02 (m). MS (m/z) 803.13 [M+H]$^+$.

Example 105

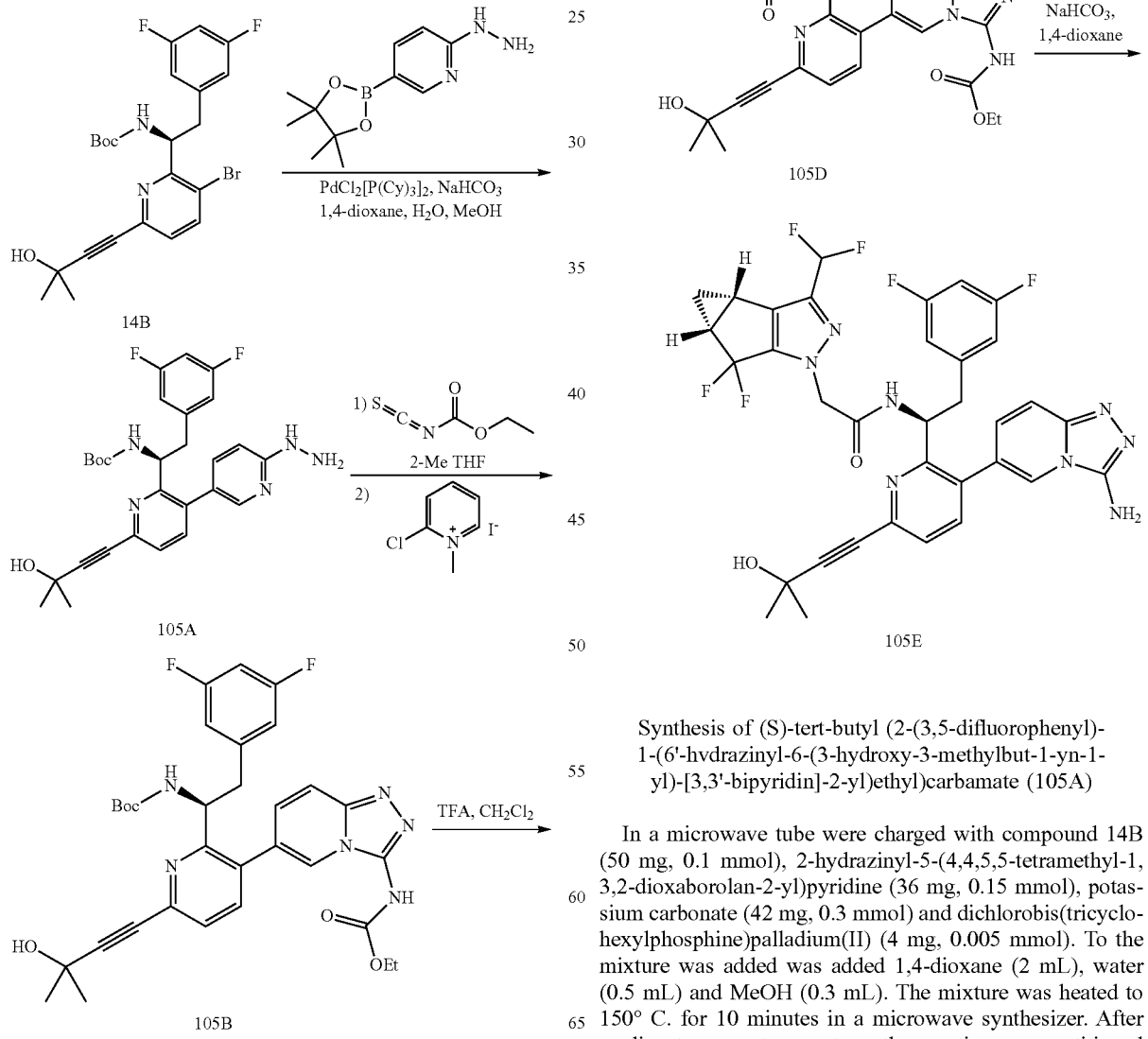

Synthesis of (S)-tert-butyl (2-(3,5-difluorophenyl)-1-(6'-hydrazinyl-6-(3-hydroxy-3-methylbut-1-yn-1-yl)-[3,3'-bipyridin]-2-yl)ethyl)carbamate (105A)

In a microwave tube were charged with compound 14B (50 mg, 0.1 mmol), 2-hydrazinyl-5-(4,4,5,5-tetramethyl-1,3,2-dioxaborolan-2-yl)pyridine (36 mg, 0.15 mmol), potassium carbonate (42 mg, 0.3 mmol) and dichlorobis(tricyclohexylphosphine)palladium(II) (4 mg, 0.005 mmol). To the mixture was added was added 1,4-dioxane (2 mL), water (0.5 mL) and MeOH (0.3 mL). The mixture was heated to 150° C. for 10 minutes in a microwave synthesizer. After cooling to room temperature, the reaction was partitioned between EtOAc and water. The organic layer was separated

311 and washed with brine, then dried over MgSO$_4$, filtered and concentrated. The residue was purified by silica gel chromatography to afford the title compound 105A. MS (m/z): 524.10 [M+H]$^+$;

Synthesis of Boc-(S)-ethyl (6-(2-(1-amino-2-(3,5-difluorophenyl)ethyl)-6-(3-hydroxy-3-methylbut-1-yn-1-yl)pyridin-3-yl)-[1,2,4]triazolo[4,3-a]pyridin-3-yl)carbamate (105B)

To a reaction mixture of compound 105A (28 mg, 0.053 mmol) in 0.5 mL 2-methyltetrahydrofuran was added ethoxycarbonyl isothiocyanate (7 mg, 0.053 mmol) and the reaction was allowed to stir at room temperature for 1 min. The solvent was removed in vacuo. The residue was dissolved in 0.5 mL of methylene chloride and to it was added 2-chloro-1-methylpyridinium iodide (12 mg, 0.046 mmol) followed by triethylamine (0.08 mL, 0.057 mmol). The reaction mixture was stirred at room temperature for 1 min. The solvent was removed in vacuo and the residue was purified by silica gel chromatography to afford the title compound 105B. MS (m/z): 621.07 [M+H]$^+$.

Synthesis of (S)-ethyl (6-(2-(1-amino-2-(3,5-difluorophenyl)ethyl)-6-(3-hydroxy-3-methylbut-1-yn-1-yl)pyridin-3-yl)-[1,2,4]triazolo[4,3-a]pyridin-3-yl)carbamate (105C)

Compound 105B (14 mg, 0.023 mmol) was dissolved in 1 mL of methylene chloride and to it was added 0.15 mL of TFA. The reaction mixture was stirred at room temperature for 40 minutes. The solvent was removed to afford the title compound 105C as a TFA salt. MS (m/z): 521.09 [M+H]$^+$

312

Synthesis of ethyl (6-(2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-6-(3-hydroxy-3-methylbut-1-yn-1-yl)pyridin-3-yl)-[1,2,4]triazolo[4,3-a]pyridin-3-yl)carbamate (105D)

The title compound (105D) was prepared according to the method presented for the synthesis of compound 37E of Example 37 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and compound 105C. MS (m/z) 767.18 [M+H]$^+$.

Synthesis of N—((S)-1-(3-(3-amino-[1,2,4]triazolo[4,3-a]pyridin-6-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (105E)

Compound 105D (15.3 mg, 0.05 mmol) was dissolved in 2 mL of 1,4-dioxane and to it was added 0.5 mL of 1M sodium bicarbonate aqueous solution. The reaction mixture was heated in microwave for 1 hour at 140° C. The solvent was removed and the residue was purified by RP-HPLC to afford the title compound 105E. $^1$H NMR (400 MHz, Methanol-d$_4$): δ 8.08 (s), 7.81-7.60 (m), 7.57-7.38 (m), 6.77-6.70 (m), 6.61 (t), 6.52-6.35 (m), 5.36 (t), 4.81 (d), 3.15 (d), 2.59-2.27 (m), 1.63 (s), 1.48-1.20 (m), 1.10-0.78 (m). MS (m/z): 695.30 [M+H]$^+$.

Example 106

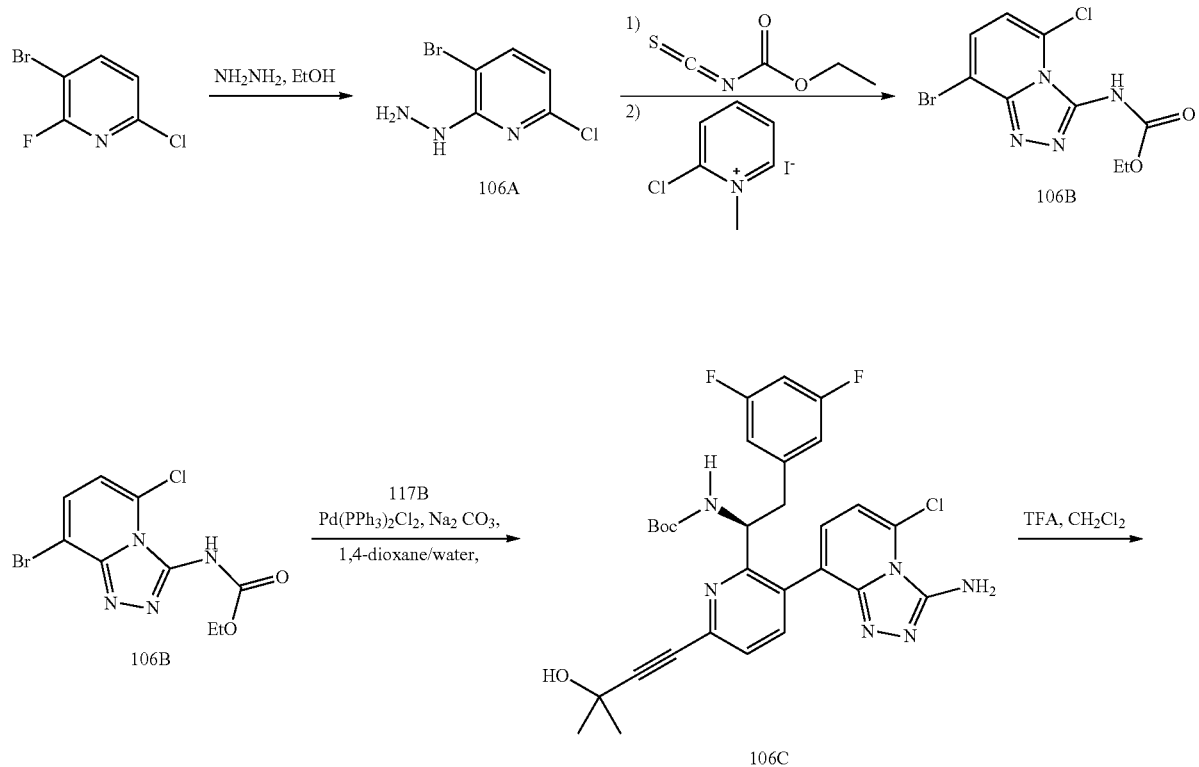

-continued

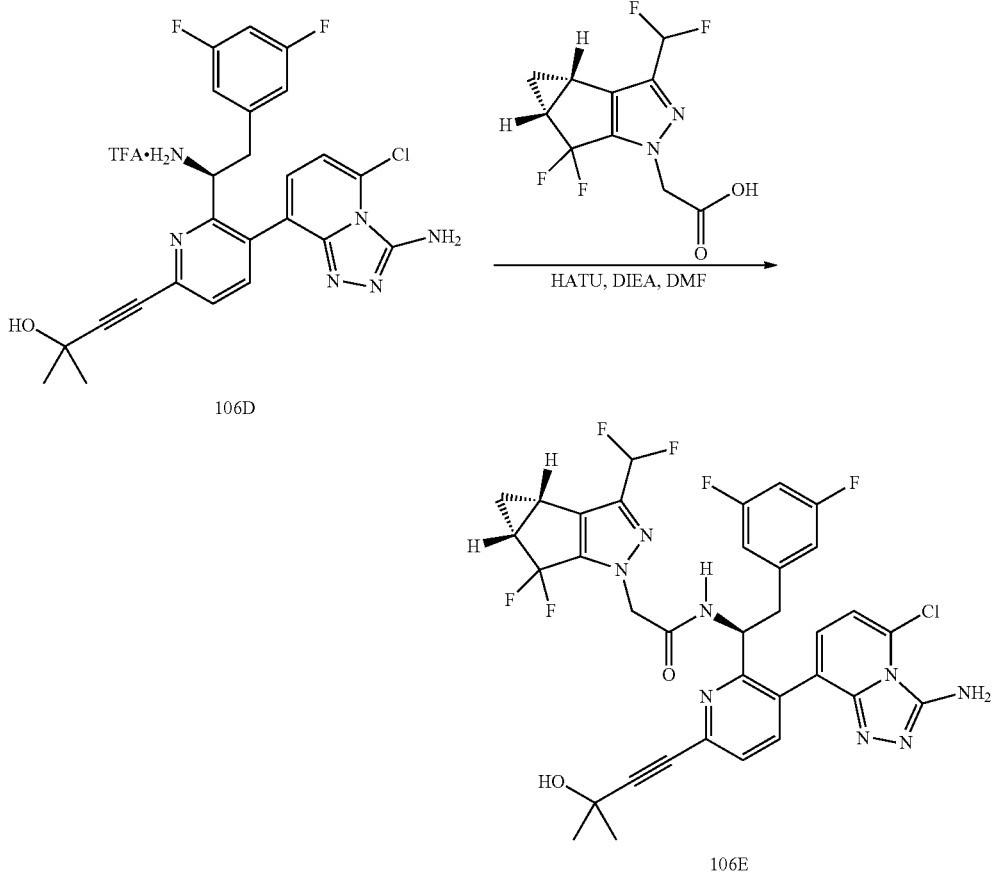

106D

106E

Synthesis of 3-bromo-6-chloro-2-hydrazinylpyridine (106A)

To a mixture of 3-bromo-6-chloro-2-fluoropyridine (6 g, 28.5 mmol) in 200 mL ethanol was added 14 mL of hydrazine monohydrate. The reaction mixture was stir at room temperature for overnight and then removed most of the solvent. The precipitate was collected by vacuum filtration to afford the title compound 106A. MS (m/z): 223.97 [M+H]$^+$.

Synthesis of ethyl (8-bromo-5-chloro-[1,2,4]triazolo[4,3-a]pyridin-3-yl)carbamate (106B)

The title compound (106B) was prepared according to the method presented for the synthesis of compound 105B of Example 105 utilizing compound 106A. MS (m/z) 321.01 [M+H]$^+$.

Synthesis of (S)-tert-butyl (1-(3-(3-amino-5-chloro-[1,2,4]triazolo[4,3-a]pyridin-8-yl)-6-(3-hydroxy-3-methylbut-1-yn-1-yl)pyridin-2-yl)-2-(3,5-difluorophenyl)ethyl)carbamate (106C)

In a microwave tube were charged with compound 117B (48 mg, 0.1 mmol), compound 106B (40 mg, 0.13 mmol), sodium carbonate (33 mg, 0.03 mmol) and PdCl$_2$[PPh$_3$]2 (8 mg, 0.01 mmol). To the mixture was added 2.5 mL of 1,4-dioxane and 0.5 mL of water. The mixture was heated to 170° C. for 20 minutes in a microwave synthesizer. After cooling to room temperature, the reaction was partitioned between EtOAc and water. The organic layer was separated and washed with brine, then dried over MgSO$_4$, filtered and concentrated. The residue was purified by reverse phase HPLC to afford the title compound 106C. MS (m/z): 583.01 [M+H]$^+$

Synthesis of (S)-4-(6-(1-amino-2-(3,5-difluorophenyl)ethyl)-5-(3-amino-5-chloro-[1,2,4]triazolo[4,3-a]pyridin-8-yl)pyridin-2-yl)-2-methylbut-3-yn-2-ol (106D)

The title compound (106D) was prepared according to the method presented for the synthesis of compound 105C of Example 105 utilizing compound 106C. MS (m/z) 483.28 [M+H]$^+$.

Synthesis of N—((S)-1-(3-(3-amino-5-chloro-[1,2,4]triazolo[4,3-a]pyridin-8-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (106E)

The title compound (106E) was prepared according to the method presented for the synthesis of compound 37E of Example 37 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and compound 106D.
$^1$H NMR (400 MHz, Methanol-d$_4$): δ 8.79 (d), 7.71 (d), 7.52

(d), 7.04 (d), 6.69-6.63 (m), 6.68 (t), 6.59-6.36 (m), 5.41-5.12 (m), 4.75-4.48 (m), 3.25-2.97 (m), 2.55-2.35 (m), 1.62 (s), 1.38 (q), 1.12-0.96 (m). MS (m/z): 729.24 [M+H]+

5.07 (m), 4.83-4.74 (m), 3.24 (dd), 3.12-2.88 (m), 2.75 (s), 2.55-2.42 (m), 1.64 (s), 1.45-1.35 (m), 1.14-1.06 (m). MS (m/z) 727.1 [M+H]+.

Example 107

Example 108

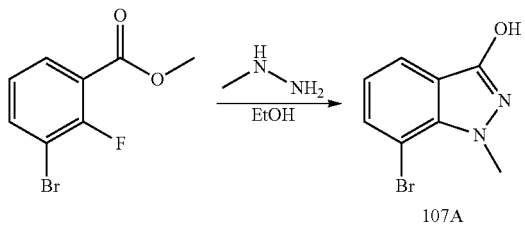

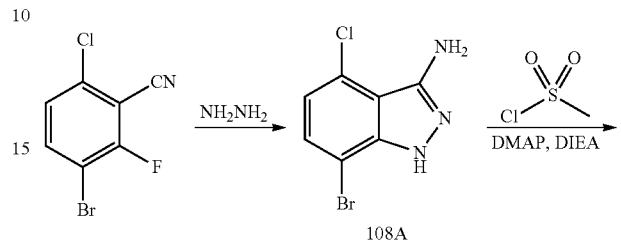

Synthesis of 7-bromo-1-methyl-1H-indazol-3-ol (107A)

To the reaction vial containing methyl 3-bromo-2-fluorobenzoate (1 g, 4.5 mmol) in ethanol (5 mL) was added methylhydrazine (0.29 mL, 6 mmol). The reaction mixture was sealed and heated to 125° C. overnight. Upon cooling, the reaction mixture was treated with water and the resulting solid was collected by filtration to give the title product 107A. MS (m/z) 229.1 [M+2H]+.

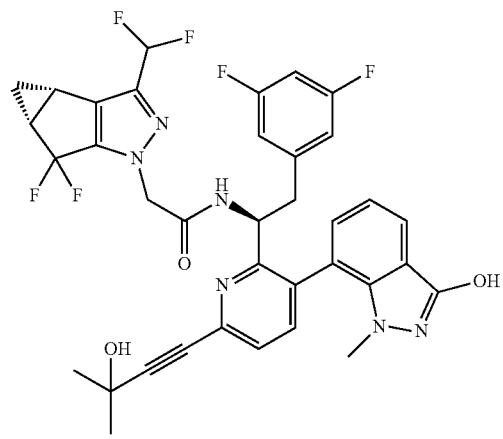

Synthesis of 7-bromo-4-chloro-1H-indazol-3-amine (108A)

In a microwave vial a solution of 3-bromo-2-fluorobenzonitrile (1g, 4.26 mmol) ethanol (5 mL) was treated with hydrazine (0.85 mL, 17 mmol), sealed, and heated to 120° C. in a microwave reactor for 35 minutes. The reaction was concentrated in vacuo and the crude product dissolved with EtOAc (30 mL) and washed with water (30 mL), then 2M NaCl (aq, 30 mL). The organics were dried with Na$_2$SO$_4$, filtered, and concentrated. Product was purified by silica chromatography to give the title compound. MS (m/z) 247.1 [M+H]+.

Synthesis of N-(7-bromo-4-chloro-1H-indazol-3-yl) methanesulfonamide (108B)

To a stirred solution of 108A (161 mg, 0.65 mmol), 4-dimethylaminopyridine (4 mg, 0.03 mmol), and N,N-diisopropylethylamine (0.28 mL, 1.6 mmol) in DCM (5 ml) at, 0° C. was added drop wise methanesulfonyl chloride (156 mg, 1.3 mmol). The ice bath was removed immediately after the addition and the reaction was warmed to room temperature and stirred for 2 h. The reaction was washed with water, dried with Na$_2$SO$_4$, filtered, and concentrated. The crude product dissolved with EtOH (10 mL) and treated with 8N NaOH (3.3 ml). The reaction mixture was heated at 60° C. for 0.5 h. The ethanol was removed under vacuum, pH to ~2 with 1.0 HCl then, extracted with EtOAc. The organics were dried with Na$_2$SO$_4$, filtered, and concentrated. The product was purified by silica chromatography to give the title compound. MS (m/z) 325.9 [M+H]+.

Synthesis of 2-((3bS,4aR)-3-(difluoromethyl)-5,5-difluoro-3b,4,4a,5-tetrahydro-1H-cyclopropa[3,4] cyclopenta[1,2-c]pyrazol-1-yl)-N—((S)-2-(3,5-difluorophenyl)-1-(6-(3-hydroxy-3-methylbut-1-yn-1-yl)-3-(1-methyl-3-oxo-2,3-dihydro-1H-indazol-7-yl) pyridin-2-yl)ethyl)acetamide (107B)

The title compound (107B) was prepared as a mixture of atropisomers according to the method presented for the synthesis of compound 117F of Example 117 utilizing 107A and 117B. $^1$H NMR (400 MHz, cd$_3$od) δ 8.61 (d), 7.79-7.63 (m), 7.52 (dd), 7.28-7.21 (m), 7.12 (t), 7.02 (t), 6.76-6.67 (m), 6.66-6.54 (m), 6.40 (d), 6.34-6.27 (m), 5.26 (t), 5.17-

Example 109

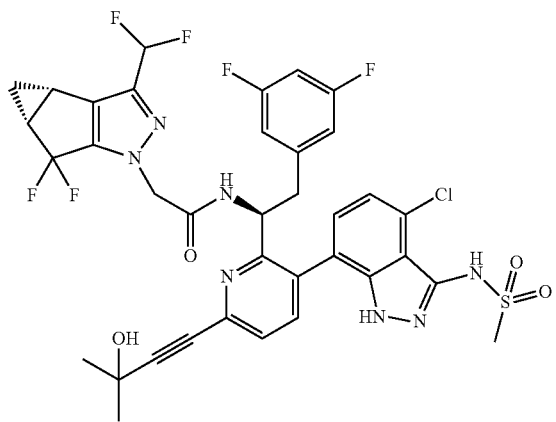

108C

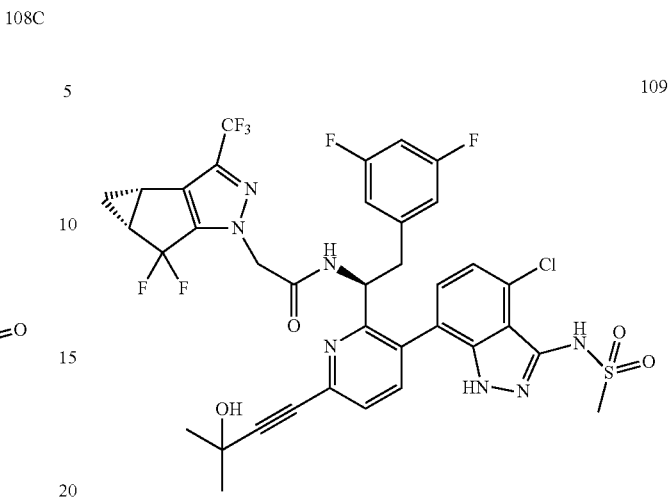

109

Synthesis of N—((S)-1-(3-(4-chloro-3-(methylsulfonamido)-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (108C)

The title compound (108C) was prepared according to the method presented for the synthesis of compound 117F of Example 117 utilizing 108B and 117B. MS (m/z) 807.1 [M+H]+. HPLC retention time 6.96 min (2-98% acetonitrile: water with 0.1% trifluoroacetic acid, 8.5 min gradient on a Phenomonex Kinetex C18 column).

Synthesis of N—((S)-1-(3-(4-chloro-3-(methylsulfonamido)-1H-indazol-7-yl)-6-(3-hydroxy-3-methylbut-1-yn-1-yl)pyridin-2-yl)-2-(3,5-difluorophenyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (109)

The title compound (109) was prepared according to the method presented for the synthesis of compound 117F of Example 117 utilizing 108B, 117B and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. MS (m/z) 824.2 [M+H]+. HPLC retention time 7.16 min (2-98% acetonitrile: water with 0.1% trifluoroacetic acid, 8.5 min gradient on a Phenomonex Kinetex C18 column).

Example 110

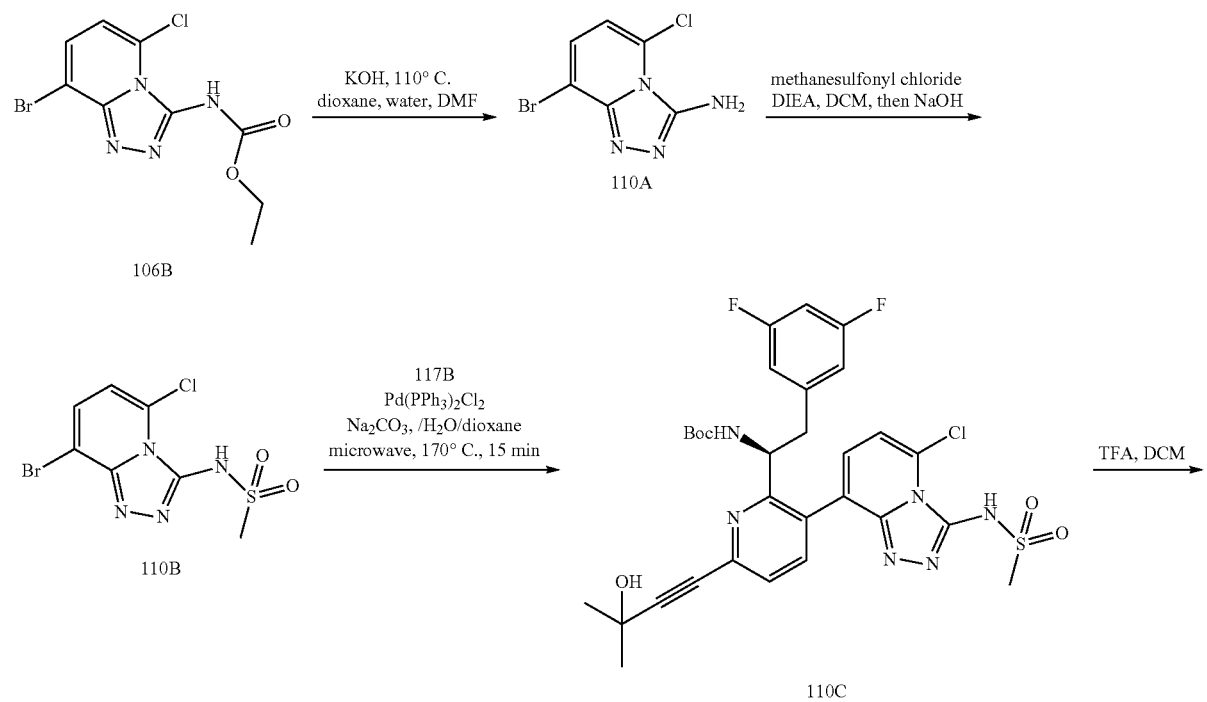

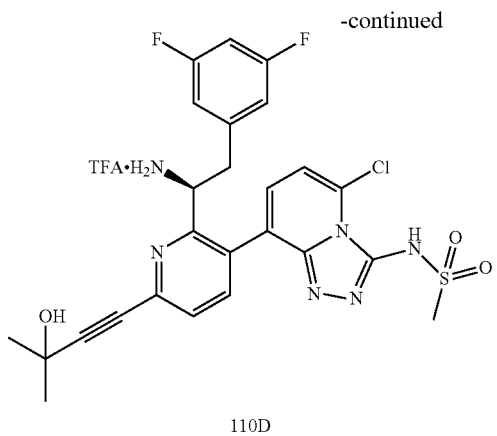

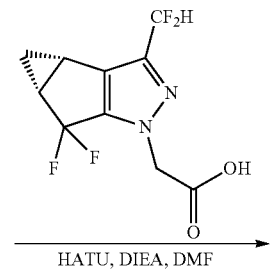

110D

110E

Synthesis of 8-bromo-5-chloro-[1,2,4]triazolo[4,3-a]pyridin-3-amine (110A)

To a solution of compound 106B (2.1 g, 6.6 mmol) in a mixture of dioxane (90 mL), water (15 mL) and DMF (9 mL) was added KOH (0.37 g, 6.6 mmol). The mixture was heated at 110° C. overnight. After removing volatiles in vacuo, the residue was purified by silica gel column to yield the title compound 110A. MS (m/z) 248.95 [M+H]$^+$.

Synthesis of N-(8-bromo-5-chloro-[1,2,4]triazolo[4,3-a]pyridin-3-yl)methanesulfonamide (110B)

To a solution of compound 110A (80 mg, 0.3 mmol) in DCM (5 mL) was added DIEA (0.42 g, 3 mmol) and methanesulfonyl chloride (0.19 g, 2 mmol). After stirred at room temperature for 5 min, the volatiles was removed in vacuo. The residue was dissolved in a mixture of THF (2 mL), MeOH (2 mL) and 2 N NaOH (2 mL) and stirred for 15 min. After removing volatiles, the residue was purified by reverse phase HPLC to yield the title compound. MS (m/z) 326.82 [M+H]$^+$.

Synthesis of (S)-tert-butyl (1-(3-(5-chloro-3-(methylsulfonamido)-[1,2,4]triazolo[4,3-a]pyridin-8-yl)-6-(3-hydroxy-3-methylbut-1-yn-1-yl)pyridin-2-yl)-2-(3,5-difluorophenyl)ethyl)carbamate (110C)

The title compound (110C) was prepared according to the method presented for the synthesis of compound 117D of Example 117 utilizing compound 110B and 117B. MS (m/z) 661.02 [M+H]$^+$.

Synthesis of (S)—N-(8-(2-(1-amino-2-(3,5-difluorophenyl)ethyl)-6-(3-hydroxy-3-methylbut-1-yn-1-yl)pyridin-3-yl)-5-chloro-[1,2,4]triazolo[4,3-a]pyridin-3-yl)methanesulfonamide TFA salt (110D)

The title compound (110D) was prepared according to the method presented for the synthesis of compound 19F of Example 19 utilizing compound 110C. MS (m/z) 561.00 [M+H]$^+$.

Synthesis of N—((S)-1-(3-(5-chloro-3-(methylsulfonamido)-[1,2,4]triazolo[4,3-a]pyridin-8-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (110E)

The title compound (110E) was prepared according to the method presented for the synthesis of compound 10A of Example 10 utilizing compound 110D and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. HPLC retention time 6.63 min (2-98% acetonitrile: water with 0.1% trifluoroacetic acid, 8.5 min gradient on a Phenomonex Kinetex C18 column 4.6×100 mm). MS (m/z) 807.16 [M+H]$^+$.

Example 111

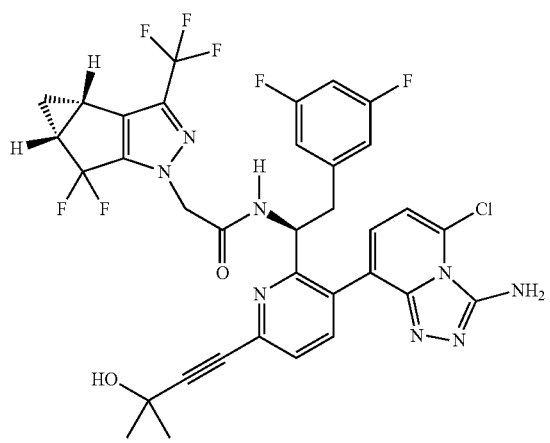

111

Synthesis of N—((S)-1-(3-(3-amino-5-chloro-[1,2,4]triazolo[4,3-a]pyridin-8-yl)-6-(3-hydroxy-3-methyl-but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (111)

The title compound (111) was prepared according to the method presented for the synthesis of compound 106E of Example 106 utilizing 2-43bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid and 106D. $^1$H NMR (400 MHz, Methanol-$d_4$): δ 8.83 (d), 7.72 (d), 7.51 (d), 6.98 (d), 6.64 (t), 6.58-6.44 (m), 5.41-5.18 (m), 4.74 (s), 3.27-2.96 (m), 2.67-2.18 (m), 1.62 (s), 1.40 (q), 1.17-0.99 (m). MS (m/z): 747.30 [M+H]$^+$

Example 112

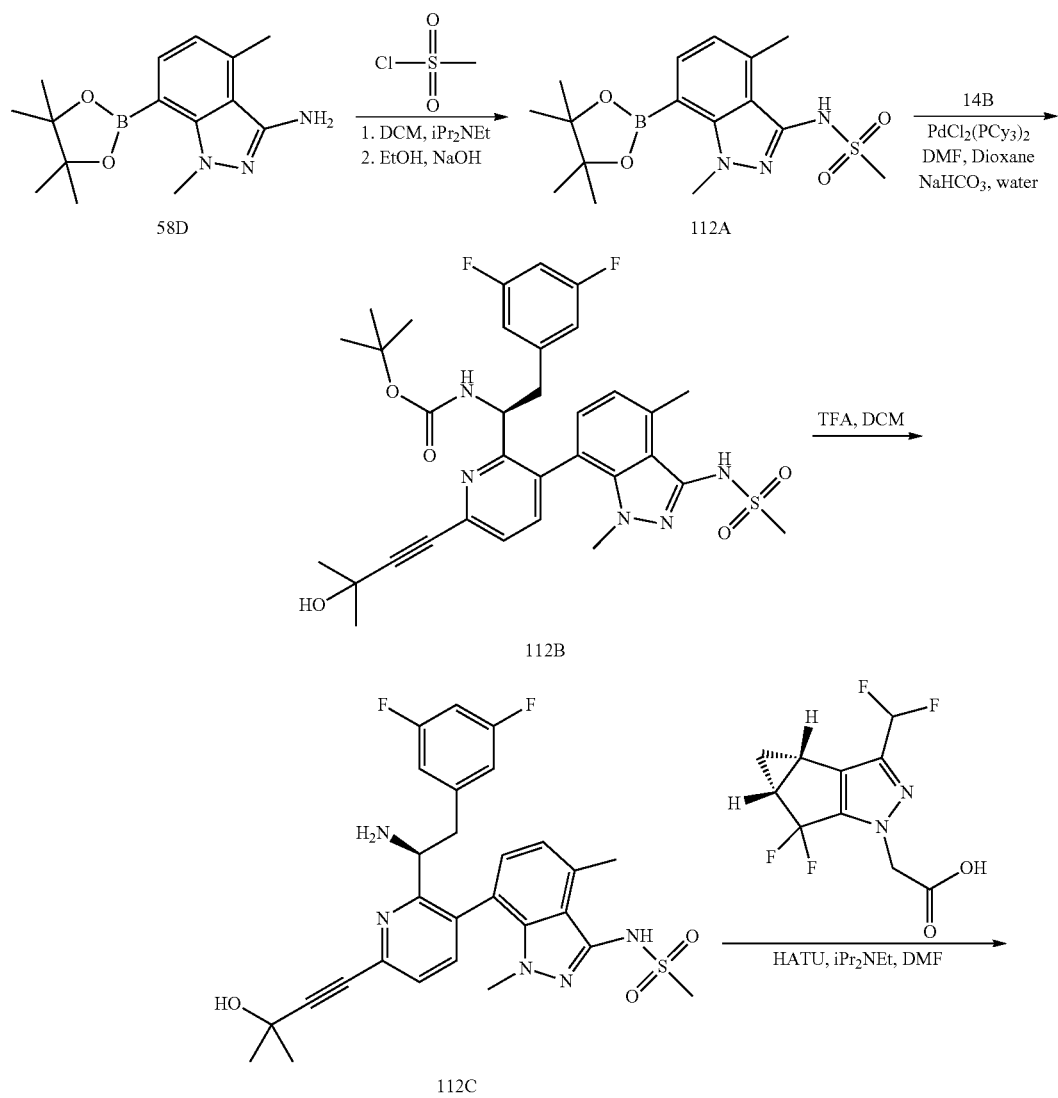

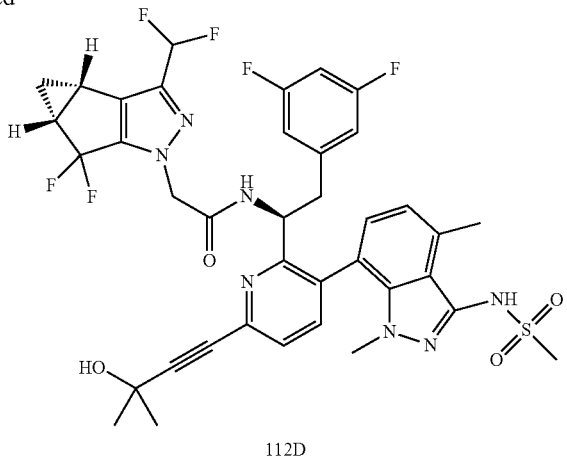

112D

Synthesis of N-(1,4-dimethyl-7-(4,4,5,5-tetramethyl-1,3,2-dioxaborolan-2-yl)-1H-indazol-3-yl)methanesulfonamide (112A)

The title compound (112A) was prepared according to the method presented for the synthesis of compound 19D of Example 19 utilizing 58D. MS (m/z) 366.1 [M+H]+.

Synthesis of (S)-tert-butyl (2-(3,5-difluorophenyl)-1-(3-(1,4-dimethyl-3-(methylsulfonamido)-1H-indazol-7-yl)-6-(3-hydroxy-3-methylbut-1-yn-1-yl)pyridin-2-yl)ethyl)carbamate (112B)

The title compound (112B) was prepared as a mixture of atropisomers according to the method presented for the synthesis of compound 19E of Example 19 utilizing 112A. MS (m/z) 654.4 [M+H]+.

Synthesis of (S)—N-(7-(2-(1-amino-2-(3,5-difluorophenyl)ethyl)-6-(3-hydroxy-3-methylbut-1-yn-1-yl)pyridin-3-yl)-1,4-dimethyl-1H-indazol-3-yl)methanesulfonamide (112C)

The title compound (112C) was prepared as a mixture of atropisomers according to the method presented for the synthesis of compound 19F of Example 19 utilizing 112B. MS (m/z) 554.2[M+H]+.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1,4-dimethyl-3-(methylsulfonamido)-1H-indazol-7-yl)-6-(3-hydroxy-3-methylbut-1-yn-1-yl)pyridin-2-yl)ethyl)acetamide (112D)

The title compound (112D) was prepared as a mixture of atropisomers according to the method presented for the synthesis of compound 10A of Example 10 utilizing 112C and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. 1H NMR (Chloroform-d) δ: 8.16-8.10 (m), 8.00 (d), 7.76 (d), 7.58 (d), 7.38 (d), 7.06 (dd), 6.86 (dd), 6.67 (t), 6.64 (dt), 6.51-6.41 (m), 6.38 (d), 6.24 (dd), 6.13 (dd), 5.62 (q), 5.06 (q), 4.78 (d), 4.69 (s), 4.35 (s), 3.32 (s), 3.29 (s), 3.11 (s), 3.10-2.91 (m), 2.87-2.78 (m), 2.55-2.34 (m), 1.71 (s), 1.45-1.34 (m), 1.20-1.07 (m) MS (m/z) 800.6 [M+H]+.

Example 113

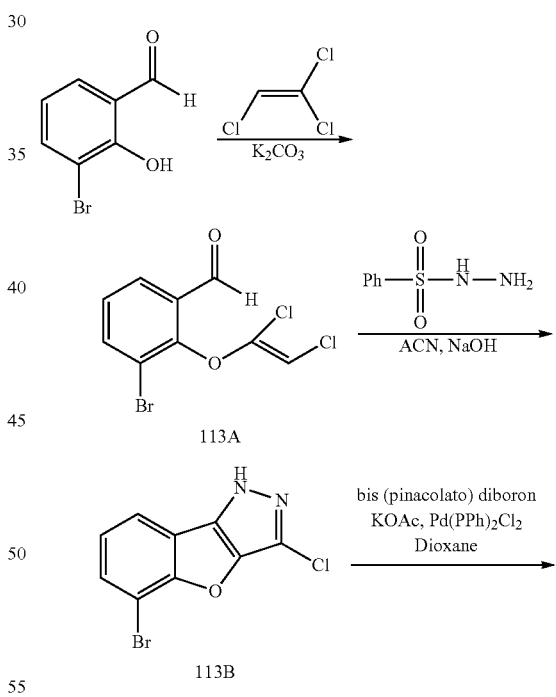

113A

113B

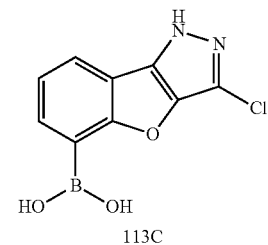

113C

Synthesis of (Z)-3-bromo-2-((1,2-dichlorovinyl) oxy)benzaldehyde (113A)

Trichloroethylene (2.68 mL, 30 mmol) was added drop wise over a period of 30 min to a solution of 3-bromo-2-hydroxybenzaldehyde (2 g, 9.9 mmol) suspended with $K_2CO_3$ (4.1 g, 30 mmol) in DMF (8 mL) at 60° C. under $N_2$. The reaction was stirred for 15 h then cooled to room temperature and partitioned between 150 mL of ethylacetate and 100 mL of water. The organic phase was washed with brine 100 mL, dried over sodium sulfate, filtered and concentrated. The crude material was purified by silica gel to give the title compound.

Synthesis of 5-bromo-3-chloro-1H-benzofuro[3,2-c] pyrazolebenzaldehyde (113B)

Benzenesulfonylhydrazide (0.57 g, 3.3 mmol) was added all at once to a solution of the 113A (0.9 g, 3.0 mmol) in acetonitrile (13 mL) at room temperature. After stirring for 2 h, aqueous 2 M NaOH (3 mL, 6 mmol) was added drop wise over 10 min. The solution was heated to 50° C. and stirred for 1 h. After cooling to room temperature, the solvents were removed under vacuum. The residue was partitioned between 20 mL EtOAc and 15 mL $H_2O$. The organic layer was dried over $MgSO_4$, filtered and solvent removed under vacuum yielding the title compound 113B.

Synthesis of (3-chloro-1H-benzofuro[3,2-c]pyrazol-5-yl)boronic acid (113C)

To 113B (200 mg, 0.73 mmol) in dioxane (5 mL) was added bis(pinacolato)diboron (262 mg, 1 mmol), potassium acetate (0.144 g, 1 mmol), and $Pd(PPh_3)_2Cl_2$ (26 mg, 0.03 mmol). The reaction mixture sealed and heated to 100° C. for 1 h. The reaction was cooled to room temperature and telescoped to the next reaction. MS (m/z) 237.1 [M+H]⁺.

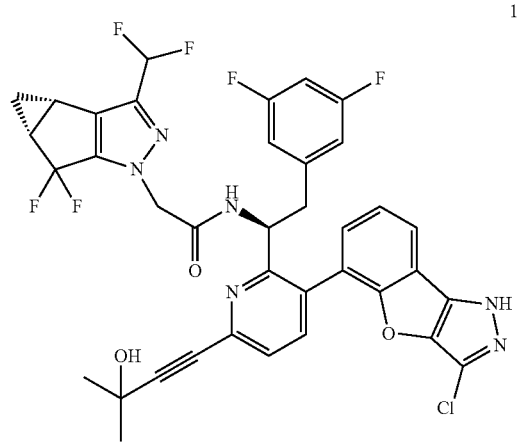

113D

Synthesis of N—((S)-1-(3-(3-chloro-1H-benzofuro [3,2-c]pyrazol-5-yl)-6-(3-hydroxy-3-methylbut-1-yn-1-yl)pyridin-2-yl)-2-(3,5-difluorophenyl)-2-((3bS,4aR)-5,5-difluoro-3-(trifluoromethyl)-3b,4,4a, 5-tetrahydro-1H-cyclopropa[3,4]cyclopenta[1,2-c] pyrazol-1-yl)acetamide (113D)

The title compound (113D) was prepared according to the method presented for the synthesis of compound 33F of Example 33 utilizing 113C and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. ¹H NMR (400 MHz, cd₃od) δ 8.88-8.60 (m, 1H), 7.80 (d), 7.70 (d), 7.51 (d), 7.35 (t), 6.44-6.17 (m), 5.50-5.27 (m), 4.80-4.74 (m), 3.12-2.72 (m), 2.55-2.48 (m), 1.64 (s), 1.45-1.35 (m), 1.14-1.06 (m). MS (m/z) 772.2 [M+H]⁺.

Example 114

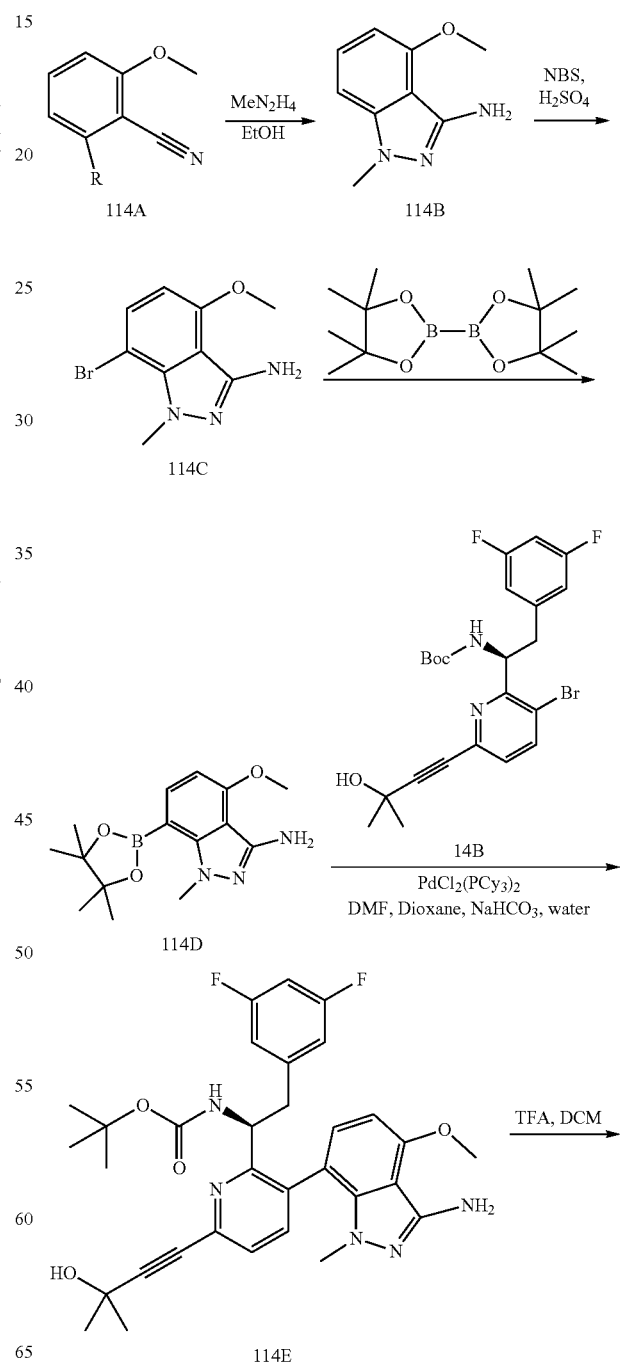

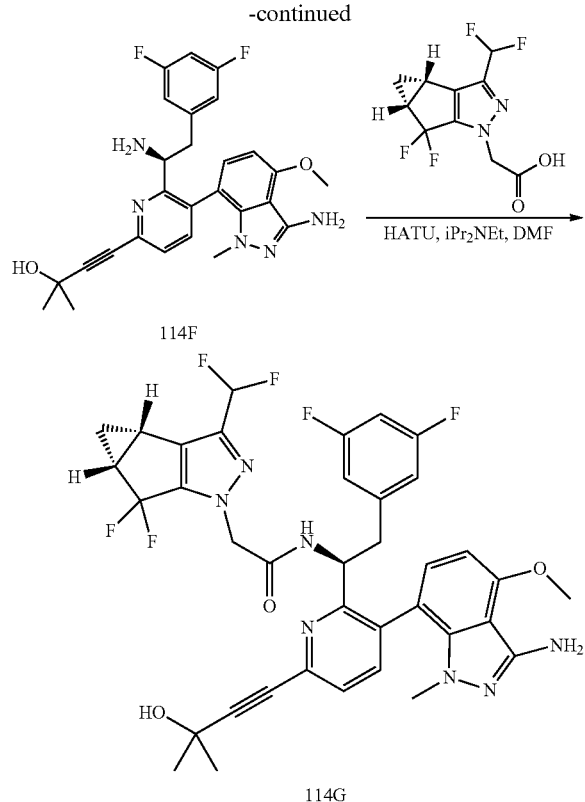

Synthesis of 4-methoxy-1-methyl-1H-indazol-3-amine (114B)

The title compound (114B) was prepared according to the method presented for the synthesis of compound 19B of Example 19 utilizing 114A. MS (m/z) 178.1 [M+H]⁺. Synthesis of 7-bromo-4-methoxy-1-methyl-1H-indazol-3-amine (114C)

A flask was charged with 114B (3.7 g, 20.9 mmol) and $H_2SO_4$ (35 mL) and cooled to 0° C. in an ice bath. Then NBS (1.9 g, 10 mmol) was added. The reaction mixture was allowed to warm to room temperature and diluted with ice water and filtered to remove solids. The mother liquor was basified with saturated $NaHCO_3$ and extracted 2× EtOAc. The organic layer was dried over sodium sulfate, concentrated, and purified by flash column chromatography to provide the title compound. MS (m/z) 256.2 [M+H]⁺.

Synthesis of 4-methoxy-1-methyl-7-(4,4,5,5-tetramethyl-1,3,2-dioxaborolan-2-yl)-1H-indazol-3-amine (114D)

The title compound (114D) was prepared according to the method presented for the synthesis of compound 19C of Example 19 utilizing 114C. MS (m/z) 304.2 [M+H]⁺. Synthesis of (S)-tert-butyl (1-(3-(3-amino-4-methoxy-1-methyl-1H-indazol-7-yl)-6-(3-hydroxy-3-methylbut-1-yn-1-yl)pyridin-2-yl)-2-(3,5-difluorophenyl)ethyl)carbamate (114E)

The title compound (114E) was prepared as a mixture of atropisomers according to the method presented for the synthesis of compound 19E of Example 19 utilizing 114D. MS (m/z) 592.1 [M+H]⁺.

Synthesis of (S)-4-(6-(1-amino-2-(3,5-difluorophenyl)ethyl)-5-(3-amino-4-methoxy-1-methyl-1H-indazol-7-yl)pyridin-2-yl)-2-methylbut-3-yn-2-ol (114F)

The title compound (114F) was prepared as a mixture of atropisomers according to the method presented for the synthesis of compound 19F of Example 19 utilizing 114E. MS (m/z) 492.2 [M+H]⁺.

Synthesis of N—((S)-1-(3-(3-amino-4-methoxy-1-methyl-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (114G)

The title compound (114G) was prepared as a mixture of atropisomers according to the method presented for the synthesis of compound 10A of Example 10 utilizing 114F and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. ¹H NMR (Methanol-d₄) δ: 8.72-8.62 (m), 7.66 (dd), 7.51 (dd), 7.19 (d), 6.87-6.65 (m), 6.65-6.51 (m), 6.44 (d), 6.40-6.30 (m), 5.34-5.26 (m), 5.11-4.99 (m), 4.79-4.71 (m), 4.02 (d), 3.28-3.22 (m), 3.14 (d), 3.07 (dd), 3.02-2.90 (m), 2.83 (s), 2.53-2.35 (m), 1.63 (d), 1.38 (q), 1.11-0.99 (m). MS (m/z) 738.6 [M+H]⁺.

Example 115

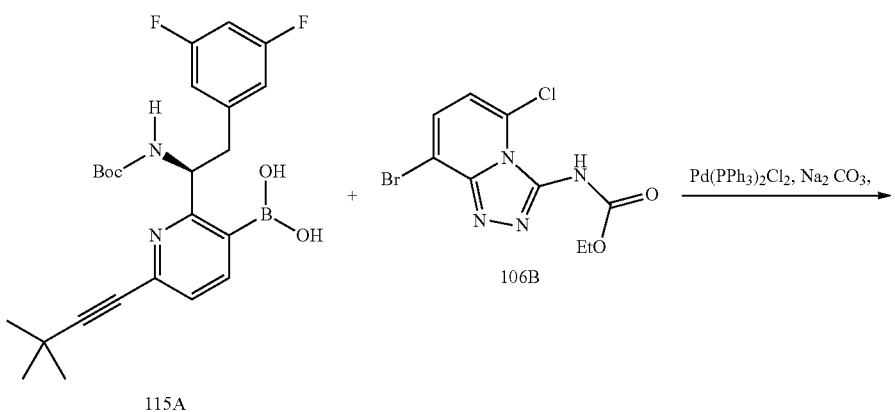

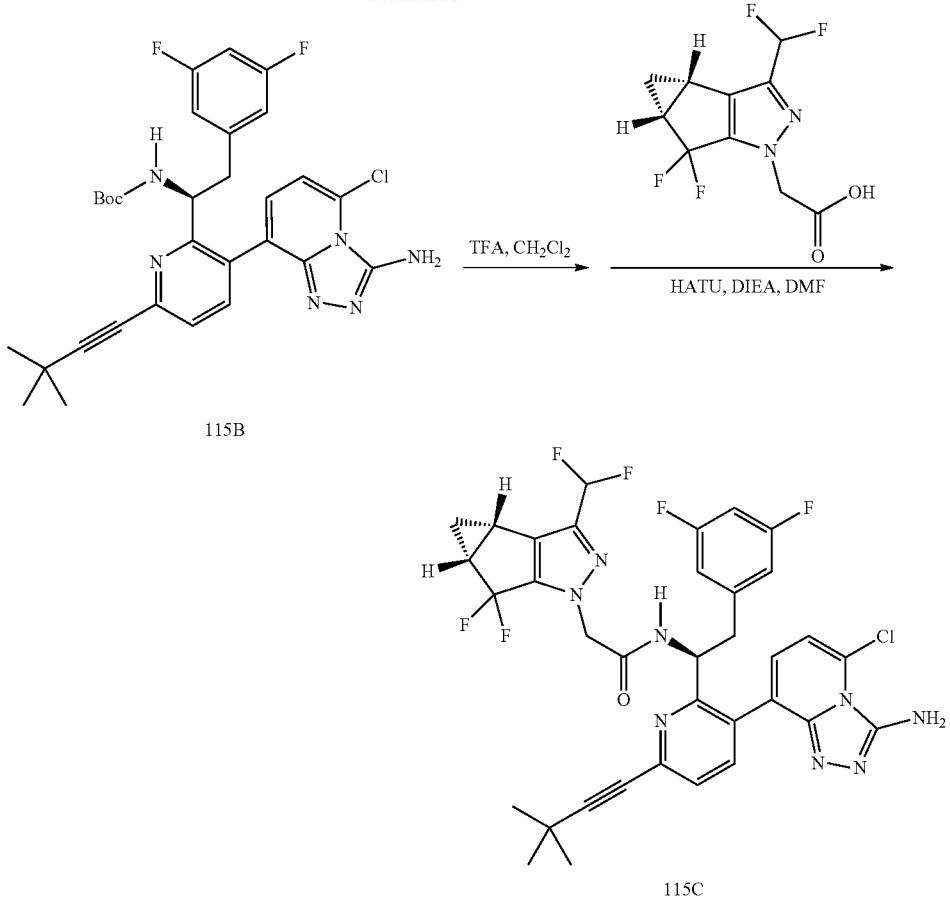

115B

115C

Synthesis of (S)-(2-(1-((tert-butoxycarbonyl)amino)-2-(3,5-difluorophenyl)ethyl)-6-(3,3-dimethylbut-1-yn-1-yl)pyridin-3-yl)boronic acid (115A)

The title compound (115A) was prepared according to the method presented for the synthesis of compound 117B of Example 117 utilizing (S)-(6-bromo-2-(1-((tert-butoxycarbonyl)amino)-2-(3,5-difluorophenyl)ethyl)pyridin-3-yl)boronic acid (117A) and 3,3-dimethylbut-1-yne. MS (m/z): 459.22 [M+H]+.

Synthesis of (S)-tert-butyl (1-(3-(3-amino-5-chloro-[1,2,4]triazolo[4,3-a]pyridin-8-yl)-6-(3,3-dimethyl-but-1-yn-1-yl)pyridin-2-yl)-2-(3,5-difluorophenyl)ethyl)carbamate (115B)

The title compound (115B) was prepared according to the method presented for the synthesis of compound 106C of Example 106 utilizing compound 1152-((3bS,4aR)-3-(A and compound 106B. MS (m/z): 581.14 [M+H]+.

Synthesis of N—((S)-1-(3-(3-amino-5-chloro-[1,2,4]triazolo[4,3-a]pyridin-8-yl)-6-(3,3-dimethylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (115C)

The title compound (115C) was prepared according to the method presented for the synthesis of compound 37E of Example 37 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and compound 115B. 1H NMR (400 MHz, Methanol-d4): δ 8.74 (d), 7.68 (d), 7.45 (d), 7.03 (d), 6.69-6.62 (m), 6.65 (t), 6.59-6.45 (m), 5.36-5.14 (m), 4.69 (s), 3.23-3.05 (m), 2.59-2.22 (m), 1.39 (s), 1.41-1.28 (m), 1.13-0.83 (m). MS (m/z): 727.41 [M+H]+.

Example 116

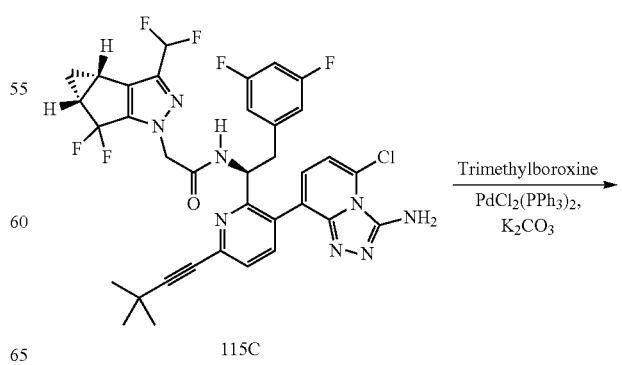

115C

-continued

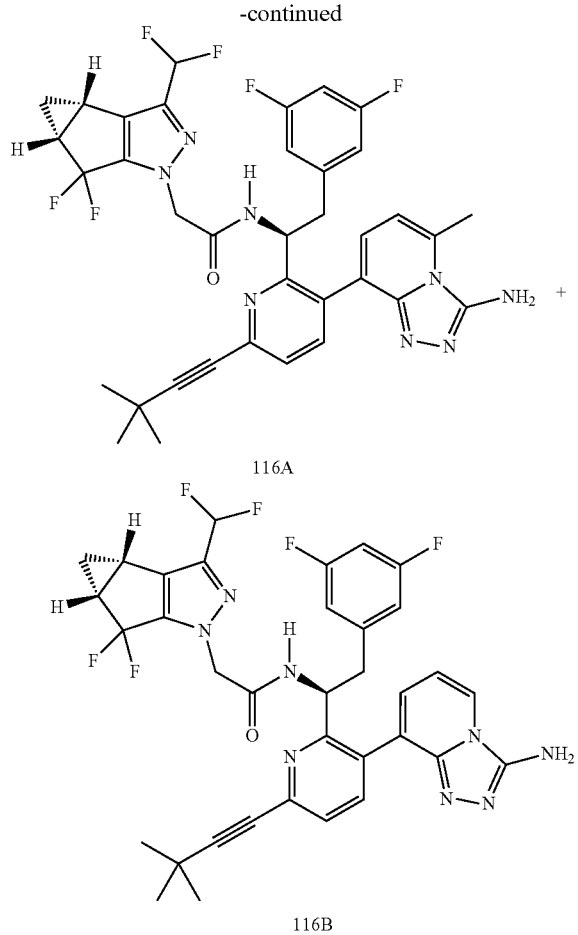

116A

116B

Synthesis of N—((S)-1-(3-(3-amino-5-methyl-[1,2,4]triazolo[4,3-a]pyridin-8-yl)-6-(3,3-dimethylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (116A)

In a microwave tube were charged with compound 115C (15 mg, 0.02 mmol), trimethylboroxine (9 μL, 0.06 mmol), potassium carbonate (8.5 mg, 0.06 mmol) and $PdCl_2[PPh_3]_2$ (1.5 mg, 0.002 mmol). To the mixture was added 1 mL of 1,4-dioxane and 0.1 mL of water. The mixture was heated to 160° C. for 20 minutes in a microwave synthesizer. After cooled to room temperature, it was partitioned between EtOAc and water. The organic layer was separated and washed with brine, then dried over $MgSO_4$, filtered and concentrated. The residue was purified by reverse phase HPLC to afford the title compound 116A. $^1$H NMR (400 MHz, Methanol-$d_4$) δ 8.82 (d), 7.67 (d), 7.47 (d), 6.87 (dd), 6.72-6.65 (m), 6.68 (t), 6.58-6.45 (m), 5.26-5.11 (m), 4.70 (s), 3.25-3.05 (m), 2.99 (d), 2.58-2.32 (m), 1.39 (s), 1.39-1.37 (m), 1.14-0.88 (m). MS (m/z) 707.30 [M+H]$^+$.

Compound 116B was obtained as a side product. MS (m/z): 693.23 [M+H]$^+$.

Example 117

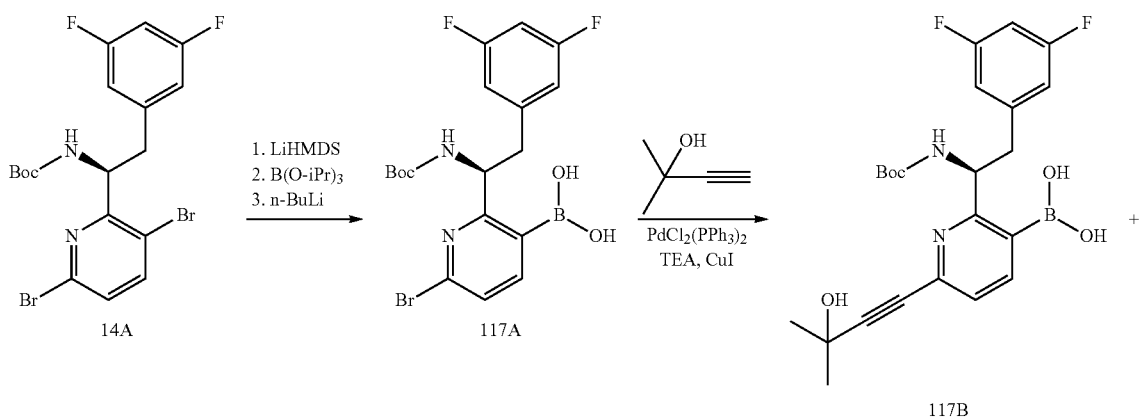

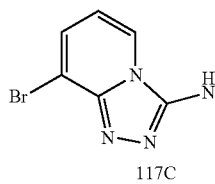

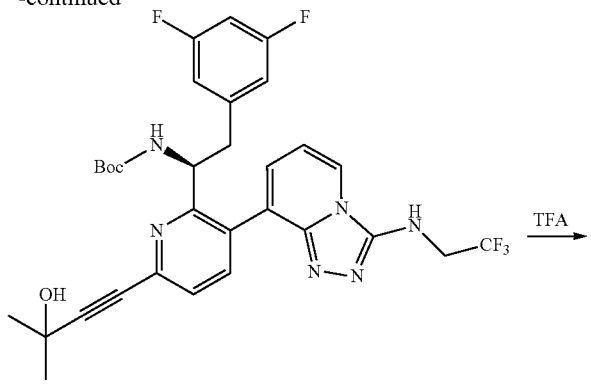

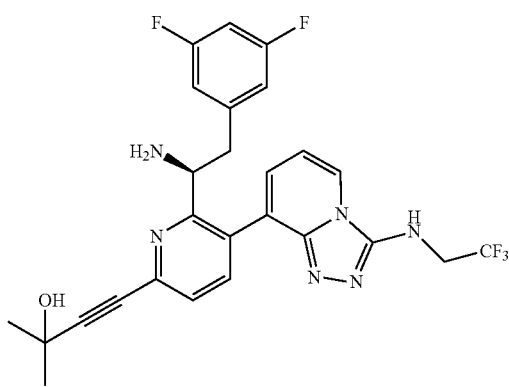

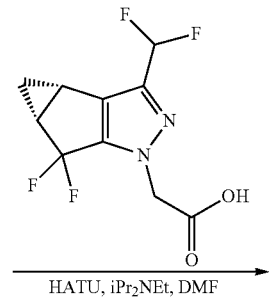

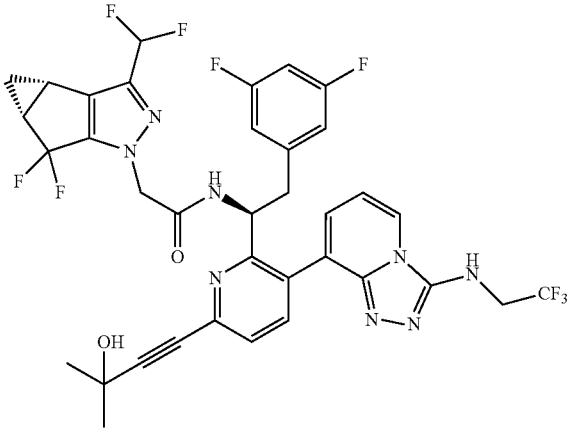

Synthesis of (S)-(6-bromo-2-(1-((tert-butoxycarbonyl)amino)-2-(3,5-difluorophenyl)ethyl)pyridin-3-yl)boronic acid (117A)

To a solution (S)-tert-butyl (1-(3,6-dibromopyridin-2-yl)-2-(3,5-difluorophenyl)ethyl)carbamate (14A) (6.2 g, 12.6 mmol) in 2-methyltetrahydrofuran (25 ml) was added dropwise 1M LiHMDS in THF (12.6 ml) at 0° C. After stirring at room temperature for 20 minutes, the reaction was concentrated in vacuo, dissolved in toluene (30 mL), concentrated in vacuo, and re-dissolved in 2-MeTHF (25 ml). To the resulting solution was added triisopropyl borate (7.11 ml, 37.8 mmol) at −78° C. followed by the dropwise addition of 1M n-butyllithium in hexanes (20 ml) over 15 minutes. After stirring for 5 minutes, the reactions were gradually warmed to 0° C., and quenched with 4M aqueous $NH_4Cl$ (75 mL). Additional 2-MeTHF (25 mL) was added and the organic layer was dried with $Na_2SO_4$, filtered, and concentrated in vacuo. The crude product was taken to the next step without further purification. MS (m/z) 456.87 $[M+H]^+$.

Synthesis of (S)-(2-(1-((tert-butoxycarbonyl)amino)-2-(3,5-difluorophenyl)ethyl)-6-(3-hydroxy-3-methylbut-1-yn-1-yl)pyridin-3-yl)boronic acid (117B)

A solution of (S)-(6-bromo-2-(1-((tert-butoxycarbonyl)amino)-2-(3,5-difluorophenyl)ethyl)pyridin-3-yl)boronic acid (117A) (5.76 g, 12.6 mmol), 2-methyl-3-butyn-2-ol (2.44 ml, 25.2 mmol), and triethylamine (7.0 ml, 50.4 mmol) in tetrahydrofuran (21 ml) was degassed with argon. To the reaction was added CuI (72 mg, 0.38 mmol) and $PdCl_2(PPh_3)_2$ (2.65 g, 0.38 mmol) and the resulting mixture was stirred at room temperature for 1 h. The reaction was concentrated in vacuo and extracted with ethyl acetate and water. The organic layer was dried with $Na_2SO_4$, filtered, concentrated in vacuo, and purified by silica chromatography to give the title compound. MS (m/z) 460.11 [M+H]+.

Synthesis of 8-bromo-N-(2,2,2-trifluoroethyl)-[1,2,4]triazolo[4,3-a]pyridin-3-amine (117C)

The title compound (117C) was prepared according to the method presented for the synthesis of 76C in Example 76 utilizing 3-bromo-2-hydrazinylpyridine and 1,1,1-trifluoro-2-isothiocyanatoethane. MS (m/z) 295.0 [M+H]+.

Synthesis of (S)-tert-butyl (2-(3,5-difluorophenyl)-1-(6-(3-hydroxy-3-methylbut-1-yn-1-yl)-3-(3-((2,2,2-trifluoroethyl)amino)-[1,2,4]triazolo[4,3-a]pyridin-8-yl)pyridin-2-yl)ethyl)carbamate (117D)

In a microwave vial, (S)-(2-(1-((tert-butoxycarbonyl)amino)-2-(3,5-difluorophenyl)ethyl)-6-(3-hydroxy-3-methylbut-1-yn-1-yl)pyridin-3-yl)boronic acid (117B, 30 mg, 0.07 mmol) was combined with 8-bromo-N-(2,2,2-trifluoroethyl)-[1,2,4]triazolo[4,3-a]pyridin-3-amine (117C, 19 mg, 0.07 mmol), $PdCl_2(PPh_3)_2$ (2 mg, 5 mol %), $K_2CO_3$ (65 ml of 2 M aqueous solution), and LiCl (1 mg) in dioxane (1 ml). Argon was bubbled into the reaction solution for 5 min. The reaction was heated in a microwave reactor at 155° C. for 15 min. After cooling to ambient temperature, the reaction was partitioned between EtOAc and water. The organics were separated, dried, and removed in vacuo and the residue was purified by column chromatography on silica to provide the title compound (117D). MS (m/z) 631.0 [M+H]+.

Synthesis of (S)-4-(6-(1-amino-2-(3,5-difluorophenyl)ethyl)-5-(3-((2,2,2-trifluoroethyl)amino)-[1,2,4]triazolo[4,3-a]pyridin-8-yl)pyridin-2-yl)-2-methylbut-3-yn-2-ol (117E)

The title compound (117E) was prepared according to the method presented for the synthesis of compound 19F of Example 19 utilizing compound 117D.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-((2,2,2-trifluoroethyl)amino)-[1,2,4]triazolo[4,3-a]pyridin-8-yl)pyridin-2-yl)ethyl)acetamide (117F)

The title compound (117F) was prepared according to the method presented for the synthesis of compound 37E of Example 37 utilizing compound 117E. $^1$H NMR (400 MHz, Methanol-$d_4$) δ 8.85 (d), 8.34 (d), 7.76 (d), 7.56 (d), 7.38 (s), 7.23 (t), 6.67 (t), 6.66-6.58 (m), 6.51-6.45 (m), 5.30-5.12 (m), 4.69 (s), 4.33-4.18 (m), 3.27-3.04 (m), 2.53-2.36 (m), 2.00 (d), 1.43-1.26 (m), 1.03 (s). MS (m/z) 777.1 [M+H]+.

Example 118

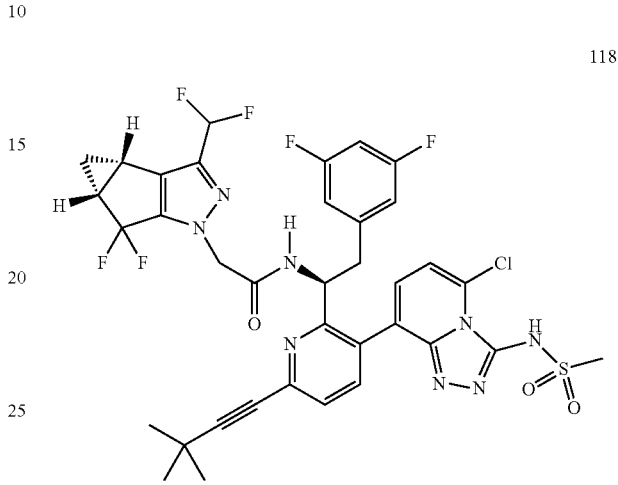

118

Synthesis of N—((S)-1-(3-(5-chloro-3-(methylsulfonamido)-[1,2,4]triazolo[4,3-a]pyridin-8-yl)-6-(3,3-dimethylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (118)

The title compound (118) was prepared according to the method presented for the synthesis of compound 19D of Example 19 utilizing compound 115C. $^1$H NMR (400 MHz, Methanol-$d_4$) δ 8.67 (d), 7.69 (d), 7.42 (d), 7.09-6.97 (m), 6.89 (d), 6.70 (t), 6.63 (t), 6.53-6.41 (m), 5.37-5.19 (m), 4.72 (s), 3.22-3.00 (m), 3.11 (s), 2.56-2.35 (m), 1.39 (s), 1.39-1.33 (m), 1.13-0.91 (m). MS (m/z): 805.78 [M+H]+.

Example 119

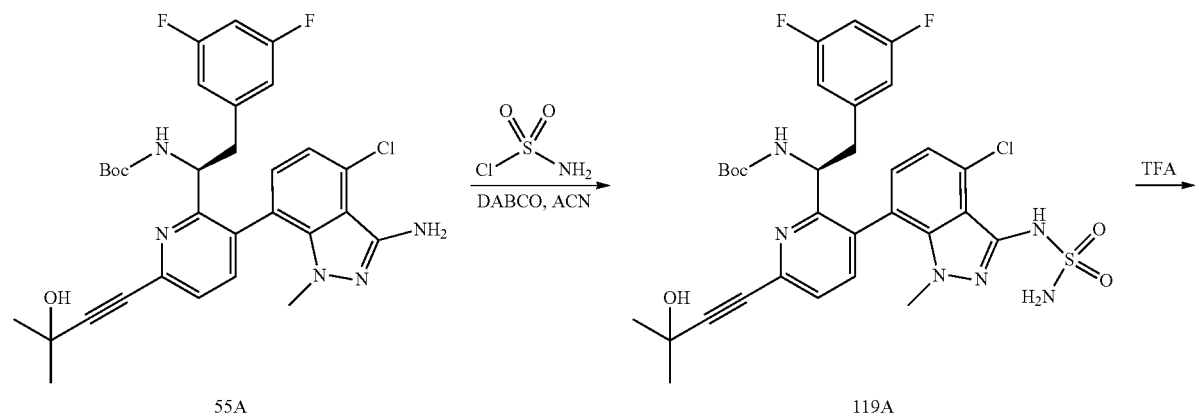

55A      119A

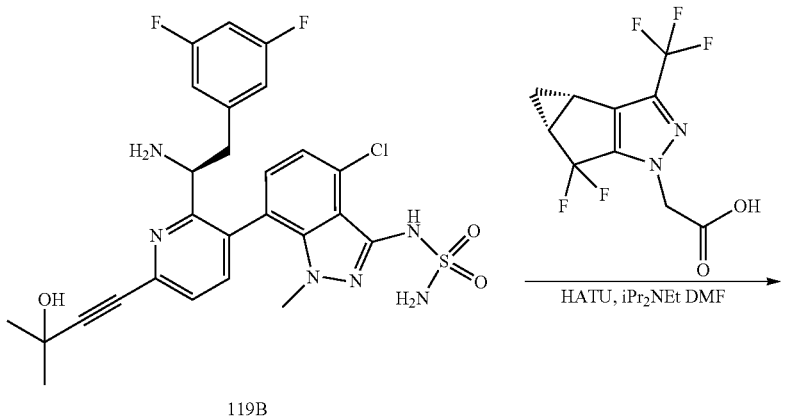

119B

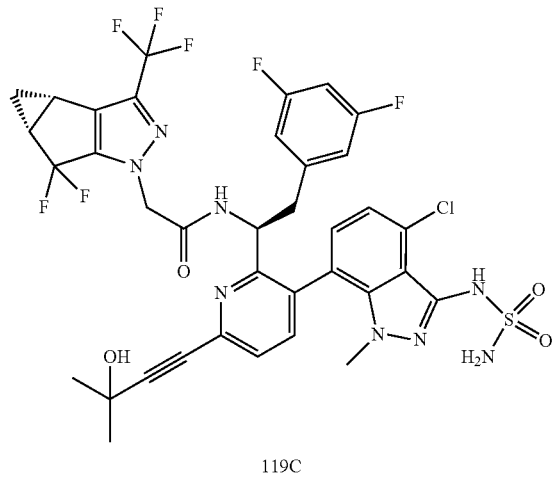

119C

Synthesis of (S)-tert-butyl (1-(3-(4-chloro-1-methyl-3-(sulfamoylamino)-1H-indazol-7-yl)-6-(3-hydroxy-3-methylbut-1-yn-1-yl)pyridin-2-yl)-2-(3,5-difluorophenyl)ethyl)carbamate (119A)

The title compound (119A) was prepared as a mixture of atropisomers according to the method presented for the synthesis of 70 in Example 70 utilizing 55A. MS (m/z) 675.0 [M+H]⁺.

Synthesis of 119B

The title compound (119B) was prepared as a mixture of atropisomers according to the method presented for the synthesis of 19F in Example 19 utilizing 119A. MS (m/z) 575.2 [M+H]⁺.

Synthesis of N—((S)-1-(3-(4-chloro-1-methyl-3-(sulfamoylamino)-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (119C)

The title compound (119C) was prepared as a mixture of atropisomers according to the method presented for the synthesis of 10A in Example 10 utilizing 119B and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, Methanol-d₄) δ 8.76 (d), 7.68 (dd), 7.53 (dd), 7.14 (q), 7.05 (d), 6.82-6.69 (m), 6.69-6.57 (m), 6.46-6.40 (m), 6.40-6.30 (m), 5.33-5.21 (m), 5.05-4.92 (m), 4.81-4.76 (m), 3.52-3.43 (m), 3.29-3.20 (m), 3.12 (dd), 3.06-2.92 (m), 2.60-2.40 (m), 1.49-1.31 (m), 1.25 (dd), 1.17-1.03 (m). MS (m/z): 839.8 [M+H]⁺.

Example 120
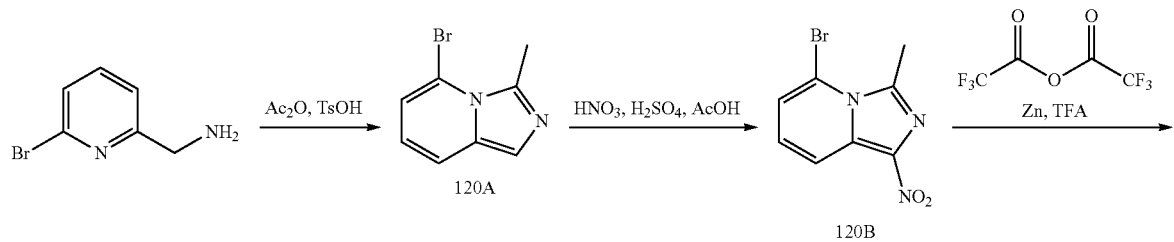
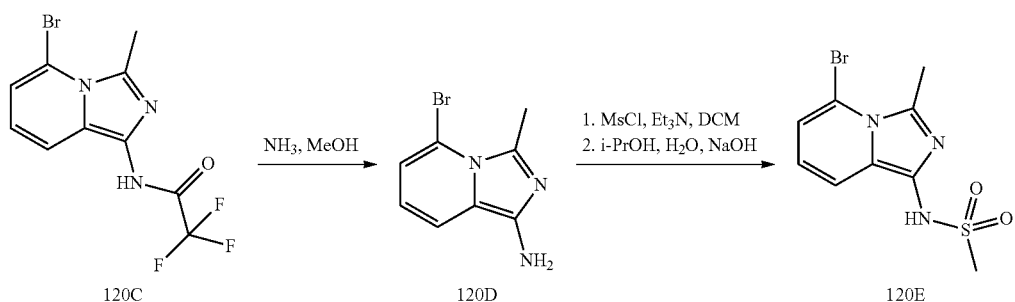
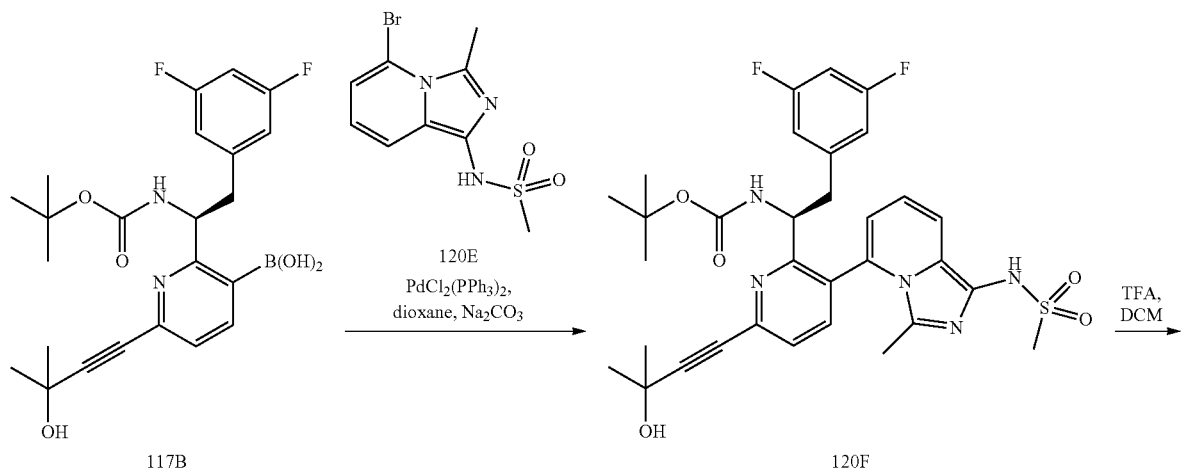
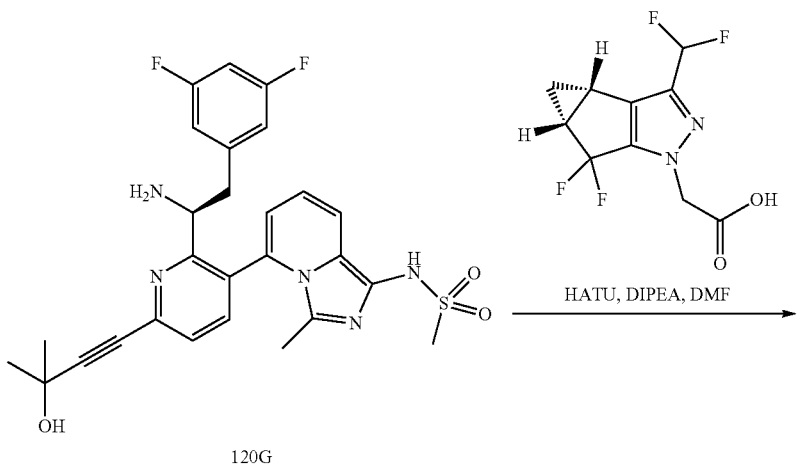

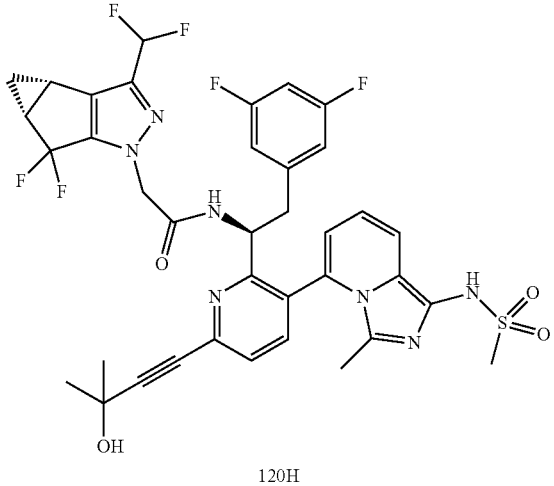 [SMILES: Cc1nc(NS(C)(=O)=O)c2cccc(-c3ccc(C#CC(C)(C)O)nc3[C@H](Cc3cc(F)cc(F)c3)NC(=O)Cn3nc(C(F)F)c4c3C(F)(F)[C@@H]3C[C@H]43)n12]

120H

Synthesis of 5-bromo-3-methylimidazo[1,5-a]pyridine (120A)

6-(Bromopyridin-2-yl)methylamine (4.0 g, 21.4 mmol) was added dropwise to acetic anhydride (10 ml) at 0° C. The reaction was warmed to room temperature and to the reaction was added p-toluenesulfonic acid (4.07 g, 20.4 mmol). The reaction was heated in a microwave reactor at 140° C. for 25 minutes. The reaction was concentrated in vacuo, the crude product was taken up in water, pH adjusted to ~9 with 1N aqueous NaOH, and extracted with twice with ethyl acetate. The organic layers were dried with $Na_2SO_4$, filtered, concentrated in vacuo, and purified by silica gel chromatography to give the title compound. MS (m/z) 213.06 [M+H]$^+$.

Synthesis of 5-bromo-3-methyl-1-nitroimidazo[1,5-a]pyridine (120B)

To 5-bromo-3-methylimidazo[1,5-a]pyridine (120A) (3.0 g, 14.2 mmol) in acetic acid (15 ml) was added dropwise a solution of 70% $HNO_3$ (0.82 ml) and conc. $H_2SO_4$ (0.82 ml) in acetic acid (8 ml). An exotherm was produced during the reaction. After stirring at room temperature for 45 mins, the resulting solution was added to stirring mixture of ice and brine (150 mL). To the chilled solution was added 8M aqueous NaOH (4.3 mL). The yellow precipitate was filtered and washed with water. The crude product was taken to the next step without further purification. MS (m/z) 255.95 [M+H]$^+$.

Synthesis of N-(5-bromo-3-methylimidazo[1,5-a]pyridin-1-yl)-2,2,2-trifluoroacetamide (120C)

To a solution of 5-bromo-3-methyl-1-nitroimidazo[1,5-a]pyridine (120B) (0.30 g, 1.17 mmol) and trifluoroacetic acid anhydride (0.5 ml, 3.51 mmol) in trifluoroacetic acid (4.2 ml) was added in portions zinc dust (0.15 g, 2.34 mmol). The reaction produces a strong exotherm. Upon completion, the reaction was concentrated in vacuo, and extracted with EtOAc and saturated aqueous $NaHCO_3$. The organic layer was dried with $Na_2SO_4$, filtered, concentrated in vacuo, and purified by silica gel chromatography eluting with ethyl acetate and hexanes to give the title compound. MS (m/z) 322.018 [M+H]$^+$.

Synthesis of 5-bromo-3-methylimidazo[1,5-a]pyridin-1-amine (120D)

A solution of N-(5-bromo-3-methylimidazo[1,5-a]pyridin-1-yl)-2,2,2-trifluoroacetamide (120C) (50 mg, 0.16 mmol) in 7N ammonia in methanol (1 ml) was heated in a microwave reactor at 70° C. for 30 minutes. The reaction was concentrated in vacuo. The resulting crude mixture was suspended in EtOAc, concentrated in vacuo, and dried under vacuum. The crude product was taken to the next step without further purification. MS (m/z) 228.12 [M+H]$^+$.

Synthesis of N-(5-bromo-3-methylimidazo[1,5-a]pyridin-1-yl)methanesulfonamide (120E)

To a solution of 5-bromo-3-methylimidazo[1,5-a]pyridin-1-amine (120D) (35 mg) and triethylamine (48 ul, 0.34 mmol) in dichloromethane (0.5 ml) was added methanesulfonyl chloride (24 μl, 0.31 mmol). After stirring at room temperature for 30 minutes, 2M methylamine in THF (0.250 mL) was added, and the reaction was concentrated in vacuo. The crude product was dissolved in 2-propanol (2.0 mL) and to the reaction was added 1.0M aqueous NaOH (2.0 mL). After stirring at room temperature for 1.5 h, the reaction was acidified with AcOH (180 uL), and the resulting mixture was concentrated in vacuo. The mixture was extracted with ethyl acetate and water. The organic layers were dried with $Na_2SO_4$, filtered, concentrated in vacuo, and purified by silica gel chromatography to give the title compound. MS (m/z) 305.88 [M+H]$^+$.

Synthesis of (S)-tert-butyl (2-(3,5-difluorophenyl)-1-(6-(3-hydroxy-3-methylbut-1-yn-1-yl)-3-(3-methyl-1-(methylsulfonamido)imidazo[1,5-a]pyridin-5-yl)pyridin-2-yl)ethyl)carbamate (120F)

A solution of N-(5-bromo-3-methylimidazo[1,5-a]pyridin-1-yl)methanesulfonamide (120E) (50 mg, 0.16 mmol), (S)-(2-(1-((tert-butoxycarbonyl)amino)-2-(3,5-difluorophenyl)ethyl)-6-(3-hydroxy-3-methylbut-1-yn-1-yl)pyridin-3-yl)boronic acid (117B) (90.8 mg, 0.20 mol), and dichlorobis(triphenylphosphine)palladium(II) (11.5 mg, 0.016 mmol) in dioxane (1.2 ml) was purged with argon. To the reaction was added 1M aqueous $Na_2CO_3$ (0.4 ml), solution was purged with argon, and heated in a microwave reactor for 30 mins at 120° C. To the resulting solution was added 5% AcOH in brine (10 mL) and was extracted twice with EtOAc. The organic layers were dried with Na₂SO₄, filtered, concentrated in vacuo, and purified by silica gel chromatography to give the title compound as a mixture of atropisomers. MS (m/z) 639.94 [M+H]⁺.

Synthesis of (S)—N-(5-(2-(1-amino-2-(3,5-difluorophenyl)ethyl)-6-(3-hydroxy-3-methylbut-1-yn-1-yl)pyridin-3-yl)-3-methylimidazo[1,5-a]pyridin-1-yl)methanesulfonamide (120G)

(S)-tert-butyl (2-(3,5-difluorophenyl)-1-(6-(3-hydroxy-3-methylbut-1-yn-1-yl)-3-(3-methyl-1-(methylsulfonamido)imidazo[1,5-a]pyridin-5-yl)pyridin-2-yl)ethyl)carbamate (120F) (75 mg, 0.12 mmol) was dissolved in DCM (1.0 mL) and TFA (0.5 mL) and stirred at room temperature for 30 mins. The resulting solution was concentrated in vacuo and extracted with ethyl acetate and saturated aqueous NaHCO₃ followed by water. The organic layer was dried with Na₂SO₄, filtered, and concentrated in vacuo. The crude product as a mixture of atropisomers was taken to the next step without further purification. MS (m/z) 540.12 [M+H]⁺.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-methyl-1-(methylsulfonamido)imidazo[1,5-a]pyridin-5-yl)pyridin-2-yl)ethyl)acetamide (120H)

The title compound (120H) was prepared as a mixture of atropisomers according to the method presented for the synthesis of compound (33F) of Example 33 utilizing (S)—N-(5-(2-(1-amino-2-(3,5-difluorophenyl)ethyl)-6-(3-hydroxy-3-methylbut-1-yn-1-yl)pyridin-3-yl)-3-methylimidazo[1,5-a]pyridin-1-yl)methanesulfonamide (120G). ¹H NMR (400 MHz, Methanol-d4) δ 8.88-8.81 (m), 8.75 (d), 7.84 (dd), 7.70-7.53 (m), 6.90 (dd), 6.83-6.74 (m), 6.73-6.65 (m), 6.58 (dd), 6.54-6.46 (m), 5.99 (dd), 5.31-5.22 (m), 5.01-4.92 (m), 4.74-4.61 (m), 3.41-3.28 (m), 3.24-3.12 (m), 3.10-2.99 (m), 2.53-2.39 (m), 1.87 (s), 1.65 (s), 1.64 (s), 1.43-1.33 (m), 1.11-1.04 (m), 1.05-0.97 (m). MS (m/z) 786.13 [M+H]⁺.

Example 121

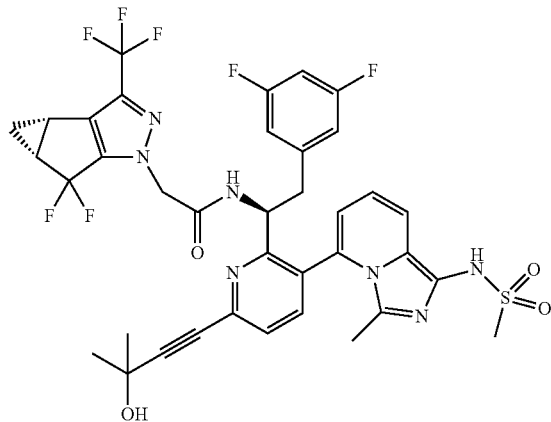

121

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(3-methyl-1-(methylsulfonamido)imidazo[1,5-a]pyridin-5-yl)pyridin-2-yl)ethyl)acetamide (121)

The title compound (121) was prepared as a mixture of atropisomers according to the method presented for the synthesis of compound (33F) of Example 33 utilizing (S)—N-(5-(2-(1-amino-2-(3,5-difluorophenyl)ethyl)-6-(3-hydroxy-3-methylbut-1-yn-1-yl)pyridin-3-yl)-3-methylimidazo[1,5-a]pyridin-1-yl)methanesulfonamide (120G) and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. ¹H NMR (400 MHz, Methanol-d₄) δ 8.97 (d), 8.83 (d), 7.84 (dd), 7.70 (dd), 7.65-7.52 (m), 6.96-6.86 (m), 6.84-6.74 (m), 6.70-6.62 (m), 6.62-6.55 (m), 6.54-6.43 (m), 5.99 (dd), 5.32-5.22 (m), 5.01-4.89 (m), 4.81-4.66 (m), 3.51-3.36 (m), 3.26-3.15 (m), 3.14-2.97 (m), 2.55-2.43 (m), 1.88 (s), 1.65 (s), 1.64 (s), 1.46 (s), 1.45-1.36 (m), 1.13 (s), 1.09-1.04 (m). MS (m/z) 804.15 [M+H]⁺.

Example 122

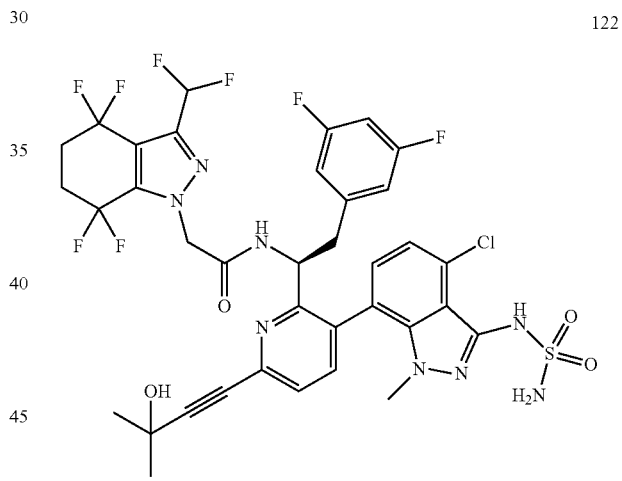

122

Synthesis of (S)—N-(1-(3-(4-chloro-1-methyl-3-(sulfamoylamino)-1H-indazol-7-yl)-6-(3-hydroxy-3-methylbut-1-yn-1-yl)pyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (122)

The title compound (122) was prepared as a mixture of atropisomers according to the method presented for the synthesis of 10A in Example 10 utilizing 119B and 2-(3-(difluoromethyl)-4,4,7,7-tetrafluoro-4,5,6,7-tetrahydro-H-indazol-1-yl)acetic acid. ¹H NMR (400 MHz, Methanol-d₄) δ 8.91-8.81 (m), 7.69 (dd), 7.53 (dd), 7.22-7.12 (m), 7.06 (d), 6.98-6.59 (m), 6.50-6.32 (m), 5.36-5.24 (m), 4.99 (d), 3.34 (s), 3.24 (dd), 3.14 (dd), 3.02 (s), 2.97 (m), 2.66-2.38 (m), 1.63 (s). MS (m/z): 859.3 [M+H]⁺.

Example 123

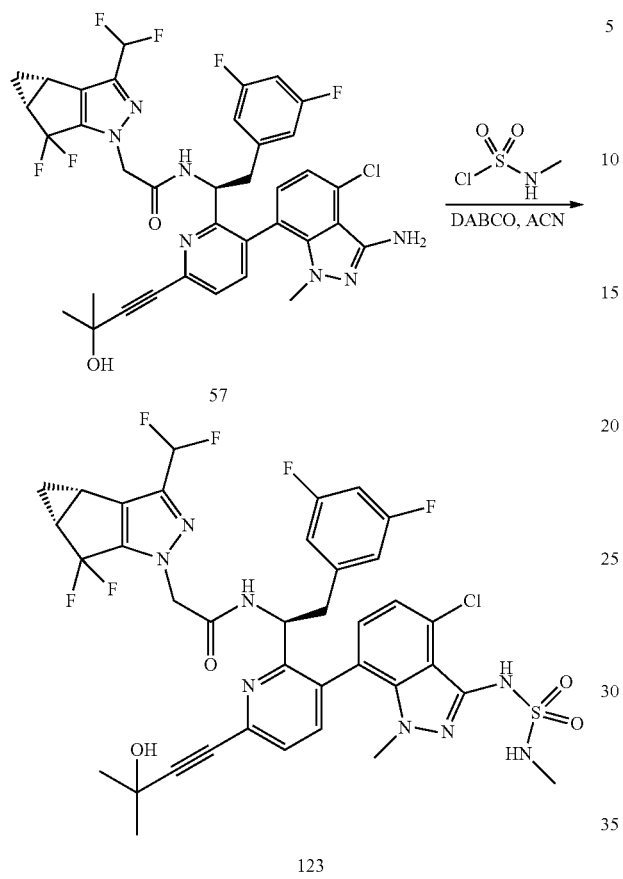

123

Synthesis of N—((S)-1-(3-(4-chloro-1-methyl-3-((N-methylsulfamoyl)amino)-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (123)

The title compound (123) was prepared as a mixture of atropisomers according to the method presented for the synthesis of 70 in Example 70 utilizing 57 and methylsulfamoyl chloride. ¹H NMR (400 MHz, Methanol-d₄) δ 8.75-8.67 (m), 7.68 (d), 7.57-7.51 (m), 7.15 (d), 7.06 (d), 6.86-6.52 (m), 6.48-6.29 (m), 5.33-5.23 (m), 4.96 (q), 4.80-4.64 (m), 3.21-3.05 (m), 3.05-2.89 (m), 2.78 (s), 2.72 (s), 2.55-2.39 (m), 1.64 (s), 1.48-1.28 (m), 1.11-0.95 (m). MS (m/z) 835.8 [M+H]⁺.

Example 124

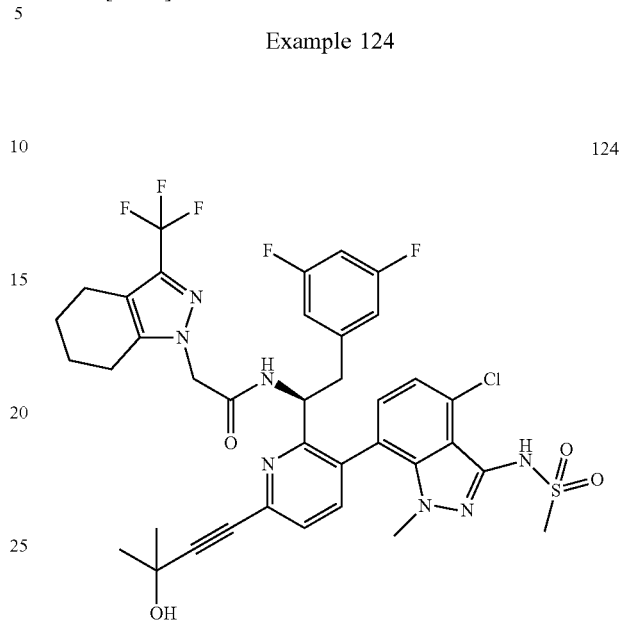

124

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-(trifluoromethyl)-4,5,6,7-tetrahydro-1H-indazol-1-yl)acetamide (124)

The title compound (124) was prepared as a mixture of atropisomers according to the method presented for the synthesis of compound 10A of Example 10 utilizing (S)—N-(7-(2-(1-amino-2-(3,5-difluorophenyl)ethyl)-6-(3-hydroxy-3-methylbut-1-yn-1-yl)pyridin-3-yl)-4-chloro-1-methyl-1H-indazol-3-yl)methanesulfonamide (19F) and 2-(3-(trifluoromethyl)-4,5,6,7-tetrahydro-1H-indazol-1-yl) acetic acid. ¹H NMR (400 MHz, Methanol-d₄) 8.68 (t), 7.71 (dd), 7.54 (dd), 7.25-7.14 (m), 7.11 (d), 6.80-6.73 (m), 6.69-6.60 (m), 6.53 (dd), 6.46-6.36 (m), 5.29-5.22 (m), 5.04-4.96 (m), 4.91-4.75 (m), 4.72 (d), 4.67 (d), 4.17 (s), 3.58 (s), 3.33 (s), 3.26 (s), 3.23 (s), 3.15 (dd), 3.04 (s), 3.02-2.94 (m), 2.65-2.43 (m), 2.40-2.28 (m), 1.85-1.69 (m), 1.64 (s), 1.64 (s). MS (m/z) 804.18 [M+H]⁺.

Examples 125 and 126

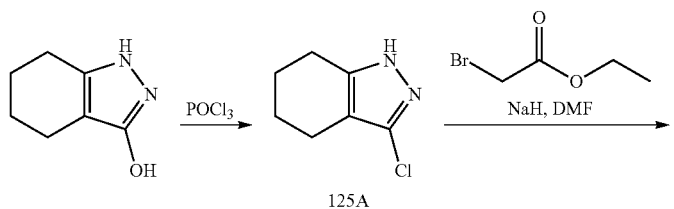

125A

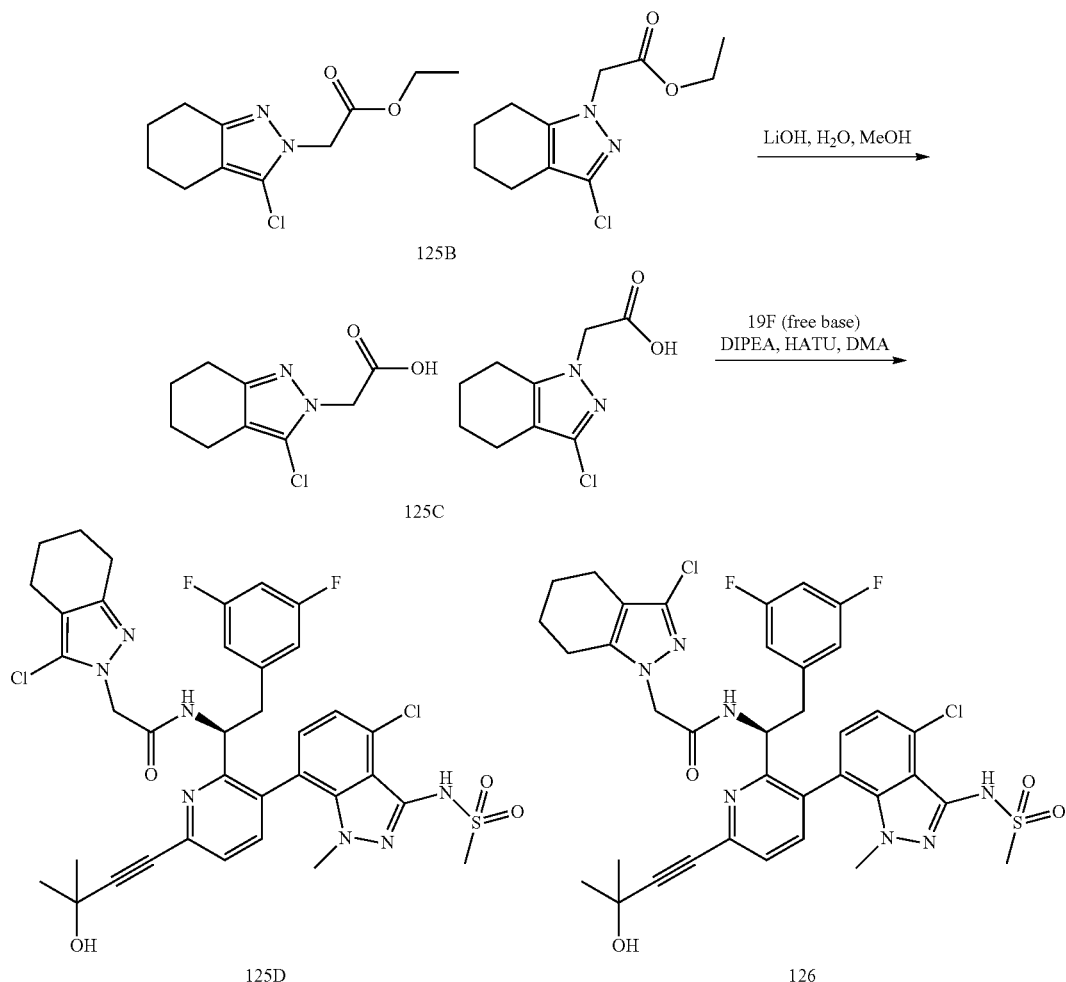

Synthesis of 3-chloro-4,5,6,7-tetrahydro-1H-indazole (125A)

A solution of 4,5,6,7-tetrahydro-1H-indazol-3-ol (0.41 g, 3.0 mmol) in trichlorophosphate (1.5 ml) was heated in a microwave reactor under argon at 225° C. for 15 minutes. The reaction was concentrated in vacuo and carefully quenched with 1.0N aqueous NaOH at 0° C. and extracted with dichloromethane. The organic layer was dried with Na$_2$SO$_4$, filtered, concentrated in vacuo and purified by silica gel chromatography to give the title compound. MS (m/z) 157.14 [M+H]$^+$.

Synthesis of a 1:5 mixture of ethyl 2-(3-chloro-4,5,6,7-tetrahydro-2H-indazol-2-yl)acetate and ethyl 2-(3-chloro-4,5,6,7-tetrahydro-1H-indazol-1-yl)acetate (125B)

To a solution of 3-chloro-4,5,6,7-tetrahydro-1H-indazole (125A) in DMF (1.6 ml) was added portionwise NaH (60% w/ mineral oil) (74.9 mg, 1.95 mmol). After stirring at room temperature for 15 mins, ethyl bromoacetate (0.22 ml, 1.95 mmol) was added dropwise at 0° C. The reaction was warmed to room temperature and stirred for 2 h. The reaction was quenched with water and extracted with ethyl acetate. The organic layer was washed with water. The organic layer was dried with Na$_2$SO$_4$, filtered, concentrated in vacuo and purified by silica gel chromatography to give the title compounds as a 1:5 mixture of ethyl 2-(3-chloro-4,5,6,7-tetrahydro-2H-indazol-2-yl)acetate and ethyl 2-(3-chloro-4,5,6,7-tetrahydro-1H-indazol-1-yl)acetate (125B). MS (m/z) 243.11 [M+H]$^+$.

Synthesis of a 1:5 mixture of 2-(3-chloro-4,5,6,7-tetrahydro-2H-indazol-2-yl)acetic acid and 2-(3-chloro-4,5,6,7-tetrahydro-H-indazol-1-yl)acetic acid (125C)

To a 1:5 mixture of ethyl 2-(3-chloro-4,5,6,7-tetrahydro-2H-indazol-2-yl)acetate and ethyl 2-(3-chloro-4,5,6,7-tetrahydro-1H-indazol-1-yl)acetate (125B) (15 mg, 61.8 mol) in methanol (250 µl) was added 2M aqueous LiOH (62 µl). The reaction was heated at 50° C. for 1.5 h. The mixture was concentrated in vacuo, extracted with 2-methyltetrahydrofuran (2 mL) and 0.1N HCl (1.3 mL). The organic layer was dried with Na$_2$SO$_4$, filtered, and concentrated in vacuo. The crude product was taken to the next step without further purification. MS (m/z) 215.14 [M+H]$^+$.

Syntheses of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-chloro-4,5,6,7-tetrahydro-2H-indazol-2-yl)acetamide (125D) and of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-chloro-4,5,6,7-tetrahydro-1H-indazol-1-yl)acetamide (126)

The title compounds (125D and 126) were both prepared as mixtures of atropisomers according to the method presented for the synthesis of compound 33F of Example 33 utilizing the free base form of (S)—N-(7-(2-(1-amino-2-(3,5-difluorophenyl)ethyl)-6-(3-hydroxy-3-methylbut-1-yn-1-yl)pyridin-3-yl)-4-chloro-1-methyl-1H-indazol-3-yl)methanesulfonamide (19F) and 1:5 mixture of 2-(3-chloro-4,5,6,7-tetrahydro-2H-indazol-2-yl)acetic acid and 2-(3-chloro-4,5,6,7-tetrahydro-1H-indazol-1-yl)acetic acid (125C). The regioisomers were separated by reverse phase HPLC to provide the title products. (125D) $^1$H NMR (400 MHz, Methanol-d4) δ 8.56-8.45 (m), 7.70 (dd), 7.53 (dd), 7.27-7.14 (m), 7.10 (d), 6.79-6.71 (m), 6.66-6.59 (m), 6.53-6.47 (m), 6.44-6.33 (m), 5.32-5.22 (m), 5.05-4.92 (m), 4.71 (d), 4.67 (s), 3.36 (s), 3.25 (s), 3.23 (s), 3.21-3.16 (m), 3.16-3.07 (m), 3.03 (s), 3.01-2.90 (m), 2.64-2.53 (m), 2.44-2.30 (m), 1.76 (dd), 1.64 (s), 1.64 (s). MS (m/z) 770.24 [M+H]$^+$. (126): $^1$H NMR (400 MHz, Methanol-d$_4$) δ 7.71 (dd), 7.53 (dd), 7.27-7.14 (m), 7.11 (d), 6.82-6.7 (m), 6.68-6.60 (m), 6.54 (d), 6.47-6.34 (m), 5.26 (dd), 5.00 (t), 4.60 (s), 4.55 (s), 3.34 (s), 3.26 (s), 3.23 (s), 3.25-3.19 (m), 3.17-3.10 (m), 3.03 (s), 3.02-2.92 (m), 2.47-2.27 (m), 1.85-1.67 (m), 1.64 (s), 1.64 (s). MS (m/z) 770.24 [M+H]$^+$.

Example 127

127

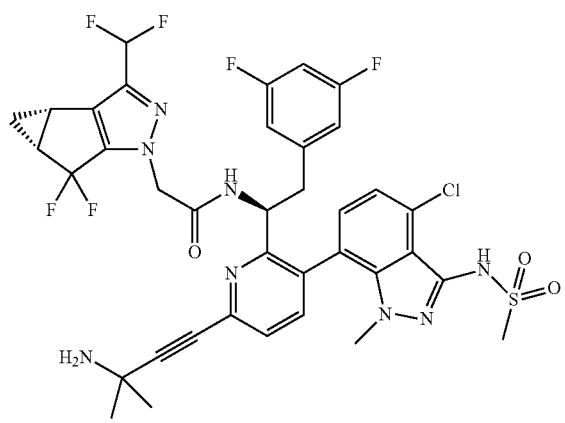

Synthesis of N—((S)-1-(6-(3-amino-3-methylbut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (127)

The title compound (127) was prepared as a mixture of atropisomers according to the method presented for the synthesis of compound 142 of Example 142 utilizing 2-methylbut-3-yn-2-amine. $^1$H NMR (400 MHz, cd$_3$od) δ 8.79 (t), 7.79 (d), 7.76 (d), 7.64 (d), 7.61 (d), 7.22-7.15 (m), 7.08 (d), 6.82-6.75 (m), 6.70-6.63 (m), 6.45-6.40 (m), 6.40-6.35 (m), 5.30-5.21 (m), 5.04-4.95 (m), 4.78 (s), 4.75 (d), 3.32 (s), 3.26 (s), 3.23 (s), 3.20-3.13 (m), 3.06-2.95 (m), 2.94 (s), 2.50 (ddt), 1.82 (s), 1.82 (s), 1.48-1.28 (m), 1.14 (dd), 1.09-1.00 (m). MS (m/z) 838.3 [M+H]$^+$.

Example 128

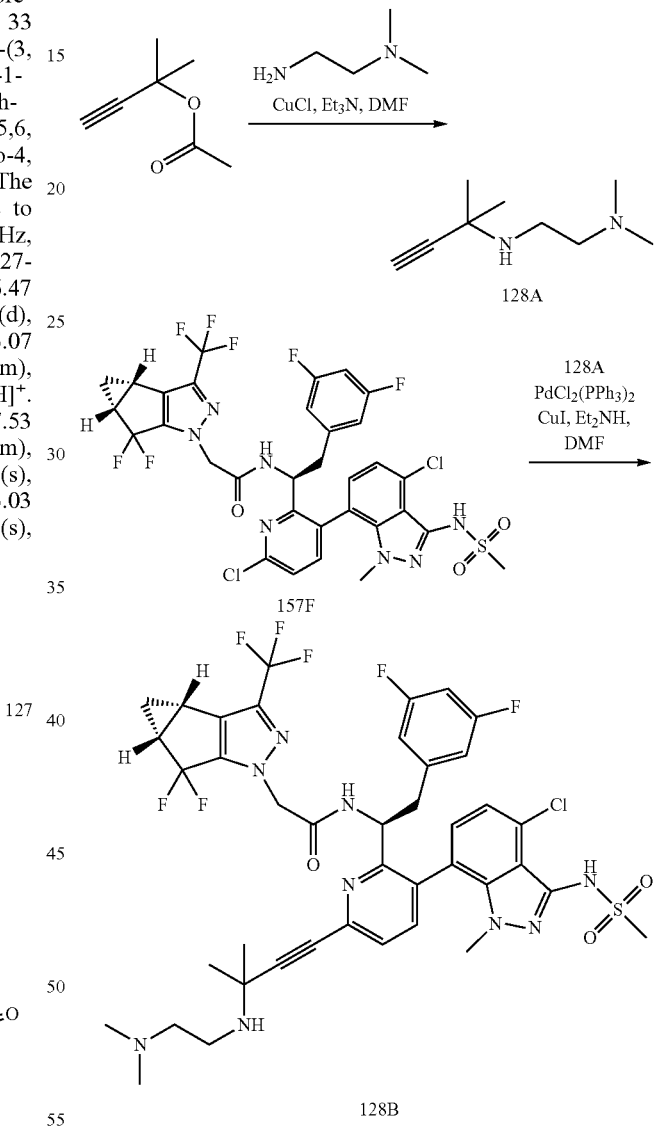

Synthesis of N1,N1-dimethyl-N2-(2-methylbut-3-yn-2-yl)ethane-1,2-diamine (128A)

Argon was bubbled through a solution of 2-methylbut-3-yn-2-yl acetate (15.96 mg, 126.5 mol), copper chloride (0.75 mg, 7.59 mol), triethylamine (17.63 µl, 126.5 mol), and N,N-dimethylethylenediamine (20.73 µl, 189.74 mol) in DMF (0.2 ml). The reaction was heated in a microwave reactor at 110° C. for 5 min. The reaction was cooled to room temperature and telescoped to the next reaction.

Synthesis of N—((S)-1-(6-(3-amino-3-methylbut-1-yn-1-yl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (128B)

Into the reaction was added 157F (20 mg, 25.3 mol) in DMF (0.2 mL), CuI (1 mg, 5.06 mol), and PdCl$_2$(PPh$_3$)$_2$ (3.55 mg, 5.06 mol). Argon was bubbled through the reaction and diethylamine (39 al, 379 mol) was added. The reaction was heated in a microwave reactor for 15 mins at 125° C. The excess amines were removed under vacuum and the product was purified by reverse phase HPLC the title product 128B as a mixture of atropisomers. $^1$H NMR (400 MHz, cd$_3$od) δ 8.76 (t), 7.76 (d), 7.73 (d), 7.64 (d), 7.61 (d), 7.21-7.16 (m), 7.07 (d), 6.82-6.74 (m), 6.69-6.62 (m), 6.45-6.40 (m), 6.37 (ddd), 5.30-5.24 (m), 4.99 (dd), 4.78 (s), 4.76 (d), 3.60-3.48 (m), 3.32 (s), 3.26 (s), 3.23 (s), 3.18-3.11 (m), 3.01 (s), 2.97 (s), 2.58-2.42 (m), 1.77 (s), 1.48-1.37 (m), 1.13 (tt), 1.10-1.03 (m). MS (m/z) 908.3 [M+H]$^+$.

Example 129

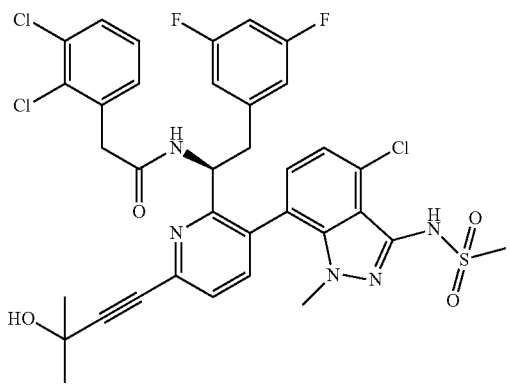

129

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(2,3-dichlorophenyl)acetamide (129)

The title compound (129) was prepared as a mixture of atropisomers according to the method presented in the synthesis of 10A in Example 10 utilizing 19F and 2-(2,3-dichlorophenyl)acetic acid. $^1$H NMR (400 MHz, Methanol-d$_4$) δ 7.70 (dd), 7.53 (dd), 7.44 (dd), 7.39 (dd), 7.28-7.05 (m), 6.80-6.69 (m), 6.68-6.61 (m), 6.60 (d), 6.48-6.36 (m), 5.35-5.20 (m), 5.06-4.92 (m), 3.67 (s), 3.62 (s), 3.22 (s), 3.20-3.11 (m), 3.07 (s), 3.00 (dd), 1.64 (s). MS (m/z) 762.3 [M+H]$^+$.

Example 130

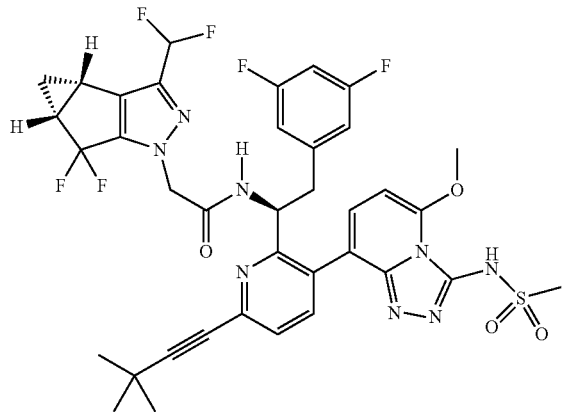

130

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3,3-dimethylbut-1-yn-1-yl)-3-(5-methoxy-3-(methylsulfonamido)-[1,2,4]triazolo[4,3-a]pyridin-8-yl)pyridin-2-yl)ethyl)acetamide (130)

To compound 115C (15 mg, 0.2 mmol) dissolved in 0.5 mL of methylene chloride was added triethylamine (37 μL, 0.2 mmol) followed by methanesulfonyl chloride (8 μL, 0.1 mmol). The reaction mixture was allowed to stir at room temperature for 30 minutes. The reaction was diluted with methylene chloride and water. The organic layer was separated, dried over sodium sulfate, filtered and concentrated. The residue was dissolved in 1 mL of methanol and to it was added 0.1 mL of 15% NaOH aqueous solution. The mixture was stirred at 40° C. for overnight then 60° C. for 7 hours. The solvent was removed and the residue was purified by RP-HPLC to afford the title compound 130. $^1$H NMR (400 MHz, Methanol-d$_4$) δ 7.68 (d), 7.43 (d), 7.22-7.11 (m), 6.70 (t), 6.63 (t), 6.53-6.43 (m), 6.27 (d), 5.28 (t), 4.71 (s), 4.12 (s), 3.26-2.89 (m), 3.18 (s), 2.52-2.40 (m), 1.40-1.31 (m), 1.39 (s), 1.09-1.00 (m). MS (m/z): 801.65 [M+H]$^+$.

Example 131

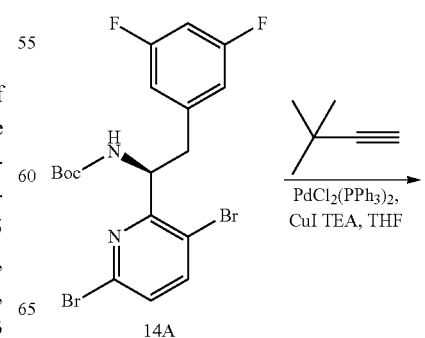

14A

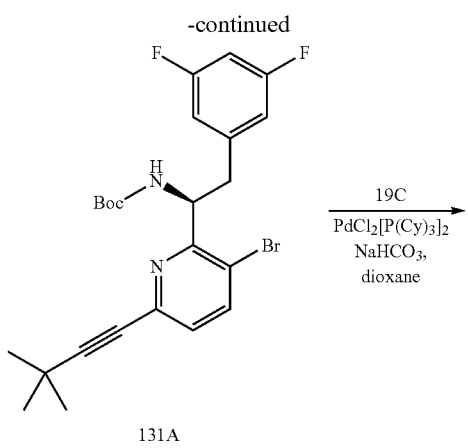

131A

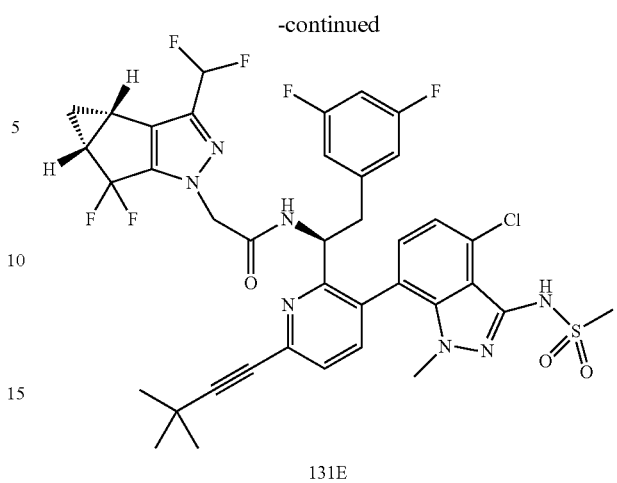

131E

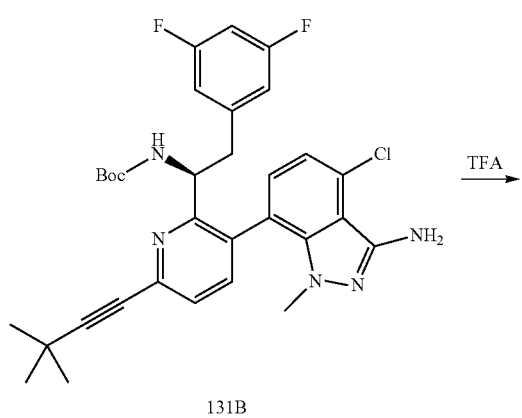

131B

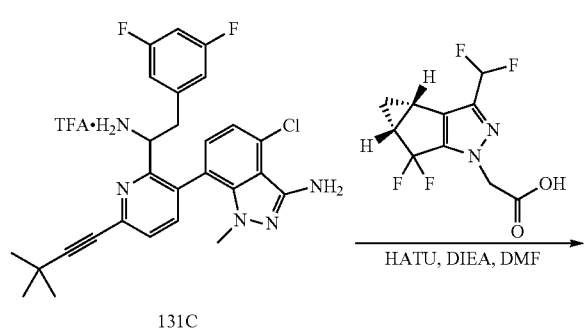

131C

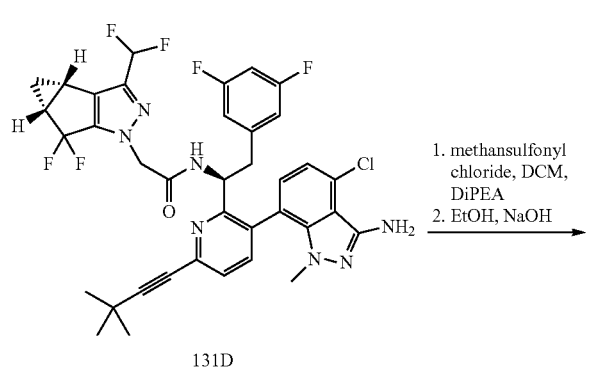

131D

Synthesis of (S)-tert-butyl (1-(3-bromo-6-(3,3-dimethylbut-1-yn-1-yl)pyridin-2-yl)-2-(3,5-difluorophenyl)ethyl)carbamate (131A)

The title compound (131A) was prepared according to the method presented for the synthesis of compound 4F of Example 4 utilizing compound 14A and 3,3-dimethylbut-1-yne. MS (m/z) 494.92 [M+H]+.

Synthesis of (S)-tert-butyl (1-(3-(3-amino-4-chloro-1-methyl-1H-indazol-7-yl)-6-(3,3-dimethylbut-1-yn-1-yl)pyridin-2-yl)-2-(3,5-difluorophenyl)ethyl)carbamate (131B)

The title compound (131B) was prepared as a mixture of atropisomers according to the method presented for the synthesis of compound 19E of Example 19 utilizing compound 131A and compound 19C. MS (m/z) 594.44 [M+H]+.

Synthesis of (S)-7-(2-(1-amino-2-(3,5-difluorophenyl)ethyl)-6-(3,3-dimethylbut-1-yn-1-yl)pyridin-3-yl)-4-chloro-1-methyl-1H-indazol-3-amine (131C)

The title compound (131C) was prepared as a mixture of atropisomers according to the method presented for the synthesis of compound 105C of Example 105 utilizing compound 131B. MS (m/z) 494.26 [M+H]+.

Synthesis of N—((S)-1-(3-(3-amino-4-chloro-1-methyl-1H-indazol-7-yl)-6-(3,3-dimethylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (131D)

The title compound 131D was prepared as a mixture of atropisomers according to the method presented for the synthesis of compound 37E of Example 37 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and compound 131C. MS (m/z) 740.35 [M+H]+.

Synthesis of N—((S)-1-(3-(4-chloro-1-methyl-3-(methylsulfonamido)-1H-indazol-7-yl)-6-(3,3-dimethylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (131E)

The title compound (131E) was prepared according to the method presented for the synthesis of compound 19D of Example 19 utilizing compound 131D. $^1$H NMR (400 MHz, Methanol-d$_4$) δ 7.67-7.63 (m), 7.49-7.44 (m), 7.17 (d), 7.06 (d), 6.90-6.47 (m), 6.79 (t), 6.47-6.20 (m), 5.33-5.23 (m), 4.95 (t), 4.79-4.49 (m), 3.33 (s), 3.24 (d), 3.13 (dd), 3.05-2.83 (m), 3.00 (s), 2.58-2.14 (m), 1.43-1.31 (m), 1.41 (s), 1.13-0.93 (m). MS (m/z): 818.15 [M+H]$^+$.

Example 132

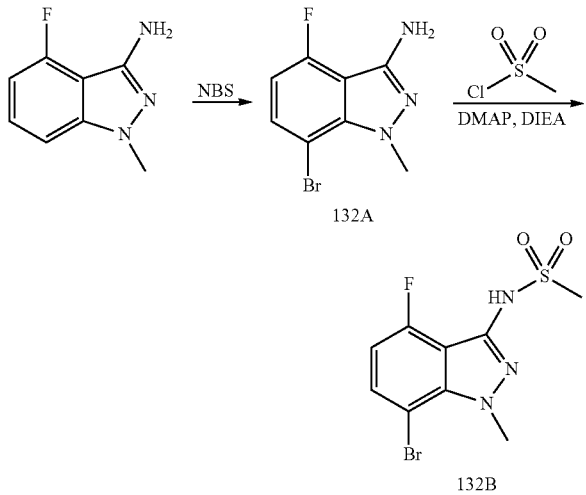

Synthesis of 7-bromo-4-fluoro-1-methyl-1H-indazol-3-amine (132A)

A solution of 4-fluoro-1-methyl-1H-indazol-3-amine (4.3 g, 26 mmol) in concentrated sulfuric acid (26 ml) was cooled to 0° C. then treated in three portions with N-bromosuccinimide (4.64 g, 26 mmol). The reaction was allowed to slowly reach room temperature and stirred for 15 h. The reaction was carefully quenched with water, filtered, and the filtrate was neutralized. The neutralized solution was then extracted with ethyl acetate, dried over sodium sulfate, filtered and concentrated. The crude material was purified by silica gel chromatography to give the title compound. MS (m/z) 246.1 [M+H]$^+$.

Synthesis of N-(7-bromo-4-fluoro-1-methyl-1H-indazol-3-yl)methanesulfonamide (132B)

The title compound was prepared similarly to 108B of Example 108 starting from 132A. MS (m/z) 320.3 [M–H]$^-$.

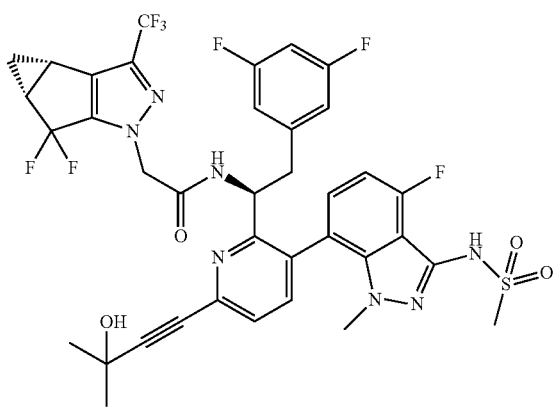

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(3-(4-fluoro-1-methyl-3-(methylsulfonamido)-1H-indazol-7-yl)-6-(3-hydroxy-3-methylbut-1-yn-1-yl)pyridin-2-yl)ethyl)acetamide (132C)

The title compound (132C) was prepared as a mixture of atropisomers according to the method presented for the synthesis of compound 117F of Example 117 utilizing 132B, 117B and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid. $^1$H NMR (400 MHz, cd$_3$od) δ 8.80-8.75 (m), 7.70 (d), 7.65-7.59 (m), 7.52 (d), 7.35-7.30 (m), 7.22-7.17 (m), 7.11-7.06 (m), 6.75-6.70 (m), 6.49-6.44 (m), 6.23-6.16 (m), 5.52-5.47 (m), 5.00-4.95 (m), 4.86 (d), 3.26 (t), 3.02-2.97 (m), 2.52-2.47 (m), 1.63 (s), 1.45-1.36 (m), 1.33-1.27 (m), 1.15-1.10 (m). MS (m/z) 822.1 [M+H]$^+$.

Example 133

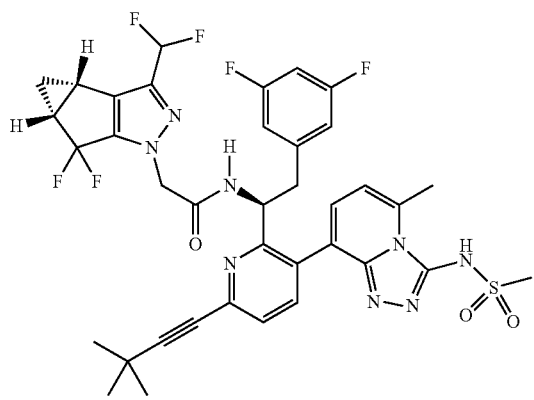

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3,3-dimethylbut-1-yn-1-yl)-3-(5-methyl-3-(methylsulfonamido)-[1,2,4]triazolo[4,3-a]pyridin-8-yl)pyridin-2-yl)ethyl)acetamide (133)

The title compound (133) was prepared according to the method presented for the synthesis of compound 19D of Example 19 utilizing compound 116A. $^1$H NMR (400 MHz, Methanol-d$_4$): δ 7.66 (d), 7.41 (dd), 7.02-6.90 (m), 6.71 (t), 6.63 (t), 6.56-6.37 (m), 5.41-5.23 (m), 4.74 (d), 3.23-2.75 (m), 3.06 (s), 2.92 (s), 2.46 (ddd), 1.45-1.32 (m), 1.39 (s), 1.11-1.01 (m). MS (m/z): 785.31 [M+H]$^+$.

Example 134

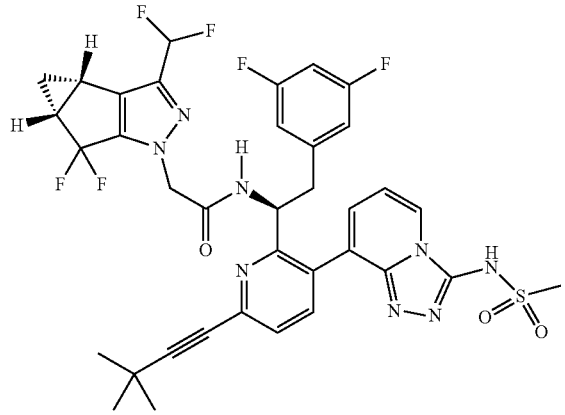

134

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3,3-dimethylbut-1-yn-1-yl)-3-(3-(methylsulfonamido)-[1,2,4]triazolo[4,3-a]pyridin-8-yl)pyridin-2-yl)ethyl)acetamide (134)

The title compound (134) was prepared according to the method presented for the synthesis of compound 19D of Example 19 utilizing compound 116B. $^1$H NMR (400 MHz, Methanol-$d_4$) δ 8.69 (d), 8.04 (dd), 7.71 (d), 7.43 (d), 7.21-7.12 (m), 6.91 (t), 6.70 (t), 6.62 (t), 6.50-6.41 (m), 5.41-5.26 (m), 4.74 (s), 3.25-3.10 (m), 3.06 (s), 2.55-2.36 (m), 1.43-1.21 (m), 1.40 (s), 1.14-0.96 (m). MS (m/z): 771.12 [M+H]$^+$.

Example 135

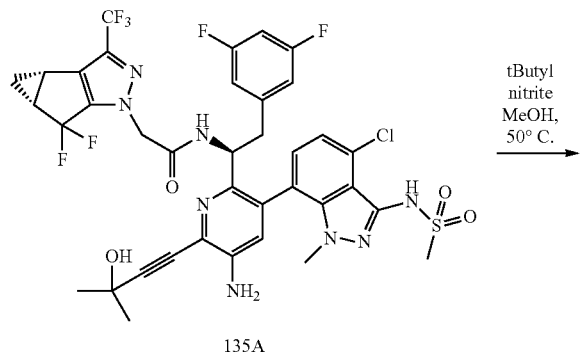

135A tButyl nitrite
MeOH,
50° C.

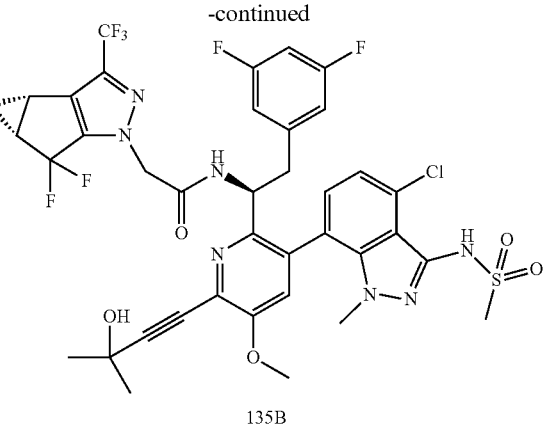

135B

Synthesis of N—((S)-1-(5-amino-3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)-2-((3bS,4aR)-5,5-difluoro-3-(trifluoromethyl)-3b,4,4a,5-tetrahydro-H-cyclopropa[3,4]cyclopenta[1,2-c]pyrazol-1-yl)acetamide (135A)

The title compound (135A) may be prepared analogously to the method presented for the synthesis of compound 139A of Example 139 utilizing 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid and compound 182H. MS (m/z): 853.26 [M+H]$^+$.

Synthesis of N—((S)-1-(3-(4-chloro-1-methyl-3-(methylsulfonamido)-1H-indazol-7-yl)-6-(3-hydroxy-3-methylbut-1-yn-1-yl)-5-methoxypyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (135B)

To a solution of compound 135A (25 mg, 0.029 mmol) in MeOH (1 mL) was added t-butyl nitrite (15 mg, 0.15 mmol). The resulting solution was heated at 50° C. for 2 h. The volatiles were removed in vacuo and residue was purified by reverse phase HPLC to yield the title compound as a mixture of atropisomers. $^1$H NMR (400 MHz, Methanol-$d_4$) δ 8.73 (dd), 7.69 (dd), 7.53 (dd), 7.34 (d), 7.22-7.10 (m), 7.05 (dd), 6.76 (t), 6.52-6.23 (m), 4.82-4.67 (m), 3.87 (d), 3.37 (s), 3.24 (d), 3.17-3.04 (m), 2.97 (q), 2.49 (s), 1.71-1.55 (m), 1.49-1.31 (m), 1.07 (s). MS (m/z) 868.24 [M+H]$^+$.

Examples 136

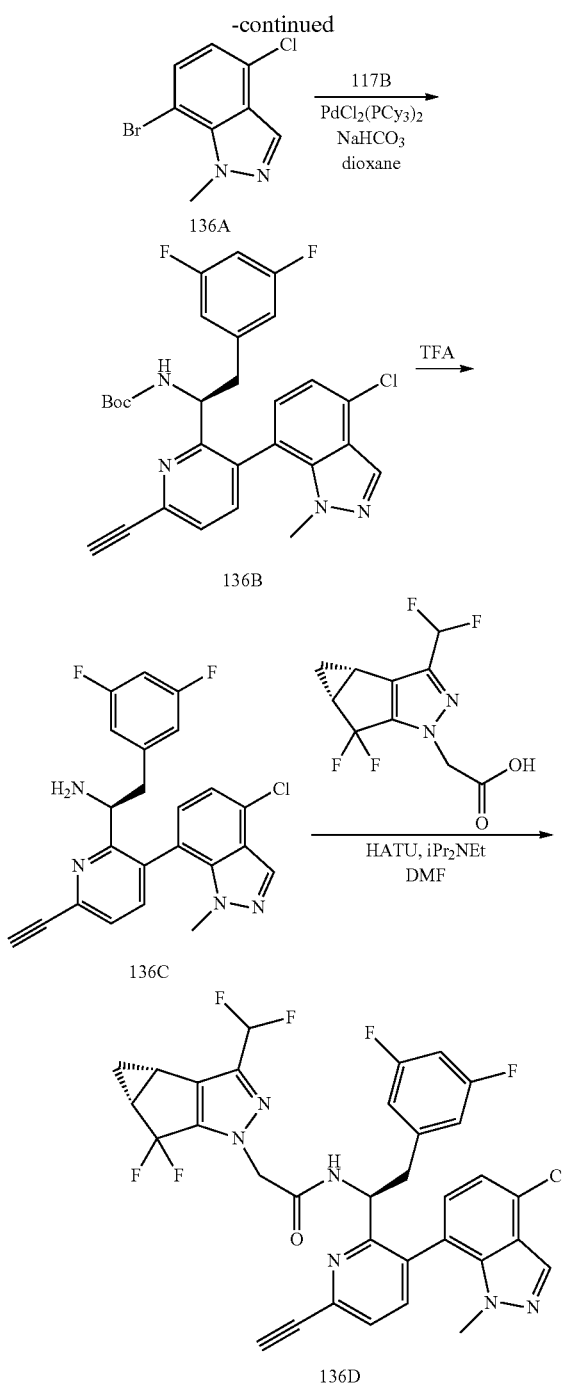

Synthesis of 7-bromo-4-chloro-1-methyl-1H-indazole (136A)

Compound 19B (150 mg, 0.58 mmol) was dissolved in Me-THF and treated with tert-butyl nitrite (0.21 ml, 1.73 mmol). The reaction was heated to 75° C. for 2 h. The reaction was diluted with EtOAc and saturated aqueous NaCl. The organics were separated, dried, and removed in vacuo and the residue was purified by column chromatography on silica to provide the title compound (136A). MS (m/z) 247.0 [M+H]$^+$.

Synthesis of (S)-tert-butyl (1-(3-(4-chloro-1-methyl-1H-indazol-7-yl)-6-ethynylpyridin-2-yl)-2-(3,5-difluorophenyl)ethyl)carbamate (136B)

In a microwave vial, (S)-(2-(1-((tert-butoxycarbonyl)amino)-2-(3,5-difluorophenyl)ethyl)-6-(3-hydroxy-3-methylbut-1-yn-1-yl)pyridin-3-yl)boronic acid (117B, 35 mg, 0.08 mmol) was combined with 7-bromo-4-chloro-1-methyl-1H-indazole (136A, 19 mg, 0.08 mmol), PdCl$_2$(PCy$_3$)$_2$ (6 mg), and NaHCO$_3$ (228 µl of 1 M aqueous solution) in dioxane (1 ml). Argon was bubbled into the reaction solution for 5 min. The reaction was heated in a microwave reactor at 155° C. for 15 min. After cooling to ambient temperature, the reaction was partitioned between EtOAc and water. The organics were separated, dried, and removed in vacuo and the residue was purified by column chromatography on silica to provide the title compound (136B). MS (m/z) 523.2 [M+H]$^+$.

Synthesis of N—((S)-1-(3-(4-chloro-1-methyl-1H-indazol-7-yl)-6-ethynylpyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (136C)

The title compound (136C) was prepared according to the method presented for the synthesis of compound 19F of Example 19 utilizing compound 136B. MS (m/z): 423.1 [M+H]$^+$.

Synthesis of N—((S)-1-(3-(4-chloro-1-methyl-1H-indazol-7-yl)-6-ethynylpyridin-2-yl)-2-(3,5-difluorophenyl)ethyl)-2-((3bS,4aR)-3-(difluoromethyl)-55-difluoro-3b,4,4a,5-tetrahydro-1H-cyclopropa[3,4]cyclopenta[1,2-c]pyrazol-1-yl)acetamide (136D)

The title compound (136D) was prepared according to the method presented for the synthesis of compound 10A of Example 10 utilizing compound 136C and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (400 MHz, DMSO-d$_6$) δ 8.89 (d), 8.23 (s), 7.87 (t), 7.66 (dd), 7.43 (d), 7.29 (d), 7.07-6.99 (m), 6.98-6.96 (m), 6.94 (t), 5.25-5.11 (m), 4.90-4.62 (m), 3.27-2.97 (m), 2.61-2.49 (m), 1.44-1.30 (m), 0.95-0.84 (m). MS (m/z): 669.1 [M+H]$^+$.

Example 137

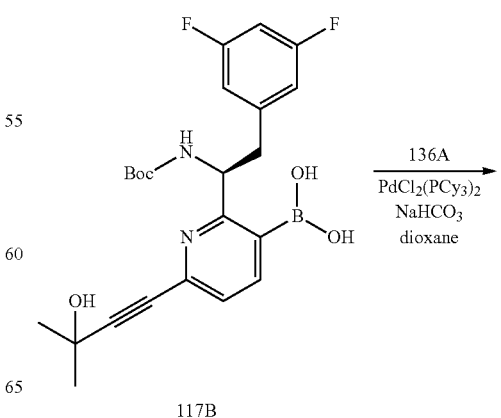

361

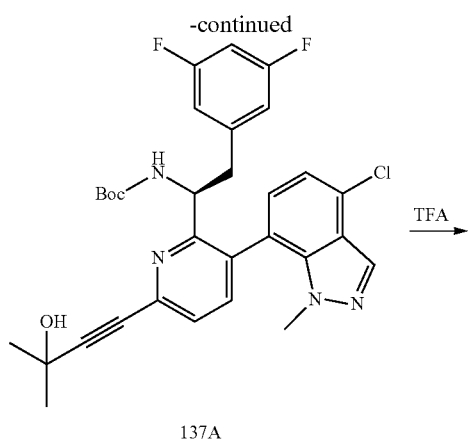

137A

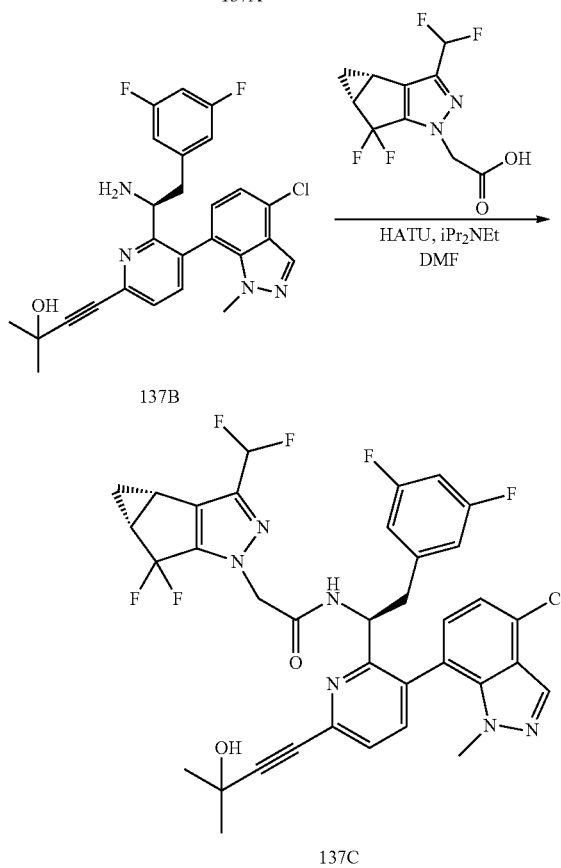

137B

137C

Synthesis of (S)-tert-butyl (1-(3-(4-chloro-1-methyl-1H-indazol-7-yl)-6-ethynylpyridin-2-yl)-2-(3,5-difluorophenyl)ethyl)carbamate (137A)

In a microwave vial, (S)-(2-(1-((tert-butoxycarbonyl)amino)-2-(3,5-difluorophenyl)ethyl)-6-(3-hydroxy-3-methylbut-1-yn-1-yl)pyridin-3-yl)boronic acid (117B, 35 mg, 0.08 mmol) was combined with 7-bromo-4-chloro-1-methyl-1H-indazole (136A, 19 mg, 0.08 mmol), PdCl$_2$(PPh$_3$)$_2$ (5 mg), and K$_2$CO$_3$ (95 µl of 2 M aqueous solution) in dioxane (1 ml). Argon was bubbled into the reaction solution for 5 min. The reaction was heated in a microwave reactor at 115° C. for 15 min. After cooling to ambient temperature, the reaction was partitioned between EtOAc and water. The organics were separated, dried, and removed in vacuo and the residue was purified by column chromatography on silica to provide the title compound as a mixture of atropisomers. MS (m/z) 581.0 [M+H]$^+$.

362

Synthesis of (S)-4-(6-(1-amino-2-(3,5-difluorophenyl)ethyl)-5-(4-chloro-1-methyl-1H-indazol-7-yl)pyridin-2-yl)-2-methylbut-3-yn-2-ol (137B)

The title compound (137B) was prepared as a mixture of atropisomers according to the method presented for the synthesis of compound 19F of Example 19 utilizing compound 137A. MS (m/z): 481.1 [M+H]$^+$.

Synthesis of N—((S)-1-(3-(4-chloro-1-methyl-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (137C)

The title compound (137C) was prepared as a mixture of atropisomers according to the method presented for the synthesis of compound 10A of Example 10 utilizing compound 137B and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (400 MHz, Methanol-d$_4$) δ 8.75-8.70 (m), 8.70-8.62 (m), 8.10-8.05 (m), 7.69 (dd), 7.53 (dd), 7.18 (s), 7.08 (d), 6.89-6.52 (m), 6.42 (d), 6.39-6.30 (m), 5.31-5.20 (m), 5.04-4.91 (m), 4.70 (d), 3.48 (t), 3.40 (s), 3.19-3.07 (m), 3.04 (s), 2.96 (dd), 2.54-2.38 (m), 1.64 (d), 1.44-1.27 (m), 1.14-0.96 (m). MS (m/z): 727.1 [M+H]$^+$.

Example 138

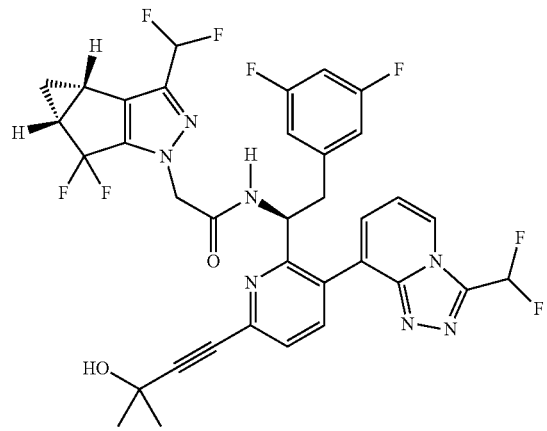

138

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-1-(3-(3-(difluoromethyl)-[1,2,4]triazolo[4,3-a]pyridin-8-yl)-6-(3-hydroxy-3-methylbut-1-yn-1-yl)pyridin-2-yl)-2-(3,5-difluorophenyl)ethyl)acetamide (138)

The title compound (138) was prepared according to the method presented for the synthesis of compound 106E of Example 106 utilizing compound 117B and 8-bromo-5-chloro-3-(difluoromethyl)-[1,2,4]triazolo[4,3-a]pyridine. $^1$H NMR (400 MHz, Methanol-d$_4$) δ 8.61 (dd), 7.78 (dd), 7.55 (d), 7.48 (t), 7.46-7.37 (m), 7.33-7.18 (m), 6.83-6.74 (m), 6.67 (t), 6.62-6.47 (m), 6.46-6.35 (m), 5.38-5.03 (m), 4.75-4.57 (m), 3.26-3.17 (m), 3.17-2.98 (m), 2.44 (ddd), 1.61 (d), 1.42-1.30 (m), 1.06-0.96 (m, 1H). MS (m/z): 730.22 [M+H]$^+$.

Example 139

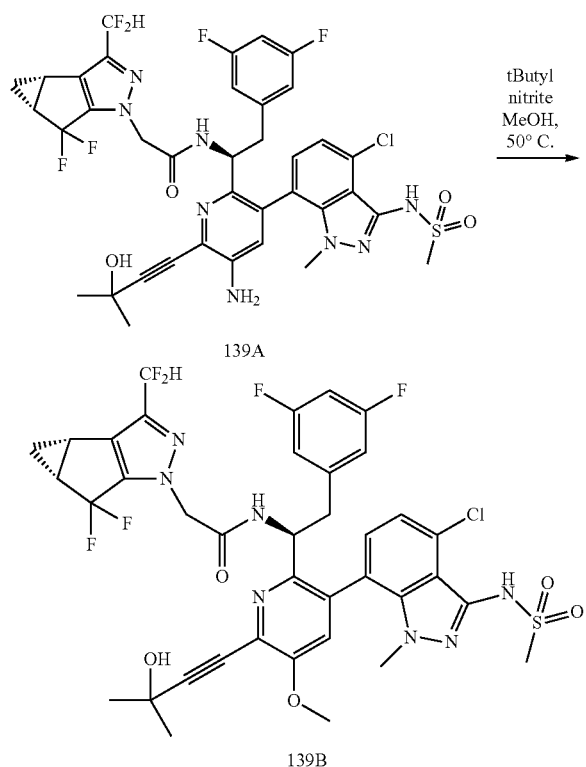

Synthesis of N—((S)-1-(5-amino-3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (139A)

The title compound (139A) was prepared as a mixture of atropisomers according to the method presented for the synthesis of compound 19G of Example 19 utilizing compound 182H. MS (m/z): 835.67 [M+H]+.

Synthesis of N—((S)-1-(3-(4-chloro-1-methyl-3-(methylsulfonamido)-1H-indazol-7-yl)-6-(3-hydroxy-3-methylbut-1-yn-1-yl)-5-methoxypyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (139B)

The title compound (139B) was prepared as a mixture of atropisomers according to the method presented for the synthesis of compound 135A of Example 135 utilizing compound 139A. ¹H NMR (400 MHz, Methanol-d₄) δ 8.62 (t), 7.75-7.47 (m), 7.34 (d), 7.21-6.96 (m), 6.90-6.64 (m), 6.53-6.21 (m), 4.78-4.60 (m), 3.86 (d), 3.36 (s), 3.24 (d), 3.15-3.07 (m), 3.01-2.90 (m), 2.61-2.35 (m), 1.64 (d), 1.37 (q), 1.28 (d), 1.03 (d). MS (m/z) 850.52 [M+H]+.

Example 140

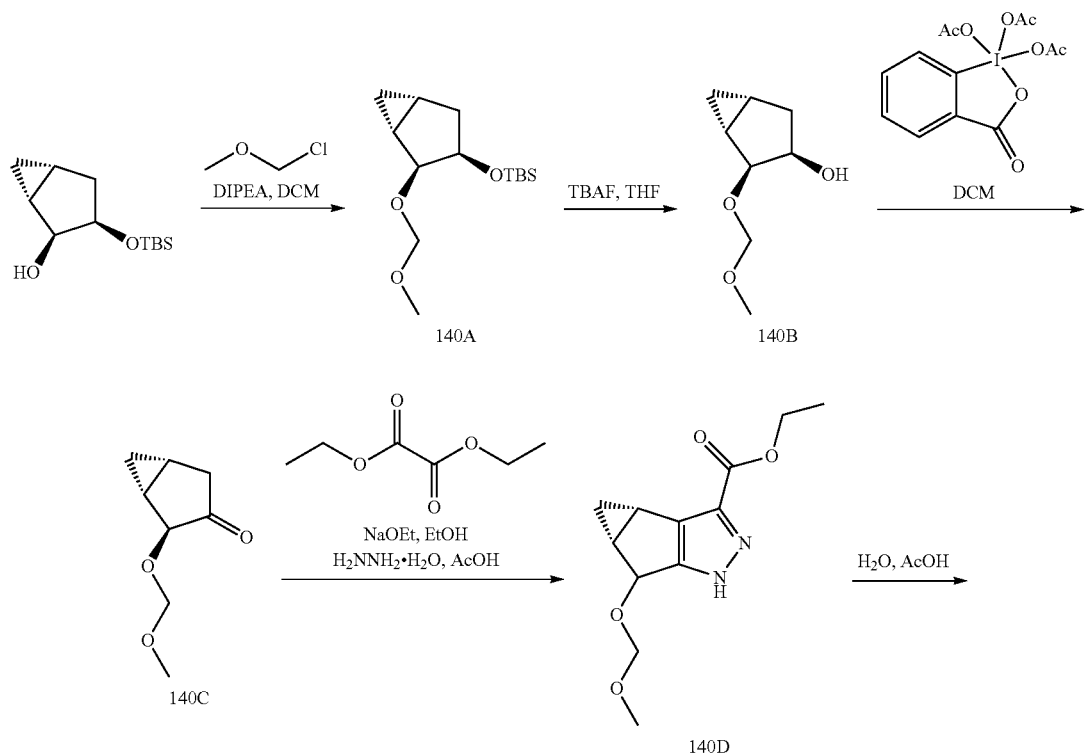

-continued
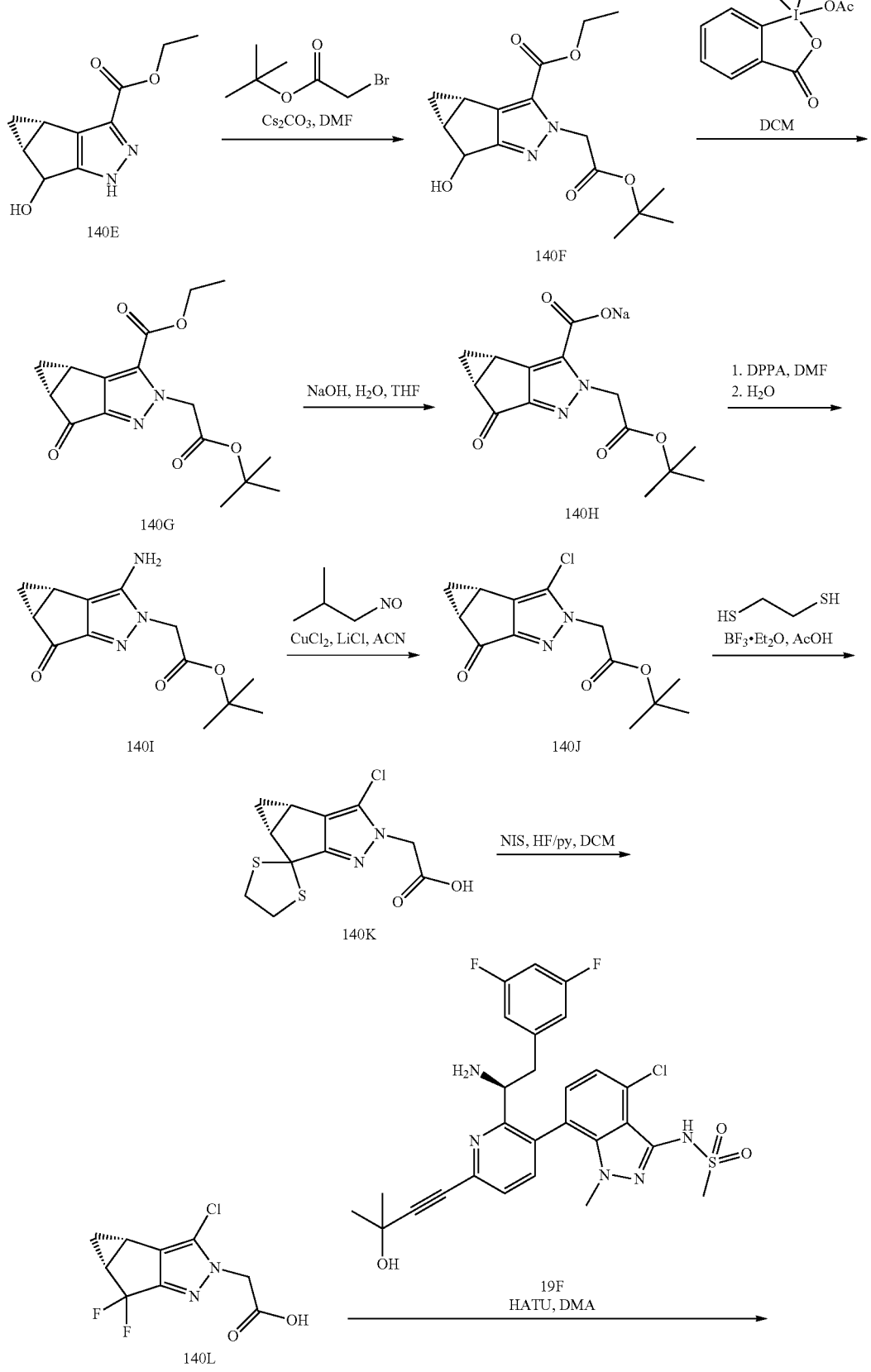

-continued

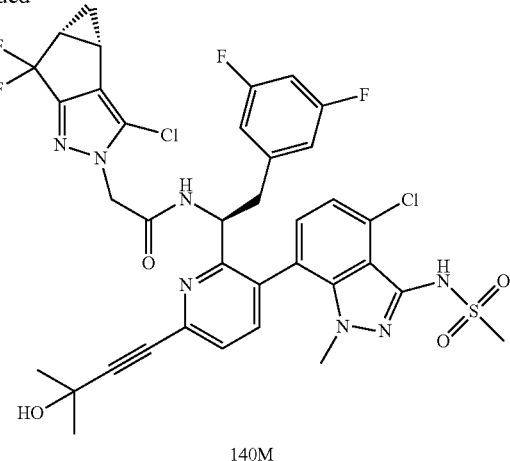

140M

Synthesis of tert-butyl(((1R,2S,3R,5R)-2-(methoxymethoxy)bicyclo[3.1.0]hexan-3-yl)oxy)dimethylsilane (140A)

To a solution of (1R,2S,3R,5R)-3-((tert-butyldimethylsilyl)oxy)bicyclo[3.1.0]hexan-2-ol (10.4 g, 45.6 mmol, synthesis previous reported in JACS, 2007, 129, 4456-4462), DIPEA (31.7 ml, 182.4 mmol), and DMAP (556 mg, 4.56 mmol) in dichloromethane (90 mL) was added chloromethyl methyl ether (14.6 ml, 182.4 mmol) at 0° C. The mixture was warmed to room temperature and stirred overnight. The resulting solution was concentrated in vacuo and extracted twice with EtOAc and water. The combined organic layers were dried over MgSO$_4$, filtered, and concentrated in vacuo. The crude product was taken to next step without further purification. $^1$H NMR (400 MHz, Chloroform-d) δ 4.09-3.99 (m, 1H), 2.50-2.38 (m, 1H), 2.05-1.96 (m, 2H), 1.84-1.76 (m, 1H), 1.57 (s, 1H), 1.31-1.14 (m, 2H), 1.06-0.99 (m, 1H), 0.95-0.81 (m, 10H), 0.07 (dd, 6H).

Synthesis of (1R,2S,3R,5R)-2-(methoxymethoxy)bicyclo[3.1.0]hexan-3-ol (140B)

To a crude solution of tert-butyl(41R,2S,3R,5R)-2-(methoxymethoxy)bicyclo[3.1.0]hexan-3-yl)oxy)dimethylsilane (140A) (12.4 g) in THF (100 ml) was added 1M tetrabutylammonium fluoride in THF (64 mL). After stirring at room temperature for 2 h, the mixture was partially concentrated in vacuo, and extracted twice with EtOAc and water. The combined organic layers were washed with brine, dried with MgSO$_4$, filtered, and concentrated in vacuo. The resulting mixture was slurried in 25% EtOAc and hexanes, solids filtered, and the filtrate was purified by silica gel chromatography to give the title compound. $^1$H NMR (400 MHz, Chloroform-d) δ 4.85-4.73 (m, 2H), 4.01-3.92 (m, 1H), 3.87-3.74 (m, 1H), 3.47-3.41 (m, 3H), 2.16-2.06 (m, 1H), 1.73-1.61 (m, 1H), 1.52-1.35 (m, 2H), 0.53-0.42 (m, 1H), 0.19-0.11 (m, 1H).

Synthesis of (1R,2S,5R)-2-(methoxymethoxy)bicyclo[3.1.0]hexan-3-one (140C)

To a mixture of (1R,2S,3R,5R)-2-(methoxymethoxy)bicyclo[3.1.0]hexan-3-ol (140B) (5.8 g, 36.7 mmol) and NaHCO$_3$ (4.62 g, 55.1 mmol) in dichloromethane (75 ml) was added in portions Dess-Martin periodinane (17.1 g, 40.37 mmol) at −15° C. The mixture was slowly warmed to room temperature and stirred for 1 h. Upon completion, the reaction was cooled to 0° C. and 1M aqueous NaHCO$_3$ (150 ml) was added. The solution was stirred until evolution of gas ceased, and the organic layer was separated. The aqueous layer was back extracted twice with dichloromethane, the organic layers were combined, dried with Na$_2$SO$_4$, filtered, and concentrated in vacuo. The resulting mixture was slurried in 25% Et$_2$O and hexanes, solids filtered, and the filtrate was concentrated in vacuo then, purified by silica gel chromatography to give the title compound. $^1$H NMR (400 MHz, Chloroform-d) δ 4.89-4.62 (m, 2H), 3.66 (s, 1H), 3.45-3.35 (m, 3H), 2.81-2.69 (m, 1H), 2.19-2.08 (m, 1H), 1.73-1.54 (m, 2H), 1.03-0.92 (m, 1H), —0.00-0.11 (m, 1H).

Synthesis of (3bS,4aR)-ethyl 5-(methoxymethoxy)-3b,4,4a,5-tetrahydro-1H-cyclopropa[3,4]cyclopenta[1,2-c]pyrazole-3-carboxylate (140D)

To a solution of (1R,2S,5R)-2-(methoxymethoxy)bicyclo[3.1.0]hexan-3-one (140C) (4.4 g, 28.2 mmol) in ethanol (28 ml) was added a solution of 21% NaOEt in EtOH (11.0 ml, 29.6 mmol) at 0° C. After stirring at room temperature for 5 minutes, diethyl oxalate (4.02 ml, 29.6 mmol) was added, and the reaction was stirred at 70° C. for 45 minutes. Upon completion, the mixture was concentrated in vacuo, dissolved in acetic acid (15 ml) and water (2 ml), and hydrazine hydrate (2.82 g, 56.4 mmol) was slowly added at 0° C. The reaction was heated in a microwave reactor at 120° C. for 10 minutes. The mixture was concentrated in vacuo and extracted with twice with 2-methyltetrahydrofuran and water. The organic layers were combined and washed with water. The organic layer was dried with Na$_2$SO$_4$, filtered, concentrated, and purified by silica gel chromatography to give the title compound. MS (m/z) 252.84 [M+H]$^+$.

Synthesis of (3bS,4aR)-ethyl 5-hydroxy-3b,4,4a,5-tetrahydro-1H-cyclopropa[3,4]cyclopenta[1,2-c]pyrazole-3-carboxylate (140E)

A solution of (3bS,4aR)-ethyl 5-(methoxymethoxy)-3b,4,4a,5-tetrahydro-1H-cyclopropa[3,4]cyclopenta[1,2-c]pyrazole-3-carboxylate (140D) (1.2 g, 4.76 mmol) in 1:1 AcOH:H$_2$O (5 ml) was heated in a microwave reactor at 130° C. for 10 minutes. The resulting mixture was concentrated in vacuo and extracted with three times with EtOAc and water. The combined organic layers were dried with Na$_2$SO$_4$, filtered, concentrated in vacuo, and partially purified by silica gel chromatography eluting with ethyl acetate and hexanes. MS (m/z) 208.98 [M+H]$^+$.

Synthesis of (3bS,4aR)-ethyl 2-(2-(tert-butoxy)-2-oxoethyl)-5-hydroxy-3b,4,4a,5-tetrahydro-2H-cyclopropa[3,4]cyclopenta[1,2-c]pyrazole-3-carboxylate (140F)

To a solution of (3bS,4aR)-ethyl 5-hydroxy-3b,4,4a,5-tetrahydro-1H-cyclopropa[3,4]cyclopenta[1,2-c]pyrazole-3-carboxylate (140E) (990 mg) in DMF (10 ml) was added cesium carbonate (2.32 g, 7.14 mmol) followed by tert-butyl bromoacetate (0.70 ml, 4.76 mmol). After heating the reaction at 45° C. for 1 h, the resulting mixture was extracted with EtOAc and water. The organic layer was dried with Na$_2$SO$_4$, filtered, concentrated in vacuo, and purified by silica gel chromatography to give the title compound. MS (m/z) 322.83 [M+H]$^+$.

Synthesis of (3bS,4aR)-ethyl 2-(2-(tert-butoxy)-2-oxoethyl)-5-oxo-3b,4,4a,5-tetrahydro-2H-cyclopropa[3,4]cyclopenta[1,2-c]pyrazole-3-carboxylate (140G)

To a solution of (3bS,4aR)-ethyl 2-(2-(tert-butoxy)-2-oxoethyl)-5-hydroxy-3b,4,4a,5-tetrahydro-2H-cyclopropa[3,4]cyclopenta[1,2-c]pyrazole-3-carboxylate (140F) (0.27 g, 0.83 mmol) in DCM (10 ml) was added Dess Martin periodinane (0.34 g, 0.91 mmol). After stirring at room temperature for 3 h, mixture was solid loaded onto silica gel and purified by silica gel chromatography to give the title compound. MS (m/z) 320.74 [M+H]$^+$.

Synthesis of sodium (3bS,4aR)-2-(2-(tert-butoxy)-2-oxoethyl)-5-oxo-3b,4,4a,5-tetrahydro-2H-cyclopropa[3,4]cyclopenta[1,2-c]pyrazole-3-carboxylate (140H)

To a solution of (3bS,4aR)-ethyl 2-(2-(tert-butoxy)-2-oxoethyl)-5-oxo-3b,4,4a,5-tetrahydro-2H-cyclopropa[3,4]cyclopenta[1,2-c]pyrazole-3-carboxylate (140G) (0.22 g, 0.69 mmol) in THF (2 ml) was added 0.25M aqueous NaOH (1.87 ml). The reaction was heated at 60° C. for 1.5 h. Upon completion, the reaction was concentrated in vacuo, and dried under vacuum. The crude product was taken to next step without further purification. MS (m/z) 291.04 [M–H]$^-$.

Synthesis of tert-butyl 2-((3bS,4aR)-3-amino-5-oxo-3b,4,4a,5-tetrahydro-2H-cyclopropa[3,4]cyclopenta[1,2-c]pyrazol-2-yl)acetate (140I)

The title compound (140I) was prepared according to the method presented for the synthesis of compound (148B) of Example 148 utilizing sodium (3bS,4aR)-2-(2-(tert-butoxy)-2-oxoethyl)-5-oxo-3b,4,4a,5-tetrahydro-2H-cyclopropa[3,4]cyclopenta[,2-c]pyrazole-3-carboxylate (140H). MS (m/z) 263.86 [M+H]$^+$.

Synthesis of tert-butyl 2-((3bS,4aR)-3-chloro-5-oxo-3b,4,4a,5-tetrahydro-2H-cyclopropa[3,4]cyclopenta[1,2-c]pyrazol-2-yl)acetate (140J)

The title compound (140J) was prepared according to the method presented for the synthesis of compound (149) of Example 149 utilizing tert-butyl 2-((3bS,4aR)-3-amino-5-oxo-3b,4,4a,5-tetrahydro-2H-cyclopropa[3,4]cyclopenta[1,2-c]pyrazol-2-yl)acetate (140I). MS (m/z) 282.73 [M+H]$^+$.

Synthesis of 2-((3bS,4aR)-3-chloro-4,4a-dihydrospiro[cyclopropa[3,4]cyclopenta[1,2-c]pyrazole-5,2'-[1,3]dithiolane]-2(3bH)-yl)acetic acid (140K)

To a solution of tert-butyl 2-((3bS,4aR)-3-chloro-5-oxo-3b,4,4a,5-tetrahydro-2H-cyclopropa[3,4]cyclopenta[1,2-c]pyrazol-2-yl)acetate (140J) (19 mg, 0.07 mmol), 1,2-ethanedithiol (11.3 µl, 0.13 mmol), and acetic acid (19.2 µl, 0.34 mmol) in dichloromethane (400 µl) was added boron trifluoride diethyl etherate (20.7 al, 0.17 mmol). After stirring at room temperature for 2 h, the mixture was dry loaded onto silica and purified by silica gel chromatography to give the title compound as a partially purified product. MS (m/z) 302.93 [M+H]$^+$.

Synthesis of 2-((3bS,4aR)-3-chloro-5,5-difluoro-3b,4,4a,5-tetrahydro-2H-cyclopropa[3,4]cyclopenta[1,2-c]pyrazol-2-yl)acetic acid (140L)

To a solution of N-iodosuccinimide (27.9 mg, 0.12 mmol) in dichloromethane (0.10 ml) was added dropwise 70% HF in pyridine (0.10 ml) at –78° C. After stirring for 15 minutes, a suspension of 140K (15 mg, 0.05 mmol) in dichloromethane (0.10 ml) was added and the reaction was gradually warmed to 0° C. over 1 h. The mixture was extracted with 2-methyltetrahydrofuran and water. The organic layer was washed with brine, dried with Na$_2$SO$_4$, filtered, and concentrated in vacuo. The product was purified by preparative TLC eluting to give the title compound. MS (m/z) 249.05 [M+H]$^+$.

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-chloro-5,5-difluoro-3b,4,4a,5-tetrahydro-2H-cyclopropa[3,4]cyclopenta[1,2-c]pyrazol-2-yl)acetamide (140M)

The title compound (140M) was prepared as a mixture of atropisomers according to the method presented for the synthesis of compound (33F) of Example 33 utilizing 19F and 2-((3bS,4aR)-3-chloro-5,5-difluoro-3b,4,4a,5-tetrahydro-2H-cyclopropa[3,4]cyclopenta[1,2-c]pyrazol-2-yl)acetic acid (140L). $^1$H NMR (400 MHz, Methanol-d$_4$) δ 8.75 (t), 7.71 (dd), 7.54 (dd), 7.27-7.15 (m), 7.10 (d), 6.81-6.72 (m), 6.69-6.59 (m), 6.50 (d), 6.46-6.36 (m), 5.30-5.21 (m), 5.05-4.95 (m), 4.81 (s), 4.77 (s), 3.35 (s), 3.26 (s), 3.28-3.21 (m), 3.23 (s), 3.19-3.12 (m), 3.03 (s), 3.04-2.97 (m), 2.45-2.32 (m), 1.94 (s), 1.64 (s), 1.64 (s), 1.42-1.25 (m), 1.01-0.96 (m), 0.96-0.92 (m). MS (m/z) 804.14[M+H]$^+$.

Example 141
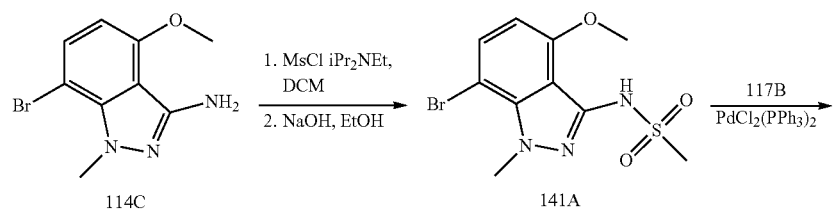
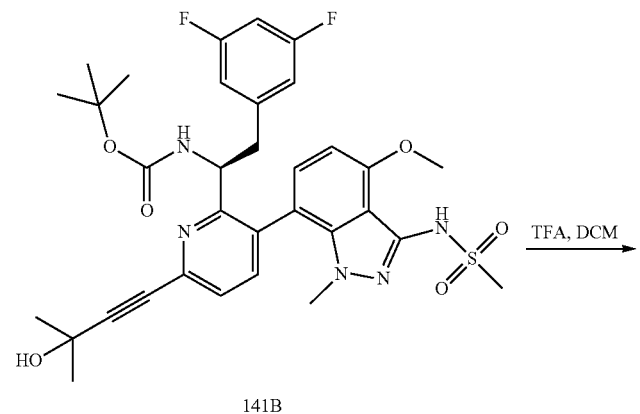
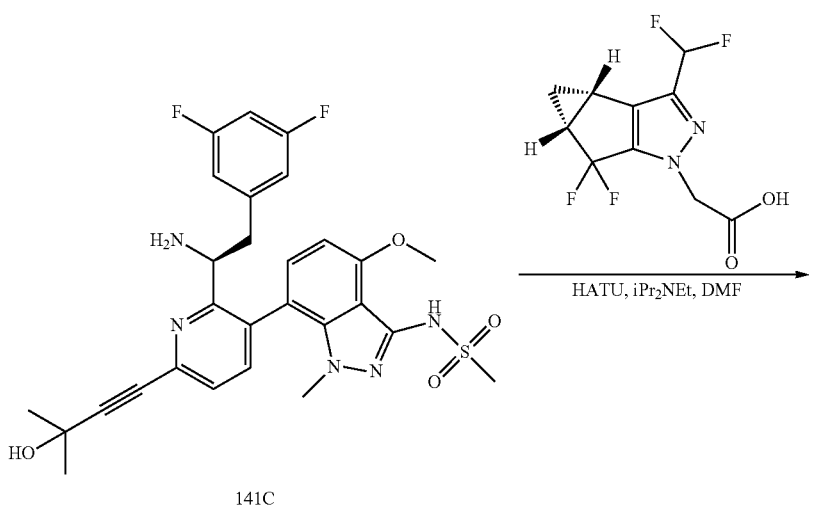
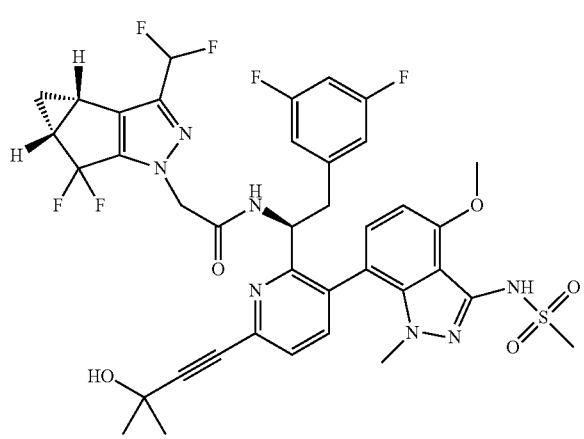

Synthesis of N-(7-bromo-4-methoxy-1-methyl-1H-indazol-3-yl)methanesulfonamide (141A)

The title compound (141A) was prepared according to the method presented for the synthesis of compound 19D of Example 19 utilizing 114C. MS (m/z) 334.1 [M+H]$^+$.

Synthesis of (S)-tert-butyl (2-(3,5-difluorophenyl)-1-(6-(3-hydroxy-3-methylbut-1-yn-1-yl)-3-(4-methoxy-1-methyl-3-(methylsulfonamido)-1H-indazol-7-yl)pyridin-2-yl)ethyl)carbamate (141B)

In a microwave vial, (117B, 30 mg, 0.07 mmol) was combined with (141A, 65 mg, 0.2 mmol), PdCl$_2$(PPh$_3$)$_2$ (5 mg, 0.007 mmol), and K$_2$CO$_3$ (0.2 ml of 2 M aqueous solution) in dioxane (1.5 ml) and DMF (0.1 ml). Nitrogen was bubbled into the reaction solution for 5 min. The reaction was heated in a microwave reactor at 120° C. for 15 min. After cooling to ambient temperature, the reaction was partitioned between EtOAc and brine. The organics were separated, dried, and removed in vacuo and the residue was purified by column chromatography on silica to provide the title compound as a mixture of atropisomers. MS (m/z) 670.3 [M+H]$^+$.

Synthesis of (S)—N-(7-(2-(1-amino-2-(3,5-difluorophenyl)ethyl)-6-(3-hydroxy-3-methylbut-1-yn-1-yl)pyridin-3-yl)-4-methoxy-1-methyl-1H-indazol-3-yl)methanesulfonamide (141C)

The title compound (141C) was prepared as a mixture of atropisomers according to the method presented for the synthesis of compound 19F of Example 19 utilizing 141B. MS (m/z) 570.1 [M+H]$^+$.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-hydroxy-3-methylbut-1-yn-1-yl)-3-(4-methoxy-1-methyl-3-(methylsulfonamido)-1H-indazol-7-yl)pyridin-2-yl)ethyl)acetamide (141D)

The title compound (141D) was prepared as a mixture of atropisomers according to the method presented for the synthesis of compound 10A of Example 10 utilizing 141C and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (Chloroform-d) δ: 7.91-7.84 (m), 7.64 (dd), 7.54-7.42 (m), 7.34-7.28 (m), 6.70 (t), 6.68-6.61 (m), 6.55-6.53 (m), 6.52-6.44 (m), 6.30-6.24 (m), 6.24-6.15 (m), 5.74-5.66 (m), 5.12-5.01 (m), 4.78 (d), 4.71 (d), 4.03 (s), 3.99 (s), 3.39 (d), 3.25 (s), 3.07 (s), 3.06-2.91 (m), 2.81-2.54 (m), 2.54-2.36 (m), 1.71 (s), 1.41 (dd), 1.30-1.22 (m), 1.22-1.10 (m). MS (m/z) 816.5 [M+H]$^+$.

Example 142

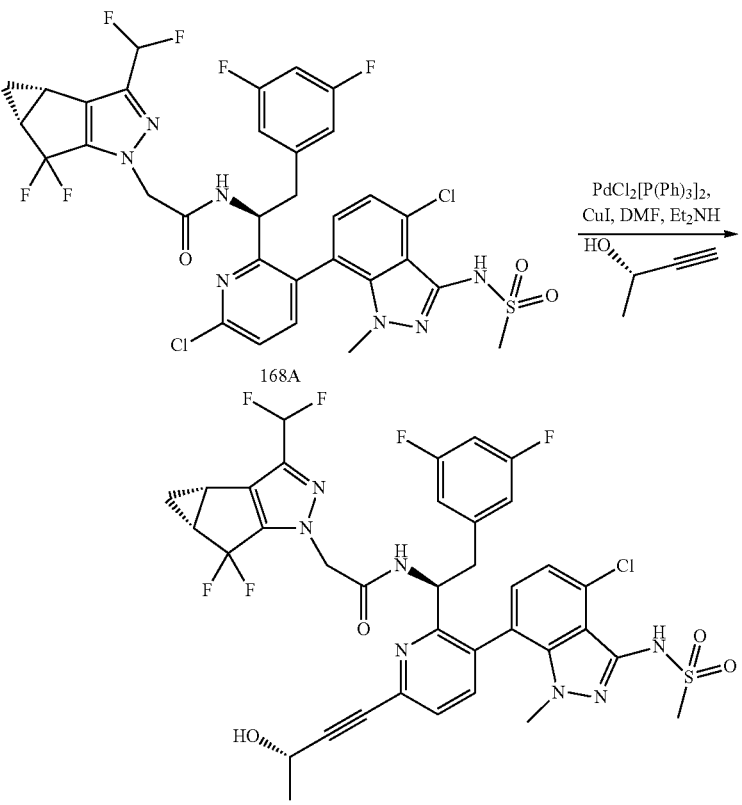

142

Synthesis of N—((S)-1-(3-(4-chloro-1-methyl-3-(methylsulfonamido)-1H-indazol-7-yl)-6-((S)-3-hydroxybut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (142)

To the reaction vial containing 168A (20 mg, 0.027 mmol) in DMF (1 mL) was added (S)-but-3-yn-2-ol (0.012 mL, 0.13 mmol), PdCl₂[P(Ph)₃]₂ (1.9 mg, 0.003 mmol), and diethylamine (0.02 mL, 0.27 mmol). The reaction mixture was flushed with argon gas for 5 min then sealed and heated in a microwave reactor to 125° C. for 20 min. Upon cooling, the reaction mixture was filtered and purified by reverse phase HPLC, to provide the title compound 142 as a mixture of atropisomers. ¹H NMR (400 MHz, cd₃od) ¹H NMR (400 MHz, cd3od) δ 8.62 (dd), 7.70 (dd), 7.54 (dd), 7.16 (s), 7.07 (d), 6.88-6.52 (m), 6.44-6.33 (m),5.31-5.23 (m), 5.02-4.92 (m), 4.82-4.64 (m), 3.33 (s), 3.24 (d), 3.18-3.08 (m), 3.04-2.91 (m), 2.53-2.39 (m), 1.57 (dd), 1.42-1.32 (m), 1.11-1.08 (m), 1.07-0.99 (m). MS (m/z) 806.1 [M+H]⁺.

Example 143

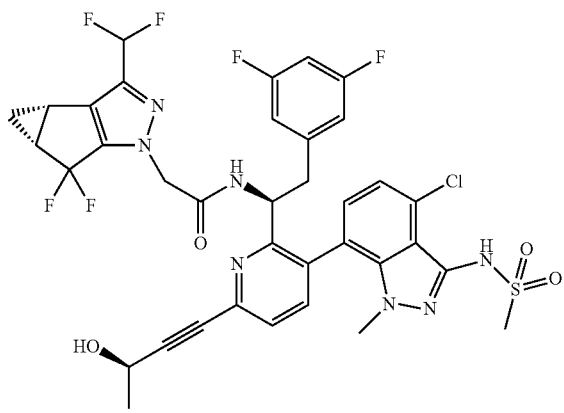

143

Synthesis of N—((S)-1-(3-(4-chloro-1-methyl-3-(methylsulfonamido)-1H-indazol-7-yl)-6-((R)-3-hydroxybut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (143)

The title compound (143) was prepared as a mixture of atropisomers according to the method presented for the synthesis of compound 142 of Example 142 utilizing (R)-but-3-yn-2-ol. ¹H NMR (400 MHz, cd₃od) δ 8.63 (dd), 7.70 (dd), 7.54 (dd), 7.16 (s), 7.06 (d), 6.88-6.52 (m), 6.44-6.33 (m),5.30-5.25 (m), 5.02-4.92 (m), 4.83-4.64 (m), 3.33 (s), 3.24 (d), 3.18-3.08 (m), 3.04-2.91 (m), 2.50-2.39 (m), 1.57 (dd), 1.38 (m), 1.05 (s), 1.03 (s). MS (m/z) 806.1 [M+H]⁺.

Example 144

144

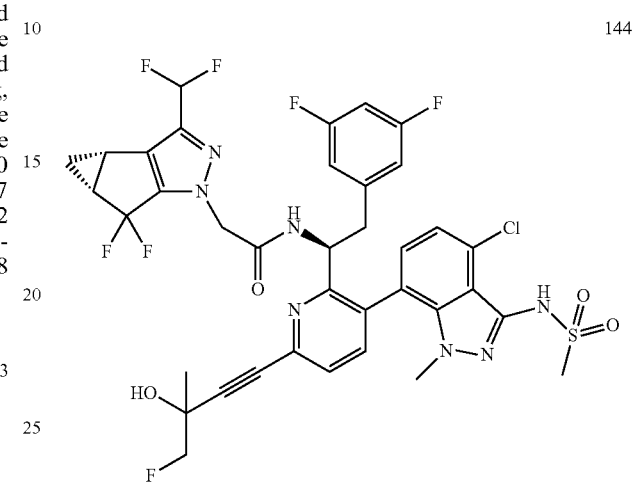

Synthesis of N-((1S)-1-(3-(4-chloro-1-methyl-3-(methylsulfonamido)-1H-indazol-7-yl)-6-(4-fluoro-3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide (144)

The title compound (144) was prepared as a mixture of atropisomers according to the method presented for the synthesis of compound 142 of Example 142 utilizing 1-fluoro-2-methylbut-3-yn-2-ol. ¹H NMR (400 MHz, cd₃od) δ 8.69 (t), 7.71 (dd), 7.56 (dd), 7.17 (s), 7.07 (d), 6.87-6.52 (m), 6.44-6.34 (m), 5.33-5.23 (m), 5.03-4.94 (m), 4.78-4.63 (m), 4.50 (d), 4.38 (d), 3.24 (d), 3.19-3.08 (m), 3.05-2.92 (m), 2.44 (ddd), 1.63 (dd), 1.39 (dd), 1.08 (s), 1.02 (s). MS (m/z) 839.1 [M+H]⁺.

Example 145

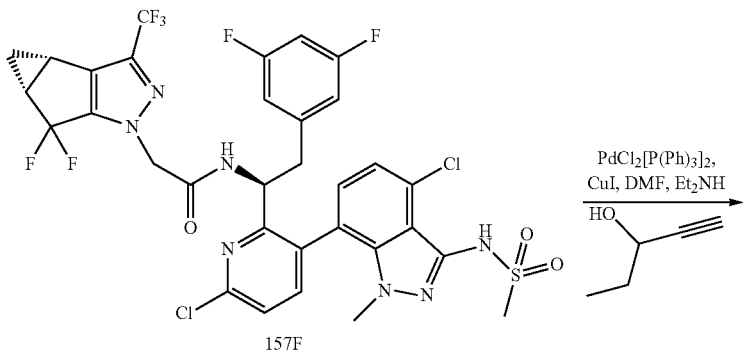

157F

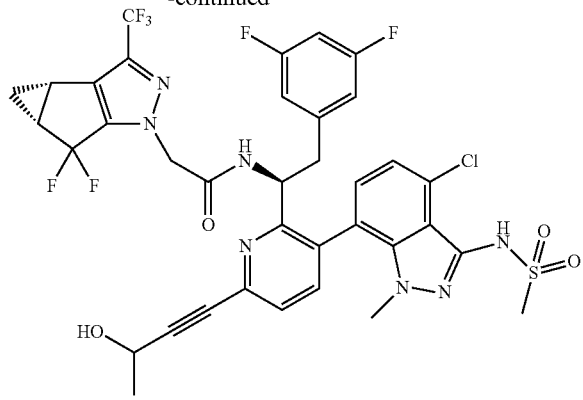

145

Synthesis of N-((1S)-1-(3-(4-chloro-1-methyl-3-(methylsulfonamido)-1H-indazol-7-yl)-6-(3-hydroxypent-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (145)

To the reaction vial containing 157F (20 mg, 0.025 mmol) in DMF (1 mL) was added pent-1-yn-3-ol (0.011 g, 0.13 mmol), Pd(PPh₃)₂Cl₂ (1.7 mg, 0.003 mmol), and diethylamine (0.02 mL, 0.25 mmol). The reaction mixture was flushed with argon gas for 5 min then sealed and heated in a microwave reactor to 125° C. for 20 min. Upon cooling, the reaction mixture was filtered and purified by reverse phase HPLC the title compound 145 as a mixture of atropisomers. $^1$H NMR (400 MHz, cd₃od) δ 8.72 (dd), 7.70 (dd), 7.54 (dd), 7.16 (d), 7.06 (d), 6.81-6.71 (m), 6.66-6.59 (m), 6.46-6.34 (m), 5.35-5.20 (m), 5.03-4.93 (m), 4.81-4.70 (m), 4.61-4.52 (m), 3.34 (s), 3.24 (d), 3.20-3.11 (m), 3.05-2.93 (m), 2.52-2.43 (m), 1.96-1.79 (m), 1.41 (dt), 1.13 (td). MS (m/z) 840.0 [M+H]⁺.

Example 146

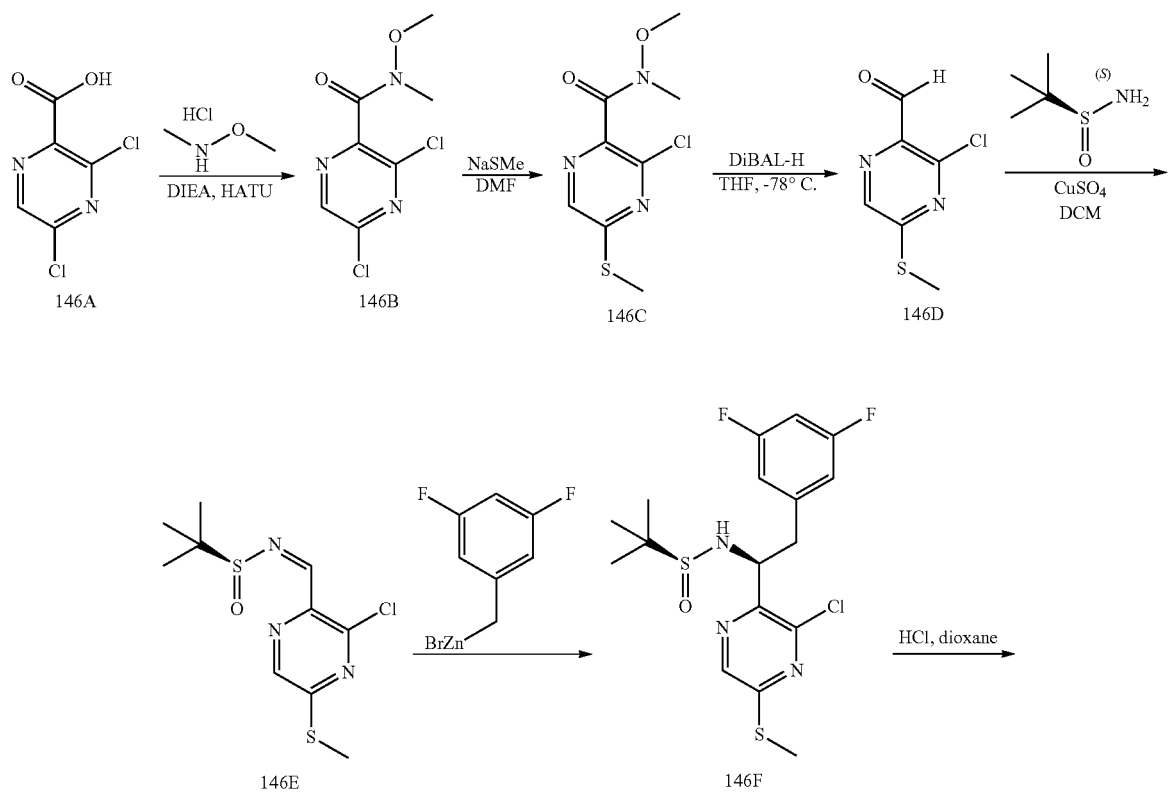

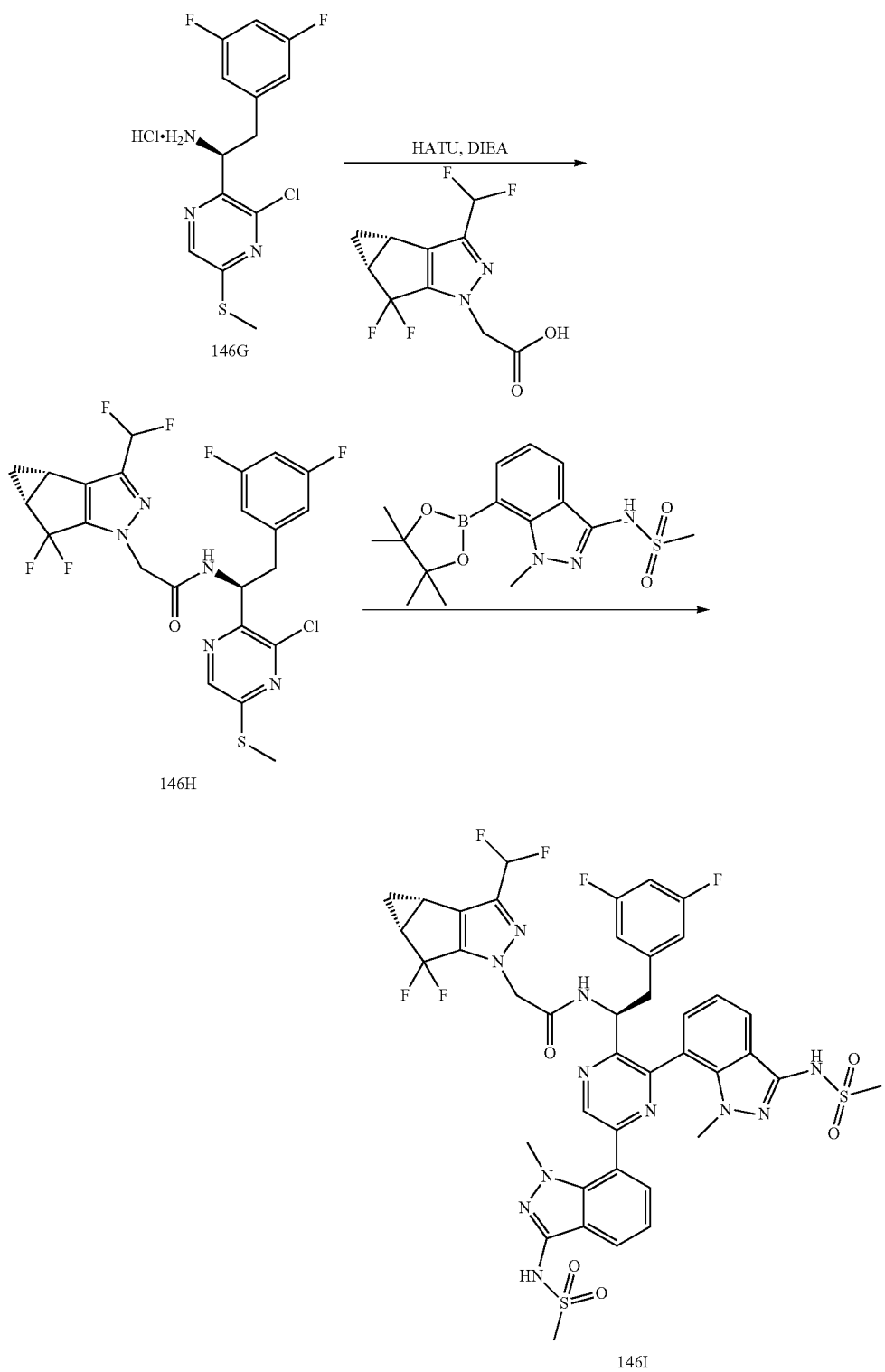

Synthesis of 3,5-dichloro-N-methoxy-N-methyl-pyrazine-2-carboxamide (146B)

To a solution of 146A (10 g, 51.82 mmol) and HATU (21.67 g, 57 mmol) in DMF (50 mL), DIEA (19.86 mL, 114 mmol) was added to the solution. After 30 minutes, N,O-dimethylhydroxyamine hydrochloride (6.09 g, 62.18 mmol) was added to the solution. The mixture was stirred for overnight. 300 mL of water was added and extracted with EtOAc three times (100 mL). The crude product was purified by flash column to provide the desired product. MS (m/z) 236 [M+H]$^+$.

Synthesis of 3-chloro-N-methyl-5-(methylthio)pyrazine-2-carboxamide (146C)

To a solution of 146B (2 g, 8.47 mmol) in DMF (10 mL), 1 eq. of sodium methanethiolate was added to the solution. After 5 hours, 0.5 eq. of sodium methanethiolate was added to the suspension. The reaction was stirred overnight then diluted with EtOAc and washed with NaHCO$_3$(aq) and brine. The organic layer was concentrated and purified by flash column to provide the title compound. MS (m/z) 248 [M+H]$^+$.

Synthesis of 3-chloro-5-(methylthio)pyrazine-2-carbaldehyde (146D)

To a solution of 146C (750 mg, 3.03 mmol) in THF at −78° C., DIBAL-H (3.33 mL, 3.33 mmol) in toluene was added to the solution slowly. Then, it was stirred for 2 hours at −78° C. 4 mL of 1 N HCl(aq) was added to the solution and warmed to 0° C. The mixture was stirred for 20 minutes at 0° C. then extracted with EtOAc twice. The organic layer was dried and concentrated and used without further purification. MS (m/z) 189 [M+H]$^+$.

Synthesis of (S,Z)—N-((3-chloro-5-(methylthio)pyrazin-2-yl)methylene)-2-methylpropane-2-sulfinamide (146E)

The title compound (146E) was prepared according to the method presented for the synthesis of compound 21C of Example 21 utilizing 146D. MS (m/z) 292 [M+H]$^+$.

Synthesis of (S)—N—((S)-1-(3-chloro-5-(methylthio)pyrazin-2-yl)-2-(3,5-difluorophenyl)ethyl)-2-methylpropane-2-sulfinamide (146F)

The title compound (146F) was prepared according to the method presented for the synthesis of compound 182D of Example 182 utilizing 146E. MS (m/z) 420 [M+H]$^+$.

Synthesis of (S)-1-(3-chloro-5-(methylthio)pyrazin-2-yl)-2-(3,5-difluorophenyl)ethanamine hydrochloride (146G)

The title compound (146G) was prepared according to the method presented for the synthesis of compound 21E of Example 21 utilizing 146F. MS (m/z) 316 [M+H]$^+$.

Synthesis of N—((S)-1-(3-chloro-5-(methylthio)pyrazin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (146H)

The title compound (146H) was prepared according to the method presented for the synthesis of compound 10A of Example 10 utilizing 146G and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. MS (m/z) 562 [M+H]$^+$.

Synthesis of N—((S)-1-(3,5-bis(1-methyl-3-(methylsulfonamido)-1H-indazol-7-yl)pyrazin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (146I)

The title compound (146I) was prepared as a mixture of atropisomers according to the method presented for the synthesis of compound 19E of Example 19 utilizing 33B and 146H. $^1$H NMR (400 MHz, Methanol-d4) δ 9.15 (d), 8.91 (s), 7.93 (t), 7.63 (d), 7.35-7.25 (m), 7.23-7.1 (m), 6.85-6.75 (m), 6.74-6.6 (m), 6.6-6.50 (m), 6.4-6.32 (m), 5.75-5.6 (m), 5.10-5.25 (m), 4.71 (s), 3.65 (s), 3.56 (s), 3.10-3.25 (m), 2.92 (s), 2.60-2.40 (m), 1.45-1.30 (m), 1.1-0.80 (m). MS (m/z) 928 [M+H]$^+$.

Example 147

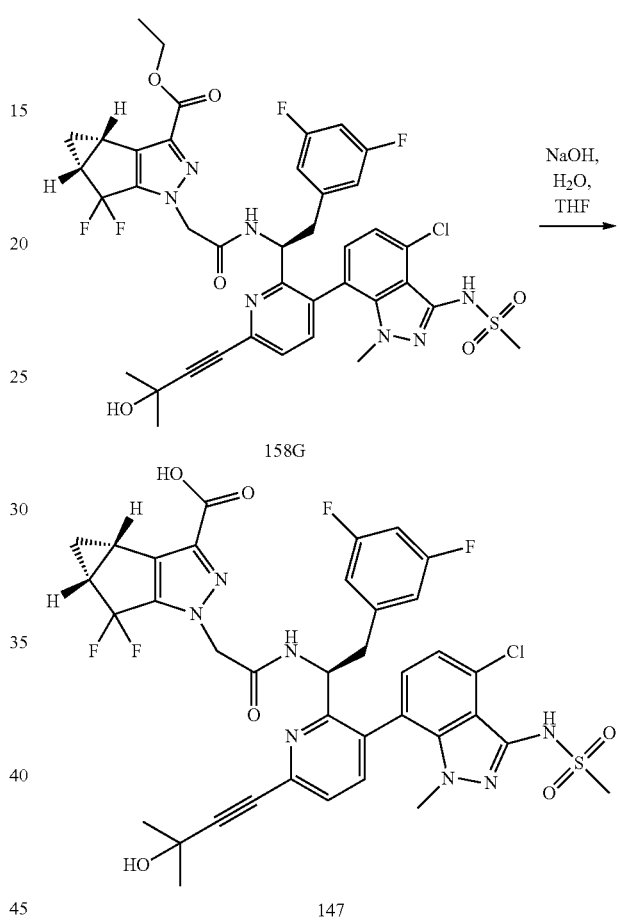

Synthesis of (3bS,4aR)-1-(2-(((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)amino)-2-oxoethyl)-5,5-difluoro-3b,4,4a,5-tetrahydro-1H-cyclopropa[3,4]cyclopenta[1,2-c]pyrazole-3-carboxylic acid (147)

A solution of 158G (0.41 g, 0.49 mmol) in THF (0.5 ml) was treated with 1M NaOH (2 ml). The reaction was stirred at room temperature for 1.5 h. The solution was acidified to pH=4 with AcOH and extracted with 2-MeTHF (2×5 mL) and water (5 mL). The organics were dried with Na$_2$SO$_4$, filtered, and concentrated. The crude material was purified by reverse phase HPLC to provide the product 147 as a mixture of atropisomers. $^1$H NMR (400 MHz, cd$_3$od) δ, 8.69 (d), 7.69 (d), 7.53 (dd), 7.19 (d), 7.06 (d), 6.81-6.71 (m), 6.63 (t), 6.46-6.35 (m), 5.32-5.23 (m), 5.03-4.93 (m), 4.85-4.80 (m), 4.72 (s), 3.36 (s), 3.26 (s), 3.23 (s), 3.22-3.09 (m), 3.05-2.92 (m), 2.63-2.51 (m), 2.50-2.39 (m), 1.65 (s), 1.64 (s), 1.49-1.35 (m), 1.15-1.07 (m), 1.08-0.97 (m). MS (m/z) 814.1 [M+H]$^+$.

Example 148

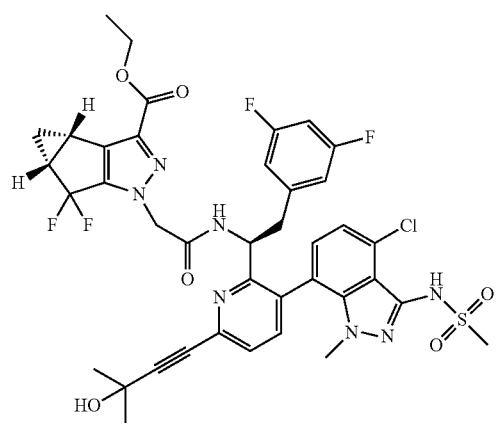

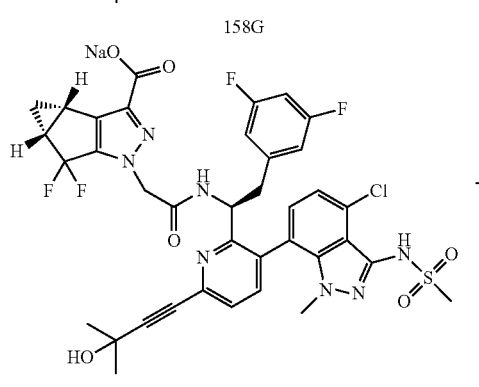

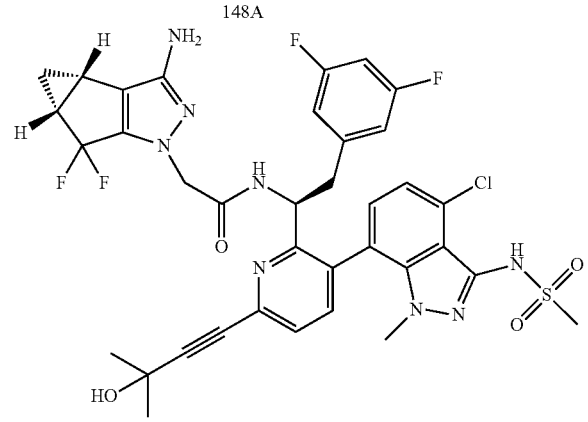

Synthesis of sodium (3bS,4aR)-1-(2-(((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)amino)-2-oxoethyl)-5,5-difluoro-3b,4,4a,5-tetrahydro-1H-cyclopropa[3,4]cyclopenta[1,2-c]pyrazole-3-carboxylate (148A)

To a solution of 158G (0.22 g, 0.26 mmol) in THF (0.65 ml) was added 1M NaOH (0.65 ml). The reaction was stirred at room temperature for 1.5 h. The solution was acidified to pH=4 with AcOH and extracted with with 2-MeTHF (2×5 mL) and brine (5 mL). The organic layer was washed with NaHCO$_3$ (10 mL). The organics were dried with Na$_2$SO$_4$, filtered, and concentrated. The product was taken to the next step without further purification. MS (m/z) 814.1 [M+H]$^+$.

Synthesis of 2-((3bS,4aR)-3-amino-5,5-difluoro-3b,4,4a,5-tetrahydro-H-cyclopropa[3,4]cyclopenta[1,2-c]pyrazol-1-yl)-N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)acetamide (148B)

To a solution of 148A (110 mg, 0.13 mmol) in DMF (1.0 ml) was added diphenyl phosphoryl azide (28.35 µl, 0.13 mmol). The reaction was stirred at room temperature for 45 min. The solution was cooled to 0° C. and water (0.75 mL) was added dropwise. The resulting solution was sealed and heated in microwave reactor at 130° C. for 15 min. The crude material treated with TFA (20 µl) and purified by prep HPLC to provide the product 148B as a mixture of atropisomers. $^1$H NMR (400 MHz, cd$_3$od) δ 8.72-8.59 (m), 7.75-7.65 (m), 7.53 (dd), 7.22-7.15 (m), 7.09 (d), 6.83-6.72 (m), 6.67-6.60 (m), 6.46-6.33 (m), 5.28 (dd), 4.96 (t), 4.90-4.70 (m), 4.69-4.52 (m), 3.35 (s), 3.26 (s), 3.25-3.22 (m), 3.20 (s), 3.17-3.10 (m), 3.04-2.91 (m), 2.51-2.33 (m), 1.65 (s), 1.47-1.31 (m), 1.15-1.06 (m), 1.03 (m). MS (m/z) 785.2 [M+H]$^+$.

Example 149

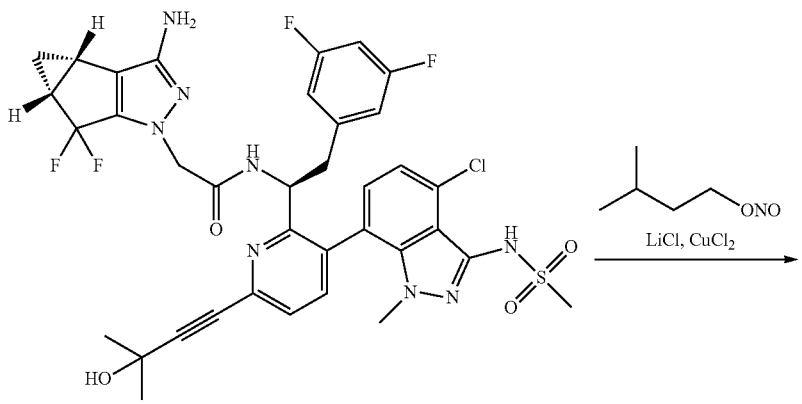

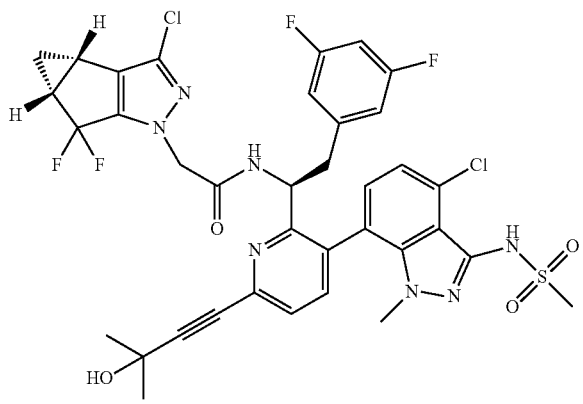

149

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-chloro-5,5-difluoro-3b,4,4a,5-tetrahydro-1H-cyclopropa[3,4]cyclopenta[1,2-c]pyrazol-1-yl)acetamide (149)

A solution of 148B (19.1 mg, 0.02 mmol), ground lithium chloride (5.16 mg, 0.12 mmol), and cupric chloride (6.54 mg, 0.05 mmol) in ACN (1 ml) was sonicated for 5 min. Isoamyl nitrite (6.51 µl, 0.05 mmol) was added and the reaction was sonicated for an additional 5 min then stirred for 45 min. The crude material was purified by prep HPLC to provide the desired product 149 as a mixture of atropisomers. $^1$H NMR (400 MHz, cd$_3$od) δ 8.67 (d), 8.62 (d), 7.69 (dd), 7.53 (dd), 7.19 (s), 7.07 (d), 6.82-6.72 (m), 6.68-6.58 (m), 6.47-6.32 (m), 5.27 (m), 5.03-4.92 (m), 4.69-4.67 (m), 4.64 (d), 3.34 (s), 3.26 (s), 3.24 (s), 3.18-3.08 (m), 3.05-2.92 (m), 2.53-2.30 (m), 1.64 (s), 1.45-1.27 (m), 1.13-1.07 (m), 1.08-1.01 (m). MS (m/z) 804.1 [M+H]$^+$.

Example 150

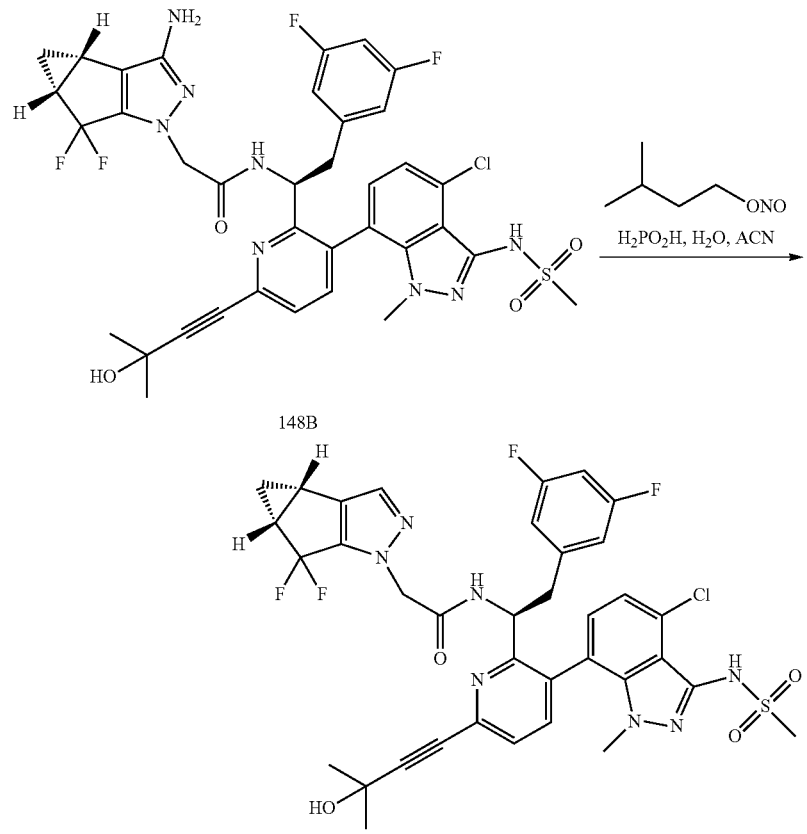

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3b,4,4a,5-tetrahydro-1H-cyclopropa[3,4]cyclopenta[1,2-c]pyrazol-1-yl)acetamide (150)

To a solution of 148B (10 mg, 0.01 mmol) in ACN (0.2 ml) and 50% hypophosphorus acid in water (50 µl) was added isoamyl nitrite (3.41 µl, 0.03 mmol). The reaction mixture was stirred at room temperature for 30 min. The crude material was purified by prep HPLC to provide the title product 150 as a mixture of atropisomers. $^1$H NMR (400 MHz, cd$_3$od) δ 8.48 (d), 8.41 (d), 7.74-7.63 (m), 7.54 (d), 7.51 (d), 7.34 (s), 7.31 (s), 7.17 (s), 7.07 (d), 6.81-6.72 (m), 6.66-6.58 (m), 6.45-6.33 (m), 5.34-5.26 (m), 5.02-4.93 (m), 4.74 (d), 4.69 (d), 3.33 (s), 3.26 (s), 3.24 (s), 3.14-3.06 (m), 3.03-2.91 (m), 2.46-2.33 (m), 1.65 (s), 1.39-1.28 (m), 1.03 (s), 1.00-0.93 (m). MS (m/z) 770.1 [M+H]$^+$.

Example 151

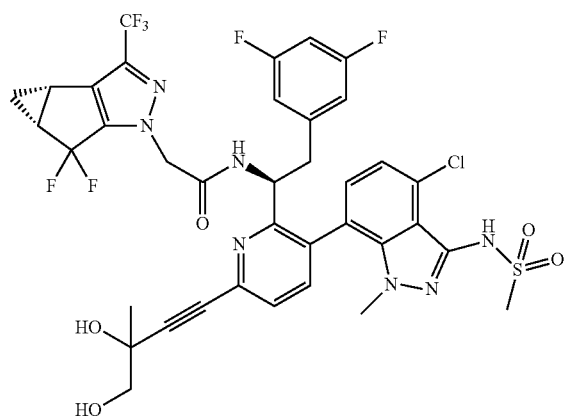

151

Synthesis of N-((1S)-1-(3-(4-chloro-1-methyl-3-(methylsulfonamido)-1H-indazol-7-yl)-6-(3,4-dihydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (151)

The title compound (151) was prepared as a mixture of atropisomers according to the method presented for the synthesis of compound 145 of Example 145 utilizing 2-methylbut-3-yne-1,2-diol. $^1$H NMR (400 MHz, cd$_3$od) δ 8.78 (d), 7.70 (dd), 7.62-7.52 (m), 7.16 (s), 7.05 (d), 6.81-6.72 (m), 6.65-6.60 (m), 6.44-6.30 (m), 5.28 (d), 4.97 (d), 4.84-4.70 (m), 3.66 (d), 3.33 (s), 3.24 (d), 3.14 (dd), 3.07-2.92 (m), 2.86 (s), 2.53-2.42 (m), 1.59 (d), 1.47-1.36 (m), 1.29 (t), 1.19-1.10 (m), 1.09-1.04 (m). MS (m/z) 854.1 [M+H]$^+$.

Example 152

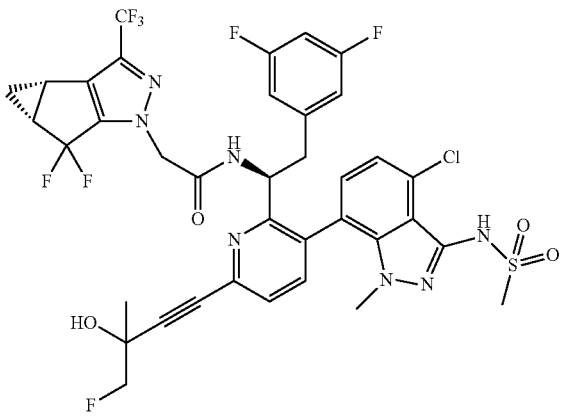

152

Synthesis of N-((1S)-1-(3-(4-chloro-1-methyl-3-(methylsulfonamido)-1H-indazol-7-yl)-6-(4-fluoro-3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (152)

The title compound (152) was prepared as a mixture of atropisomers according to the method presented for the synthesis of compound 145 of Example 145 utilizing 1-fluoro-2-methylbut-3-yn-2-ol. $^1$H NMR (400 MHz, cd$_3$od) δ 7.71 (dd), 7.64-7.51 (m), 7.22-7.12 (m), 7.06 (d), 6.81-6.71 (m),6.68-6.58 (m), 6.44-6.33 (m), 5.30-5.21 (m), 4.98 (t), 4.85-4.70 (m), 4.50 (d), 4.38 (d), 3.24 (d), 3.20-3.11 (m), 3.06-2.93 (m), 2.56-2.43 (m), 1.62 (s), 1.47-1.27 (m),1.16-1.10 (m), 1.09-1.04 (s). MS (m/z) 858.0 [M+H]$^+$.

Example 153

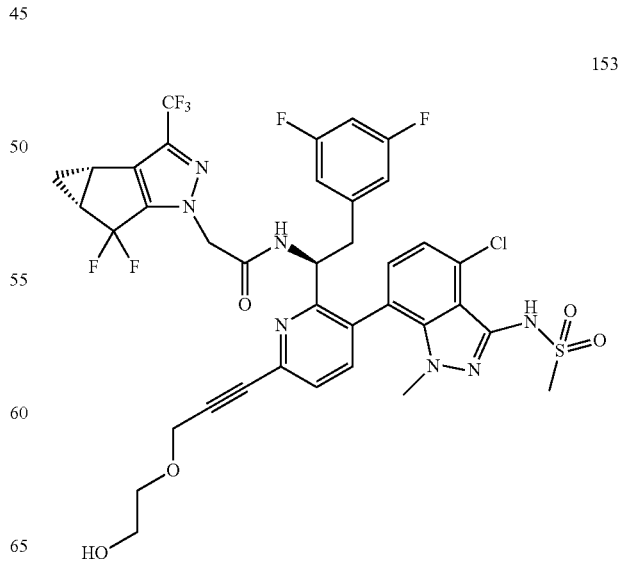

153

Synthesis of N—((S)-1-(3-(4-chloro-1-methyl-3-(methylsulfonamido)-1H-indazol-7-yl)-6-(3-(2-hydroxyethoxy)prop-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (153)

The title compound (153) was prepared as a mixture of atropisomers according to the method presented for the synthesis of compound 145 of Example 145 utilizing 2-(prop-2-yn-1-yloxy)ethanol. $^1$H NMR (400 MHz, cd$_3$od) δ 8.67 (d), 7.71 (dd), 7.62-7.52 (m), 7.17 (d), 7.07 (d), 6.81-6.71 (m), 6.68-6.60 (m), 6.45-6.34 (m), 5.29-5.24 (m), 4.98 (q), 4.84-4.70 (m), 4.54 (d), 3.86-3.80 (m), 3.80-3.66 (m), 3.36-3.31 (m), 3.28-3.09 (m), 2.98 (d), 2.52-2.44 (m), 1.40 (q), 1.16-1.11 (m), 1.10-1.05 (m). MS (m/z) 854.2 [M+H]$^+$.

Example 154

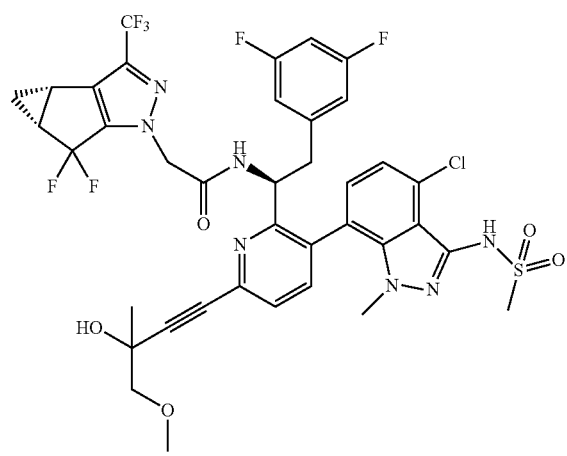

154

Synthesis of N-((1S)-1-(3-(4-chloro-1-methyl-3-(methylsulfonamido)-1H-indazol-7-yl)-6-(3-hydroxy-4-methoxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (154)

The title compound (154) was prepared as a mixture of atropisomers according to the method presented for the synthesis of compound 145 of Example 145 utilizing 1-methoxy-2-methylbut-3-yn-2-ol. $^1$H NMR (400 MHz, cd$_3$od) δ 8.67 (d), 7.71 (dd), 7.62-7.52 (m), 7.17 (d), 7.07 (d), 6.81-6.71 (m), 6.64 (d), 6.45-6.34 (m), 5.26 (s), 4.98 (q), 4.84-4.70 (m), 4.62 (s), 4.54 (d), 3.86-3.80 (m), 3.80-3.66 (m), 3.34 (s), 3.28-3.09 (m), 2.98 (d), 2.48 (dd), 1.40 (q), 1.14 (m), 1.07 (m). MS (m/z) 869.1 [M+H]$^+$.

Example 155

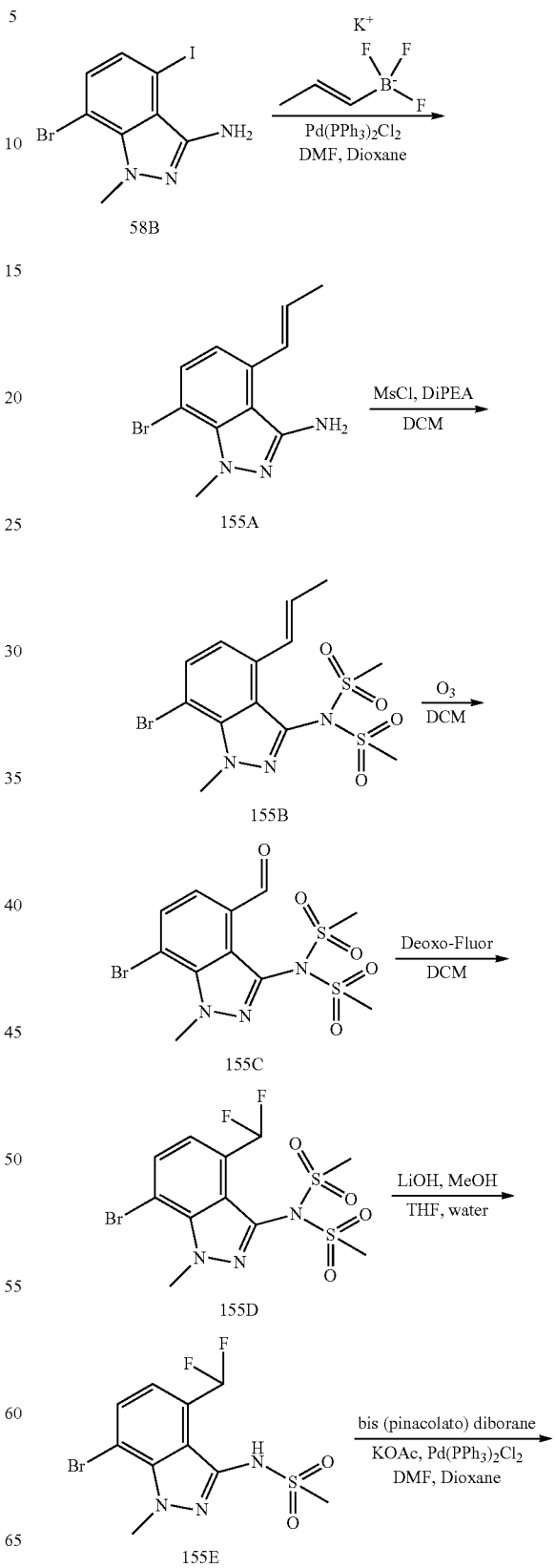

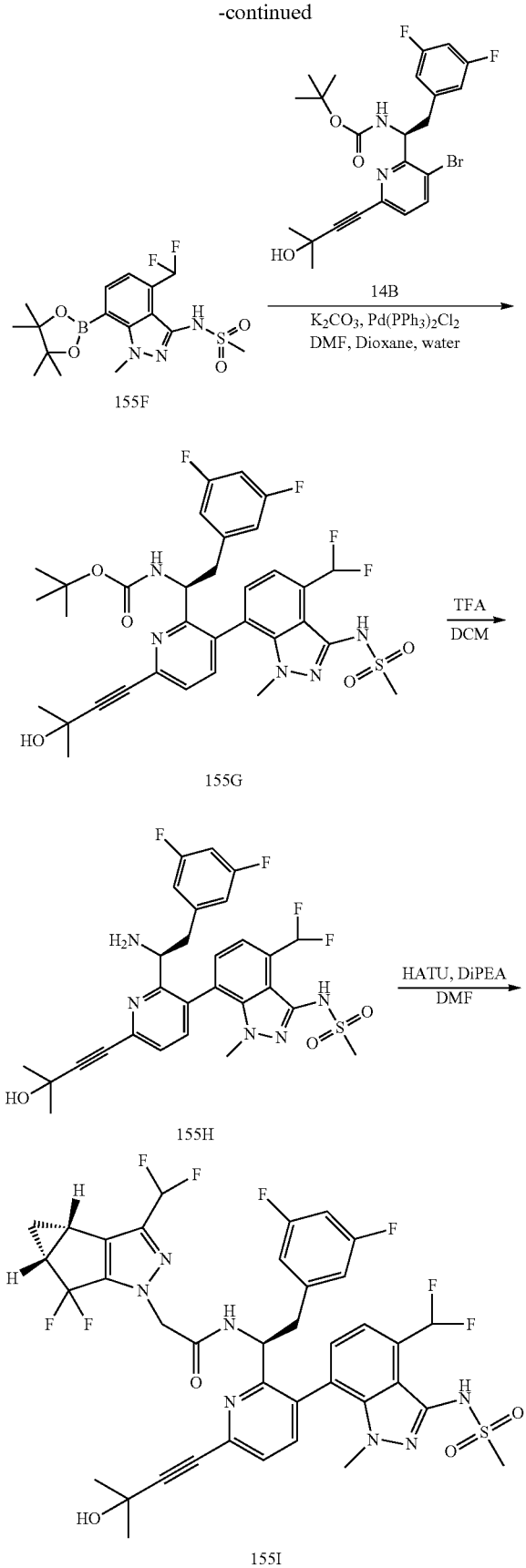

Synthesis of (E)-7-bromo-1-methyl-4-(prop-1-en-1-yl)-1H-indazol-3-amine (155A)

To 58B (7.4 g, 21.0 mmol) in dioxane (40 mL) and DMF (40 ml) was added potassium trifluoro(prop-1-en-1-yl)borate (3.7 g, 25.2 mmol), 2M K$_2$CO$_3$ in water (21.0 ml), and Pd(PPh$_3$)$_2$Cl$_2$ (740.0 mg, 1.1 mmol). The reaction mixture was stirred for 2 hours at 100° C. The reaction was cooled, diluted with EtOAc and brine. The mixture was extracted 2× with EtOAc, the organic layer was dried over sodium sulfate, was concentrated and purified by flash column chromatography to provide the title compound. MS (m/z) 266.3 [M+H]$^+$.

Synthesis of (E)-N-(7-bromo-1-methyl-4-(prop-1-en-1-yl)-1H-indazol-3-yl)-N-(methylsulfonyl)methanesulfonamide (155B)

To 155A (3.7 g, 13.9 mmol) in DCM (100 mL) was added N,N-diisopropylethylamine (9.7 ml, 55.6 mmol) then the reaction was cooled in an ice bath and methanesulfonyl chloride (3.2 ml, 41.7 mmol) was added. The reaction mixture was stirred for 30 minutes at 0° C. The reaction was diluted with water and extracted 2× with DCM. The organic layer was dried over sodium sulfate and concentrated. The mixture was purified by flash column chromatography to provide the title compound. MS (m/z) 421.9 [M+H]$^+$.

Synthesis of N-(7-bromo-4-formyl-1-methyl-1H-indazol-3-yl)-N-(methylsulfonyl)methanesulfonamide (155C)

A round bottom is charged with 155B (2.7 g, 6.4 mmol) and DCM (100 mL). The mixture was cooled to −78° C. and ozone was bubbled into the reaction. Once the conversion was complete, DMS was added to quench the reaction under stirring for 30 minutes. To the stirring mixture a saturated sodium thiosulfate solution was added and the mixture was allowed to warm to room temperature and stirred another 30 minutes. The layers were separated and the water layer was extracted again with DCM. The combined organic layers were dried over sodium sulfate and concentrated. The residue was dissolved in DCM and followed by the addition of hexane. The mixture was filtered to provide the title compound. MS (m/z) 410.0 [M+H]$^+$.

Synthesis of N-(7-bromo-4-(difluoromethyl)-1-methyl-1H-indazol-3-yl)-N-(methylsulfonyl)methanesulfonamide (155D)

A teflon flask was charged with 155C (650 mg, 1.6 mmol) and DCM (100 mL). The mixture was cooled to 0° C. and Deoxo-Fluor (0.4 ml, 2.4 mmol) was added into the reaction and then the mixture was allowed to warm to room temperature. The mixture is stirred for 8 hours and checked. Another equivalent of Deoxo-Fluor was added and the mixture was stirred overnight. The mixture is diluted with water and extracted 2× with DCM. The organic layers are dried over sodium sulfate and concentrated. The residue was dissolved in DCM followed by the addition of hexane. The mixture was filtered to provide the title compound. MS (m/z) 431.9 [M+H]$^+$.

Synthesis of N-(7-bromo-4-(difluoromethyl)-1-methyl-1H-indazol-3-yl)methanesulfonamide (155E)

To 155D (5.9 g, 13.7 mmol), THF (50 ml) and MeOH (20 ml) was added a saturated solution of LiOH (10 ml) and water (10 ml). The mixture was stirred for 10 minutes, then diluted with water and extracted 2× EtOAc. The organic layers were dried over sodium sulfate and concentrated. The residue was dissolved in DCM followed by the addition of hexane. The mixture was filtered to provide the title compound. MS (m/z) 354.6 [M+H]$^+$.

Synthesis of N-(4-(difluoromethyl)-1-methyl-7-(4,4,5,5-tetramethyl-1,3,2-dioxaborolan-2-yl)-1H-indazol-3-yl)methanesulfonamide (155F)

The title compound (155F) was prepared according to the method presented for the synthesis of compound 19C of Example 19 utilizing 155E. MS (m/z) 402.3 [M+H]$^+$.

Synthesis of (S)-tert-butyl (1-(3-(4-(difluoromethyl)-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)carbamate (155G)

To 14B (100 mg, 0.2 mmol) in dioxane (8 mL) and DMF (2 ml) was added 2N K$_2$CO$_3$ (0.2 ml), and Pd(PPh$_3$)$_2$Cl$_2$ (7.1 mg, 0.01 mmol). The reaction mixture was stirred at 110° C., then 155F (170 mg, 0.4 mml) dissolved in dioxane (4 ml) and DMF (2 ml) was slower added into the reaction by syringe. The reaction was cooled after 8 hours, diluted with EtOAc and brine. The mixture was extracted 2× with EtOAc, the organic layer was dried over sodium sulfate, was concentrated and purified by flash column chromatography to provide the title compound as a mixture of atropisomers. MS (m/z) 689.8 [M+H]$^+$.

Synthesis of (S)—N-(7-(2-(1-amino-2-(3,5-difluorophenyl)ethyl)-6-(3-hydroxy-3-methylbut-1-yn-1-yl)pyridin-3-yl)-4-(difluoromethyl)-1-methyl-1H-indazol-3-yl)methanesulfonamide (155H)

The title compound (155H) was prepared as a mixture of atropisomers according to the method presented for the synthesis of compound 19F of Example 19 utilizing 155G. MS (m/z) 590.1 [M+H]$^+$.

Synthesis of N—((S)-1-(3-(4-(difluoromethyl)-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (155I)

The title compound (155I) was prepared as a mixture of atropisomers according to the method presented for the synthesis of compound 10A of Example 10 utilizing 155H and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (Chloroform-d) δ: 7.60 (dd), 7.53 (dd), 7.49-7.38 (m), 7.30-7.19 (m), 7.14 (s), 6.83-6.78 (m), 6.70 (t), 6.69-6.62 (m), 6.34 (d), 6.25-6.14 (m), 4.95 (q), 4.75-4.69 (m), 3.59-3.42 (m), 3.35 (s), 3.01-2.88 (m), 2.56-2.36 (m), 1.72 (s), 1.46-1.37 (m), 1.19-1.09 (m). MS (m/z) 836.2 [M+H]$^+$.

Example 156

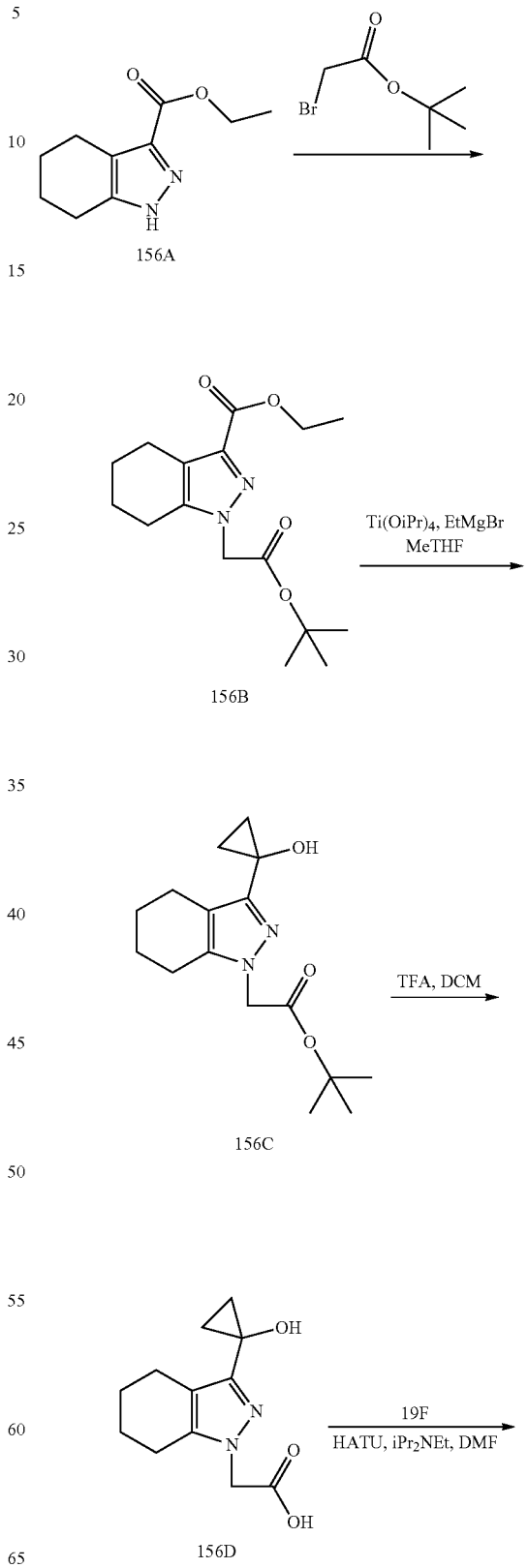

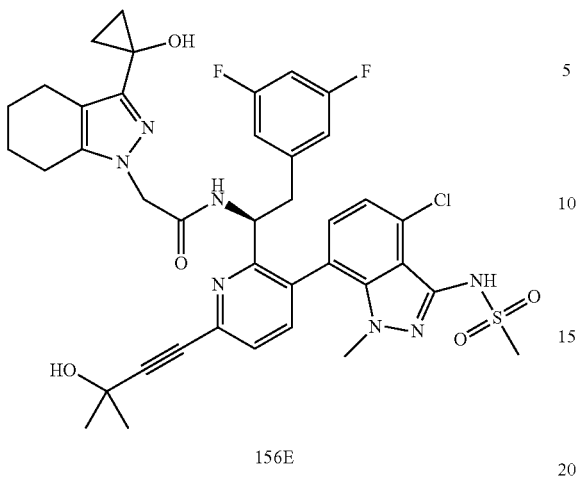

156E

Synthesis of ethyl 1-(2-(tert-butoxy)-2-oxoethyl)-4,5,6,7-tetrahydro-1H-indazole-3-carboxylate (156B)

To 156A (2 g, 10.3 mmol) in MeTHF (100 mL) and DMF (5 ml) was added Cs$_2$CO$_3$ (4.0 g, 12.3 mmol) and tert-butyl 2-bromoacetate (2.3 ml, 15.5 mmol). The reaction mixture was stirred for 4 hours. Solids were filtered, the eluent was concentrated and purified by flash column chromatography to provide the title compound. MS (m/z) 309.6 [M+H]$^+$.

Synthesis of tert-butyl 2-(3-(1-hydroxycyclopropyl)-4,5,6,7-tetrahydro-1H-indazol-1-yl)acetate (156C)

To 156B (300 mg, 1.0 mmol) in MeTHF (20 mL) was added titanium (iv) isopropoxide (2.9 ml, 9.73 mmol). To the stirring mixture 3M EµMgBr (3.2 ml) was slowly added. The reaction mixture was stirred for 1 hour. The reaction was diluted with EtOAc and brine. The mixture was extracted 2× with EtOAc, the organic layer was dried over sodium sulfate, was concentrated and purified by flash column chromatography to provide the title compound. MS (m/z) 293.0 [M+H]$^+$.

Synthesis of 2-(3-(1-hydroxycyclopropyl)-4,5,6,7-tetrahydro-1H-indazol-1-yl)acetic acid (156D)

To 156C (20 mg, 0.07 mmol) in DCM (2 mL) was added TFA (0.5 ml). The reaction mixture was stirred for 0.5 hours at RT. The reaction was concentrated and then diluted with 1 N HCl and extracted 2× with DCM. The water layer was lyophilized to provide the title compound. MS (m/z) 237.1 [M+H]$^+$.

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-(1-hydroxvcyclopropyl)-4,5,6,7-tetrahydro-1H-indazol-1-yl)acetamide (156E)

The title compound (156E) was prepared as a mixture of atropisomers according to the method presented for the synthesis of compound 10A of Example 10 utilizing 156D and 19F. $^1$H NMR (Methanol-d$_4$) δ: 7.76-7.68 (m), 7.53 (dd), 7.25-7.14 (m), 6.64 (tt), 6.39 (dd), 5.27 (dd), 4.64 (d), 3.28-3.21 (m), 3.21-3.10 (m), 3.04 (s), 2.98 (dd), 2.67-2.55 (m), 2.47-2.37 (m), 1.86-1.69 (m), 1.64 (s), 1.10-0.97 (m). MS (m/z) 792.3 [M+H]$^+$.

Example 157

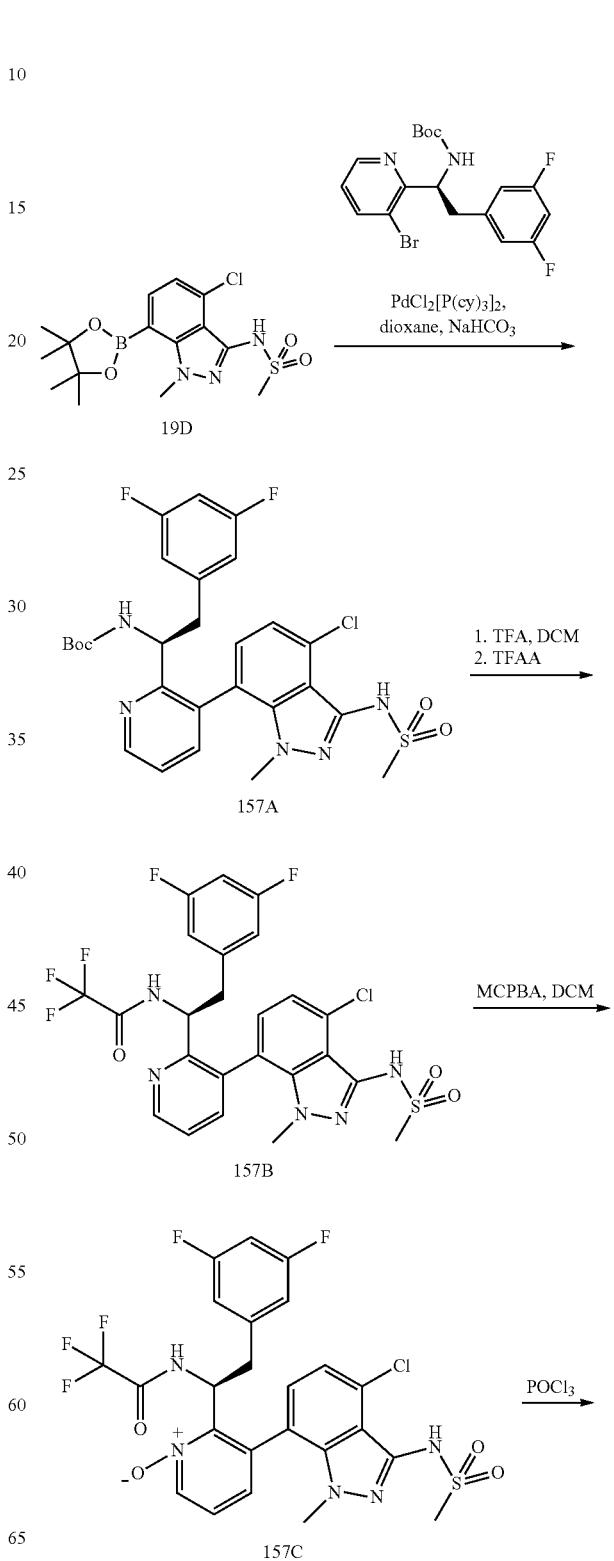

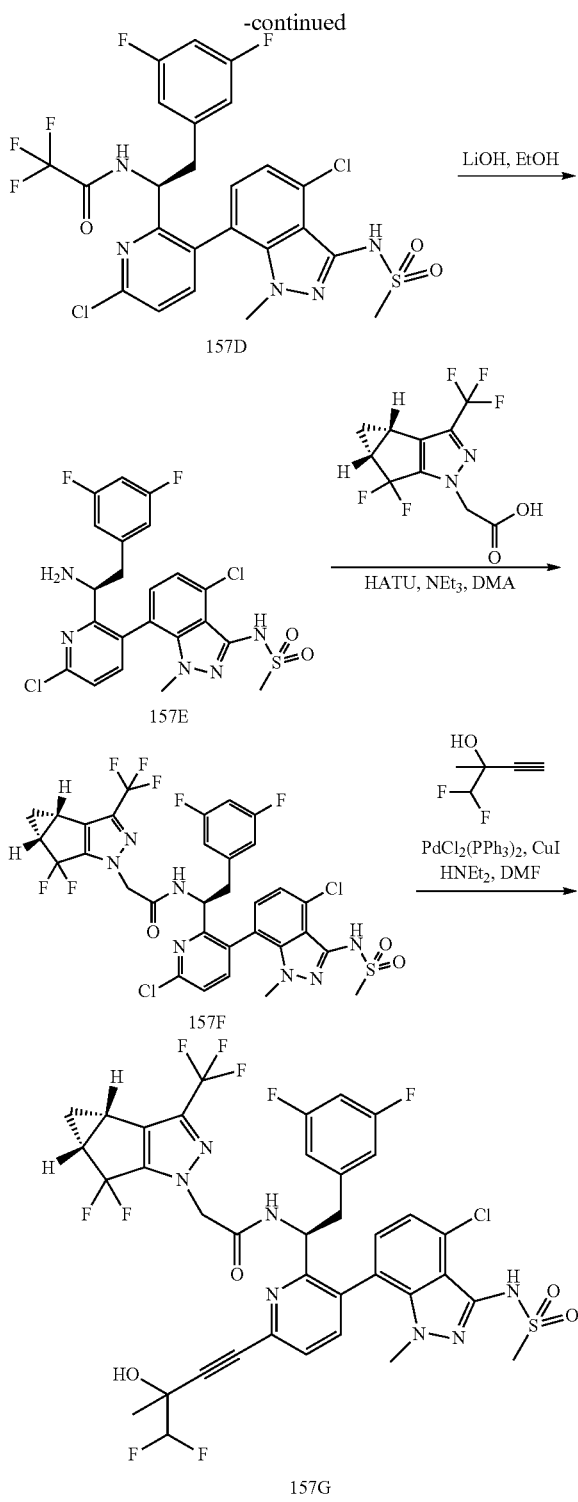

mmol), and PdCl$_2$[P(cy)$_3$]$_2$ (89.0 mg, 0.121 mmol) were suspended in 1,4-dioxane (12 mL) and 1.0 M aqueous NaHCO$_3$ (4 mL). The reaction mixture was degassed by bubbling argon for 5 minutes then sealed and heated at 150° C. for 15 minutes in a microwave reactor. Upon cooling, the reaction mixture was diluted with water and extracted with three portions of EtOAc. The combined organic layers were dried over Na$_2$SO$_4$, filtered, concentrated in vacuo, and purified by silica gel column chromatography to give the title compound 157A. MS (m/z) 591.72 [M+H]$^+$.

Synthesis of (S)—N-(1-(3-(4-chloro-1-methyl-3-(methylsulfonamido)-1H-indazol-7-yl)pyridin-2-yl)-2-(3,5-difluorophenyl)ethyl)-2,2,2-trifluoroacetamide (157B)

To (S)-tert-butyl (1-(3-(4-chloro-1-methyl-3-(methylsulfonamido)-1H-indazol-7-yl)pyridin-2-yl)-2-(3,5-difluorophenyl)ethyl)carbamate (157A, 3.39 g, 5.73 mmol) in DCM (5 mL) was added trifluoroacetic acid (5 mL). The reaction mixture was stirred at room temperature for 2.5 hours. Upon complete removal of the Boc protecting group, trifluoroacetic anhydride (2.02 mL, 14.31 mmol) was added. The reaction mixture was stirred at room temperature for 30 minutes. Upon completion, the reaction mixture was filtered through celite, concentrated in vacuo, taken in EtOAc, and carefully neutralized with 1M aqueous NaHCO$_3$ until the aqueous layer was at pH 10. The organic layer was collected and the aqueous layer extracted once more with EtOAc. The combined organic layers were dried over Na$_2$SO$_4$, filtered, concentrated in vacuo, and purified by silica gel column chromatography to give the title compound 157B. MS (m/z) 588.14 [M+H]$^+$.

Synthesis of (S)-3-(4-chloro-1-methyl-3-(methylsulfonamido)-1H-indazol-7-yl)-2-(2-(3,5-difluorophenyl)-1-(2,2,2-trifluoroacetamido)ethyl)pyridine 1-oxide (157C)

To a solution of (S)—N-(1-(3-(4-chloro-1-methyl-3-(methylsulfonamido)-1H-indazol-7-yl)pyridin-2-yl)-2-(3,5-difluorophenyl)ethyl)-2,2,2-trifluoroacetamide (157B, 8.0 g, 13.61 mmol) in DCM (70 mL) was added MCPBA (3.659 g, 16.33 mmol) in 4 portions over a 15 minute period. The reaction mixture was stirred at room temperature for 16 hours. Upon completion, the reaction was quenched with 1M aqueous NaHSO$_3$ and saturated aqueous NaHCO$_3$. The organic layer was collected and the aqueous layer was extracted an additional time with DCM. The combined organic layers were dried over Na$_2$SO$_4$, filtered, concentrated in vacuo, and purified by silica gel column chromatography to give the title compound 157C. MS (m/z) 604.10 [M+H]$^+$.

Synthesis of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (157D)

Synthesis of (S)-tert-butyl (1-(3-(4-chloro-1-methyl-3-(methylsulfonamido)-1H-indazol-7-yl)pyridin-2-yl)-2-(3,5-difluorophenyl)ethyl)carbamate (157A)

(S)-tert-butyl (1-(3-bromopyridin-2-yl)-2-(3,5-difluorophenyl)ethyl)carbamate (1.0 g, 2.42 mmol), N-(4-chloro-1-methyl-7-(4,4,5,5-tetramethyl-1,3,2-dioxaborolan-2-yl)-1H-indazol-3-yl)methanesulfonamide (19D, 1.12 g, 2.90

(S)-3-(4-chloro-1-methyl-3-(methylsulfonamido)-1H-indazol-7-yl)-2-(2-(3,5-difluorophenyl)-1-(2,2,2-trifluoroacetamido)ethyl)pyridine 1-oxide (157C, 1.0 g, 1.66 mmol) was taken in POCl$_3$ (2.32 mL, 24.84 mmol). The reaction mixture was heated at 115° C. for 2 hours. Upon cooling, the reaction was concentrated in vacuo, taken in DCM, and vigorously stirred with saturated aqueous NaHCO$_3$ for 1 hour. The organic layer was collected, and the aqueous layer was extracted an additional time with DCM. The combined organic layers were dried over Na₂SO₄, filtered, concentrated in vacuo, and purified by silica gel column chromatography to give the title compound 157D. MS (m/z) 622.13 [M+H]⁺.

Synthesis of (S)—N-(7-(2-(1-amino-2-(3,5-difluorophenyl)ethyl)-6-chloropyridin-3-yl)-4-chloro-1-methyl-1H-indazol-3-yl)methanesulfonamide (157E)

To a solution of (S)—N-(1-(6-chloro-3-(4-chloro-1-methyl-3-(methylsulfonamido)-1H-indazol-7-yl)pyridin-2-yl)-2-(3,5-difluorophenyl)ethyl)-2,2,2-trifluoroacetamide (157D, 870 mg, 1.40 mmol) in EtOH (16 mL) was added 2M aqueous LiOH (7.0 mL, 13.98 mmol). The reaction was heated at 130° C. for 10 minutes. Upon cooling, the reaction mixture was acidified with 2N aqueous HCl until at pH 5. The reaction mixture was then concentrated in vacuo and taken in EtOAc. To the solution was added saturated aqueous NaHCO₃ until the aqueous layer was at pH 10. The organic layer was collected, and the aqueous layer was extracted an additional time with EtOAc. The combined organic layers were dried over Na₂SO₄, filtered, concentrated in vacuo, and used without further purification. MS (m/z) 526.06 [M+H]⁺.

Synthesis of N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (157F)

To a solution of crude (S)—N-(7-(2-(1-amino-2-(3,5-difluorophenyl)ethyl)-6-chloropyridin-3-yl)-4-chloro-1-methyl-1H-indazol-3-yl)methanesulfonamide (157E, 400 mg, 0.76 mmol) in DMA (6 mL) was added NEt₃ (0.32 mL, 2.28 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (160.6 mg, 0.61 mmol), then HATU (173.4 mg, 0.46 mmol). The reaction mixture was stirred at room temperature for 15 minutes, then additional HATU (86.7 mg, 0.23 mmol) was added. The reaction mixture was stirred at room temperature for an additional 15 minutes. Upon completion, the reaction mixture was concentrated in vacuo and purified by silica gel column chromatography to give the title compound 157F. MS (m/z) 790.12 [M+H]⁺.

Synthesis of N-((1S)-1-(3-(4-chloro-1-methyl-3-(methylsulfonamido)-1H-indazol-7-yl)-6-(4,4-difluoro-3-hydroxy-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (157G)

N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (157F, 20 mg, 0.025 mmol), 1,1-difluoro-2-methylbut-3-yn-2-ol (15.2 mg, 0.126 mmol), PdCl₂(PPh₃)₂ (1.8 mg, 0.003 mmol), and CuI (0.5 mg, 0.003 mmol) were taken in DMF (0.25 mL). To the reaction mixture was added diethylamine (26 µL, 0.253 mmol), and the reaction mixture was degassed by bubbling argon for 5 minutes then sealed and heated at 125° C. for 30 minutes in a microwave reactor. Upon cooling, the reaction mixture was filtered and purified by reverse phase HPLC to give the title compound 157G as a mixture of atropisomers. ¹H NMR (400 MHz, Methanol-d₄) δ 8.88-8.78 (m), 7.74 (dd), 7.60 (dd), 7.24-7.13 (m), 7.10-7.05 (m), 6.77 (t), 6.64 (t), 6.46-6.33 (m), 5.82 (t), 5.35-5.23 (m), 5.00 (q), 4.82 (s), 4.79 (s), 4.76 (s), 3.34 (s), 3.26 (s), 3.23 (s), 3.20-3.10 (m), 3.07-2.93 (m), 2.58-2.37 (m), 1.63 (s), 1.50-1.34 (m), 1.18-1.11 (m), 1.10-1.01 (m). MS (m/z) 874.07 [M+H]⁺.

Example 158

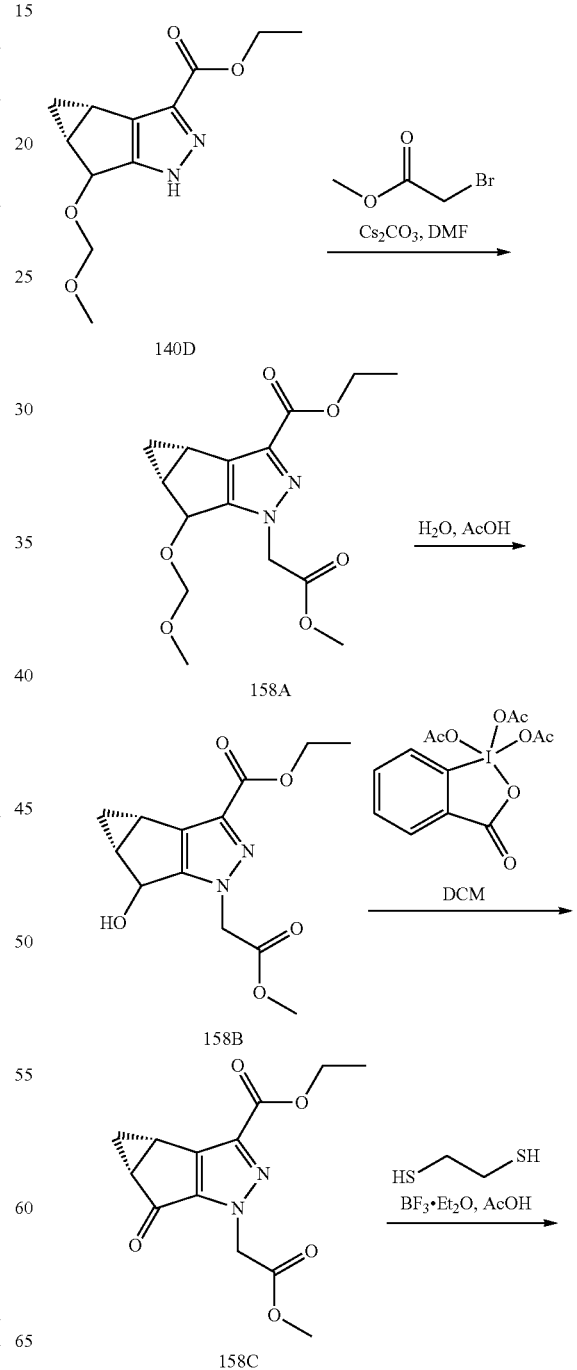

-continued

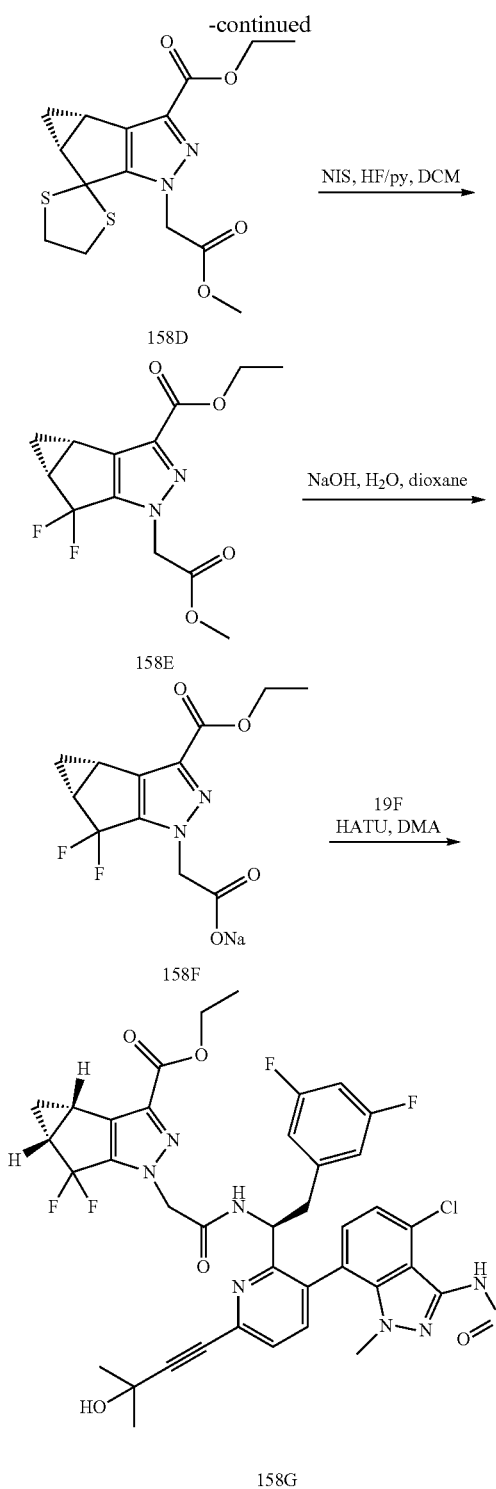

Synthesis of (3bS,4aR)-ethyl 1-(2-methoxy-2-oxo-ethyl)-5-(methoxymethoxy)-3b,4,4a,5-tetrahydro-1H-cyclopropa[3,4]cyclopenta[1,2-c]pyrazole-3-carboxylate (158A)

To a solution of (3bS,4aR)-ethyl 5-(methoxymethoxy)-3b,4,4a,5-tetrahydro-1H-cyclopropa[3,4]cyclopenta[1,2-c]pyrazole-3-carboxylate (140D) (3.3 g, 13.1 mmol) in DMF (12 ml) was added portionwise potassium t-butoxide (1.61 g, 14.39 mmol) at 0° C. To the reaction was added 2-methyl-tetrahydrofuran (12 ml) followed by a dropwise addition of methyl bromoacetate (1.36 ml, 14.4 mmol). After gradually warming to room temperature and stirring for 1 h, the reaction was extracted with EtOAc and water. The organic layer was washed with water. The organics layer was dried with Na$_2$SO$_4$, filtered, and concentrated in vacuo. The crude product was taken to next step without further purification. MS (m/z) 324.96 [M+H]$^+$.

Synthesis of (3bS,4aR)-ethyl 5-hydroxy-1-(2-methoxy-2-oxoethyl)-3b,4,4a,5-tetrahydro-1H-cyclopropa[3,4]cyclopenta[1,2-c]pyrazole-3-carboxylate (158B)

To a solution of (3bS,4aR)-ethyl 1-(2-methoxy-2-oxoethyl)-5-(methoxymethoxy)-3b,4,4a,5-tetrahydro-1H-cyclopropa[3,4]cyclopenta[1,2-c]pyrazole-3-carboxylate (158A) (4.2 g) in acetic acid (15 ml) was added water (30 ml). After stirring at reflux for 2 h, the reaction was concentrated in vacuo. The resulting mixture was diluted with dioxane (40 ml) and concentrated in vacuo. The crude product was dissolved in dichloromethane (20 ml), dried with Na$_2$SO$_4$, filtered, and concentrated in vacuo. The crude product was taken to next step without further purification. MS (m/z) 281.02 [M+H]$^+$.

Synthesis of (3bS,4aR)-ethyl 1-(2-methoxy-2-oxoethyl)-5-oxo-3b,4,4a,5-tetrahydro-1H-cyclopropa[3,4]cyclopenta[1,2-c]pyrazole-3-carboxylate (158C)

To a solution of 156B (3.63 g, 12.95 mmol) in DCM (30 mL) was added Dess-Martin periodinane (4.87 g, 12.95 mmol). The reaction was stirred at room temperature overnight. The reaction mixture was filtered through celite, solid loaded onto silica and purified by silica gel chromatography to give the title compound. MS (m/z) 278.9 [M+H]$^+$.

Synthesis of (3bS,4aR)-ethyl 1-(2-methoxy-2-oxoethyl)-1,3b,4,4a-tetrahydrospiro[cyclopropa[3,4]cyclopenta[1,2-c]pyrazole-5,2'-[1,3]dithiolane]-3-carboxylate (158D)

To a solution of 158C (0.69 g, 2.61 mmol), 1,2-ethanedithiol (0.44 ml, 5.22 mmol), acetic acid (0.75 ml, 13.06 mmol) in DCM (10 ml) was added boron trifluoride diethyl etherate (0.81 ml, 6.53 mmol). The reaction was stirred at room temperature for 2 days. The reaction mixture was concentrated, solid loaded onto silica and purified by silica chromatography to give the title compound 158D. MS (m/z) 354.9 [M+H]$^+$.

Synthesis of (3bS,4aR)-ethyl 5,5-difluoro-1-(2-methoxy-2-oxoethyl)-3b,4,4a,5-tetrahydro-1H-cyclopropa[3,4]cyclopenta[1,2-c]pyrazole-3-carboxylate (158E)

To suspension of N-iodosuccinimide, 98% (1.35 g, 6.0 mmol) in DCM (5 ml) was added dropwise 70% HF in pyridine (5 ml) at −78° C. After stirring for 15 min 158D (0.85 g, 2.39 mmol) in DCM (5 ml) was added and the reaction was slowly warmed to −30° C. and stirred at that temperature for 1 h. The resulting solution was carefully poured onto ice containing 1.0 N NaHCO$_3$. The product was extracted with ethyl acetate, washed with NaHSO$_3$, brine and water. The combined organic layers were dried with Na$_2$SO$_4$, filtered, and concentrated. The crude material was purified by silica chromatography to give the title compound 158E. MS (m/z) 300.9 [M+H]$^+$.

Synthesis of sodium 2-((3bS,4aR)-3-(ethoxycarbonyl)-5,5-difluoro-3b,4,4a,5-tetrahydro-1H-cyclopropa[3,4]cyclopenta[1,2-c]pyrazol-1-yl)acetate (158F)

To a solution of 158E (0.16 g, 532.87 μmol) in dioxane (3 ml) was added dropwise 1M NaOH (0.55 ml). The reaction was stirred at room temperature for 0.5 h. An additional 0.500 mL of 1M NaOH was added and stirred for an additional 0.5 h. The reaction was concentrated, diluted with DMA (3 mL) and concentrated until dryness. The crude product was taken to next step without further purification. MS (m/z) 286.9 [M+H]$^+$.

Synthesis of (3bS,4aR)-ethyl 1-(2-(((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)amino)-2-oxoethyl)-5,5-difluoro-3b,4,4a,5-tetrahydro-1H-cyclopropa[3,4]cyclopenta[1,2-c]pyrazole-3-carboxylate (158G)

To a solution of 19F (305.45 mg, 532.1 μmol) and 158F (164 mg, 532.1 μmol) in DMA (2 mL) was added HATU (212.31 mg, 558.7 μmol). The reaction was stirred at room temperature for 0.5 h. The reaction was diluted with 0.1 M NaCl (10 mL) and extracted with ethyl acetate (2×10 mL). The combined organic layers was washed with water (20 mL), dried with Na$_2$SO$_4$, filtered, and concentrated. The crude material was purified by silica chromatography to give the title compound 158G as a mixture of atropisomers. $^1$H NMR (400 MHz, cd$_3$od) δ 8.77 (d), 8.75-8.68 (m), 8.43 (dd), 7.70 (t), 7.57-7.48 (m), 7.22-7.15 (m), 7.06 (d), 6.81-6.72 (m), 6.68-6.59 (m), 6.41 (dd), 5.30-5.19 (m), 4.99 (q), 4.82 (d), 4.73 (s), 4.42-4.31 (m), 3.36 (s), 3.34-3.27 (m), 3.25 (s), 3.22 (s), 3.17 (dd), 3.04-2.97 (m), 2.96 (s), 2.63-2.39 (m), 1.65 (s), 1.64 (s), 1.49-1.32 (m), 1.14-1.07 (m), 1.07-0.99 (m). MS (m/z) 842.2 [M+H]$^+$.

Example 159

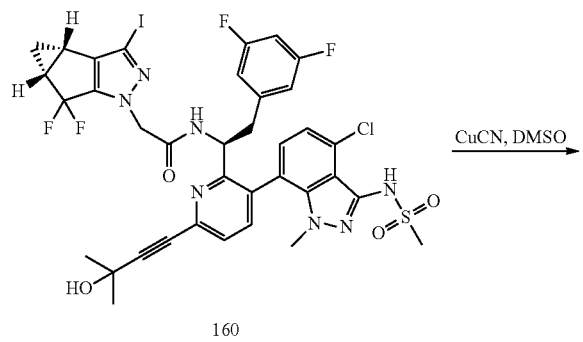

160

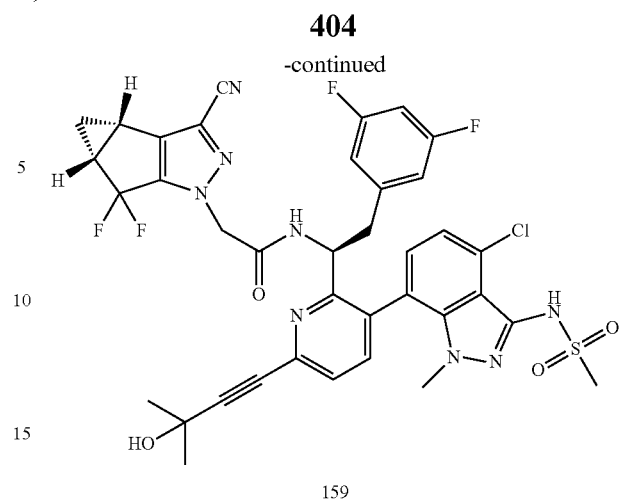

159

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-cyano-5,5-difluoro-3b,4,4a,5-tetrahydro-1H-cyclopropa[3,4]cyclopenta[1,2-c]pyrazol-1-yl)acetamide (159)

To a solution of 160 (11 mg, 12.2 mol) in DMSO (0.2 ml) was added cuprous cyanide (2.7 mg, 30.7 mol). The reaction mixture sealed and heated to 180° C. for 0.5 h. The reaction was cooled rt, diluted with ethyl acetate, and washed with water. The organic phase was then dried with Na$_2$SO$_4$, filtered and concentrated. The crude material was purified by prep HPLC to provide the product 159 as a mixture of atropisomers. $^1$H NMR (400 MHz, cd$_3$od) δ 8.87-8.78 (m), 7.73-7.66 (m), 7.58-7.48 (m), 7.18 (s), 7.07 (d), 6.81-6.71 (m), 6.68-6.58 (m), 6.48-6.32 (m), 5.32-5.20 (m), 5.03-4.91 (m), 4.80 (d), 3.34 (s), 3.25 (s), 3.24 (s), 3.15 (dd), 3.06-2.93 (m), 2.63-2.47 (m), 1.64 (s), 1.45 (dd), 1.19-1.14 (m), 1.11-1.06 (m). MS (m/z) 795.1 [M+H]$^+$.

Example 160

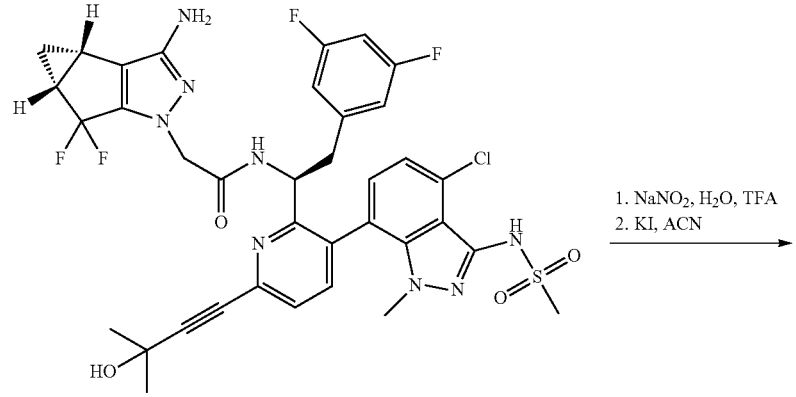

148B

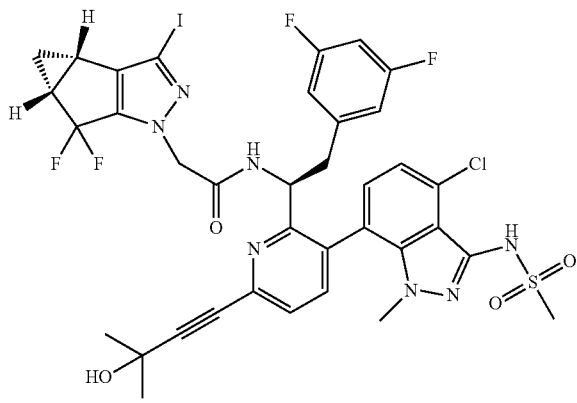

160

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-5,5-difluoro-3-iodo-3b,4,4a,5-tetrahydro-1H-cyclopropa[3,4]cyclopenta[1,2-c]pyrazol-1-yl)acetamide (160)

To a solution of 148B (75 mg, 95.5 mol) in trifluoroacetic acid (0.5 ml) and water (0.2 mL was added sodium nitrite (1M in water, 0.3 mL) followed by stirring for 15 min at room temperature. The reaction mixture was then treated with potassium iodide (238 mg, 1.4 mmol), acetonitrile (0.8 mL) and stirred for an additional 1.5 h. The reaction was basified with 1M NaHCO₃, quenched with 1M NaHSO₃, and extracted with ethyl acetate (20 mL). The organic phase was then dried with Na₂SO₄, filtered and concentrated. The crude material was purified by prep HPLC to provide the product 160 as a mixture of atropisomers. $^1$H NMR (400 MHz, cd₃od) 67.75-7.63 (m), 7.58-7.48 (m), 7.18 (s), 7.12-7.02 (m), 6.82-6.72 (m), 6.68-6.58 (m), 6.46-6.32 (m), 5.32-5.22 (m), 4.96 (t), 4.76-4.56 (m), 3.34 (s), 3.30-3.22 (m), 3.26 (s), 3.25 (s), 3.20-3.06 (m), 3.04-2.91 (m), 2.51-2.35 (m), 2.30-2.16 (m), 2.03 ( ), 1.65 (s), 1.42-1.27 (m), 1.10-1.04 (m), 1.04-0.99 (m). MS (m/z) 896.0 [M+H]⁺.

Example 161

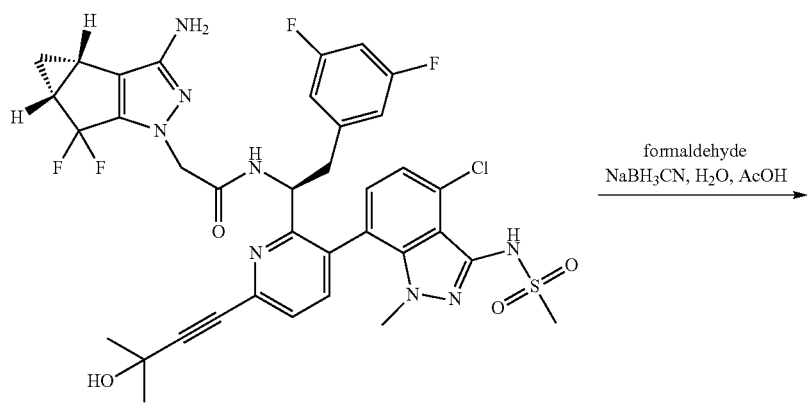

148B

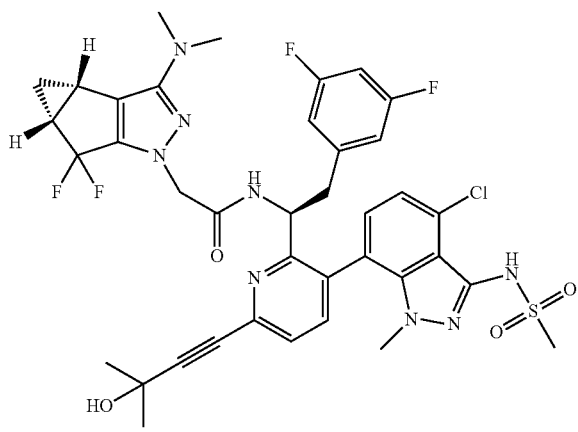

161

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-(dimethylamino)-5,5-difluoro-3b,4,4a,5-tetrahydro-1H-cyclopropa[3,4]cyclopenta[1,2-c]pyrazol-1-yl)acetamide (161)

To a solution of 148B (10 mg, 12.7 μmol) in acetic acid (0.1 ml) and formaldehyde (35% in water, 6.7 μl, 63.6 μmol) was added sodium cyanoborohydride (1.7 mg, 26.7 mol) followed by stirring for 16 h at rt. The reaction mixture was diluted with ACN and purified by prep HPLC to provide the product 161 as a mixture of atropisomers. $^1$H NMR (400 MHz, cd$_3$od) δ 7.74-7.64 (m), 7.58-7.48 (m), 7.16 (q), 7.07 (d), 6.82-6.72 (m), 6.68-6.56 (m), 6.45-6.30 (m), 5.28 (dd), 4.95 (t), 4.51 (d), 4.47 (d), 3.33 (s), 3.26 (s), 3.25 (s), 3.27-3.18 (m), 3.09 (dd), 2.98 (s), 2.92 (s), 2.92 (s), 2.49-2.40 (m), 2.40-2.28 (m), 1.65 (s), 1.41-1.29 (m), 1.09-0.98 (m). MS (m/z) 813.2 [M+H]$^+$.

Example 162

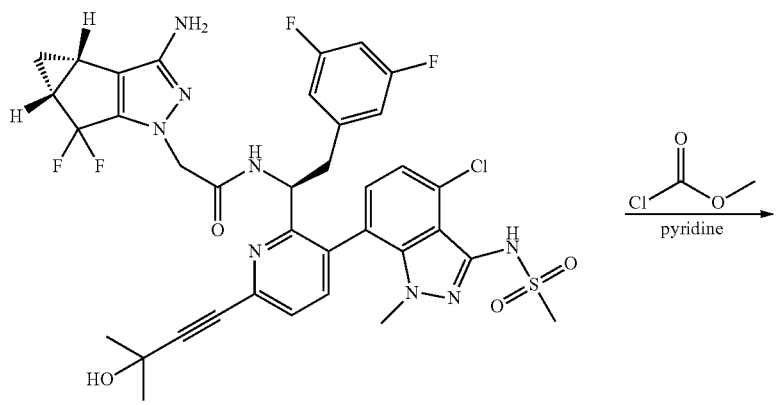

148B

-continued

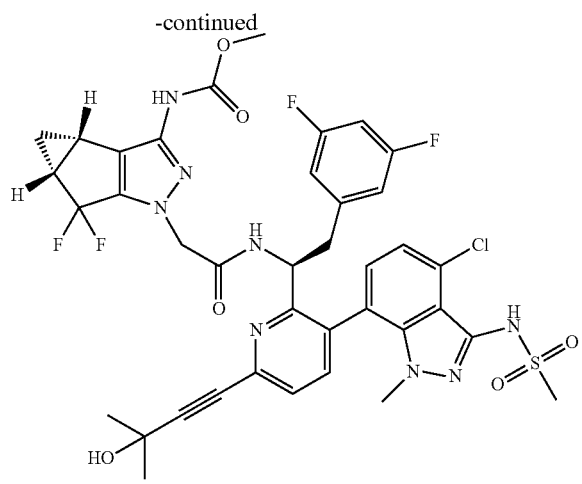

162

Synthesis of methyl ((3bS,4aR)-1-(2-(((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)amino)-2-oxoethyl)-5,5-difluoro-3b,4,4a,5-tetrahydro-1H-cyclopropa[3,4]cyclopenta[1,2-c]pyrazol-3-yl)carbamate (162)

To a solution of 148B (6 mg, 7.64 μmol) in DCM (0.1 ml) was added pyridine (3.08 μl, 38.21 μmol) followed by methylchloroformate (0.7 mg, 7.18 μmol) then stirred for 30 min at rt. The reaction was concentrated and the product was purified by prep HPLC to provide the product 162 as a mixture of atropisomers. $^1$H NMR (400 MHz, cd$_3$od) δ 7.72-7.65 (m), 7.54 (d), 7.51 (d), 7.17 (s), 7.06 (d), 6.81-6.73 (m), 6.67-6.59 (m), 6.44-6.33 (m), 5.27 (dd), 4.96 (t), 4.59 (d), 4.54 (d), 3.76 (s), 3.75 (s), 3.34 (s), 3.26 (s), 3.23 (s), 3.15-3.07 (m), 3.04-2.91 (m), 2.61 (s), 2.37-2.22 (m), 1.64 (s), 1.37-1.25 (m), 1.06-0.99 (m), 0.99-0.93 (m). MS (m/z) 843.2 [M+H]$^+$.

Example 163

Synthesis of 2-((3bS,4aR)-3-acetamido-5,5-difluoro-3b,4,4a,5-tetrahydro-1H-cyclopropa[3,4]cyclopenta[1,2-c]pyrazol-1-yl)-N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)acetamide (163)

The title compound (163) was prepared as a mixture of atropisomers according to the method presented for the synthesis of compound 162 of Example 162 utilizing acetyl chloride. $^1$H NMR (400 MHz, cd$_3$od) δ 7.69 (t), 7.54 (d), 7.51 (d), 6.80-6.74 (m), 6.67-6.60 (m), 6.44-6.33 (m), 5.27 (dd), 4.96 (t), 4.61 (s), 4.56 (d), 3.34 (s), 3.26 (s), 3.23 (s), 3.16-3.07 (m), 3.02-2.92 (m), 2.68-2.56 (m), 2.34-2.23 (m), 2.12 (s), 2.11 (s), 1.64 (s), 1.36-1.25 (m), 1.03-0.98 (m), 0.98-0.92 (m). MS (m/z) 827.1 [M+H]$^+$.

Example 164

163

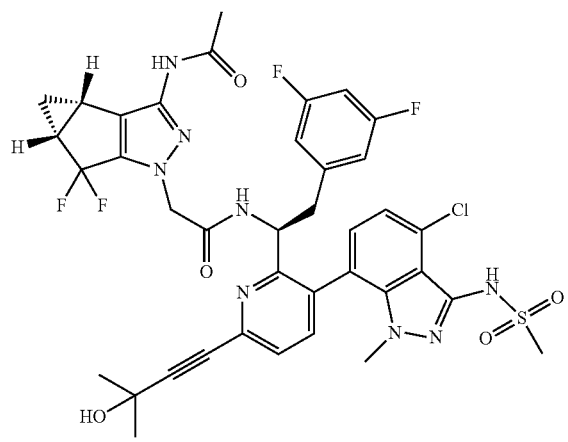

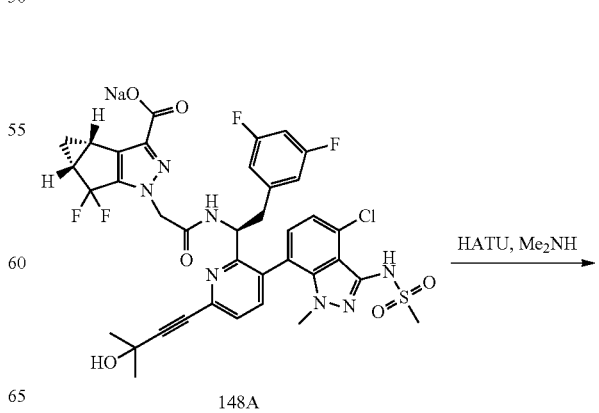

148A

411
-continued

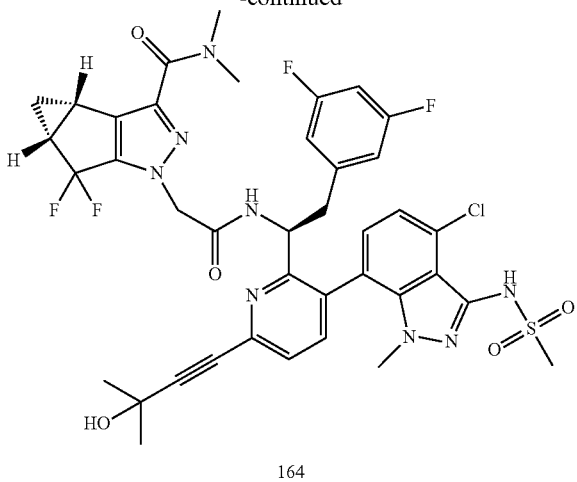

164

Synthesis of (3bS,4aR)-1-(2-(((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)amino)-2-oxoethyl)-5,5-difluoro-N,N-dimethyl-3b,4,4a,5-tetrahydro-1H-cyclopropa[3,4]cyclopenta[1,2-c]pyrazole-3-carboxamide (164)

To a solution of 148A (6 mg, 7.18 μmol) in DMA (100 μl) was added a solution of HATU (2.73 mg, 7.18 μmol) in DMA (50 μl) followed by dimethylamine (2M in THF, 50 μl, 0.1 mmol), then stirred for 16 h at rt. The reaction mixture was concentrated, filtered, and purified by reverse phase HPLC to provide the product 164 as a mixture of atropisomers. 1H NMR (400 MHz, cd₃od) δ 8.64 (d), 8.59 (d), 7.76-7.65 (m), 7.54 (d), 7.51 (d), 7.16 (s), 7.08 (d), 6.80-6.72 (m), 6.66-6.60 (m), 6.44 (d), 6.42-6.34 (m), 5.28 (dd), 4.98 (t), 4.78 (s), 4.73 (d), 3.34 (s), 3.33 (s), 3.28 (s), 3.25 (s), 3.23 (s), 3.15-3.07 (m), 3.09 (s), 3.07 (s), 3.03-2.92 (m), 2.57-2.38 (m), 1.66-1.61 (m), 1.43-1.26 (m), 1.13-1.07 (m), 1.03 (dt). MS (m/z) 841.1 [M+H]⁺.

Example 165

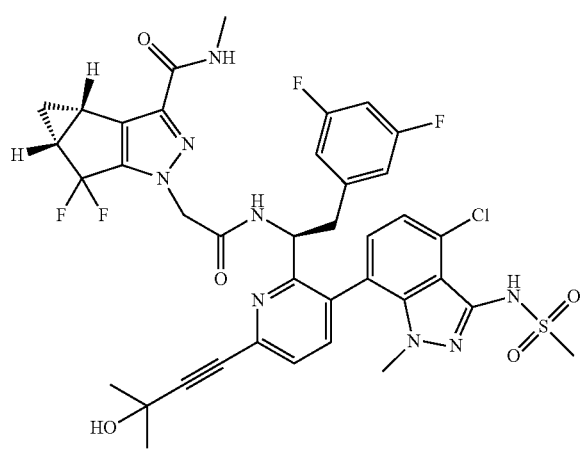

165

412

Synthesis of (3bS,4aR)-1-(2-(((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)amino)-2-oxoethyl)-5,5-difluoro-N-methyl-3b,4,4a,5-tetrahydro-1H-cyclopropa[3,4]cyclopenta[1,2-c]pyrazole-3-carboxamide (165)

The title compound (165) was prepared as a mixture of atropisomers according to the method presented for the synthesis of compound 164 of Example 164 utilizing methylamine. 1H NMR (400 MHz, cd₃od) δ 8.65-8.60 (m), 7.18-7.07 (m), 6.79-6.61 (m), 7.73-7.65 (m), 7.54 (d), 7.51 (d), 7.17 (s), 7.08 (d), 6.81-6.71 (m), 6.65-6.57 (m), 6.45 (d), 6.42-6.34 (m), 5.29 (dd), 4.97 (t), 4.78 (s), 4.72 (d), 3.34 (s), 3.25 (s), 3.21 (s), 3.24-3.11 (m), 3.02-2.93 (m), 2.88 (s), 2.87 (s), 2.69-2.52 (m), 2.51-2.36 (m), 1.64 (s), 1.45-1.24 (m), 1.10-1.02 (m), 1.02-0.95 (m). MS (m/z) 827.2 [M+H]⁺.

Example 166

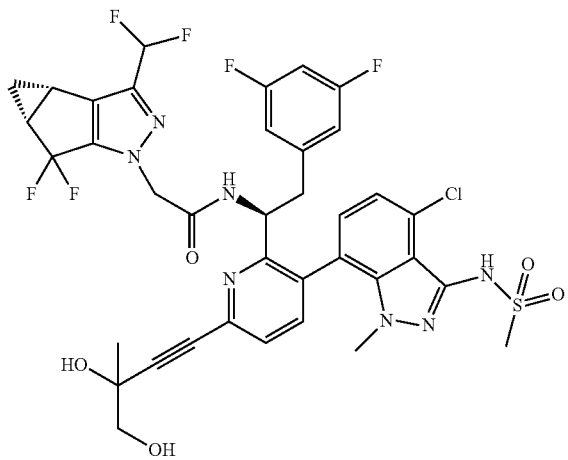

166

Synthesis of N-((1S)-1-(3-(4-chloro-1-methyl-3-(methylsulfonamido)-1H-indazol-7-yl)-6-(3,4-dihydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (166)

The title compound (166) was prepared as a mixture of atropisomers according to the method presented for the synthesis of compound 142 of Example 142 utilizing 2-methylbut-3-yne-1,2-diol. ¹H NMR (400 MHz, cd₃od) ¹H NMR (400 MHz, Methanol-d4) δ 8.68 (d), 7.70 (dd), 7.62-7.52 (m), 7.17 (s), 7.06 (d), 6.88-6.66 (m), 6.65-6.52 (m), 6.44-6.32 (m), 5.00-4.93 (m), 4.78-4.64 (m), 3.67 (s), 3.24 (d), 3.02-2.92 (m), 2.49-2.42 (m), 1.59 (s), 1.40-1.34 (m), 1.12-1.07 (m), 1.05-0.98 (s). MS (m/z) 837.9 [M+H]⁺.

Example 167

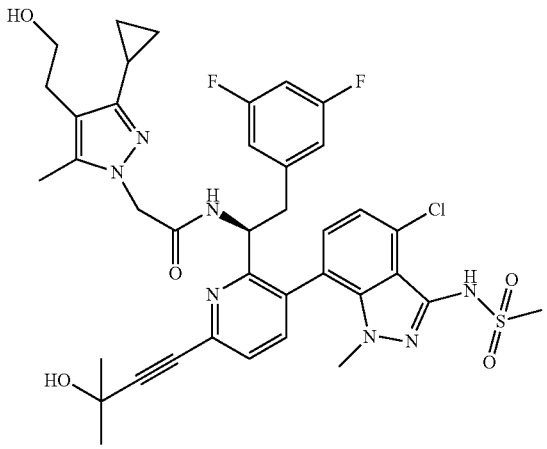

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-cyclopropyl-4-(2-hydroxyethyl)-5-methyl-1H-pyrazol-1-yl)acetamide (167)

The title compound (167) was prepared as a mixture of atropisomers according to the method presented in the synthesis of 10A in Example 10 utilizing 19F and 2-(3-cyclopropyl-4-(2-hydroxyethyl)-5-methyl-1H-pyrazol-1-yl) acetic acid (prepared as described in US2012045761). $^1$H NMR (400 MHz, Methanol-$d_4$) δ 7.71 (dd), 7.53 (dd), 7.27-7.15 (m), 7.12 (d), 6.80-6.70 (m), 6.69-6.58 (m), 6.55 (d), 6.44-6.29 (m), 5.33-5.22 (m), 5.03-4.93 (m), 4.73-4.52 (m), 3.69-3.53 (m), 3.32 (s), 3.27-3.21 (m), 3.17-3.08 (m), 3.05 (s), 2.99-2.85 (m), 2.76-2.60 (m), 2.11 (s), 2.01 (s), 1.88-1.78 (m), 1.64 (s), 0.93-0.86 (m), 0.79-0.70 (m). MS (m/z) 780.8 [M+H]$^+$.

Example 168

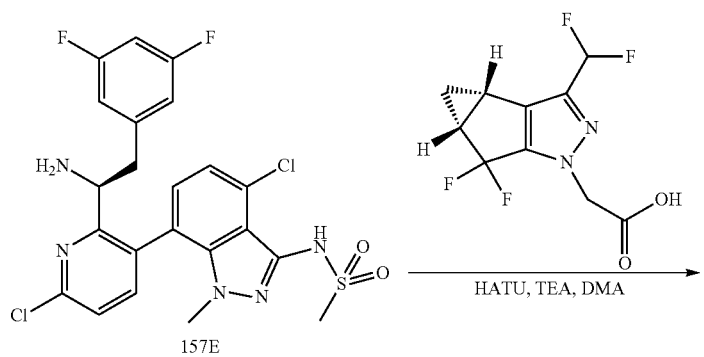

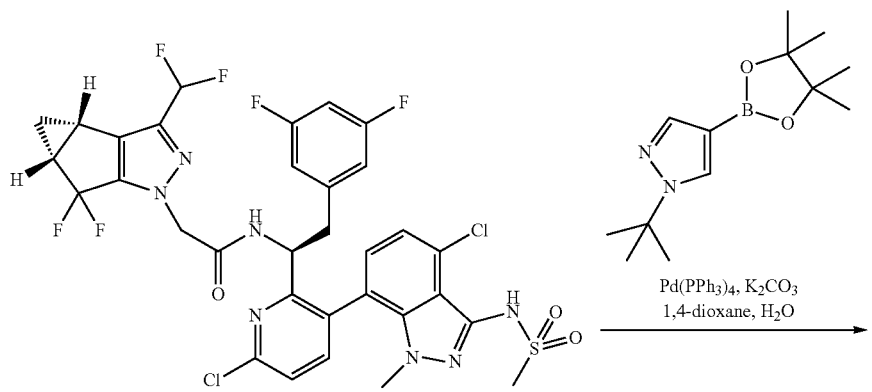

-continued

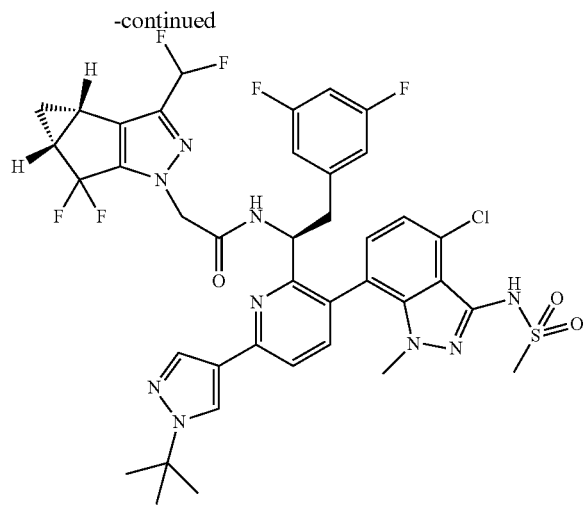

168B

Synthesis of N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (168A)

The title compound (168A) was prepared according to the method presented for the synthesis of compound 157F of Example 157 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. MS (m/z) 772.03 [M+H]⁺.

Synthesis of N—((S)-1-(6-(1-(tert-butyl)-1H-pyrazol-4-yl)-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (168B)

N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (168A, 20 mg, 0.026 mmol), 1-t-Butylpyrazole-4-boronic acid, pinacol ester (7.77 mg, 0.031 mmol), Pd(PPh$_3$)$_4$ (1.50 mg, 0.001 mmol), and K$_2$CO$_3$ (10.7 mg, 0.078 mmol) were suspended in 1,4-dioxane (0.2 mL). To the suspension was added water (0.05 mL). The resulting reaction mixture was degassed by bubbling argon for 60 seconds then sealed and heated thermally at 110° C. for 3.5 hours. Upon completion, the reaction mixture was filtered, concentrated in vacuo, taken in DMF, and purified by reverse phase HPLC to give the title compound 168B as a mixture of atropisomers. $^1$H NMR (400 MHz, Methanol-d$_4$) δ 8.51 (s), 8.50 (s), 8.25 (s), 8.22 (d), 7.70 (t), 7.68-7.60 (m), 7.17 (s), 7.08 (s), 7.06 (s), 6.87-6.51 (m), 6.46-6.33 (m), 5.34-5.24 (m), 4.98 (dd), 4.81 (s), 4.79 (s), 4.77 (s), 3.38 (s), 3.26 (s), 3.24 (s), 3.22-3.17 (m), 3.04 (s), 2.98 (dd), 2.53-2.36 (m), 1.70 (s), 1.46-1.27 (m), 1.08 (m), 1.00 (m). MS (m/z) 860.21 [M+H]⁺.

Example 169

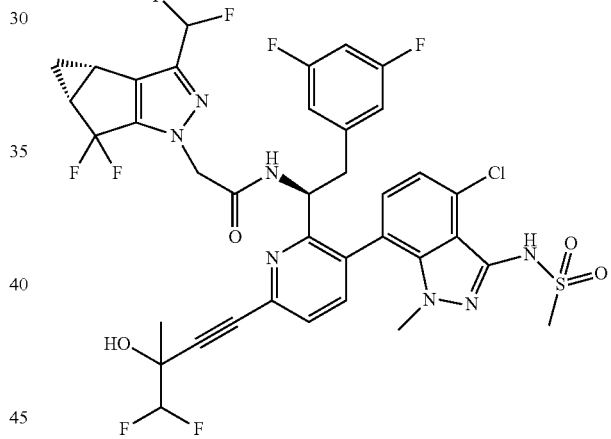

169

Synthesis of N-((1S)-1-(3-(4-chloro-1-methyl-3-(methylsulfonamido)-1H-indazol-7-yl)-6-(4,4-difluoro-3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (169)

The title compound (169) was prepared as a mixture of atropisomers according to the method presented for the synthesis of compound 142 of Example 142 utilizing 1,1-difluoro-2-methylbut-3-yn-2-ol. $^1$H NMR (400 MHz, cd$_3$od) δ 8.73 (t), 7.77-7.68 (d), 7.64-7.59 (m), 7.22-7.13 (m), 7.07 (dd), 6.87-6.51 (m), 6.46-6.34 (m), 5.82 (t), 5.37-5.21 (m), 5.04-4.93 (m), 4.78-4.63 (m), 3.24 (d), 3.05-2.93 (m), 2.45 (m), 1.63 (s), 1.47-1.32 (m), 1.08 (s), 1.01 (s). MS (m/z) 857.1 [M+H]⁺.

Example 170

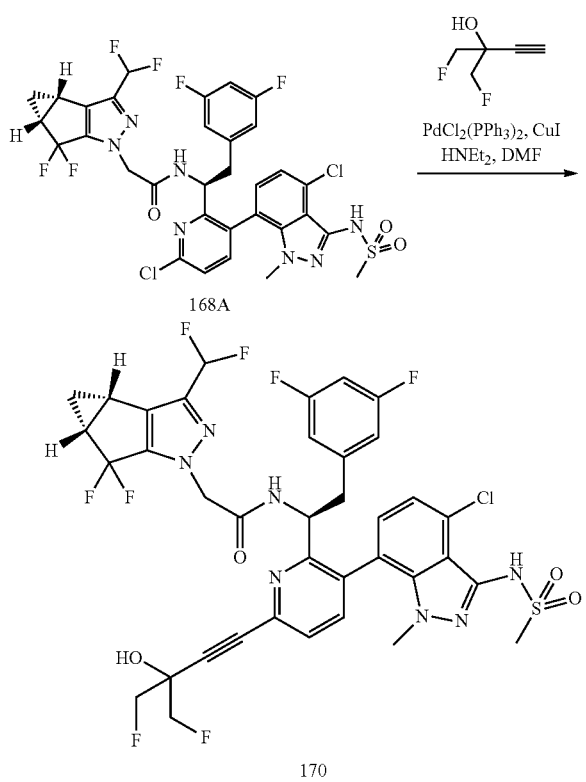

Synthesis of N—((S)-1-(3-(4-chloro-1-methyl-3-(methylsulfonamido)-1H-indazol-7-yl)-6-(4-fluoro-3-(fluoromethyl)-3-hydroxybut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (170)

N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (168A, 20 mg, 0.025 mmol), 1-fluoro-2-(fluoromethyl)but-3-yn-2-ol (15.5 mg, 0.129 mmol), PdCl$_2$(PPh$_3$)$_2$ (1.8 mg, 0.003 mmol), and CuI (0.5 mg, 0.003 mmol) were suspended in DMF (0.25 mL). To the reaction mixture was added diethylamine (27 µL, 0.259 mmol), and the reaction mixture was degassed by bubbling argon for 5 minutes then sealed and heated at 125° C. for 30 minutes in a microwave reactor. Upon cooling, the reaction mixture was filtered and purified by reverse phase HPLC. Fractions containing the product were pooled and lyophilized to give the title compound 170 as a mixture of atropisomers. $^1$H NMR (400 MHz, Methanol-d$_4$) δ 8.72 (t), 7.74 (dd), 7.61 (dd), 7.22-7.14 (m), 7.09 (s), 7.07 (s), 6.87-6.53 (m), 6.46-6.35 (m), 5.35-5.26 (m), 4.99 (q), 4.76 (s), 4.72 (s), 4.70 (s), 4.66 (d), 4.54 (d), 3.33 (s), 3.26 (s), 3.23 (s), 3.18-3.09 (m), 3.05-2.91 (m), 2.54-2.37 (m), 1.45-1.33 (m), 1.09 (s), 1.02 (s). MS (m/z) 856.09 [M+H]$^+$.

Example 171

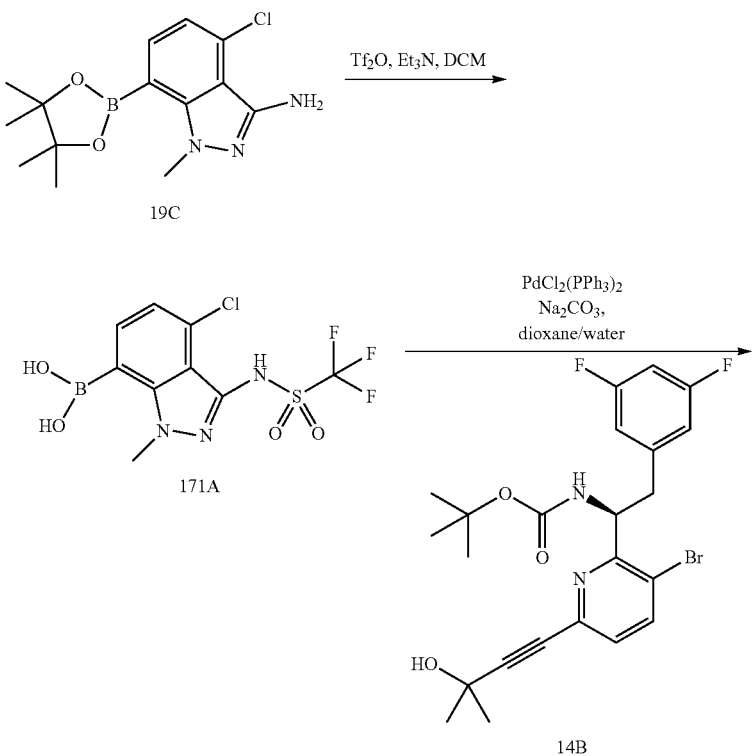

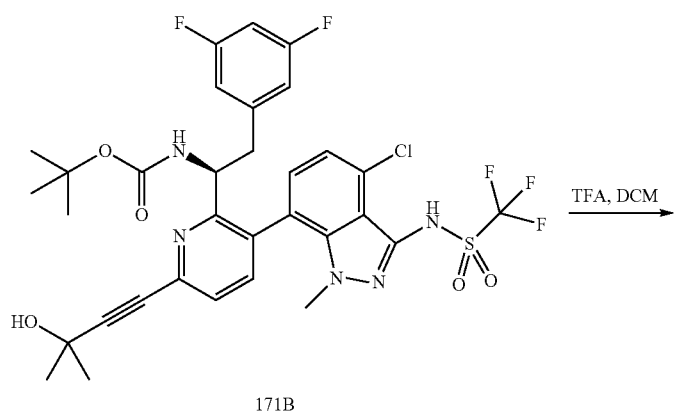

171B

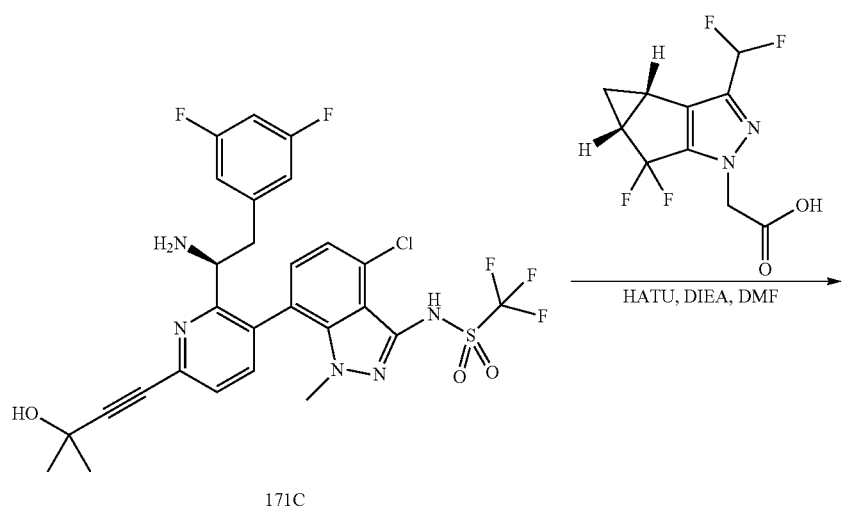

171C

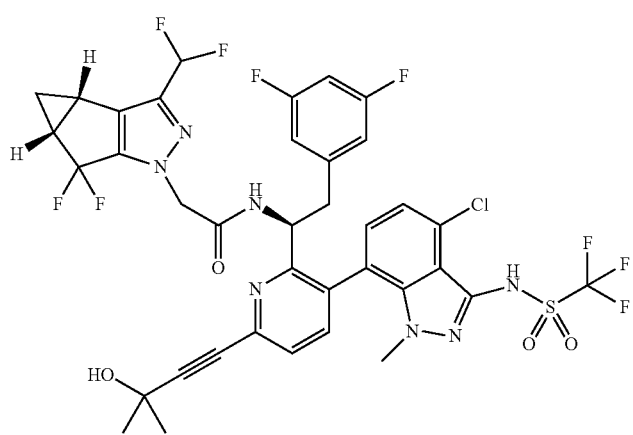

171D

Synthesis of (4-chloro-1-methyl-3-(trifluoromethylsulfonamido)-1H-indazol-7-yl)boronic acid (171A)

4-chloro-1-methyl-7-(4,4,5,5-tetramethyl-1,3,2-dioxaborolan-2-yl)-1H-indazol-3-amine (19C) (0.20 g, 0.65 mmol) was dissolved in dichloromethane (10 mL) and triethylamine (0.36 mL, 2.6 mmol). The mixture was cooled to 0° C. and triflic anhydride (0.55 g, 1.95 mmol) was added dropwise. After stirring for 30 minutes the reaction was quenched with water (10 mL) and extracted with dichloromethane (3×20 mL). The combined extracts were washed with brine and evaporated under vacuum. The residue was dissolved in ethanol (10 mL) and cooled to 0° C. 50% aqueous KOH solution (0.2 mL) was added dropwise and stirring was continued for 30 minutes. The mixture was acidified with 1N aqueous HCl. The formed precipitate was filtered and dried to give the title compound. MS (m/z) 358.0 [M+H]$^+$.

Synthesis of (S)-tert-butyl (1-(3-(4-chloro-1-methyl-3-(trifluoromethylsulfonamido)-1H-indazol-7-yl)-6-(3-hydroxy-3-methylbut-1-yn-1-yl)pyridin-2-yl)-2-(3,5-difluorophenyl)ethyl)carbamate (171B)

(4-chloro-1-methyl-3-(trifluoromethylsulfonamido)-1H-indazol-7-yl)boronic acid (171A, 26 mg, 0.073 mmol), (S)-tert-butyl (1-(3-bromo-6-(3-hydroxy-3-methylbut-1-yn-1-yl)pyridin-2-yl)-2-(3,5-difluorophenyl)ethyl)carbamate (14B, 36 mg, 0.073 mmol), and PdCl$_2$(PPh$_3$)$_2$ (5.1 mg, 0.007 mmol) were suspended in 1,4-dioxane (1 mL) and 1.0 M aqueous NaHCO$_3$ (1 mL). The reaction mixture was heated at 150° C. for 15 minutes in a microwave reactor. After cooling, the reaction mixture was diluted with EtOAc (50 mL), washed with water and brine, concentrated in vacuo, and purified by silica gel column chromatography, eluting with 20-100% EtOAc in hexanes to give the title compound. MS (m/z) 728.3 [M+H]$^+$.

Synthesis of (S)—N-(7-(2-(1-amino-2-(3,5-difluorophenyl)ethyl)-6-(3-hydroxy-3-methylbut-1-yn-1-yl)pyridin-3-yl)-4-chloro-1-methyl-1H-indazol-3-yl)-1,1,1-trifluoromethanesulfonamide (171C)

To a solution of (S)-tert-butyl (1-(3-(4-chloro-1-methyl-3-(trifluoromethylsulfonamido)-1H-indazol-7-yl)-6-(3-hydroxy-3-methylbut-1-yn-1-yl)pyridin-2-yl)-2-(3,5-difluorophenyl)ethyl)carbamate (171B, 43 mg, 0.059 mmol) in DCM (1 mL) was added trifluoroacetic acid (1 mL). The reaction mixture was stirred at room temperature for 3 hours and then concentrated in vacuo and azeotroped once with toluene (20 mL) to give the title compound. MS (m/z) 628.2 [M+H]$^+$.

Synthesis of N—((S)-1-(3-(4-chloro-1-methyl-3-(trifluoromethylsulfonamido)-1H-indazol-7-yl)-6-(3-hydroxy-3-methylbut-1-yn-1-yl)pyridin-2-yl)-2-(3,5-difluorophenyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (171D)

To a solution of crude (S)—N-(7-(2-(1-amino-2-(3,5-difluorophenyl)ethyl)-6-((2-hydroxyethyl)(methyl)amino)pyridin-3-yl)-4-chloro-1-methyl-1H-indazol-3-yl)methanesulfonamide (171C, 44 mg, 0.059 mmol) in DMF (1 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15.6 mg, 0.059 mmol), and HATU (27 mg, 0.071 mmol) followed by diisopropylethylamine (31 µL, 0.177 mmol). After stirring for two hours at ambient temperature, the reaction mixture was filtered and purified by reverse phase HPLC to provide the title compound as a mixture of atropisomers. $^1$H NMR (400 MHz, DMSO-d$_6$) δ 9.11 (d), 8.95 (d), 7.87 (d), 7.83 (d), 7.51 (d), 7.26 (d), 7.19 (s), 7.12-6.74 (m), 6.62-6.56 (m), 6.49-6.35 (m), 4.95 (q), 4.79-4.54 (m), 3.26 (s), 3.06 (s), 3.31-2.92 (m), 2.58-2.38 (m), 1.52 (s), 1.42-1.30 (m), 0.95-0.78 (m). MS (m/z) 874.2 [M+H]$^+$.

Example 172

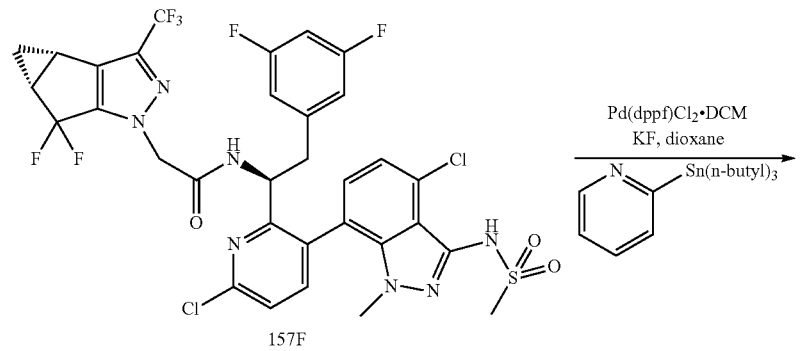

157F

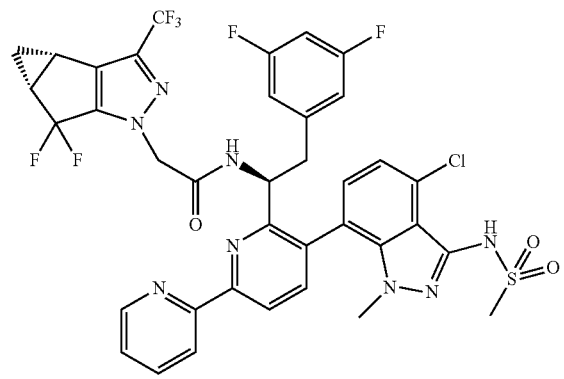

172

423

Synthesis of N—((S)-1-(5-(4-chloro-1-methyl-3-(methylsulfonamido)-1H-indazol-7-yl)-[2,2'-bipyridin]-6-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (172)

To the reaction vial containing 157F (20 mg, 0.025 mmol) in dioxane (0.25 mL) was added 2-(tributylstannyl)pyridine (0.01 mL, 0.027 mmol), Pd(dppf)Cl$_2$.DCM (1.2 mg, 0.001 mmol), and KF (4 mg, 0.75 mmol). The reaction mixture was flushed with argon gas for 5 min then sealed and heated in a microwave reactor to 135° C. for 30 min. Upon cooling, the reaction mixture was filtered and purified by reverse phase HPLC to provide the title compound 172 as a mixture of atropisomers. $^1$H NMR (400 MHz, cd$_3$od) δ 9.90-9.8 (m), 8.80-8.76 (m), 8.74-8.70 (m), 8.52-8.45 (m), 7.98-7.88 (m, 1H), 7.30-7.04 (m), 6.82-6.71 (m), 6.51-6.34 (m), 5.45-5.35 (m), 5.14-5.05 (m), 4.98-4.86 (m), 3.35 (s), 3.21-3.00 (m), 2.60-2.38 (m), 1.42-1.22 (m), 1.19-1.09 (m,), 1.06-1.00 (m). MS (m/z) 833.2 [M+H]$^+$.

Example 173

424

Synthesis of N—((S)-1-(3-(4-chloro-1-methyl-3-(methylsulfonamido)-1H-indazol-7-yl)-6-(1-methyl-1H-pyrazol-4-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (173)

N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (157F, 20 mg, 0.025 mmol), 1-methylpyrazole-4-boronic acid (3.8 mg, 0.030 mmol), Pd(PPh$_3$)$_4$ (1.5 mg, 0.001 mmol), and K$_2$CO$_3$ (10.5 mg, 0.076 mmol) were suspended in 1,4-dioxane (0.2 mL). To the suspension was added water (0.05 mL). The resulting reaction mixture was degassed by bubbling argon for 60 seconds then sealed and heated thermally at 110° C. for 2 hours. Upon completion, the reaction mixture was filtered, concentrated in vacuo, taken in DMF, and purified by reverse phase HPLC to give the title compound 173 as a mixture of atropisomers. $^1$H NMR (400 MHz, Methanol-d$_4$) δ 8.39 (s), 8.35 (s), 8.23 (s), 8.20 (s), 7.71-7.60 (m), 7.15 (s), 7.06 (d), 6.76 (tt), 6.63 (tt), 6.49-6.41 (m), 6.41-6.34 (m), 5.24 (dd), 4.99 (dd), 4.03 (s), 4.02 (s), 3.46-3.41 (m), 3.39 (s), 3.26 (s), 3.24 (s), 3.23-3.17 (m), 3.07-2.95 (m), 2.59-2.38 (m), 1.49-1.34 (m), 1.17-1.11 (m), 1.09-1.03 (m). MS (m/z) 836.16 [M+H]$^+$.

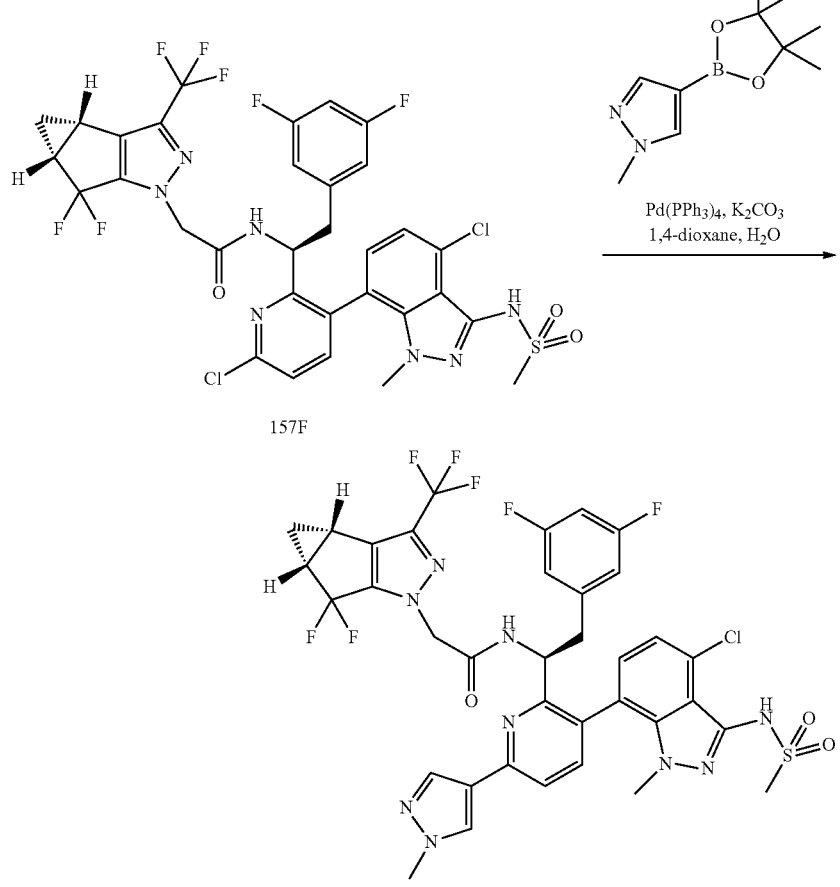

Example 174

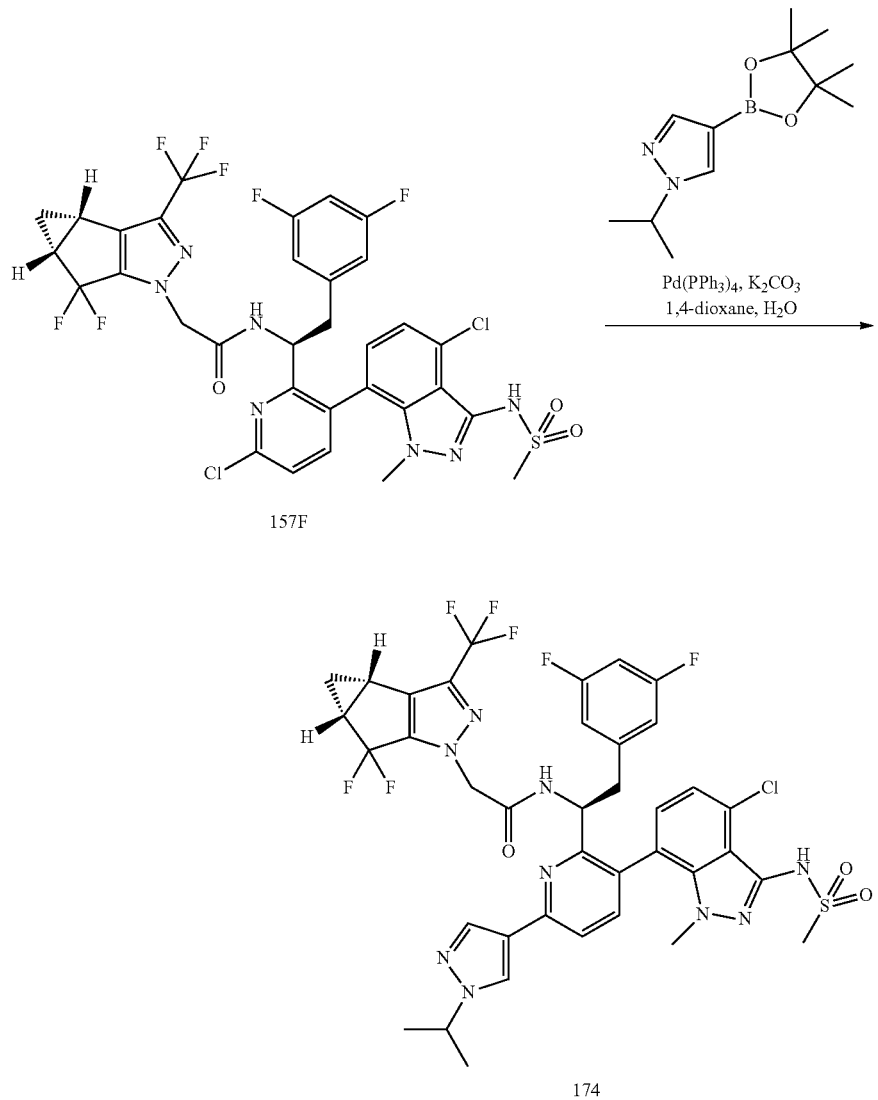 [SMILES: Cn1nc(NS(C)(=O)=O)c2c(Cl)ccc(-c3ccc(Cl)nc3[C@H](Cc3cc(F)cc(F)c3)NC(=O)Cn3nc(C(F)(F)F)c4c3C(F)(F)[C@@H]3C[C@H]43)c21 ; CC(C)n1cc(B2OC(C)(C)C(C)(C)O2)cn1 ; CC(C)n1cc(-c2ccc(-c3ccc(Cl)c4c(NS(C)(=O)=O)nn(C)c34)c([C@H](Cc3cc(F)cc(F)c3)NC(=O)Cn3nc(C(F)(F)F)c4c3C(F)(F)[C@@H]3C[C@H]43)n2)cn1]

Synthesis of N—((S)-1-(3-(4-chloro-1-methyl-3-(methylsulfonamido)-1H-indazol-7-yl)-6-(1-isopropyl-1H-pyrazol-4-yl)pyridin-2-yl)-2-(3,5-difluorophenyl)ethyl)-2-((3b,4aR)-5,5-difluoro-3-(trifluoromethyl)-3b,4,4a,5-tetrahydro-1H-cyclopropa[3,4]cyclopenta[1,2-c]pyrazol-1-yl)acetamide (174)

The title compound (174) was prepared as a mixture of atropisomers according to the method presented for the synthesis of compound 173 of Example 173 utilizing 1-isopropylpyrazole-4-boronic acid, pinacol ester. $^1$H NMR (400 MHz, Methanol-$d_4$) δ 8.46 (s), 8.44 (s), 8.24 (s), 8.22 (s), 7.72-7.60 (m), 7.16 (s), 7.06 (d), 6.76 (tt), 6.68-6.57 (m), 6.49-6.42 (m), 6.41-6.33 (m), 5.26 (dd), 4.99 (dd), 4.86 (s), 4.70-4.58 (m), 3.47-3.40 (m), 3.39 (s), 3.37-3.34 (m), 3.26 (s), 3.24 (s), 3.23-3.16 (m), 3.09-2.93 (m), 2.59-2.37 (m), 1.61 (d), 1.49-1.34 (m), 1.17-1.11 (m), 1.09-1.02 (m). MS (m/z) 864.20 [M+H]$^+$.

Example 175

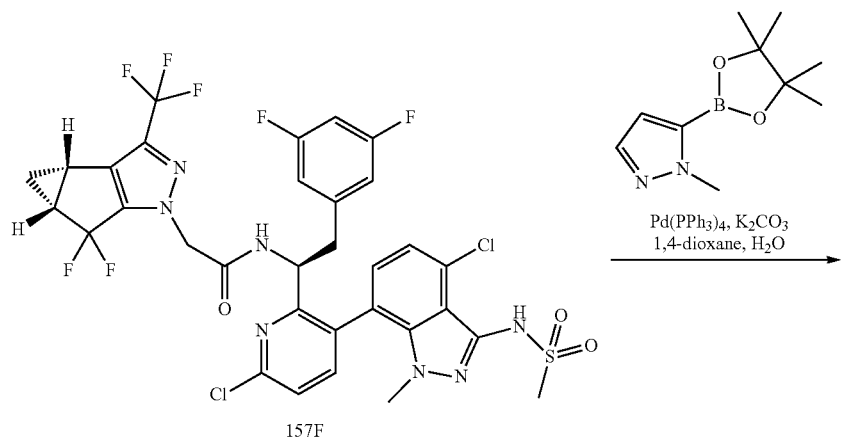

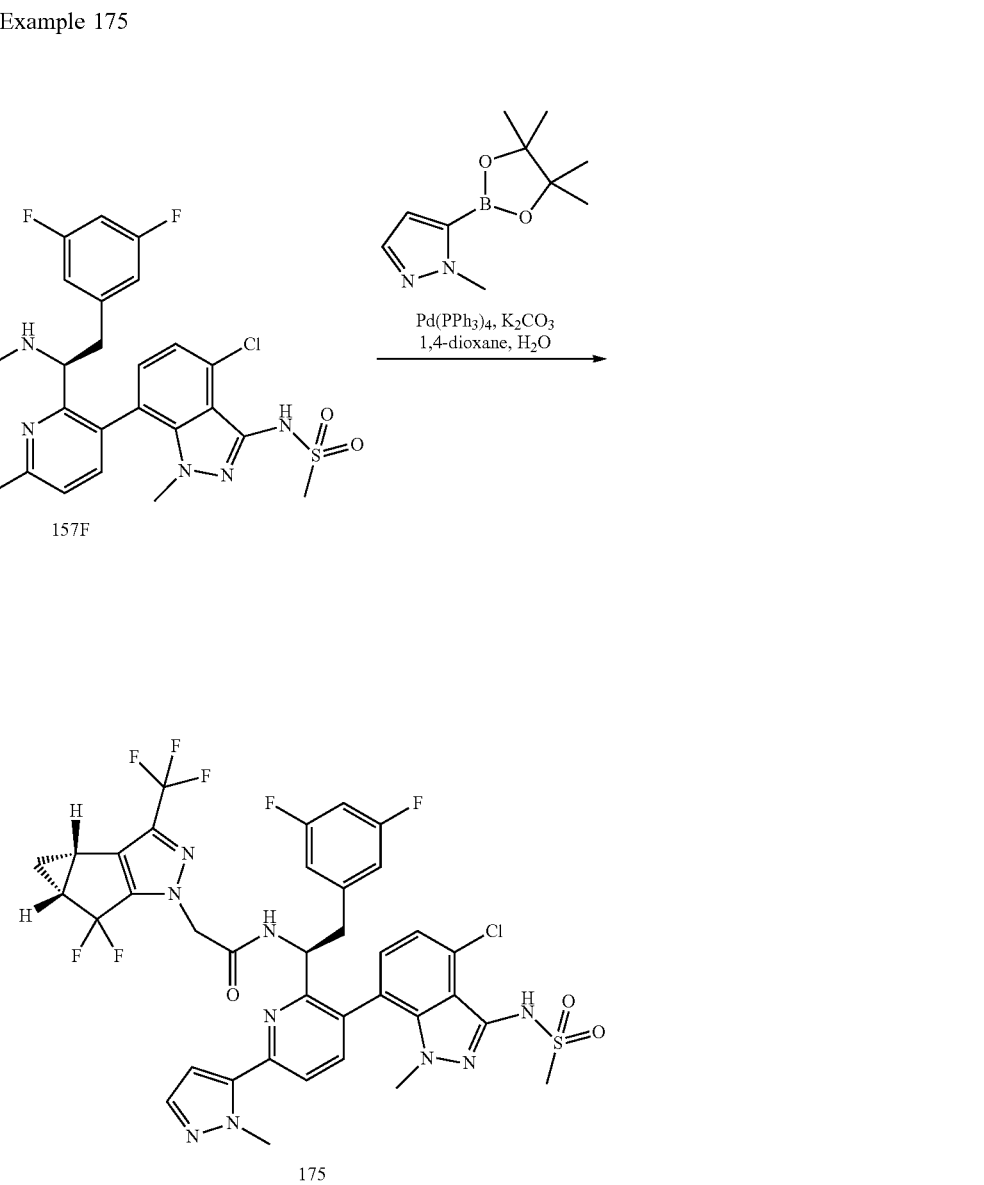

Synthesis of N—((S)-1-(3-(4-chloro-1-methyl-3-(methylsulfonamido)-1H-indazol-7-yl)-6-(1-methyl-1H-pyrazol-5-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (175)

The title compound (175) was prepared as a mixture of atropisomers according to the method presented for the synthesis of compound 173 of Example 173 utilizing 1-methyl-1H-pyrazole-5-boronic acid pinacol ester. $^1$H NMR (400 MHz, Methanol-d$_4$) δ 7.87-7.78 (m), 7.59 (d), 7.31 (d), 7.20 (d), 7.11 (d), 6.90 (d), 6.88 (d), 6.79 (tt), 6.63 (tt), 6.55-6.51 (m), 6.47-6.37 (m), 5.40 (dd), 5.07 (dd), 4.78 (s), 4.77 (s), 4.43 (s), 4.34 (s), 3.39 (s), 3.25 (s), 3.24-3.21 (m), 3.15-3.12 (m), 3.11-3.02 (m), 2.59-2.35 (m), 1.47-1.33 (m), 1.15-1.08 (m), 1.06-0.98 (m). MS (m/z) 836.15 [M+H]$^+$.

Example 176

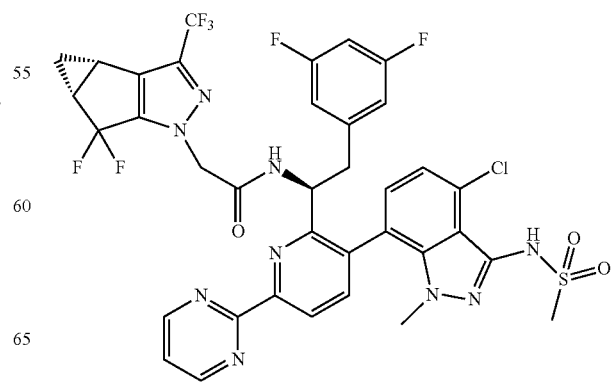

176

Synthesis of N—((S)-1-(3-(4-chloro-1-methyl-3-(methylsulfonamido)-1H-indazol-7-yl)-6-(pyrimidin-2-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (176)

The title compound (176) was prepared as a mixture of atropisomers according to the method presented for the synthesis of compound 172 of Example 172 utilizing 2-(tributylstannyl)pyrimidine. $^1$H NMR (400 MHz, cd$_3$od) δ 9.90-9.86 (m), 9.84-9.80 (m), 8.80-8.75 (m, 1H), 8.74 (d), 8.47 (d), 7.92 (t), 7.25-7.12 (m), 6.80-6.50 (m), 6.45-6.40 (m), 5.45-5.38 (m), 5.15-5.05 (m), 4.90-4.81 (m), 3.37 (s), 3.18-3.04 (m), 2.50-2.39 (m), 1.44-1.25 (m), 1.15-1.09 (m), 1.08-0.97 (m). MS (m/z) 835.1 [M+H]$^+$.

Example 177

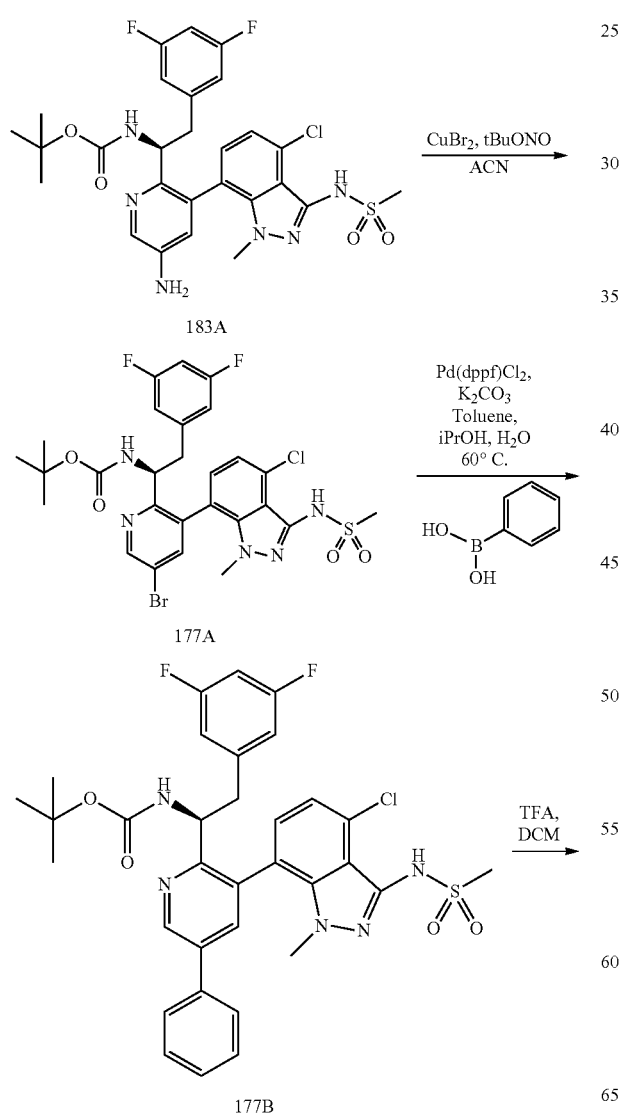

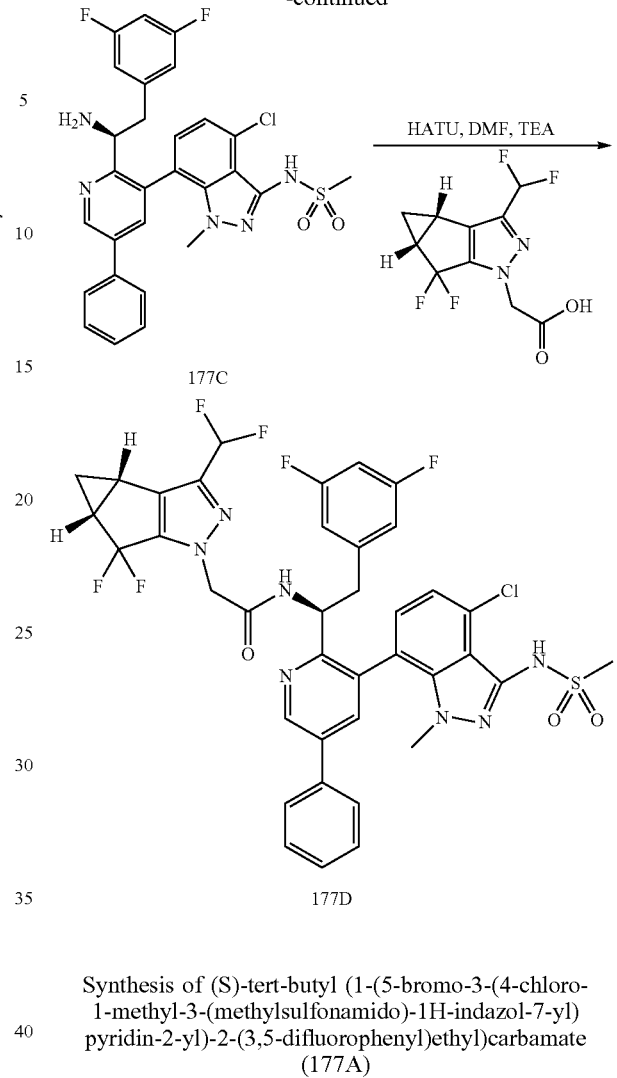

Synthesis of (S)-tert-butyl (1-(5-bromo-3-(4-chloro-1-methyl-3-(methylsulfonamido)-1H-indazol-7-yl)pyridin-2-yl)-2-(3,5-difluorophenyl)ethyl)carbamate (177A)

Compound 183A (0.500 g, 0.82 mmol) was added to a stirred suspension of t-BuONO (0.15 mL, 1.24 mmol) and CuBr$_2$ (0.276 g, 1.24 mmol) in acetonitrile with ice bath, the suspension was allowed to warm up to room temperature and stirred overnight. Aqueous ammonium chloride was added. The mixture was extracted with EtOAc. The organic layer was dried with MgSO$_4$, concentrated and purified by silica gel column to afford the title compound as mixture of atropisomers (177A). MS (m/z) 670 [M+H]$^+$.

Synthesis of (S)-tert-butyl (1-(3-(4-chloro-1-methyl-3-(methylsulfonamido)-1H-indazol-7-yl)-5-phenylpyridin-2-yl)-2-(3,5-difluorophenyl)ethyl)carbamate (177B)

Compound 177A (31.3 mg, 0.047 mmol), phenylbronic acid (6.3 mg, 0.051 mmol), K$_2$CO$_3$ (39 mg, 0.28 mmol) and Pd(dppf)Cl$_2$ (14 mg, 0.019 mmol) were mixed together. Toluene (1 mL), iPrOH (0.5 mL) and water (1 mL) were added. The vial was capped tight, stirred at 60° C. for 30 minutes. The reaction mixture was diluted with EtOAc, washed with brine, dried with MgSO$_4$ and concentrated. The crude was purified by silica gel column to afford the title compound as mixture of atropisomers (177B). MS (m/z) 668 [M+H]$^+$.

Synthesis of (S)—N-(7-(2-(1-amino-2-(3,5-difluorophenyl)ethyl)-5-phenylpyridin-3-yl)-4-chloro-1-methyl-1H-indazol-3-yl)methanesulfonamide (177C)

Compound 177B (21.7 mg, 0.032 mmol) was dissolved in DCM (1 mL). TFA (0.5 mL) was added. The resultant solution was stirred at ambient temperature for 2 hours. The reaction was concentrated to afford title compound as mixture of atropisomers (177C). MS (m/z) 568 [M+H]$^+$.

Synthesis of N—((S)-1-(3-(4-chloro-1-methyl-3-(methylsulfonamido)-1H-indazol-7-yl)-5-phenylpyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (177D)

Compound 177C (18.4 mg, 0.032 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (8.6 mg, 0.032 mmol) were dissolved in DMF (1 mL). TEA (23 uL, 0.162 mmol) and HATU (18.5 mg, 0.049 mmol) were added. Upon completion, a few drops of 1M HCl were added. The reaction was purified by HPLC to afford the title compound as mixture of atropisomers (177D). $^1$H NMR (400 MHz, Acetonitrile-d3) δ 9.04 (dd), 7.99 (dd), 7.82-7.73 (m), 7.69 (d), 7.59-7.43 (m), 7.34 (d), 7.29-7.18 (m), 7.15 (d), 6.90 (d), 6.85-6.73 (m), 6.69-6.58 (m), 6.49-6.36 (m), 5.30 (q), 4.96 (q), 4.69 (d), 3.33 (s), 3.28 (s), 3.27 (s), 3.20-2.91 (m), 2.58-2.40 (m), 1.40 (q), 1.09-0.97 (m). MS (m/z) 814 [M+H]$^+$.

Example 178

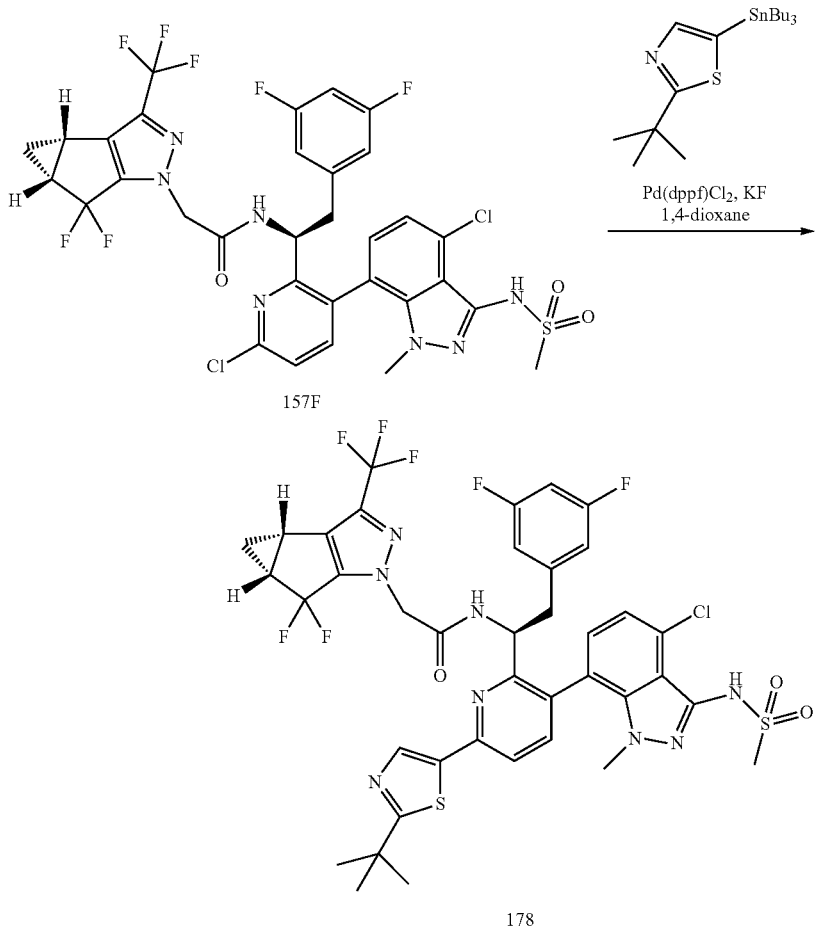

Synthesis of N—((S)-1-(6-(2-(tert-butyl)thiazol-5-yl)-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (178)

N—((S)-1-(6-chloro-3-(4-chloro-1-methyl-3-(methylsulfonamido)-1H-indazol-7-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (157F, 20 mg, 0.025 mmol), 2-(tert-butyl)-5-(tributylstannyl)thiazole (12.03 mg, 0.028 mmol), Pd(dppf)Cl$_2$ (1.1 mg, 0.001 mmol), and KF (4.4 mg, 0.076 mmol) were suspended in 1,4-dioxane (0.25 mL). The resulting reaction mixture was degassed by bubbling argon for 60 seconds then sealed and heated at 130° C. for 30 minutes in a microwave reactor. Upon cooling, the reaction mixture was filtered, concentrated in vacuo, taken in DMF, and purified by reverse phase HPLC to give the title compound 178 as a mixture of atropisomers. $^1$H NMR (400

MHz, Methanol-d$_4$) δ 8.40 (s), 7.91 (dd), 7.76 (d), 7.74 (d), 7.20-7.13 (m), 7.08 (d), 6.77 (tt), 6.65 (tt), 6.55-6.47 (m), 6.45-6.38 (m), 5.20 (dd), 5.02 (dd), 4.80 (s), 3.41 (s), 3.26 (s), 3.25 (s), 3.09-2.98 (m), 2.95 (s), 2.60-2.39 (m), 1.71 (s), 1.70 (s), 1.69 (s), 1.48-1.34 (m), 1.17-1.11 (m), 1.09-1.03 (m). MS (m/z) 897.04 [M+H]$^+$.

Example 179

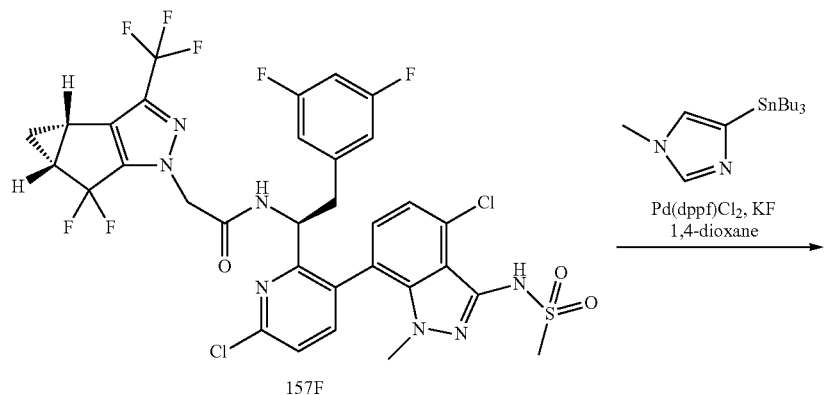

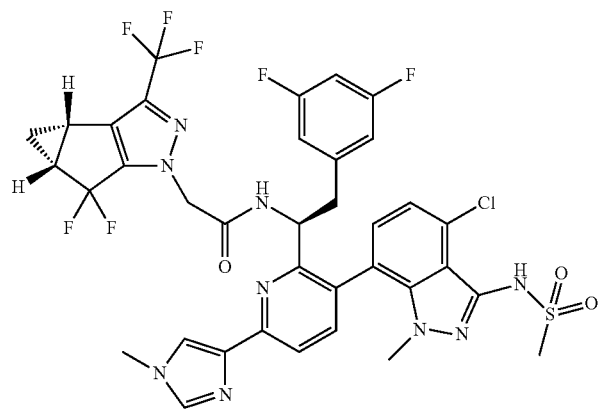

Synthesis of N—((S)-1-(3-(4-chloro-1-methyl-3-(methylsulfonamido)-1H-indazol-7-yl)-6-(1-methyl-1H-imidazol-4-yl)pyridin-2-yl)-2-(3,5-difluorophenyl)ethyl)-2-((3b,4aR)-5,5-difluoro-3-(trifluoromethyl)-3b,4,4a,5-tetrahydro-1H-cyclopropa[3,4]cyclopenta[1,2-c]pyrazol-1-yl)acetamide (179)

The title compound (179) was prepared as a mixture of atropisomers according to the method presented for the synthesis of compound 178 of Example 178 utilizing 1-methyl-4-(tributylstannyl)-1H-imidazole. $^1$H NMR (400 MHz, Methanol-d$_4$) δ 8.89 (s), 8.84 (s), 8.29 (s), 8.25 (s), 7.94-7.82 (m), 7.19 (s), 7.07 (d), 6.78 (tt), 6.64 (tt), 6.48-6.41 (m), 6.37 (dd), 5.35 (dd), 5.05 (dd), 4.81 (s), 4.77 (s), 4.05 (s), 4.04 (s), 3.36 (s), 3.27 (s), 3.25 (s), 3.23-3.18 (m), 3.12-2.98 (m), 2.59-2.41 (m), 1.48-1.37 (m), 1.33-1.26 (m), 1.16-1.10 (m), 1.09-1.03 (m). MS (m/z) 836.15 [M+H]$^+$.

Example 180
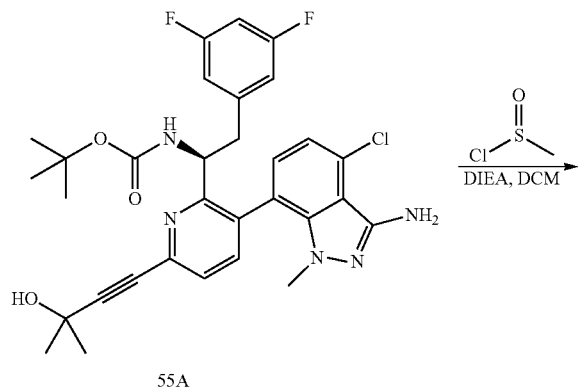
55A
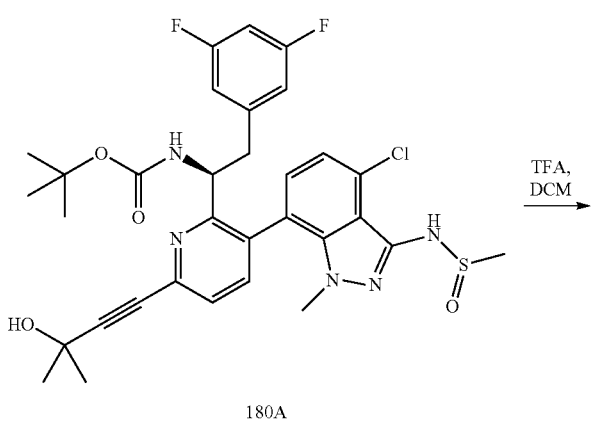
180A
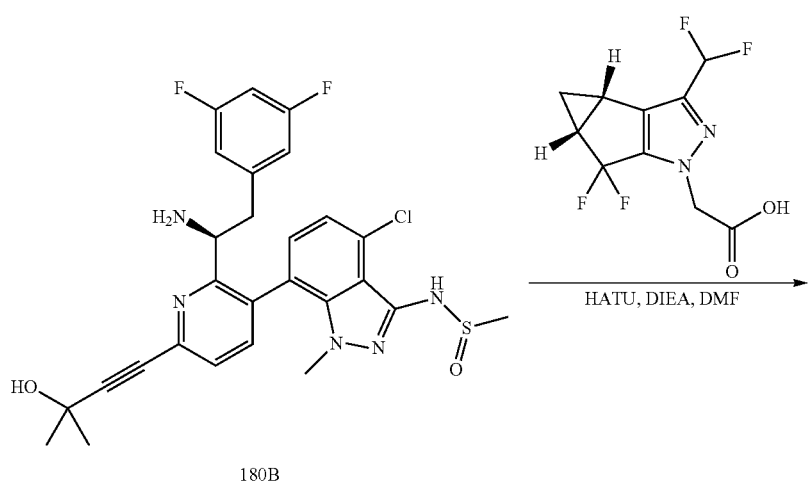
180B

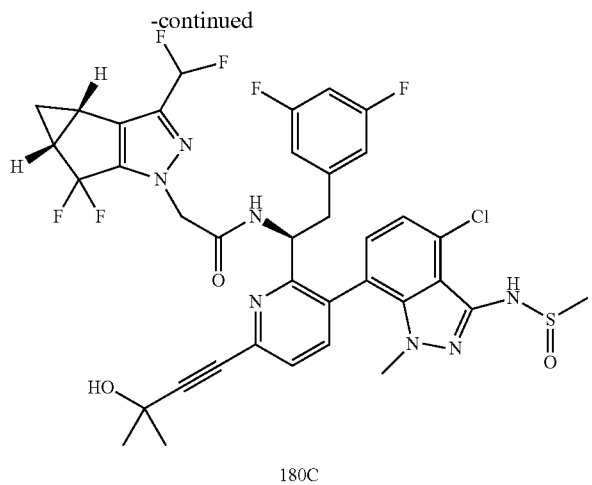

180C

Synthesis of tert-butyl ((1S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)carbamate (180A)

(S)-tert-butyl (1-(3-(3-amino-4-chloro-1-methyl-1H-indazol-7-yl)-6-(3-hydroxy-3-methylbut-1-yn-1-yl)pyridin-2-yl)-2-(3,5-difluorophenyl)ethyl)carbamate (55A, 61 mg, 0.102 mmol) was dissolved in dichloromethane (2 mL) and diisopropylethylamine (0.071 mL, 0.409 mmol). The mixture was cooled to 0° C. and methanesulfinyl chloride (30.3 mg, 0.307 mmol) was added dropwise. After stirring at ambient temperature overnight the reaction mixture was diluted with ethyl acetate (50 mL), washed with water and brine and evaporated under vacuum. Purification on silica gel gave the title compound. MS (m/z) 658.3 [M+H]$^+$.

Synthesis of N-(7-(2-((S)-1-amino-2-(3,5-difluorophenyl)ethyl)-6-(3-hydroxy-3-methylbut-1-yn-1-yl)pyridin-3-yl)-4-chloro-1-methyl-1H-indazol-3-yl)methanesulfinamide (180B)

To a solution of tert-butyl ((1S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)carbamate (180A, 50 mg, 0.076 mmol) in DCM (1 mL) was added trifluoroacetic acid (1 mL). The reaction mixture was stirred at room temperature for 3 hours and then concentrated in vacuo and azeotroped once with toluene (20 mL) to give the title compound. MS (m/z) 558.2 [M+H]$^+$.

Synthesis of N-((1S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (180C)

To a solution of crude N-(7-(2-((S)-1-amino-2-(3,5-difluorophenyl)ethyl)-6-(3-hydroxy-3-methylbut-1-yn-1-yl)pyridin-3-yl)-4-chloro-1-methyl-1H-indazol-3-yl)methanesulfinamide (180B, 52 mg, 0.076 mmol) in DMF (1 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (20 mg, 0.076 mmol), and HATU (34.7 mg, 0.091 mmol) followed by diisopropylethylamine (66 µL, 0.38 mmol). After stirring for two hours at ambient temperature, the reaction mixture was filtered and purified by reverse phase HPLC to provide the title compound as a mixture of diastereomers and atropisomers. $^1$H NMR (400 MHz, DMSO-d$_6$) δ 8.99-8.60 (m), 7.85-7.70 (m), 7.55 (d), 7.05-6.70 (m), 6.56-6.28 (m), 4.93-4.49 (m), 3.30-2.59 (m), 2.96 (s), 2.65 (s), 2.48-2.30 (m), 1.72-1.66 (m), 1.42-1.30 (m), 0.95-0.78 (m). MS (m/z) 804.2 [M+H]$^+$.

Example 181

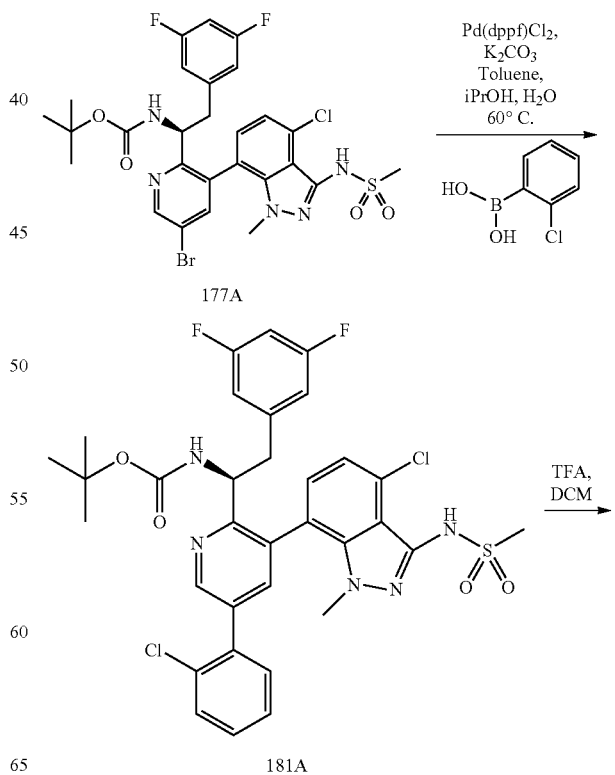

-continued

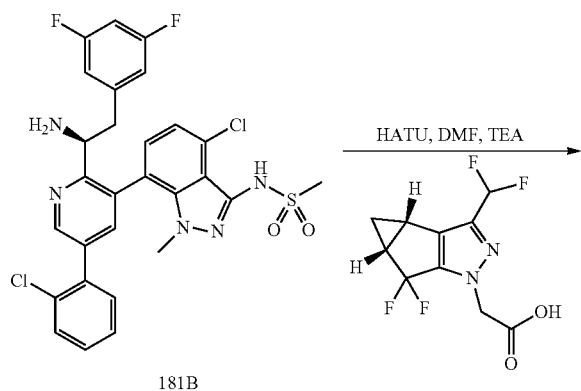

181B

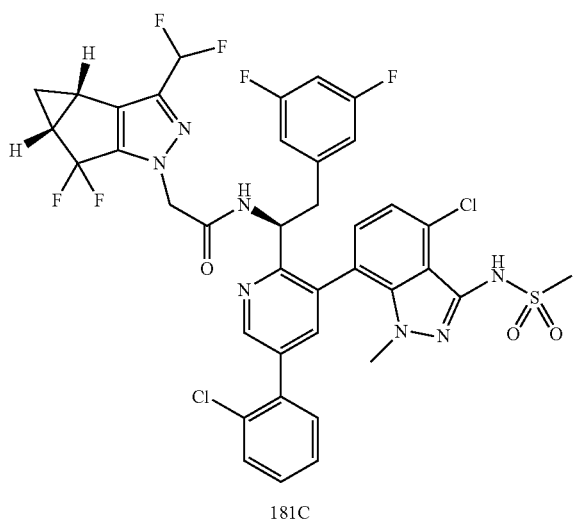

181C

Synthesis of (S)-tert-butyl (1-(3-(4-chloro-1-methyl-3-(methylsulfonamido)-1H-indazol-7-yl)-5-(2-chlorophenyl)pyridin-2-yl)-2-(3,5-difluorophenyl)ethyl) carbamate (181A)

The title compound as mixture of atropisomers (181A) was prepared according to the method presented for the synthesis of compound 177B of Example 177 utilizing compound 177A and 2-chlorophenylbronic acid. MS (m/z) 702 [M+H]+.

Synthesis of (S)—N-(7-(2-(1-amino-2-(3,5-difluorophenyl)ethyl)-5-(2-chlorophenyl)pyridin-3-yl)-4-chloro-1-methyl-1H-indazol-3-yl)methanesulfonamide (181A)

The title compound as mixture of atropisomers (181B) was prepared according to the method presented for the synthesis of compound 177C of Example 177 utilizing compound 181A. MS (m/z) 602 [M+H]+.

Synthesis of N—((S)-1-(3-(4-chloro-1-methyl-3-(methylsulfonamido)-1H-indazol-7-yl)-5-(2-chlorophenyl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (181C)

The title compound as mixture of atropisomers (181C) was prepared according to the method presented for the synthesis of compound 177D of Example 177 utilizing compound 181B and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. ¹H NMR (400 MHz, DMSO-d6) δ 9.82 (s), 9.75 (s), 9.07 (d), 8.94 (d), 8.87 (dd), 7.97 (d), 7.90 (d), 7.69-7.39 (m), 7.23-6.74 (m), 6.54 (d), 6.44 (d), 5.03 (q), 4.90-4.53 (m), 3.32 (s), 3.23-2.89 (m), 2.60-2.37 (m), 1.47-1.30 (m), 0.83 (s). MS (m/z) 848 [M+H]+.

Example 182

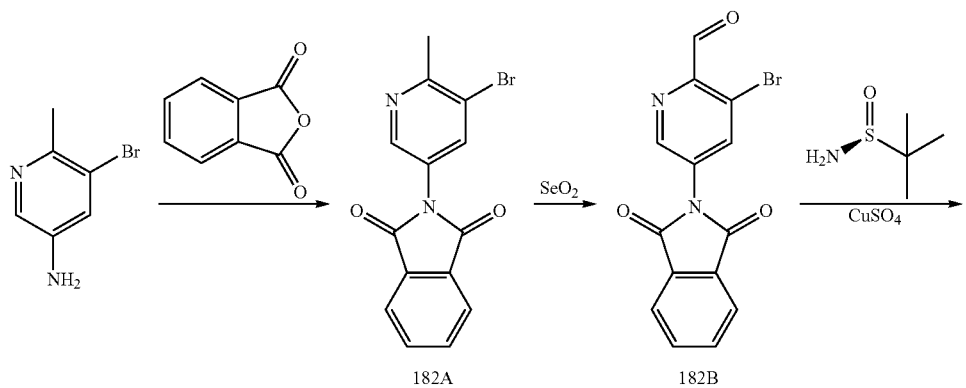

-continued
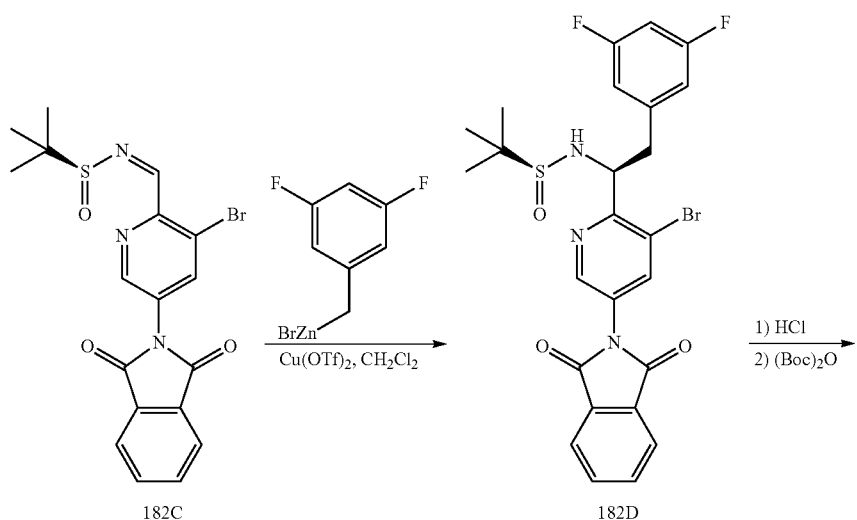
182C → 182D
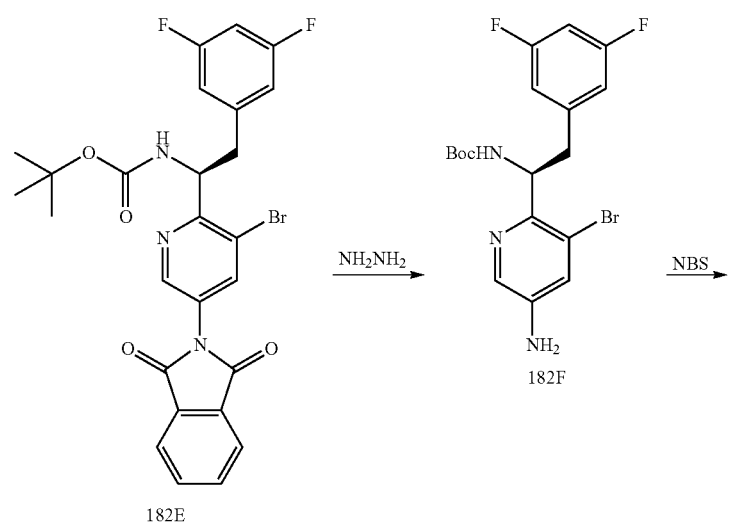
182E → 182F
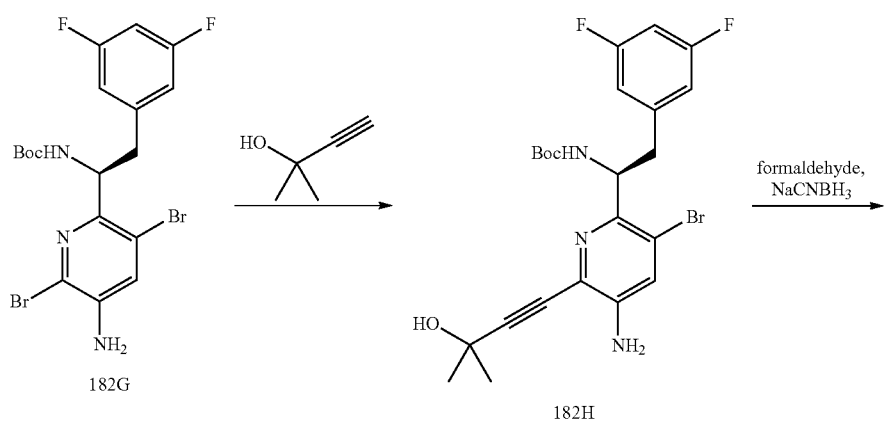
182G → 182H -continued
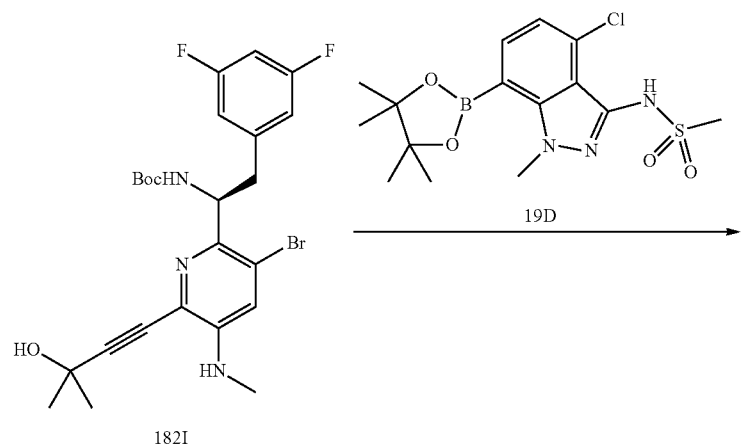
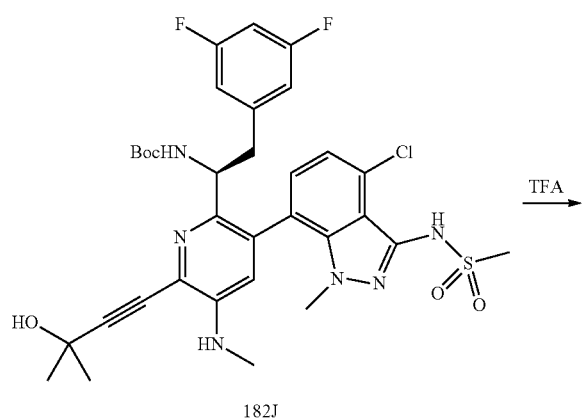
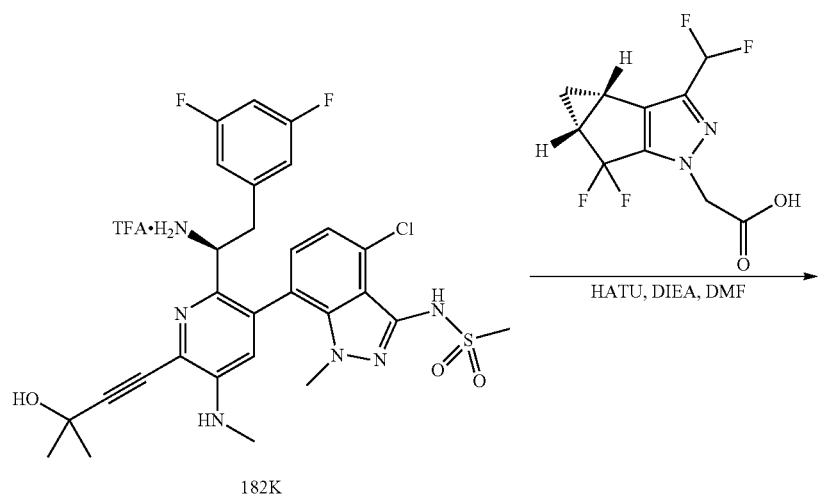

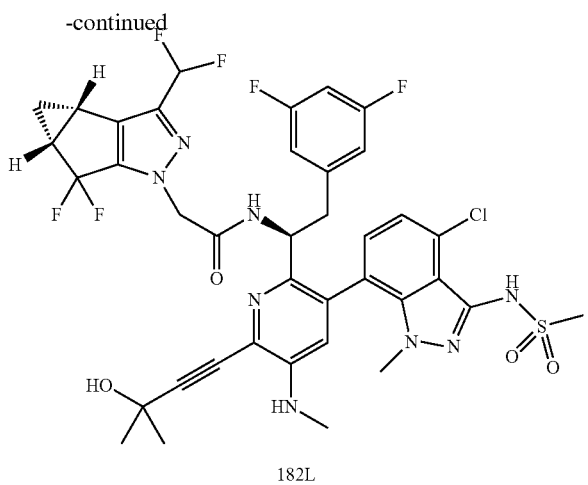

182L

Synthesis of 2-(5-bromo-6-methylpyridin-3-yl)isoindoline-1,3-dione (182A)

A mixture of phthalic anhydride (3.7 g, 25 mmol), 5-bromo-6-methylpyridin-3-amine (3.9 g, 20.85 mmol) and sodium acetate (1.5 g, 25 mmol) in glacial acetic acid (44 ml) was refluxed for overnight. After cooling down to room temperature, the precipitate was collected by vacuum filtration and washed with water. Then it was dried under high vacuum to afford the title compound 182A. MS (m/z) 318.91 [M+H]$^+$.

Synthesis of 3-bromo-5-(1,3-dioxoisoindolin-2-yl)picolinaldehyde (182B)

To a microwave tube was charged with compound 182A (1.5 g, 4.73 mmol) and selenium dioxide (682 mg, 6.15 mmol). To it was added 14 mL of 1,2-dimethoxyethane and the microwave tube was sealed. The reaction mixture was heated in a 130° C. heating bath for 20 hours. The reaction mixture was cooled down and the solids filtered off. The filtrate was concentrated to afford the title compound 182B. $^1$H NMR (400 MHz, DMSO) δ 10.04 (s, 1H), 8.95 (d, J=1.9 Hz, 1H), 8.41 (d, J=1.7 Hz, 1H), 8.07-7.84 (m, 4H).

Synthesis of (S,Z)—N-((3-bromo-5-(1,3-dioxoisoindolin-2-yl)pyridin-2-yl)methylene)-2-methylpropane-2-sulfinamide (182C)

Copper(II) sulfate (anhydrous, 5.8 g, 36.2 mmol) was added to a solution of 3-bromo-5-(1,3-dioxoisoindolin-2-yl)picolinaldehyde (182B, 6 g, 18 mmol) and (S)-2-methylpropane-2-sulfinamide (2.2 g, 18 mmol) in CH$_2$Cl$_2$ (60 mL). The reaction mixture was stirred at ambient temperature for 2 hours and then filtered and washed with CH$_2$Cl$_2$. The filtrate was concentrated and the residue was purified by silica gel chromatography eluting with EtOAc and methylene chloride to yield the title compound 182C. MS (m/z) 433.87 [M+H]$^+$.

Synthesis of (S)—N—((S)-1-(3-bromo-5-(1,3-dioxoisoindolin-2-yl)pyridin-2-yl)-2-(3,5-difluorophenyl)ethyl)-2-methylpropane-2-sulfinamide (182D)

To a solution of compound (182C, 3.7 g, 8.5 mmol) and Cu(OTf)$_2$ (154 mg, 0.4 mmol) in methylene chloride (30 ml) at 0° C. was added (3,5-difluorobenzyl)zinc bromide (0.5 M in THF, 25.5 ml, 12.8 mmol) dropwise. The reaction stirred at room temperature for one hour. Ammonium chloride (aq, 100 ml) was added to the reaction and the mixture was extracted with methylene chloride (2×100 ml). The organic layer was dried over Na$_2$SO$_4$, filtered and concentrated. The reaction mixture was purified by silica gel chromatography then by reverse phase HPLC to afford the title compound 182D. MS (m/z) 563.83 [M+H]$^+$.

Synthesis of (S)-tert-butyl 1-(3-bromo-5-(1,3-dioxoisoindolin-2-yl)pyridin-2-yl)-2-(3,5-difluorophenyl)ethylcarbamate (182E)

Compound 182D (2.6 g, 4.6 mmol) was dissolved in 40 mL of methanol and cooled to 0° C. To it was added 4N HCl/1,4-dioxane (4.6 ml). The reaction mixture was allowed to stir at room temperature for 10 minutes and concentrated to afford product (S)-2-(6-(1-amino-2-(3,5-difluorophenyl)ethyl)-5-bromopyridin-3-yl)isoindoline-1,3-dione hydrochloride. To the mixture of the above HCl salt (~4.6 mmol) and Di-tert-Butyl dicarbonate (1 g, 4.6 mmol) in 50 mL of CH$_2$Cl$_2$ was added triethylamine (1.28 mL, 9.2 mmol) at 0° C. The reaction mixture was stirred for overnight and concentrated in vacuo. The residue was partitioned between EtOAc and water. The organic layer was washed with brine, dried over MgSO4, filtered and concentrated. Then it was purified on silica gel chromatography to yield the title compound 182E. MS (m/z) 559.71 [M+H]$^+$.

Synthesis of (S)-tert-butyl (1-(5-amino-3-bromopyridin-2-yl)-2-(3,5-difluorophenyl)ethyl)carbamate (182F)

To a mixture of compound 182E (1.5 g, 2.7 mmol) in 27 ml of ethanol, 0.9 ml of hydrazine monohydrate was added and stirred at room temperature for 2 hours. More ethanol was added to the reaction mixture. The precipitate was filtered off and the filtrate was concentrated. The residue was diluted with ethyl acetate, and washed with water and then with a saturated sodium chloride solution. The organic layer was dried over anhydrous magnesium sulfate, and concentrated under reduced pressure. The residue was subjected to silica gel column chromatography to give the title compound 182F. MS (m/z) 427.83 [M+H]$^+$.

Synthesis of (S)-tert-butyl (1-(5-amino-3,6-dibromopyridin-2-yl)-2-(3,5-difluorophenyl)ethyl)carbamate (182G)

A solution of compound 182F (960 mg, 2.24 mmol) in 20 mL of acetonitrile was cooled to 0° C. and treated with N-Bromosuccinimide (399 mg, 2.24 mmol) as a solution in 20 mL of acetonitrile. The reaction mixture was partitioned with EtOAc and saturated aqueous NaHCO$_3$. The organic layer was separated and washed with brine, then dried over MgSO$_4$ and concentrated in vacuo. The residue was purified by silica gel chromatography to afford the title compound 182G. MS (m/z): 507.52 [M+H]$^+$.

Synthesis of (S)-tert-butyl (1-(5-amino-3-bromo-6-(3-hydroxy-3-methylbut-1-yn-1-yl)pyridin-2-yl)-2-(3,5-difluorophenyl)ethyl)carbamate (182H)

The title compound (182H) was prepared according to the method presented for the synthesis of compound 4F of Example 4 utilizing compound 182G. MS (m/z) 511.87 [M+H]$^+$. Synthesis of (S)-tert-butyl (1-(3-bromo-6-(3-hydroxy-3-methylbut-1-yn-1-yl)-5-(methylamino)pyridin-2-yl)-2-(3,5-difluorophenyl)ethyl)carbamate (182I):

Compound 182H (200 mg, 0.39 mmol) was dissolved in 2 mL of acetonitrile, to it was added formaldehyde (0.1 mL, 37% in H$_2$O) and acetic acid (0.2 mL, 4 mmol) followed by slow addition of sodium cyanoborohydride solution (1.2 mL, 1M in THF). The reaction mixture was allowed to stir at room temperature for 3 hours and quenched by adding aqueous sodium bicarbonate. It was extracted with ethyl acetate. The organic layer was washed with water, dried over Na$_2$SO$_4$ and concentrated under reduced pressure. The crude product was purified by RP-HPLC to afford the title compound 182I. MS (m/z): 525.99 [M+H]$^+$.

Synthesis of (S)-tert-butyl (1-(3-(4-chloro-1-methyl-3-(methylsulfonamido)-1H-indazol-7-yl)-6-(3-hydroxy-3-methylbut-1-yn-1-yl)-5-(methylamino)pyridin-2-yl)-2-(3,5-difluorophenyl)ethyl)carbamate (182J)

The title compound (182J) was prepared as a mixture of atropisomers according to the method presented for the synthesis of compound 19E of Example 19 utilizing compound 182I and compound 19D. MS (m/z) 703.35 [M+H]$^+$.

Synthesis of (S)—N-(7-(2-(1-amino-2-(3,5-difluorophenyl)ethyl)-6-(3-hydroxy-3-methylbut-1-yn-1-yl)-5-(methylamino)pyridin-3-yl)-4-chloro-1-methyl-1H-indazol-3-yl)methanesulfonamide (182K)

The title compound (182K) was prepared as a mixture of atropisomers according to the method presented for the synthesis of compound 105C of Example 105 utilizing compound 182J. MS (m/z) 603.17 [M+H]$^+$.

Synthesis of N—((S)-1-(3-(4-chloro-1-methyl-3-(methylsulfonamido)-1H-indazol-7-yl)-6-(3-hydroxy-3-methylbut-1-yn-1-yl)-5-(methylamino)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (182L)

The title compound (182L) was prepared as a mixture of atropisomers according to the method presented for the synthesis of compound 37E of Example 37 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and compound 182K. $^1$H NMR (400 MHz, Methanol-d$_4$) δ 7.00 (d), 6.82 (d), 6.76 (tt), 6.70 (t), 6.43-6.30 (m), 6.24 (d), 4.78-4.56 (m), 3.39 (s), 3.22 (s), 3.16-2.99 (m), 2.98-2.88 (m), 2.84 (s), 2.52-2.31 (m), 1.66 (d), 1.49-1.21 (m), 1.12-0.86 (m). MS (m/z) 849.90 [M+H]$^+$.

Example 183

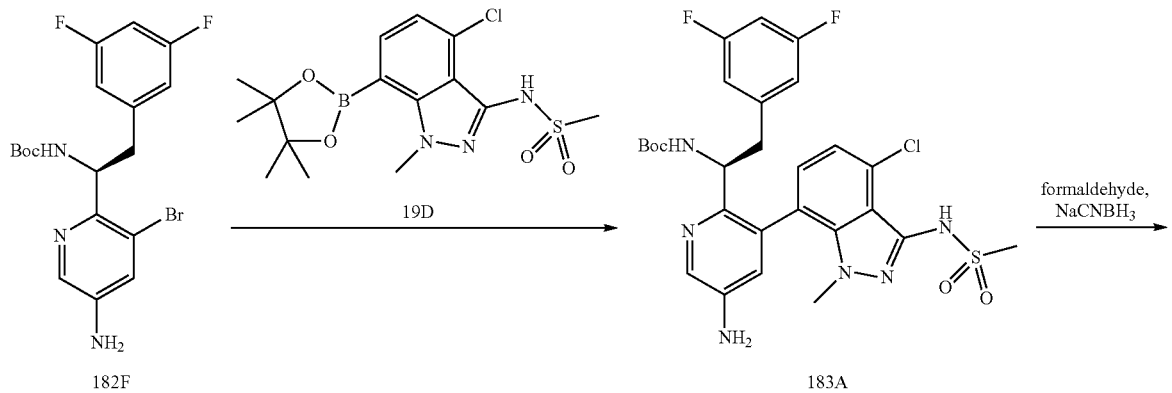

-continued
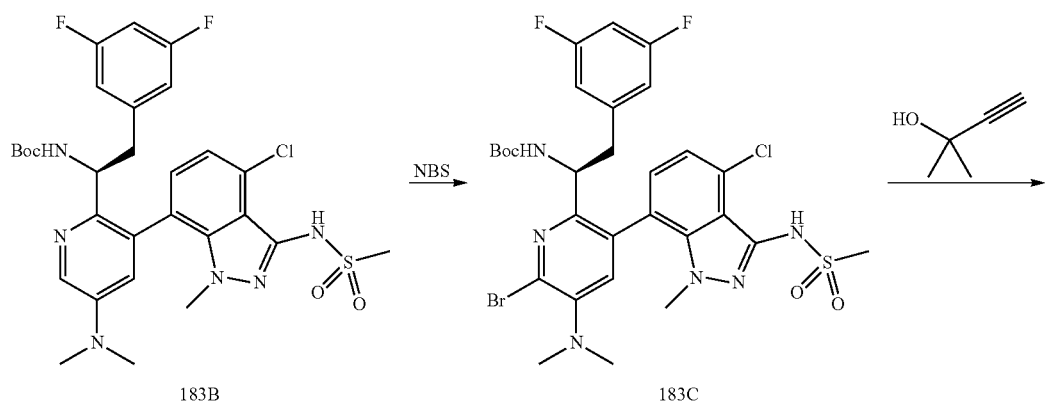
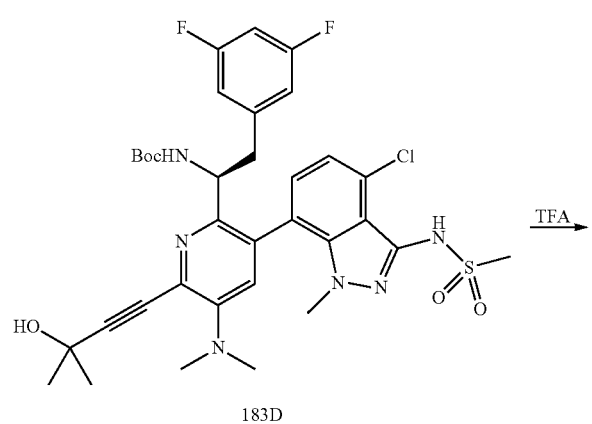
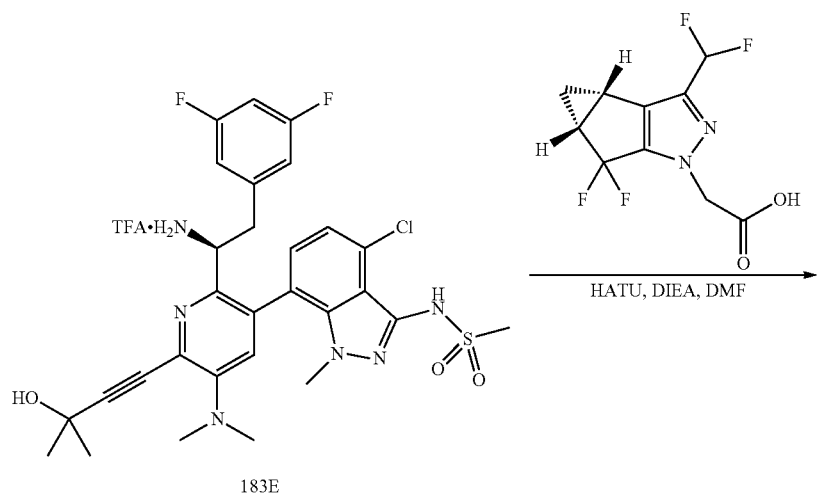

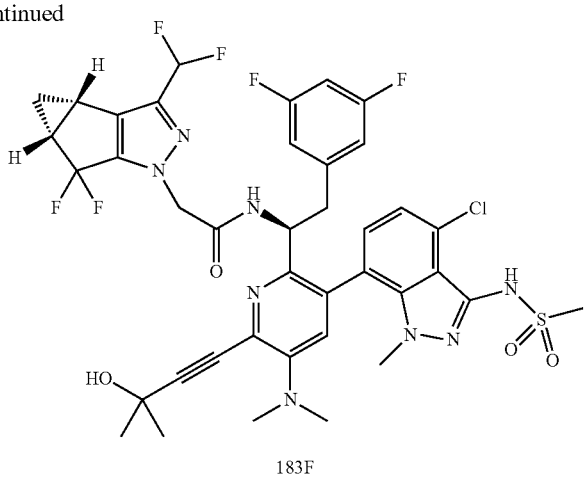

183F

Synthesis of (S)-tert-butyl (1-(5-amino-3-(4-chloro-1-methyl-3-(methylsulfonamido)-1H-indazol-7-yl)pyridin-2-yl)-2-(3,5-difluorophenyl)ethyl)carbamate (183A)

The title compound (183A) was prepared as a mixture of atropisomers according to the method presented for the synthesis of compound 19E of Example 19 utilizing compound 182F and compound 19D. MS (m/z) 606.88 [M+H]⁺.

Synthesis of (S)-tert-butyl (1-(3-(4-chloro-1-methyl-3-(methylsulfonamido)-1H-indazol-7-yl)-5-(dimethylamino)pyridin-2-yl)-2-(3,5-difluorophenyl)ethyl)carbamate (183B)

The title compound (183B) was prepared as a mixture of atropisomers according to the method presented for the synthesis of compound 182I of Example 182 utilizing compound 183A. MS (m/z) 635.48 [M+H]⁺.

Synthesis of (S)-tert-butyl (1-(6-bromo-3-(4-chloro-1-methyl-3-(methylsulfonamido)-1H-indazol-7-yl)-5-(dimethylamino)pyridin-2-yl)-2-(3,5-difluorophenyl)ethyl)carbamate (183C)

The title compound (183C) was prepared as a mixture of atropisomers according to the method presented for the synthesis of compound 182G of Example 182 utilizing compound 183B. MS (m/z) 714.81 [M+H]⁺.

Synthesis of (S)-tert-butyl (1-(3-(4-chloro-1-methyl-3-(methylsulfonamido)-1H-indazol-7-yl)-5-(dimethylamino)-6-(3-hydroxy-3-methylbut-1-yn-1-yl)pyridin-2-yl)-2-(3,5-difluorophenyl)ethyl)carbamate (183D)

The title compound (183D) was prepared as a mixture of atropisomers according to the method presented for the synthesis of compound 4F of Example 4 utilizing compound 183C. MS (m/z) 717.62 [M+H]⁺.

Synthesis of (S)—N-(7-(2-(1-amino-2-(3,5-difluorophenyl)ethyl)-5-(dimethylamino)-6-(3-hydroxy-3-methylbut-1-yn-1-yl)pyridin-3-yl)-4-chloro-1-methyl-1H-indazol-3-yl)methanesulfonamide (183E)

The title compound (183E) was prepared as a mixture of atropisomers according to the method presented for the synthesis of compound 105C of Example 105 utilizing compound 183D. MS (m/z) 617.09 [M+H]⁺.

Synthesis of N—((S)-1-(3-(4-chloro-1-methyl-3-(methylsulfonamido)-1H-indazol-7-yl)-5-(dimethylamino)-6-(3-hydroxy-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (183F)

The title compound (183F) was prepared as a mixture of atropisomers according to the method presented for the synthesis of compound 37E of Example 37 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and compound 183E. ¹H NMR (400 MHz, Methanol-d₄) δ 7.26-7.10 (m), 7.03 (d), 6.76 (t), 6.69 (t), 6.60 (t), 6.52-6.33 (m), 6.32 (d), 4.85-4.78 (m), 4.78-4.60 (m), 3.37 (s), 3.23 (d), 3.10 (dd), 2.99 (d), 2.98-2.74 (m), 2.45 (ddd), 1.66 (s), 1.48-1.30 (m), 1.17-0.92 (m).). MS(m/z): 863.19 [M+H]⁺.

Example 184

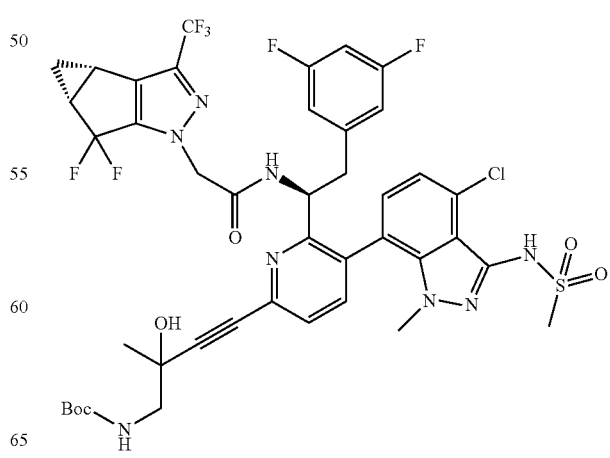

184

Synthesis of tert-butyl (4-(5-(4-chloro-1-methyl-3-(methylsulfonamido)-1H-indazol-7-yl)-6-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-2-yl)-2-hydroxy-2-methylbut-3-yn-1-yl)carbamate (184)

The title compound (184) was prepared as a mixture of atropisomers according to the method presented for the synthesis of compound 145 of Example 145 utilizing tert-butyl (2-hydroxy-2-methylbut-3-yn-1-yl)carbamate. MS (m/z) 953.9 [M+H]$^+$. HPLC retention time 7.54 min and 7.69 min (2-98% acetonitrile: water with 0.1% trifluoroacetic acid, 8.5 min gradient on a Phenomonex Kinetex C18 column).

Example 185

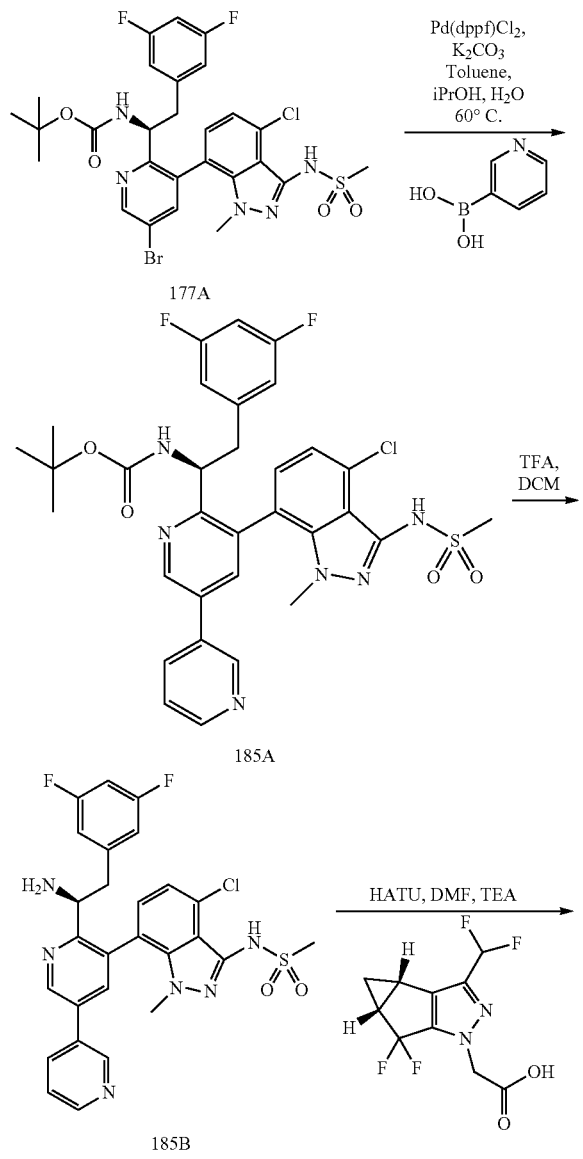

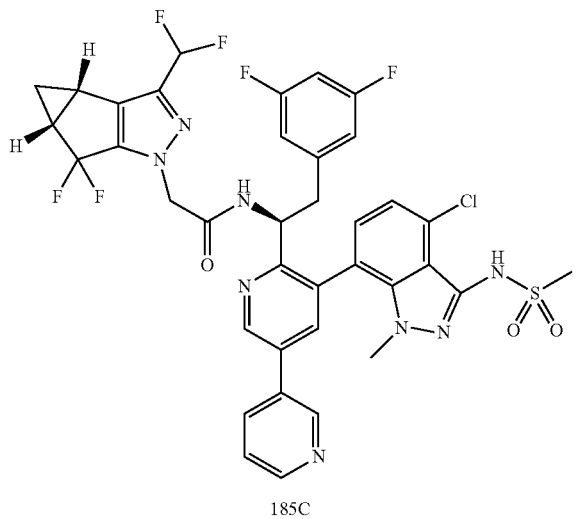 [SMILES: Cn1nc(NS(C)(=O)=O)c2c(Cl)ccc(-c3cc(-c4ccccc4)cnc3[C@H](Cc3cc(F)cc(F)c3)NC(=O)Cn3nc(C(F)F)c4c3C(F)(F)[C@@H]3C[C@H]43)c21]

185C

Synthesis of (S)-tert-butyl (1-(5-(4-chloro-1-methyl-3-(methylsulfonamido)-1H-indazol-7-yl)-[3,3'-bipyridin]-6-yl)-2-(3,5-difluorophenyl)ethyl)carbamate (185A)

The title compound as mixture of atropisomers (185A) was prepared according to the method presented for the synthesis of compound 177B of Example 177 utilizing compound 177A and 3-pyridineboronic acid. MS (m/z) 669 [M+H]$^+$.

Synthesis of (S)—N-(7-(6-(1-amino-2-(3,5-difluorophenyl)ethyl)-[3,3'-bipyridin]-5-yl)-4-chloro-1-methyl-1H-indazol-3-yl)methanesulfonamide (185B)

The title compound as mixture of atropisomers (185B) was prepared according to the method presented for the synthesis of compound 177C of Example 177 utilizing compound 185A. MS (m/z) 569 [M+H]$^+$.

Synthesis of N—((S)-1-(5-(4-chloro-1-methyl-3-(methylsulfonamido)-1H-indazol-7-yl)-[3,3'-bipyridin]-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (185C)

The title compound as mixture of atropisomers (185C) was prepared according to the method presented for the synthesis of compound 177D of Example 177 utilizing compound 185B. $^1$H NMR (400 MHz, Acetonitrile-d3) δ 9.07 (t), 8.96 (dd), 8.66 (dd), 8.15-8.06 (m), 8.03 (dd), 7.56-7.44 (m), 7.35 (d), 7.28 (d), 7.22 (d), 7.16 (dd), 6.93-6.87 (m), 6.86-6.72 (m), 6.69-6.57 (m), 6.48-6.34 (m), 5.37-5.29 (q), 4.98 (q), 4.78-4.59 (m), 3.36-2.91 (m), 2.49 (dtd), 1.41 (p), 1.05 (t). MS (m/z) 815 [M+H]$^+$.

Example 186

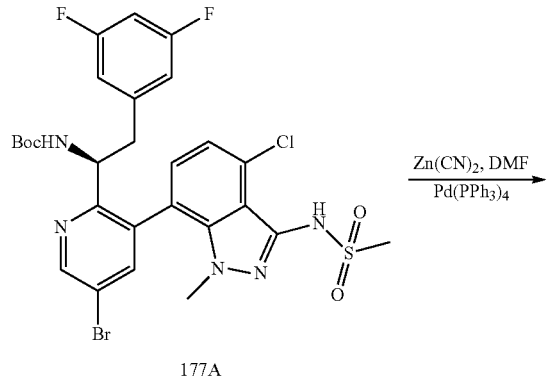

177A

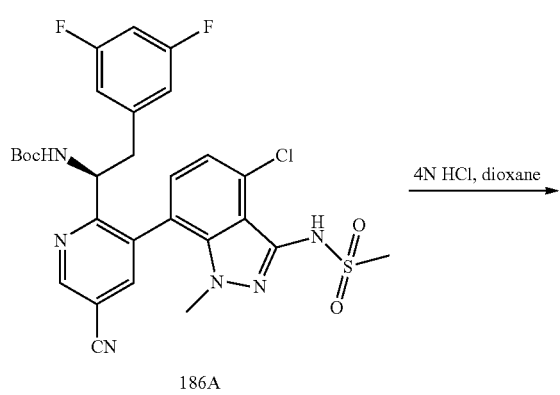

186A

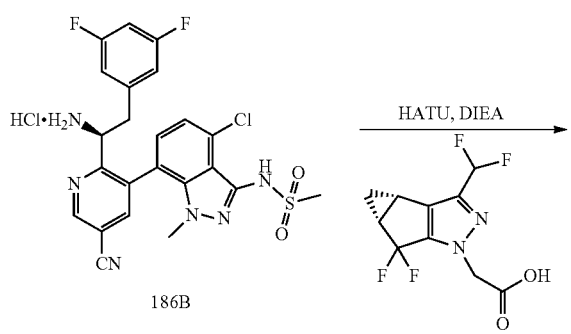

186B

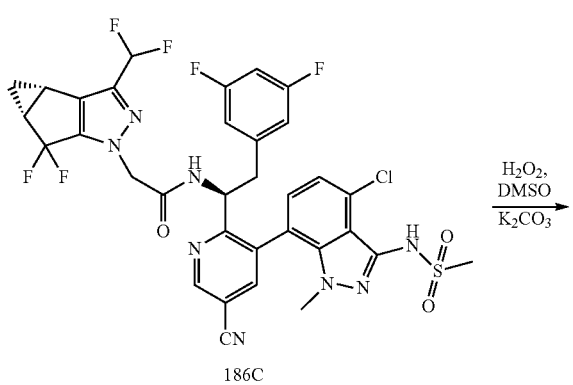

186C

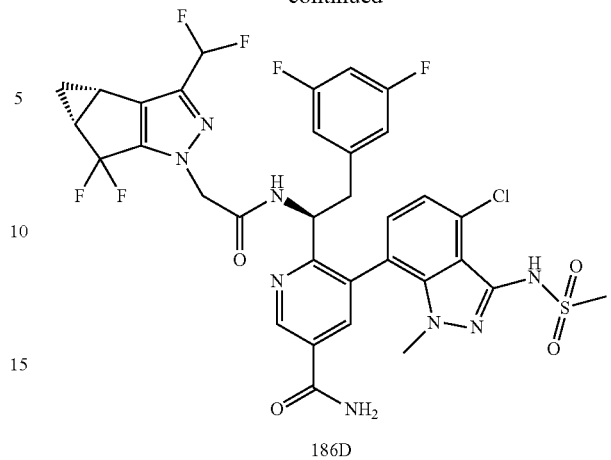

186D

Synthesis of (S)-tert-butyl (1-(3-(4-chloro-1-methyl-3-(methylsulfonamido)-1H-indazol-7-yl)-5-cyano-pyridin-2-yl)-2-(3,5-difluorophenyl)ethyl)carbamate (186A)

To a suspension of 177A (140 mg, 0.21 mmol) in anhydrous/degassed DMF (1.5 ml) was treated with Zn(CN)$_2$ (14.7 mg, 0.125 mmol), and tetrakis(triphenylphosphine)palladium(0) (24.1 mg, 0.021 mmol). The mixture was heated at 90° C. for 16 hours under a nitrogen atmosphere. The reaction mixture was allowed to cool to ambient temperature and poured into EtOAc (50 ml). The organic layer was washed with brine, dried (MgSO$_4$), and concentrated under reduced pressure. The residue was purified on flash column to provide the title compound as a mixture of atropisomers. MS (m/z) 617 [M+H]$^+$.

Synthesis of (S)—N-(7-(2-(1-amino-2-(3,5-difluoro-phenyl)ethyl)-5-cyanopyridin-3-yl)-4-chloro-1-methyl-1H-indazol-3-yl)methanesulfonamide hydrochloride (186B)

The title compound (186B) was prepared as a mixture of atropisomers according to the method presented for the synthesis of compound 21E of Example 21 utilizing 186A. MS (m/z) 517 [M+H]$^+$.

Synthesis of N—((S)-1-(3-(4-chloro-1-methyl-3-(methylsulfonamido)-1H-indazol-7-yl)-5-cyanopyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (186C)

The title compound (186C) was prepared as a mixture of atropisomers according to the method presented for the synthesis of compound 10A of Example 10 utilizing 186B and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. MS (m/z) 763 [M+H]$^+$.

Synthesis of 5-(4-chloro-1-methyl-3-(methylsulfonamido)-1H-indazol-7-yl)-6-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)nicotinamide (186D)

To a suspension of 186C (21 mg, 0.028 mmol) and K$_2$CO$_3$ (38 mg, 0.28 mmol) in DMSO, H$_2$O$_2$ (30 wt. % in H$_2$O, 0.028 mL, 0.28 mmol) was added to the suspension slowly. After 10 minutes, the mixture was filtered and purified by reverse phase HPLC to provide the title compound as a mixture of atropisomers. ¹H NMR (400 MHz, Methanol-d4)
¹H NMR (400 MHz, Methanol-d4) δ 9.26 (t), 8.73 (t), 8.14 (dd), 7.31-7.14 (m), 7.09 (d), 6.77 (tt), 6.72 (t), 6.68-6.59 (m), 6.49-6.30 (m), 5.35-5.25 (m), 5.08-5.00 (m), 4.78-4.68 (m), 3.25 (d), 3.18-3.09 (m), 3.05-2.93 (m), 2.65 (s), 2.44 (ddd), 1.39 (dq), 1.01 (h). MS (m/z) 781 [M+H]⁺.
Example 187
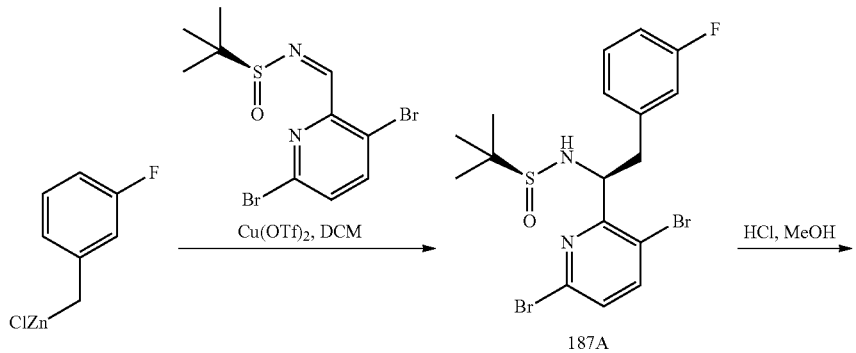
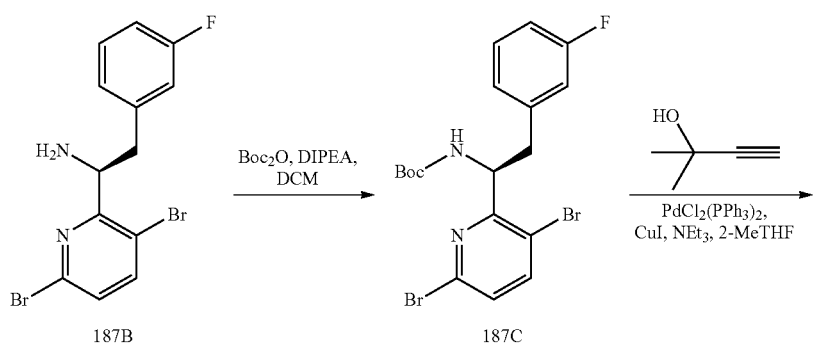
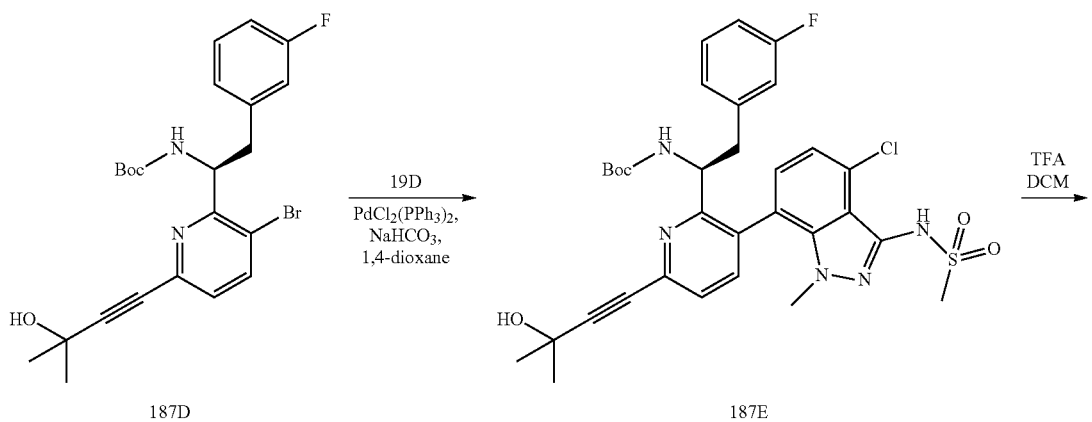

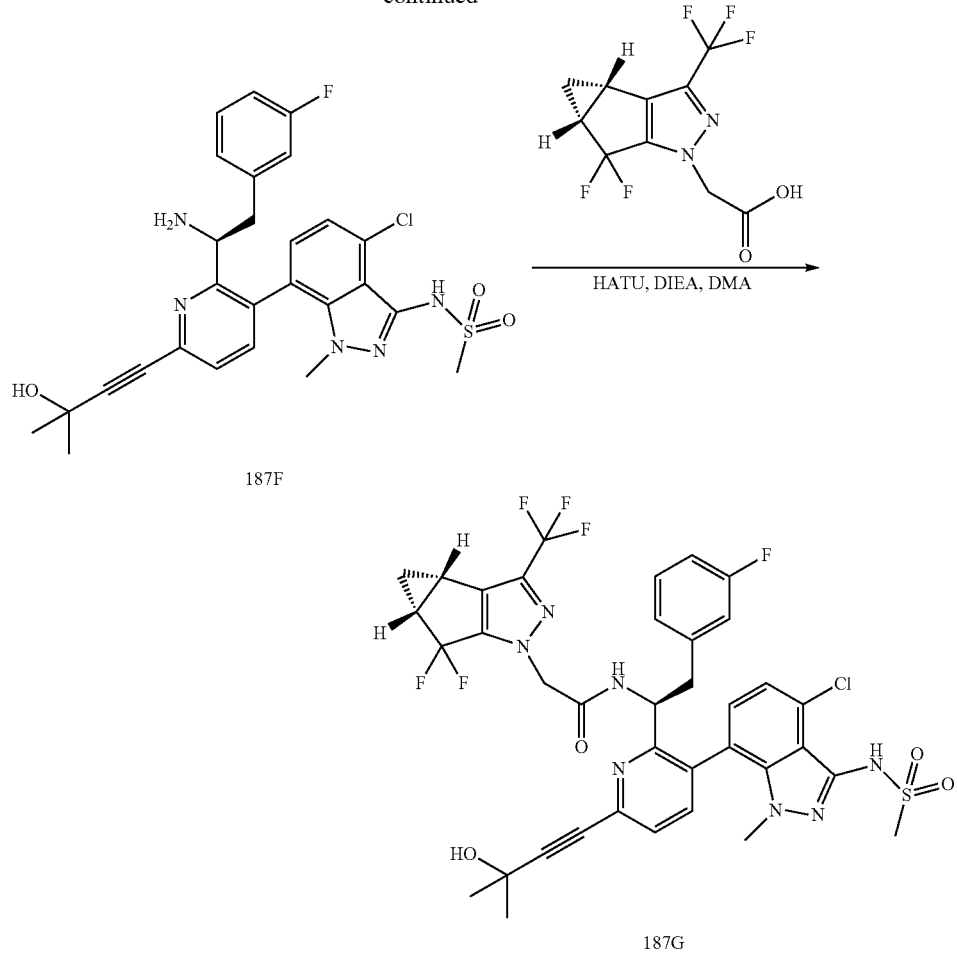

Synthesis of (S)—N—((S)-1-(3,6-dibromopyridin-2-yl)-2-(3-fluorophenyl)yl)-2-methylpropane-2-sulfinamide (187A)

To a solution of (S,Z)—N-((3,6-dibromopyridin-2-yl)methylene)-2-methylpropane-2-sulfinamide (1.0 g, 2.717 mmol) and Cu(OTf)₂ (49.1 mg, 0.136 mmol) in DCM (10 mL) was added 3-fluorobenzyl zinc chloride (0.5M in THF, 7.6 mL, 3.803 mmol) dropwise over 7 minutes at 0° C. The reaction mixture was stirred at 0° C. for 1 hour, then quenched with saturated aqueous NH₄Cl and diluted with EtOAc. The organic layer was collected, and the aqueous layer was extracted an additional time with EtOAc. The combined organic layers were dried over Na₂SO₄, filtered, concentrated, and purified by silica gel column chromatography to provide the title compound 187A. MS (m/z) 476.93, 478.84, 480.79 [M+H]⁺.

Synthesis of (S)-1-(3,6-dibromopyridin-2-yl)-2-(3-fluorophenyl)ethanamine (187B)

To a solution of (S)—N—((S)-1-(3,6-dibromopyridin-2-yl)-2-(3-fluorophenyl)ethyl)-2-methylpropane-2-sulfinamide (187A, 714.2 mg, 1.493 mmol) in MeOH (3.7 mL) was added HCl (4M in 1,4-dioxane, 3.7 mL, 14.93 mmol). The reaction mixture was stirred at room temperature for 30 minutes. Upon completion, the reaction mixture was concentrated in vacuo to provide the title compound 187B, which was used without purification. MS (m/z) 373.08, 374.92, 376.86 [M+H]⁺.

Synthesis of (S)-tert-butyl (1-(3,6-dibromopyridin-2-yl)-2-(3-fluorophenyl)ethyl)carbamate (187C)

To a solution of (S)-1-(3,6-dibromopyridin-2-yl)-2-(3-fluorophenyl)ethanamine (187B, 558.62 mg, 1.493 mmol) in DCM was added DIPEA (0.52 mL, 2.987 mmol). The reaction mixture was cooled to 0° C., then Boc₂O (358.6 mg, 1.643 mmol) was added. The reaction mixture was warmed to room temperature and stirred at room temperature for 2.5 hours. Upon completion, the reaction mixture was concentrated in vacuo and purified by silica gel column chromatography to provide the title compound 187C. MS (m/z) 472.71, 474.68, 476.68 [M+H]⁺.

Synthesis of (S)-tert-butyl (1-(3-bromo-6-(3-hydroxy-3-methylbut-1-yn-1-yl)pyridin-2-yl)-2-(3-fluorophenyl)ethyl)carbamate (187D)

A solution of (S)-tert-butyl (1-(3,6-dibromopyridin-2-yl)-2-(3-fluorophenyl)ethyl)carbamate (187C, 200.0 mg, 0.422 mmol) in 2-MeTHF was degassed by bubbling argon for 60 seconds. To the degassed solution were added NEt₃ (0.18 mL, 1.268 mmol) and 2-methyl-3-butyn-2-ol (62 μL, 0.633 mmol) followed by CuI (2.4 mg, 0.013 mmol) and PdCl$_2$(PPh$_3$)$_2$ (8.9 mg, 0.013 mmol). The reaction mixture was stirred at room temperature for 30 minutes. Upon completion, the reaction mixture was diluted with water and extracted three times with EtOAc. The combined organic layers were dried over Na$_2$SO$_4$, filtered, concentrated in vacuo, and purified by silica gel column chromatography to provide the title compound 187D. MS (m/z) 476.91, 478.83 [M+H]$^+$.

Synthesis (S)-tert-butyl (1-(3-(4-chloro-1-methyl-3-(methylsulfonamido)-1H-indazol-7-yl)-6-(3-hydroxy-3-methylbut-1-yn-1-yl)pyridin-2-yl)-2-(3-fluorophenyl)ethyl)carbamate (187E)

(S)-tert-butyl (1-(3-bromo-6-(3-hydroxy-3-methylbut-1-yn-1-yl)pyridin-2-yl)-2-(3-fluorophenyl)ethyl)carbamate (187D, 189.7 mg, 0.397 mmol), N-(4-chloro-1-methyl-7-(4,4,5,5-tetramethyl-1,3,2-dioxaborolan-2-yl)-1H-indazol-3-yl)methanesulfonamide (19D, 214.6 mg, 0.556 mmol), and PdCl$_2$(PPh$_3$)$_2$ (27.9 mg, 0.04 mmol) were taken in 1,4-dioxane (10 mL) and NaHCO$_3$ (1 M in water, 1.19 mL, 1.19 mmol). The resulting solution was degassed by bubbling argon for 5 minutes, then the reaction flask was sealed and the reaction heated at 150° C. for 20 minutes in a microwave reactor. Upon cooling, the reaction mixture was filtered, concentrated in vacuo, and purified by silica gel column chromatography to provide the title compound 187E as a mixture of atropisomers. MS (m/z) 655.92 [M+H]$^+$.

Synthesis of (S)—N-(7-(2-(1-amino-2-(3-fluorophenyl)ethyl)-6-(3-hydroxy-3-methylbut-1-yn-1-yl)pyridin-3-yl)-4-chloro-1-methyl-1H-indazol-3-yl)methanesulfonamide (187F)

To a solution of (S)-tert-butyl (1-(3-(4-chloro-1-methyl-3-(methylsulfonamido)-1H-indazol-7-yl)-6-(3-hydroxy-3-methylbut-1-yn-1-yl)pyridin-2-yl)-2-(3-fluorophenyl)ethyl) carbamate (187E, 257.3 mg, 0.392 mmol) in DCM (4 mL) was added TFA (4 mL). The reaction mixture was stirred at room temperature for 1 hour 15 minutes. Upon completion, the reaction mixture was concentrated in vacuo to provide the title compound 187F as a mixture of atropisomers which was used without further purification. MS (m/z) 556.15 [M+H]$^+$.

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3-fluorophenyl)ethyl)-2-((3b,4aR)-5,5-difluoro-3-(trifluoromethyl)-3b,4,4a,5-tetrahydro-1H-cyclopropa[3,4]cyclopenta[1,2-c]pyrazol-1-yl)acetamide (187G)

To a solution of (S)—N-(7-(2-(1-amino-2-(3-fluorophenyl)ethyl)-6-(3-hydroxy-3-methylbut-1-yn-1-yl)pyridin-3-yl)-4-chloro-1-methyl-1H-indazol-3-yl)methanesulfonamide (187F, 218.0 mg, 0.392 mmol) in DMA (3 mL) was added NEt$_3$ (0.16 mL, 1.176 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (77.5 mg, 0.274 mmol), then HATU (104.4 mg, 0.274 mmol) at room temperature. The reaction mixture was stirred at room temperature for 15 minutes. Upon completion, the reaction mixture was filtered and purified by reverse phase HPLC. Fractions containing the product were pooled and lyophilized to give the title compound 187G as a mixture of atropisomers. $^1$H NMR (400 MHz, Methanol-d$_4$) δ 8.80-8.70 (m), 7.65 (dd), 7.51 (dd), 7.22-7.11 (m), 6.99 (d), 6.96-6.89 (m), 6.77 (t), 6.60-6.46 (m), 6.15-6.07 (m), 5.37-5.25 (m), 5.02-4.93 (m), 4.84 (s), 4.80 (s), 4.78 (s), 4.74 (s), 3.26 (s), 3.23 (s), 3.21-3.11 (m), 3.04-2.94 (m), 2.82 (s), 2.61-2.39 (m), 1.65 (s), 1.50-1.35 (m), 1.19-1.12 (m), 1.11-1.02 (m). MS (m/z) 820.12 [M+H]$^+$.

Example 188

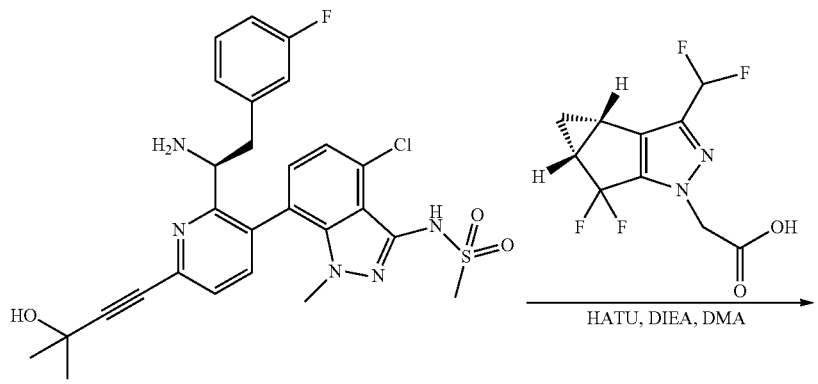

187F

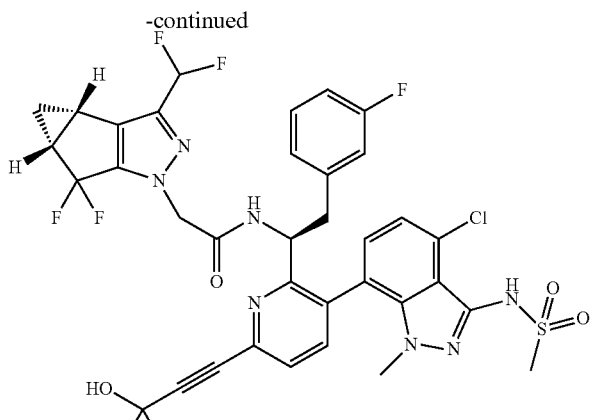

188

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3-fluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (188)

The title compound (188) was prepared as a mixture of atropisomers according to the method presented for the synthesis of compound 187G of Example 187 utilizing 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid. $^1$H NMR (400 MHz, Methanol-d$_4$) δ 8.72-8.62 (m), 7.65 (dd), 7.57-7.44 (m), 7.33 (dd), 7.22-7.11 (m), 6.99 (d), 6.98-6.65 (m), 6.61-6.46 (m), 6.14 (d), 6.13 (d), 5.31 (dd), 4.96 (dd), 4.79 (s), 4.74 (s), 4.72 (s), 4.68 (s), 3.26 (s), 3.22 (s), 3.20-3.11 (m), 3.04-2.92 (m), 2.83 (s), 2.55-2.39 (m), 1.65 (s), 1.45-1.32 (m), 1.15-1.07 (m), 1.07-0.98 (m). MS (m/z) 802.15 [M+H]$^+$.

Example 189

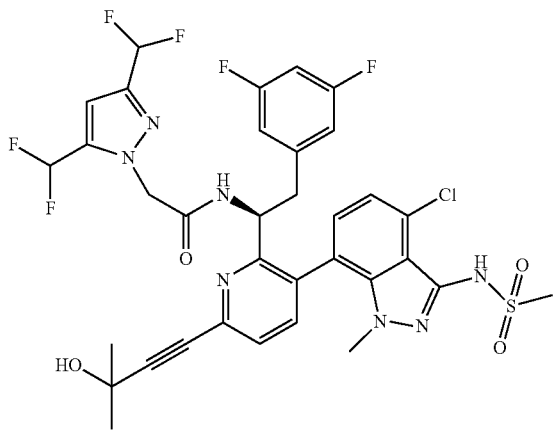

189

Synthesis of (S)-2-(3,5-bis(difluoromethyl)-1H-pyrazol-1-yl)-N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)acetamide (189)

The title compound (189) was prepared as a mixture of atropisomers according to the method presented in the synthesis of 10A in Example 10 utilizing 19F and 2-(3,5-bis(difluoromethyl)-1H-pyrazol-1-yl)acetic acid. $^1$H NMR (400 MHz, Methanol-d$_4$) δ 7.70 (dd), 7.53 (dd), 7.18 (q), 7.07 (d), 7.01-6.56 (m), 6.42 (d), 6.40-6.31 (m), 5.26 (dd), 5.04-4.86 (m), 3.25 (s), 3.21 (s), 3.15 (dd), 3.04-2.93 (m), 1.64 (s). MS (m/z) 783.1 [M+H]$^+$.

Example 190

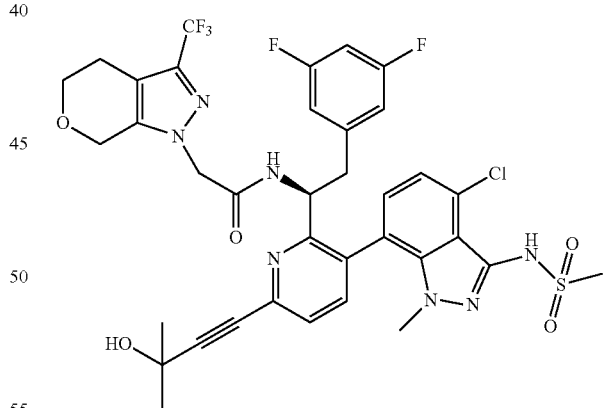

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(3-(trifluoromethyl)-4,5-dihydropyrano[3,4-c]pyrazol-1(7H)-yl)acetamide (190)

The title compound (190) was prepared as a mixture of atropisomers according to the method presented in the synthesis of 10A in Example 10 utilizing 19F and 2-(3-

(trifluoromethyl)-4,5-dihydropyrano[3,4-c]pyrazol-1(7H)-yl)acetic acid. $^1$H NMR (400 MHz, Methanol-d$_4$) δ 7.71 (dd), 7.53 (dd), 7.17 (q), 7.09 (d), 6.82-6.69 (m), 6.68-6.59 (m), 6.42 (dd), 5.28-5.19 (m), 5.01-4.92 (m), 4.69 (t), 4.52 (s), 3.92-3.78 (m), 3.25 (d), 3.20-3.09 (m), 3.01 (s), 2.96 (dd), 2.73-2.59 (m), 1.64 (s). MS (m/z) 807.0 [M+H]$^+$.

Example 191

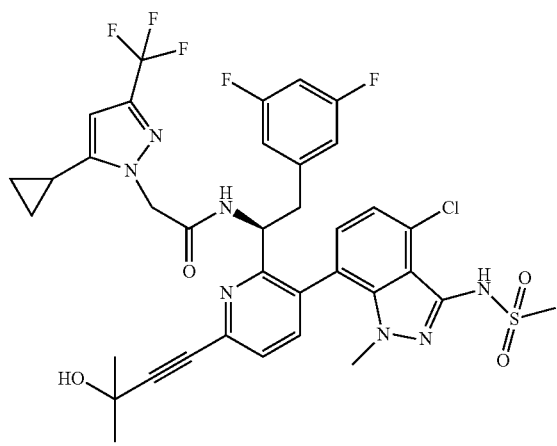

191

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(5-cyclopropyl-3-(trifluoromethyl)-1H-pyrazol-1-yl)acetamide (191)

The title compound (191) was prepared as a mixture of atropisomers according to the method presented in the synthesis of 10A in Example 10 utilizing 19F and 2-(5-cyclopropyl-3-(trifluoromethyl)-1H-pyrazol-1-yl)acetic acid. $^1$H NMR (400 MHz, Methanol-d$_4$) δ 7.71 (dd), 7.53 (dd), 7.27 (d), 7.17 (d), 7.10 (d), 6.80-6.72 (m), 6.67-6.58 (m), 6.52 (d), 6.45-6.33 (m), 6.24 (s), 6.19 (s), 5.37-5.22 (m), 5.05-4.95 (m), 4.90 (d), 3.23 (d), 3.21-3.08 (m), 3.05 (s), 3.03-2.93 (m), 1.64 (s), 1.59-1.47 (m), 1.04-0.90 (m), 0.69-0.55 (m). MS (m/z) 791.0 [M+H]$^+$.

Example 192

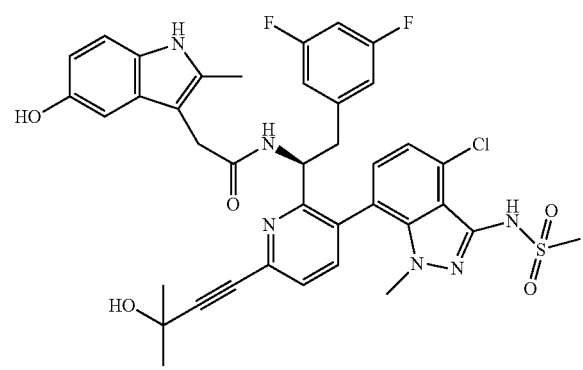

192

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(5-hydroxy-2-methyl-1H-indol-3-yl)acetamide (192)

The title compound (192) was prepared as a mixture of atropisomers according to the method presented in the synthesis of 10A in Example 10 utilizing 19F and 2-(5-hydroxy-2-methyl-H-indol-3-yl)acetic acid. $^1$H NMR (400 MHz, Methanol-d$_4$) δ 7.63 (dd), 7.46 (dd), 7.13-7.03 (m), 7.03-6.92 (m), 6.74-6.54 (m), 6.46 (d), 6.35 (d), 6.26 (d), 5.29-5.18 (m), 5.04-4.89 (m), 3.47 (d), 3.43 (s), 3.22 (d), 3.18-3.08 (m), 2.97 (s), 2.95-2.75 (m), 2.31 (s), 2.28 (s), 1.65 (s). MS (m/z) 761.5 [M+H]$^+$.

Example 193

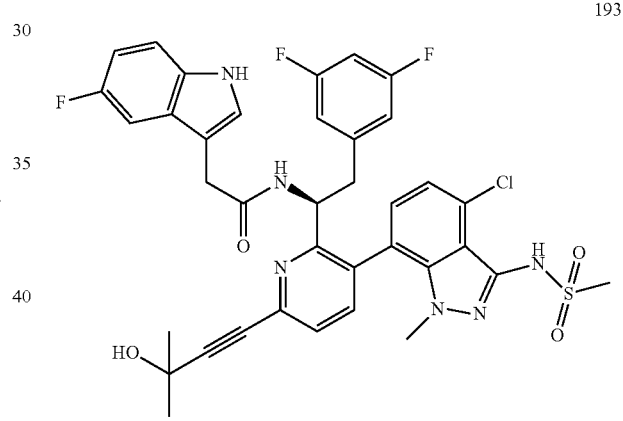

193

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(5-fluoro-1H-indol-3-yl)acetamide (193)

The title compound (193) was prepared as a mixture of atropisomers according to the method presented in the synthesis of 10A in Example 10 utilizing 19F and 2-(5-fluoro-1H-indol-3-yl)acetic acid. $^1$H NMR (400 MHz, Methanol-d$_4$) δ 7.63 (d), 7.53-7.43 (m), 7.34-7.24 (m), 7.18-7.06 (m), 7.02 (dd), 6.91-6.77 (m), 6.74-6.64 (m), 6.64-6.56 (m), 6.49 (d), 6.43-6.30 (m), 5.26-5.16 (m), 5.05-4.95 (m), 3.64-3.39 (m), 3.24 (s), 3.23 (s), 3.14-2.80 (m), 1.64 (s). MS (m/z) 749.5 [M+H]$^+$.

Example 194

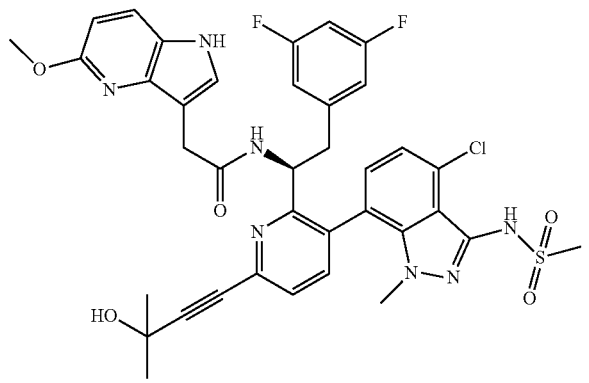

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(5-methoxy-1H-pyrrolo[3,2-b]pyridin-3-yl)acetamide (194)

The title compound (194) was prepared as a mixture of atropisomers according to the method presented in the synthesis of 10A in Example 10 utilizing 19F and 2-(5-methoxy-1H-pyrrolo[3,2-b]pyridin-3-yl)acetic acid. $^1$H NMR (400 MHz, Methanol-$d_4$) δ 8.32-8.20 (m), 7.77-7.59 (m), 7.56-7.49 (m), 7.17 (dd), 7.09-6.97 (m), 6.94 (d), 6.72 (d), 6.57-6.48 (m), 6.38 (d), 6.29 (d), 5.29-5.17 (m), 5.12-5.00 (m), 4.18-4.14 (m), 4.03 (d), 3.69-3.45 (m), 3.29-3.18 (m), 3.20-3.03 (m), 3.03-2.90 (m), 1.65 (s). MS (m/z) 762.3 [M+H]$^+$.

Example 195

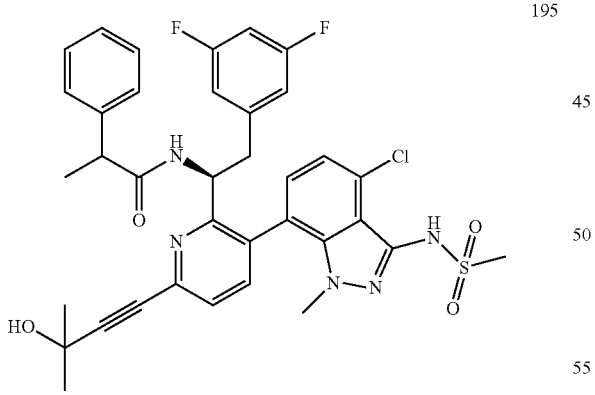

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-phenylpropanamide (195)

The title compound (195) was prepared as a mixture of atropisomers according to the method presented in the synthesis of 10A in Example 10 utilizing 19F and 2-phenylpropanoic acid. $^1$H NMR (400 MHz, Methanol-$d_4$) δ 7.71 (dd), 7.63-7.42 (m), 7.37-7.05 (m), 6.81-6.72 (m), 6.69 (d), 6.67-6.52 (m), 6.49 (d), 6.47-6.39 (m), 6.35-6.24 (m), 5.28-5.22 (m), 5.08-5.00 (m), 5.00-4.95 (m), 3.72-3.49 (m), 3.39 (s), 3.29-3.22 (m), 3.18-2.95 (m), 2.91 (s), 2.88-2.84 (m), 2.81 (s), 1.64 (s), 1.35 (dd), 1.32-1.19 (m). MS (m/z) 706.8 [M+H]$^+$.

Example 196

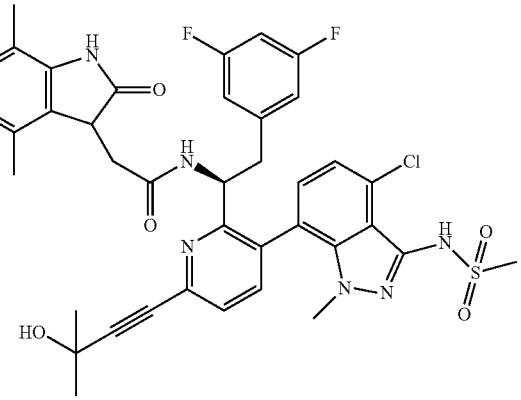

Synthesis of N—((S)-1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(4,7-dimethyl-2-oxoindolin-3-yl)acetamide (196)

The title compound (196) was prepared as a mixture of atropisomers according to the method presented in the synthesis of 10A in Example 10 utilizing 19F and 2-(4,7-dimethyl-2-oxoindolin-3-yl)acetic acid. $^1$H NMR (400 MHz, Methanol-$d_4$) δ 7.69-7.61 (m), 7.61-7.41 (m), 7.16 (d), 7.12-7.06 (m), 7.03 (d), 6.89-6.76 (m), 6.76-6.68 (m), 6.67 (d), 6.64-6.54 (m), 6.49 (d), 6.43-6.36 (m), 6.34 (d), 5.18 (s), 5.14-5.06 (m), 4.83-4.75 (m), 3.67-3.57 (m), 3.57-3.43 (m), 3.36 (s), 3.25 (dd), 3.21-3.11 (m), 3.10-2.97 (m), 2.97-2.68 (m), 2.35-2.06 (m), 1.71-1.59 (m). MS (m/z) 776.1 [M+H]$^+$.

Example 197

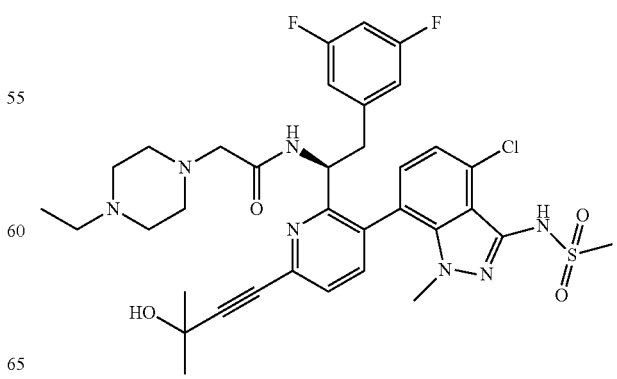

469

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(4-ethylpiperazin-1-yl)acetamide (197)

The title compound (197) was prepared as a mixture of atropisomers according to the method presented in the synthesis of 10A in Example 10 utilizing 19F and 2-(4-ethylpiperazin-1-yl)acetic acid. $^1$H NMR (400 MHz, Methanol-d$_4$) δ 7.75 (dd), 7.54 (dd), 7.35 (d), 7.27 (d), 7.20 (d), 6.82 (d), 6.80-6.73 (m), 6.69-6.62 (m), 6.50-6.37 (m), 5.47-5.39 (m), 5.07 (dd), 3.40 (s), 3.27 (s), 3.23-2.87 (m), 1.63 (s), 1.35 (td). MS (m/z) 729.0 [M+H]$^+$.

Example 198

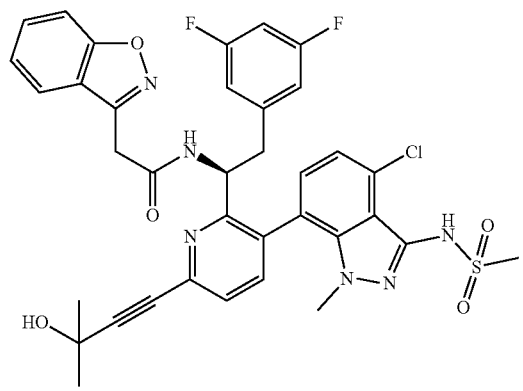

198

Synthesis of (S)-2-(benzo[d]isoxazol-3-yl)-N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)acetamide (198)

The title compound (198) was prepared as a mixture of atropisomers according to the method presented in the synthesis of 10A in Example 10 utilizing 19F and 2-(benzo[d]isoxazol-3-yl)acetic acid. $^1$H NMR (400 MHz, Methanol-d$_4$) δ 7.72-7.63 (m), 7.60 (d), 7.59-7.49 (m), 7.37-7.30 (m), 7.31-7.24 (m), 7.16 (d), 7.11 (d), 7.00 (d), 6.74-6.66 (m), 6.58 (d), 6.47-6.38 (m), 5.30-5.22 (m), 5.07-4.95 (m), 3.93-3.76 (m), 3.24 (s), 3.21-3.10 (m), 3.08-2.93 (m), 1.65 (s). MS (m/z) 733.2 [M+H]$^+$.

Example 199

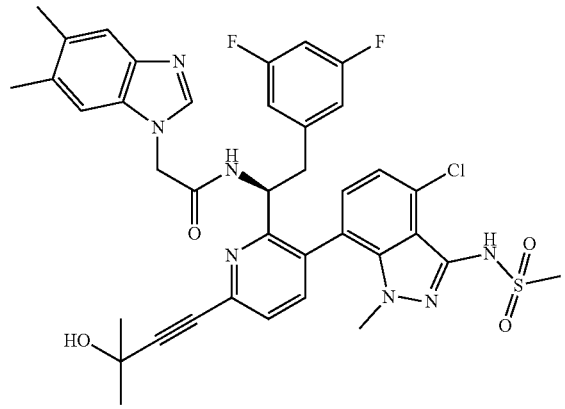

199

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(5,6-dimethyl-1H-benzo[d]imidazol-1-yl)acetamide (199)

The title compound (199) was prepared as a mixture of atropisomers according to the method presented in the synthesis of 10A in Example 10 utilizing 19F and 2-(5,6-dimethyl-1H-benzo[d]imidazol-1-yl)acetic acid. $^1$H NMR (400 MHz, Methanol-d$_4$) δ 9.19 (s), 9.07 (s), 7.74 (dd), 7.63-7.50 (m), 7.49-7.33 (m), 7.27 (s), 7.24-6.99 (m), 6.74-6.56 (m), 6.47-6.34 (m), 5.38-5.29 (m), 5.22-4.91 (m), 4.03 (s), 3.25 (d), 3.23-3.19 (m), 3.14 (s), 3.09-2.95 (m), 2.52-2.38 (m), 1.65 (s). MS (m/z) 761.1 [M+H]$^+$.

Example 200

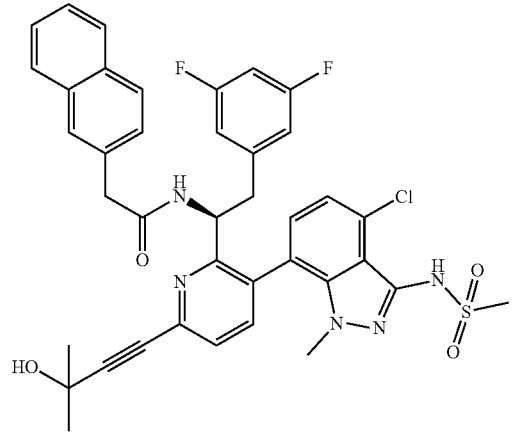

200

Synthesis of (S)—N-(1-(3-(4-chloro-1-methyl-3-(methylsulfonamido)-1H-indazol-7-yl)-6-(3-hydroxy-3-methylbut-1-yn-1-yl)pyridin-2-yl)-2-(3,5-difluorophenyl)ethyl)-2-(naphthalen-2-yl)acetamide (200)

The title compound (200) was prepared as a mixture of atropisomers according to the method presented in the synthesis of 10A in Example 10 utilizing 19F and 2-(naphthalen-2-yl)acetic acid. $^1$H NMR (400 MHz, Methanol-$d_4$) δ 7.86-7.69 (m), 7.69-7.62 (m), 7.59 (s), 7.55-7.49 (m), 7.50-7.37 (m), 7.34 (d), 7.25-7.19 (m), 7.10 (dd), 6.99 (d), 6.84 (d), 6.71-6.62 (m), 6.60-6.57 (m), 6.55 (dd), 6.47-6.34 (m), 5.24-5.16 (m), 5.02 (t), 3.64-3.44 (m), 3.24 (s), 3.20 (s), 3.18-3.11 (m), 3.10 (d), 3.03-2.93 (m), 1.64 (s). MS (m/z) 742.8 [M+H]$^+$.

Example 201

Large scale preparation of (S)—N-(1-(3-(4-chloro-1-methyl-3-(methylsulfonamido)-1H-indazol-7-yl)-6-(3-hydroxy-3-methylbut-1-ynyl)pyridin-2-yl)-2-(3,5-difluorophenyl)ethyl)-2-((3bS,4aR)-5,5-difluoro-3-(difluoromethyl)-3b,4,4a,5-tetrahydro-1H-cyclopropa[3,4]cyclopenta[1,2-c]pyrazol-1-yl)acetamide (19G).

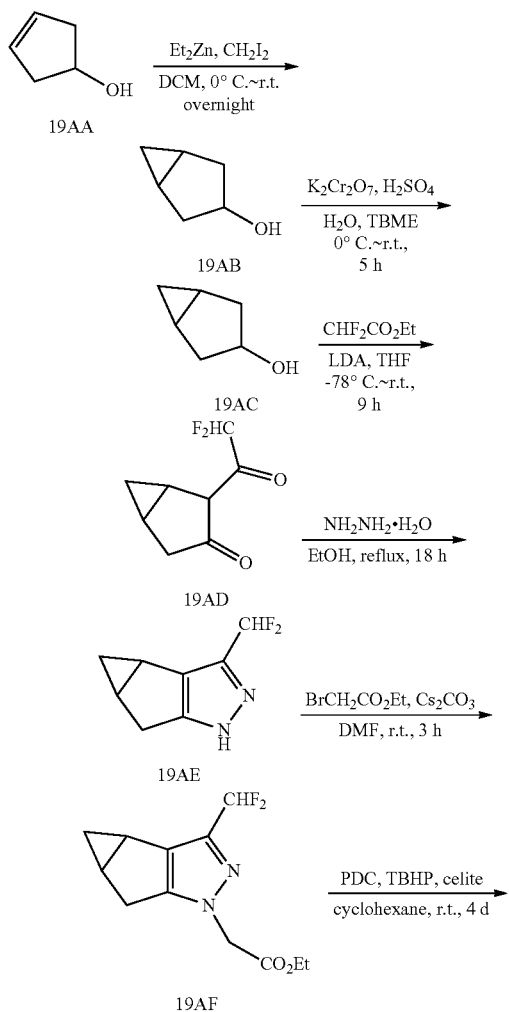

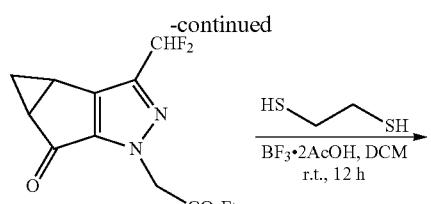

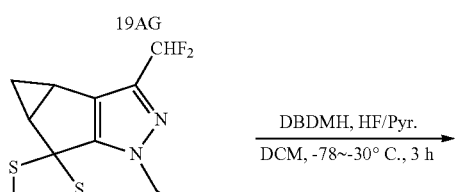

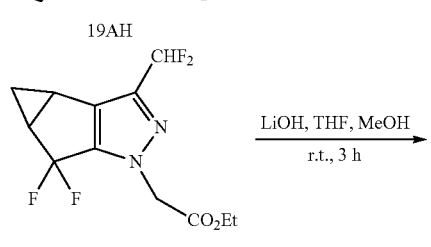

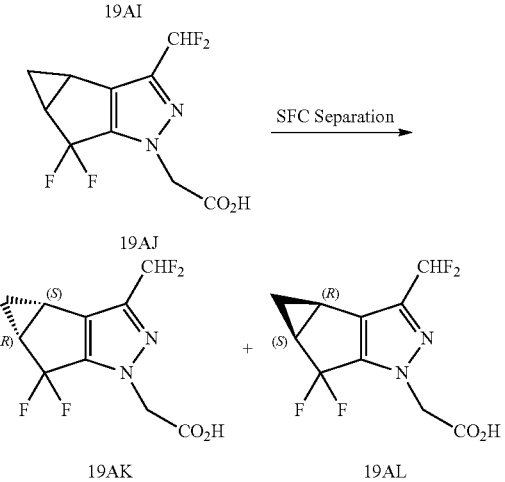

Synthesis of bicyclo[3.1.0]hexan-3-ol (19AB)

Et$_2$Zn (1M in hexane, 2.37 L, 2.37 mol) was added drop-wise to a solution of compound 19AA (100 g, 1.19 mol) in DCM (800 ml) under N$_2$ at 0-5° C. The mixture was stirred at 0-5° C. for 30 min, then CH$_2$I$_2$ (636 g, 2.37 mol) in DCM (200 ml) was added drop-wise in 1 h at 0-5° C. The resulting mixture was stirred at room temperature overnight. The mixture was added slowly to ice-cold aq. NH$_4$Cl (1.5 L). The mixture was filtered. The aqueous phase was extracted with DCM (2L×3). The combined organic layer was dried over MgSO$_4$, concentrated in vacuo to give crude residue, which was purified by distillation (20 mmHg, 80° C.-82° C.) to give compound 19AB. $^1$H NMR: (400 MHz, CDCl$_3$) δ 4.35 (t, J=6.4 Hz, 1H), 2.10-2.06 (m, 2H), 1.70 (d, J=14.0 Hz, 2H), 1.65 (s, 1H), 1.27-1.24 (m, 2H), 0.52-0.47 (m, 2H).

Synthesis of bicyclo[3.1.0]hexan-3-one (19AC)

To a solution of K$_2$Cr$_2$O$_7$ (240 g, 0.82 mol) in H$_2$O (2 L), H$_2$SO$_4$ (240 g, 2.45 mol) was added drop-wise at room temperature. The mixture was stirred at room temperature for 1 h. The system was cooled to 0° C., compound 19AB (100 g, 1.02 mol) in TBME (2 L) was added drop-wise. The reaction mixture was stirred at room temperature for 4 h. The organic layer was separated. The aqueous layer was extracted with TBME (1 L×3). The combined organic layer was dried over MgSO$_4$, filtered, concentrated in vacuo to give the crude product, which was purified by distillation (20 mmHg, 60° C.-62° C.) to give compound 19AC. $^1$H NMR (400 MHz, CDCl$_3$) δ 2.57-2.52 (m, 2H), 2.13-2.08 (m, 2H), 1.50-1.47 (m, 2H), 0.88-0.85 (m, 1H), 0.08-0.01 (m, 1H).

Synthesis of 2-(2,2-difluoroacetyl)bicyclo[3.1.0]hexan-3-one (19AD)

To the solution of compound 19AC (100 g, 1.04 mol) in THF (1 L), LDA (700 ml, 1.05 mol, 1.5M in THF) was added drop-wise under N$_2$ over a period of 2 h. The resulting mixture was stirred 1 h at −78° C. Ethyl difluoroacetate (142 g, 1.14 mol) in THF (500 ml) was added drop-wise over a period of 1 h and the reaction was stirred 1 h at −78° C. The reaction was warmed to room temperature and stirred for 4 h. The reaction was quenched by aqueous 1N HCl (1.5 L) and then partitioned between EA (1.0 L) and aqueous citric acid (300 ml). The organic layer was separated and washed with brine. Solvents were removed in vacuo to give compound 19AD which was used for the next step without further purification. $^1$H NMR (400 MHz, CDCl$_3$) δ 6.17 (t, J=53.6 Hz, 1H), 2.78-2.73 (m, 1H), 2.44-2.39 (m, 1H), 2.25-2.24 (m, 1H), 1.70-1.69 (m, 1H), 1.22-1.14 (m, 1H), 0.31-0.27 (m, 1H).

Synthesis of 3-(difluoromethyl)-3b,4,4a,5-tetrahydro-1H-cyclopropa[3,4]cyclopenta[1,2-c]pyrazole (19AE)

N$_2$H$_4$.H$_2$O (104 g, 2.08 mol) was added drop-wise in 30 min to the solution of compound 19AD (380 g, 2.08 mol) in EtOH (4 L) at room temperature The mixture was stirred at reflux overnight. The mixture was concentrated in vacuo then purified by silica gel column chromatography (PE: EA=10:1-5:1) to give compound 19AE. MS (m/z): 171.1 [M+H]$^+$. $^1$H NMR (400 MHz, CDCl$_3$) δ 6.74 (t, J=55.6 Hz, 1H), 2.99-2.94 (m, 1H), 2.82-2.78 (m, 1H), 2.13-2.07 (m, 2H), 1.14-1.08 (m, 1H), 0.30-0.27 (m, 1H).

Synthesis of ethyl 2-(3-(difluoromethyl)-3b,4,4a,5-tetrahydro-1H-cyclopropa[3,4]cyclopenta[1,2-c]pyrazol-1-yl)acetate (19AF)

To a solution of compound 19AE (201 g, 1.18 mol) in DMF (2 L), ethyl bromoacetate (207 g, 1.24 mol) and Cs$_2$CO$_3$ (404 g, 1.24 mol) were added in one portion at room temperature. The mixture was stirred at room temperature for 3 h. The mixture was poured into H$_2$O (4 L) and then extracted with EA (2 L×3). The combined organic phase was washed with brine (2 L×3), dried over MgSO$_4$, and concentrated in vacuo. The crude product was purified by silica gel column chromatography (PE: EA=20:1-8:1) to obtain a mixture of N1 and N2 alkylation isomers. An additional purification from PE/EA (10/1) provided compound 19AF. MS (m/z): 257.1 [M+H]$^+$. $^1$H NMR (400 MHz, CDCl$_3$) δ 6.61 (t, J=55.2 Hz, 1H), 4.70 (dd, J=17.2, 11.2 Hz, 2H), 4.23 (q, J=7.2 Hz, 2H), 2.91 (dd, J=16.0, 6.0 Hz, 1H), 2.72 (d, J=16.4 Hz, 1H), 2.17-2.09 (m, 1H), 1.28 (t, J=7.2 Hz, 3H), 1.10-1.07 (m, 1H), 0.33-0.30 (m, 1H).

Synthesis of ethyl 2-(3-(difluoromethyl)-5-oxo-3b,4,4a,5-tetrahydro-1H-cyclopropa[3,4]cyclopenta[1,2-c]pyrazol-1-yl)acetate (19AG)

Compound 19AF (102 g, 0.39 mol) and celite 545 (390 g) were added to cyclohexane (3.5 L) and the mixture was stirred at 10° C. PDC (599 g, 1.59 mol) was added in one portion followed by TBHP (289 ml, 1.59 mol) drop-wise in 30 min at 10° C. The reaction was slowly warmed to room temperature and stirred for 4 days. The reaction was filtered through celite and filter cake was washed with EtOAc (600 ml). The combined organic layer was stirred with saturated aqueous Na$_2$S$_2$O$_3$ (1000 ml) for 1 h. The organic layer was separated and treated with half saturated FeSO$_4$ (300 ml), washed with brine and dried over Na$_2$SO$_4$. Solvents were removed in vacuo to give crude product, which was additionally purified from PE (300 ml) to give compound 19AG. MS (m/z): 271.1 [M+H]$^+$. $^1$H NMR (400 MHz, CDCl$_3$) δ 6.67 (t, J=54.8 Hz, 1H), 4.94 (s, 2H), 4.23 (q, J=7.2 Hz, 2H), 2.79-2.78 (m, 1H), 2.59-2.56 (m, 1H), 1.70-1.65 (m, 2H), 1.28 (t, J=6.8 Hz, 3H).

Synthesis of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate (19AH)

To compound 19AG (148.5 g, 0.55 mol) in DCM (2.0 L) was added ethane-1,2-dithiol (88.0 g, 0.94 mol) in one portion and the solution was stirred at room temperature. BF$_3$.2AcOH (175.8 g, 0.94 mol) was added to above solution. The reaction was stirred at room temperature for 12 h. The system was cooled to 0° C. and quenched with saturated aqueous NaHCO$_3$ (1000 ml). The organic layer was separated, washed with brine (500 ml) and dried over Na$_2$SO$_4$. Solvents were removed in vacuo and the residue was purified by silica gel column chromatography (PE: EtOAc=30:1-10:1) to provide compound 19AH. MS (m/z): 347.1 [M+H]$^+$. $^1$H NMR (400 MHz, CDCl$_3$) δ 6.61 (t, J=55.0 Hz, 1H), 4.90 (dd, J=17.2, 10.8 Hz, 2H), 4.21 (q, J=4.8 Hz, 2H), 3.51-3.45 (m, 4H), 2.60-2.58 (m, 1H), 2.43-2.42 (m, 1H), 1.29-1.23 (m, 4H), 0.63-0.61 (m, 1H).

Synthesis of ethyl 2-(3-(difluoromethyl)-5,5-difluoro-3b,4,4a,5-tetrahydro-1H-cyclopropa[3,4]cyclopenta[1,2-c]pyrazol-1-yl)acetate (19AI)

A solution of DBDMH (99 g, 0.35 mol) in dry DCM (120 mL) was cooled to −78° C. in a teflon bottle. HF/Py (120 mL) was added drop-wise over a period of 30 min. The reaction was stirred at −78° C. for 30 min. Then a solution of compound 19AH (40 g, 0.12 mol) in dry DCM (80 mL) was added drop-wise over a period of 15 min at −78° C. The resulting mixture was stirred for 30 min at this temperature, then slowly warm to −30° C. and stirred for 1.5 h. The reaction mixture was slowly poured into aq. NaHCO$_3$ (500 mL) and extracted with EA (500 mL×3). The combined organic layer was washed with 10% aq. Na$_2$S$_2$O$_3$ (500 mL), brine (500 mL) and dried over Na$_2$SO$_4$. Solvents were removed in vacuo to afford the crude product, which was further purified by column chromatography (PE: EA=80:1 to 50:1) to give compound 19AI. MS (m/z): 293.2 [M+H]$^+$. $^1$H NMR (400 MHz, CDCl$_3$) δ 6.63 (t, J=54.8 Hz, 1H), 4.83 (s, 2H), 4.24 (q, J=7.2 Hz, 2H), 2.48-2.45 (m, 2H), 1.38-1.36 (m, 1H), 1.28 (t, J=7.2 Hz, 3H), 1.13-1.12 (m, 1H).

Synthesis of 2-(3-(difluoromethyl)-5,5-difluoro-3b,4,4a,5-tetrahydro-1H-cyclopropa[3,4]cyclopenta[1,2-c]pyrazol-1-yl)acetic acid (19AJ)

To a solution of compound 19AI (50 g, 171 mmol) in THF (87.5 mL) and MeOH (350 mL) was added the solution of LiOH (6.2 g, 257 mmol) in H₂O (350 mL). The mixture was stirred at 20° C. for 3 h. The mixture was concentrated to remove most of THF and MeOH, the aqueous was acidified by 1N HCl to adjust pH to 2-3, then extracted with EA (600 mL×2). The organic phase was separated and combined, dried over Na₂SO₄, filtered and concentrated in vacuum to give compound 19AJ.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (19AK) and 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid (19AL)

Compound 19AJ was separated by SFC (ChiralPak IC-10 u, 300×50 mm I.D., mobile phase: CO₂/isopropanol (0.1% NH₃.H₂O), 35% gradient, 200 mL/min flow rate, 38° C. column temperature, detection at 220 nm) to give compound 19AK (79.3 g) and 19AL (80.8 g). 19AK: MS (m/z): 265.0 [M+H]⁺; ¹H NMR: (400 MHz, DMSO-d₆) δ 13.43 (br, 1H), 7.04 (t, J=54.0 Hz, 1H), 4.99-4.87 (m, 2H), 2.62-2.57 (m, 2H), 1.46-1.41 (m, 1H), 0.96 (s, 1H). 19AL: MS (m/z): 265.0 [M+H]⁺; ¹H NMR: (400 MHz, DMSO-d₆) δ 13.42 (br, 1H), 7.04 (t, J=54.0 Hz, 1H), 4.99-4.88 (m, 2H), 2.63-2.51 (m, 2H), 1.46-1.41 (m, 1H), 0.97 (s, 1H).

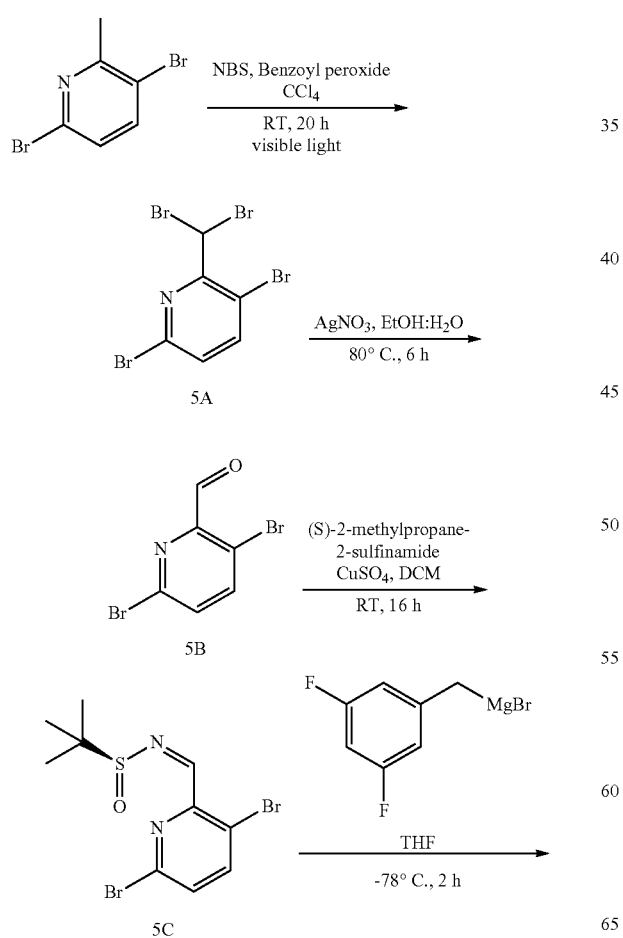

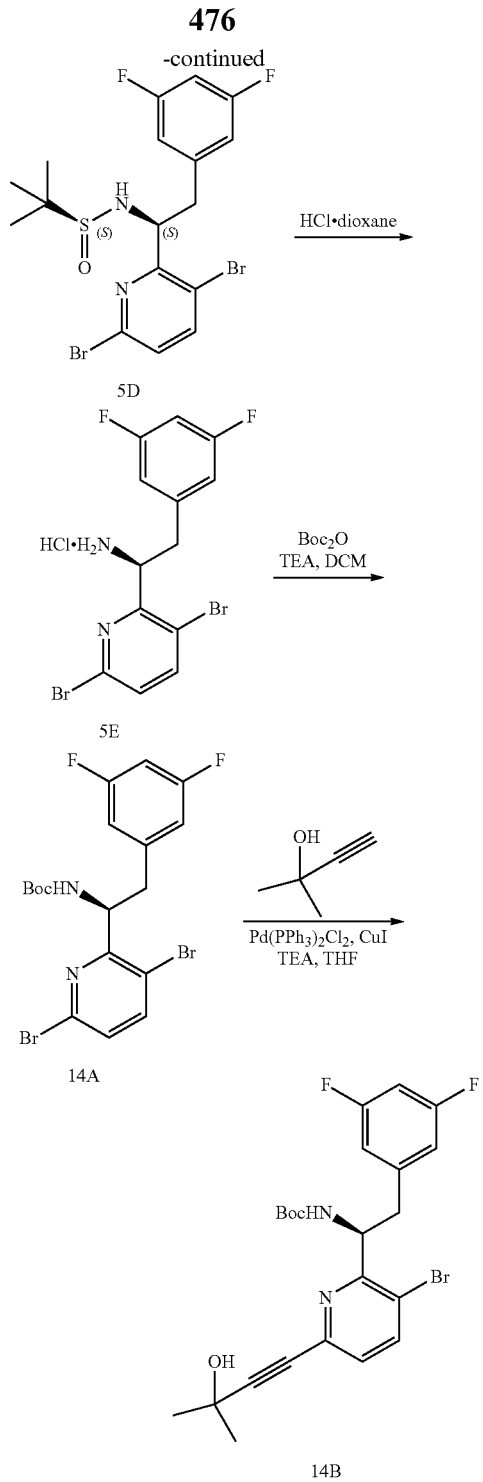

Synthesis of 3,6-dibromo-2-(dibromomethyl)pyridine (5A)

To a stirred solution of 3,6-dibromo-2-methylpyridine (200.0 g, 797.06 mmol) in CCl₄ (4000 mL), benzoyl peroxide (192.89 g, 797.06 mmol) followed by NBS (565.0 g, 3188.0 mmol) was added at room temperature. After addition was completed, the resulting reaction mixture was stirred in presence of white light 400 watt bulb at room temperature for 20 h. The reaction mixture was stirred at room temperature for 20 h. The reaction mixture was filtered and washed with CCl₄ (2×800 mL). The filtrate was evaporated under reduced pressure which was further purified by column chromatography on silica gel using 0-5% EA in hexane as an eluent to afford compound 5A. MS (m/z): 409.66 [M+H]⁺.

Synthesis of 3,6-dibromopicolinaldehyde (5B)

To a solution of compound 5A (100.0 g, 244.67 mmol) in EtOH (1000 mL) at 80° C., aqueous silver nitrate (103.9 g, 611.6 mmol, in 300 mL water) was added drop-wise, in 1 h at same temperature. After addition was completed, the resulting reaction mixture was stirred to reflux for another 5 h. The reaction mixture was cooled to room temperature and filtered. The filtrate was evaporated under reduced pressure and the resultant crude was diluted with water (1000 mL). The aqueous layer was extracted with ethyl acetate (3×400 mL). The combined organic layers were washed with water (2×400 mL), dried over sodium sulfate and distilled off under reduced pressure gave compound 5B. MS (m/z): 265.96. [M+H]⁺

Synthesis of (S,Z)—N-((3,6-dibromopyridin-2-yl)methylene)-2-methylpropane-2-sulfinamide (5C)

To a stirred solution of compound 5B (68.0 g, 256.7 mmol) in DCM (1400 mL), copper (II) sulfate anhydrous (102.3 g, 641.75 mmol) was added followed by (S)-2-methylpropane-2-sulfinamide (37.3 g, 308.0 mmol) at room temperature. The resulting suspension was stirred at room temperature for 16 h. The reaction mixture was filtered and washed with DCM (100 mL). The eluent was evaporated under reduced pressure. The resultant crude compound was recrystallized from diethyl ether (300 mL) to provide compound 5C. MS (m/z) 368.86 [M+H]⁺

Synthesis of (S)—N—((S)-1-(3,6-dibromopyridin-2-yl)-2-(3,5-difluorophenyl)ethyl)-2-methylpropane-2-sulfinamide (5D)

To a stirred solution of compound 5C (20.0 g, 54.33 mmol) in dry THF (300 mL), at −78° C. a solution of 3,5-difluorobenzylmagnesium bromide (260.8 mL, 0.2M in ether, 65.20 mmol) was added drop-wise in 1 h at −78° C. After addition was completed, the resulting reaction mixture was stirred at −78° C. for 1 h. The reaction mixture was quenched with aqueous NH₄Cl (200 mL) at same temperature. Organic layer was separated and aqueous layer was extracted with EtOAc (3×150 mL). The combined organic layers were washed with water (2×200 mL) and brine, dried over Na₂SO₄. The solvent was distilled off under reduced pressure and the resultant crude compound was purified by column chromatography on silica-gel using 0-18% EA in hexane as an eluent to provide compound 5D. MS (m/z) 496.99 [M+H]⁺

Synthesis of (S)-1-(3,6-dibromopyridin-2-yl)-2-(3,5-difluorophenyl)ethanamine hydrochloride (5E)

To a solution of compound 5D (53 g, 107 mmol) in methanol (100 mL) was slowly added 4 N HCl in dioxane (30 mL) at room temperature. Upon completion of the reaction, the volatiles were removed in vacuo. The resulting solid was suspended in ether (200 mL) and collected by filtration to provide compound 5E. MS (m/z) 393.17 [M+H]⁺

Synthesis of (S)-tert-butyl 1-(3,6-dibromopyridin-2-yl)-2-(3,5-difluorophenyl)ethylcarbamate (14A)

To a suspension of compound 5E (5 g, 11.7 mmol) in DCM (50 mL) was added di-tert-butyl dicarbonate (3.1 g, 14 mmol) and triethylamine (2.4 g, 23 mmol) at room temperature. Upon completion of the reaction, the volatiles were removed in vacuo. The resulting residue was dissolved in EtOAc and washed with saturated aqueous ammonium chloride and brine. The organic layer was dried over sodium sulfate. The solvent was distilled off under reduced pressure and the resultant crude compound was purified by column chromatography on silica-gel using ethyl acetate in hexane as an eluent to provide compound 14A. MS (m/z) 492.96 [M+H]⁺

Synthesis of (S)-tert-butyl (1-(3-bromo-6-(3-hydroxy-3-methylbut-1-yn-1-yl)pyridin-2-yl)-2-(3,5-difluorophenyl)ethyl)carbamate (14B)

A solution of compound 14A (570 mg, 1.16 mmol), 3-methyl butynol (179 µL, 1.74 mmol), CuI (6 mg, 0.03 mmol), Pd(PPh₃)₂Cl₂ (20 mg, 0.03 mmol) and triethylamine (0.5 mL) in THF (2 mL) was degassed with argon for 15 min. The resulting solution was then heated at 35° C. for 2 h. Upon completion of the reaction, the mixture was filtered through a pad of celite and washed with ethyl acetate. The combined organic layers were washed with aqueous NH₄Cl, water and brine, dried over Na₂SO₄. The solvent was distilled off under reduced pressure and the resultant crude compound was purified by column chromatography on silica-gel using ethyl acetate in hexane as an eluent to provide compound 14B. MS (m/z) 496.90 [M+H]⁺

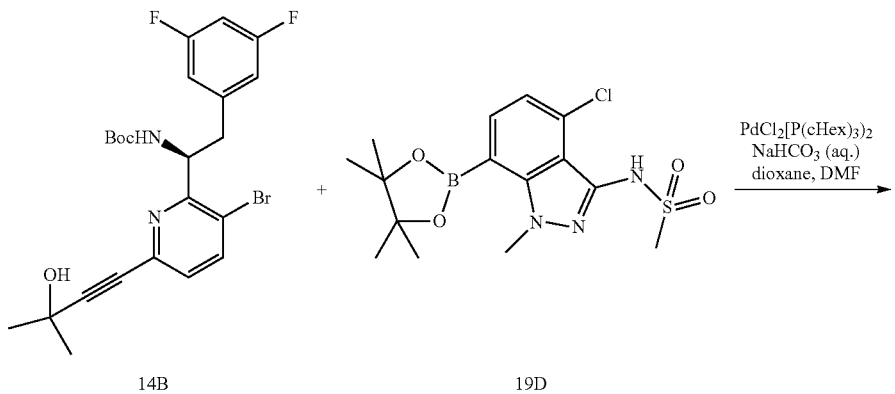

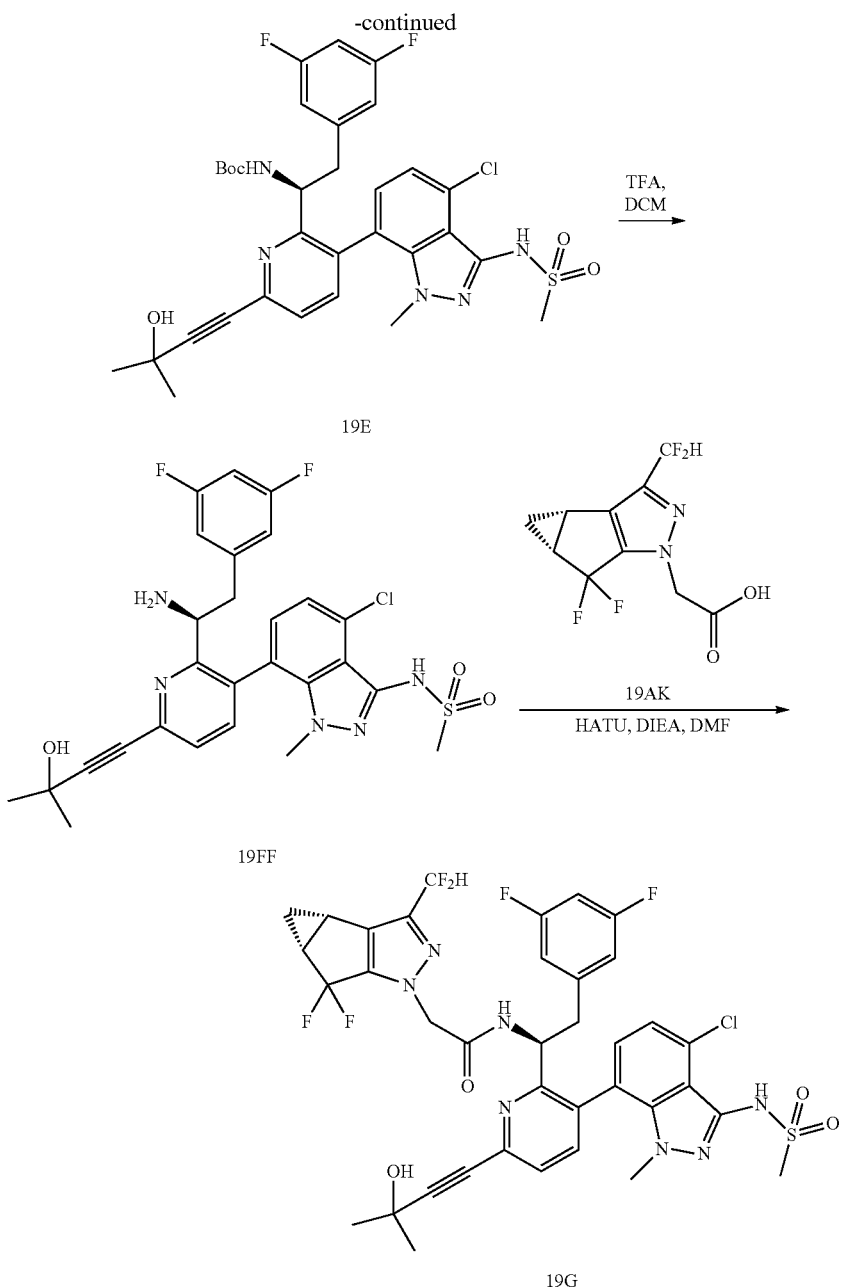

Synthesis of (S)-tert-butyl 1-(3-(4-chloro-1-methyl-3-(methylsulfonamido)-1H-indazol-7-yl)-6-(3-hydroxy-3-methylbut-1-ynyl)pyridin-2-yl)-2-(3,5-difluorophenyl)ethylcarbamate (19E)

To a flask of 14B (4000 mg, 8.075 mmol) in dioxane (150 mL) and DMF (75 ml) was added N-(4-chloro-1-methyl-7-(4,4,5,5-tetramethyl-1,3,2-dioxaborolan-2-yl)-1H-indazol-3-yl)methanesulfonamide (3114 mg, 8.075 mmol), 1N sodium bicarbonate (20.2 ml, 20.2 mmol), and dichlorobis(tricyclohexylphosphine)palladium(II) (715.3 mg, 0.97 mmol). The reaction mixture was degassed by $N_2$ for 30 minutes and then moved to oil bath at 150° C. for 45 minutes. The reaction was cooled to room temperature and filtered. The filtrate was concentrated and dissolved in EtOAc (300 mL) and washed with brine twice. The organic layer was dried over sodium sulfate, concentrated and purified by column chromatography on silica-gel using 50-90% EtOAc in hexane as an eluent to provide 19E. MS (m/z) 674.7 [M+H]$^+$.

Synthesis of (S)—N-(7-(2-(1-amino-2-(3,5-difluorophenyl)ethyl)-6-(3-hydroxy-3-methylbut-1-ynyl)pyridin-3-yl)-4-chloro-1-methyl-1H-indazol-3-yl)methanesulfonamide TFA salt (19FF)

To a flask of 19E (1 g, 1.48 mmol), 10 mL of 40% of TFA in dichloromethane was added to the flask. The mixture was neutralized by $NaHCO_3$ (aq) and extracted with EtOAc (200 mL twice). The organic layer was concentrated and dried to provide 0.85 g of the desired product 19FF that was used without further purification. MS (m/z) 574.4 [M+H]$^+$. Synthesis of (S)—N-(1-(3-(4-chloro-1-methyl-3-(methylsulfonamido)-1H-indazol-7-yl)-6-(3-hydroxy-3-methylbut-1-ynyl)pyridin-2-yl)-2-(3,5-difluorophenyl)ethyl)-2-((3bS,4aR)-5,5-difluoro-3-(difluoromethyl)-3b,4,4a,5-tetrahydro-1H-cyclopropa[3,4]cyclopenta[1,2-c]pyrazol-1-yl)acetamide (19G)

To a flask of 19FF (850 mg, 1.48 mmol) and DIEA (0.5 mL, 2.96 mmol) in 20 mL DMF, 19AK (350 mg, 1.33 mmol) and HATU (507 mg, 1.33 mmol) in 10 mL of DMF was added to the mixture slowly at 0° C. The mixture was diluted with EtOAc (300 mL) and washed with NaHCO$_3$. The organic layer was concentrated and purify by column chromatography on silica-gel using 50-80% EtOAc in hexane as an eluent to provide 19G. MS (m/z) 820.8 [M+H]$^+$.

Example 202

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word

483

"about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein. In one aspect, about a value includes and intends that value per se. For example, about x includes and intends x per se.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

EMBODIMENTS

Provided below are certain embodiments.

Embodiment I-1

A compound of formula I:

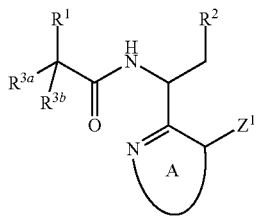

I wherein:
A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with one or more (e.g., 1 or 2) $Z^3$ groups;

$R^1$ is 6-12 membered aryl, 5-12 membered heteroaryl or 3-12 membered heterocycle, wherein any 6-12 membered

484 aryl, 5-12 membered heteroaryl or 3-12 membered heterocycle of $R^1$ is optionally substituted with one or more (e.g., 1, 2, 3, 4 or 5) $Z^4$ groups;

$R^2$ is phenyl, 5-membered monocyclic-heteroaryl, 6-membered monocyclic-heteroaryl or $(C_3-C_7)$carbocycle, wherein any phenyl, 5-membered monocyclic-heteroaryl, 6-membered monocyclic-heteroaryl or $(C_3-C_7)$carbocycle of $R^2$ is optionally substituted with one or more (e.g., 1, 2, 3, 4 or 5) $Z^5$ groups;

each $R^{3a}$ and $R^{3b}$ is independently selected from H, halogen, $(C_1-C_3)$alkyl and $(C_1-C_3)$haloalkyl, or $R^{3a}$ is selected from H, $(C_1-C_3)$alkyl and $(C_1-C_3)$haloalkyl and $R^{3b}$ is selected from —OH and —CN;

$Z^1$ is selected from 6-12 membered aryl, 5-14 membered heteroaryl and 3-14 membered heterocycle, wherein any 6-12 membered aryl, 5-14 membered heteroaryl and 3-14 membered heterocycle of $Z^1$ is optionally substituted with one or more (e.g., 1, 2, 3, 4 or 5) $Z^{1a}$ or $Z^b$;

each $Z^{1a}$ is independently selected from $(C_3-C_7)$carbocycle, 6-12 membered aryl, 5-12 membered heteroaryl, 3-12 membered heterocycle, halogen, —CN, —$OR^{n1}$, —OC(O)$R^{p1}$, —OC(O)$NR^{q1}R^{r1}$, —$SR^{n1}$, —S(O)$R^{p1}$, —S(O)$_2$OH, —S(O)$_2R^{p1}$, —S(O)$_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2R^{p1}$, —$NR^{n1}S(O)_2NR^{q1}R^{r1}$, $NO_2$, —C(O)$R^{n1}$, —C(O)$OR^{n1}$, —C(O)$NR^{q1}R^{r1}$ and —S(O)$_2NR^{n1}COR^{p1}$, wherein any $(C_3-C_7)$carbocycle, 6-12 membered aryl, 5-12 membered heteroaryl and 3-12 membered heterocycle of $Z^{1a}$ is optionally substituted with one or more (e.g., 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with one or more (e.g., 1, 2, 3, 4 or 5) $Z^{1c}$ groups;

each $Z^{1c}$ is independently selected from $(C_3-C_7)$carbocycle, phenyl, 5-6 membered monocyclic-heteroaryl, 3-7 membered heterocycle, halogen, —CN, —$OR^{n2}$, —OC(O)$R^{p2}$, —OC(O)$NR^{q2}R^{r2}$, —$SR^{n2}$, —S(O)$R^{p2}$, —S(O)$_2$OH, —S(O)$_2R^{p2}$, —S(O)$_2NR^{q2}R^{r2}$, —$NR^{q2}R^{r2}$, —$NR^{n2}COR^{p2}$, —$NR^{n2}CO_2R^{p2}$, —$NR^{n2}CONR^{q2}R^{r2}$, —$NR^{n2}S(O)_2R^{p2}$, —$NR^{n2}S(O)_2OR^{p2}$, —$NR^{n2}S(O)_2NR^{q2}R^{r2}$, $NO_2$, —C(O)$R^{n2}$, —C(O)$OR^{n2}$, —C(O)$NR^{q2}R^{r2}$, halophenyl, 5-6 membered haloheteroaryl, 3-7 membered haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R^{n1}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{n1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{n1}$ is optionally substituted with one or more (e.g., 1, 2, 3, 4 or 5) $Z^{1c}$ groups;

each $R^{p1}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{p1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{p1}$ is optionally substituted with one or more (e.g., 1, 2, 3, 4 or 5) $Z^{1c}$ groups;

$R^{q1}$ and $R^{r1}$ are each independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{q1}$ or $R^{r1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{q1}$ or $R^{r1}$ is optionally substituted with one or more (e.g., 1, 2, 3, 4 or 5) $Z^{1c}$ groups, or $R^{q1}$ and $R^{r1}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{1c}$ or $Z^{1d}$ groups;

each $R^{n2}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl;

each $R^{p2}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl;

$R^{q2}$ and $R^{r2}$ are each independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl, or $R^{q2}$ and $R^{r2}$ together with the nitrogen to which they are attached form a 5, 6 or 7-membered heterocycle;

$Z^2$ is selected from $(C_2-C_8)$alkenyl, $(C_2-C_8)$alkynyl, 6-12 membered aryl, 5-12 membered C-linked-heteroaryl, 3-12 membered C-linked-heterocycle, —C(O)$R^{n3}$ and —C(O)NR$^{q3}$R$^{r3}$, wherein any 6-12 membered aryl, 5-12 membered C-linked-heteroaryl and 3-12 membered C-linked-heterocycle of $Z^2$ is optionally substituted with one or more (e.g., 1, 2, 3, 4 or 5) $Z^{2b}$ or $Z^{2c}$ groups, and wherein any $(C_2-C_8)$alkenyl and $(C_2-C_8)$alkynyl of $Z^2$ is optionally substituted with one or more (e.g., 1, 2, 3, 4, or 5) $Z^{2c}$ groups;

each $Z^{2a}$ is independently selected from $(C_3-C_7)$carbocycle, 6-12 membered aryl, 5-12 membered heteroaryl, 3-12 membered heterocycle, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$, wherein any $(C_3-C_7)$carbocycle, 6-12 membered aryl, 5-12 membered heteroaryl and 3-12 membered heterocycle of $Z^{2a}$ is optionally substituted with one or more (e.g., 1, 2, 3, 4 or 5) $Z^{2b}$ or $Z^{2c}$ groups;

each $Z^{2b}$ is independently selected from $(C_1-C_4)$alkyl, $(C_1-C_4)$heteroalkyl and $(C_1-C_4)$haloalkyl;

each $Z^{2c}$ is independently selected from halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^4$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$;

each $R^{n3}$ is independently selected from H, $(C_1-C_4)$alkyl, $(C_2-C_4)$alkenyl, $(C_3-C_7)$carbocycle, 3-12 membered heterocycle, 5-12 membered heteroaryl and 6-12 membered aryl, wherein any $(C_3-C_7)$carbocycle, 3-12 membered heterocycle, 5-12 membered heteroaryl and 6-12 membered aryl of $R^{n3}$ is optionally substituted with one or more (e.g., 1, 2, 3, 4 or 5) $Z^{2b}$ or $Z^{2c}$ groups, and wherein any $(C_1-C_4)$alkyl, $(C_2-C_4)$alkenyl and $(C_2-C_4)$alkynyl of $R^{n3}$ is optionally substituted with one or more (e.g., 1, 2, 3, 4 or 5) $Z^{2a}$ groups;

$R^{q3}$ and $R^{r3}$ are each independently selected from H, $(C_1-C_4)$alkyl, $(C_2-C_4)$alkenyl, $(C_3-C_7)$carbocycle, 3-12 membered heterocycle, 5-12 membered heteroaryl and 6-12 membered aryl, wherein any $(C_3-C_7)$carbocycle, 3-12 membered heterocycle, 5-12 membered heteroaryl and 6-12 membered aryl of $R^{q3}$ or $R^{r3}$ is optionally substituted with one or more (e.g., 1, 2, 3, 4 or 5) $Z^{2b}$ or $Z^{2c}$ groups, and wherein any $(C_1-C_4)$alkyl and $(C_2-C_4)$alkenyl of $R^{q3}$ or $R^{r3}$ is optionally substituted with one or more (e.g., 1, 2, 3, 4 or 5) $Z^{2a}$ groups, or $R^{q3}$ and $R^{r3}$ together with the nitrogen to which they are attached form a heterocycle or heteroaryl, wherein the heterocycle or heteroaryl is optionally substituted with one or more (e.g., 1, 2, 3, 4 or 5) $Z^{2b}$ or $Z^{2c}$ groups;

each $R^{n4}$ is independently selected from H, $(C_1-C_4)$alkyl, $(C_2-C_8)$alkenyl, $(C_2-C_8)$alkynyl, $(C_1-C_4)$haloalkyl and $(C_1-C_4)$heteroalkyl;

each $R^{p4}$ is independently selected from $(C_1-C_8)$alkyl, $(C_2-C_4)$alkenyl, $(C_2-C_4)$alkynyl, $(C_1-C_4)$haloalkyl and $(C_1-C_4)$heteroalkyl;

$R^{q4}$ and $R^{r4}$ are each independently selected from H, $(C_1-C_4)$alkyl, $(C_2-C_4)$alkenyl, $(C_2-C_4)$alkynyl, $(C_1-C_4)$haloalkyl and $(C_1-C_4)$heteroalkyl;

each $Z^3$ is independently selected from halogen, $(C_1-C_4)$alkyl, —OH, —CN, $(C_1-C_4)$heteroalkyl and $(C_1-C_4)$haloalkyl;

each $Z^4$ is independently selected from $(C_1-C_8)$alkyl, $(C_2-C_8)$alkenyl, $(C_2-C_8)$alkynyl, $(C_3-C_7)$carbocycle, halogen, —CN, —OR$^{n5}$, —OC(O)R$^{p5}$, —OC(O)NR$^{q5}$R$^{r5}$, —SR$^{n5}$, —S(O)R$^{p5}$, —S(O)$_2$OH, —S(O)$_2$R$^{p5}$, —S(O)$_2$NR$^{q5}$R$^{r5}$, —NR$^{q5}$R$^{r5}$, —NR$^{n5}$COR$^{p5}$, —NR$^{n5}$CO$_2$R$^{p5}$, —NR$^{n5}$CONR$^{q5}$R$^{r5}$, —NR$^{n5}$S(O)$_2$R$^{p5}$, —NR$^{n5}$S(O)$_2$OR$^5$, —NR$^{n5}$S(O)$_2$NR$^{q5}$R$^{r5}$, NO$_2$, —C(O)R$^{n5}$, —C(O)OR$^{n5}$ and —C(O)NR$^{q5}$R$^{r5}$, wherein any $(C_3-C_7)$carbocycle, of $Z^4$ is optionally substituted with one or more (e.g., 1, 2, 3, 4 or 5) $Z^{4a}$ or $Z^{4b}$ groups, and wherein any $(C_1-C_8)$alkyl, $(C_2-C_8)$alkenyl and $(C_2-C_8)$alkynyl of $Z^4$ is optionally substituted with one or more (e.g., 1, 2, 3, 4 or 5) $Z^{4a}$ groups;

each $Z^{4a}$ is independently selected from halogen, —CN, —OR$^{n6}$, —OC(O)R$^{p6}$, —OC(O)NR$^{q6}$R$^{r6}$, —SR$^{n6}$, —S(O)R$^{p6}$, —S(O)$_2$OH, —S(O)$_2$R$^{p6}$, —S(O)$_2$NR$^{q6}$R$^{r6}$, —NR$^{q6}$R$^{r6}$, —NR$^{n6}$COR$^{p6}$, —NR$^{n6}$CO$_2$R$^{p6}$, —NR$^{n6}$CONR$^{q6}$R$^{r6}$, —NR$^{n6}$S(O)$_2$R$^{p6}$, —NR$^{n6}$S(O)$_2$R$^{p6}$, —NR$^{n6}$S(O)$_2$NR$^{q6}$R$^{r6}$, NO$_2$, —C(O)R$^{n6}$, —C(O)OR$^{n6}$ and —C(O)NR$^{q6}$R$^{r6}$;

each $Z^{4b}$ is independently selected from $(C_1-C_4)$alkyl, $(C_2-C_4)$alkenyl $(C_2-C_4)$alkynyl and $(C_1-C_4)$haloalkyl;

each $R^{n5}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p5}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q5}$ and $R^{r5}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{n6}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p6}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q6}$ and $R^{r6}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $Z^5$ is independently selected from $(C_1-C_6)$alkyl, halogen, —CN and —OR$^{n7}$, wherein any $(C_1-C_6)$alkyl of $Z^5$ is optionally substituted with one or more (e.g., 1, 2, 3, 4 or 5) halogen; and each $R^{n7}$ is independently selected from H, $(C_1-C_3)$alkyl, $(C_1-C_3)$haloalkyl and $(C_3-C_7)$carbocycle;

or a pharmaceutically acceptable salt thereof.

Embodiment I-2

The compound of Embodiment I-1 which is a compound of formula Ia:

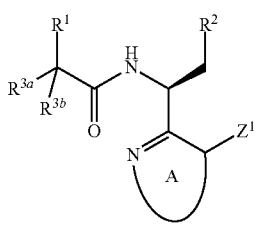

Ia or a pharmaceutically acceptable salt thereof.

Embodiment I-3

The compound of Embodiment I-1 or Embodiment I-1-2 wherein $R^{1a}$ and $R^{3b}$ are each H.

Embodiment I-4

The compound of any one of Embodiments I-1 to I-3 wherein $R^2$ is phenyl or a 5-membered monocyclic-heteroaryl, wherein any phenyl or 5-membered monocyclic-heteroaryl of $R^2$ is optionally substituted with one or more $Z^5$ groups.

Embodiment I-5

The compound of any one of Embodiments I-1 to I-3 wherein $R^2$ is phenyl optionally substituted with one or more $Z^5$ groups.

Embodiment I-6

The compound of any one of Embodiments I-1 to I-5 wherein each $Z^5$ is halogen.

Embodiment I-7

The compound of any one of Embodiments I-1 to I-5 wherein each $Z^5$ is fluoro.

Embodiment I-8

The compound of Embodiment I-1 or Embodiment I-2 wherein $R^2$ is 3,5-difluorophenyl.

Embodiment I-9

The compound of Embodiment I-1 which is a compound of formula Ig:

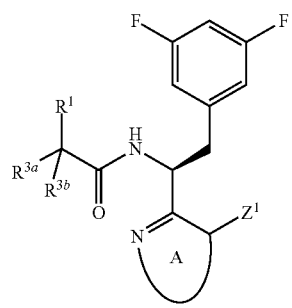

Ig or a pharmaceutically acceptable salt thereof.

Embodiment I-10

The compound of Embodiment I-1 which is a compound of formula Ie:

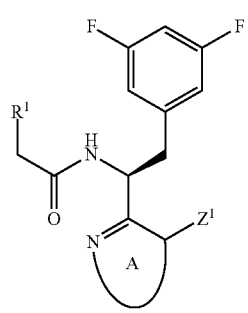

Ie or a pharmaceutically acceptable salt thereof.

Embodiment I-11

The compound of any one of Embodiments I-1 to I-10 wherein A is pyridinyl, pyrimidinyl, pyrazinyl or pyridazinyl, wherein any pyridinyl, pyrimidinyl, pyrazinyl or pyridazinyl of A is substituted with one $Z^1$ group at the position shown, one $Z^2$ group, and optionally substituted with one or more $Z^3$ groups.

Embodiment I-12

The compound of any one of Embodiments I-1 to I-10 wherein A is pyridinyl, wherein any pyridinyl of A is substituted with one $Z^1$ group at the position shown, one $Z^2$ group, and optionally substituted with one or more $Z^3$ groups.

Embodiment I-13

The compound of any one of Embodiments I-1 to I-12 wherein A is substituted with one $Z^1$ group at the position shown and one $Z^2$ group.

Embodiment I-14

The compound of any one of Embodiments I-1 to I-10 wherein A-$Z^1$ is selected from:

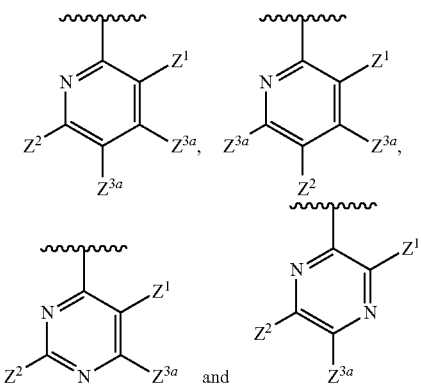

wherein each $Z^{3a}$ is independently selected from H and $Z^3$.

Embodiment I-15

The compound of any one of Embodiments I-1 to I-10 wherein A-$Z^1$ is selected from:

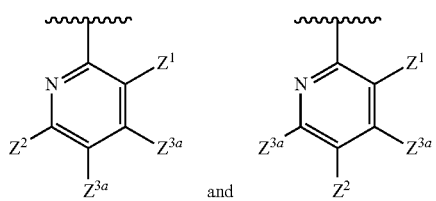

wherein each $Z^{3a}$ is independently selected from H and $Z^3$.

Embodiment I-16

The compound of any one of Embodiments I-1 to I-10 wherein A-$Z^1$ is:

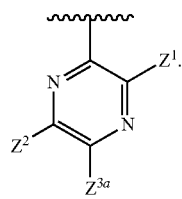

wherein each $Z^{3a}$ is independently selected from H and $Z^3$.

Embodiment I-17

The compound of any one of Embodiments I-1 to I-10 wherein A-$Z^1$ is:

wherein $Z^{3a}$ is selected from H and $Z^3$.

Embodiment I-18

The compound of any one of Embodiments I-1 to I-10 wherein A-$Z^1$ is:

wherein $Z^{3a}$ is selected from H and $Z^3$.

Embodiment I-19

The compound of any one of Embodiments I-14 to I-18 wherein each $Z^{3a}$ is H.

Embodiment I-20

The compound of any one of Embodiments I-1 to I-19 wherein $Z^1$ is selected from phenyl, 5-14 membered heteroaryl and 3-14 membered heterocycle, wherein any phenyl, 5-14 membered heteroaryl and 3-14 membered heterocycle of $Z^1$ is optionally substituted with one or more $Z^{1a}$ or $Z^{1b}$ groups.

Embodiment I-21

The compound of any one of Embodiments I-1 to I-19 wherein $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more $Z^{1a}$ or $Z^{1b}$ groups.

Embodiment I-22

The compound of any one of Embodiments I-1 to I-19 wherein $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle, wherein the 5-6 membered monocyclic-heteroaryl, 8-10 membered bicyclic-heteroaryl, 8-10 membered bicyclic-heterocycle and 9-12 membered tricyclic-heterocycle have 1-11 carbon atoms and 1-5 heteroatoms in the ring system, and wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more $Z^{1a}$ or $Z^{1b}$ groups.

Embodiment I-23

The compound of any one of Embodiments I-1 to I-19 wherein $Z^1$ is selected from 8-10 membered bicyclic-heteroaryl and 8-10 membered bicyclic-heterocycle, wherein any from 8-10 membered bicyclic-heteroaryl and 8-10 membered bicyclic-heterocycle of $Z^1$ is optionally substituted with one or more $Z^{1a}$ or $Z^{1b}$ groups.

Embodiment I-24

The compound of any one of Embodiments I-1 to I-19 wherein $Z^1$ is selected from 8-10 membered bicyclic-heteroaryl and 8-10 membered bicyclic-heterocycle, wherein

491 the 8-10 membered bicyclic-heteroaryl and 8-10 membered bicyclic-heterocycle have 3-9 carbon atoms and 1-5 heteroatoms in the ring system, and wherein any 8-10 membered bicyclic-heteroaryl and 8-10 membered bicyclic-heterocycle of $Z^1$ is optionally substituted with one or more $Z^{1a}$ or $Z^{1b}$ groups.

Embodiment I-25

The compound of any one of Embodiments I-1 to I-19 wherein $Z^1$ is selected from phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl, wherein any phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl of $Z^1$ is optionally substituted with one or more $Z^{1a}$ or $Z^{1b}$ groups.

Embodiment I-26

The compound of any one of Embodiments I-1 to I-19 wherein $Z^1$ is selected from phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydorquinazolin-8-yl, wherein any phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydorquinazolin-8-yl of $Z^1$ is optionally substituted with one or more $Z^{1a}$ or $Z^{1b}$ groups.

Embodiment I-27

The compound of any one of Embodiments I-1 to I-26 wherein each $Z^{1a}$ is independently selected from halogen, —$OR^{n1}$, $NR^{q1}R^{r1}$, and —$C(O)NR^{q1}R^{r1}$

Embodiment I-28

The compound of any one of Embodiments I-1 to I-26 wherein each $Z^{1a}$ is independently selected from halogen and —$C(O)NR^{q1}R^{r1}$.

Embodiment I-29

The compound of any one of Embodiments I-1 to I-26 wherein $R^{n1}$, $R^{q1}$ and $R^{r1}$ are each H.

Embodiment I-30

The compound of any one of Embodiments I-1 to I-19 wherein $Z^1$ is selected from:

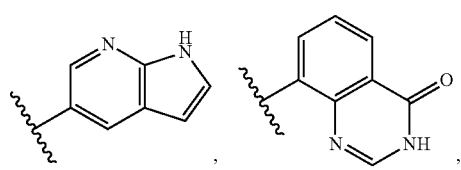

492

-continued

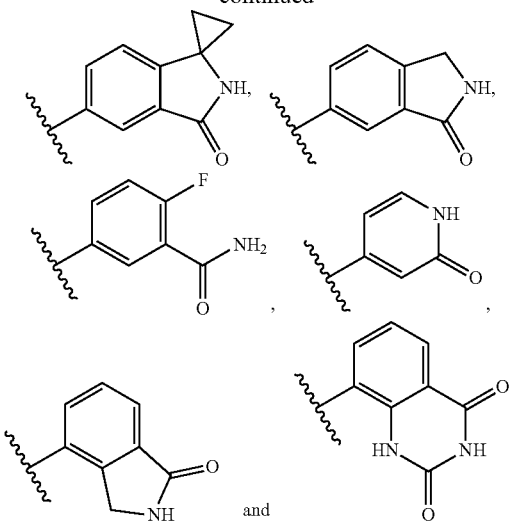

Embodiment I-31

The compound of any one of Embodiments I-1 to I-30 wherein $Z^2$ is selected from $(C_2-C_8)$alkynyl, 6-12 membered aryl, 5-12 membered C-linked-heteroaryl, 3-12 membered C-linked-heterocycle and —$C(O)NR^{q3}R^{r3}$, wherein any 6-12 membered aryl, 5-12 membered C-linked-heteroaryl and 3-12 membered C-linked-heterocycle of $Z^2$ is optionally substituted with one or more $Z^{2b}$ or $Z^{2c}$ groups, and wherein any $(C_2-C_8)$alkynyl of $Z^2$ is optionally substituted with one or more $Z^{2c}$ groups.

Embodiment I-32

The compound of any one of Embodiments I-1 to I-30 wherein $Z^2$ is selected from $(C_2-C_8)$alkynyl, phenyl, 5-6 membered C-linked-monocyclic-heteroaryl, 8-10 membered C-linked-bicyclic-heteroaryl, 8-10 membered C-linked-bicyclic-heterocycle and —$C(O)NR^{q3}R^{r3}$, wherein any phenyl, 5-6 membered C-linked-monocyclic-heteroaryl, 8-10 membered C-linked-bicyclic-heteroaryl and 8-10 membered C-linked-bicyclic-heterocycle of $Z^2$ is optionally substituted with one or more $Z^{2b}$ or $Z^{2c}$ groups, and wherein any $(C_2-C_8)$alkynyl of $Z^2$ is optionally substituted with one or more $Z^{2c}$ groups.

Embodiment I-33

The compound of any one of Embodiments I-1 to I-30 wherein $Z^2$ is selected from $(C_2-C_8)$alkynyl, phenyl, 5-6 membered C-linked-monocyclic-heteroaryl, 8-10 membered C-linked-bicyclic-heteroaryl, 8-10 membered C-linked-bicyclic-heterocycle and —$C(O)NR^{q3}R^{r3}$, wherein the 5-6 membered C-linked-monocyclic-heteroaryl, 8-10 membered C-linked-bicyclic-heteroaryl and 8-10 membered C-linked-bicyclic-heterocycle have 1-9 carbon atoms and 1-4 heteroatoms in the ring system, and wherein any phenyl, 5-6 membered C-linked-monocyclic-heteroaryl, 8-10 membered C-linked-bicyclic-heteroaryl, 8-10 membered and C-linked-bicyclic-heterocycle of $Z^2$ is optionally substituted with one or more $Z^{2b}$ or $Z^{2c}$ groups, and wherein any $(C_2-C_8)$alkynyl of $Z^2$ is optionally substituted with one or more $Z^{2c}$ groups.

Embodiment I-34

The compound of any one of Embodiments I-1 to I-30 wherein $Z^2$ is selected from 4-methylpentynyl, phenyl, pyridinyl, 1H-2-oxo-pyridinyl, triazolyl, 1-oxoisoindolinyl, 1H-pyrrolo[2,3-b]pyridinyl and —C(O)NR$^{q3}$R$^{r3}$, wherein any phenyl, pyridinyl, 2-oxopyridinyl, triazolyl, 1-oxoisoindolinyl and 1H-pyrrolo[2,3-b]pyridinyl of $Z^2$ is optionally substituted with one or more $Z^{2b}$ or $Z^{2c}$ groups, and wherein any 4-methylpentynyl of $Z^2$ is optionally substituted with one or more $Z^2$ groups.

Embodiment I-35

The compound of any one of Embodiments I-1 to I-30 wherein $Z^2$ is selected from 4-methylpentyn-1-yl, phenyl, pyridin-4-yl, 1H-2-oxo-pyridin-2-yl, triazol-4-yl, 1-oxoisoindolin-6-yl, 1H-pyrrolo[2,3-b]pyridine-5-yl and —C(O)NR$^{q3}$R$^{r3}$, wherein any phenyl, pyridin-4-yl, 2-hydroxypyridin-2-yl, triazol-4-yl, 1-oxoisoindolin-6-yl and 1H-pyrrolo[2,3-b]pyridine-5-yl of $Z^2$ is optionally substituted with one or more $Z^{2b}$ or $Z^{2c}$ groups, and wherein any 4-methylpentyn-1-yl of $Z^2$ is optionally substituted with one or more $Z^{2c}$ groups.

Embodiment I-36

The compound of any one of Embodiments I-1 to I-35 wherein $Z^2$ is optionally substituted with one or more $Z^{2c}$ groups.

Embodiment I-37

The compound of any one of Embodiments I-1 to I-36 wherein R$^{q3}$ and R$^{r3}$ are each H.

Embodiment I-38

The compound of any one of Embodiments I-1 to I-37 wherein each $Z^{2c}$ is independently selected from halogen, —OR$^{n4}$ and —C(O)NR$^{q4}$R$^{r4}$

Embodiment I-39

The compound of any one of Embodiments I-1 to I-38 wherein R$^{n4}$ is H or methyl, and R$^{q4}$ and R$^{r4}$ are each H.

Embodiment I-40

The compound of any one of Embodiments I-1 to I-30 wherein $Z^2$ is selected from:

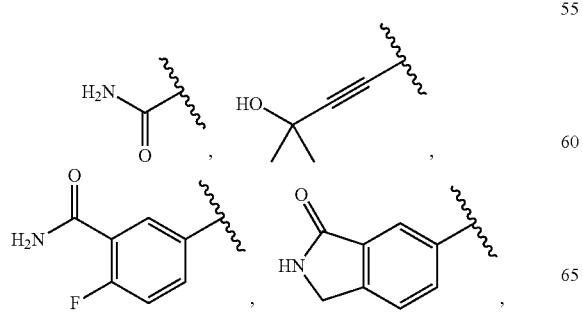

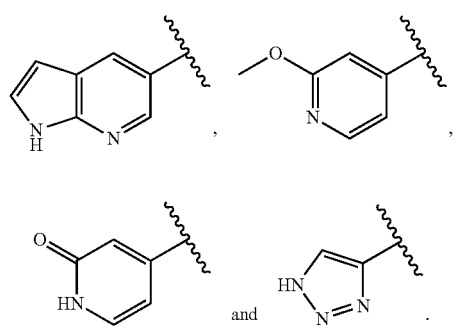

and

Embodiment I-41

The compound of any one of Embodiments I-1 to I-10 wherein A-$Z^1$ is selected from:

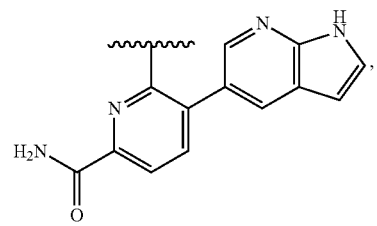

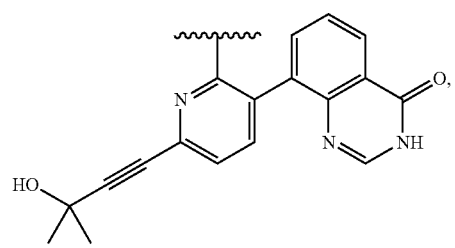

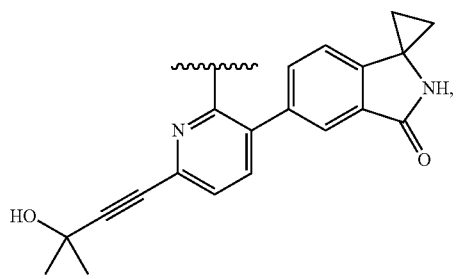

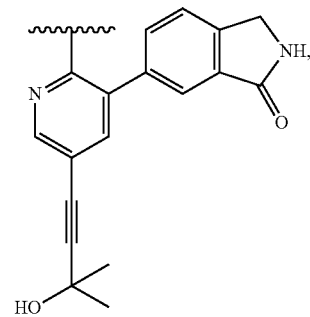

495
-continued
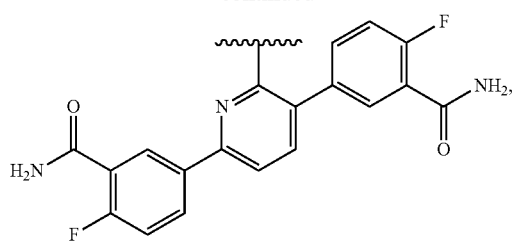
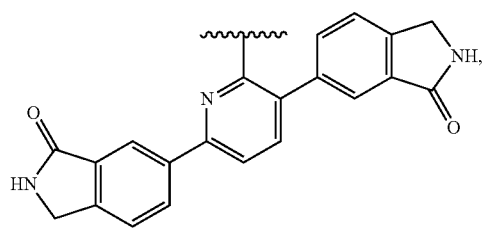
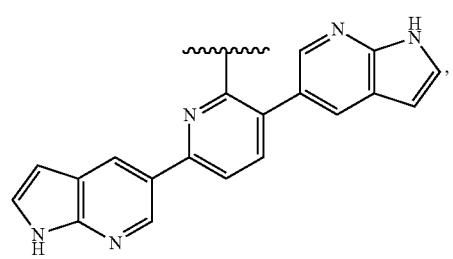
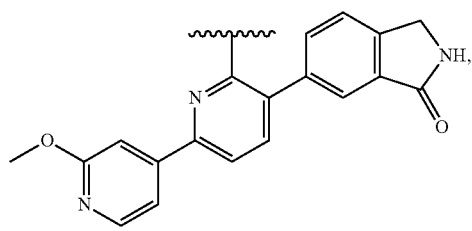
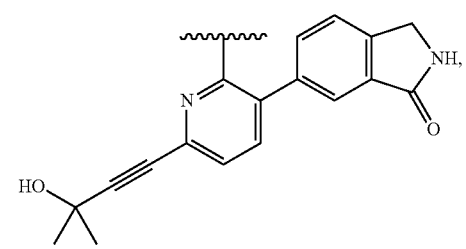
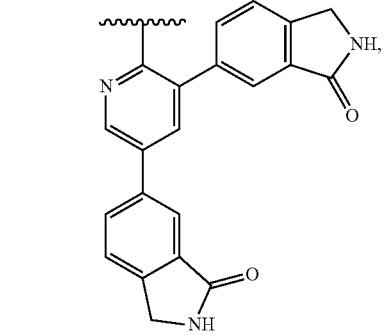
496
-continued
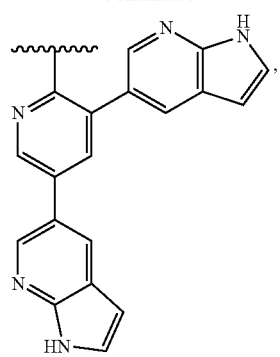
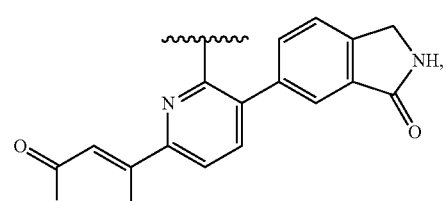
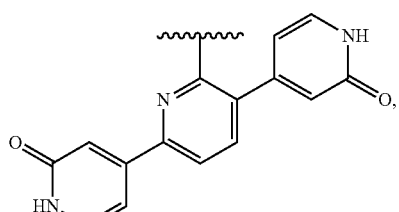
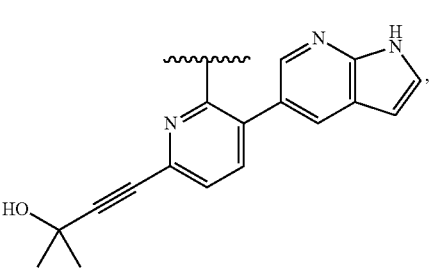
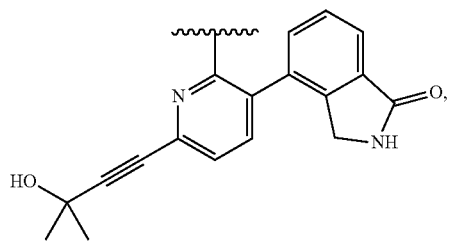
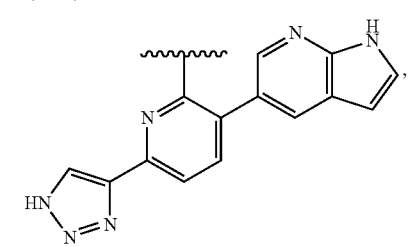

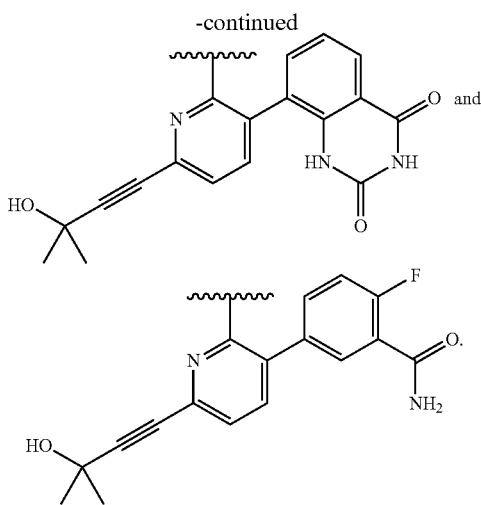

Embodiment I-42

The compound of any one of Embodiments I-1 to I-41 wherein $R^1$ is a 5-12 membered heteroaryl, wherein any 5-12 membered heteroaryl of $R^1$ is optionally substituted with one or more $Z^4$ groups.

Embodiment I-42

The compound of any one of Embodiments I-1 to I-41 wherein $R^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of $R^1$ is optionally substituted with one or more $Z^4$ groups.

Embodiment I-44

The compound of any one of Embodiments I-1 to I-41 wherein $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl have 4-10 carbon atoms and 1-5 heteroatoms in the ring system, and wherein any 8-12 membered bicyclic-heteroaryl or 8-12 membered tricyclic-heteroaryl of $R^1$ is optionally substituted with one or more $Z^4$ groups.

Embodiment I-45

The compound of any one of Embodiments I-1 to I-41 wherein $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl contains at least one partially unsaturated ring, and wherein any 8-12 membered bicyclic-heteroaryl or 8-12 membered tricyclic-heteroaryl of $R^1$ is optionally substituted with one or more (e.g., 1, 2, 3, 4 or 5) $Z^4$ groups.

Embodiment I-46

The compound of any one of Embodiments I-1 to I-41 wherein $R^1$ has the following formula IIb:

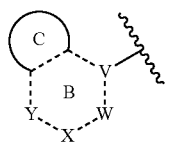

wherein:
C together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with one or more (e.g. 1, 2, 3, 4 or 5) $Z^4$ groups; and
B is a 5 or 6 membered monocyclic-heteroaryl having 1, 2 or 3 nitrogen atoms;
V is C or N;
W is $CZ^{4c}$, $NZ^{4c}$ or N;
X is $CZ^{4c}$, $NZ^{4c}$ or N;
Y is $CZ^{4c}$, N or absent;
the dashed bonds are selected from single bonds and double bonds, wherein the dashed bonds, V, W, X and Y are selected so that the 5 or 6 membered monocyclic-heteroaryl B is aromatic; and
each $Z^{4c}$ is independently selected from H or $Z^4$.

Embodiment I-47

The compound of any one of Embodiments I-1 to I-41 wherein $R^1$ has the following formula IId:

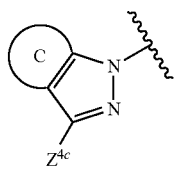

wherein:
C together with the two carbon atoms to which it is attached forms a 3-7 membered monocyclic-carbocycle, 5-9 membered bicyclic-carbocycle, 3-7 membered monocyclic-heterocycle or 5-9 membered bicyclic heterocycle, wherein any 3-7 membered monocyclic-carbocycle, 5-9 membered bicyclic-carbocycle, 3-7 membered monocyclic-heterocycle or 5-9 membered bicyclic heterocycle of C is optionally substituted with one or more (e.g. 1, 2, 3, 4 or 5) $Z^4$ groups; and
each $Z^{4c}$ is independently selected from H or $Z^4$.

Embodiment I-48

The compound of any one of Embodiments I-1 to I-41 wherein $R^1$ is selected from 3b,4,4a,5-tetrahydro-1H-cyclopropa[3,4]cyclopenta[1,2-c]pyrazolyl and 4,5,6,7-tetrahydro-indazolyl, wherein any 3b,4,4a,5-tetrahydro-1H-cyclopropa[3,4]cyclopenta[1,2-c]pyrazolyl and 4,5,6,7-tetrahydro-indazolyl of $R^1$ is optionally substituted with one or more $Z^4$ groups.

Embodiment I-49

The compound of any one of Embodiments I-1 to I-41 wherein $R^1$ is selected from 3b,4,4a,5-tetrahydro-1H-cyclopropa[3,4]cyclopenta[1,2-c]pyrazol-1-yl and 4,5,6,7-tetrahydro-indazol-1-yl, wherein any 3b,4,4a,5-tetrahydro-1H-cyclopropa[3,4]cyclopenta[1,2-c]pyrazol-1-yl and 4,5,6,7-tetrahydro-indazol-1-yl of $R^1$ is optionally substituted with one or more $Z^4$ groups.

Embodiment I-50

The compound of any one of Embodiments I-1 to I-49 wherein each $Z^4$ is independently selected from $(C_1-C_6)$alkyl and halogen, wherein any $(C_1-C_6)$alkyl of $Z^4$ is optionally substituted with one or more halogen.

Embodiment I-51

The compound of any one of Embodiments I-1 to I-49 wherein each $Z^4$ is independently selected from fluoro, trifluoromethyl and difluoromethyl.

Embodiment I-52

The compound of any one of Embodiments I-1 to I-41 wherein $R^1$ is selected from:

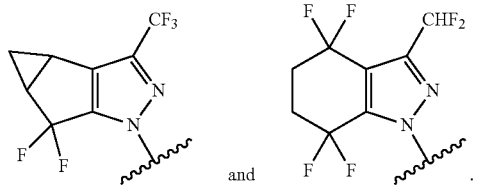 [SMILES: *n1nc(C(F)(F)F)c2c1C(F)(F)C1CC21 ; *n1nc(C(F)F)c2c1C(F)(F)CCC2(F)F]

Embodiment I-53

The compound of any one of Embodiments I-1 to I-41 wherein $R^1$ is selected from:

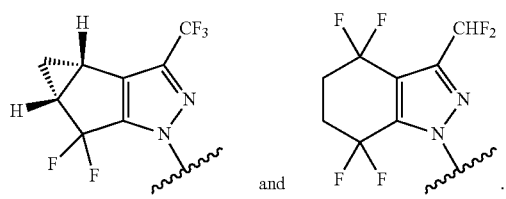 [SMILES: *n1nc(C(F)(F)F)c2c1C(F)(F)[C@@H]1C[C@H]21 ; *n1nc(C(F)F)c2c1C(F)(F)CCC2(F)F]

Embodiment I-54

The compound of Embodiment I-1 selected from:

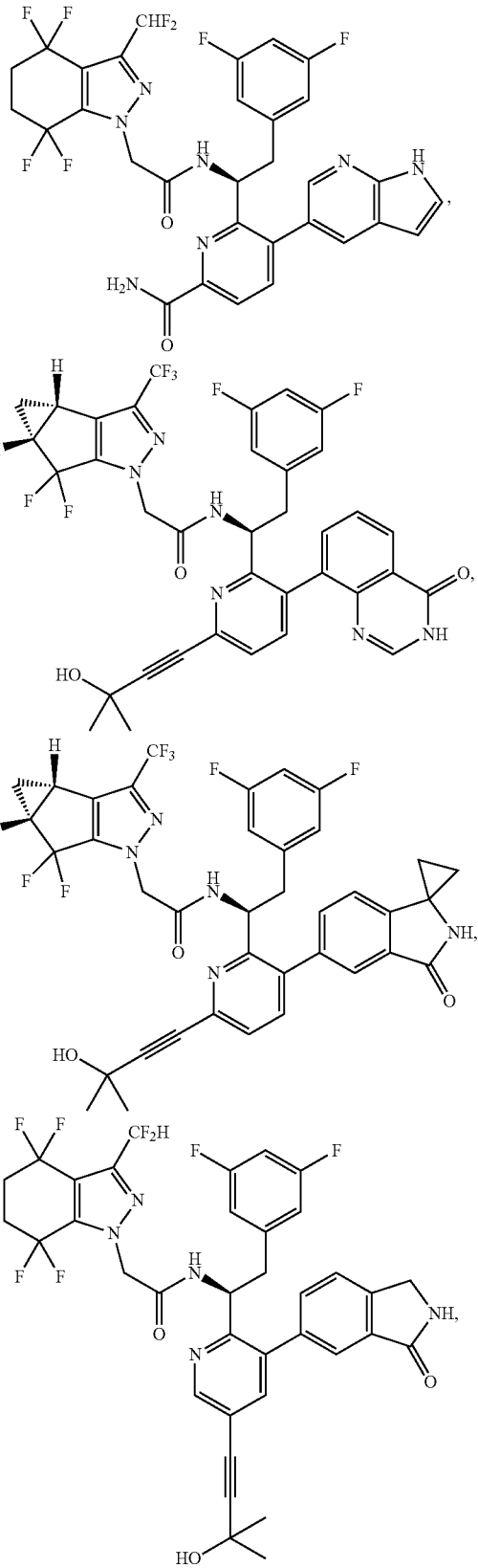

501
-continued
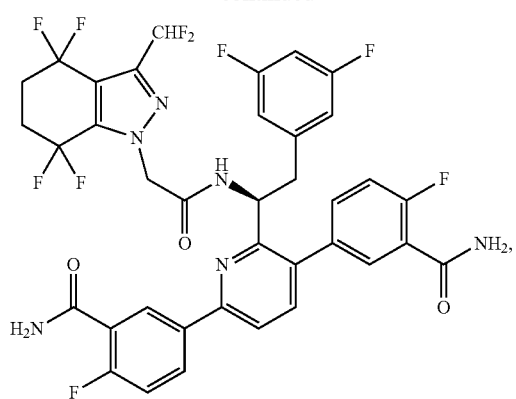
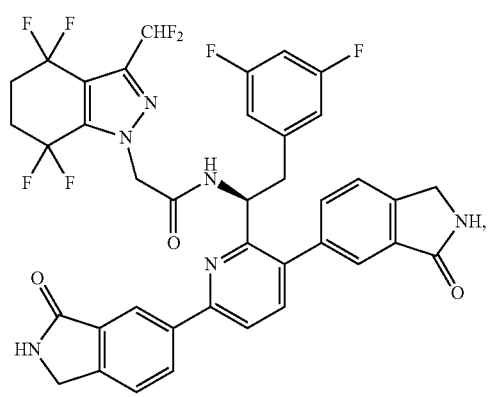
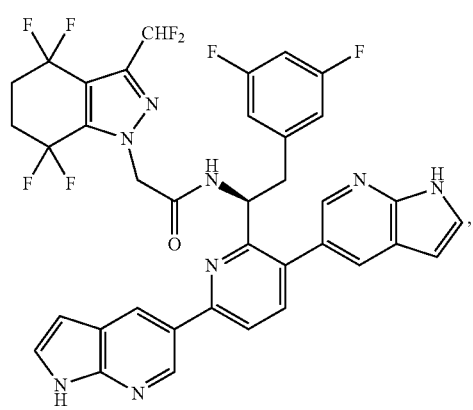
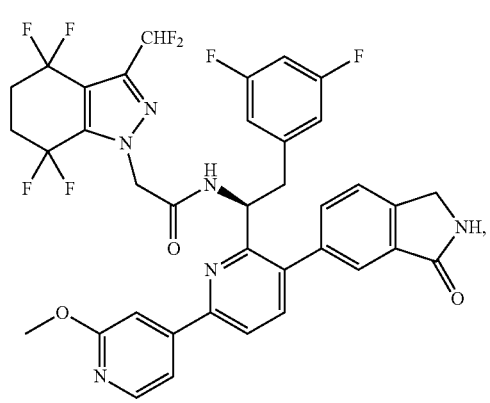
502
-continued
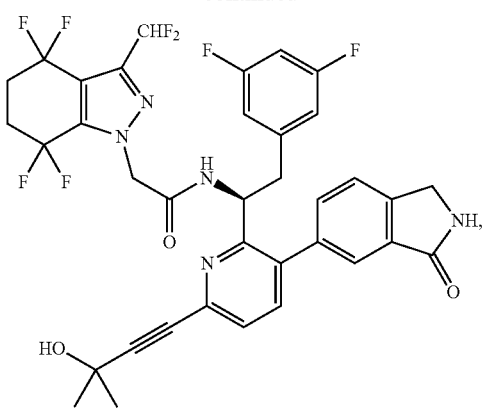
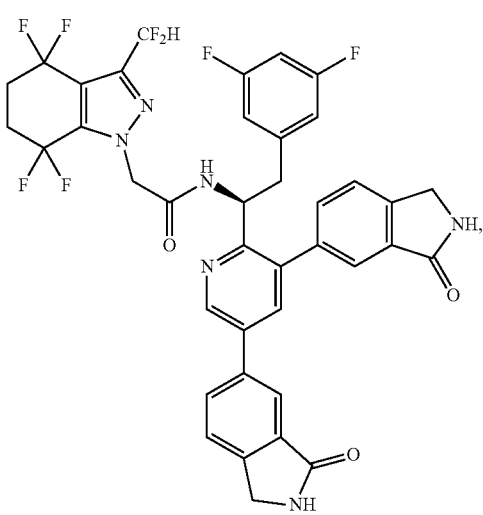
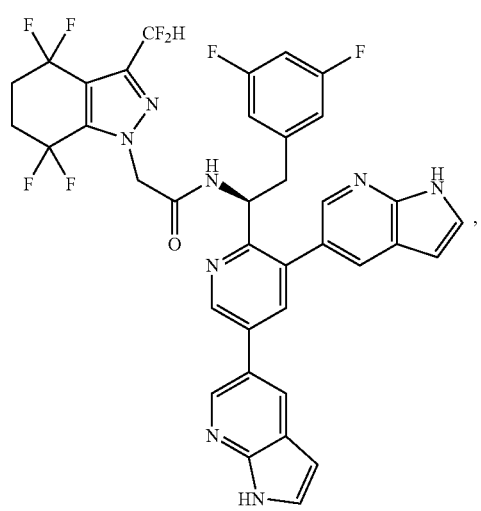

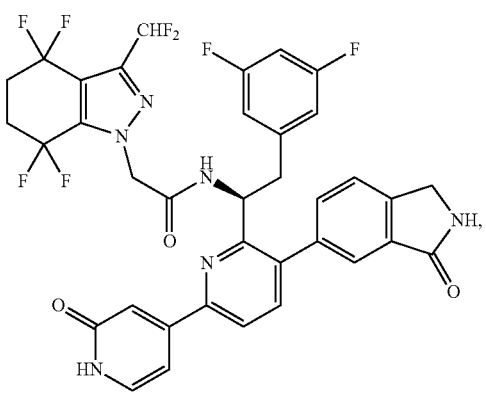

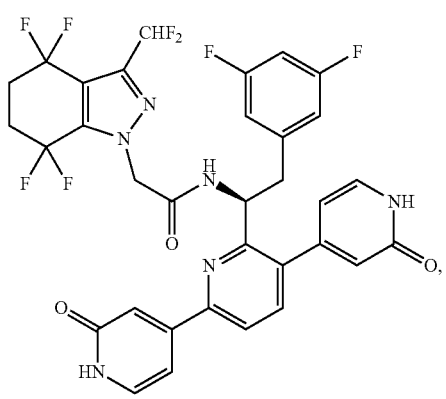

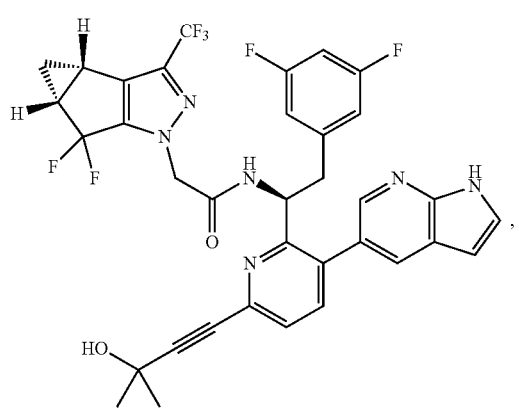

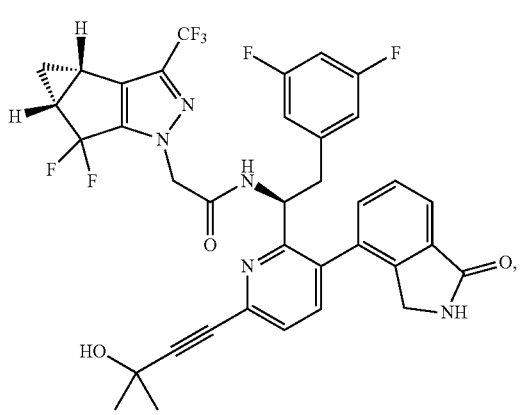

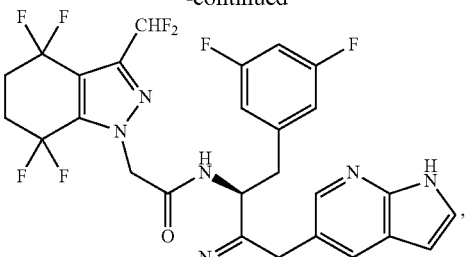

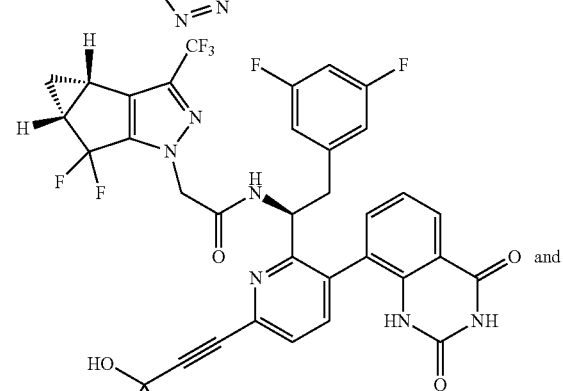

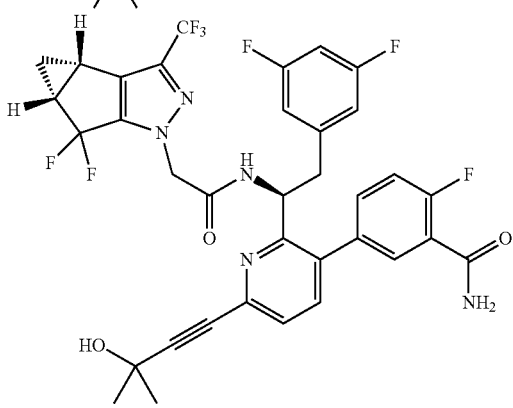

and pharmaceutically acceptable salts thereof.

Embodiment I-55

A pharmaceutical composition comprising a compound of formula I as described in any one of Embodiments I-1 to I-54, or a pharmaceutically acceptable salt thereof, and a pharmaceutically acceptable carrier.

Embodiment I-56

A method for treating a Retroviridae virus infection in a mammal comprising administering a therapeutically effective amount of a compound of any one of Embodiments I-1 to I-54, or a pharmaceutically acceptable salt thereof, to the mammal.

Embodiment I-57

The method of claim 56 wherein the Retroviridae virus infection is an HIV virus infection.

Embodiment I-58

A method for treating an HIV infection in a mammal comprising administering to the mammal in need thereof a therapeutically effective amount of a compound of formula I as described in any one of Embodiments I-1 to I-54, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

Embodiment I-59

A compound of formula I as described in any of Embodiments I-1 to I-54, or a pharmaceutically acceptable salt thereof for use in medical therapy.

Embodiment I-60

A compound of formula I as described in any one of Embodiments I-1 to I-54 or a pharmaceutically acceptable salt thereof, for the prophylactic or therapeutic treatment of a Retroviridae virus infection or an HIV virus infection.

Embodiment I-61

The use of a compound as described in any one of Embodiments I-1 to I-54 or a pharmaceutically acceptable salt thereof, for the manufacture of a medicament for treating a Retroviridae virus infection or an HIV virus infection in a mammal.

Embodiment I-62

A compound or method as described herein
Also provided below are certain embodiments.

Embodiment II-1

A compound of formula I:

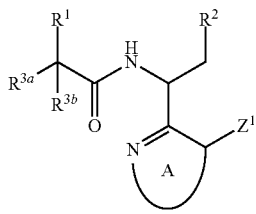

I wherein:

A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with one or more (e.g., 1 or 2) $Z^3$ groups;

$R^1$ is 6-12 membered aryl, 5-12 membered heteroaryl or 3-12 membered heterocycle, wherein any 6-12 membered aryl, 5-12 membered heteroaryl or 3-12 membered heterocycle of $R^1$ is optionally substituted with one or more (e.g., 1, 2, 3, 4 or 5) $Z^4$ groups;

$R^2$ is phenyl, 5-membered monocyclic-heteroaryl, 6-membered monocyclic-heteroaryl or $(C_3-C_7)$carbocycle, wherein any phenyl, 5-membered monocyclic-heteroaryl, 6-membered monocyclic-heteroaryl or $(C_3-C_7)$carbocycle of $R^2$ is optionally substituted with one or more (e.g., 1, 2, 3, 4 or 5) $Z^5$ groups;

each $R^{3a}$ and $R^{3b}$ is independently selected from H, halogen, $(C_1-C_3)$alkyl and $(C_1-C_3)$haloalkyl, or $R^{3a}$ is selected from H, $(C_1-C_3)$alkyl and $(C_1-C_3)$haloalkyl and $R^{3b}$ is selected from —OH and —CN;

$Z^1$ is selected from 6-12 membered aryl, 5-14 membered heteroaryl and 3-14 membered heterocycle, wherein any 6-12 membered aryl, 5-14 membered heteroaryl and 3-14 membered heterocycle of $Z^1$ is optionally substituted with one or more (e.g., 1, 2, 3, 4 or 5) $Z^{1a}$ or $Z^b$;

each $Z^{1a}$ is independently selected from $(C_3-C_7)$carbocycle, 6-12 membered aryl, 5-12 membered heteroaryl, 3-12 membered heterocycle, halogen, —CN, —$OR^{n1}$, —OC(O)$R^{p1}$, —OC(O)$NR^{q1}R^{r1}$, —$SR^{n1}$, —S(O)$R^{p1}$, —S(O)$_2$OH, —S(O)$_2R^{p1}$, —S(O)$_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2R^{p1}$, —$NR^{n1}S(O)_2NR^{q1}R^{r1}$, $NO_2$, —C(O)$R^{n1}$, —C(O)$OR^{n1}$, —C(O)$NR^{q1}R^{r1}$ and —S(O)$_2NR^{n1}COR^{p1}$, wherein any $(C_3-C_7)$carbocycle, 6-12 membered aryl, 5-12 membered heteroaryl and 3-12 membered heterocycle of $Z^{1a}$ is optionally substituted with one or more (e.g., 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with one or more (e.g., 1, 2, 3, 4 or 5) $Z^{1c}$ groups;

each $Z^{1c}$ is independently selected from $(C_3-C_7)$carbocycle, phenyl, 5-6 membered monocyclic-heteroaryl, 3-7 membered heterocycle, halogen, —CN, —$OR^{n2}$, —OC(O)$R^{p2}$, —OC(O)$NR^{q2}R^{r2}$, —$SR^{n2}$, —S(O)$R^{p2}$, —S(O)$_2$OH, —S(O)$_2R^{p2}$, —S(O)$_2NR^{n2}R^{r2}$, —$NR^{q2}R^{r2}$, —$NR^{n2}COR^{p2}$, —$NR^{n2}CO_2R^{p2}$, —$NR^{n2}CONR^{q2}R^{r2}$, —$NR^{n2}S(O)_2R^{p2}$, —$NR^{n2}S(O)_2OR^{p2}$, —$NR^{n2}S(O)_2NR^{q2}R^{r2}$, $NO_2$, —C(O)$R^{n2}$, —C(O)$OR^{n2}$, —C(O)$NR^{q2}R^{r2}$, halophenyl, 5-6 membered haloheteroaryl, 3-7 membered haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R^{n1}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{n1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{n1}$ is optionally substituted with one or more (e.g., 1, 2, 3, 4 or 5) $Z^{1c}$ groups;

each $R^{p1}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{p1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{p1}$ is optionally substituted with one or more (e.g., 1, 2, 3, 4 or 5) $Z^{1c}$ groups;

$R^{q1}$ and $R^{r1}$ are each independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{q1}$ or $R^{r1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{q1}$ or $R^{r1}$ is optionally substituted with one or more (e.g., 1, 2, 3, 4 or 5) $Z^{1c}$ groups, or $R^{q1}$ and $R^{r1}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{1c}$ or $Z^{1d}$ groups;

each $R^{n2}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl;

each $R^{p2}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl;

$R^{q2}$ and $R^{r2}$ are each independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1-C_8)$haloalkyl and $(C_1-C_8)$heteroalkyl, or $R^{q2}$ and $R^{r2}$ together with the nitrogen to which they are attached form a 5, 6 or 7-membered heterocycle;

$Z^2$ is selected from $(C_2-C_8)$alkenyl, $(C_2-C_8)$alkynyl, 6-12 membered aryl, 5-12 membered C-linked-heteroaryl, 3-12 membered C-linked-heterocycle, —C(O)$R^{n3}$ and —C(O)NR$^{q3}$R$^{r3}$, wherein any 6-12 membered aryl, 5-12 membered C-linked-heteroaryl and 3-12 membered C-linked-heterocycle of $Z^2$ is optionally substituted with one or more (e.g., 1, 2, 3, 4 or 5) $Z^{2b}$ or $Z^{2c}$ groups, and wherein any $(C_2-C_8)$alkenyl and $(C_2-C_8)$alkynyl of $Z^2$ is optionally substituted with one or more (e.g., 1, 2, 3, 4, or 5) $Z^{2c}$ groups;

each $Z^{2a}$ is independently selected from $(C_3-C_7)$carbocycle, 6-12 membered aryl, 5-12 membered heteroaryl, 3-12 membered heterocycle, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$, wherein any $(C_3-C_7)$carbocycle, 6-12 membered aryl, 5-12 membered heteroaryl and 3-12 membered heterocycle of $Z^{2a}$ is optionally substituted with one or more (e.g., 1, 2, 3, 4 or 5) $Z^{2b}$ or $Z^{2c}$ groups;

each $Z^{2b}$ is independently selected from $(C_1-C_4)$alkyl, $(C_1-C_4)$heteroalkyl and $(C_1-C_4)$haloalkyl;

each $Z^{2c}$ is independently selected from halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^4$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$;

each $R^{n3}$ is independently selected from H, $(C_1-C_4)$alkyl, $(C_2-C_4)$alkenyl, $(C_3-C_7)$carbocycle, 3-12 membered heterocycle, 5-12 membered heteroaryl and 6-12 membered aryl, wherein any $(C_3-C_7)$carbocycle, 3-12 membered heterocycle, 5-12 membered heteroaryl and 6-12 membered aryl of $R^{n3}$ is optionally substituted with one or more (e.g., 1, 2, 3, 4 or 5) $Z^{2b}$ or $Z^{2c}$ groups, and wherein any $(C_1-C_4)$alkyl, $(C_2-C_4)$alkenyl and $(C_2-C_4)$alkynyl of $R^{n3}$ is optionally substituted with one or more (e.g., 1, 2, 3, 4 or 5) $Z^{2a}$ groups;

$R^{q3}$ and $R^{r3}$ are each independently selected from H, $(C_1-C_4)$alkyl, $(C_2-C_4)$alkenyl, $(C_3-C_7)$carbocycle, 3-12 membered heterocycle, 5-12 membered heteroaryl and 6-12 membered aryl, wherein any $(C_3-C_7)$carbocycle, 3-12 membered heterocycle, 5-12 membered heteroaryl and 6-12 membered aryl of $R^{q3}$ or $R^{r3}$ is optionally substituted with one or more (e.g., 1, 2, 3, 4 or 5) $Z^{2b}$ or $Z^{2c}$ groups, and wherein any $(C_1-C_4)$alkyl and $(C_2-C_4)$alkenyl of $R^{q3}$ or $R^{r3}$ is optionally substituted with one or more (e.g., 1, 2, 3, 4 or 5) $Z^{2a}$ groups, or $R^{q3}$ and $R^{r3}$ together with the nitrogen to which they are attached form a heterocycle or heteroaryl, wherein the heterocycle or heteroaryl is optionally substituted with one or more (e.g., 1, 2, 3, 4 or 5) $Z^{2b}$ or $Z^{2c}$ groups;

each $R^{n4}$ is independently selected from H, $(C_1-C_4)$alkyl, $(C_2-C_8)$alkenyl, $(C_2-C_8)$alkynyl, $(C_1-C_4)$haloalkyl and $(C_1-C_4)$heteroalkyl;

each $R^{p4}$ is independently selected from $(C_1-C_8)$alkyl, $(C_2-C_4)$alkenyl, $(C_2-C_4)$alkynyl, $(C_1-C_4)$haloalkyl and $(C_1-C_4)$heteroalkyl;

$R^{q4}$ and $R^{r4}$ are each independently selected from H, $(C_1-C_4)$alkyl, $(C_2-C_4)$alkenyl, $(C_2-C_4)$alkynyl, $(C_1-C_4)$haloalkyl and $(C_1-C_4)$heteroalkyl;

each $Z^3$ is independently selected from halogen, $(C_1-C_4)$alkyl, —OH, —CN, $(C_1-C_4)$heteroalkyl and $(C_1-C_4)$haloalkyl;

each $Z^4$ is independently selected from $(C_1-C_8)$alkyl, $(C_2-C_8)$alkenyl, $(C_2-C_8)$alkynyl, $(C_3-C_7)$carbocycle, halogen, —CN, —OR$^{n5}$, —OC(O)R$^{p5}$, —OC(O)NR$^{q5}$R$^{p5}$, —SR$^{n5}$, —S(O)R$^{p5}$, —S(O)$_2$OH, —S(O)$_2$R$^{p5}$, —S(O)$_2$NR$^{q5}$R$^{r5}$, —NR$^{q5}$R$^{r5}$, —NR$^{n5}$COR$^{p5}$, —NR$^{n5}$CO$_2$R$^{p5}$, —NR$^{n5}$CONR$^{q5}$R$^{r5}$, —NR$^{n5}$S(O)$_2$R$^{p5}$, —NR$^{n5}$S(O)$_2$OR$^5$, —NR$^{n5}$S(O)$_2$NR$^{q5}$R$^5$, NO$_2$, —C(O)R$^{n5}$, —C(O)OR$^{n5}$ and —C(O)NR$^{q5}$R$^{r5}$, wherein any $(C_3-C_7)$carbocycle, of $Z^4$ is optionally substituted with one or more (e.g., 1, 2, 3, 4 or 5) $Z^{4a}$ or $Z^{4b}$ groups, and wherein any $(C_1-C_8)$alkyl, $(C_2-C_8)$alkenyl and $(C_2-C_8)$alkynyl of $Z^4$ is optionally substituted with one or more (e.g., 1, 2, 3, 4 or 5) $Z^{4a}$ groups;

each $Z^{4a}$ is independently selected from halogen, —CN, —OR$^{n6}$, —OC(O)R$^{p6}$, —OC(O)NR$^{q6}$R$^{r6}$, —SR$^{n6}$, —S(O)R$^{p6}$, —S(O)$_2$OH, —S(O)$_2$R$^{p6}$, —S(O)$_2$NR$^{q6}$R$^{r6}$, —NR$^{q6}$R$^{r6}$, —NR$^{n6}$COR$^{p6}$, —NR$^{n6}$CO$_2$R$^{p6}$, —NR$^{n6}$CONR$^{q6}$R$^{r6}$, —NR$^{n6}$S(O)$_2$R$^{p6}$, —NR$^{n6}$S(O)$_2$OR$^{p6}$, —NR$^{n6}$S(O)$_2$NR$^{q6}$R$^{r6}$, NO$_2$, —C(O)R$^{n6}$, —C(O)OR$^{n6}$ and —C(O)NR$^{q6}$R$^{r6}$;

each $Z^{4b}$ is independently selected from $(C_1-C_4)$alkyl, $(C_2-C_4)$alkenyl $(C_2-C_4)$alkynyl and $(C_1-C_4)$haloalkyl;

each $R^{n5}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p5}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q5}$ and $R^{r5}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{n6}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p6}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q6}$ and $R^{r6}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $Z^5$ is independently selected from $(C_1-C_6)$alkyl, halogen, —CN and —$OR^{n7}$, wherein any $(C_1-C_6)$alkyl of $Z^5$ is optionally substituted with one or more (e.g., 1, 2, 3, 4 or 5) halogen; and each $R^{n7}$ is independently selected from H, $(C_1-C_3)$alkyl, $(C_1-C_3)$haloalkyl and $(C_3-C_7)$carbocycle;

or a pharmaceutically acceptable salt thereof.

Embodiment II-2

The compound of Embodiment II-1 which is a compound of formula Ia:

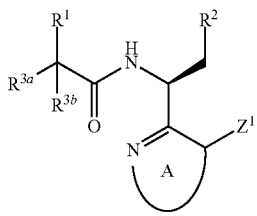

Ia or a pharmaceutically acceptable salt thereof.

Embodiment II-3

The compound of Embodiment II-1 or Embodiment II-2 wherein $R^{1a}$ and $R^{3b}$ are each H.

Embodiment II-4

The compound of any one of Embodiments II-1-3 wherein $R^2$ is phenyl or a 5-membered monocyclic-heteroaryl, wherein any phenyl or 5-membered monocyclic-heteroaryl of $R^2$ is optionally substituted with one or more $Z^5$ groups.

Embodiment II-5

The compound of any one of Embodiments II-1 to 11-3 wherein $R^2$ is phenyl optionally substituted with one or more $Z^5$ groups.

Embodiment II-6

The compound of any one of Embodiments II-1 to II-5 wherein each $Z^5$ is halogen.

Embodiment II-7

The compound of any one of Embodiments II-1 to II-5 wherein each $Z^5$ is fluoro.

Embodiment II-8

The compound of Embodiment II-1 or Embodiment II-2 wherein $R^2$ is 3,5-difluorophenyl.

Embodiment II-9

The compound of Embodiment II-1 which is a compound of formula Ig:

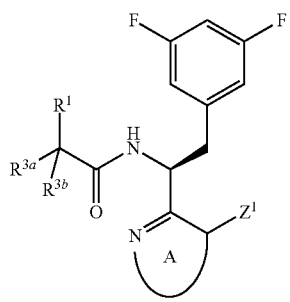

Ig or a pharmaceutically acceptable salt thereof.

Embodiment II-10

The compound of Embodiment II-1 which is a compound of formula Ie:

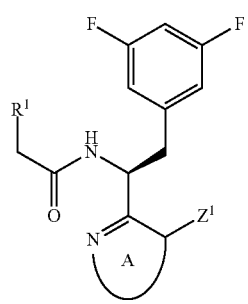

Ie or a pharmaceutically acceptable salt thereof.

Embodiment II-11

The compound of any one of Embodiments II-1 to II-10 wherein A is pyridinyl, pyrimidinyl, pyrazinyl or pyridazinyl, wherein any pyridinyl, pyrimidinyl, pyrazinyl or pyridazinyl of A is substituted with one $Z^1$ group at the position shown, one $Z^2$ group, and optionally substituted with one or more $Z^3$ groups.

Embodiment II-12

The compound of any one of Embodiments II-1 to II-10 wherein A is pyridinyl, wherein any pyridinyl of A is substituted with one $Z^1$ group at the position shown, one $Z^2$ group, and optionally substituted with one or more $Z^3$ groups.

Embodiment II-13

The compound of any one of Embodiments II-1 to II-12 wherein A is substituted with one $Z^1$ group at the position shown and one $Z^2$ group.

Embodiment II-14

The compound of any one of Embodiments II-1 to II-10 wherein A-$Z^1$ is selected from:

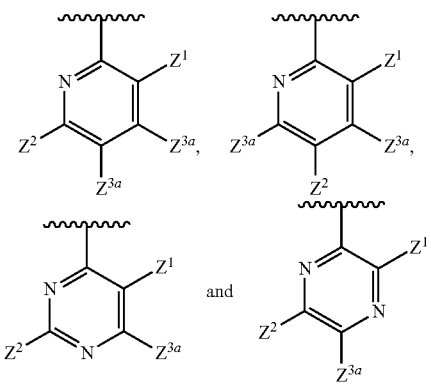

wherein each $Z^{1a}$ is independently selected from H and $Z^3$.

Embodiment II-15

The compound of any one of Embodiments II-1 to II-10 wherein A-$Z^1$ is selected from:

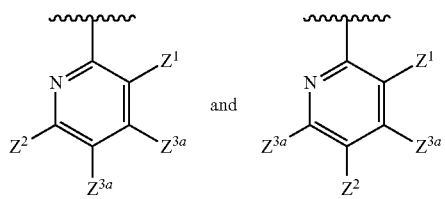

wherein each $Z^{3a}$ is independently selected from H and $Z^3$.

Embodiment II-16

The compound of any one of Embodiments II-1 to II-10 wherein A-$Z^1$ is:

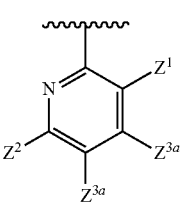

wherein each $Z^{3a}$ is independently selected from H and $Z^3$.

Embodiment II-17

The compound of any one of Embodiments II-1 to II-10 wherein A-$Z^1$ is:

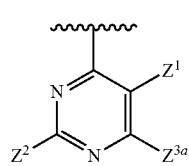

wherein $Z^{3a}$ is selected from H and $Z^3$.

Embodiment II-18

The compound of any one of Embodiments II-1 to II-10 wherein A-$Z^1$ is:

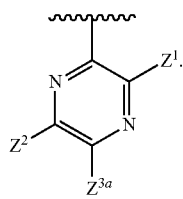

wherein $Z^{3a}$ is selected from H and $Z^3$.

Embodiment II-19

The compound of any one of Embodiments II-14 to II-18 wherein each $Z^3$a is H.

Embodiment II-20

The compound of any one of Embodiments II-1 to II-19 wherein $Z^1$ is selected from phenyl, 5-14 membered heteroaryl and 3-14 membered heterocycle, wherein any phenyl, 5-14 membered heteroaryl and 3-14 membered heterocycle of $Z^1$ is optionally substituted with one or more $Z^{1a}$ or $Z^{1b}$ groups.

Embodiment II-21

The compound of any one of Embodiments II-1 to II-19 wherein $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more $Z^{1a}$ or $Z^{1b}$ groups.

Embodiment II-22

The compound of any one of Embodiments II-1 to II-19 wherein $Z^1$ is selected from phenyl, 5-6 membered monocyclic-heteroaryl, 8-10 membered bicyclic-heteroaryl, 8-10 membered bicyclic-heterocycle and 9-12 membered tricyclic-heterocycle, wherein the 5-6 membered monocyclic-heteroaryl, 8-10 membered bicyclic-heteroaryl, 8-10 membered bicyclic-heterocycle and 9-12 membered tricyclic-heterocycle have 1-11 carbon atoms and 1-5 heteroatoms in the ring system, and wherein any phenyl, 5-6 membered monocyclic-heteroaryl, 8-10 membered bicyclic-heteroaryl, 8-10 membered bicyclic-heterocycle and 9-12 membered tricyclic-heterocycle of $Z^1$ is optionally substituted with one or more $Z^{1a}$ or $Z^{1b}$ groups.

Embodiment II-23

The compound of any one of Embodiments II-1 to II-19 wherein $Z^1$ is selected from 8-10 membered bicyclic-heteroaryl and 8-10 membered bicyclic-heterocycle, wherein any from 8-10 membered bicyclic-heteroaryl and 8-10 membered bicyclic-heterocycle of $Z^1$ is optionally substituted with one or more $Z^{1a}$ or $Z^{1b}$ groups.

Embodiment II-24

The compound of any one of Embodiments II-1 to II-19 wherein $Z^1$ is selected from 8-10 membered bicyclic-heteroaryl and 8-10 membered bicyclic-heterocycle, wherein the 8-10 membered bicyclic-heteroaryl and 8-10 membered bicyclic-heterocycle have 3-9 carbon atoms and 1-5 heteroatoms in the ring system, and wherein any 8-10 membered bicyclic-heteroaryl and 8-10 membered bicyclic-heterocycle of $Z^1$ is optionally substituted with one or more $Z^{1a}$ or $Z^{1b}$ groups.

Embodiment II-25

The compound of any one of Embodiments II-1 to II-19 wherein $Z^1$ is selected from phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl, wherein any phenyl, 1H-pyrrolo[2,3-b]pyridinyl, 1-oxoisoindolinyl, 4-oxo-3,4-dihydroquinazolinyl, 3-oxospiro[cyclopropane-1,1'-isoindolin]-yl, 1H-2-oxo-pyridinyl and 2,4-dioxo-1,2,3,4-tetrahydorquinazolinyl of $Z^1$ is optionally substituted with one or more $Z^{1a}$ or $Z^{1b}$ groups.

Embodiment II-26

The compound of any one of Embodiments II-1 to II-19 wherein $Z^1$ is selected from phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl, wherein any phenyl, 1H-pyrrolo[2,3-b]pyridin-5-yl, 1-oxoisoindolin-5-yl, 1-oxoisoindolin-4-yl, 4-oxo-3,4-dihydroquinazolin-8-yl, 3'-oxospiro[cyclopropane-1,1'-isoindolin]-5'-yl, 1H-2-oxo-pyridin-4-yl and 2,4-dioxo-1,2,3,4-tetrahydroquinazolin-8-yl of $Z^1$ is optionally substituted with one or more $Z^{1a}$ or $Z^{1b}$ groups.

Embodiment II-27

The compound of any one of Embodiments II-1 to II-19 wherein $Z^1$ is 1H-indazol-7-yl, wherein $Z^1$ is optionally substituted with one or more $Z^{1a}$ or $Z^{1b}$ groups.

Embodiment II-28

The compound of any one of Embodiments II-1 to II-27 wherein each $Z^{1a}$ is independently selected from halogen, —$OR^{n1}$, $NR^{q1}R^{r1}$, and —$C(O)NR^{q1}R^{r1}$.

Embodiment II-29

The compound of any one of Embodiments II-1 to II-27 wherein each $Z^{1a}$ is independently selected from halogen and —$NR^{n1}S(O)_2R^{p1}$.

Embodiment II-30

The compound of any one of Embodiments II-1 to II-27 wherein each $Z^{1b}$ is independently selected from $(C_1-C_8)$ alkyl.

Embodiment II-31

The compound of any one of Embodiments II-1 to II-27 wherein each $Z^{1a}$ is independently selected from halogen and —$NR^{n1}S(O)_2R^{p1}$ and each $Z^{1b}$ is independently selected from $(C_1-C_8)$alkyl.

Embodiment II-32

The compound of any one of Embodiments II-1 to 11-27 wherein each $Z^{1a}$ is independently selected from halogen and —$C(O)NR^{q1}R^{r1}$.

Embodiment II-33

The compound of any one of Embodiments II-1 to 11-27 wherein $R^{n1}$, $R^{q1}$ and $R^{r1}$ are each H.

Embodiment II-34

The compound of any one of Embodiments II-1 to 11-19 wherein $Z^1$ is selected from:

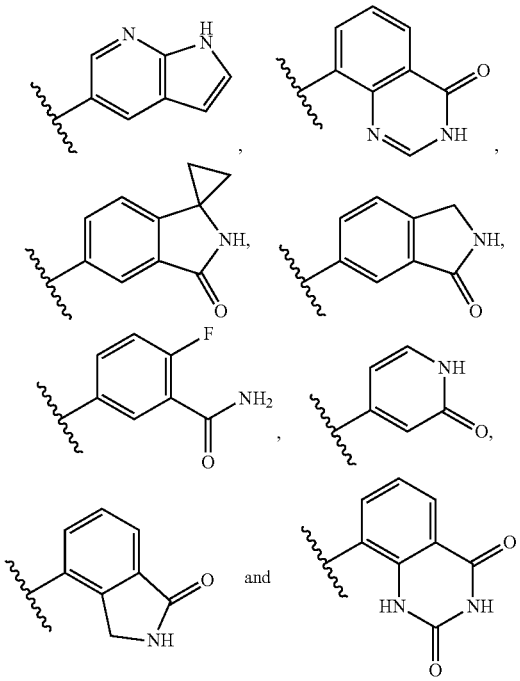

Embodiment II-35

The compound of any one of Embodiments II-1 to 11-19 wherein $Z^1$ is

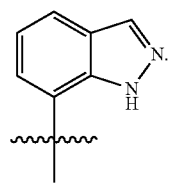 [SMILES: *c1cccc2cn[nH]c12]

Embodiment II-36

The compound of any one of Embodiments II-1 to 11-19 wherein $Z^1$ is selected from

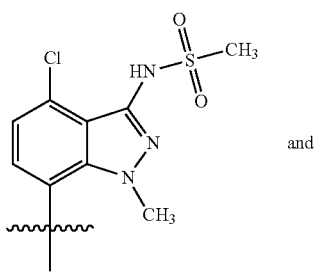

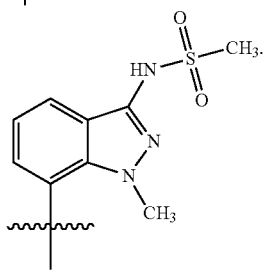

Embodiment II-37

The compound of any one of Embodiments II-1 to 11-36 wherein $Z^2$ is selected from $(C_2-C_8)$alkynyl, 6-12 membered aryl, 5-12 membered C-linked-heteroaryl, 3-12 membered C-linked-heterocycle and $-C(O)NR'^{13}R'^3$, wherein any 6-12 membered aryl, 5-12 membered C-linked-heteroaryl and 3-12 membered C-linked-heterocycle of $Z^2$ is optionally substituted with one or more $Z^{2b}$ or $Z^{2c}$ groups, and wherein any $(C_2-C_8)$alkynyl of $Z^2$ is optionally substituted with one or more $Z^{2c}$ groups.

Embodiment II-38

The compound of any one of Embodiments II-1 to II-36 wherein $Z^2$ is selected from $(C_2-C_8)$alkynyl, phenyl, 5-6 membered C-linked-monocyclic-heteroaryl, 8-10 membered C-linked-bicyclic-heteroaryl, 8-10 membered C-linked-bicyclic-heterocycle and $-C(O)NR^{q3}R'^3$, wherein any phenyl, 5-6 membered C-linked-monocyclic-heteroaryl, 8-10 membered C-linked-bicyclic-heteroaryl and 8-10 membered C-linked-bicyclic-heterocycle of $Z^2$ is optionally substituted with one or more $Z^{2b}$ or $Z^{2c}$ groups, and wherein any $(C_2-C_8)$alkynyl of $Z^2$ is optionally substituted with one or more $Z^2$ groups.

Embodiment II-39

The compound of any one of Embodiments II-1 to II-36 wherein $Z^2$ is selected from $(C_2-C_8)$alkynyl, phenyl, 5-6 membered C-linked-monocyclic-heteroaryl, 8-10 membered C-linked-bicyclic-heteroaryl, 8-10 membered C-linked-bicyclic-heterocycle and $-C(O)NR^{q3}R'^3$, wherein the 5-6 membered C-linked-monocyclic-heteroaryl, 8-10 membered C-linked-bicyclic-heteroaryl and 8-10 membered C-linked-bicyclic-heterocycle have 1-9 carbon atoms and 1-4 heteroatoms in the ring system, and wherein any phenyl, 5-6 membered C-linked-monocyclic-heteroaryl, 8-10 membered C-linked-bicyclic-heteroaryl, 8-10 membered and C-linked-bicyclic-heterocycle of $Z^2$ is optionally substituted with one or more $Z^{2b}$ or $Z^{2c}$ groups, and wherein any $(C_2-C_8)$alkynyl of $Z^2$ is optionally substituted with one or more $Z^{2c}$ groups.

Embodiment II-40

The compound of any one of Embodiments II-1 to II-36 wherein $Z^2$ is selected from 4-methylpentynyl, phenyl, pyridinyl, 1H-2-oxo-pyridinyl, triazolyl, 1-oxoisoindolinyl, 1H-pyrrolo[2,3-b]pyridinyl and $-C(O)NR^{q3}R'^3$, wherein any phenyl, pyridinyl, 2-oxopyridinyl, triazolyl, 1-oxoisoindolinyl and 1H-pyrrolo[2,3-b]pyridinyl of $Z^2$ is optionally substituted with one or more $Z^{2b}$ or $Z^{2c}$ groups, and wherein any 4-methylpentynyl of $Z^2$ is optionally substituted with one or more $Z^2$ groups.

Embodiment II-41

The compound of any one of Embodiments II-1 to II-36 wherein $Z^2$ is selected from 4-methylpentyn-1-yl, phenyl, pyridin-4-yl, 1H-2-oxo-pyridin-2-yl, triazol-4-yl, 1-oxoisoindolin-6-yl, 1H-pyrrolo[2,3-b]pyridine-5-yl and $-C(O)NR^{q3}R'^3$, wherein any phenyl, pyridin-4-yl, 2-hydroxypyridin-2-yl, triazol-4-yl, 1-oxoisoindolin-6-yl and 1H-pyrrolo[2,3-b]pyridine-5-yl of $Z^2$ is optionally substituted with one or more $Z^{2b}$ or $Z^{2c}$ groups, and wherein any 4-methylpentyn-1-yl of $Z^2$ is optionally substituted with one or more $Z^{2c}$ groups.

Embodiment II-42

The compound of any one of Embodiments II-1 to 11-41 wherein $Z^2$ is optionally substituted with one or more $Z^{2c}$ groups.

Embodiment II-43

The compound of any one of Embodiments II-1 to 11-42 wherein $R^{q3}$ and $R'^3$ are each H.

Embodiment II-44

The compound of any one of Embodiments II-1 to 11-43 wherein each $Z^{2c}$ is independently selected from halogen, $-OR^{n4}$ and $-C(O)NR^{q4}R'^4$.

Embodiment II-45

The compound of any one of Embodiments II-1 to 11-44 wherein $R^{n4}$ is H or methyl, and $R^{q4}$ and $R'^4$ are each H.

Embodiment II-46

The compound of any one of Embodiments II-1 to 11-36 wherein $Z^2$ is selected from:

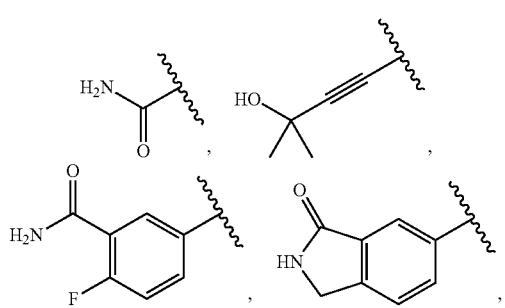

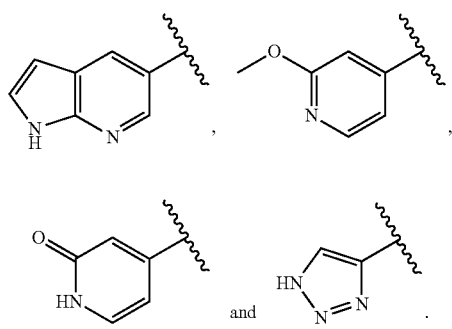
Embodiment II-47
The compound of any one of Embodiments II-1 to II-36 wherein $Z^2$ is selected from:
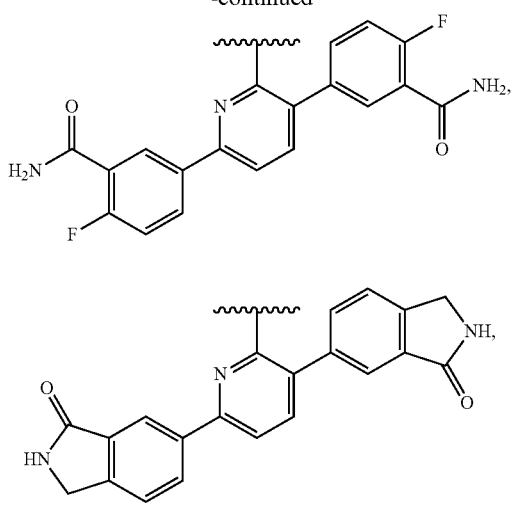
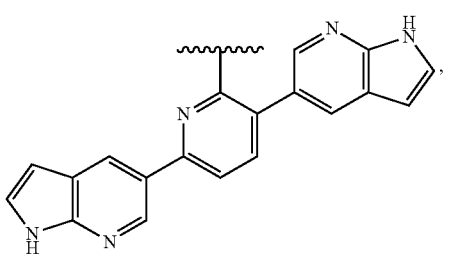
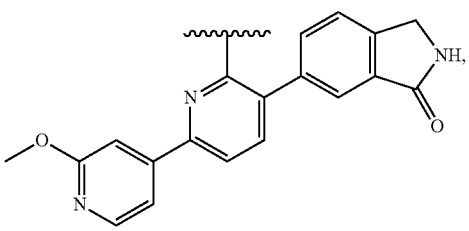
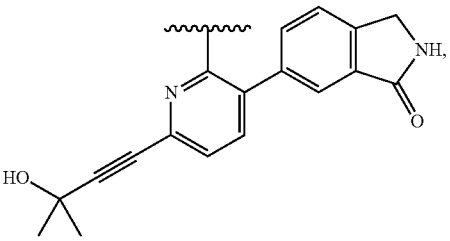
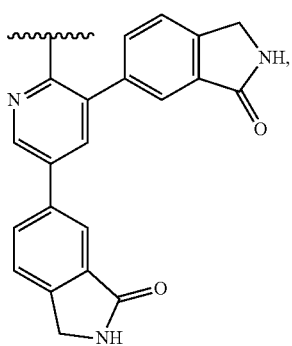

519

-continued

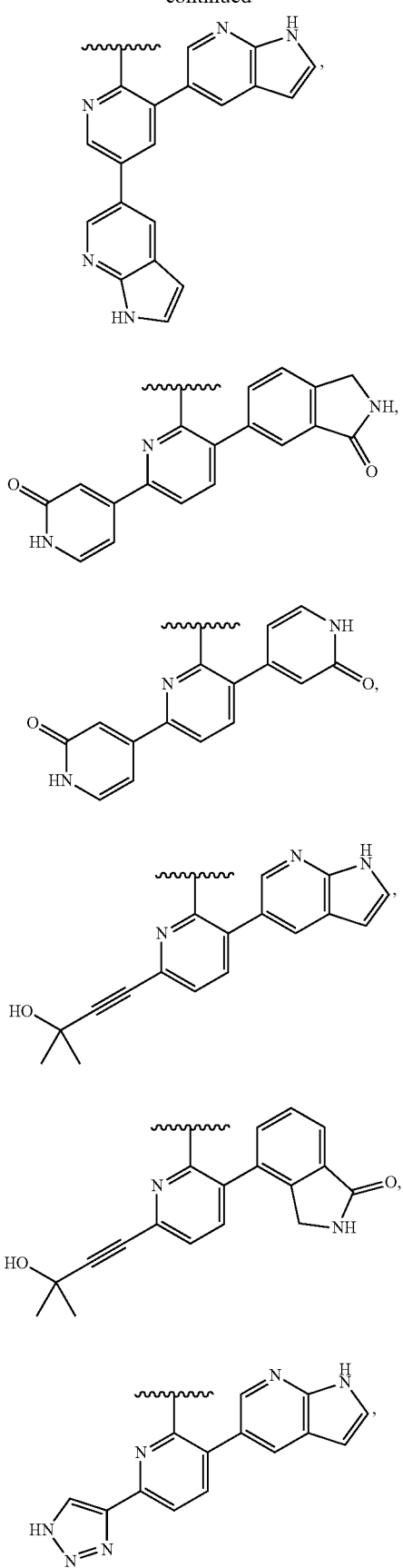

520

-continued

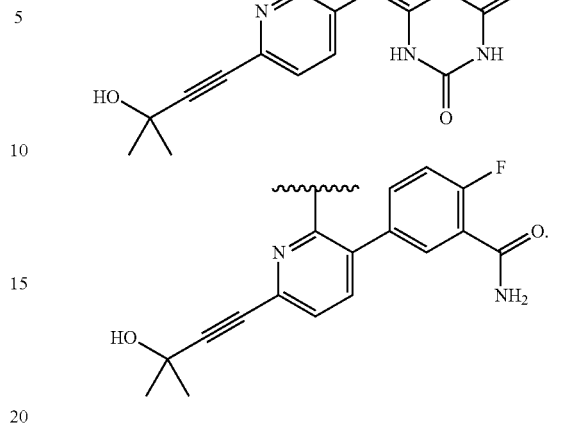

Embodiment II-48

The compound of any one of Embodiments II-1 to II-10 wherein A-Z$^1$ is selected from:

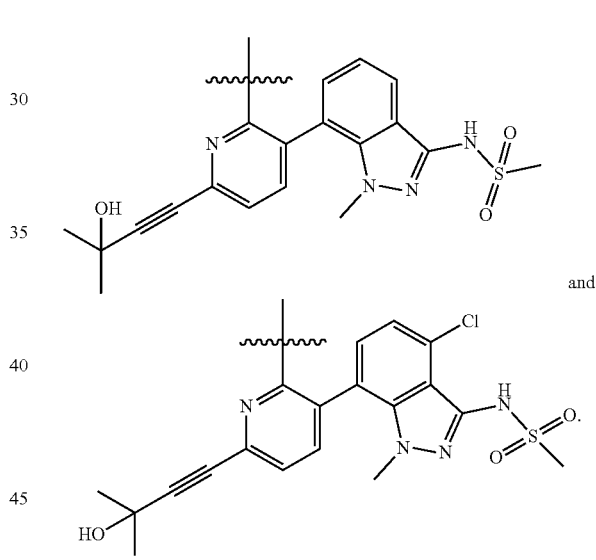

Embodiment II-49

The compound of any one of Embodiments II-1 to II-48 wherein R$^1$ is a 5-12 membered heteroaryl, wherein any 5-12 membered heteroaryl of R$^1$ is optionally substituted with one or more Z$^4$ groups.

Embodiment II-50

The compound of any one of Embodiments II-1 to II-48 wherein R$^1$ is a 8-12 membered bicyclic-heteroaryl or 8-12 membered tricyclic-heteroaryl, wherein any 8-12 membered bicyclic-heteroaryl or 8-12 membered tricyclic-heteroaryl of R$^1$ is optionally substituted with one or more Z$^4$ groups.

Embodiment II-51

The compound of any one of Embodiments II-1 to II-48 wherein R$^1$ is a 8-12 membered bicyclic-heteroaryl or 8-12 membered tricyclic-heteroaryl, wherein the 8-12 membered bicyclic-heteroaryl or 8-12 membered tricyclic-heteroaryl have 4-10 carbon atoms and 1-5 heteroatoms in the ring system, and wherein any 8-12 membered bicyclic-heteroaryl or 8-12 membered tricyclic-heteroaryl of $R^1$ is optionally substituted with one or more $Z^4$ groups.

Embodiment II-52

The compound of any one of Embodiments II-1 to II-48 wherein $R^1$ is a 8-12 membered bicyclic-heteroaryl or 8-12 membered tricyclic-heteroaryl, wherein the 8-12 membered bicyclic-heteroaryl or 8-12 membered tricyclic-heteroaryl contains at least one partially unsaturated ring, and wherein any 8-12 membered bicyclic-heteroaryl or 8-12 membered tricyclic-heteroaryl of $R^1$ is optionally substituted with one or more (e.g., 1, 2, 3, 4 or 5) $Z^4$ groups.

Embodiment II-53

The compound of any one of Embodiments II-1 to II-48 wherein $R^1$ has the following formula IIb:

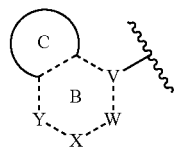

IIb wherein:
C together with the two carbon atoms of ring B to which it is attached forms a 3-7 membered monocyclic-carbocycle, 5-8 membered bicyclic-carbocycle, 3-7 membered monocyclic-heterocycle or 5-8 membered bicyclic heterocycle, wherein any 3-7 membered monocyclic-carbocycle, 5-8 membered bicyclic-carbocycle, 3-7 membered monocyclic-heterocycle or 5-8 membered bicyclic heterocycle of C is optionally substituted with one or more (e.g. 1, 2, 3, 4 or 5) $Z^4$ groups; and
B is a 5 or 6 membered monocyclic-heteroaryl having 1, 2 or 3 nitrogen atoms;
V is C or N;
W is $CZ^{4c}$, $NZ^{4c}$ or N;
X is $CZ^{4c}$, $NZ^{4c}$ or N;
Y is $CZ^{4c}$, N or absent;
the dashed bonds are selected from single bonds and double bonds, wherein the dashed bonds, V, W, X and Y are selected so that the 5 or 6 membered monocyclic-heteroaryl B is aromatic; and
each $Z^{4c}$ is independently selected from H or $Z^4$.

Embodiment II-54

The compound of any one of Embodiments II-1 to II-48 wherein $R^1$ has the following formula IId:

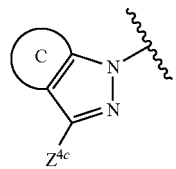

IId wherein:
C together with the two carbon atoms to which it is attached forms a 3-7 membered monocyclic-carbocycle, 5-9 membered bicyclic-carbocycle, 3-7 membered monocyclic-heterocycle or 5-9 membered bicyclic heterocycle, wherein any 3-7 membered monocyclic-carbocycle, 5-9 membered bicyclic-carbocycle, 3-7 membered monocyclic-heterocycle or 5-9 membered bicyclic heterocycle of C is optionally substituted with one or more (e.g. 1, 2, 3, 4 or 5) $Z^4$ groups; and
each $Z^{4c}$ is independently selected from H or $Z^4$.

Embodiment II-55

The compound of any one of Embodiments II-1 to II-48 wherein $R^1$ is selected from 3b,4,4a,5-tetrahydro-1H-cyclopropa[3,4]cyclopenta[1,2-c]pyrazolyl and 4,5,6,7-tetrahydro-indazolyl, wherein any 3b,4,4a,5-tetrahydro-1H-cyclopropa[3,4]cyclopenta[1,2-c]pyrazolyl and 4,5,6,7-tetrahydro-indazolyl of $R^1$ is optionally substituted with one or more $Z^4$ groups.

Embodiment 56

The compound of any one of Embodiments II-1 to II-48 wherein $R^1$ is selected from 3b,4,4a,5-tetrahydro-1H-cyclopropa[3,4]cyclopenta[1,2-c]pyrazol-1-yl and 4,5,6,7-tetrahydro-indazol-1-yl, wherein any 3b,4,4a,5-tetrahydro-1H-cyclopropa[3,4]cyclopenta[1,2-c]pyrazol-1-yl and 4,5,6,7-tetrahydro-indazol-1-yl of $R^1$ is optionally substituted with one or more $Z^4$ groups.

Embodiment II-57

The compound of any one of Embodiments II-1 to II-56 wherein each $Z^4$ is independently selected from $(C_1-C_6)$alkyl and halogen, wherein any $(C_1-C_6)$alkyl of $Z^4$ is optionally substituted with one or more halogen.

Embodiment II-58

The compound of any one of Embodiments II-1 to II-56 wherein each $Z^4$ is independently selected from fluoro, trifluoromethyl and difluoromethyl.

Embodiment II-59

The compound of any one of Embodiments II-1 to II-48 wherein $R^1$ is selected from:

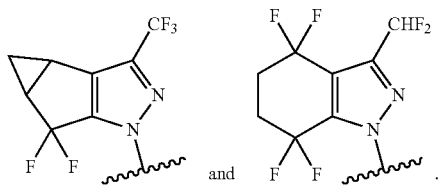 [SMILES: *n1nc(C(F)(F)F)c2c1C(F)(F)C1CC21 ; *n1nc(C(F)F)c2c1C(F)(F)CCC2(F)F]

Embodiment II-60

The compound of any one of Embodiments II-1 to II-48 wherein $R^1$ is

523
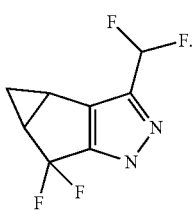 [SMILES: FC(F)c1n[nH]c2c1C1CC1C2(F)F]
Embodiment II-61
The compound of any one of Embodiments II-1 to 11-48 wherein R¹ is selected from:
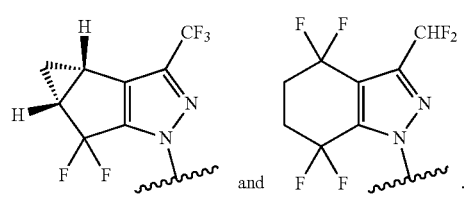 [SMILES: *n1nc(C(F)(F)F)c2c1C(F)(F)[C@@H]1C[C@H]21 ; *n1nc(C(F)F)c2c1C(F)(F)CCC2(F)F]
Embodiment II-62
The compound of any one of Embodiments II-1 to 11-48 wherein R¹ is
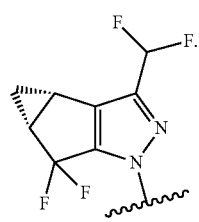 [SMILES: *n1nc(C(F)F)c2c1C(F)(F)[C@@H]1C[C@H]21]
Embodiment II-63
The compound of Embodiment II-1 selected from:
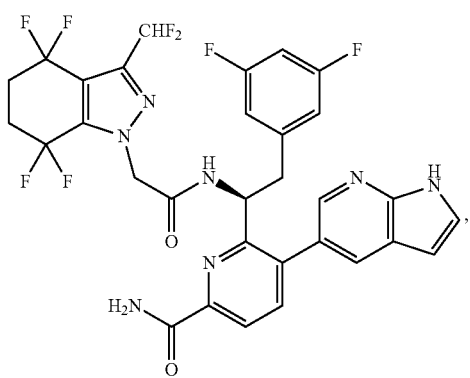
524
-continued
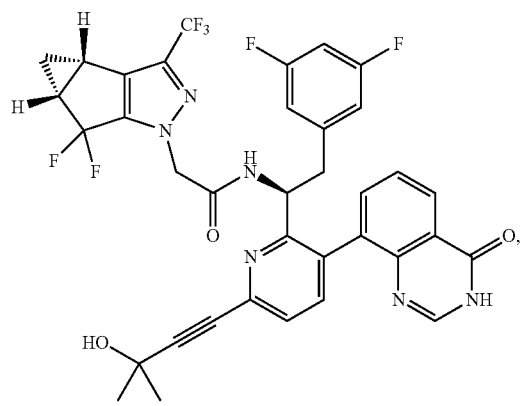
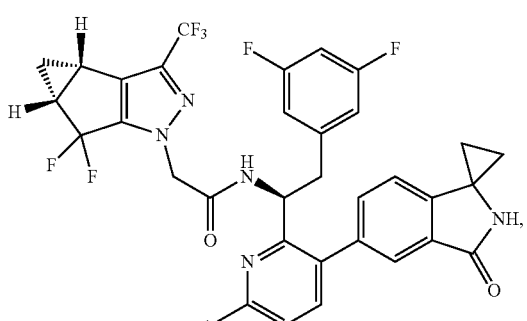
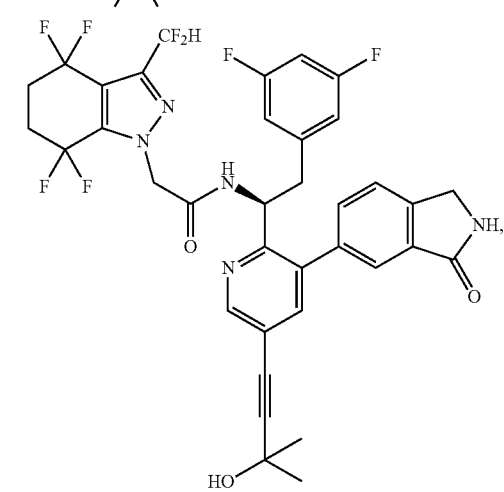
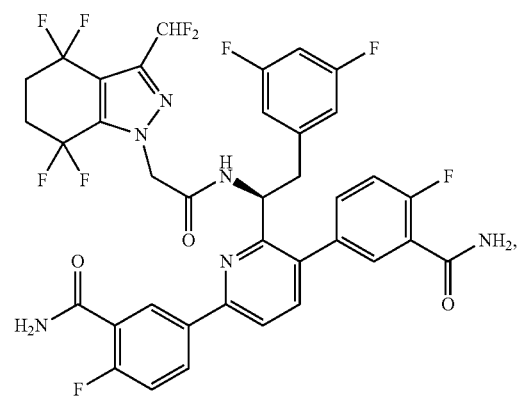

525
-continued
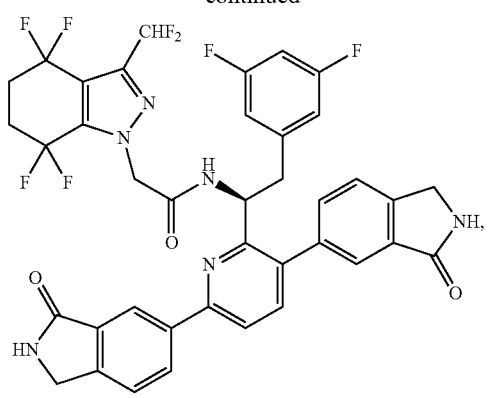
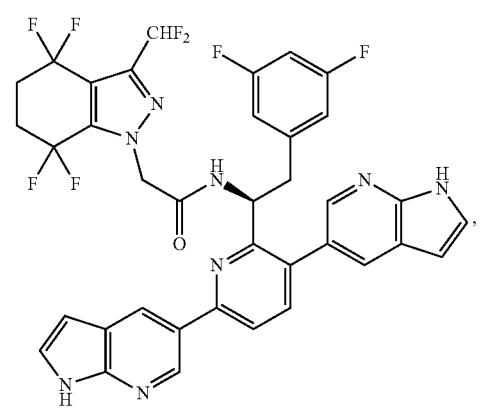
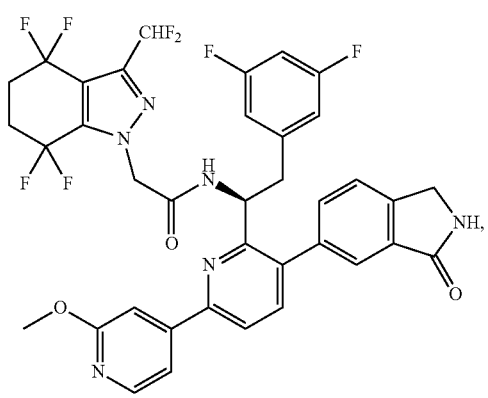
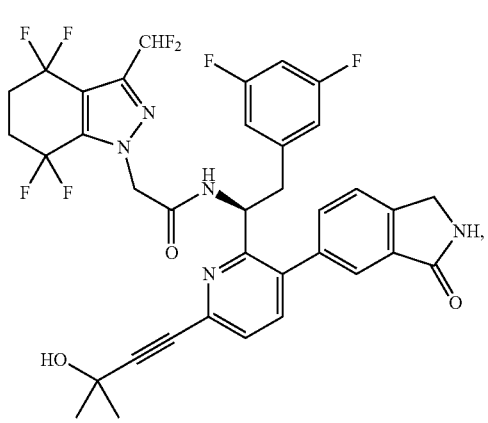
526
-continued
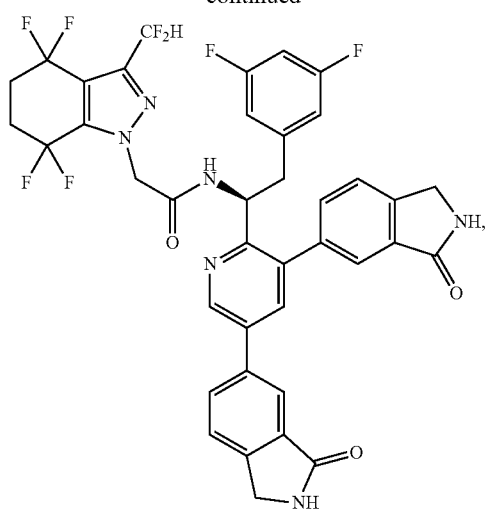
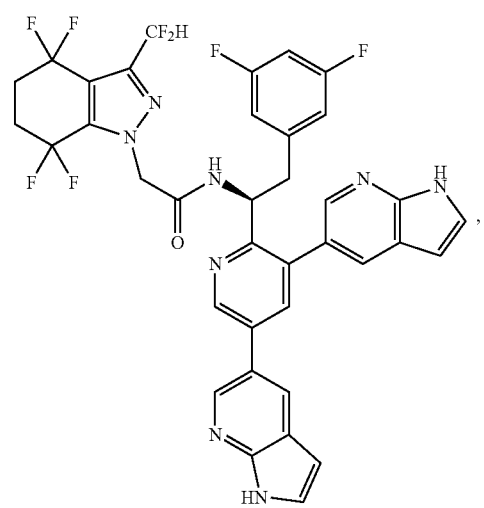
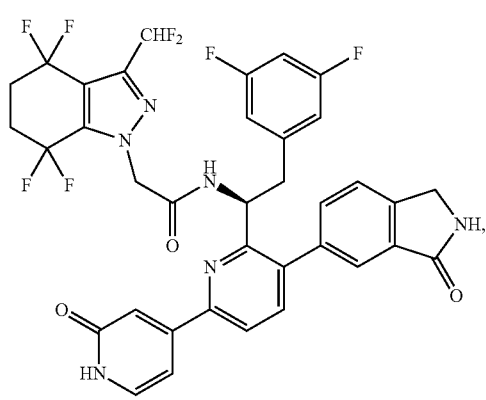

527
-continued
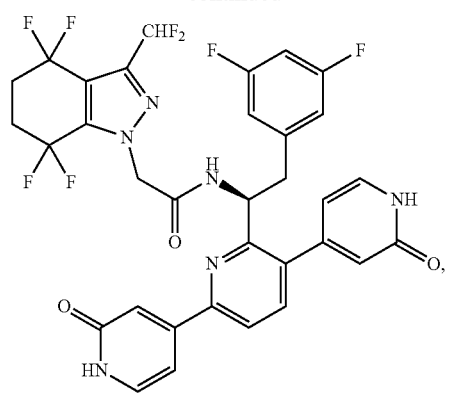
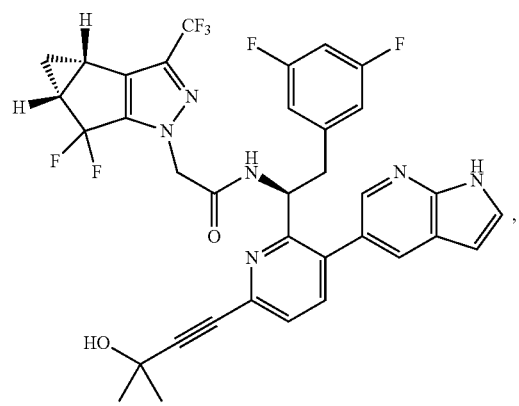
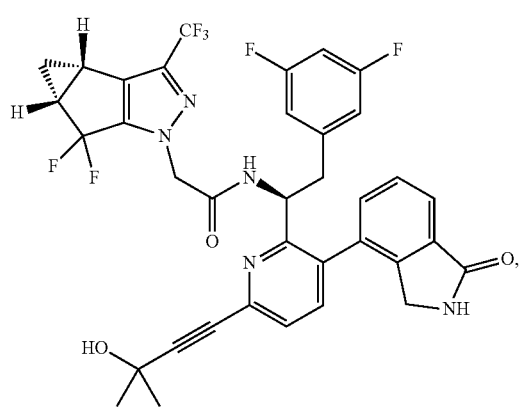
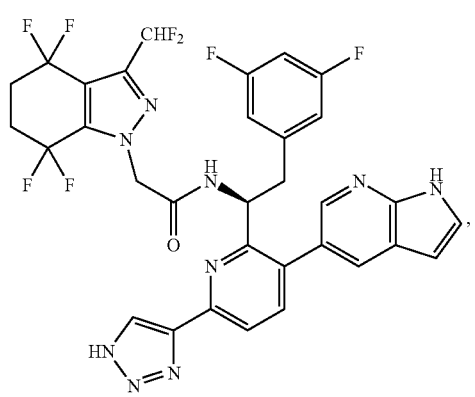
528
-continued
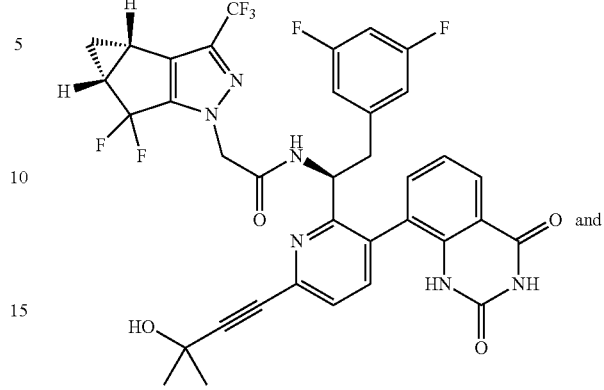
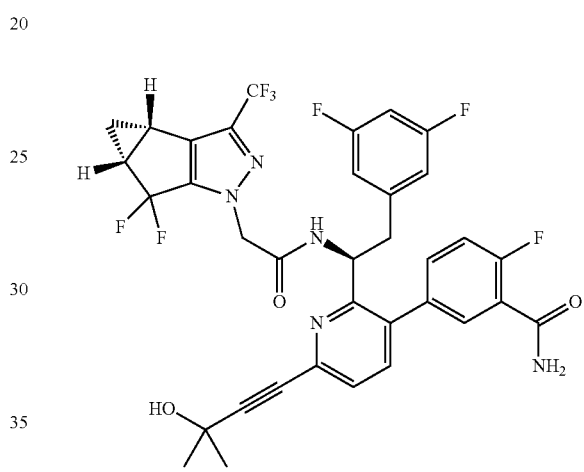
and pharmaceutically acceptable salts thereof.
Embodiment II-641
The compound of Embodiment II-1 selected from:
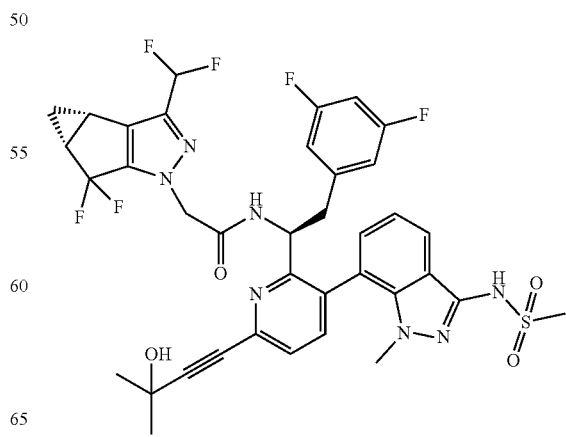
and 529
-continued

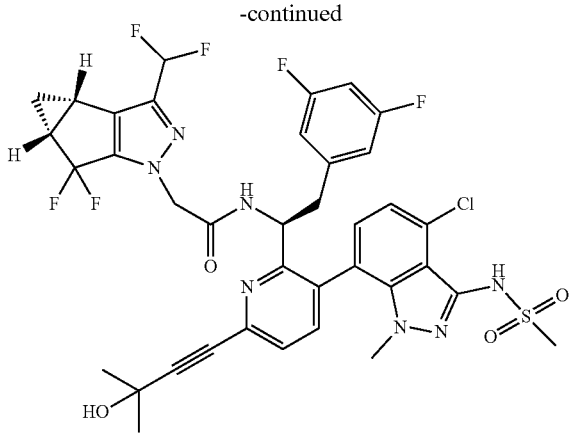

and pharmaceutically acceptable salts thereof.

Embodiment II-65

A pharmaceutical composition comprising a compound of formula I as described in any one of Embodiments II-1 to 11-64, or a pharmaceutically acceptable salt thereof, and a pharmaceutically acceptable carrier.

Embodiment II-66

A method for treating a Retroviridae virus infection in a mammal comprising administering a therapeutically effective amount of a compound of any one of Embodiments II-1 to 11-64, or a pharmaceutically acceptable salt thereof, to the mammal.

Embodiment II-67

The method of Embodiment II-66 wherein the Retroviridae virus infection is an HIV virus infection.

Embodiment II-68

A method for treating an HIV infection in a mammal comprising administering to the mammal in need thereof a therapeutically effective amount of a compound of formula I as described in any one of Embodiments II-1 to 11-64, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

Embodiment II-69

A compound of formula I as described in any of Embodiments II-1 to II-44, or a pharmaceutically acceptable salt thereof for use in medical therapy.

Embodiment II-70

A compound of formula I as described in any one of Embodiments II-1 to II-44 or a pharmaceutically acceptable salt thereof, for the prophylactic or therapeutic treatment of a Retroviridae virus infection or an HIV virus infection.

Embodiment II-71

The use of a compound as described in any one of Embodiments II-1 to II-44 or a pharmaceutically acceptable salt thereof, for the manufacture of a medicament for treating a Retroviridae virus infection or an HIV virus infection in a mammal.

Embodiment II-72

A compound or method as described herein.
What is claimed is:
1. A compound of formula IIIe:

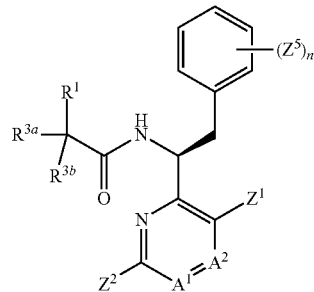

IIIe wherein
  $A^1$ is OH, C—$Z^3$, or nitrogen;
  $A^2$ is CH or nitrogen;
  $R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;
  each $R^{3a}$ and $R^{3b}$ is independently H or $(C_1$-$C_3)$alkyl;
  $Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;
  each $Z^{1a}$ is independently $(C_3$-$C_7)$carbocycle, 5-12 membered heteroaryl, 3-12 membered heterocycle, halogen, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, —C(O)R$^{n1}$, —C(O)OR$^{n1}$, —C(O)Nr$^{q1}$R$^{r1}$ and —S(O)$_2$NR$^{n1}$COR$^{p1}$, wherein any $(C_3$-$C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;
  each $Z^{1b}$ is independently $(C_1$-$C_8)$alkyl optionally substituted with 1, 2, 3, 4 or 5 halogen, which are the same or different;
  each $Z^{1c}$ is independently halogen, —CN, —OH, —NH$_2$, —C(O)N$^{q2}$R$^{r2}$, or $(C_1$-$C_8)$heteroalkyl;
  each $Z^{1d}$ is independently $(C_1$-$C_8)$alkyl or $(C_1$-$C_8)$haloalkyl;

each $R^{n1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{n1}$ is optionally substituted with 1, 2, 3, 4 or 5 $Z^{1c}$ groups, wherein the $Z^{1c}$ groups are the same or different;

each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is $(C_2-C_8)$alkenyl, $(C_2-C_8)$alkynyl, 6-12 membered aryl, 5-12 membered C-linked-heteroaryl, 3-12 membered C-linked-heterocycle, —C(O)$R^{n3}$, or —C(O)NR$^{q3}$R$^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, wherein the $Z^{2b}$ and $Z^{2c}$ groups are the same or different, and wherein any $(C_2-C_8)$alkenyl or $(C_2-C_8)$alkynyl of $Z^2$ is optionally substituted with 1, 2, 3, 4, or 5 $Z^{2c}$ groups, wherein the $Z^{2c}$ groups are the same or different;

each $R^{n3}$ is independently H or $(C_1-C_4)$alkyl;

each $R^{q3}$ and $R^{r3}$ is independently H or $(C_1-C_4)$alkyl;

each $Z^{2b}$ is independently oxo, $(C_1-C_4)$alkyl, $(C_1-C_4)$heteroalkyl or $(C_1-C_4)$haloalkyl;

each $Z^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, or —C(O)NR$^{q4}$R$^{r4}$;

each $R^{n4}$ is independently H, $(C_1-C_4)$alkyl, $(C_1-C_4)$haloalkyl, or $(C_1-C_4)$heteroalkyl, each $R^{p4}$ is independently $(C_1-C_8)$alkyl, $(C_1-C_4)$haloalkyl, or $(C_1-C_4)$heteroalkyl;

each $R^{q4}$ and $R^{r4}$ is independently H, $(C_1-C_4)$alkyl, $(C_1-C_4)$haloalkyl, or $(C_1-C_4)$heteroalkyl;

each $Z^3$ is independently a $(C_1-C_4)$heteroalkyl, each $Z^4$ is independently oxo, $(C_1-C_8)$alkyl, $(C_3-C_7)$carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any $(C_3-C_7)$carbocycle or $(C_1-C_8)$alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —OR$^{n6}$;

each $R^{n5}$, $R^{p5}$, $R^{q5}$, $R^{r5}$, and $R^{n6}$ is independently H or $(C_1-C_4)$alkyl;

each $Z^5$ is independently halogen, which may be same or different; and n 0, 1, 2, or 3;

or a pharmaceutically acceptable salt thereof.

2. The compound of claim 1 or a pharmaceutically acceptable salt thereof, wherein $R^1$ is

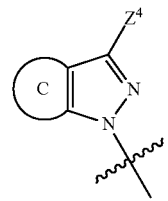

wherein
C together with the two carbon atoms to which it is attached forms a 3-7 membered monocyclic-carbocycle or 5-9 membered bicyclic-carbocycle, wherein any 3-7 membered monocyclic-carbocycle or 5-9 membered bicyclic-carbocycle of C is optionally substituted with 1, 2, 3, or 4 $Z^4$ groups, wherein the $Z^4$ groups are the same or different.

3. The compound of claim 1, or a pharmaceutically acceptable salt thereof, wherein $R^1$ is

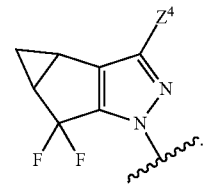

4. The compound of claim 1, or a pharmaceutically acceptable salt thereof, wherein $Z^1$ is

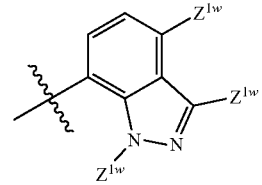

wherein each $Z^{1w}$ is independently $Z^{1a}$, $Z^{1b}$, or H.

5. The compound of claim 4, or a pharmaceutically acceptable salt thereof, wherein:

each $Z^{1a}$ is independently halogen, —CN, —OR$^{n1}$, —NR$^{n1}$S(O)$_2$R$^{p1}$, —NR$^{n1}$S(O)$_2$NR$^{q1}$R$^{r1}$, —NR$^{q1}$R$^{r1}$, —NR$^{n1}$COR$^{p1}$, —NR$^{n1}$CONR$^{q1}$R$^{r1}$, or —NR$^{n1}$CO$_2$R$^{p1}$;

each $Z^{1b}$ is independently (C$_1$-C$_8$alkyl), wherein the (C$_1$-C$_8$alkyl) is optionally substituted with 1, 2, or 3 halogen, which are the same or different; and at least one of $Z^{1w}$ is $Z^{1a}$ or $Z^{1b}$.

6. The compound of claim 5, or a pharmaceutically acceptable salt thereof, wherein each $Z^{1a}$ is independently halogen, —NR$^{n1}$S(O)$_2$R$^{p1}$, or —NR$^{n1}$S(O)$_2$NR$^{q1}$R$^{r1}$.

7. The compound of claim 1, or a pharmaceutically acceptable salt thereof, wherein the moiety

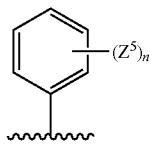

is

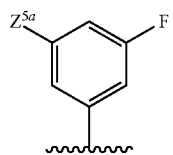

wherein $Z^{5a}$ is H or halogen.

8. The compound of claim 1, or a pharmaceutically acceptable salt thereof, wherein A$^1$ is CH or C—Z$^3$; and A$^2$ is CH.

9. The compound of claim 1, or a pharmaceutically acceptable salt thereof, wherein R$^{3a}$ and R$^{3b}$ are each H.

10. The compound of claim 1, or a pharmaceutically acceptable salt thereof, wherein R$^{3a}$ is methyl and R$^{3b}$ is H.

11. The compound of claim 1, or a pharmaceutically acceptable salt thereof, wherein Z$^2$ is (C$_2$-C$_8$)alkynyl, optionally substituted with 1, 2, or 3 Z$^{2c}$ groups.

12. The compound of claim 11, or a pharmaceutically acceptable salt thereof, wherein each Z$^{2c}$ is independently halogen, —OR$^{n4}$, NR$^{q4}$R$^{r4}$, —NR$^{n4}$CO$_2$R$^{p4}$, —C(O)OR$^{n4}$, or —C(O)NR$^{q4}$R$^{r4}$.

13. The compound of claim 1, or a pharmaceutically acceptable salt thereof, wherein R$^1$ optionally substituted with 1, 2, 3, 4, or 5 Z$^4$ groups is

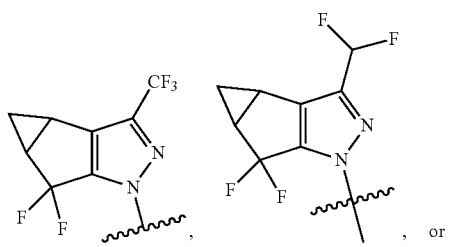

, or

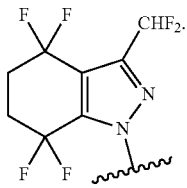

14. The compound of claim 1, or a pharmaceutically acceptable salt thereof, wherein Z$^1$ is phenyl, 5-6 membered monocyclic-heteroaryl, 8-10 membered bicyclic-heteroaryl, 8-10 membered bicyclic-heterocycle, or 9-12 membered tricyclics heterocycle, wherein any phenyl, 5-6 membered monocyclic-heteroaryl, 8-10 membered bicyclic-heteroaryl, 8-10 membered bicyclic-heterocycle, or 9-12 membered tricyclic-heterocycle of Z$^1$ is optionally substituted with 1, 2, 3, 4, or 5 $Z^{1a}$ or $Z^{1b}$ groups.

15. A compound or a pharmaceutically acceptable salt thereof, which is

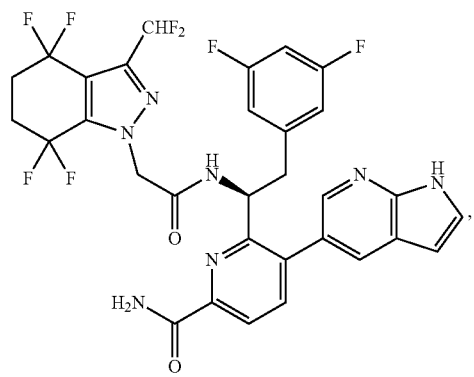

,

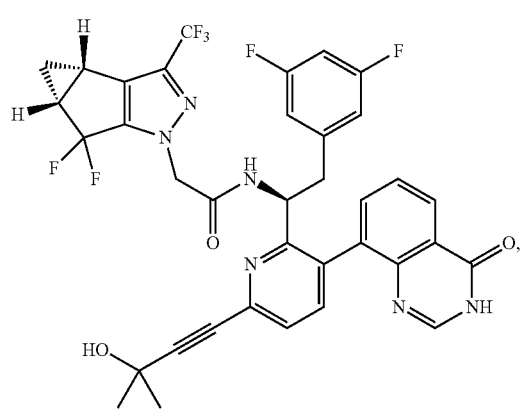

535
-continued
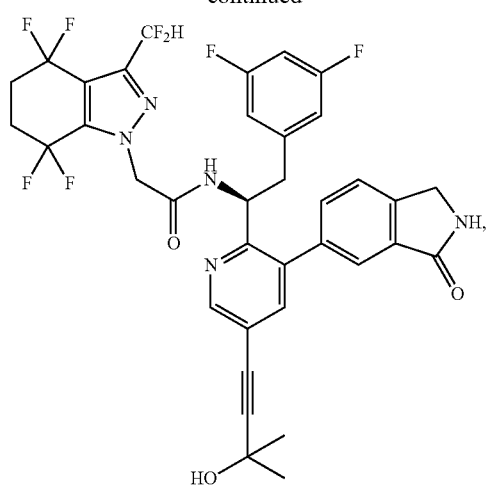
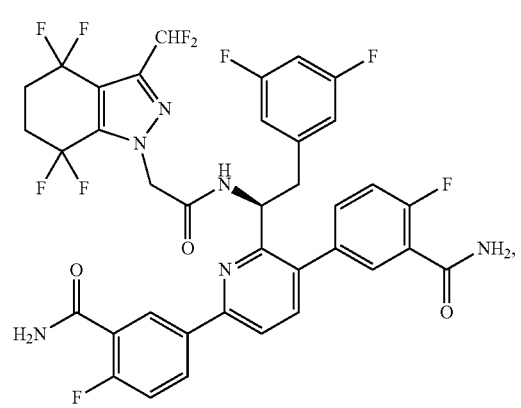
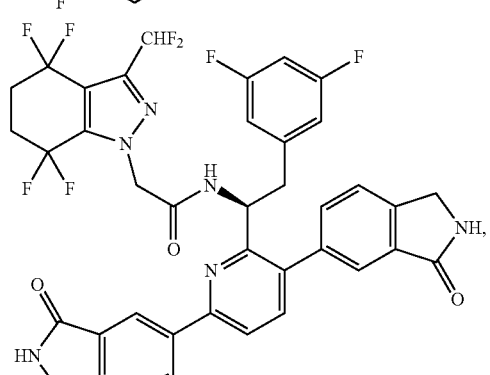
536
-continued
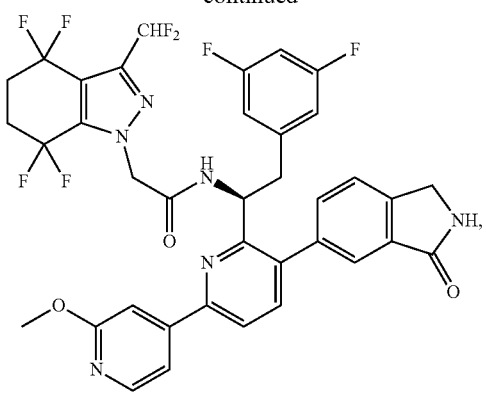
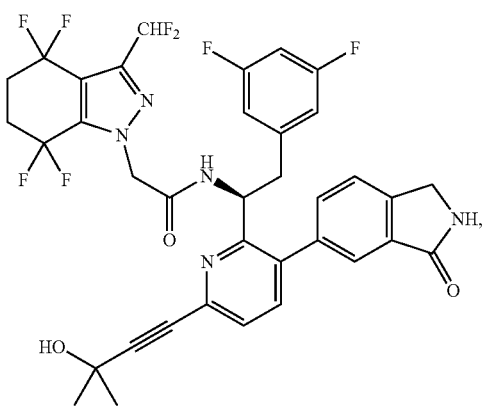
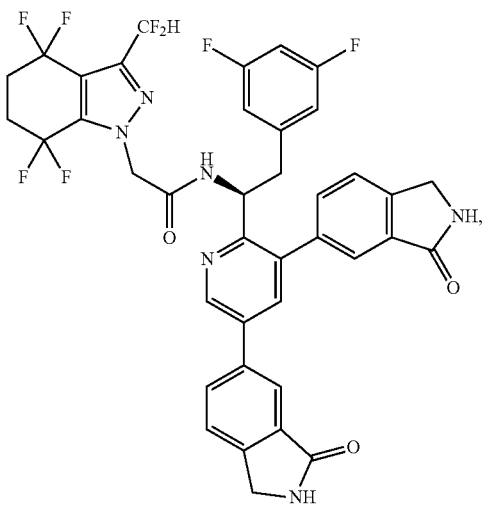

537
-continued
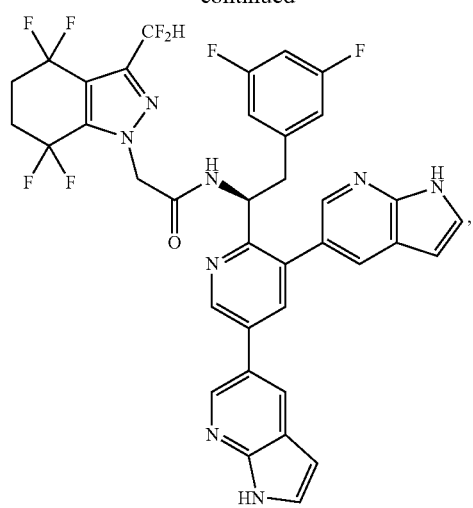
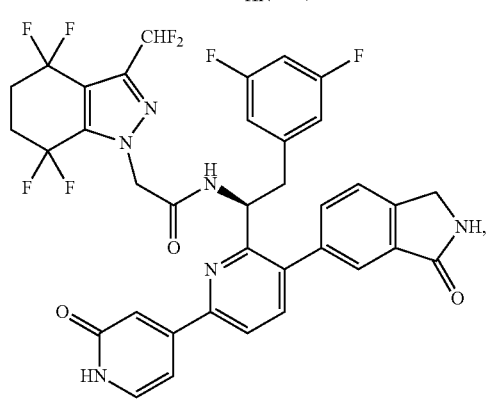
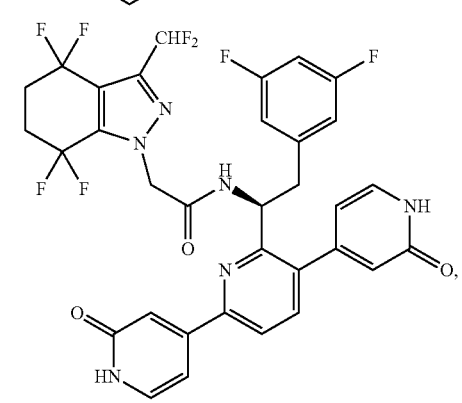
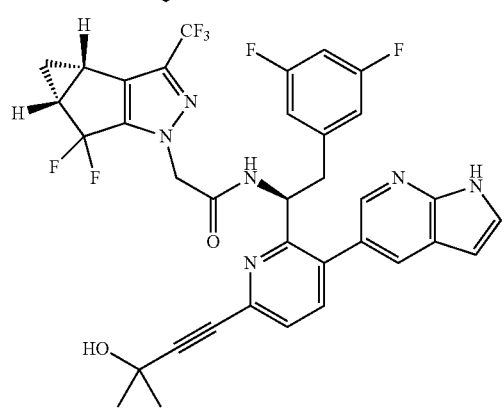
538
-continued
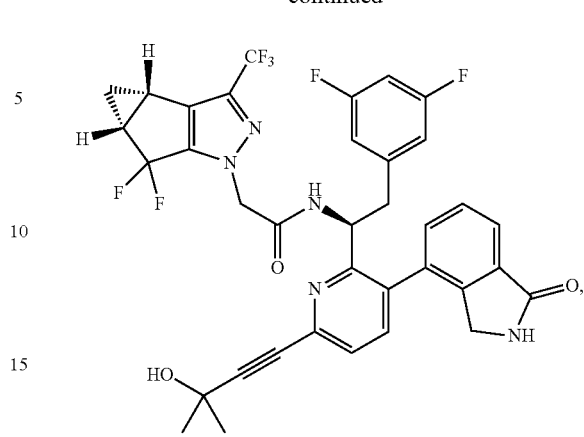
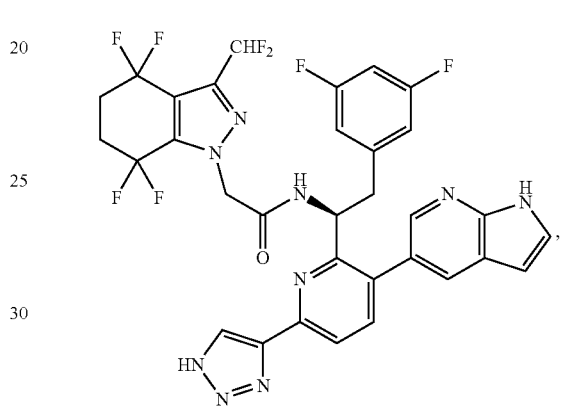
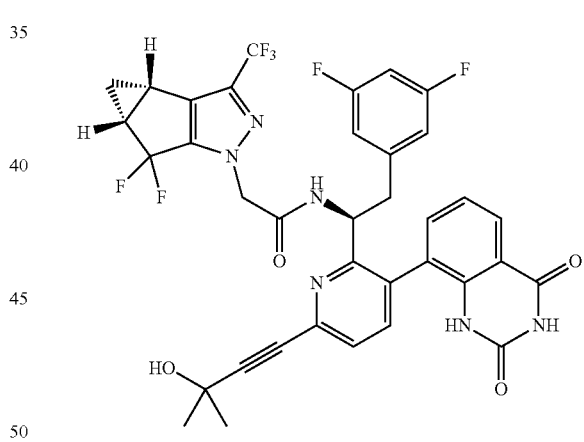
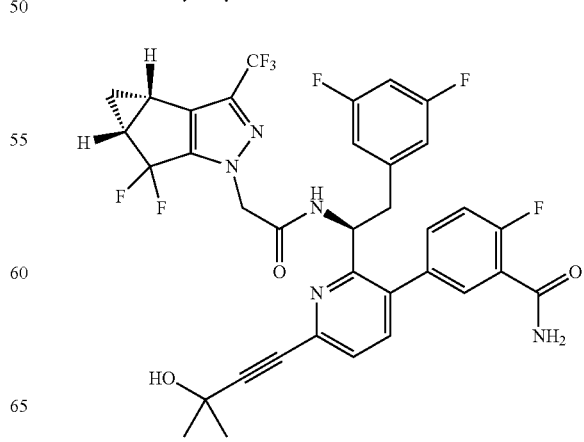

539
-continued
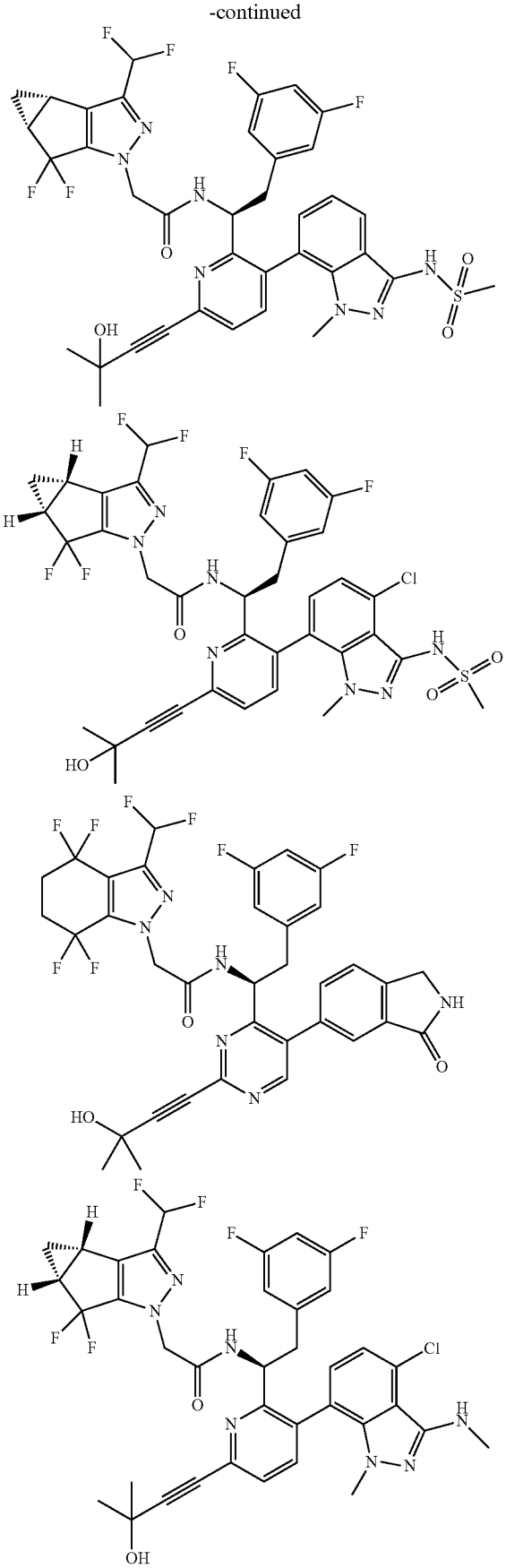
540
-continued
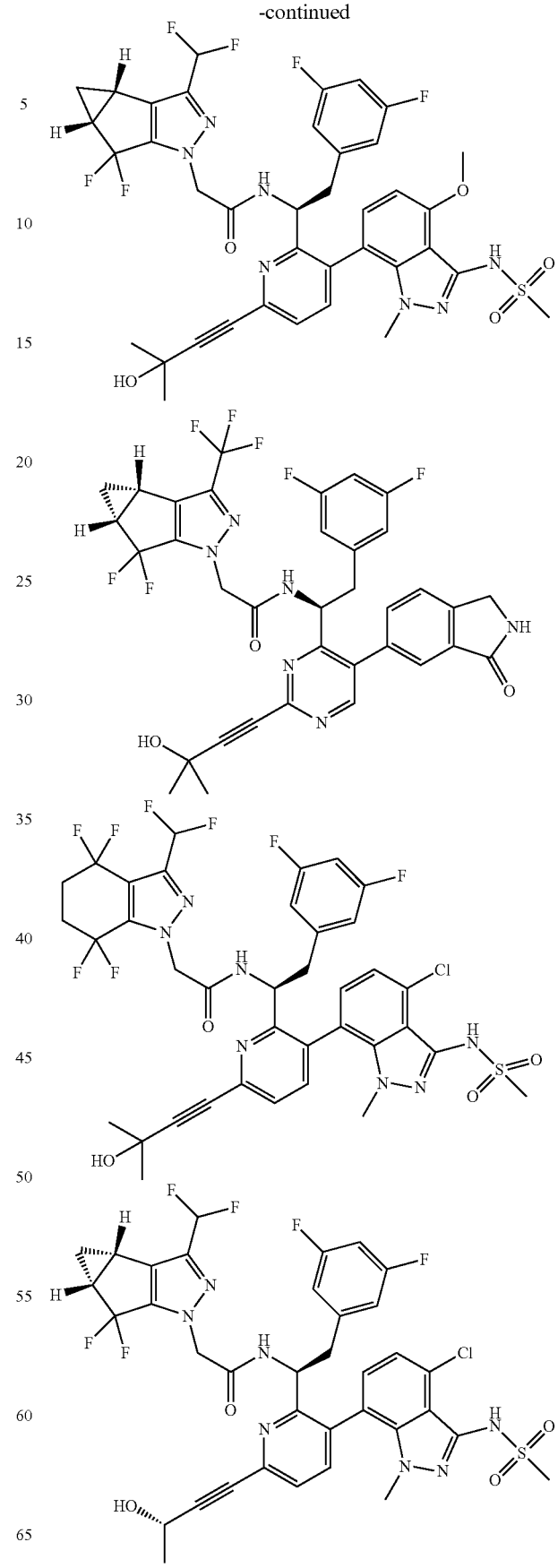

541
-continued
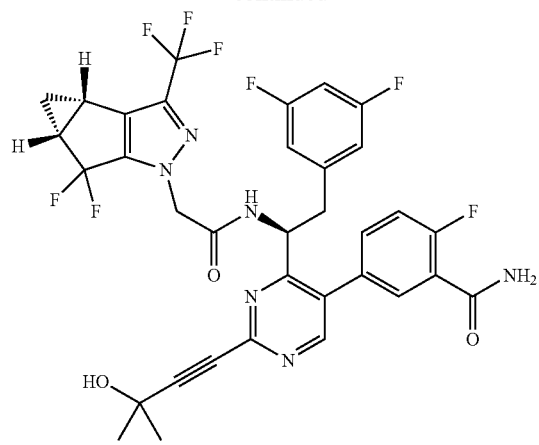
542
-continued
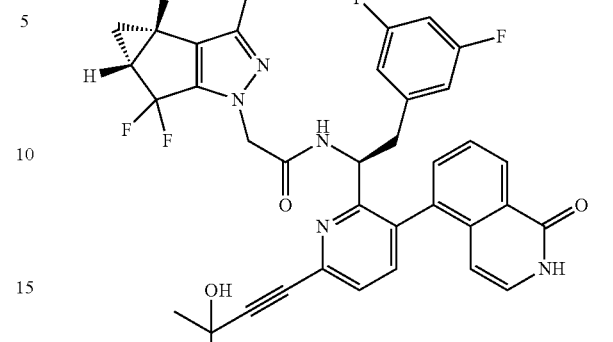
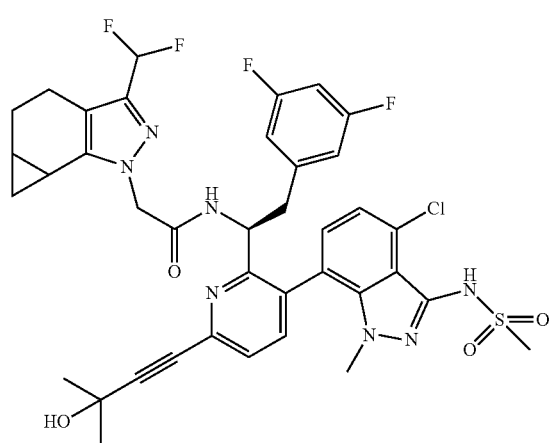
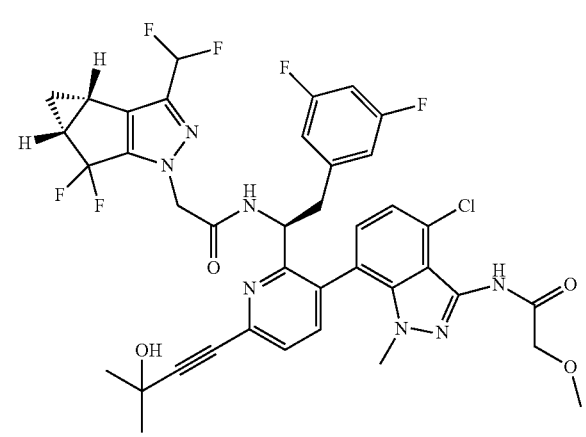
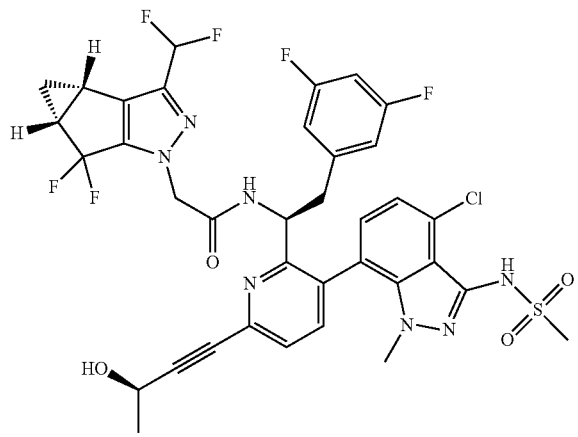
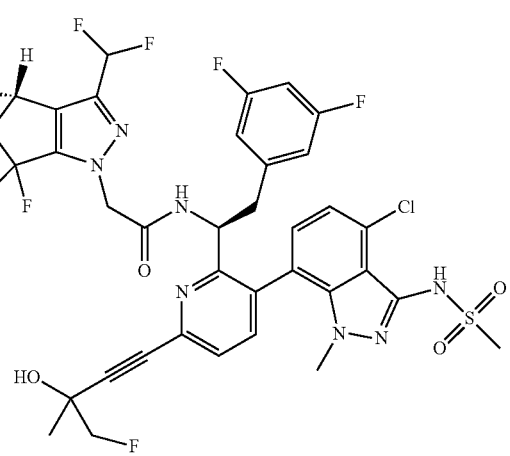

543
-continued
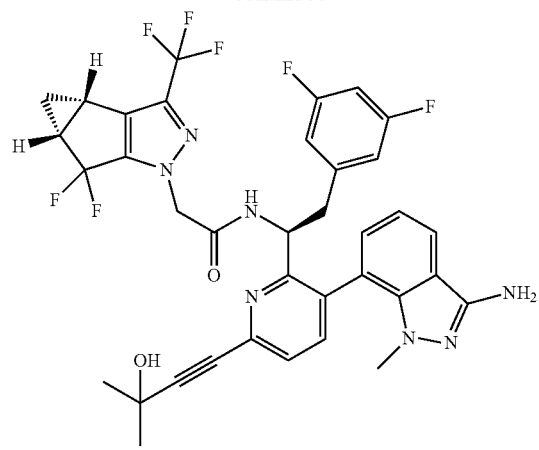
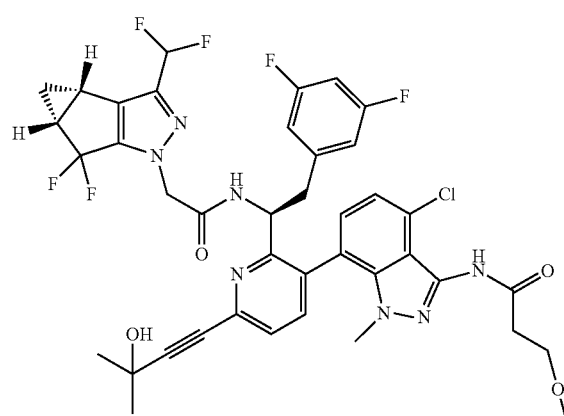
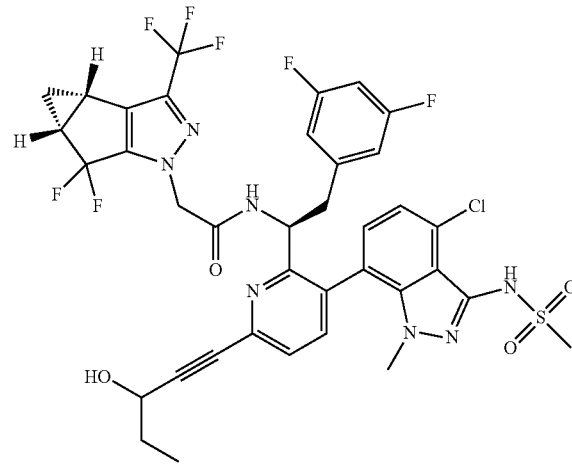
544
-continued
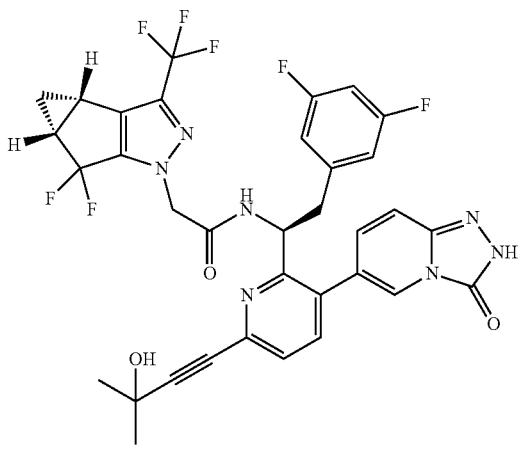
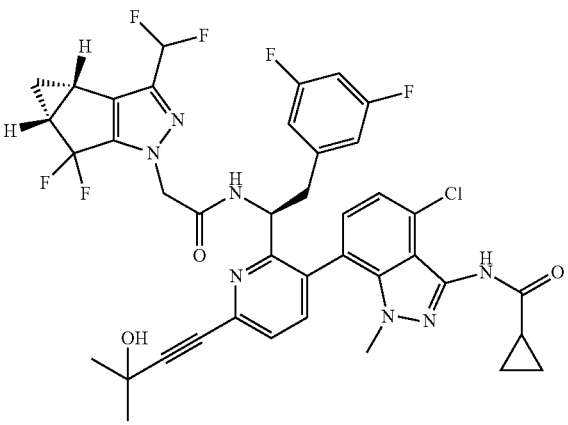
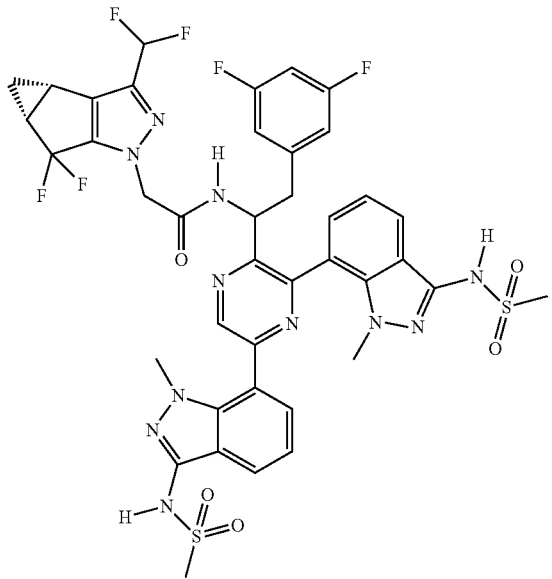

545
-continued
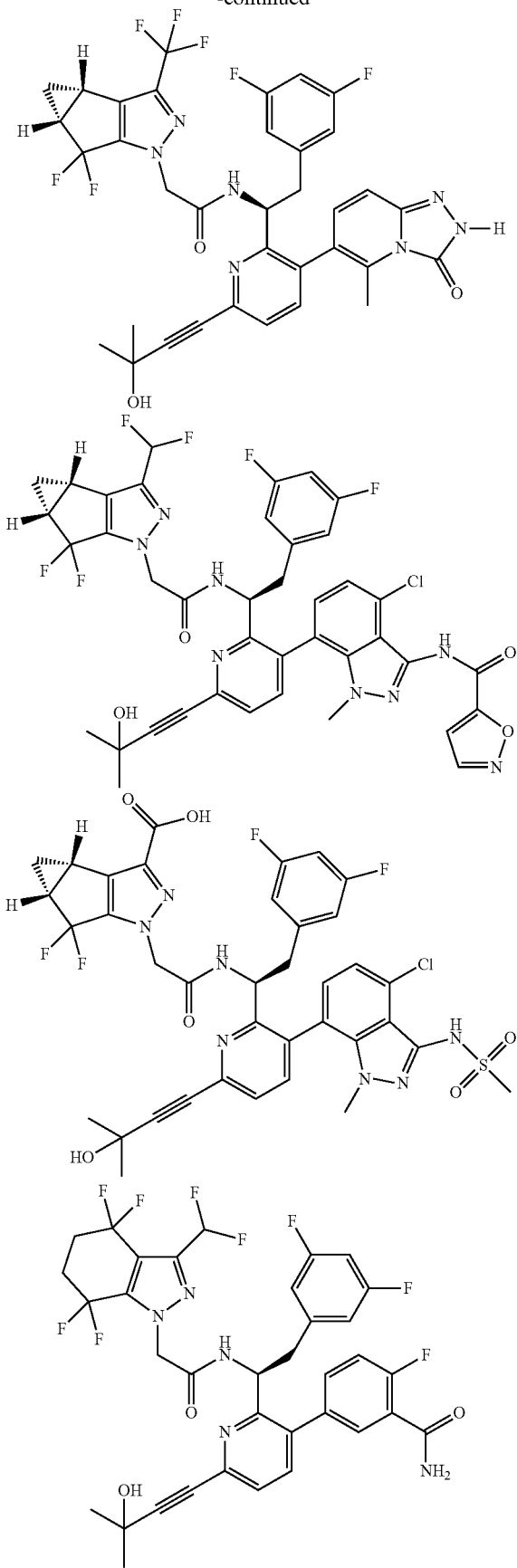
546
-continued
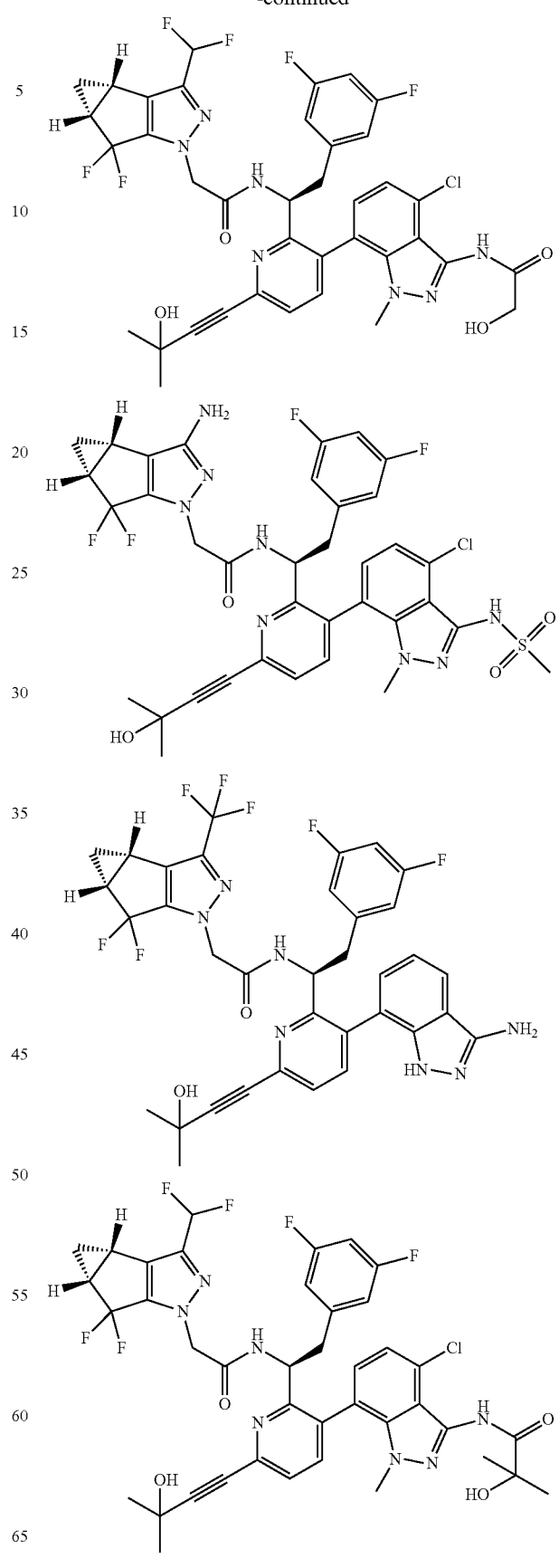

547
-continued
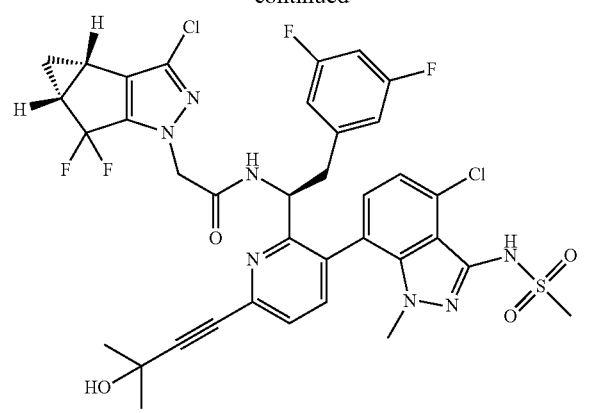
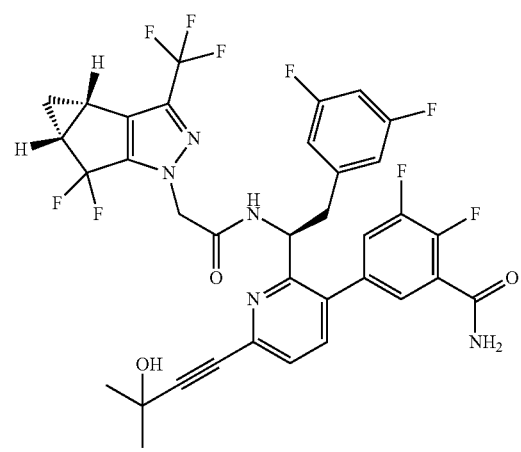
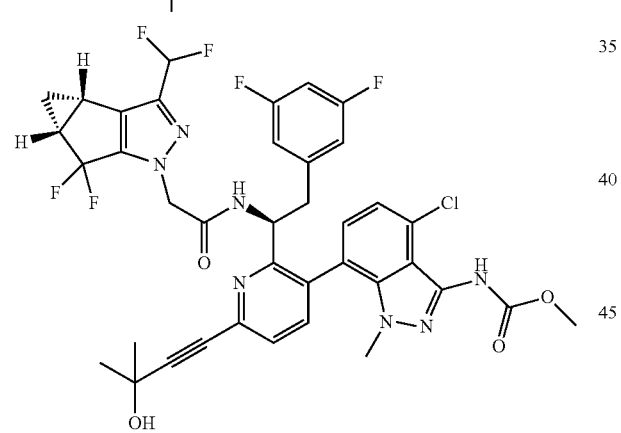
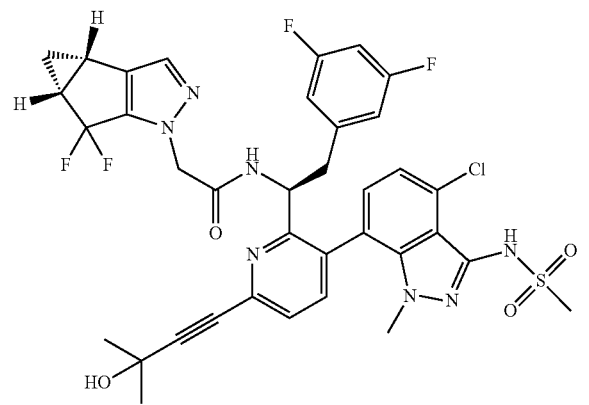
548
-continued
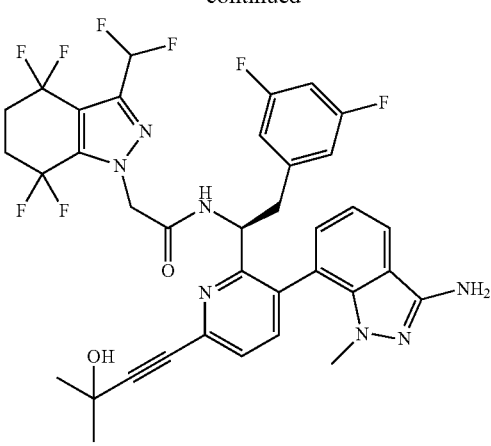
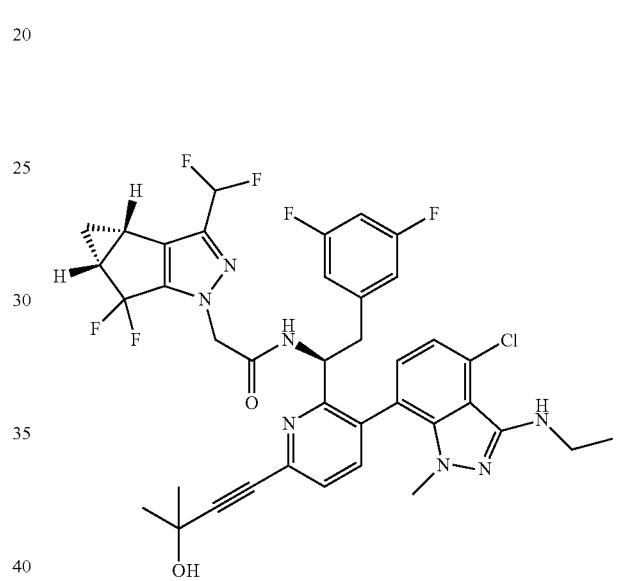
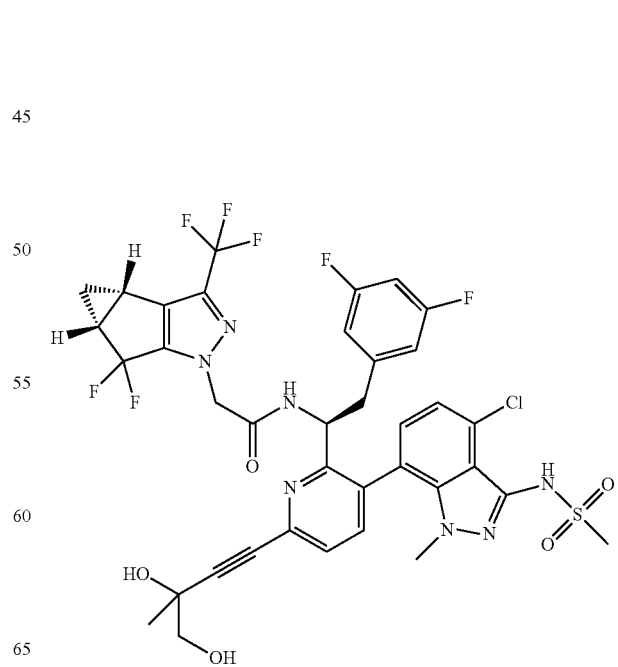

549
-continued
550
-continued
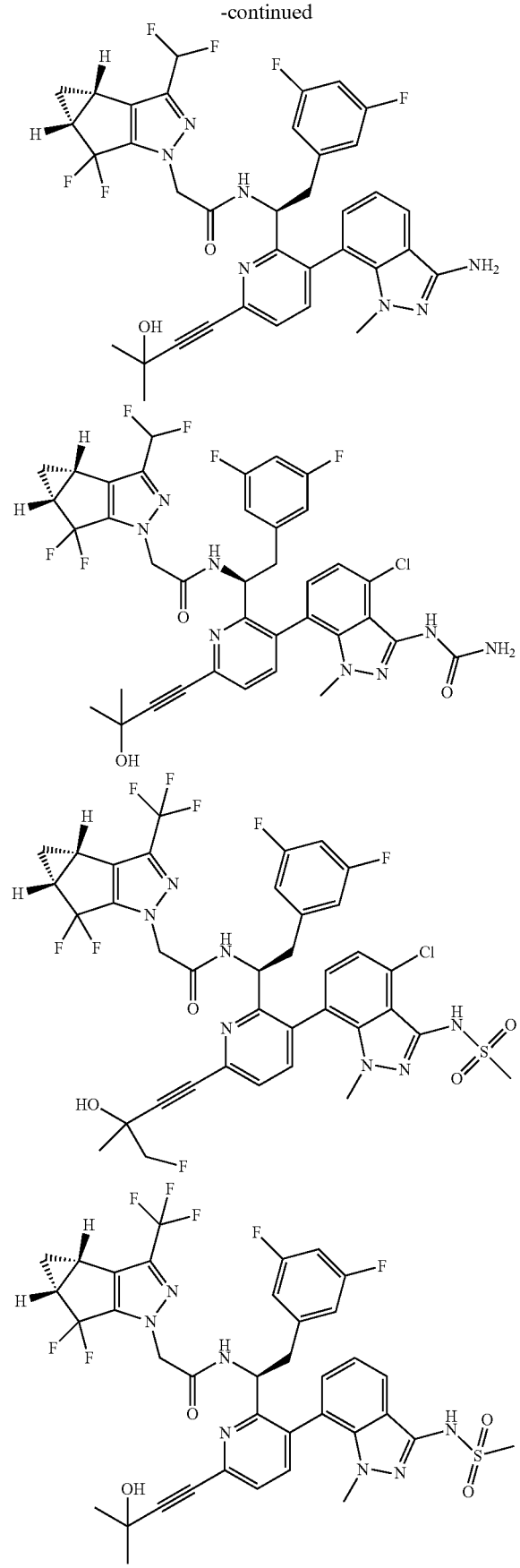
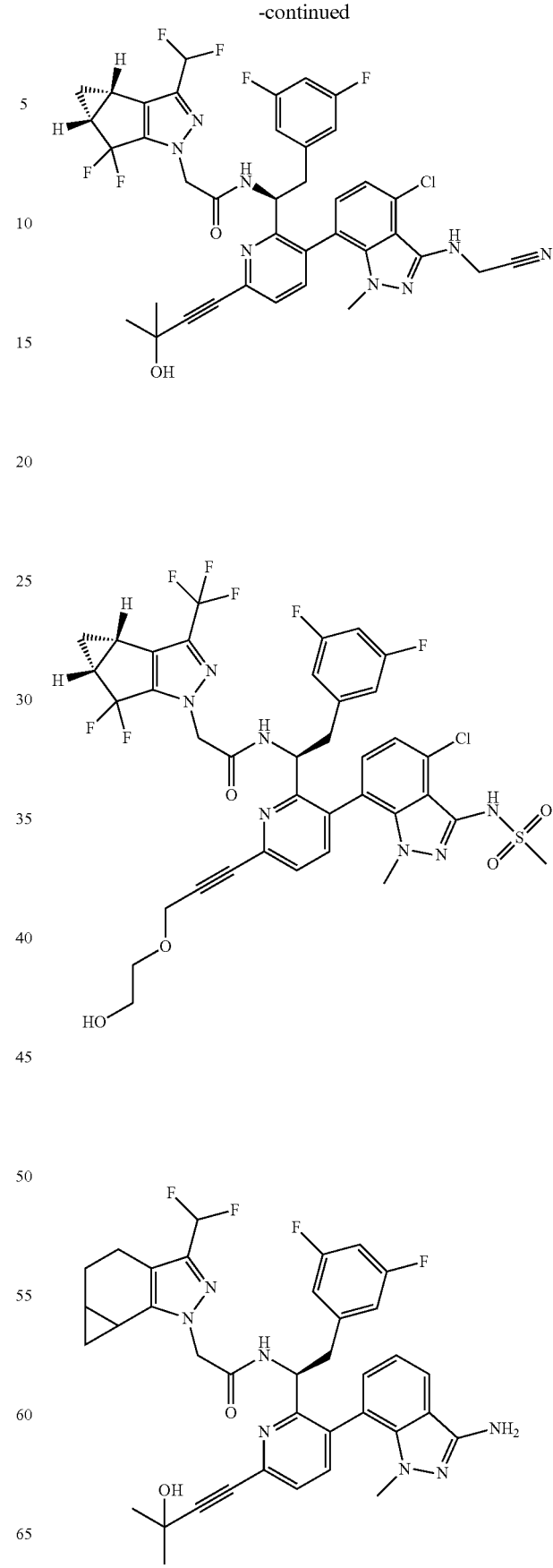

551
-continued
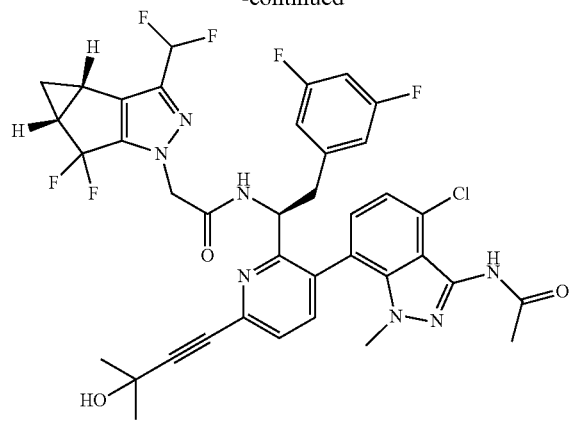
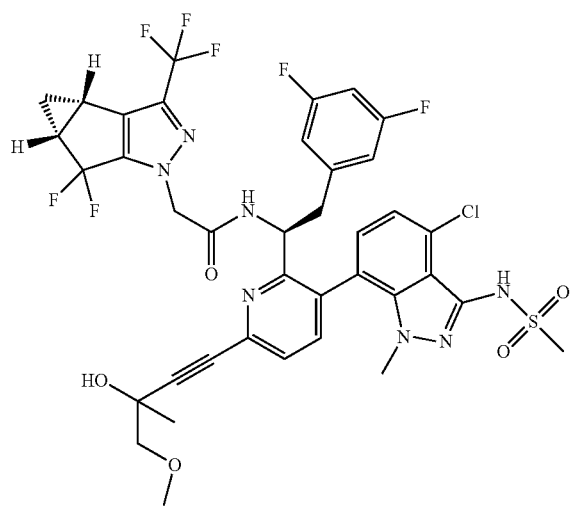
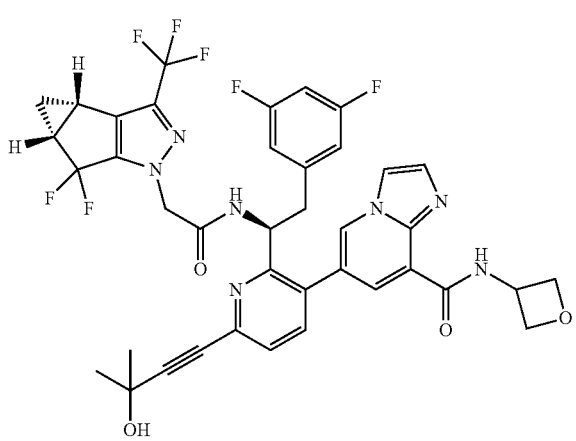
552
-continued
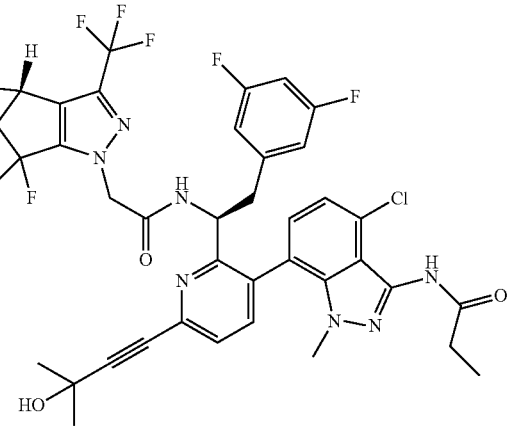
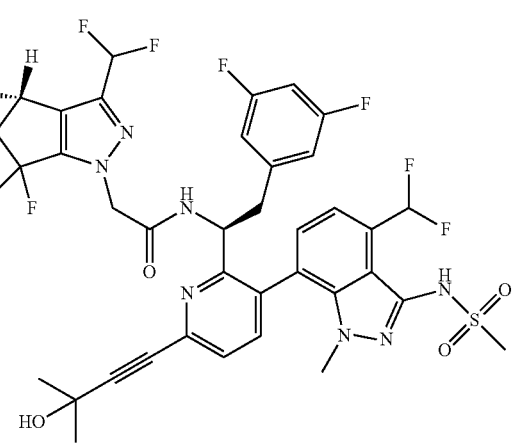
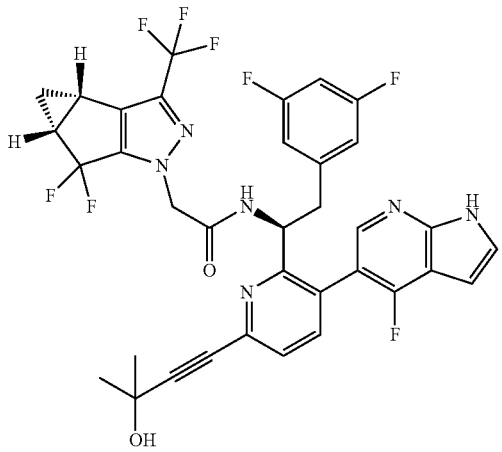

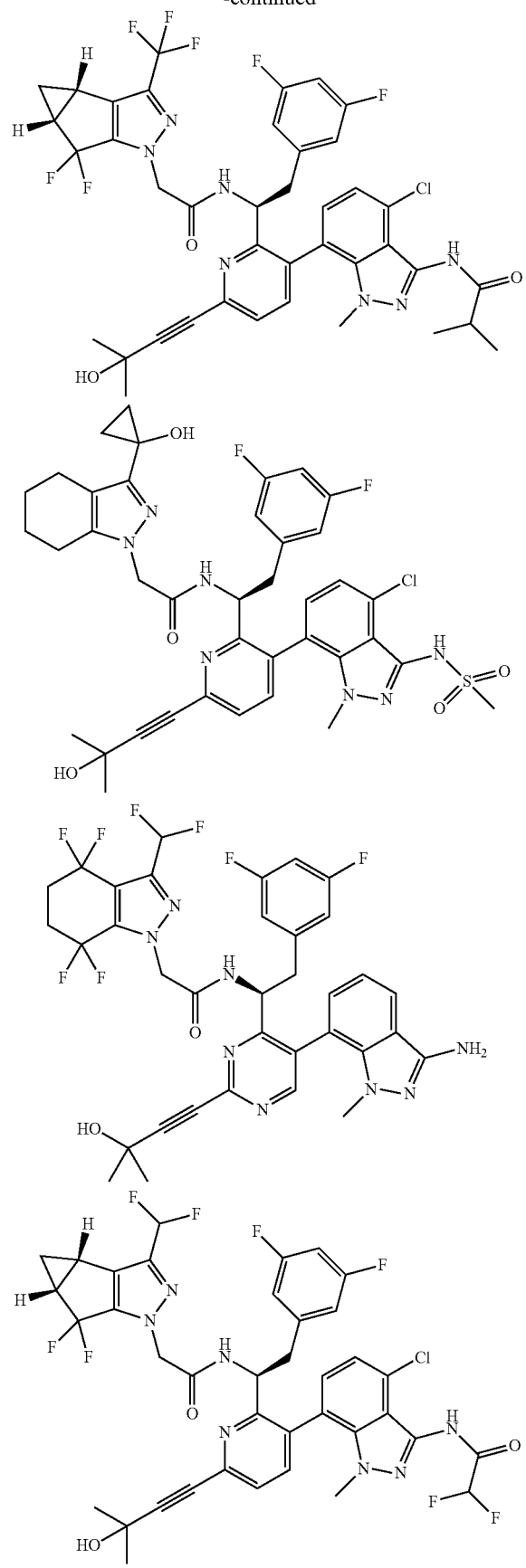
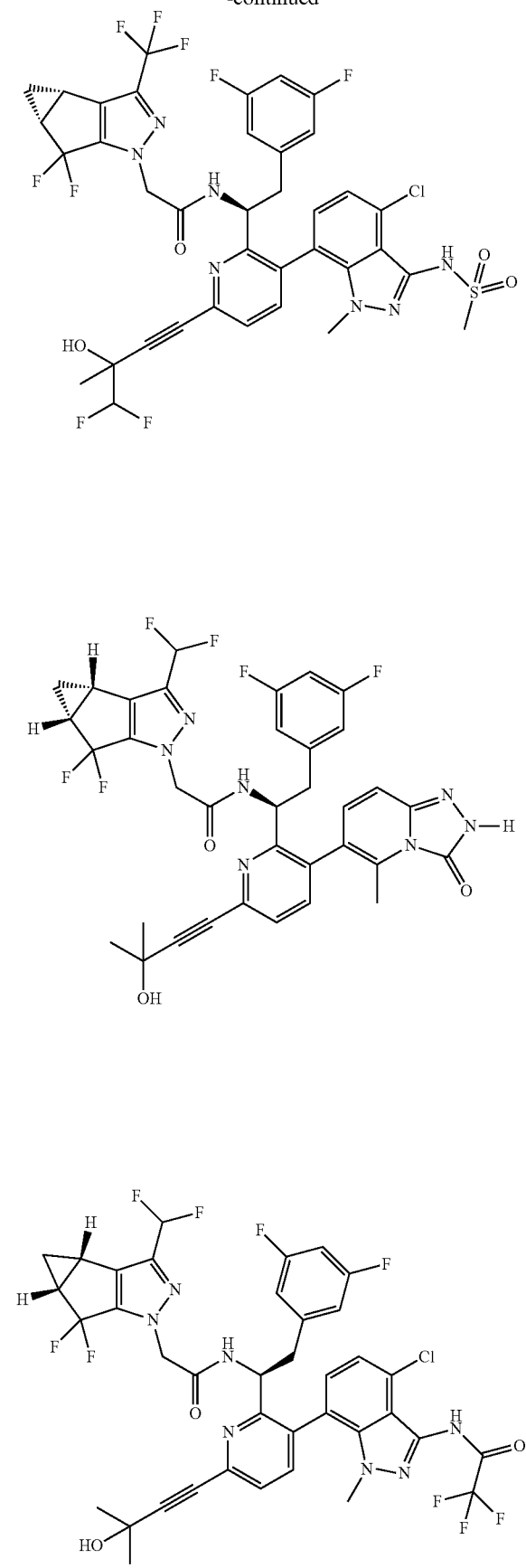

555
-continued
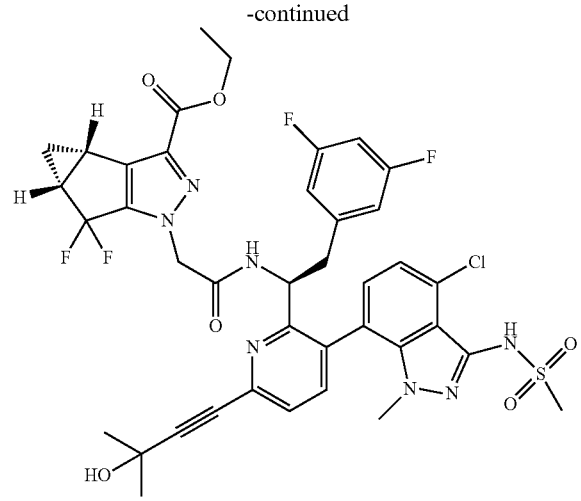
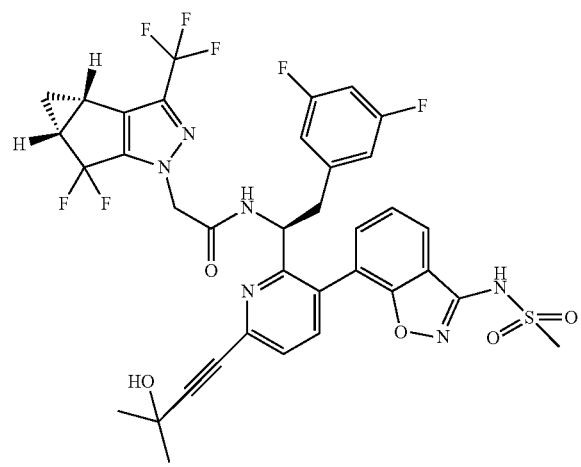
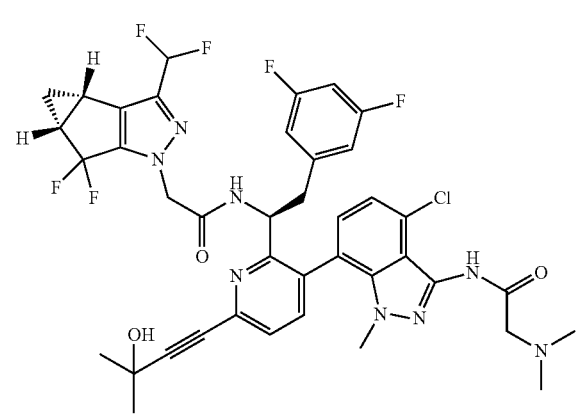
556
-continued
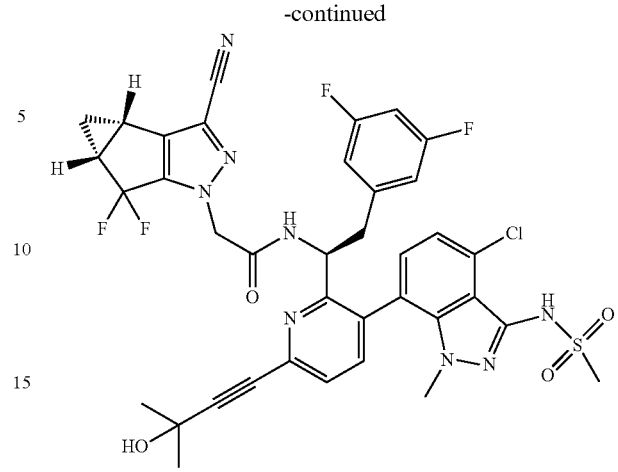
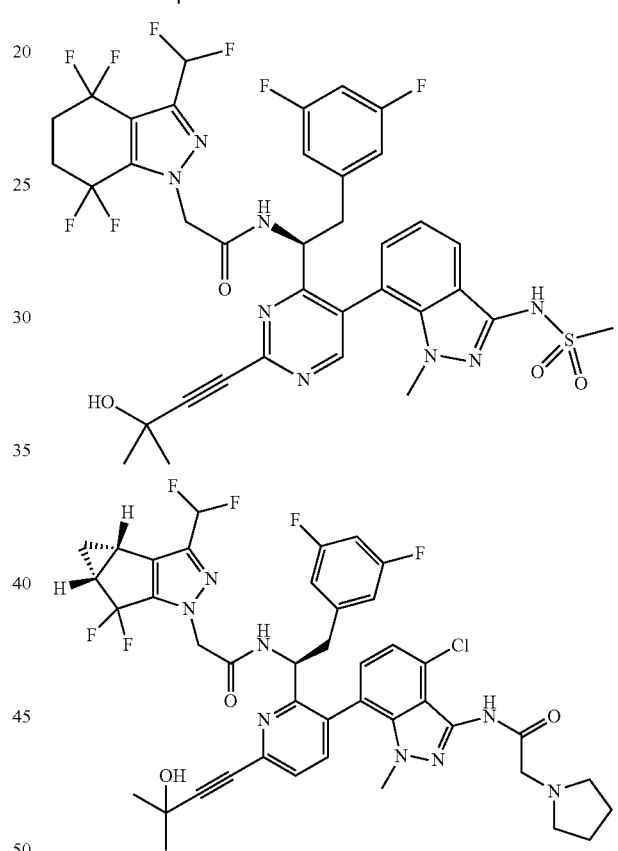
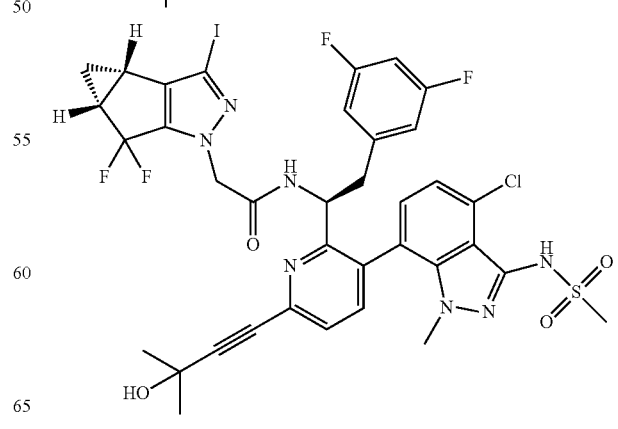

557
-continued
558
-continued
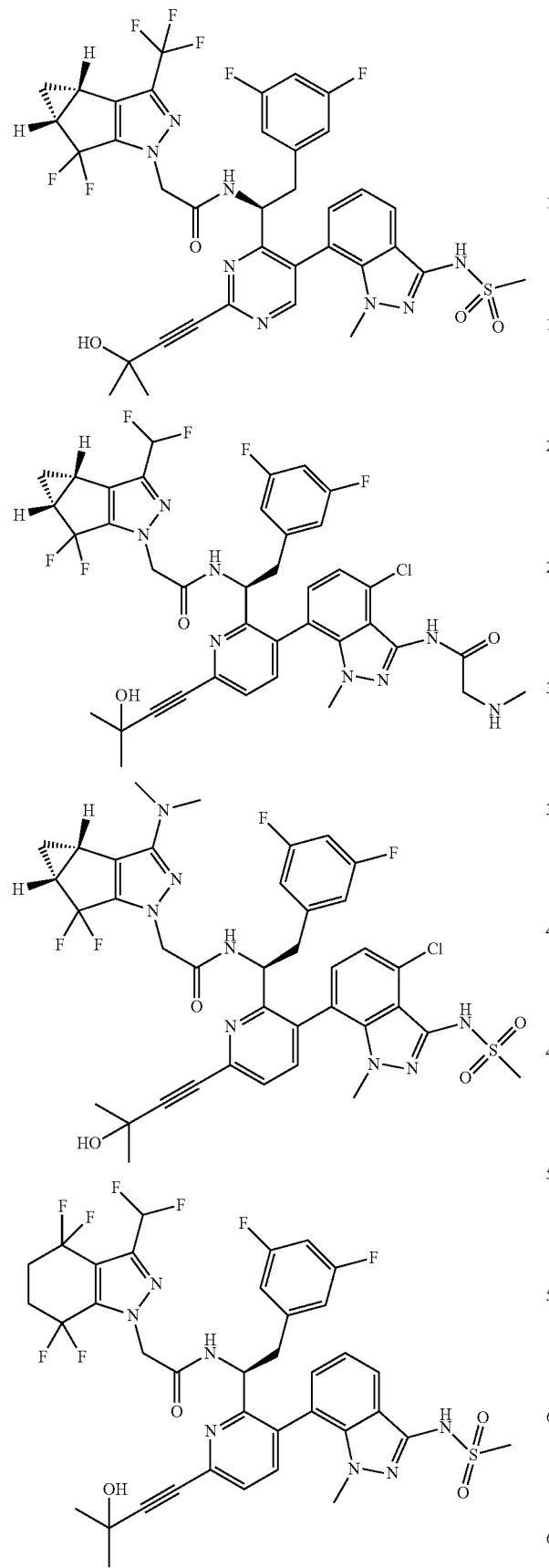
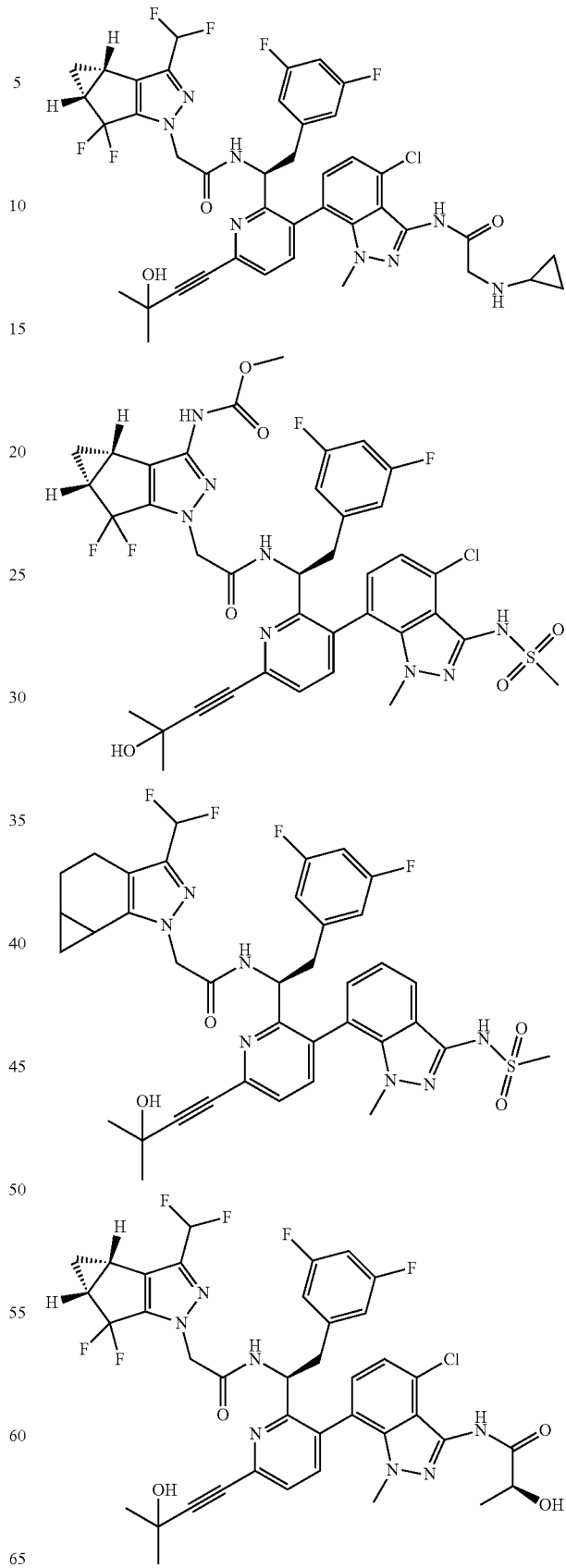

559
-continued
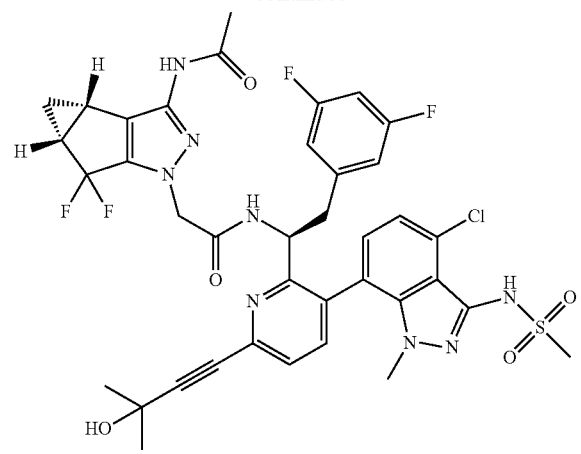
560
-continued
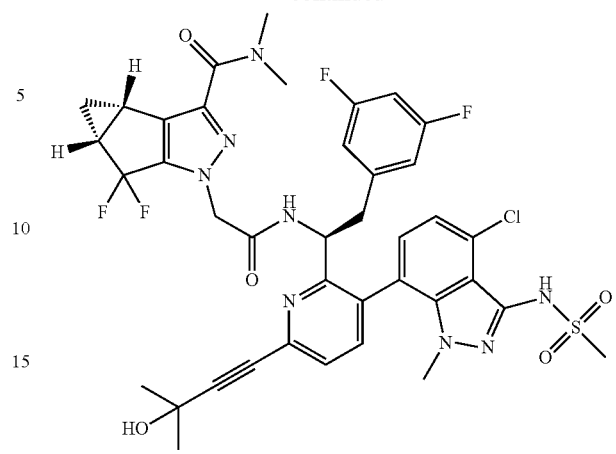
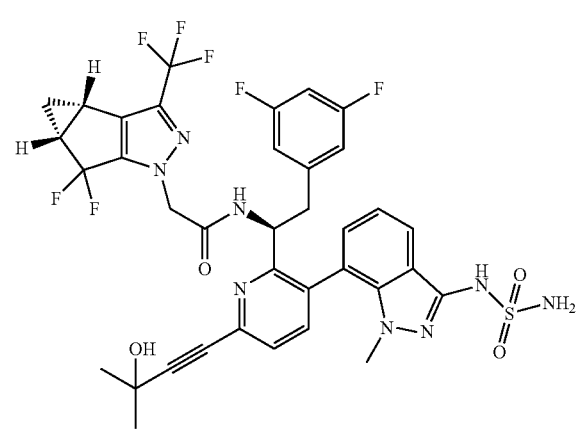
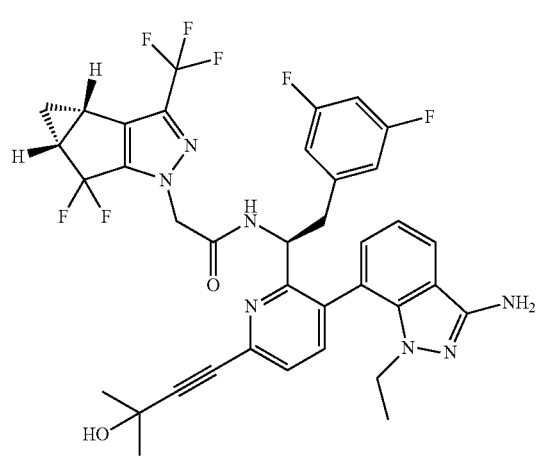
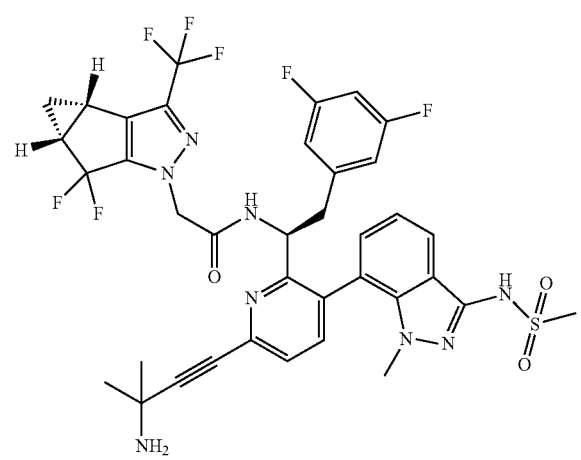
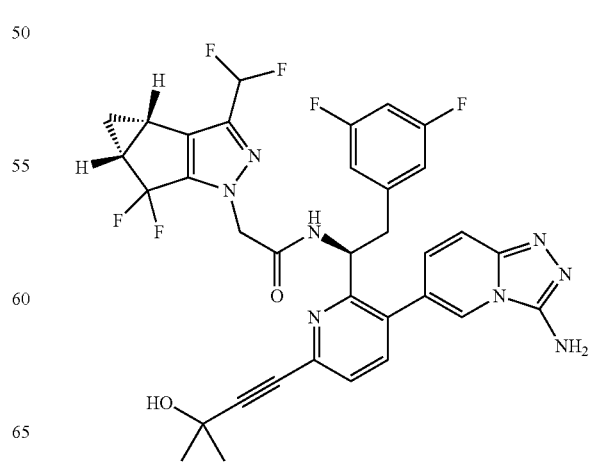

561
-continued
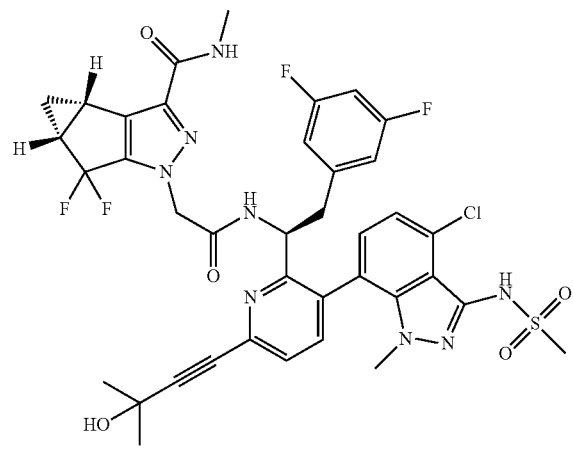
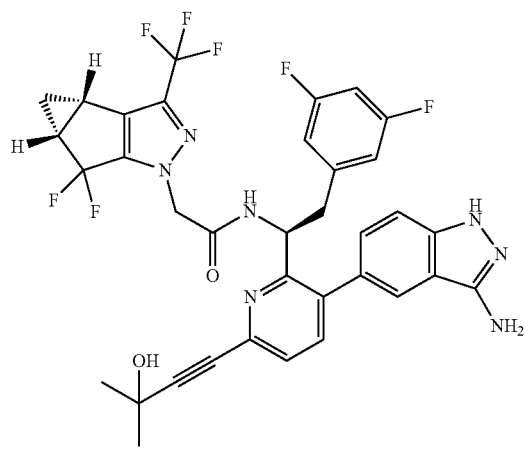
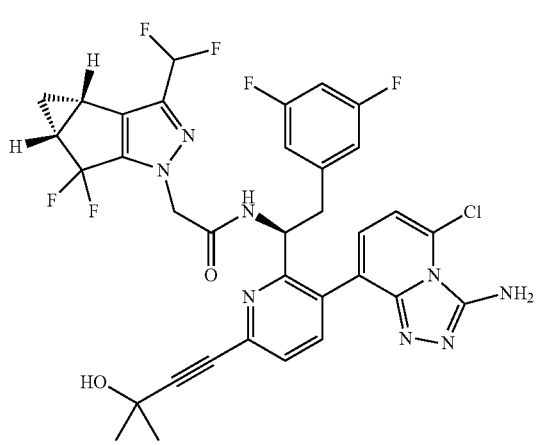
562
-continued
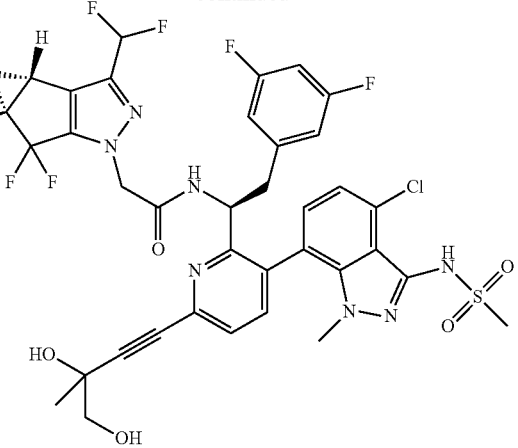
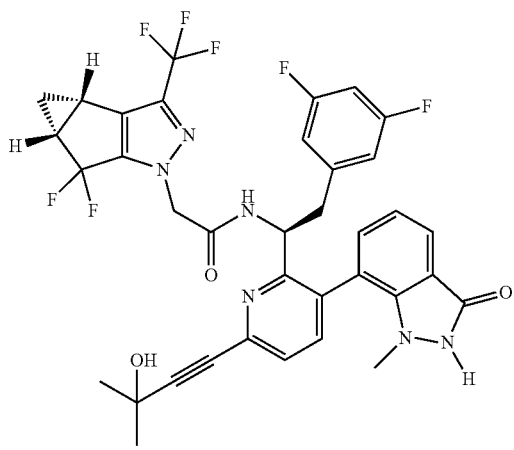

| 563 -continued | 564 -continued |
|---|---|
| 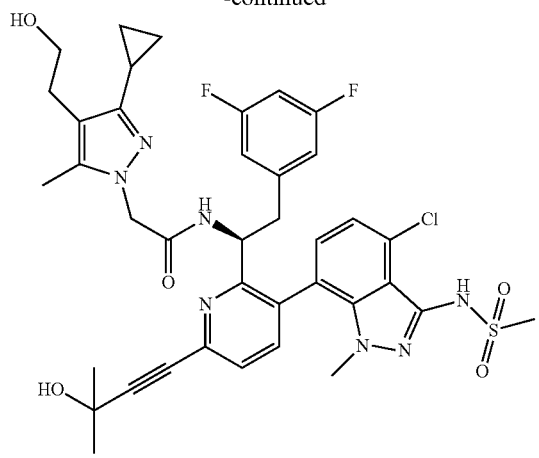 | 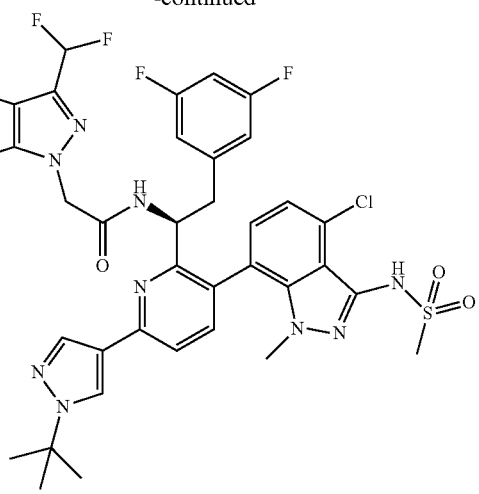 |
| 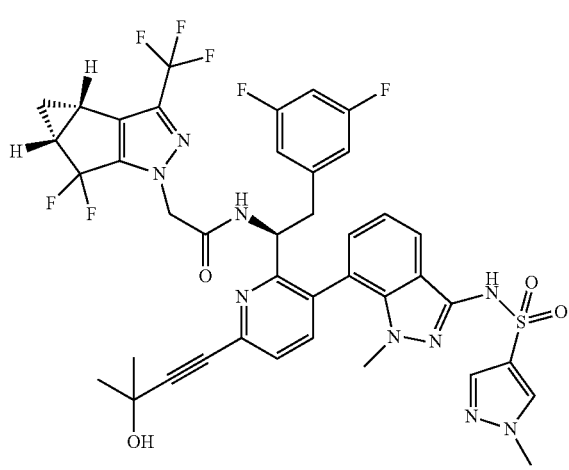 | 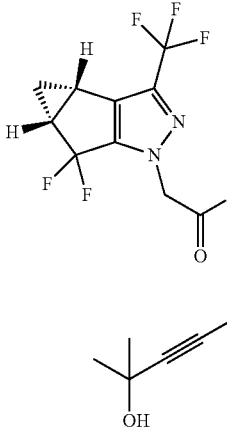 |
| 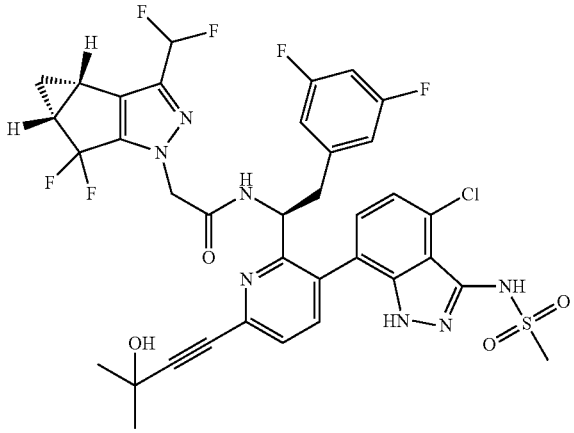 | 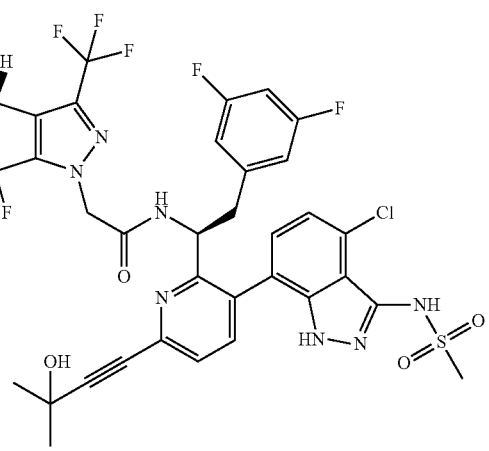 |

565
-continued
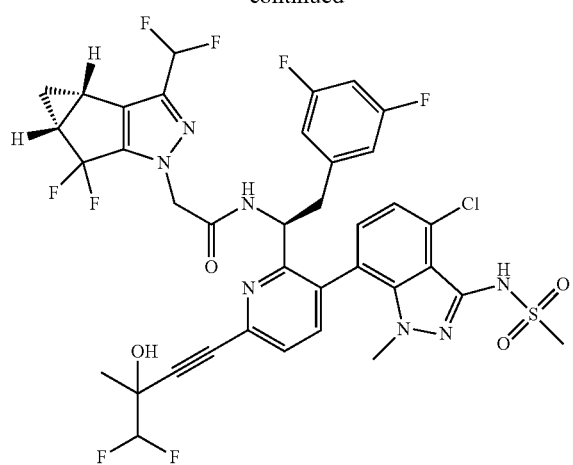
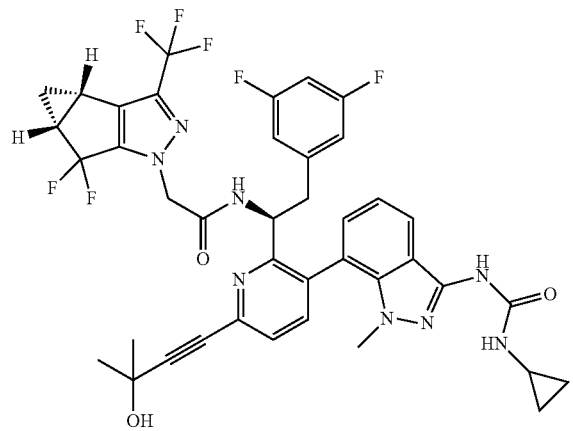
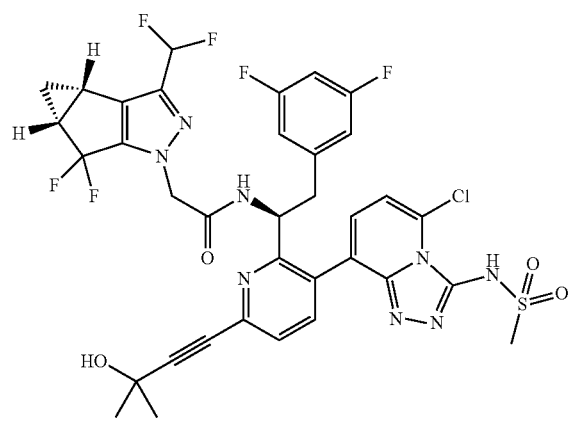
566
-continued
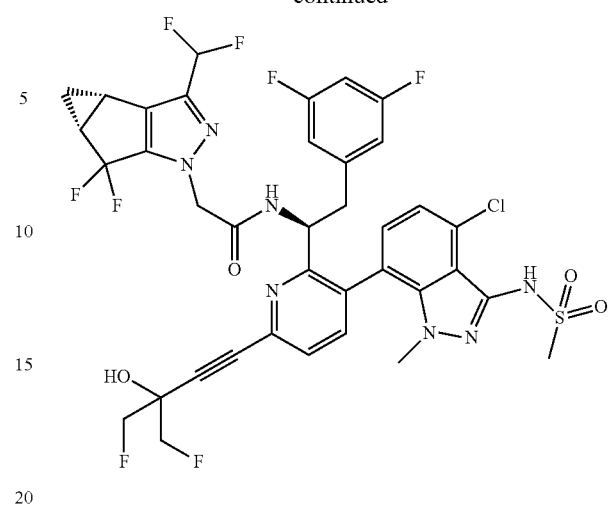
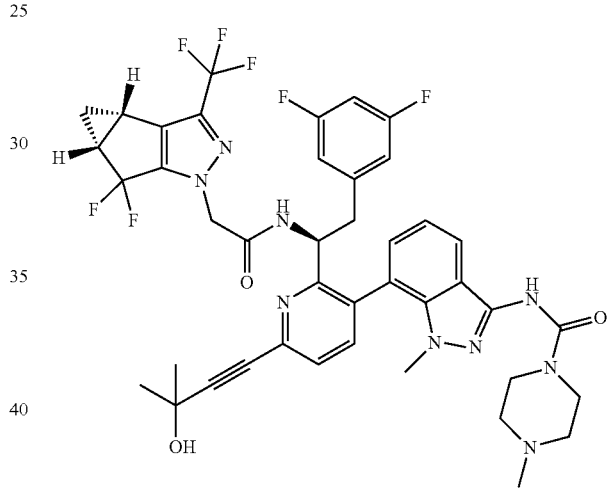
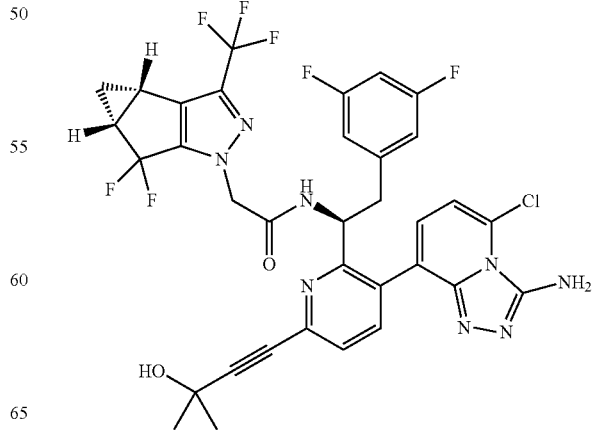

567
-continued
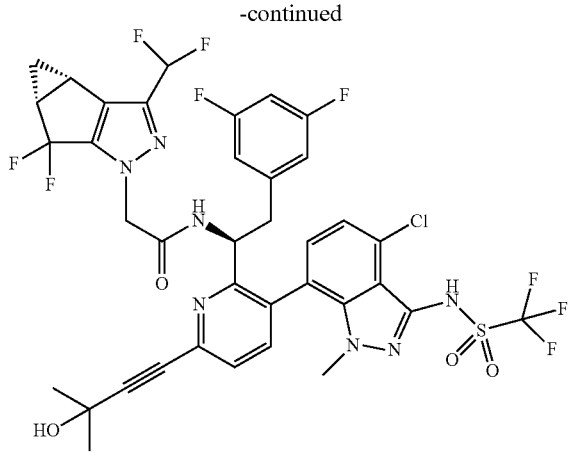
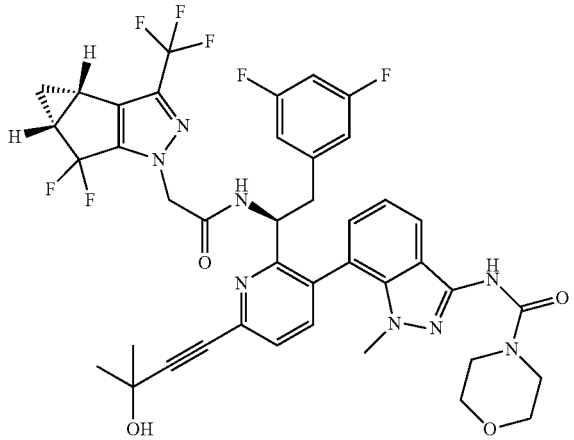
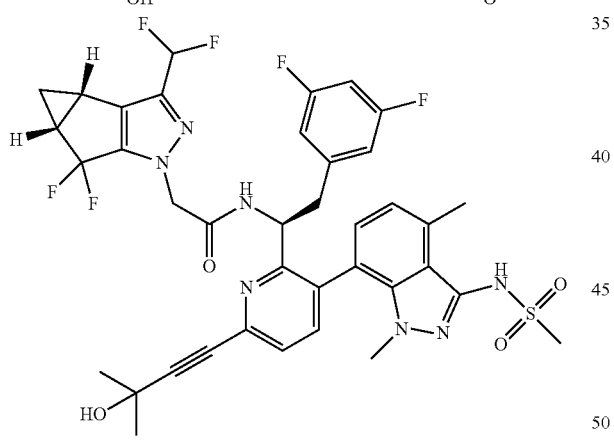
568
-continued
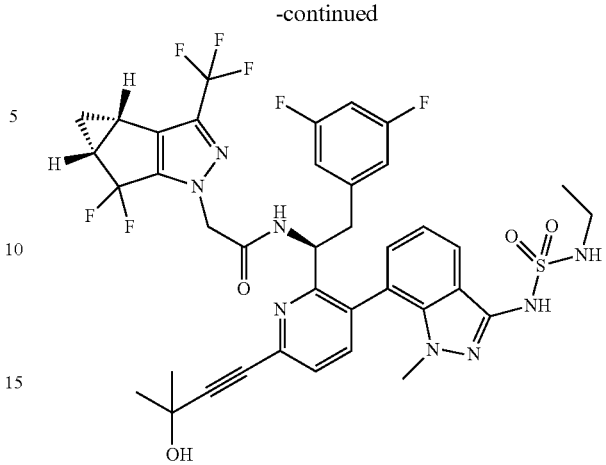
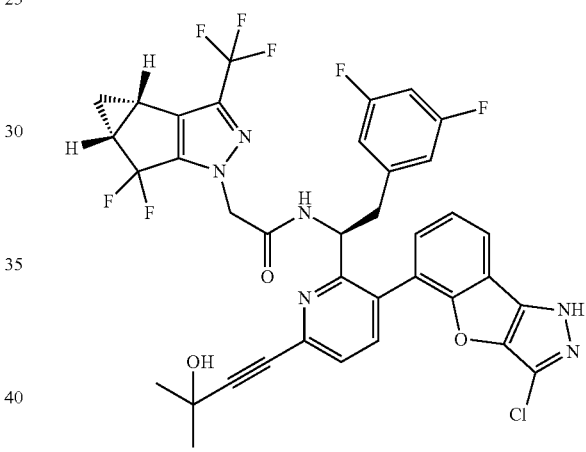
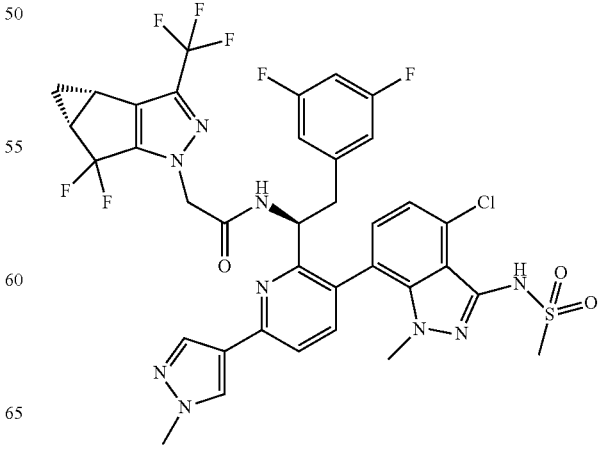

569
-continued
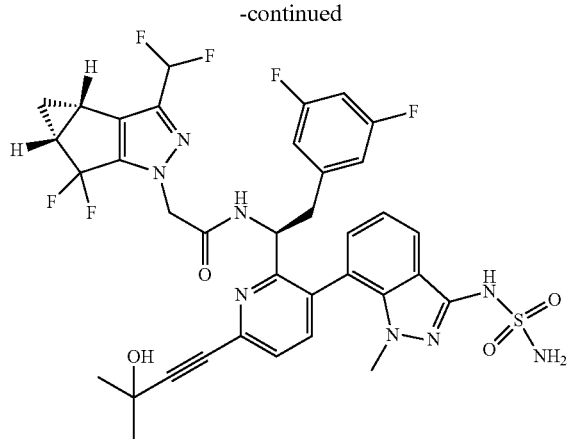
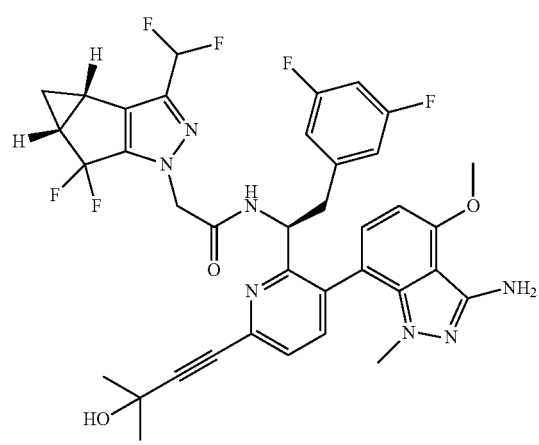
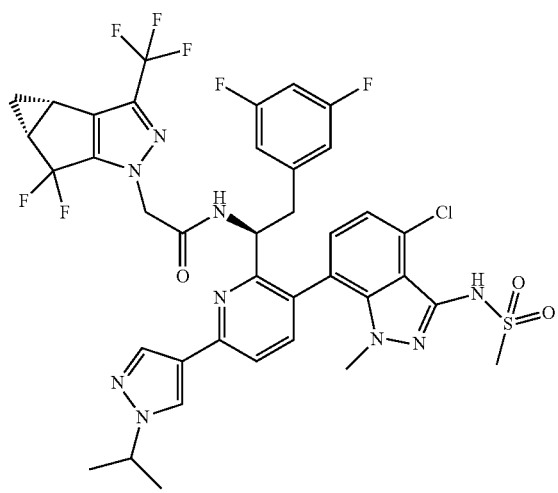
570
-continued
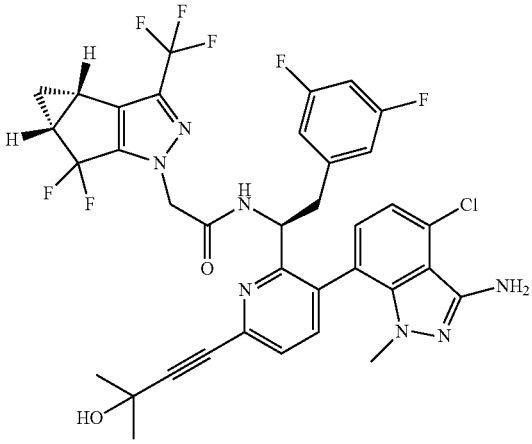
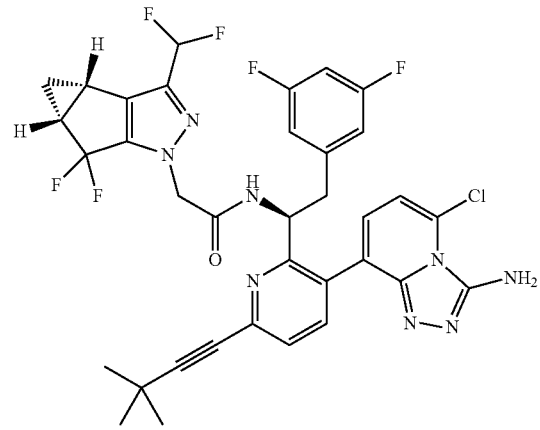
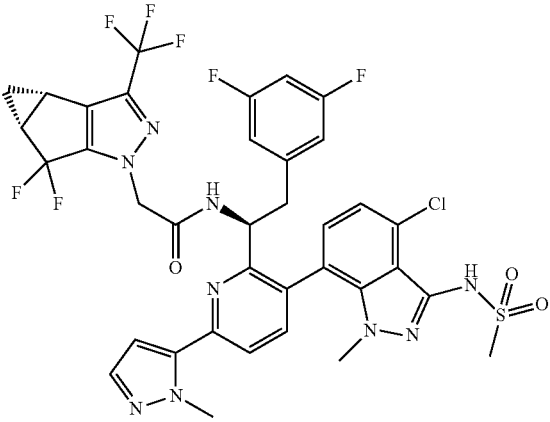

571
-continued
572
-continued
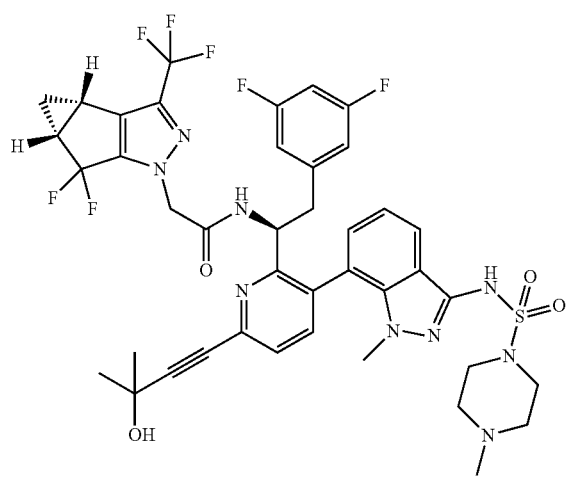
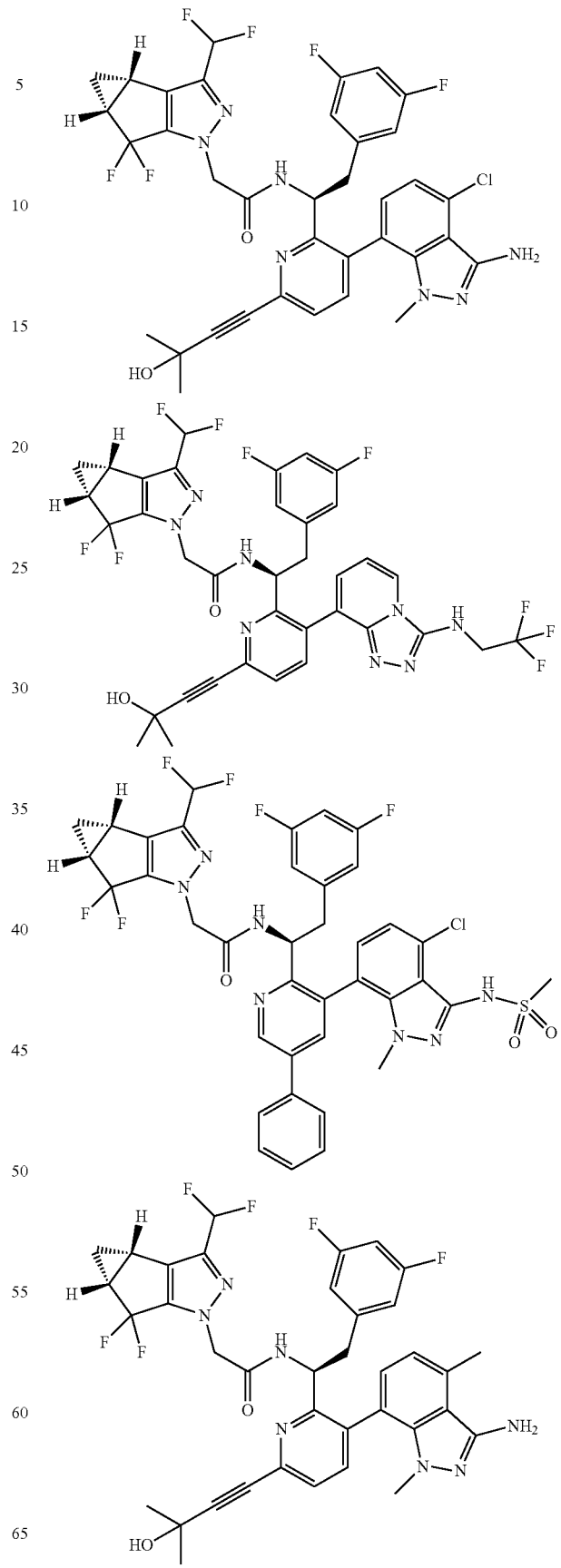

573
-continued
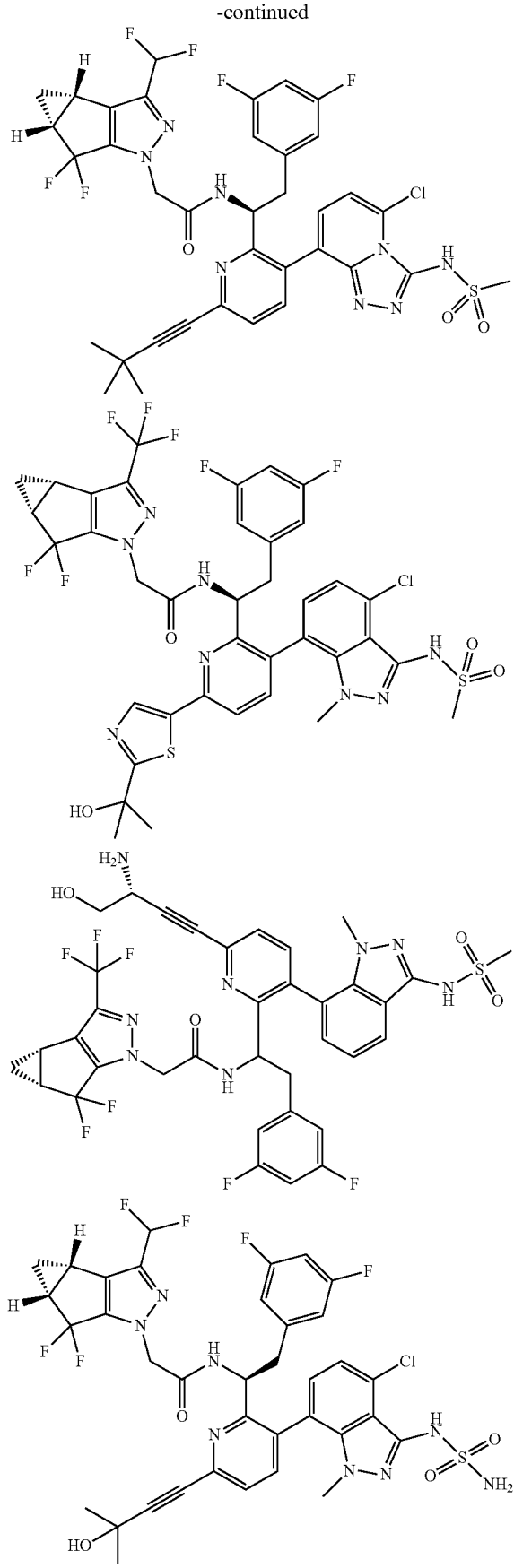
574
-continued
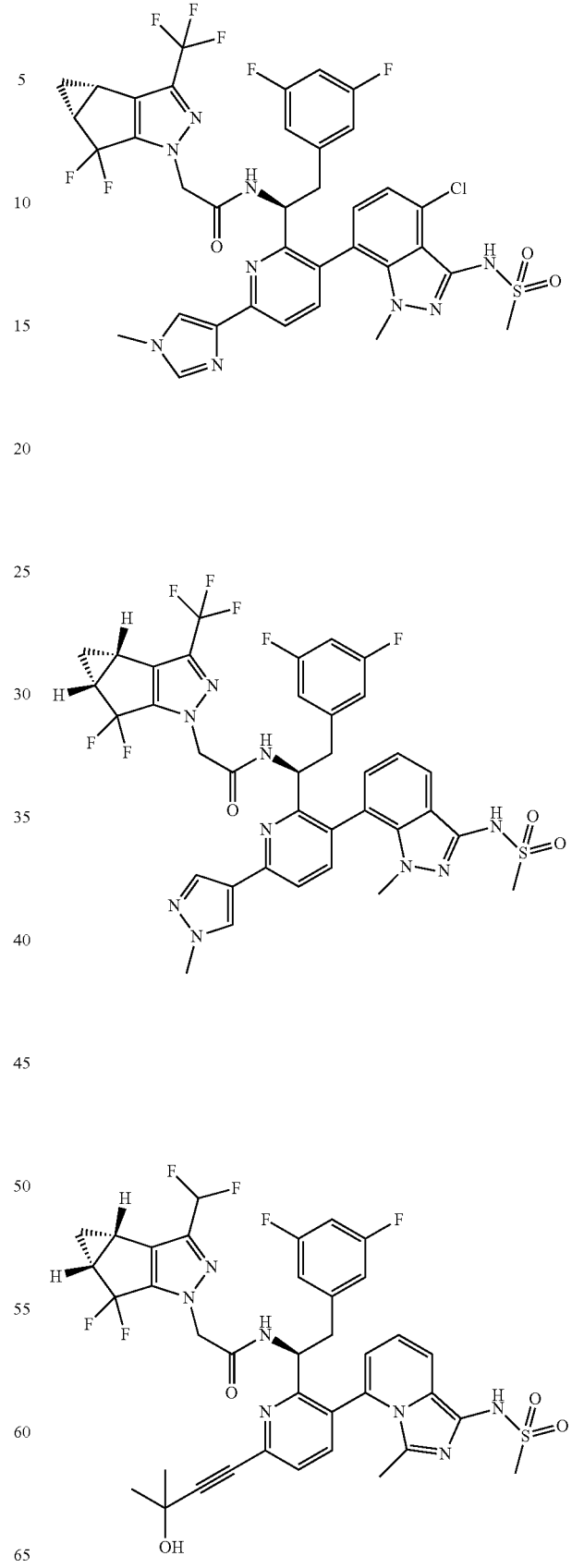

575
-continued
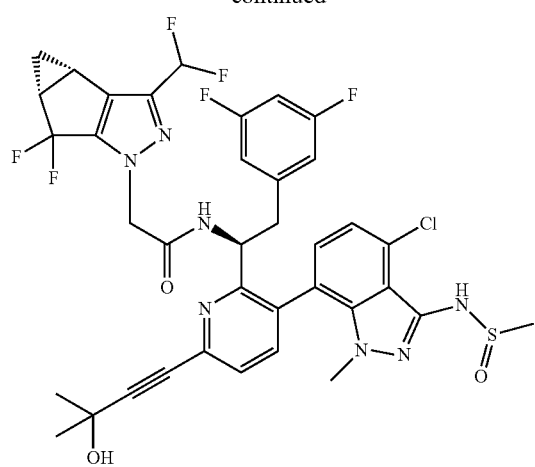
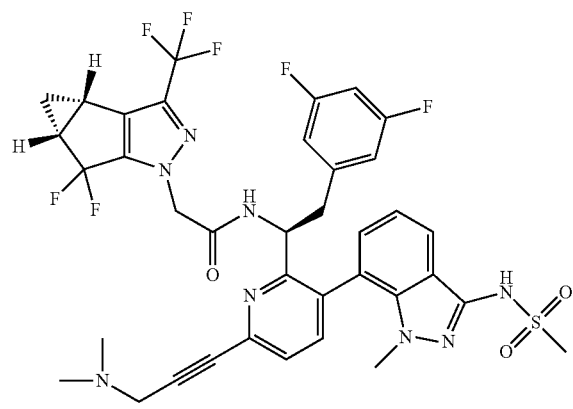
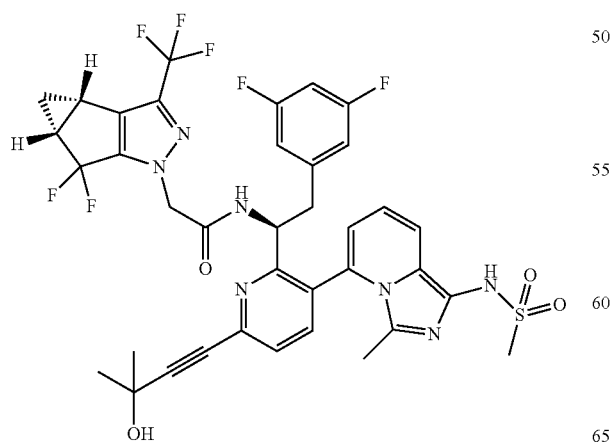
576
-continued
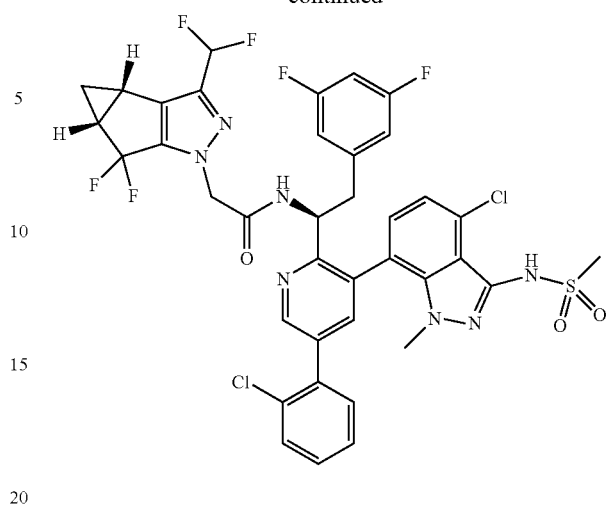
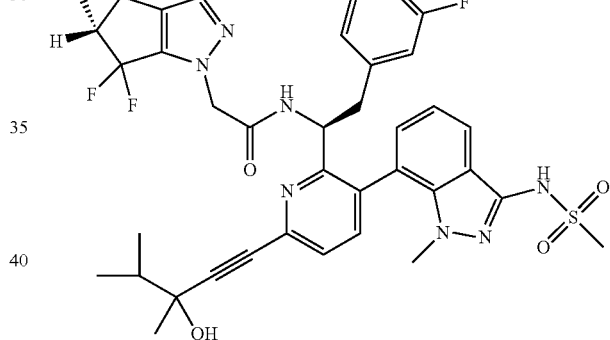
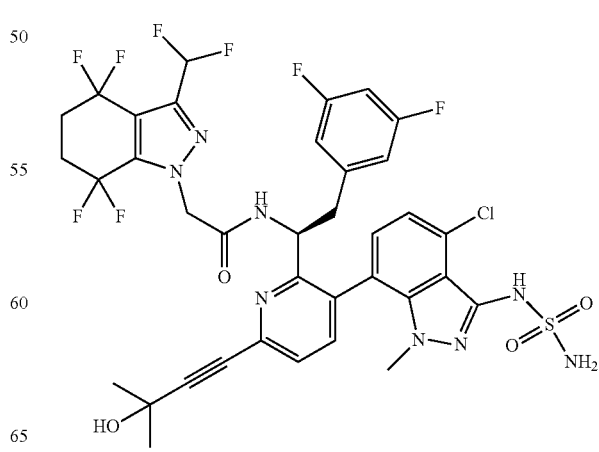

577
-continued
578
-continued
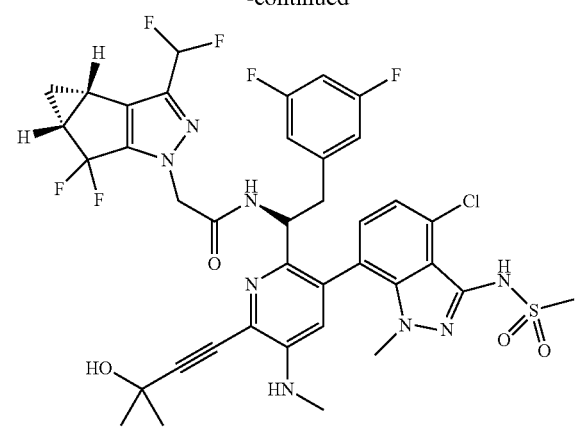
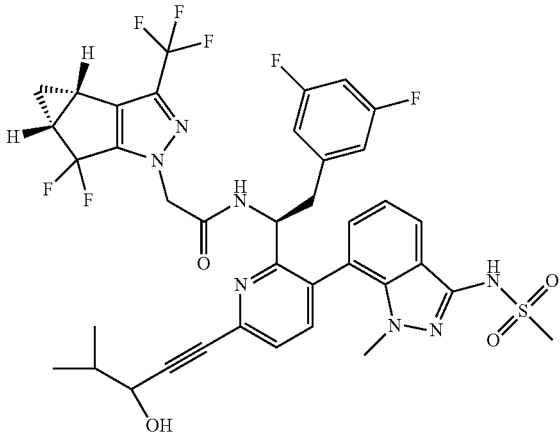

579
-continued
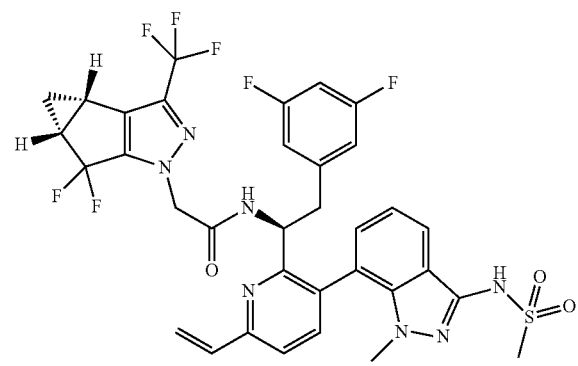
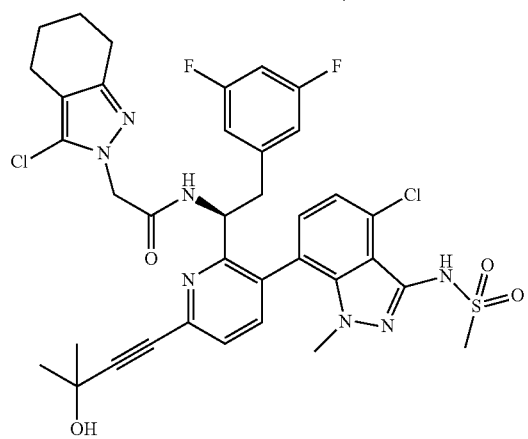
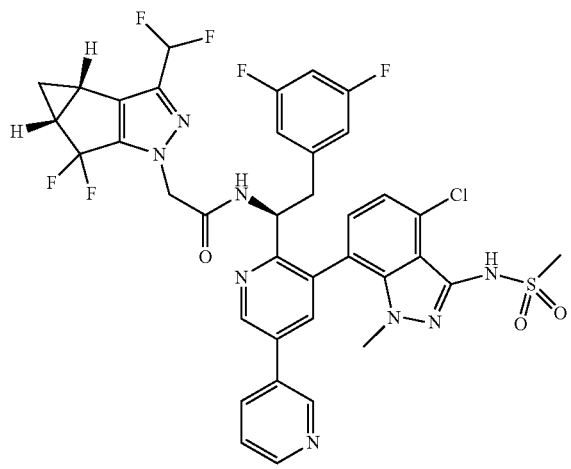
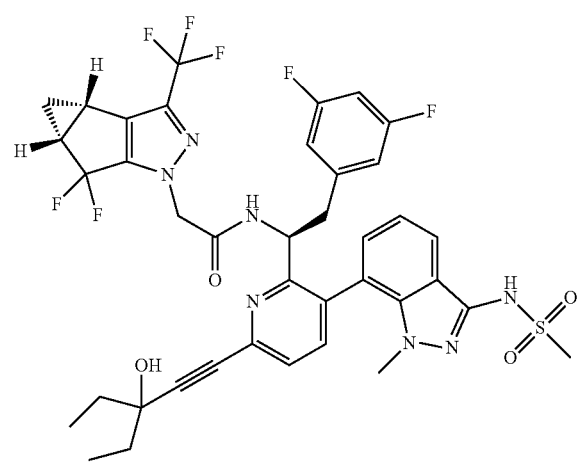
580
-continued
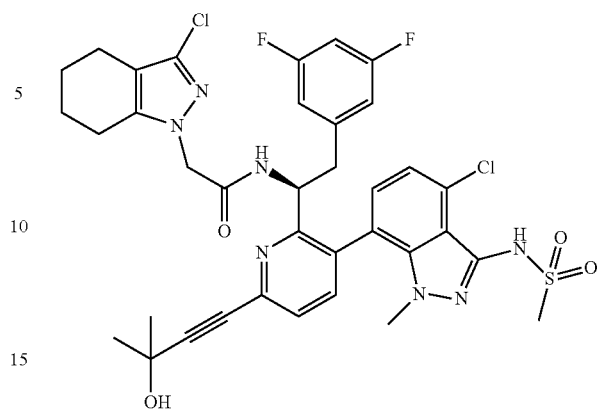
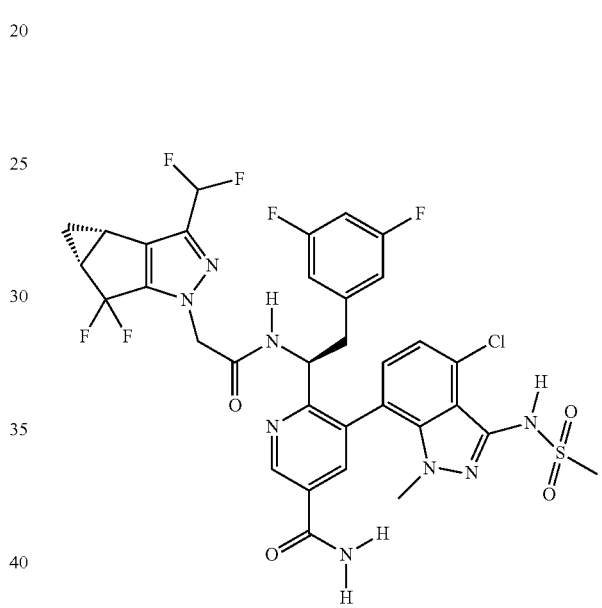
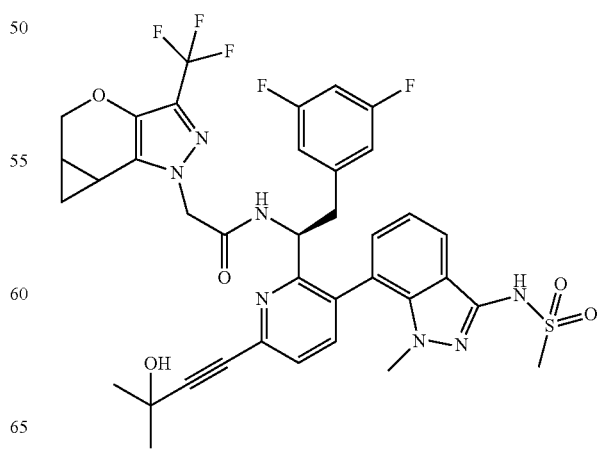

581
-continued
582
-continued
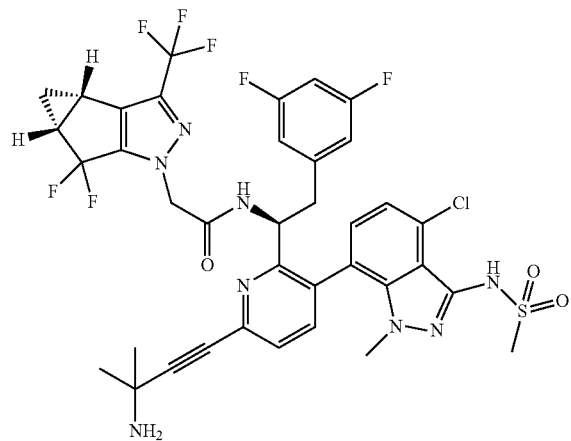
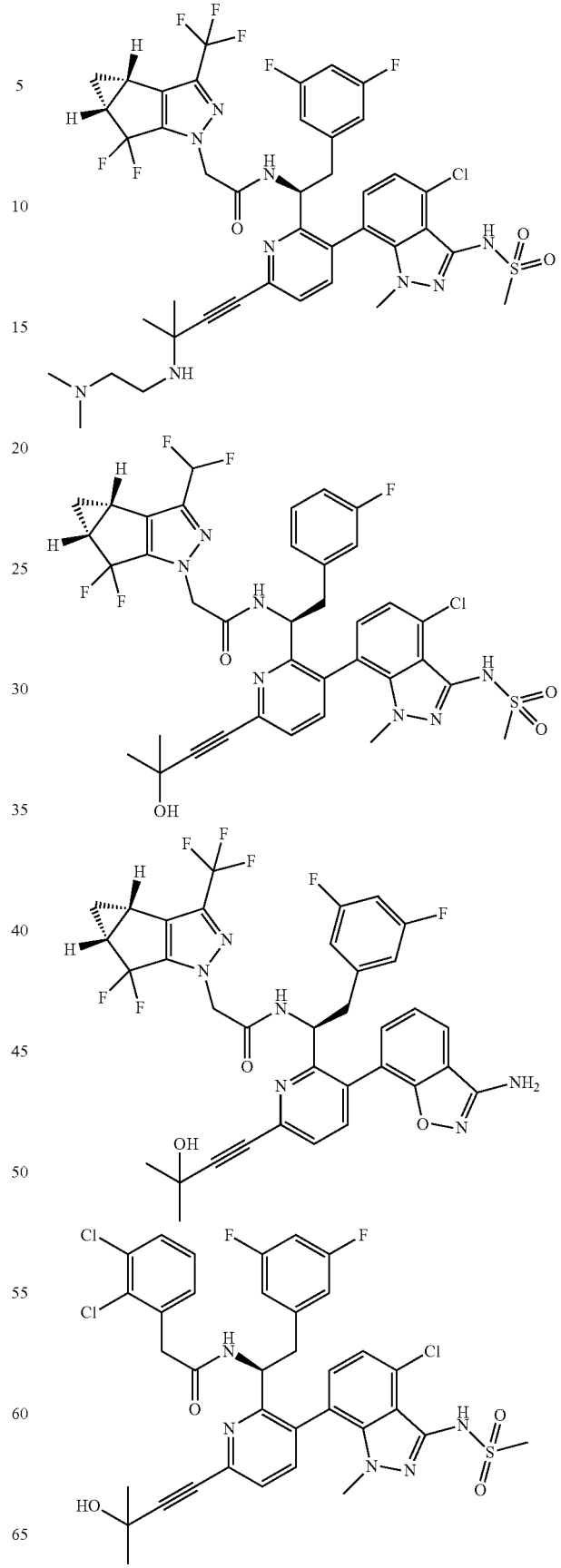

583
-continued
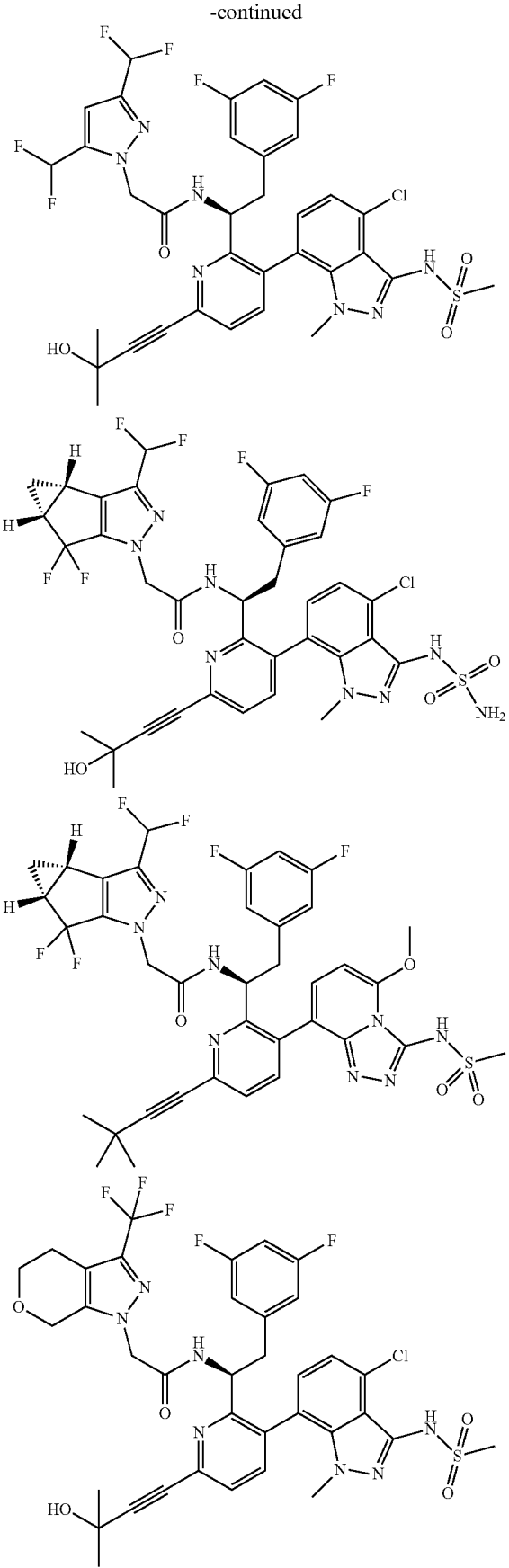
584
-continued
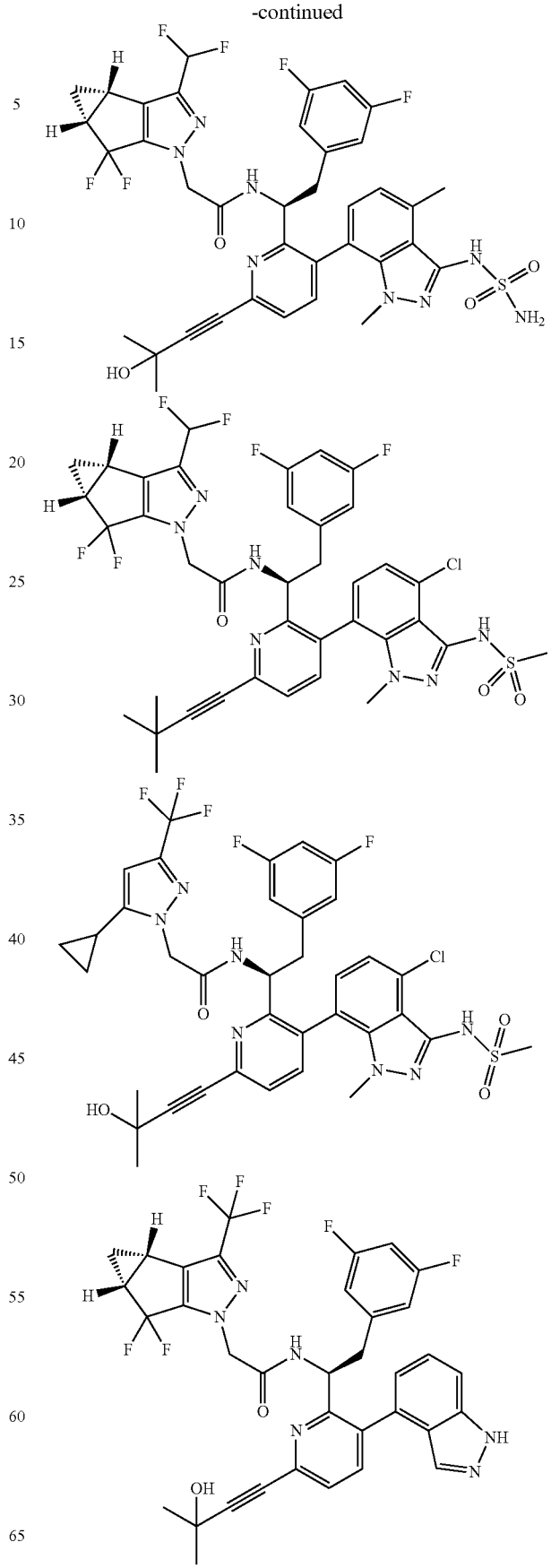

585
-continued
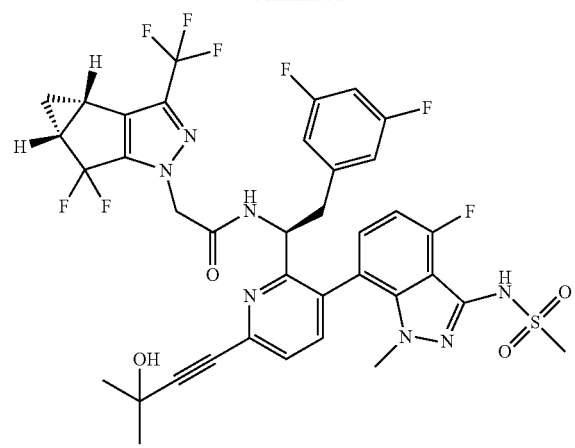
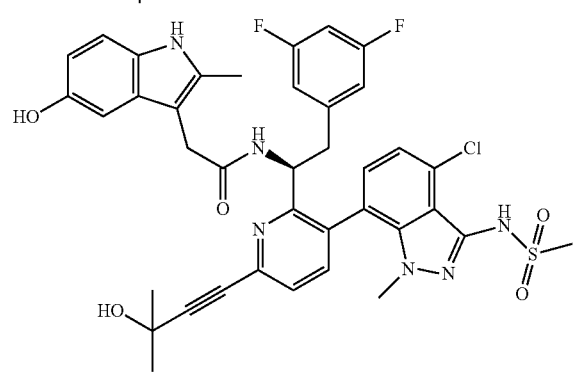
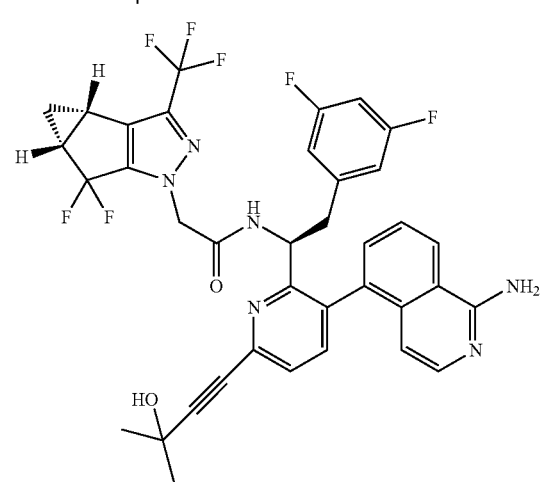
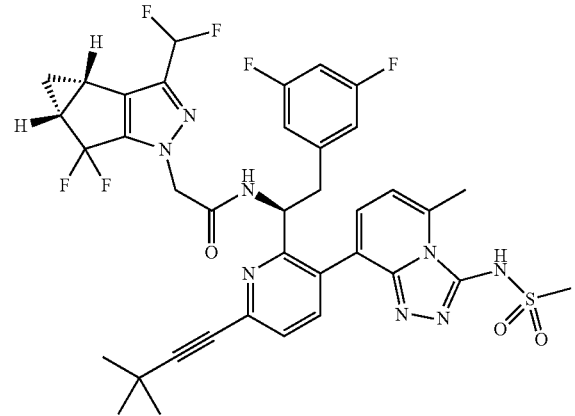
586
-continued
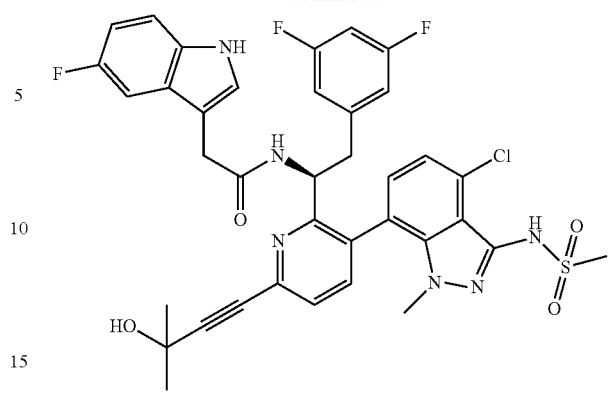
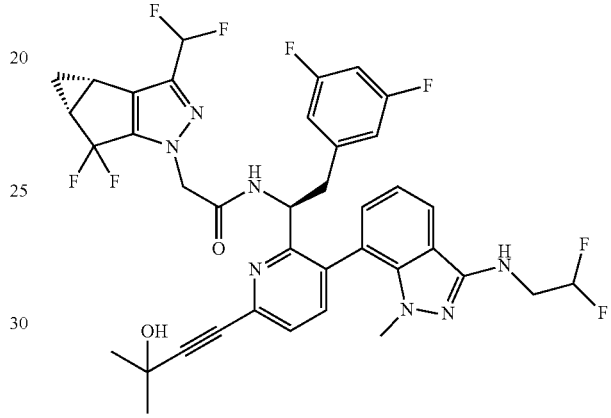
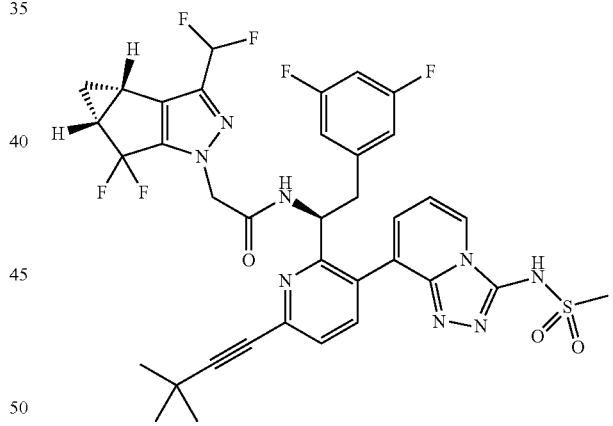
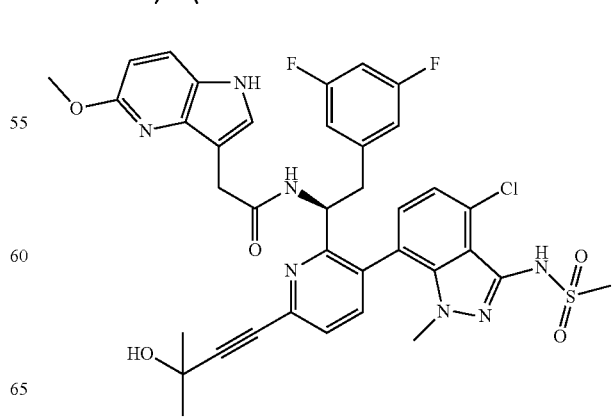

587
-continued
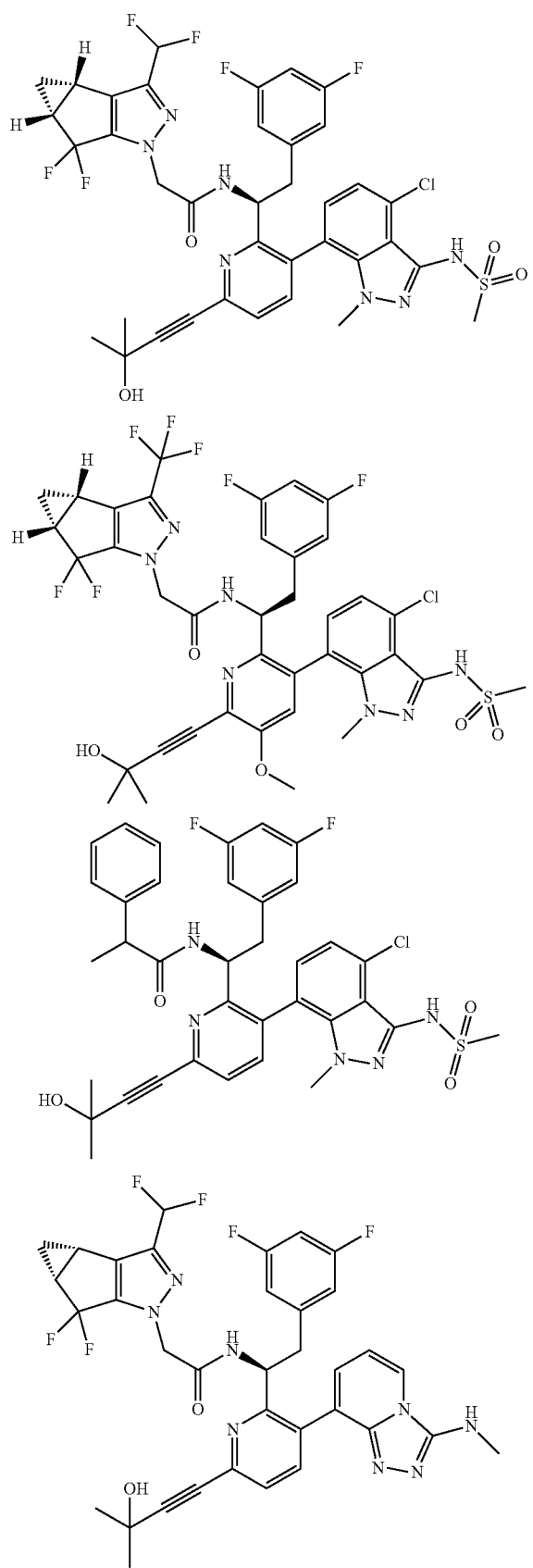
588
-continued
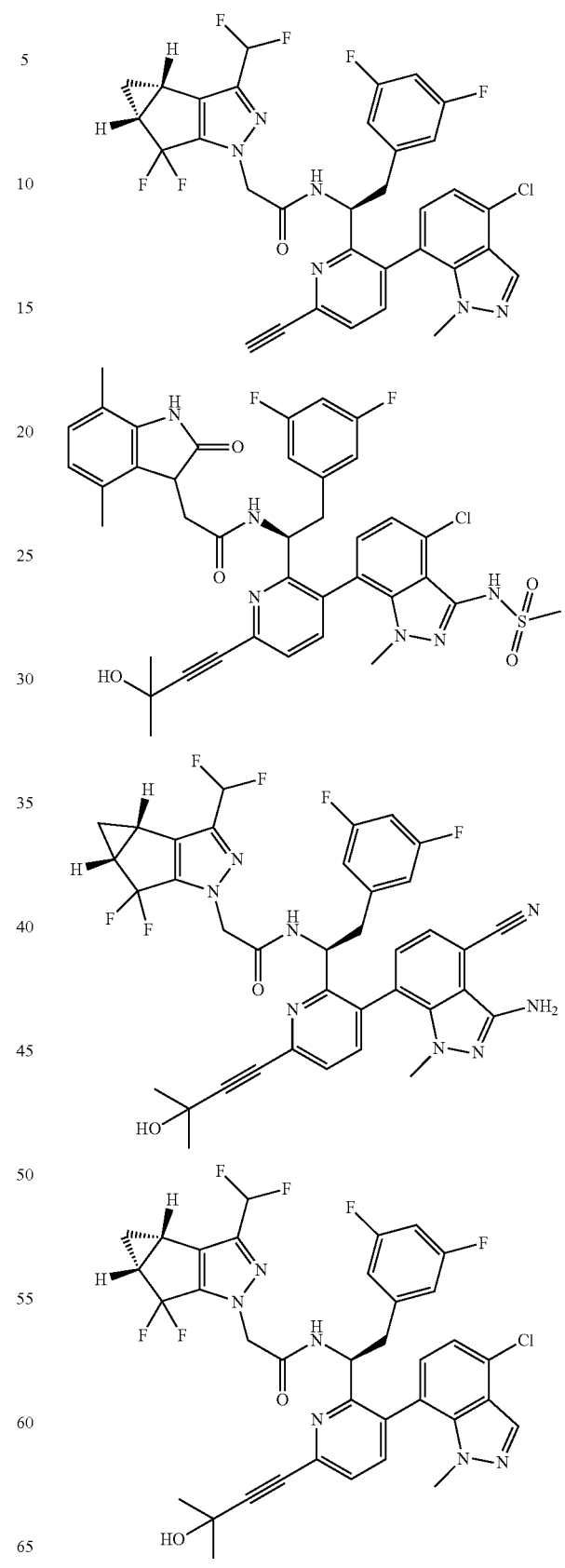

589
-continued
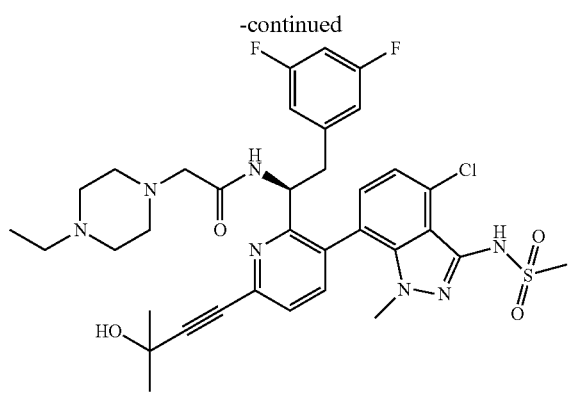
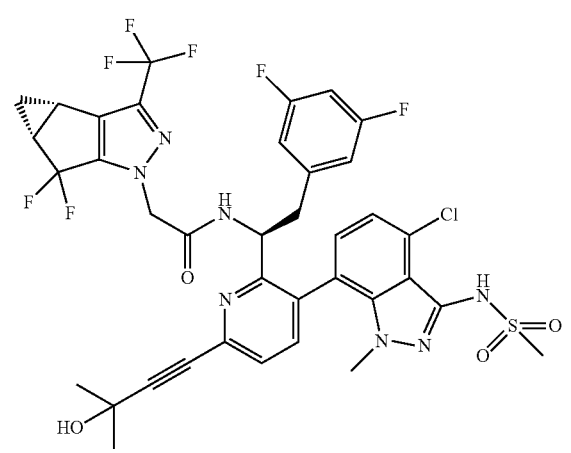
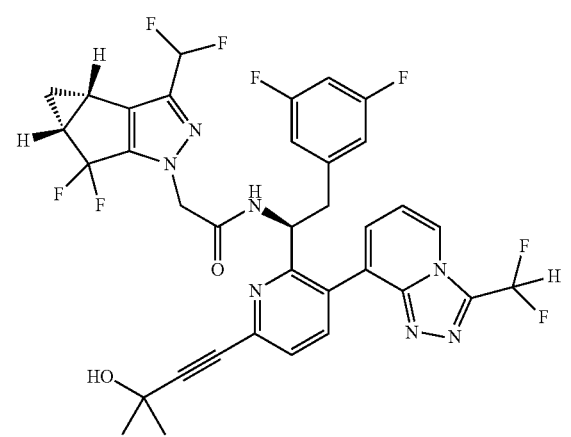
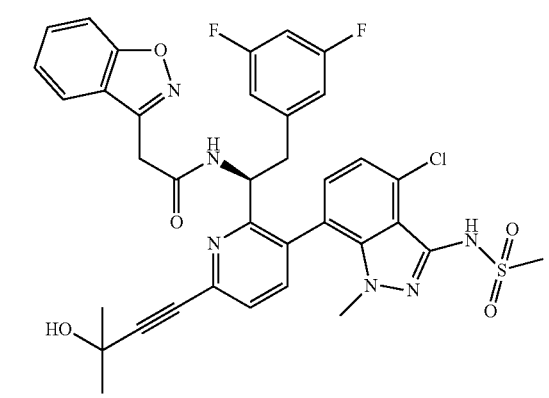
590
-continued
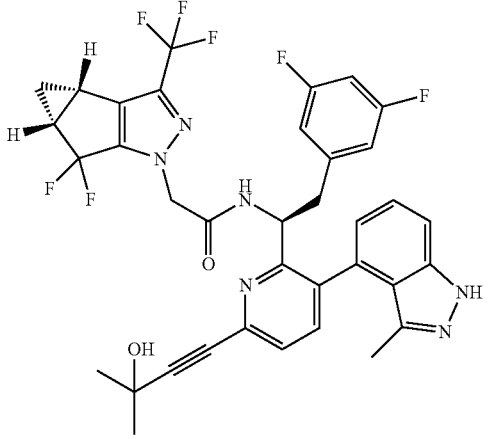
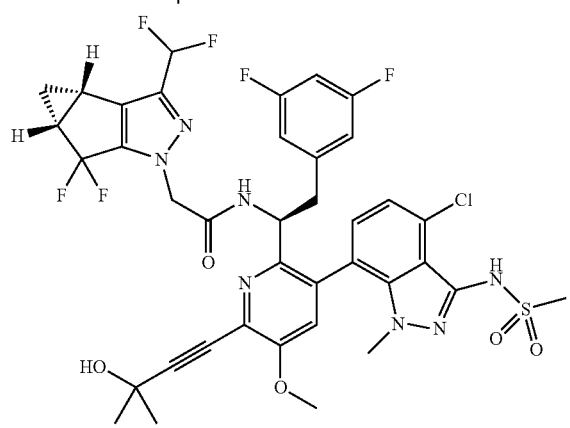
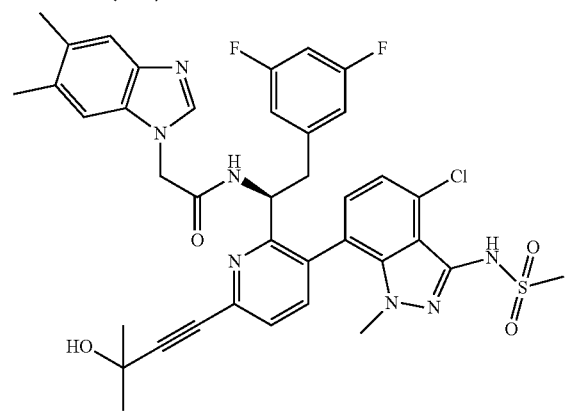
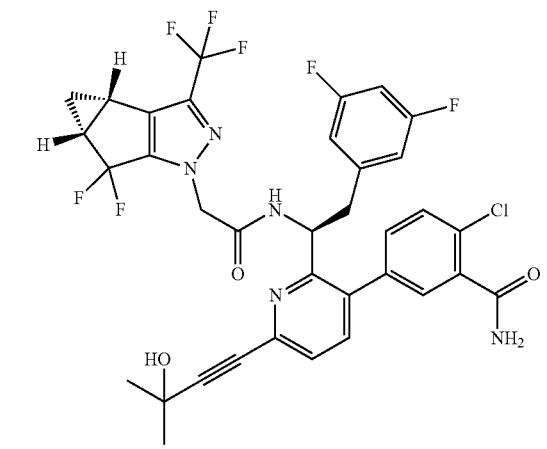

-continued

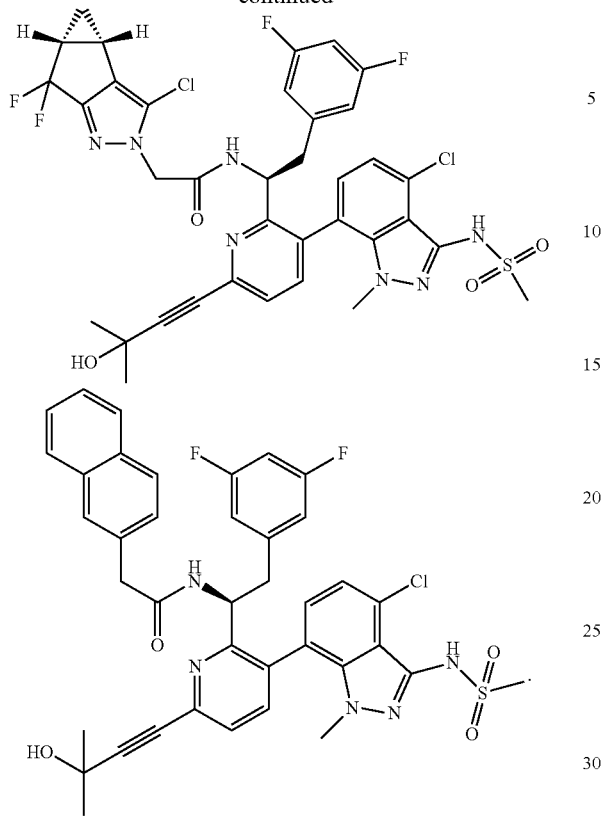

16. A pharmaceutical composition comprising a compound of claim 1, or a pharmaceutically acceptable salt thereof, and a pharmaceutically acceptable carrier.

17. A pharmaceutical composition comprising a compound of claim 1, or a pharmaceutically acceptable salt thereof, and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor or combinations thereof.

18. A method for treating a HIV infection in a patient in need thereof comprising administering a therapeutically effective amount of a compound of claim 1, or a pharmaceutically acceptable salt thereof, to the patient.

19. A method for treating an HIV infection in a patient in need thereof comprising administering to the patient a therapeutically effective amount of a compound of claim 1, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor or combinations thereof.

20. A compound of formula IIIe:

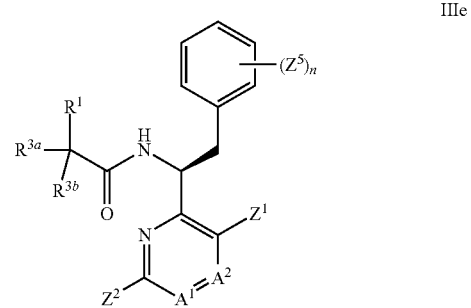

IIIe wherein
$A^1$ is CH;
$A^2$ is CH;
$R^1$ has the following formula:

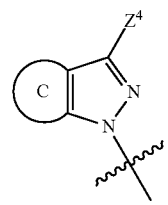

wherein
C together with the two carbon atoms to which it is attached forms a 3-7 membered monocyclic-carbocycle or 5-9 membered bicyclic-carbocycle, wherein any 3-7 membered monocyclic-carbocycle or 5-9 membered bicyclic-carbocycle of C is optionally substituted with 1, 2, 3, or 4 $Z^4$ groups, wherein the $Z^4$ groups are the same or different;
$R^{3a}$ and $R^{3b}$ are each H;
$Z^1$ is

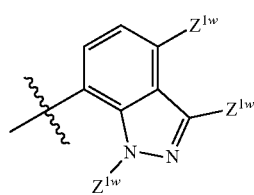

wherein each $Z^{1w}$ is independently $Z^{1a}$, $Z^{1b}$, or H
each $Z^{1a}$ is independently $(C_3-C_7)$carbocycle, 5-12 membered heteroaryl, 3-12 membered heterocycle, halogen, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$ NR$^{q1}$R$^{r1}$, —NR$^{q1}$R$^{p1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, —C(O)R$^{n1}$, —C(O)OR$^{n1}$, —C(O)NR$^{q1}$R$^{r1}$ and —S(O)$_2$ NR$^{n1}$COR$^{p1}$, wherein any $(C_3-C_7)$carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;
each $Z^{1b}$ is independently $(C_1-C_8)$alkyl optionally substituted with 1, 2, 3, 4 or 5 halogen, which are the same or different;

each $Z^{1c}$ is independently halogen —CN, —OH, —NH$_2$, —C(O)NR$^{q2}$R$^{r2}$, or (C$_1$-C$_8$)heteroalkyl;

each $Z^{1d}$ is independently (C$_1$-C$_8$)alkyl or (C$_1$-C$_8$)haloalkyl;

each R$^{n1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any (C$_1$-C$_8$)alkyl of R$^{n1}$ is optionally substituted with 1, 2, 3, 4 or 5 $Z^{1c}$ groups, wherein the $Z^{1c}$ groups are the same or different;

each R$^{p1}$ is independently (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{P1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any (C$_1$-C$_8$)alkyl of R$^{p1}$ is optionally substituted with 1, 2, 3, 4 or 5 $Z^{1c}$ groups, wherein the $Z^{1c}$ groups are the same or different;

each R$^{q1}$ and R$^{r1}$ is independently H, (C$_1$-C$_8$)alkyl, (C$_3$-C$_7$)carbocycle, 3-7 membered heterocycle, or 5-6 membered monocyclic-heteroaryl, wherein any (C$_3$-C$_7$)carbocycle, 3-7 membered heterocycle, or 5-6 membered monocyclic-heteroaryl of R$^{q1}$ or R$^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any (C$_1$-C$_8$)alkyl of R$^{q1}$ or R$^{r1}$ is optionally substituted with 1, 2, 3, 4 or 5 $Z^{1c}$ groups, wherein the $Z^{1c}$ groups are the same or different, or R$^{q1}$ and R$^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;

each R$^{q2}$ and R$^{r2}$ is independently H, (C$_1$-C$_8$)alkyl, (C$_3$-C$_7$)carbocycle, or R$^{q2}$ and R$^{r2}$ together with the nitrogen to which they are attached form a 5, 6, or 7-membered heterocycle;

$Z^2$ is (C$_2$-C$_8$)alkynyl, optionally substituted with 1, 2, 3, 4, or 5 $Z^{2c}$ groups, wherein the $Z^{2c}$ groups are the same or different;

each $Z^{2c}$ is independently oxo, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, —NO$_2$, —C(O)R$^{n4}$, —C(O)OR$^{n4}$, or —C(O)NR$^{q4}$R$^{r4}$;

each R$^{n4}$ is independently H, (C$_1$-C$_4$)alkyl, (C$_1$-C$_4$)haloalkyl, or (C$_1$-C$_4$)heteroalkyl;

each R$^{p4}$ is independently (C$_1$-C$_8$)alkyl, (C$_1$-C$_4$)haloalkyl, or (C$_1$-C$_4$)heteroalkyl;

each R$^{q4}$ and R$^{r4}$ is independently H, (C$_1$-C$_4$)alkyl, (C$_1$-C$_4$)haloalkyl, or (C$_1$-C$_4$)heteroalkyl;

each $Z^4$ is independently oxo, (C$_1$-C$_8$)alkyl, (C$_3$-C$_7$)carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any (C$_3$-C$_7$)carbocycle or (C$_1$-C$_8$)alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —OR$^{n6}$;

each R$^{n5}$, R$^{p5}$, R$^{q5}$, R$^{r5}$, and R$^{n6}$ is independently H or (C$_1$-C$_4$)alkyl;

each $Z^5$ is independently halogen, which may be same or different; and n is 0, 1, 2, or 3;

or a pharmaceutically acceptable salt thereof.

21. The compound of claim 20, or a pharmaceutically acceptable salt thereof, wherein the moiety

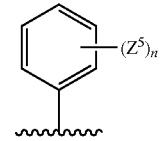

is

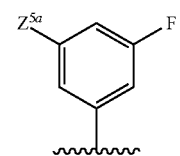

wherein $Z^{5a}$ is H or halogen.

22. The compound of claim 20, or a pharmaceutically acceptable salt thereof, wherein $Z^2$ is of the formula:

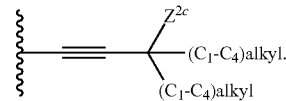

23. The compound of claim 20, or a pharmaceutically acceptable salt thereof, wherein:

each $Z^{1a}$ is independently halogen, —CN, —OR$^{n1}$, —NR$^{n1}$S(O)$_2$R$^{p1}$, —NR$^{n1}$S(O)$_2$NR$^{q1}$R$^{r1}$, —NR$^{q1}$R$^{r1}$, —NR$^{n1}$COR$^{p1}$, —NR$^{n1}$CONR$^{q1}$R$^{r1}$, or —NR$^{n1}$CO$_2$R$^{p1}$;

each $Z^{1b}$ is independently (C$_1$-C$_8$alkyl), wherein the (C$_1$-C$_8$alkyl) is optionally substituted with 1, 2, or 3 halogen, which are the same or different; and at least one of $Z^{1w}$ is $Z^{1a}$ or $Z^{1b}$.

24. The compound of claim 20, or a pharmaceutically acceptable salt thereof, wherein R$^1$ is

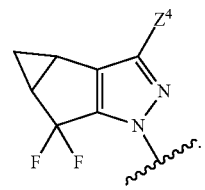

25. The compound of claim 20, or a pharmaceutically acceptable salt thereof, wherein R$^1$ optionally substituted with 1, 2, 3, or 4 $Z^4$ groups is

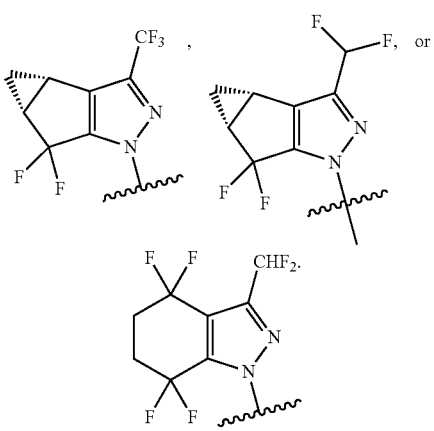

26. A pharmaceutical composition comprising a compound of claim 20, or a pharmaceutically acceptable salt thereof, and a pharmaceutically acceptable carrier.

27. A pharmaceutical composition comprising a compound of claim 20, or a pharmaceutically acceptable salt thereof, and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor or combinations thereof.

28. A method for treating a HIV infection in a patient in need thereof comprising administering a therapeutically effective amount of a compound of claim 20, or a pharmaceutically acceptable salt thereof, to the patient.

29. A method for treating an HIV infection in a patient in need thereof comprising administering to the patient a therapeutically effective amount of a compound of claim 20, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor or combinations thereof.

30. A compound of formula IIIe:

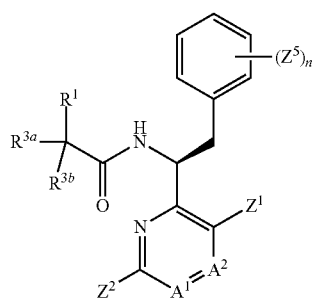

IIIe wherein
$A^1$ is CH;
$A^2$ is CH;
$R^1$ is:

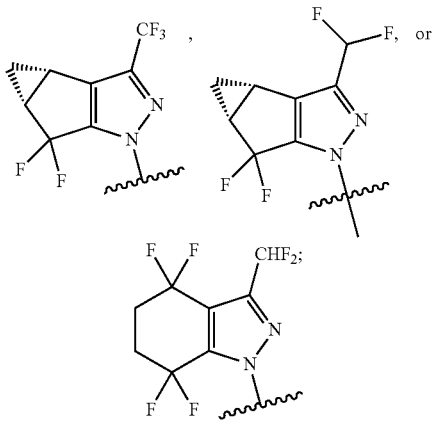

$R^{3a}$ and $R^{3b}$ are each R
$Z^1$ is

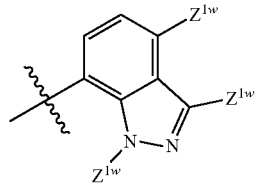

wherein each $Z^{1w}$ is independently $Z^{1a}$, $Z^{1b}$, or H;
each $Z^{1a}$ is independently halogen, —CN, —$OR^{n1}$, —$NR^{n1}S(O)_2R^{p1}$, —$NR^{n1}S(O)_2NR^{q1}R^{r1}$, —$NR^{q1}R^{r1}$, —$NR^{n1}COR^{p1}$, —$NR^{n1}CONR^{q1}R^{r1}$, or —$NR^{n1}CO_2R^{p1}$;
each $Z^{1b}$ is independently ($C_1$-$C_8$alkyl), wherein the ($C_1$-$C_8$alkyl) is optionally substituted with 1, 2, or 3 halogen, which are the same or different; and at least one of $Z^{1w}$ is $Z^{1a}$ or $Z^{1b}$;
each $Z^{1c}$ is independently halogen, —CN, —OH, —$NH_2$, —C(O) $NR^{q2}R^{r2}$, or ($C_1$-$C_8$) heteroalkyl;
each $Z^{1d}$ is independently ($C_1$-$C_8$) alkyl or ($C_1$-$C_8$)haloalkyl;
each $R^{n1}$ is independently H, ($C_1$-$C_8$) alkyl, ($C_3$-$C_7$) carbocycle, 3-7 membered heterocycle, or 5-6 membered monocyclic-heteroaryl, wherein any ($C_3$-$C_7$)carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any ($C_1$-$C_8$)alkyl of $R^{n1}$ is optionally substituted with 1, 2, 3, 4 or 5 $Z^{1c}$ groups, wherein the $Z^{1c}$ groups are the same or different;
each $R^{p1}$ is independently ($C_1$-$C_8$)alkyl, ($C_3$-$C_7$)carbocycle, 3-7 membered heterocycle, or 5-6 membered monocyclic-heteroaryl, wherein any ($C_3$-$C_7$)carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any ($C_1$-$C_8$)alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is of the formula:

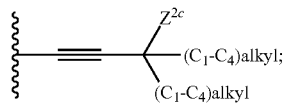

$Z^{2c}$ is oxo, halogen, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2 R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2 R^{p4}$, —$NR^{n4}S(O)_2OR^{p4}$, —$NR^{n4}S(O)_2 NR^{q4}R^{r4}$, —$NO_2$, —$C(O)R^{n4}$, —$C(O)OR^{n4}$, or —$C(O)NR^{q4}R^{r4}$;

each $R^{n4}$ is independently H, $(C_1-C_4)$alkyl, $(C_1-C_4)$haloalkyl, or $(C_1-C_4)$heteroalkyl;

each $R^{p4}$ is independently $(C_1-C_8)$alkyl, $(C_1-C_4)$haloalkyl, or $(C_1-C_4)$heteroalkyl;

each $R^{q4}$ and $R^{r4}$ is independently H, $(C_1-C_4)$alkyl, $(C_1-C_4)$haloalkyl, or $(C_1-C_4)$heteroalkyl; and the moiety

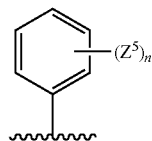

is

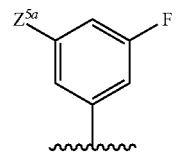

wherein $Z^{5a}$ is H or halogen;

or a pharmaceutically acceptable salt thereof.

31. A pharmaceutical composition comprising a compound of claim 30, or a pharmaceutically acceptable salt thereof, and a pharmaceutically acceptable carrier.

32. A pharmaceutical composition comprising a compound of claim 30, or a pharmaceutically acceptable salt thereof, and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

33. A method for treating a HIV infection in a patient in need thereof comprising administering a therapeutically effective amount of a compound of claim 30, or a pharmaceutically acceptable salt thereof, to the patient.

34. A method for treating an HIV infection in a patient in need thereof comprising administering to the patient a therapeutically effective amount of a compound of claim 30, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor and combinations thereof.

\* \* \* \* \*

UNITED STATES PATENT AND TRADEMARK OFFICE
CERTIFICATE OF CORRECTION

PATENT NO. : 9,951,043 B2  
APPLICATION NO. : 14/771779  
DATED : April 24, 2018  
INVENTOR(S) : Gediminas Brizgys et al.

Page 1 of 3

It is certified that error appears in the above-identified patent and that said Letters Patent is hereby corrected as shown below:

In the Claims

Column 530, Claim 1, Line 16, delete "Hie:" and insert -- IIIe: --;

Column 530, Claim 1, Line 33, delete "OH," and insert -- CH --;

Column 530, Claim 1, Line 55, delete "—C(O)Nr$^{q1}$R$^{r1}$" and insert -- —C(O)NR$^{q1}$R$^{r1}$ --;

Column 530, Claim 1, Line 65, delete "—C(O)N$^{q2}$R$^{r2}$," and insert -- —C(O)NR$^{q2}$R$^{r2}$, --;

Column 531, Claim 1, Line 61, delete "—NR$^{n4}$CONR$^{q4}$R$^{n4}$," and insert -- —NR$^{n4}$CONR$^{q4}$R$^{r4}$, --;

Column 531, Claim 1, Line 65, delete "heteroalkyl," and insert -- heteroalkyl; --;

Column 532, Claim 1, Line 3, delete "heteroalkyl," and insert -- heteroalkyl; --;

Column 532, Claim 1, Line 16, delete "n 0," and insert -- n is 0, --;

Column 533, Claim 13, Line 54, delete "R$^1$ optionally" and insert -- R$^1$ is optionally --;

Column 534, Claim 14, Line 18, "tricyclics heterocycle," and insert -- tricyclic-heterocycle, --;

Signed and Sealed this  
Third Day of July, 2018

Andrei Iancu  
*Director of the United States Patent and Trademark Office*

CERTIFICATE OF CORRECTION (continued)
U.S. Pat. No. 9,951,043 B2

Column 573, Claim 15, Lines 51-67, delete

"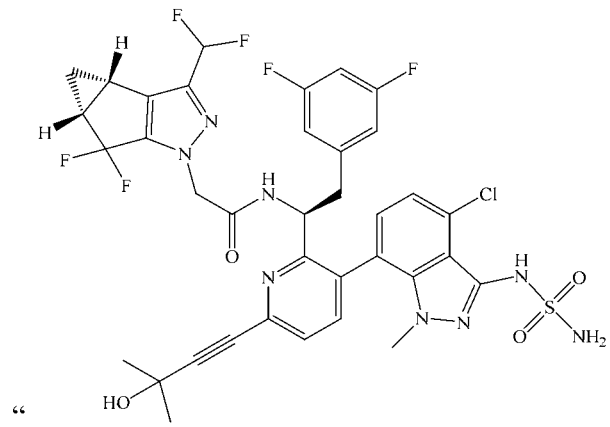" and insert

--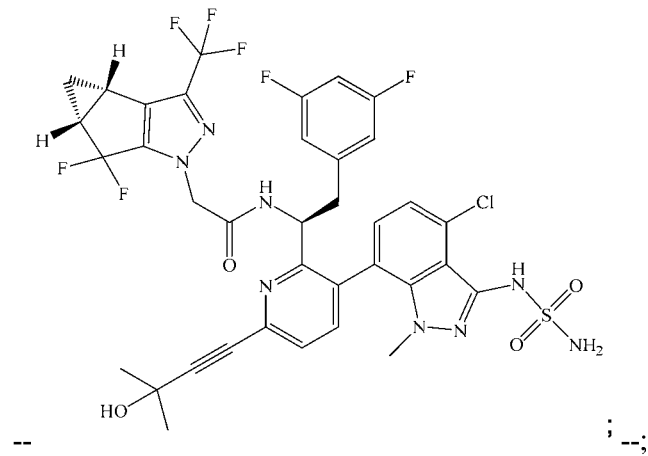; --;

CERTIFICATE OF CORRECTION (continued)
U.S. Pat. No. 9,951,043 B2

Column 587, Claim 15, Lines 1-19, delete

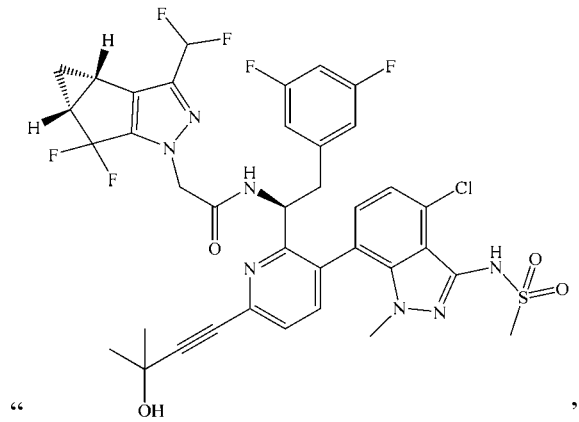

" and insert

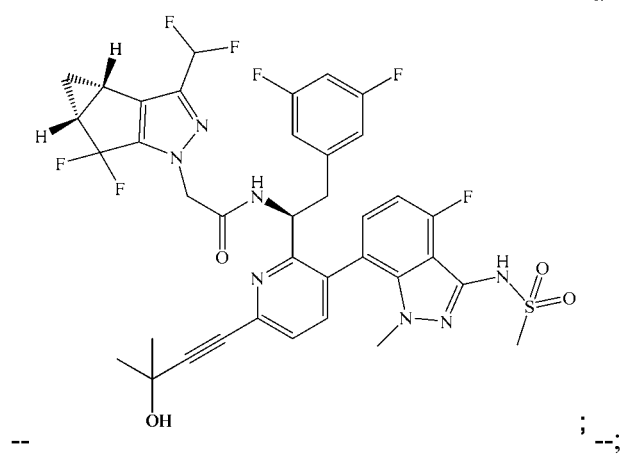

--;

Column 592, Claim 20, Line 32, delete "wherein" and insert -- wherein: --;

Column 592, Claim 20, Line 56, delete "—NR$^{q1}$R$^{p1}$," and insert -- —NR$^{q1}$R$^{r1}$, --;

Column 593, Claim 20, Line 1, delete "halogen —CN" and insert -- halogen, —CN --;

Column 593, Claim 20, Line 19, delete "R$^{P1}$" and insert -- R$^{p1}$ --;

Column 594, Claim 25, Line 66, delete "R$^1$ optionally" and insert -- R$^1$ is optionally --;

Column 596, Claim 30, Line 24, delete "R" and insert -- H; --;

Column 596, Claim 30, Line 44, delete "—C(O) NR$^{q2}$R$^{r2}$," and insert -- —C(O)NR$^{q2}$R$^{r2}$, --.